US007294695B2

(12) United States Patent
Baker et al.

(10) Patent No.: US 7,294,695 B2
(45) Date of Patent: Nov. 13, 2007

(54) PRO10268 POLYPEPTIDES

(75) Inventors: Kevin P. Baker, Darnestown, MD (US); Dan L. Eaton, San Rafael, CA (US); Ellen Filvaroff, San Francisco, CA (US); Audrey Goddard, San Francisco, CA (US); J. Christopher Grimaldi, San Francisco, CA (US); Austin L. Gurney, Belmont, CA (US); Victoria Smith, Burlingame, CA (US); Jean Philippe Stephan, Millbrae, CA (US); Colin K. Watanabe, Moraga, CA (US); William I. Wood, Hillsborough, CA (US); Zemin Zhang, Foster City, CA (US); Sherman Fong, Alameda, CA (US)

(73) Assignee: Genentech, Inc., South San Francisco, CA (US)

( * ) Notice: Subject to any disclaimer, the term of this patent is extended or adjusted under 35 U.S.C. 154(b) by 357 days.

(21) Appl. No.: 10/243,189

(22) Filed: Sep. 12, 2002

(65) Prior Publication Data

US 2006/0074033 A1 Apr. 6, 2006

Related U.S. Application Data

(63) Continuation of application No. 10/197,942, filed on Jul. 18, 2002, now abandoned, which is a continuation of application No. PCT/US01/27099, filed on Aug. 29, 2001, and a continuation-in-part of application No. PCT/US00/30873, filed on Nov. 10, 2000.

(60) Provisional application No. 60/177,118, filed on Jan. 20, 2000.

(51) Int. Cl.
*C07K 14/00* (2006.01)

(52) U.S. Cl. .................................................... 530/350

(58) Field of Classification Search ................ 500/350; 530/300; 536/23.5

See application file for complete search history.

(56) References Cited

U.S. PATENT DOCUMENTS 5,536,637 A 7/1996 Jacobs ........................... 435/6

FOREIGN PATENT DOCUMENTS

EP 1 067 182 A2 * 1/2001

OTHER PUBLICATIONS

Haynes et al. Proteome analysis: biological assay or data archive? Electrophoresis 1998; vol. 19(11), pp. 1862-1871.*

Hancock WS. Do we have enough Biomarkers? J. Proteome Research 2004; vol. 3(4), p. 685.*

Hu et al. Analysis of genomic and proteonic data using advanced literature mining. J. Proteome Res. 2003; vol. 2(4), pp. 405-412.*

Wang et al. mRNA differential display: application in the discovery of novel pharmacoliogical targets. Trends Pharmacol. Sci. 1996; vol. 17(8):276-279.*

Henikoff et al. Gene families: the taxonomy of protein paralogs and chimeras. Science 1997; vol. 278(5338), pp. 609-614.*

Lian et al. (Blood 98:513-524, 2001).*

Fessler et al. (J. Biol. Chem. 277:31291-31302, 2002).*

Czupalla et al (Proteomics (2005) 5:3868-3875).*

Kwong et al (Genomics (2005) 26:142-158).*

Chen et al (Mol. Cellular Proteomics (2002) 1:304-313).*

Conrad; et al (Mol. Cell Proteomics (2005) 4(9) :1284-1296).*

Ginestier et al (Am. J. Pathol. (2002) 161:1223-1233).*

Anderson et al (Electrophoresis (1997) 18:533-537).*

Washburn (Proc. Natl. Acad. Sci. (2003) 100 (6):3107-3112).*

Meric et al (Molecular Cancer Therapeutics (2002) 1:971-979).*

Gokman-Polar (Cancer Research (2001) 61:1375-1381).*

Pennica et al (Proc. Natl. Acad. Sci. USA (1998) 95:14717-14722).*

Li et al (J. Theoretical Biology (2002) 219:539-551).*

Ding et al (Bioinformatics (2003) 19(10):1259-66).*

Sawiris et al (Cancer Research (2002) 62:2923-2928).*

Klein et al., "Selection for genes encoding secreted proteins and receptors" *Proc. Nat. Acad. Sci. USA* 93:7108-7113 (1996).

Orntoft et al., Mol. and Cell. Proteomics, 1:37-45 (2002).

Abe, N., et al., "An Increased High-Mobility Group A2 Expression Level is Associated with malignant Phenotype in Pancreatic Exocrine Tissue," *Br J Cancer*—89(11):2104-9 (2003) Abstract.

Ando, M., et al., "Selective Apoptosis of Natural Killer-Cell Tumours by I-Asparaginase," *Br J Haematol.*,—130(6):860-8 (2005) Abstract.

Aust, G., et al., "Human Thyroid Carcinoma Cell Lines and Normal Thyrocytes: Expression and Regulation of Matrix Metalloproteinase Inhibitor-1 Messenger-RNA and Protein," *Thyroid*—7(5):713-24 (1997) Abstract.

Barnes, V.L., et al., "Expression of Embryonic Fibronectin Isoform EIIIA Parallels Alpha-Smooth Muscle Actin in Maturing and Diseased Kidney," *J Histochem Cytochem.*—47(6):787-98 (1999) Absract.

Bea, S., et al., "BMI-1 Gene Amplification and Overexpression in Hematological Malignancies Occur Mainly in Mantle Cell Lymphonas," *Cancer Res.*—61(6):2409-12 (2001) Abstract.

(Continued)

*Primary Examiner*—J. E. Angell
(74) *Attorney, Agent, or Firm*—Mark T. Kresnak; Elizabeth M. Barnes; Ginger R. Dreger

(57) ABSTRACT

The present invention is directed to novel polypeptides and to nucleic acid molecules encoding those polypeptides. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention and to methods for producing the polypeptides of the present invention.

6 Claims, 115 Drawing Sheets

OTHER PUBLICATIONS

Blaschke, V., et al., "Rapid Quantitation of Proinflammatory and Chemoattractant Cytokine Expression in Small Tissue Samples and Monocyte-Derived Dendritic Cells: Validation of a New Real-Time RT-PCR Technology," *J Immunol Methods.*—246(1-2):79-90 (2000) Abstract.

Buckley, A.R., et al., "Butyrate-Induced Reversal of Dexamethasone Resistance in Autonomous Rat Nb2 Lymphoma Cells," *Apoptosis.*—2(6):518-28 (1997) Abstract.

Caberlotto, L. et al., "Alterations in Neuropeptide Y Levels and Y1 Binding Sites in the Flinders Sensitive Line Rats, A Genetic Animal Model of Depression," *Neurosci Lett.*—265(3):191-4 (1999) Abstract.

Caberlotto, L., et al., "Neurokinin 1 Receptor and Relative Abundance of the Short and Long Isoforms in the Human Brain," *Eur J Neurosci.*—17(9):1736-46 (2003) Abstract.

Chol, D., et al., "Characterization of Cyclin D2 Expression in Human Endometrium," *J Soc Gynecol Investig.*—9(1):41-6 (2002) Abstract.

Couvelard, A., et al., "Human Chorionic Gonadotrophin Beta Expression in Malignant Barrett's Oesophagus," *Virchows Arch.*—445(3):279-84 (2004) Abstract.

Dagenais, A., et al., "Downregulation of EnaC Activity and Expression by TNF-Alpha in Alveolar Epithelial Cells," *Am J. Physio Lung Cell Mol Physiol.* 286(2):L301-11 (2004) Abstract.

De Boer, C.J., et al., "Involement of the CCNDI Gene in Hairy Cell Leukemia," *Ann Oncol.*—7(3):251-6 (1996) Abstract.

Debieve, F., et al., "Inhibin and Activin Production and Subunit Expression in Human Placental Cells Cultured in Vitro," *Mol Hum Reprod.*—6(8):743-9 (2000) Abstract.

Dong, Z., et al., "Expression of Membrane-Type Matrix Metalloproteinases 4, 5, and 6 in Mouse Corneas Infected with P. Aeruginosa," *Invest Opthalmol Vis Sci*—42(13):3223-(2001) Abstract.

Duchrow, M., et al., "Assessment of Proliferative Activity in Colorectal Carcinomas by Quantitative Reverse Transcriptase-Polymerase Chain Reaction (RT-PCR)," *Cancer Invest.*—19(6):588-96 (2001) Abstract.

Dyer, J., et al., "Molecular Characterisation of Carbohydrate Digestion and Absorption in Equine Small Intestine," *Equine Vet J.*—34(4):349-58 (2002) Abstract.

Egwuagu, C.E., et al., "Suppressors of Cytokine Signaling Proteins are Differentially Expressed in Th1 and Th2 Cells: Implications for Th Cell Lineage Commitment and Maintenance," *J Immunol.*—168(7):3181-7 (2002) Abstract.

El-Ghrably, I.A., et al., "Intravitreal Invading Cells Contribute to Vitreal Cytokine-Milieu in Proliferative Vitreoretinopathy," *Br J Opthalmol.*—85(4):461-70 (2001) Abstract.

Eleore, L., et al., "Modulation of the Glutamatergic Receptors (AMPA and NMDA) and of Glutamate Vesicular Transporter 2 in the Rat Facial Nucleus after Axotomy," *Neuroscience*—136(1):147-60 (2005) Abstract.

Forsberg, H., et al., "Altered Levels of Scavenging Enzymes in Embryos Subjected to a Diabetic Environment," *Free Radic Res.*—24(6):451-9 (1996) Abstract.

Freyschuss, B., et al., "Induction of the Estrogen Receptor by Growth Hormone and Glucocorticoid Substitution in Priminary Cultures of Rat Hepatocytes," *Endocrinology*—133(4):1548-54 (1993) Abstract.

Fu, K., et al., "Cyclin D1-Negative Mantle Cell Lymphoma: A Clinocopathologic Study Based on Gene Expression Profiling," *Blood*—106(13):4315-21 (2005) Abstract.

Fuchs, A.R., et al., "Oxytocin Receptors in Bovine Cervix:Distrubution and Gene Expression During the Estrous Cycle," *Biol Reprod.*— 54(3):700-8 (1996) Abstract.

Furuta, J., et al., "Silencing of the Thrombomodulin Gene in Human Malignant Melanoma," *Melanoma Res.*—15(1):15-20 (2005) Abstract.

Futcher, B., et al., "A Sampling of the Yeast Proteome," *Mol Cell Biol.*,—19(11):7357-68 (1999) Abstract.

George, J., et al., "Pre-translational Regulation of Cytochrome P450 Genes is Responsible for Disease-Specific Changes of Individual P450 Enzymes Among Patients with Cirrhosis," *Biochem Pharmacol.*—49(7):873-81 (1995) Abstract.

Giroux, M., et al., "Cyclooxygenase-2 Expression in Macrophages: Modulation by Protein Kinase C-alpha," *J Immunol.*—165(7):3985-91 (2000) Abstract.

Gnatenko, D.V., et al., "Transcript Profiling of Human Platelets Using Microarray and Serial Analysis of Gene Expression," *Blood*—101(6):2285-93 (2003) Abstract.

Godbout, R., et al., "Overexpression of DEAD Box Protein (DDX1) in Neuroblastoma and Retinoblastoma Cell Lines," *J Biol Chem*,—273(33):21161-8 (1998) Abstract.

Goldenberg, R.C., et al., "Modulation of Gap Junction Mediated Intercellular Communication in TM3 Leydig Cells," *J Endocrinol.*— 177(2):327-35 (2003) Abstract.

Goleblowski, F., et al., "Expression Level of Ubc9 Protein in Rat Tissues," *Acta Biochim Pol.*—50(4):1065-73 (2003) Abstract.

Grem, J.L., et al., "Thymidine Kinase, Thymidylate Synthase, and Dihydropyrimidine Dehydrogenase Profiles of Cell Lines of the National Cancer Institute's Anticancer Drug Screen," *Clin Cancer Res.*—7(4):999-1009 (2001) Abstract.

Grenback, E., et al., "Galanin Pituitary Adenomas," *Regul Pept*,—117(2):127-39 (2004) Abstract.

Gromova, I., et al., "Protein Abundance and mRNA Levels of the Adipocyte-Type Fatty Acid Binding Protein Correlate in Non-Invasive and Invasive Bladder Transitional Cell Carcinomas," *Int J. Oncol.*—13(2):379-83 (1998) Abstract.

Guo, Y., et al., "The Pathogenic Role of Macrophage Migration Inhibitory Factor in Acute Respiratory Distress Syndrome," Zhinghua Jie He He Hu Xi Za Zhi—25(6):337-40 (2002) Abstract.

Habu, Y., et al., "Restored Expression and Activity of Organic Ion Transporters rOAT1, rOAT3 and rOCT2 after Hyperuricemia in the Rat Kidney," *Biochem Pharmacol*—69(6):993-9 (2005) Abstract.

Hahn, M.E., et al., "Regulation of Cytochrome P4501A1 in Teleosts: Sustained Induction of CYP1A1 mRNA, Protein, and Catalytic Activity by 2,3,7,8-Tetrachlorodibenzofuran in the Marine Fish Stenotomus Chrysops," *Toxicol Appl Pharmacol.*—127(2):187-98 (1994) Abstract.

Hahnel, R., et al., "Expression of the pS2 Gene in Breast Tissues Assessed by pS2-mRNA Analysis and pS2-Protein Radioimmunoassay," *Breast Cancer Res Treat.*—24(1):71-4 (1992) Abstract.

Hamilton, L.M., et al., "The role of the Epidermal Growth Factor Receptor in Sustaining Neutrophil Inflammation in Severe Asthma," *Clin Exp Allergy.*—33(2):233-40 (2003) Abstract.

Hassett, C., et al., "Human Hepatic Microsomal Epoxide Hydrolase: Comparative Analysis of Polymorphic Expression," *Arch Biochem Biophys.*—337(2):275-83 (1997) Abstract.

Holten-Andersen, M.N., et al., "Localization of Tissue Inhibitor of Metalloproteinases 1 (TIMP-1) in Human Colorectal Adenoma and Adenocarcinoma," *Int J Cance*,—113(2):198-206 (2005) Abstract.

Huang, Y.H., et al., "Tissue Plasminogen Activator Induced by Dengue Virus Infection of Human Endothelial Cells," *J Med Virol.*—70(4):610-6 (2003) Abstract.

Huettner, P.C., et al., "Neu Oncogene Expression in Ovarian Tumors: A Quantitative Study," *Mod Pathol.*—5(3):250-6 (1992) Abstract.

Hui, P., et al., "Real-time Quantitative RT-PCR of Cyclin D1 mRNA in Mantle Cell Lymphoma: Comparison with FISH and Immunohistochemistry," Leuk Lymphoma. 44(8):1385-94 (2003) Abstract.

Husain, I., et al., "Elevation of Topoisomerase I Messenger RNA, Protein, and Catalytic Activity in Human Tumors: Demonstration of Tumor-Type Specificity and Implications for Cancer Chemotherapy," *Cancer Res.*—54(2):539-46 (1994) Abstract.

Ihmann, T., et al., "High-level mRNA Quantification of Proliferation Marker pKl-67 is Correlated with Favorable Prognosis in Colorectal Carcinoma," *J Cancer Res Clin Oncol.*—130(12):749-56 (2004) Abstract.

Ikegami, T., et al., "Modulation of Glucagon Receptor Expression and Response in Transfected Human Embryonic Kidney Cells," *Am J Physiol Cell Physiol.*—281(4):C1396-402 (2001) Abstract.

Jacquemin, E., et al., "Developmental Regulation of Acidic Fibroblast Growth Factor (aFGF) Expression in Bovine Retina," *Int J Biol.*—37(3):417-23 (1993) Abstract.
Jaime, M., et al., "The p21 (Cip1) Protein, A Cyclin Inhibitor, Regulates the Levels and the Intracellular Localization of CDC25A in Mice Regenerating Livers," *Hepatology*—35(5):1063-71 (2002) Abstract.
Janssens, N., et al., "Alteration of Frizzled Expression In renal Cell Carcinoma," *Tumour Biol.*—25(4):161-71 (2004) Abstract.
Jungbluth, A.A., et al., "Immunohistochemical Analysis of NY-ESO-1 Antigen Expression in Normal and Malignant Human Tissues," *Int J. Cancer*—92(6):856-60 (2001) Abstract.
Kalabis, G.M., et al., "Multidrug Resistance Phosphoglycoprotein (ABCB1) in the Mouse Placenta: Fetal Protection," *Biol Reprod.*—73(4):591-7 (2005) Abstract.
Kammaori, M., et al., "Expression of Human Telomerase Reverse Transcriptase Gene and Protein, and of Estrogen amd Progesterone Receptors, in Breast Tumors: Preliminary Data from Neo-Adjuvant Chemotherapy," *Int J Oncol.*—27(5):1257-63 (2005) Abstract.
Khal, J., et al., "Expression of the Ubiquitin-Proteasome Pathway and Muscle Loss in Experimental Cancer Cachexi," *Br J Cancer*—93(7):774-80 (2005), Abstract.
Khal, J., et al., "Increased Expression of Proteasome Subunits in Skeletal Muscle of Cancer Patients with Weight Loss," *Int J. Biochem Cell Biol.*—37(10):2196-206 (2005) Abstract.
Kogo, H., et al., "Cell Type-Specific Occurrence of Caveolin-1alpha and -1beta in the Lung caused by Expression of Distinct mRNAs," *J Biol Chem.*—279(24):25574-81 (2004) Abstract.
Kommoss, F., et al., "Oncogene and Growth Factor Expression in Ovarian Cancer," *Acta Obstet Gynecol Scand Suppl.*—155:19-24 (1992) Abstract.
Kumar, U., et al., "Somatostatin Receptors in Primary Human Breast Cancer: Quantitative Analysis of mRNA for Subtypes 1-5 and Correlation with Receptor Protein Expression and Tumor Pathology," *Breast Cancer Res. Treat.*—92(2):175-86 (2005) Abstract.
Kuo, C.C., et al., "A Transcriptomic and Proteomic Analysis of the Effect of CpG-ODN on Human THP-1 Monocytic Leukemia Cells," *Proteomics*—5(4):894-906 (2005) Abstract.
Landmark, B.F., et al., "Cellular Location and Age-dependent Changes of the regulatory Subunits of cAMP-dependent Protein Kinase in Rat Testis," *J Reprod Fertil.*—99(2):323-34 (1993) Abstract.
Lassmann, S., et al., "Quantification of CK20 Gene and Protein Expression in Colorectal Cancer by RT-PCR and Immunohistochemistry Reveals Inter- and Intratumour Heterogeneity," *J Pathol.*—198(2):198-206 (2002) Abstract.
Legrand, O., et al., "Expression of the Multidrug Resistance-Associated Protein (MRP) mRNA and Protein in Normal Peripheral Blood and Bone Marrow Haemopoietic Cells," *Br J, Haematol.*—94(1):23-33 (1996) Abstract.
Lemstrom, K.B., et al., "Vascular Endothelial Growth Factor Enhances Cardiac Allograft Arteriosclerosis," *Circulation*—105(21):2524-30 (2002) Abstract.
Li, Z.B., et al., "Enhanced Expressions of Arachidonic Acid-Sensitive Tandem-Pore Domain Potassium Channels in Rat Experimental Acute Cerebral Ischemia," *Biochem Biophys Res Commun.*— 327(4):1163-9 (2005) Abstract.
Li, Y., et al., "Retinal Preconditioning and the Induction of Heat-Shock Protein 27," *Invest Ophthalmol Vis Sci.*—44(3):1299-304 (2003) Abstract.
Lindberg, P., et al., "Increasing Expression of Tissue Plasminogen Activator and Plasminogen Activator Inhibitor Type 2 in Dog Gingival Tissues with Progressive Inflammation," *Arch Oral Biol.*— 46(1):23-31 (2001) Abstract.
Macabeo-Ong, M., et al., "Effect of Duration of Fixation on Quantitative Reverse Transcription Polymerase Chain Reaction Analyses," 15(9):979-87 (2002) Abstract.
Maruyama, H., et al., "Id-1 and Id-2 are Overexpressed in Pancreatic Cancer and in Dysplastic Lesions in Chronic Pancreatitis," *Am J Pathol.*—155(3):815-22 (1999) Abstract.
Meehan, T.P., et al., "Tightly Regulated and Inducible Expression of a Yoked Hormone-Receptor Complex in HEK 293 Cells," *J Mol Endocrinol.*—32(1):247-55 (2004) Abstract.
Mendoza-Rodriguez, C.A., et al., "C-fos and Estrogen Receptor Gene Expression Pattern in the Rat Uterine Epithelium During the Estrous Cycle," *Mol Reprod Dev.* 64(4):379-88 (2003) Abstract.
Meoni, P., et al., "[3H]MK-801 Binding and the mRNA for the NMDARI Subunit of the NMDA Receptor are Differentially Distributed in Human and Rat Forebrain," *Brain Res Mol Res.*—54(1):13-23 (1998) Abstract.
Mezzano, S.A., et al., "Overexpression of Chemokines, Fibrogenic Cytokines, and Myofibroblasts in Human Membranous Nephropathy," *Kiney Int.*—57(1):147-58 (2000) Abstract.
Mingrone, G., et al., "Decreased Uncoupling Protein Expression and Intramyocytic Triglyceride Depletion in Formerly Obese Subjects," *Obes Res.*—11(5):632-40 (2003) Abstract.
Miralles, C.P., et al., "Differential Expression of the Short and Long Forms of the Gamma 2 Subunit of the GABAA/benzodiazepine Receptors," *Brain Res Mol Res.*—24(1-4):129-39 (1994) Abstract.
Mizrachi, D., et al., "Follicle-stimulating Hormone Receptor and Its Messenger Ribonucleic Acid are Present in the Bovine Cervix and Can Regulate Cervical Prostanoid Synthesis," *Biol Reprod.*—61(3):776-84 (1999) Abstract.
Monaghan, P., et al., "The Alpha(v)beta6 Integrin Receptor for Foot-and-Mouth Disease Virus is Expressed Constitutively on the Epithelial Cells Targeted in Cattle," *J Gen Virol.*—86(PT 10):2769-80 (2005) Abstract.
Montuori, N., et al., "Urokinase-Mediated Posttranscriptional Regualtion of Urokinase-Receptor Expression in Non Small Cell Lung Carcinoma," *Int J Cancer*—105(3):353-60 (2003) Abstract.
Munaut , C.,et al., "Vascular Endothelial Growth Factor Expression Correlates with Matrix Metalloproteinases MT1-MMP, MMP-2 and MMP-9 in Human Glioblastomas," *Int J Cancer*—106(6):848-55 (2003) Abstract.
Nie, Y., et al., "DNA Hypermethylation is a Mechanism for Loss of Expression of the HLA Class I Genes in Human Esophageal Squamous Cell Carcinomas," *Carcinogenesis*—22(10):1615-23 (2001) Abstract.
Nuciforo, P.G., et al., "Molecular and Immunohistochemical Analysis of HER2/neu Oncogene in Synovial Sarcoma," *Hum Pathol.*—34(7):639-45 (2003) Abstract.
Oberringer, M., et al., "Differential Expression of Heat Shock Protein 70 in Well Healing and Chronic Human Wound Tissue," *Biochem Biophys Res Commun.*—214(3):1009-14 (1995) Abstract.
Orntoft, T.F., et al., "Genome-wide Study of Gene Copy Numbers, Transcripts, and Proteins Levels in Pairs of Non-Invasive and Invasive Human Transitional Cell Carcincomas," *Mol Cell Proteomics.*—1(1):37-45 (2002) Abstract.
Orntoft, T.F., et al., "Genome-Wide Study of Gene Copy Numbers, Transcripts, and Protein Levels in Pairs of Non-Invasive and Invasive Human Transitional Cell Carcinomas," *Molecular & Cellular Proteomics*—1:37-45 (2002).
Pachmann, K., et al., "Expression of bcr-abl mRNA in Individual Chronic Myelogenous Leukaemia Cells as determined by in Situ Amplification," *Br J. Haematol*—112(3):749-59 (2001) Abstract.
Pairon, J.C., et al., "Cell Localization and Regulation of Expression of Cytochrome P450 1A1 and 2B1 in Rat Lung after Induction with 3-Methylcholanthrene Using mRNA Hybridization and Immunohistochemistry," *Am J Respir Cell Mol Biol.*—11(4):386-96 (1994) Abstract.
Papotti, M., et al., "Correlative Immunohistochemical and Reverse Transcriptase Polymerase Chain Reaction Analysis of Somatostatin Receptor Type 2 in Neuroendocrine Tumors of the Lung," *Diagn Mol Pathol.*—9(1):47-57 (2000) Abstract.
Papotti, M., et al., "Expression of Somatostatin Receptor Types 1-5 in 81 Cases if Gastrointestinal and Pancreatic Endocrine Tumors. A correlative Immunohistochemical and Reverse-Transcriptase Polymerase Chain Reaction Analysis," *Virchows Arch.*—440(5):461-75 (2002) Abstract.
Paredes, J., et al., "P-Cadherin Overexpression is an Indicator of Clinical Outcome in Invasive Breast Carcinomas and is Associated with CDH3 Promoter Hypomethylation," *Clin Cancer Res.*—11(16):5869-77 (2005) Abstract.

Politis, I., et al., "Mammary-Derived Growth Inhibitor Protein and Messenger Ribonucleic Acid Concentrations in Different Physiological States of the Gland," *J Dairy Sci.*—75(6):1423-9 (1992) Abstract.

Preesman, A.H., et al., "T-Cell Receptor V Beta-family Usage in Primary Cutaneous and Primary Nodal T-cell non-Hodgkin's Lymphomas," *J Invest Dermatol.*—99(5):587-93 (1992) Abstract.

Pullig, O., et al., "Matrilin-3 in Human Articular Cartilage: Increased Expression in Osteoarthritis," *Osteoarthritis Cartilage*—10(4):253-63 (2002) Abstract.

Rey, C., et al., "Up-regulation of Mitochondrial Peripheral Benzodiazepine Receptor Expression by Tumor Necrosis Factor Alpha in Testicular Leydig Cells. Possible Involvement in Cell Survival," *Biochem Pharmacol.*—60(11):1636-46 (2000) Abstract.

Rudiowski, C., et al., "GLUT1 Messenger RNA and Protein Induction Rrelates to the Malignant Transformation of Cervical Cancer," *Am J. Clin Pathol.*—120(5):691-8 (2003) Abstract.

Sasaki, T., et al., "Expression and Distribution of Laminin Alpha1 and Alpha2 Chains in Embryonic and Adult Mouse Tissues: An Immunochemical Approach," *Exp Cell Res.*—275(2):189-99 (2002) Abstract.

Sedelies, K.A., et al., "Discordant Regulation of Granzyme H and Granzyme B Expression in Human Lymphocytes," *J Biol Chem.*—279(25):26581-7 (2004) Abstract.

Shen, Y., et al., "BCL2 Protein Expression Parallels its mRNA level in normal and Maligent B Cells," *Blood*—104(9):2936-9 (2004) Abstract.

Shinohara, Y., et al., "Quantitative Determinations of the Steady Transcript Levels of Hexokinase Isozymes and Glucose Transporter Isoforms in Normal Rat Tissues and the Malignant Tumor Cell Line AH130," *Biochim Biophys Acta*—1368(1):129-36 (1998) Abstract.

Silvers, A.L., et al., "UVA Irradiation-Induced Activation of Activator Protein-1 is Correlated with Induced Expression of AP-1 Family Memebers in the Human Keratinocyte Cell Line HaCat," *Photochem Photbiol.*—75(3):302-10 (2002) Abstract.

Song, L., et al., "Rat Kidney Glutamyl Aminopeptidase (aminopeptidase A): Molecular Identity and Cellular Localization," *Am J. Physiol.*—267(4 Pt 2):F546-57 (1994) Abstract.

Spaziani, E.P., et al., "Tumor Necrosis Factor-Alpha Upregulates the Prostaglandin E2 EP1 Receptor Subtype and the Cyclooxgenase-2 Isoform in Cultured Amnion WISH Cells," *J Interferon Cytokine Res.*—18(12):1039-44 (1998) Abstract.

Spika, I., et al., "Transcriptional Activity of Potent Glucocorticoids: Relevance of Glucocorticord Receptor Isoforms and Drug Metabolites," *Skin Pharmacol Appl Skin Physiol.*—16(3):143-50 (2003) Abstract.

Splinter, P.L., et al., "Specific Inhibition of AQP1 Water Channels in Isolated Rat Intrahepatic Bile Duct Units by Small Interfering RNAs," *J Biol Chem*—278(8):6268-74 (2003) Abstract.

Stearns, M.E., et al., "Type IV Collagenase (M(*r*) 72,000) Expression in Human Prostate: Benign and Malignant Tissue," *Cancer Res.*—53(4):878-83 (1993) Abstract.

Stein, R., et al., "The Decompensated Detrusor III: Impact of Bladder Outlet Obstruction on Sarcoplasmic Endoplasmic Reticulum Protein and Gene Expression," *J Urol.*—164(3Pt 2):1026-30 (2000) Abstract.

Strickland, I., et al. , "TNF-Alpha and IL-8 are Upregulated in the Epidermis of Normal Human Skin after UVB Exposure: Correlation with Nuetrophil Accumulation and E-Selectin Expression," *J Invest Dermatol.*—108(5):763-8 (1997) Abstract.

Strutz, F., et al., "Basic Fibroblast Growth Factor Expression is Increased in Human Renal Fibrogenesis and May Mediate Acutocrine Fibroblast Proliferation," *Kidney Int.*—57(4):1521-38 (2000) Abstract.

Takahashi, K., et al., "Adiposity Elevates Plasma MCP-1 Levels Leading to the Increased CD11b-Positive Monocytes in Mice," *J Biol. Chem.*—278(47):46654-60 (2003) Abstract.

Takimoto, Y., et al., "Augmented Expression of Neuronal Nitric Oxide Synthase in the Atria Parasympthetically Decreases Heart Rate During Acute Myocardial Infarction in Rats," *Circulation*—105(4):490-6 (2002) Abstract.

Telek, G., et al., "Differential Upregulation of Cellular Adhesion Molecules at the Sites of Oxidative Stress in Experimental Acute Pancreatitis," *J Surg Res.*—96(1):56-67 (2001) Abstract.

Timchenko, L., et al., "Myotonic Dystrophy: An Unstable CTG Repeat in a Protein Kinase Gene," *Semin Cell Biol.*—6(1):13-9 (1995) Abstract.

Torronen, R., et al., "Induction of Class 3 Aldehyde Dehydrogenase in the Mouse Hepatoma Cell Line Hepa-1 by Various Chemicals," *Chem Biol. Interact.*—83(2):107-19 (1992) Abstract.

Ullmannova, V., et al., "Relationship Between Cyclin D1 and p21 (Waf1/Clp1) During Differentiation of Human Myeloid Leukemia Cell Lines," *Leuk Res.*—27(12):1115-23 (2003) Abstract.

Van Beers, E.H., et al., "Intestinal Carbamoyl Phosphate Synthase I in Human and Rat. Expression during Development Shows Species Differences and Mosaic Expression in Duodenum of Both Species," *J Histochem Cytochem.*—46(2):231-40 (1998) Abstract.

Van Der Wilt, C.L., et al., "Expression of Deoxycytidine Kinase in Leukaemic Cells Compared with Solid Tumour Cell Lines, Liver Metastases and Normal Liver," *Eur J Cancer*—39(5):691-7 (2003) Abstract.

Waldherr, R., et al., "Expression of Cytokines and Growth Factors in Human Glomerulonephritides," *Pediatr Nephrol.*—7(4):471-8 (1993) Abstract.

Walmer, D.K., et al., "Malignant Transformation of the Human Endometrium is associated with Overexpression of Lactoferrin Messenger RNA and Protein," *Cancer Res.*—55(5):1168-75 (1995) Abstract.

Wang, J., et al., "Cell Proliferation in Human Soft Tissue Tumors Correlates with Platelet-derived Growth Factor B Chain Expression: An Immunohistochemical and in Situ Hybridization Study," *Cancer Res.*—54(2):560-4 (1994) Abstract.

Wang, J., et al., "Expression of Cadherins and Catenins in Paired Tumor and Non-neoplastic Primary Prostate Cultures and Corresponding Prostatectomy Specimens," *Urol Res.*—28(5):308-15 (2000) Abstract.

Wang, L.G., et al., "Down-Regulation of Prostate-Specific Antigen Expression by Finasteride through Inhibition of Complex Formation Between Androgen Receptor and Steroid Receptor-binding Consensus in the Promoter of the PSA Gene in LNCaP Cells," *Cancer Res.*—57(4):714-9 (1997) Abstract.

Weterman, M.A., et al., "Expression of Calcyclin in Human Melanocytic Lesions," *Cancer Res.*—53(24):6061-6 (1993) Abstract.

Williams, E.T., et al., "Estrogen Regulation of the Cytochrome P450 3A Subfamily in Humans," J Pharmacol Exp Ther. 311(2):728-35 (2004) Abstract.

Wojtaszek, P.A., et al., "Severely Decreased MARCKS Expression Correlates with Ras Reversion but not with Mitogenic Responsiveness" *Oncogene*—8(3):755-60 (1993) Abstract.

Zhong, W., et al., "Expression of Superoxide Dismutases, Catalase, and Glutathione Peroxidase in Glioma Cells," *Free Radic Biol Med.*—27(11-12):1334-45 (1999) Abstract.

Xi, L., et al., "Expression of Human Telomerase Reverse Transcriptase in Cervix Cancer and its Significance," Zhonghua Fu Chan Ke Za Zhi—40(6):407-10 (2005) Abstract.

Alberts, B., et al., Molecular Biology of the Cell (3rd ed. 1994) Cell 3rd at 453 Figure 9-2 of Cell 3rd Cell 3rd at 403.

Alberts, B., et al., Molecular Biology of the Cell (4rd ed.) In Cell 4th, Figure 6-3 on p. 302 Figure 6-90 on p. 364 of Cell 4th Cell 4th at 364 Cell 4th at 379 (2002).

Aust, G., et al., "Human Throid Carcinoma Cell Lines and Normal Thyrocytes: Expression and Regulation of Matrix Metalloproteinase-1 and Tissue Matrix Metalloproteinase Inhibitor-' Messenger-RNA and Protein," *Thyroid*—7(5):713-724 (1997).

Beà, S., et al., "BMI-1 Gene Amplification and Overexpression in Hematological Malignancies Occur Mainly in Mantle Cell Lymphomas," *Cancer Research*—61:2409-2412 (2001).

Beer, et al, "Gene-expression profiles predict survival of patients with lung adenocarcinoma," *Nature Biomedicine*—98(6):816-824 (2002).

Futcher, B., et al., "A Sampling of the Yeast Proteome," *Molecular and Cellular Biology*—19(11):7357-7368 (1999).

Gnatenko, D.V., et al., "Transcript Profiling of Human Platelets Using Microarray and Serial Analysis of Gene Expression," *Blood*—101(6):2285-2293 (2003).

Greenbaum, D., et al., "Analysis of mRNA Expression and Protein Abundance Data: An Approach for the Comparison of the Enrichment of Features in the Cellular Population of Proteins and Transcripts," *Bioinformatics!*—18(4):585-496 (2002).

Gromova, I., et al., "Protein Abundancy and mRNA Levels of the Adipocyte-Type Fatty Acid Binding Protein Correlate in Non-Invasive and Invasive Bladder Transitional Cell Carcinomas," *International Journal of Oncology*—13(2) 6 pages (1998).

Hähnel, E., et al., "Expression of the pS2 Gene in Breast Tissues Assessed by pS2-mRNA Analysis and pS2-Protein Radioimmunoassay," *Breast Cancer Research and Treatment*—24:71-74 (1992).

Hirsch, F.R., et al., "Early Detection of Lung Cancer: Clinical Perspectives of Recent Advances in Biology and Radiology," *Clinical Cancer Research*—7:5-22 (2001).

Holten-Andersen, M.D., et al., "Localization of Tissue Inhibitor of Metalloproteinases 1 (TIMP-1) in Human Colorectal Adenoma and Adenocarcinoma," *Int. J. Cancerl*—113:198-206 (2005).

Janssens, N., et al., "Alteration of Frizzled Expression in Renal Cell Carcinoma," *Tumor Biology*—25:161-171 (2004).

Kammori, M., et al., "Expression of Human Telomerase Reverse Transcriptase Gene and Protein, and of Estrogen and Progesterone Receptors, in Breast Tumors: Preliminary Data from Neo-Adjuvant Chemotherapy", International *Journal of Oncology*—27(5) (2005).

Kuo, C.C., et al., "A Transcriptomic and Proteomic Analysis of the Effect of CpG-ODN on Human THP-1 Monocytic Leukemia Cells," *Proteomics*—5:894-906 (2005).

Lewin, B., Genes VI (1997 *Genes VI* at 847-848.

Meric, F., et al., "Translation Initiation in Cancer: A Novel Target for Therapy," *Molecular Cancer Therapeutics*—1:971-979 (2002).

Munaut, C., et al., "Vascular Endothelial Growth Factor Expression Correlates With Matrix Metalloproteinases MT1-NMP, MNP-2 and NMP-9 in Human Glioblastomas," *Int. J. Cancer*—106:848-855 (2003).

Maruyama, H., et al., "Id-1 and Id-2 are Overexpressed in Pancreatic Cancer and in Dysplastic Lesions in Chronic Pancreatitis," *American Journal of Pathology*—155(3):815-822 (1999).

Nuciforo, P. G., et al., "Molecular and Immunohistochemical Analysis of HER2/neu Oncogene in Synovial Sarcoma," *Human Pathology*—34(7):639-645 (2003).

Papotti, M., et al., "Correlative Immunohistochemical and Reverse Transcriptase Polymerase Chain Reaction Analysis of Somatostatin Receptor Type 2 in Neuroendocrine Tumors of the Lung," *Diagnostic Molecular Pathology*—9(1):47-57 (2000).

Walmer, D. K., et al., "Malignant Transformation of the Human Endometrium is Associated with Overexpression of Lactoferrin Messenger RNA and Protein," *Cancer Research*—55(5):1168-1174 (1995).

Wang, J., et al., "Expression of Cadherins and Catenins in Paired Tumor and non-Neoplastic Primary Prostate Cultures and Corresponding Prostatectomy Specimens," *Urol Resl*—28:308-315 (2000).

Zhigang, Z., et al., "Prostate Stem Cell Antigen (PSCA) Express in Human Prostate Cancer Tissues and its Potential Role in Prostate Carinogenesis and Progession of Prostate Cancer," *World Journal of Surgical Oncology*—2-13 (2004).

Dayhoff, Accession No. P_ABG34066, WO200224888-A2, Pub date: Mar. 28, 2002, Baker et al.

Dayhoff, Accession No. P_AAB47298, WO200140465-A2, Pub date: Jun. 7, 2001, Fong et al.

Dayhoff, Accession No. P_AAB88464, EP1067182-A2, Pub date: Jan. 10, 2001, Ota et al.

Dayhoff, CAC39828, EP1067182-A 295, Jan. 10, 2001, Ota, et al.

Dayhoff, BAC11697, Direct Submission, Submitted Mar. 20, 2002, Isogai et al.

Dayhoff, Accession No. P_AAU83229, WO200202621-A2, Pub date: Jan. 10, 2002, Sheppard, et al.

Dayhoff, CAD28377, WO0202621-A 309, Jan. 10, 2002, Sheppard, et al.

Genbank, Accession No. AX164143, WO140465-1 15, Jun. 7, 2001, Fong et al.

Genbank, Accession No. AX136373, EP 1067182-A 295, Jan. 10, 2001, Ota et al.

Genbank, Accession No. AK075558, Direct Submission, Submitted Mar. 20, 2002, Isogai et al.

Genbank Accession No. BD123639, JP 2002017376-A 148, Jan. 22, 2002, Ota et al.

* cited by examiner

FIGURE 1

CGGACGCGTGGGTGCGAGGCGAAGGTGACCGGGGACCGAGCATTTCAGATCTGCTCGGTAGA
CCTGGTGCACCACCACCATGTTGGCTGCAAGGCTGGTGTGTCTCCGGACACTACCTTCTAGG
GTTTTCCACCCAGCTTTCACCAAGGCCTCCCCTGTTGTGAAGAATTCCATCACGAAGAATCA
ATGGCTGTTAACACCTAGCAGGGAATATGCCACCAAAACAAGAATTGGGATCCGGCGTGGGA
GAACTGGCCAAGAACTCAAAGAGGCAGCATTGGAACCATCGATGGAAAAAATATTTAAAATT
GATCAGATGGGAAGATGGTTTGTTGCTGGAGGGGCTGCTGTTGGTCTTGGAGCATTGTGCTA
CTATGGCTTGGGACTGTCTAATGAGATTGGAGCTATTGAAAAGGCTGTAATTTGGCCTCAGT
ATGTCAAGGATAGAATTCATTCCACCTATATGTACTTAGCAGGGAGTATTGGTTTAACAGCT
TTGTCTGCCATAGCAATCAGCAGAACGCCTGTTCTCATGAACTTCATGATGAGAGGCTCTTG
GGTGACAATTGGTGTGACCTTTGCAGCCATGGTTGGAGCTGGAATGCTGGTACGATCAATAC
CATATGACCAGAGCCCAGGCCCAAAGCATCTTGCTTGGTTGCTACATTCTGGTGTGATGGGT
GCAGTGGTGGCTCCTCTGACAATATTAGGGGGTCCTCTTCTCATCAGAGCTGCATGGTACAC
AGCTGGCATTGTGGGAGGCCTCTCCACTGTGGCCATGTGTGCGCCCAGTGAAAAGTTTCTGA
ACATGGGTGCACCCCTGGGAGTGGGCCTGGGTCTCGTCTTTGTGTCCTCATTGGGATCTATG
TTTCTTCCACCTACCACCGTGGCTGGTGCCACTCTTTACTCAGTGGCAATGTACGGTGGATT
AGTTCTTTTCAGCATGTTCCTTCTGTATGATACCCAGAAAGTAATCAAGCGTGCAGAAGTAT
CACCAATGTATGGAGTTCAAAAATATGATCCCATTAACTCGATGCTGAGTATCTACATGGAT
ACATTAAATATATTTATGCGAGTTGCAACTATGCTGGCAACTGGAGGCAACAGAAAGAAATG
AAGTGACTCAGCTTCTGGCTTCTCTGCTACATCAAATATCTTGTTTAATGGGGCAGATATGC
ATTAAATAGTTTGTACAAGCAGCTTTCGTTGAAGTTTAGAAGATAAGAAACATGTCATCATA
TTTAAATGTTCCGGTAATGTGATGCCTCAGGTCTGCCTTTTTTTCTGGAGAATAAATGCAGT
AATCCTCTCCCAAATAAGCACACACATTTTCAATTCTCATGTTTGAGTGATTTTAAAATGTT
TTGGTGAATGTGAAAACTAAAGTTTGTGTCATGAGAATGTAAGTCTTTTTTCTACTTTAAAA
TTTAGTAGGTTCACTGAGTAACTAAAATTTAGCAAACCTGTGTTTGCATATTTTTTTGGAGT
GCAGAATATTGTAATTAATGTCATAAGTGATTTGGAGCTTTGGTAAAGGGACCAGAGAGAAG
GAGTCACCTGCAGTCTTTTGTTTTTTTAAATACTTAGAACTTAGCACTTGTGTTATTGATTA
GTGAGGAGCCAGTAAGAAACATCTGGGTATTTGGAAACAAGTGGTCATTGTTACATTCATTT
GCTGAACTTAACAAAACTGTTCATCCTGAAACAGGCACAGGTGATGCATTCTCCTGCTGTTG
CTTCTCAGTGCTCTCTTTCCAATATAGATGTGGTCATGTTTGACTTGTACAGAATGTTAATC
ATACAGAGAATCCTTGATGGAATTATATATGTGTGTTTTACTTTTGAATGTTACAAAAGGAA
ATAACTTTAAAACTATTCTCAAGAGAAAATATTCAAAGCATGAAATATGTTGCTTTTTCCAG
AATACAAACAGTATACTCATG

FIGURE 2

MLAARLVCLRTLPSRVFHPAFTKASPVVKNSITKNQWLLTPSREYATKTRIGIRRGRTGQEL
KEAALEPSMEKIFKIDQMGRWFVAGGAAVGLGALCYYGLGLSNEIGAIEKAVIWPQYVKDRI
HSTYMYLAGSIGLTALSAIAISRTPVLMNFMMRGSWVTIGVTFAAMVGAGMLVRSIPYDQSP
GPKHLAWLLHSGVMGAVVAPLTILGGPLLIRAAWYTAGIVGGLSTVAMCAPSEKFLNMGAPL
GVGLGLVFVSSLGSMFLPPTTVAGATLYSVAMYGGLVLFSMFLLYDTQKVIKRAEVSPMYGV
QKYDPINSMLSIYMDTLNIFMRVATMLATGGNRKK

FIGURE 3

CCAATCGCCCGGTGCGGTGGTGCAGGGTCTCGGGCTAGTCATGGCGTCCCCGTCTCGGAGACTGCAGACTAAAC
CAGTCATTACTTGTTTCAAGAGCGTTCTGCTAATCTACACTTTTATTTTCTGGATCACTGGCGTTATCCTTCTT
GCAGTTGGCATTTGGGGCAAGGTGAGCCTGGAGAATTACTTTTCTCTTTTAAATGAGAAGGCCACCAATGTCCC
CTTCGTGCTCATTGCTACTGGTACCGTCATTATTCTTTTGGGCACCTTTGGTTGTTTTGCTACCTGCCGAGCTT
CTGCATGGATGCTAAAACTGTATGCAATGTTTCTGACTCTCGTTTTTTTGGTCGAACTGGTCGCTGCCATCGTA
GGATTTGTTTTCAGACATGAGATTAAGAACAGCTTTAAGAATAATTATGAGAAGGCTTTGAAGCAGTATAACTC
TACAGGAGATTATAGAAGCCATGCAGTAGACAAGATCCAAAATACGTTGCATTGTTGTGGTGTCACCGATTATA
GAGATTGGACAGATACTAATTATTACTCAGAAAAAGGATTTCCTAAGAGTTGCTGTAAACTTGAAGATTGTACT
CCACAGAGAGATGCAGACAAAGTAAACAATGAAGGTTGTTTTATAAAGGTGATGACCATTATAGAGTCAGAAAT
GGGAGTCGTTGCAGGAATTTCCTTTGGAGTTGCTTGCTTCCAACTGATTGGAATCTTTCTCGCCTACTGCCWCT
CTCGTGCCATAACAAATAACCAGTATGAGATAGTGTAACCCAATGTATCTGTGGGCCTATTCCTCTCTACCTTT
AAGGACATTTAGGGTCCCCCCTGTGAATTAGAAAGTTGCTTGGCTGGAGAACTGACAACACTACTTACTGATAG
ACCAAAAAACTACACCAGTAGGTTGATTCAATCAAGATGTATGTAGACCTAAAACTACACCAATAGGCTGATTC
AATCAAGATCCGTGCTCGCAGTGGGCTGATTCAATCAAGATGTATGTTTGCTATGTTCTAAGTCCACCTTCTAT
CCCATTCATGTTAGATCGTTGAAACCCTGTATCCCTCTGAAACACTGGAAGAGCTAGTAAATTGTAAATGAAGT

FIGURE 4

MASPSRRLQTKPVITCFKSVLLIYTFIFWITGVILLAVGIWGKVSLENYFSLLNEKATNVPF
VLIATGTVIILLGTFGCFATCRASAWMLKLYAMFLTLVFLVELVAAIVGFVFRHEIKNSFKN
NYEKALKQYNSTGDYRSHAVDKIQNTLHCCGVTDYRDWTDTNYYSEKGFPKSCCKLEDCTPQ
RDADKVNNEGCFIKVMTIIESEMGVVAGISFGVACFQLIGIFLAYCXSRAITNNQYEIV

Important features of the protein:
Signal peptide:
amino acids 1-42

Transmembrane domains:
amino acids 19-42, 61-83, 92-114, 209-230,

N-glycosylation site.
amino acids 134-138

Tyrosine kinase phosphorylation site.
amino acids 160-168, 160-169

N-myristoylation site.
amino acids 75-81, 78-84, 210-216, 214-220, 226-232

Prokaryotic membrane lipoprotein lipid attachment site.
amino acids 69-80, 211-222

FIGURE 5

GGGGCCGCGGTCTAGGGCGGCTACGTGTGTTGCCATAGCGACCATTTTGCATTAACTGGTTG
GTAGCTTCTATCCTGGGGGCTGAGCGACTGCGGGCCAGCTCTTCCCCTACTCCCTCTCGGCT
CCTTGTGGCCCAAAGGCCTAACCGGGGTCCGGCGGTCTGGCCTAGGGATCTTCCCCGTTGCC
CCTTTGGGGCGGGATGGCTGCGGAAGAAGAAGACGAGGTGGAGTGGGTAGTGGAGAGCATCG
CGGGGTTCCTGCGAGGCCCAGACTGGTCCATCCCCATCTTGGACTTTGTGGAACAGAAATGT
GAAGTTAACTGCAAAGGAGGGCATGTGATAACTCCAGGAAGCCCAGAGCCGGTGATTTTGGT
GGCCTGTGTTCCCCTTGTTTTTGATGATGAAGAAGAAAGCAAATTGACCTATACAGAGATTC
ATCAGGAATACAAAGAACTAGTTGAAAAGCTGTTAGAAGGTTACCTCAAAGAAATTGGAATT
AATGAAGATCAATTTCAAGAAGCATGCACTTCTCCTCTTGCAAAGACCCATACATCACAGGC
CATTTTGCAACCTGTGTTGGCAGCAGAAGATTTTACTATCTTTAAAGCAATGATGGTCCAGA
AAAACATTGAAATGCAGCTGCAAGCCATTCGAATAATTCAAGAGAGAAATGGTGTATTACCT
GACTGCTTAACCGATGGCTCTGATGTGGTCAGTGACCTTGAACACGAAGAGATGAAAATCCT
GAGGGAAGTTCTTAGAAAATCAAAAGAGGAATATGACCAGGAAGAAGAAAGGAAGAGGAAAA
AACAGTTATCAGAGGCTAAAACAGAAGAGCCCACAGTGCATTCCAGTGAAGCTGCAATAATG
AATAATTCCCAAGGGGATGGTGAACATTTTGCACACCCACCCTCAGAAGTTAAAATGCATTT
TGCTAATCAGTCAATAGAACCTTTGGGAAGAAAAGTGGAAAGGTCTGAAACTTCCTCCCTCC
CACAAAAAGGCCTGAAGATTCCTGGCTTAGAGCATGCGAGCATTGAAGGACCAATAGCAAAC
TTATCAGTACTTGGAACAGAAGAACTTCGGCAACGAGAACACTATCTCAAGCAGAAGAGAGA
TAAGTTGATGTCCATGAGAAAGGATATGAGGACTAAACAGATACAAAATATGGAGCAGAAAG
GAAAACCCACTGGGGAGGTAGAGGAAATGACAGAGAAACCAGAAATGACAGCAGAGGAGAAG
CAAACATTACTAAAGAGGAGATTGCTTGCAGAGAAACTCAAAGAAGAAGTTATTAATAAGTA
ATAATTAAGAACAATTTAACAAAATGGAAGTTCAAATTGTCTTAAAAATAAATTATTTAGTC
CTTACACTG

FIGURE 6

MAAEEEDEVEWVVESIAGFLRGPDWSIPILDFVEQKCEVNCKGGHVITPGSPEPVILVACVP
LVFDDEEESKLTYTEIHQEYKELVEKLLEGYLKEIGINEDQFQEACTSPLAKTHTSQAILQP
VLAAEDFTIFKAMMVQKNIEMQLQAIRIIQERNGVLPDCLTDGSDVVSDLEHEEMKILREVL
RKSKEEYDQEEERKRKKQLSEAKTEEPTVHSSEAAIMNNSQGDGEHFAHPPSEVKMHFANQS
IEPLGRKVERSETSSLPQKGLKIPGLEHASIEGPIANLSVLGTEELRQREHYLKQKRDKLMS
MRKDMRTKQIQNMEQKGKPTGEVEEMTEKPEMTAEEKQTLLKRRLLAEKLKEEVINK

N-glycosylation sites.
amino acids 224-228, 246-250, 285-289

N-myristoylation site.
amino acids 273-279

Amidation site.
amino acids 252-256

Cytosolic fatty-acid binding proteins.
amino acids 78-108

FIGURE 7

GGGAACGGAAA<u>ATG</u>GCGCCTCACGGCCCGGGTAGTCTTACGACCCTGGTGCCCTGGGCTGCCGCCCTGCTCCTC
GCTCTGGGCGTGGAAAGGGCTCTGGCGCTACCCGAGATATGCACCCAATGTCCAGGGAGCGTGCAAAATTTGTC
AAAAGTGGCCTTTTATTGTAAAACGACACGAGAGCTAATGCTGCATGCCCGTTGCTGCCTGAATCAGAAGGGCA
CCATCTTGGGGCTGGATCTCCAGAACTGTTCTCTGGAGGACCCTGGTCCAAACTTTCATCAGGCACATACCACT
GTCATCATAGACCTGCAAGCAAACCCCCTCAAAGGTGACTTGGCCAACACCTTCCGTGGCTTTACTCAGCTCCA
GACTCTGATACTGCCACAACATGTCAACTGTCCTGGAGGAATTAATGCCTGGAATACTATCACCTCTTATATAG
ACAACCAAATCTGTCAAGGGCAAAAGAACCTTTGCAATAACACTGGGGACCCAGAAATGTGTCCTGAGAATGGA
TCTTGTGTACCTGATGGTCCAGGTCTTTTGCAGTGTGTTTGTGCTGATGGTTTCCATGGATACAAGTGTATGCG
CCAGGGCTCGTTCTCACTGCTTATGTTCTTCGGGATTCTGGGAGCCACCACTCTATCCGTCTCCATTCTGCTTT
GGGCGACCCAGCGCCGAAAAGCCAAGACTTCA<u>TGA</u>ACTACATAGGTCTTACCATTGACCTAAGATCAATCTGAA
CTATCTTAGCCCAGTCAGGGAGCTCTGCTTCCTAGAAAGGCATCTTTCGCCAGTGGATTCGCCTCAAGGTTGAG
GCCGCCATTGGAAGATGAAAAATTGCACTCCCTTGGTGTAGACAAATACCAGTTCCCATTGGTGTTGTTGCCTA
TAATAAACACTTTTTCTTTTTTNAAAAAAAAAAAAAAAAAAAA

FIGURE 8

Signal Peptide:
Amino acids 1-30

Transmembrane:
Amino acids 198-212

MAPHGPGSLTTLVPWAAALLLALGVERALALPEICTQCPGSVQNLSKVAFYCKTTRELMLHA
RCCLNQKGTILGLDLQNCSLEDPGPNFHQAHTTVIIDLQANPLKGDLANTFRGFTQLQTLIL
PQHVNCPGGINAWNTITSYIDNQICQGQKNLCNNTGDPEMCPENGSCVPDGPGLLQCVCADG
FHGYKCMRQGSFSLLMFFGILGATTLSVSILLWATQRRKAKTS

FIGURE 9

GGGGGAGAAGGCGGCCGAGCCCCAGCTCTCCGAGCACCGGGTCGGAAGCCGCGACCCGAGCC
GCGCAGGAAGCTGGGACCGGAACCTCGGCGGACCCGGCCCCACCCAACTCACCTGCGCAGGT
CACCAGCACCCTCGGAACCCAGAGGCCCGCGCTCTGAAGGTGACCCCCCTGGGGAGGAAGGC
GATGGCCCCTGCGAGGACGATGGCCCGCGCCCGCCTCGCCCCGGCCGGCATCCCTGCCGTCG
CCTTGTGGCTTCTGTGCACGCTCGGCCTCCAGGGCACCCAGGCCGGGCCACCGCCCGCGCCC
CCTGGGCTGCCCGCGGGAGCCGACTGCCTGAACAGCTTTACCGCCGGGGTGCCTGGCTTCGT
GCTGGACACCAACGCCTCGGTCAGCAACGGAGCTACCTTCCTGGAGTCCCCCACCGTGCGCC
GGGGCTGGGACTGCGTGCGCGCCTGCTGCACCACCCAGAACTGCAACTTGGCGCTAGTGGAG
CTGCAGCCCGACCGCGGGGAGGACGCCATCGCCGCCTGCTTCCTCATCAACTGCCTCTACGA
GCAGAACTTCGTGTGCAAGTTCGCGCCCAGGGAGGGCTTCATCAACTACCTCACGAGGGAAG
TGTACCGCTCCTACCGCCAGCTGCGGACCCAGGGCTTTGGAGGGTCTGGGATCCCCAAGGCC
TGGGCAGGCATAGACTTGAAGGTACAACCCCAGGAACCCCTGGTGCTGAAGGATGTGGAAAA
CACAGATTGGCGCCTACTGCGGGGTGACACGGATGTCAGGGTAGAGAGGAAAGACCCAAACC
AGGTGGAACTGTGGGGACTCAAGGAAGGCACCTACCTGTTCCAGCTGACAGTGACTAGCTCA
GACCACCCAGAGGACACGGCCAACGTCACAGTCACTGTGCTGTCCACCAAGCAGACAGAAGA
CTACTGCCTCGCATCCAACAAGGTGGGTCGCTGCCGGGGCTCTTTCCCACGCTGGTACTATG
ACCCCACGGAGCAGATCTGCAAGAGTTTCGTTTATGGAGGCTGCTTGGGCAACAAGAACAAC
TACCTTCGGGAAGAAGAGTGCATTCTAGCCTGTCGGGGTGTGCAAGGTGGGCCTTTGAGAGG
CAGCTCTGGGGCTCAGGCGACTTTCCCCCAGGGCCCCTCCATGGAAAGGCGCCATCCAGTGT
GCTCTGGCACCTGTCAGCCCACCCAGTTCCGCTGCAGCAATGGCTGCTGCATCGACAGTTTC
CTGGAGTGTGACGACACCCCCAACTGCCCCGACGCCTCCGACGAGGCTGCCTGTGAAAAATA
CACGAGTGGCTTTGACGAGCTCCAGCGCATCCATTTCCCCAGTGACAAAGGGCACTGCGTGG
ACCTGCCAGACACAGGACTCTGCAAGGAGAGCATCCCGCGCTGGTACTACAACCCCTTCAGC
GAACACTGCGCCCGCTTTACCTATGGTGGTTGTTATGGCAACAAGAACAACTTTGAGGAAGA
GCAGCAGTGCCTCGAGTCTTGTCGCGGCATCTCCAAGAAGGATGTGTTTGGCCTGAGGCGGG
AAATCCCCATTCCCAGCACAGGCTCTGTGGAGATGGCTGTCACAGTGTTCCTGGTCATCTGC
ATTGTGGTGGTGGTAGCCATCTTGGGTTACTGCTTCTTCAAGAACCAGAGAAAGGACTTCCA
CGGACACCACCACCACCCACCACCCACCCCTGCCAGCTCCACTGTCTCCACTACCGAGGACA
CGGAGCACCTGGTCTATAACCACACCACCCGGCCCCTCTGAGCCTGGGTCTCACCGGCTCTC
ACCTGGCCCTGCTTCCTGCTTGCCAAGGCAGAGGCCTGGGCTGGGAAAAACTTTGGAACCAG
ACTCTTGCCTGTTTCCCAGGCCCACTGTGCCTCAGAGACCAGGGCTCCAGCCCCTCTTGGAG
AAGTCTCAGCTAAGCTCACGTCCTGAGAAAGCTCAAAGGTTTGGAAGGAGCAGAAAACCCTT
GGGCCAGAAGTACCAGACTAGATGGACCTGCCTGCATAGGAGTTTGGAGGAAGTTGGAGTTT
TGTTTCCTCTGTTCAAAGCTGCCTGTCCCTACCCCATGGTGCTAGGAAGAGGAGTGGGGTGG
TGTCAGACCCTGGAGGCCCCAACCCTGTCCTCCCGAGCTCCTCTTCCATGCTGTGCGCCCAG
GGCTGGGAGGAAGGACTTCCCTGTGTAGTTTGTGCTGTAAAGAGTTGCTTTTTGTTTATTTA
ATGCTGTGGCATGGGTGAAGAGGAGGGGAAGAGGCCTGTTTGGCCTCTCTGTCCTCTCTTCC
TCTTCCCCCAAGATTGAGCTCTCTGCCCTTGATCAGCCCCACCCTGGCCTAGACCAGCAGAC
AGAGCCAGGAGAGGCTCAGCTGCATTCCGCAGCCCCCACCCCCAAGGTTCTCCAACATCACA
GCCCAGCCCACCCACTGGGTAATAAAAGTGGTTTGTGGAAAAAAAAAAAAAAAAAAAAAAAA

FIGURE 10

MAPARTMARARLAPAGIPAVALWLLCTLGLQGTQAGPPPAPPGLPAGADCLNSFTAGVPGFV
LDTNASVSNGATFLESPTVRRGWDCVRACCTTQNCNLALVELQPDRGEDAIAACFLINCLYE
QNFVCKFAPREGFINYLTREVYRSYRQLRTQGFGGSGIPKAWAGIDLKVQPQEPLVLKDVEN
TDWRLLRGDTDVRVERKDPNQVELWGLKEGTYLFQLTVTSSDHPEDTANVTVTVLSTKQTED
YCLASNKVGRCRGSFPRWYYDPTEQICKSFVYGGCLGNKNNYLREEECILACRGVQGGPLRG
SSGAQATFPQGPSMERRHPVCSGTCQPTQFRCSNGCCIDSFLECDDTPNCPDASDEAACEKY
TSGFDELQRIHFPSDKGHCVDLPDTGLCKESIPRWYYNPFSEHCARFTYGGCYGNKNNFEEE
QQCLESCRGISKKDVFGLRREIPIPSTGSVEMAVTVFLVICIVVVVAILGYCFFKNQRKDFH
GHHHHPPPTPASSTVSTTEDTEHLVYNHTTRPL signal sequence:
Amino acids 1-35 transmembrane domain:
Amino acids 466-483

N-glycosylation sites:
Amino acids 66-70;235-239;523-527

N-myristoylation sites:
Amino acids 29-35;43-49;161-167;212-218;281-287;282-288;285-291;
310-316;313-319;422-428;423-429;426-432

Cell attachment sequence:
Amino acids 193-199

Pancreatic trypsin inhibitor (Kunitz) family signatures:
Amino acids 278-298;419-438

FIGURE 11

```
GTGCTGGGCTTTTTCAGACAAGTGCATCTCCTAACCAGGTCACATTTCAGCCGCGACCCACTCTCCGCCAGTCA
CCGGAGGCAGACCGCGGGAGGAGAGCTGAGGACAGCCGCGTGCGCTTCGCCAGCAGCGGGGTGGGAGGAAGGAC
ATTAAAATACTGCAGAAGTCAAGACCCCCCCAGGTCGAACCCAGACCACG**ATG**CGCGCCCCGGGCTGCGGGCGG
CTGGTGCTGCCGCTGCTGCTCCTGGCCGCGGCAGCCCTGGCCGAAGGCGACGCCAAGGGGCTCAAGGAGGGCGA
GACCCCCGGCAATTTCATGGAGGACGAGCAATGGCTGTCGTCCATCTCGCAGTACAGCGGCAAGATCAAGCACT
GGAACCGCTTCCGAGACGAAGTGGAGGATGACTATATCAAGAGCTGGGAGGACAATCAGCAAGGAGATGAAGCC
CTGGATACCACCAAGGACCCCTGCCAGAAGGTGAAGTGCAGCCGCCACAAGGTGTGCATTGCCCAGGGCTACCA
GCGGGCCATGTGCATCAGTCGCAAGAAGCTGGAGCACAGGATCAAGCAGCCGACCGTGAAACTCCATGGAAACA
AAGACTCCATCTGCAAGCCCTGCCACATGGCCCAGCTTGCCTCTGTCTGCGGCTCAGATGGCCACACTTACAGC
TCTGTGTGTAAGCTGGAGCAACAGGCGTGCCTGAGCAGCAAGCAGCTGGCGGTGCGATGCGAGGGCCCCTGCCC
CTGCCCCACGGAGCAGGCTGCCACCTCCACCGCCGATGGCAAACCAGAGACTTGCACCGGTCAGGACCTGGCTG
ACCTGGGAGATCGGCTGCGGGACTGGTTCCAGCTCCTTCATGAGAACTCCAAGCAGAATGGCTCAGCCAGCAGT
GTAGCCGGCCCGGCCAGCGGGCTGGACAAGAGCCTGGGGGCCAGCTGCAAGGACTCCATTGGCTGGATGTTCTC
CAAGCTGGACACCAGTGCTGACCTCTTCCTGGACCAGACGGAGCTGGCCGCCATCAACCTGGACAAGTACGAGG
TCTGCATCCGTCCCTTCTTCAACTCCTGTGACACCTACAAGGATGGCCGGGTCTCTACTGCTGAGTGGTGCTTC
TGCTTCTGGAGGGAGAAGCCCCCCTGCCTGGCAGAGCTGGAGCGCATCCAGATCCAGGAGGCCGCCAAGAAGAA
GCCAGGCATCTTCATCCCGAGCTGCGACGAGGATGGCTACTACCGGAAGATGCAGTGTGACCAGAGCAGCGGTG
ACTGCTGGCGTGTGGACCAGCTGGGCCTGGAGCTGACTGGCACGCGCACGCATGGGAGCCCCGACTGCGATGAC
ATCGTGGGCTTCTCGGGGGACTTTGGAAGCGGTGTCGGCTGGGAGGATGAGGAGGAGAAGGAGACGGAGGAAGC
AGGCGAGGAGGCCGAGGAGGAGGAGGGCGAGGCAGGCGAGGCTGACGACGGGGGCTACATCTGG**TAG**ACGCCCT
CAGGAGCCGGCTGCCGGGGGGGACTCAACAGCAGAGCTCTGAGCAGCAGCAGGCAACTTCGAGAACGGATCCAG
AAATGCAGTCAGAAGGACCCTGCTCCACCTGGGGGGACTGGGAGTGTGAGTGTGCATGGCATGTGTGTGGCACA
GATGGCTGGGACGGGTGACAGTGTGAGTGCATGTGTGCATGCATGTGTGTATGTGTGTGTGTGTGGCATGCG
CTGACAAATGTGTCCTTGATCCACACTGCTCCTGGCAGAGTGAGTCACCCAAAGGCCCCTTCGGCCTCCTTGTA
GCTGTTTTCTTTCCTTTTGTTGTTGGTTTTAAAATACATTCACACACAAATACAAAAAAAAAAAAAAAAAAAAA
AAAAAAAAAAAAAAAAAAAAAAAAAAAAAAAAAAAAAAAAAAAAAAA
```

FIGURE 12

MRAPGCGRLVLPLLLLAAAALAEGDAKGLKEGETPGNFMEDEQWLSSISQYSGKIKHWNRFRDEVEDDYIKSWE
DNQQGDEALDTTKDPCQKVKCSRHKVCIAQGYQRAMCISRKKLEHRIKQPTVKLHGNKDSICKPCHMAQLASVC
GSDGHTYSSVCKLEQQACLSSKQLAVRCEGPCPCPTEQAATSTADGKPETCTGQDLADLGDRLRDWFQLLHENS
KQNGSASSVAGPASGLDKSLGASCKDSIGWMFSKLDTSADLFLDQTELAAINLDKYEVCIRPFFNSCDTYKDGR
VSTAEWCFCFWREKPPCLAELERIQIQEAAKKKPGIFIPSCDEDGYYRKMQCDQSSGDCWRVDQLGLELTGTRT
HGSPDCDDIVGFSGDFGSGVGWEDEEEKETEEAGEEAEEEEGEAGEADDGGYIW

FIGURE 13

TGCGGCGACCGTCGTACACCATGGGCCTCCACCTCCGCCCCTACCGTGTGGGGCTGCTCCCG
GATGGCCTCCTGTTCCTCTTGCTGCTGCTAATGCTGCTCGCGGACCCAGCGCTCCCGGCCGG
ACGTCACCCCCCAGTGGTGCTGGTCCCTGGTGATTTGGGTAACCAACTGGAAGCCAAGCTGG
ACAAGCCGACAGTGGTGCACTACCTCTGCTCCAAGAAGACCGAAAGCTACTTCACAATCTGG
CTGAACCTGGAACTGCTGCTGCCTGTCATCATTGACTGCTGGATTGACAATATCAGGCTGGT
TTACAACAAAACATCCAGGGCCACCCAGTTTCCTGATGGTGTGGATGTACGTGTCCCTGGCT
TTGGGAAGACCTTCTCACTGGAGTTCCTGGACCCCAGCAAAAGCAGCGTGGGTTCCTATTTC
CACACCATGGTGGAGAGCCTTGTGGGCTGGGGCTACACACGGGGTGAGGATGTCCGAGGGGC
TCCCTATGACTGGCGCCGAGCCCCAAATGAAAACGGGCCCTACTTCCTGGCCCTCCGCGAGA
TGATCGAGGAGATGTACCAGCTGTATGGGGGCCCCGTGGTGCTGGTTGCCCACAGTATGGGC
AACATGTACACGCTCTACTTTCTGCAGCGGCAGCCGCAGGCCTGGAAGGACAAGTATATCCG
GGCCTTCGTGTCACTGGGTGCGCCCTGGGGGGGCGTGGCCAAGACCCTGCGCGTCCTGGCTT
CAGGAGACAACAACCGGATCCCAGTCATCGGGCCCCTGAAGATCCGGGAGCAGCAGCGGTCA
GCTGTCTCCACCAGCTGGCTGCTGCCCTACAACTACACATGGTCACCTGAGAAGGTGTTCGT
GCAGACACCCACAATCAACTACACACTGCGGGACTACCGCAAGTTCTTCCAGGACATCGGCT
TTGAAGATGGCTGGCTCATGCGGCAGGACACAGAAGGGCTGGTGGAAGCCACGATGCCACCT
GGCGTGCAGCTGCACTGCCTCTATGGTACTGGCGTCCCCACACCAGACTCCTTCTACTATGA
GAGCTTCCCTGACCGTGACCCTAAAATCTGCTTTGGTGACGGCGATGGTACTGTGAACTTGA
AGAGTGCCCTGCAGTGCCAGGCCTGGCAGAGCCGCCAGGAGCACCAAGTGTTGCTGCAGGAG
CTGCCAGGCAGCGAGCACATCGAGATGCTGGCCAACGCCACCACCCTGGCCTATCTGAAACG
TGTGCTCCTTGGGCCCTGACTCCTGTGCCACAGGACTCCTGTGGCTCGGCCGTGGACCTGCT
GTTGGCCTCTGGGGCTGTCATGGCCCACGCGTTTTGCAAAGTTTGTGACTCACCATTCAAGG
CCCCGAGTCTTGGACTGTGAAGCATCTGCCATGGGGAAGTGCTGTTTGTTATCCTTTCTCTG
TGGCAGTGAAGAAGGAAGAAATGAGAGTCTAGACTCAAGGGACACTGGATGGCAAGAATGCT
GCTGATGGTGGAACTGCTGTGACCTTAGGACTGGCTCCACAGGGTGGACTGGCTGGGCCCTG
GTCCCAGTCCCTGCCTGGGGCCATGTGTCCCCCTATTCCTGTGGGCTTTTCATACTTGCCTA
CTGGGCCCTGGCCCCGCAGCCTTCCTATGAGGGATGTTACTGGGCTGTGGTCCTGTACCCAG
AGGTCCCAGGGATCGGCTCCTGGCCCCTCGGGTGACCCTTCCCACACACCAGCCACAGATAG
GCCTGCCACTGGTCATGGGTAGCTAGAGCTGCTGGCTTCCCTGTGGCTTAGCTGGTGGCCAG
CCTGACTGGCTTCCTGGGCGAGCCTAGTAGCTCCTGCAGGCAGGGGCAGTTTGTTGCGTTCT
TCGTGGTTCCCAGGCCCTGGGACATCTCACTCCACTCCTACCTCCCTTACCACCAGGAGCAT
TCAAGCTCTGGATTGGGCAGCAGATGTGCCCCCAGTCCCGCAGGCTGTGTTCCAGGGGCCCT
GATTTCCTCGGATGTGCTATTGGCCCCAGGACTGAAGCTGCCTCCCTTCACCCTGGGACTGT
GGTTCCAAGGATGAGAGCAGGGGTTGGAGCCATGGCCTTCTGGGAACCTATGGAGAAAGGGA
ATCCAAGGAAGCAGCCAAGGCTGCTCGCAGCTTCCCTGAGCTGCACCTCTTGCTAACCCCAC
CATCACACTGCCACCCTGCCCTAGGGTCTCACTAGTACCAAGTGGGTCAGCACAGGGCTGAG
GATGGGGCTCCTATCCACCCTGGCCAGCACCCAGCTTAGTGCTGGGACTAGCCCAGAAACTT
GAATGGGACCCTGAGAGAGCCAGGGGTCCCCTGAGGCCCCCCTAGGGGCTTTCTGTCTGCCC
CAGGGTGCTCCATGGATCTCCCTGTGGCAGCAGGCATGGAGAGTCAGGGCTGCCTTCATGGC
AGTAGGCTCTAAGTGGGTGACTGGCCACAGGCCGAGAAAAGGGTACAGCCTCTAGGTGGGGT
TCCCAAAGACGCCTTCAGGCTGGACTGAGCTGCTCTCCCACAGGGTTTCTGTGCAGCTGGAT
TTTCTCTGTTGCATACATGCCTGGCATCTGTCTCCCCTTGTTCCTGAGTGGCCCCACATGGG
GCTCTGAGCAGGCTGTATCTGGATTCTGGCAATAAAAGTACTCTGGATGCTGTAAAAAAAAA
AAAAAAAAAAAAAA

FIGURE 14

></usr/seqdb2/sst/DNA/Dnaseqs.min/ss.DNA44189
><subunit 1 of 1, 412 aa, 1 stop
><MW: 46658, pI: 6.65, NX(S/T): 4
MGLHLRPYRVGLLPDGLLFLLLLLMLLADPALPAGRHPPVVLVPGDLGNQLEAKLDKPTV
VHYLCSKKTESYFTIWLNLELLLPVIIDCWIDNIRLVYNKTSRATQFPDGVDVRVPGFGK
TFSLEFLDPSKSSVGSYFHTMVESLVGWGYTRGEDVRGAPYDWRRAPNENGPYFLALREM
IEEMYQLYGGPVVLVAHSMGNMYTLYFLQRQPQAWKDKYIRAFVSLGAPWGGVAKTLRVL
ASGDNNRIPVIGPLKIREQQRSAVSTSWLLPYNYTWSPEKVFVQTPTINYTLRDYRKFFQ
DIGFEDGWLMRQDTEGLVEATMPPGVQLHCLYGTGVPTPDSFYYESFPDRDPKICFGDGD
GTVNLKSALQCQAWQSRQEHQVLLQELPGSEHIEMLANATTLAYLKRVLLGP

Signal peptide:
Amino acids 1-28

Potential lipid substrate binding site:
Amino acids 147-164

N-glycosylation sites:
Amino acids 99-103;273-277;289-293;398-402

Lipases, serine proteins family:
Amino acids 189-202

Beta-transducin family Trp-Asp repeat:
Amino acids 353-366

Tyrosine kinase phosphorylation site:
Amino acids 165-174;178-186

N-myristoylation sites:
Amino acids 200-206;227-233;232-238;316-322

FIGURE 15

CAGAGCAGATA<u>ATG</u>GCAAGCATGGCTGCCGTGCTCACCTGGGCTCTGGCTCTTCTTTCAGCG
TTTTCGGCCACCCAGGCACGGAAAGGCTTCTGGGACTACTTCAGCCAGACCAGCGGGGACAA
AGGCAGGGTGGAGCAGATCCATCAGCAGAAGATGGCTCGCGAGCCCGCGACCCTGAAAGACA
GCCTTGAGCAAGACCTCAACAATATGAACAAGTTCCTGGAAAAGCTGAGGCCTCTGAGTGGG
AGCGAGGCTCCTCGGCTCCCACAGGACCCGGTGGGCATGCGGCGGCAGCTGCAGGAGGAGTTG
GAGGAGGTGAAGGCTCGCCTCCAGCCCTACATGGCAGAGGCGCACGAGCTGGTGGGCTGGAA
TTTGGAGGGCTTGCGGCAGCAACTGAAGCCCTACACGATGGATCTGATGGAGCAGGTGGCCC
TGCGCGTGCAGGAGCTGCAGGAGCAGTTGCGCGTGGTGGGGGAAGACACCAAGGCCCAGTTG
CTGGGGGGCGTGGACGAGGCTTGGGCTTTGCTGCAGGGACTGCAGAGCCGCGTGGTGCACCA
CACCGGCCGCTTCAAAGAGCTCTTCCACCCATACGCCGAGAGCCTGGTGAGCGGCATCGGGC
GCCACGTGCAGGAGCTGCACCGCAGTGTGGCTCCGCACGCCCCCGCCAGCCCCGCGCGCCTC
AGTCGCTGCGTGCAGGTGCTCTCCCGGAAGCTCACGCTCAAGGCCAAGGCCCTGCACGCACG
CATCCAGCAGAACCTGGACCAGCTGCGCGAAGAGCTCAGCAGAGCCTTTGCAGGCACTGGGA
CTGAGGAAGGGGCCGGCCCGGACCCC<u>TAG</u>ATGCTCTCCGAGGAGGTGCGCCAGCGACTTCAG
GCTTTCCGCCAGGACACCTACCTGCAGATAGCTGCCTTCACTCGCGCCATCGACCAGGAGAC
TGAGGAGGTCCAGCAGCAGCTGGCGCCACCTCCACCAGGCCACAGTGCCTTCGCCCCAGAGT
TTCAACAAACAGACAGTGGCAAGGTTCTGAGCAAGCTGCAGGCCCGTCTGGATGACCTGTGG
GAAGACATCACTCACAGCCTTCATGACCAGGGCCACAGCCATCTGGGGGACCCCTGAGGATC
TACCTGCCCAGGCCCATTCCCAGCTTCTTGTCTGGGGAGCCTTGGCTCTGAGCCTCTAGCAT
GGTTCAGTCCTTGAAAGTGGCCTGTTGGGTGGAGGGTGGAAGGTCCTGTGCAGGACAGGGAG
GCCACCAAAGGGGCTGCTGTCTCCTGCATATCCAGCCTCCTGCGACTCCCCAATCTGGATGC
ATTACATTCACCAGGCTTTGCAAAAAAAAAAAAAAAAAAAAAAAAAAAAAAAAAAAAAAA
AAAAAA

FIGURE 16

></usr/seqdb2/sst/DNA/Dnaseqs.min/ss.DNA48303
><subunit 1 of 1, 274 aa, 1 stop
><MW: 30754, pI: 7.77, NX(S/T): 0
MASMAAVLTWALALLSAFSATQARKGFWDYFSQTSGDKGRVEQIHQQKMAREPATLKDSL
EQDLNNMNKFLEKLRPLSGSEAPRLPQDPVGMRRQLQEELEEVKARLQPYMAEAHELVGW
NLEGLRQQLKPYTMDLMEQVALRVQELQEQLRVVGEDTKAQLLGGVDEAWALLQGLQSRV
VHHTGRFKELFHPYAESLVSGIGRHVQELHRSVAPHAPASPARLSRCVQVLSRKLTLKAK
ALHARIQQNLDQLREELSRAFAGTGTEEGAGPDP

Important features of the protein:
Signal peptide:
Amino acids 1-23

Glycosaminoglycan attachment site:
Amino acids 200-204 cAMP- and cGMP-dependent protein kinase phosphorylation site:
Amino acids 233-237

N-myristoylation sites:
Amino acids 165-171;265-271

FIGURE 17

CTAAGAGGACAAGATGAGGCCCGGCCTCTCATTTCTCCTAGCCCTTCTGTTCTTCCTTGGCC
AAGCTGCAGGGGATTTGGGGGATGTGGGACCTCCAATTCCCAGCCCCGGCTTCAGCTCTTTC
CCAGGTGTTGACTCCAGCTCCAGCTTCAGCTCCAGCTCCAGGTCGGGCTCCAGCTCCAGCCG
CAGCTTAGGCAGCGGAGGTTCTGTGTCCCAGTTGTTTTCCAATTTCACCGGCTCCGTGGATG
ACCGTGGGACCTGCCAGTGCTCTGTTTCCCTGCCAGACACCACCTTTCCCGTGGACAGAGTG
GAACGCTTGGAATTCACAGCTCATGTTCTTTCTCAGAAGTTTGAGAAAGAACTTTCTAAAGTG
AGGGAATATGTCCAATTAATTAGTGTGTATGAAAAGAAACTGTTAAACCTAACTGTCCGAAT
TGACATCATGGAGAAGGATACCATTTCTTACACTGAACTGGACTTCGAGCTGATCAAGGTAG
AAGTGAAGGAGATGGAAAAACTGGTCATACAGCTGAAGGAGAGTTTTGGTGGAAGCTCAGAA
ATTGTTGACCAGCTGGAGGTGGAGATAAGAAATATGACTCTCTTGGTAGAGAAGCTTGAGAC
ACTAGACAAAAACAATGTCCTTGCCATTCGCCGAGAAATCGTGGCTCTGAAGACCAAGCTGA
AAGAGTGTGAGGCCTCTAAAGATCAAAACACCCCTGTCGTCCACCCTCCTCCCACTCCAGGG
AGCTGTGGTCATGGTGGTGTGGTGAACATCAGCAAACCGTCTGTGGTTCAGCTCAACTGGAG
AGGGTTTTCTTATCTATATGGTGCTTGGGGTAGGGATTACTCTCCCCAGCATCCAAACAAAG
GACTGTATTGGGTGGCGCCATTGAATACAGATGGGAGACTGTTGGAGTATTATAGACTGTAC
AACACACTGGATGATTTGCTATTGTATATAAATGCTCGAGAGTTGCGGATCACCTATGGCCA
AGGTAGTGGTACAGCAGTTTACAACAACAACATGTACGTCAACATGTACAACACCGGGAATA
TTGCCAGAGTTAACCTGACCACCAACACGATTGCTGTGACTCAAACTCTCCCTAATGCTGCC
TATAATAACCGCTTTTCATATGCTAATGTTGCTTGGCAAGATATTGACTTTGCTGTGGATGA
GAATGGATTGTGGGTTATTTATTCAACTGAAGCCAGCACTGGTAACATGGTGATTAGTAAAC
TCAATGACACCACACTTCAGGTGCTAAACACTTGGTATACCAAGCAGTATAAACCATCTGCT
TCTAACGCCTTCATGGTATGTGGGGTTCTGTATGCCACCCGTACTATGAACACCAGAACAGA
AGAGATTTTTTACTATTATGACACAAACACAGGGAAAGAGGGCAAACTAGACATTGTAATGC
ATAAGATGCAGGAAAAAGTGCAGAGCATTAACTATAACCCTTTTGACCAGAAACTTTATGTC
TATAACGATGGTTACCTTCTGAATTATGATCTTTCTGTCTTGCAGAAGCCCCAGTAAGCTGT
TTAGGAGTTAGGGTGAAAGAGAAAATGTTTGTTGAAAAAATAGTCTTCTCCACTTACTTAGA
TATCTGCAGGGGTGTCTAAAAGTGTGTTCATTTTGCAGCAATGTTTAGGTGCATAGTTCTAC
CACACTAGAGATCTAGGACATTTGTCTTGATTTGGTGAGTTCTCTTGGGAATCATCTGCCTC
TTCAGGCGCATTTTGCAATAAAGTCTGTCTAGGGTGGGATTGTCAGAGGTCTAGGGGCACTG
TGGGCCTAGTGAAGCCTACTGTGAGGAGGCTTCACTAGAAGCCTTAAATTAGGAATTAAGGA
ACTTAAAACTCAGTATGGCGTCTAGGGATTCTTTGTACAGGAAATATTGCCCAATGACTAGT
CCTCATCCATGTAGCACCACTAATTCTTCCATGCCTGGAAGAAACCTGGGGACTTAGTTAGG
TAGATTAATATCTGGAGCTCCTCGAGGGACCAAATCTCCAACTTTTTTTCCCCTCACTAGC
ACCTGGAATGATGCTTTGTATGTGGCAGATAAGTAAATTTGGCATGCTTATATATTCTACAT
CTGTAAAGTGCTGAGTTTTATGGAGAGAGGCCTTTTTATGCATTAAATTGTACATGGCAAATAA
ATCCCAGAAGGATCTGTAGATGAGGCACCTGCTTTTTCTTTTCTCTCATTGTCCACCTTACT
AAAAGTCAGTAGAATCTTCTACCTCATAACTTCCTTCCAAAGGCAGCTCAGAAGATTAGAAC
CAGACTTACTAACCAATTCCACCCCCCACCAACCCCCTTCTACTGCCTACTTTAAAAAAATT
AATAGTTTTCTATGGAACTGATCTAAGATTAGAAAAATTAATTTTCTTTAATTTCATTATGG
ACTTTTATTTACATGACTCTAAGACTATAAGAAAATCTGATGGCAGTGACAAAGTGCTAGCA
TTTATTGTTATCTAATAAAGACCTTGGAGCATATGTGCAACTTATGAGTGTATCAGTTGTTG
CATGTAATTTTTGCCTTTGTTTAAGCCTGGAACTTGTAAGAAAATGAAAATTTAATTTTTTT
TTCTAGGACGAGCTATAGAAAAGCTATTGAGAGTATCTAGTTAATCAGTGCAGTAGTTGGAA
ACCTTGCTGGTGTATGTGATGTGCTTCTGTGCTTTTGAATGACTTTATCATCTAGTCTTTGT
CTATTTTTCCTTTGATGTTCAAGTCCTAGTCTATAGGATTGGCAGTTTAAATGCTTTACTCC
CCCTTTTAAAATAAATGATTAAAATGTGCTTTGAAAAAAAAAAAAAAAAAAAAAAAAAAAA

FIGURE 18

</usr/seqdb2/sst/DNA/Dnaseqs.min/ss.DNA48320
<subunit 1 of 1, 510 aa, 1 stop
<MW: 57280, pI: 5.61, NX(S/T): 6

```
MRPGLSFLLALLFFLGQAAGDLGDVGPPIPSPGFSSFPGVDSSSSFSSSSRSGSSSSRSL
GSGGSVSQLFSNFTGSVDDRGTCQCSVSLPDTTFPVDRVERLEFTAHVLSQKFEKELSKV
REYVQLISVYEKKLLNLTVRIDIMEKDTISYTELDFELIKVEVKEMEKLVIQLKESFGGS
SEIVDQLEVEIRNMTLLVEKLETLDKNNVLAIRREIVALKTKLKECEASKDQNTPVVHPP
PTPGSCGHGGVVNISKPSVVQLNWRGFSYLYGAWGRDYSPQHPNKGLYWVAPLNTDGRLL
EYYRLYNTLDDLLLYINARELRITYGQGSGTAVYNNNMYVNMYNTGNIARVNLTTNTIAV
TQTLPNAAYNNRFSYANVAWQDIDFAVDENGLWVIYSTEASTGNMVISKLNDTTLQVLNT
WYTKQYKPSASNAFMVCGVLYATRTMNTRTEEIFYYYDTNTGKEGKLDIVMHKMQEKVQS
INYNPFDQKLYVYNDGYLLNYDLSVLQKPQ
```

Important features:

Signal peptide:
Amino acids 1-20

N-glycosylation sites:
Amino acids 72-76;136-140;193-197;253-257;352-356;
411-415

Tyrosine kinase phosphorylation site:
Amino acids 449-457

N-myristoylation sites:
Amino acids 16-22;39-45;53-59;61-67;63-69;81-87;
249-255;326-332;328-334;438-444

Legume lectins beta-chain proteins:
Amino acids 20-40

HBGF/FGF family proteins:
Amino acids 338-366

FIGURE 19

GCACCGCAGACGGCGCGGATCGCAGGGAGCCGGTCCGCCGCCGGAACGGGAGCCTGGGTGTG
CGTGTGGAGTCCGGACTCGTGGGAGACGATCGCGATGAACACGGTGCTGTCGCGGGCGAACT
CACTGTTCGCCTTCTCGCTGAGCGTGATGGCGGCGCTCACCTTCGGCTGCTTCATCACCACC
GCCTTCAAAGACAGGAGCGTCCCGGTGCGGCTGCACGTCTCGCGGATCATGCTAAAAAATGT
AGAAGATTTCACTGGACCTAGAGAAAGAAGTGATCTGGGATTTATCACATTTGATATAACTG
CTGATCTAGAGAATATATTTGATTGGAATGTTAAGCAGTTGTTTCTTTATTTATCAGCAGAA
TATTCAACAAAAAATAATGCTCTGAACCAAGTTGTCCTATGGGACAAGATTGTTTTGAGAGG
TGATAATCCGAAGCTGCTGCTGAAAGATATGAAAACAAAATATTTTTTCTTTGACGATGGAA
ATGGTCTCAAGGGAAACAGGAATGTCACTTTGACCCTGTCTTGGAACGTCGTACCAAATGCT
GGAATTCTACCTCTTGTGACAGGATCAGGACACGTATCTGTCCCATTTCCAGATACATATGA
AATAACGAAGAGTTATTAAATTATTCTGAATTTGAAACAAAAA

FIGURE 20

></usr/seqdb2/sst/DNA/Dnaseqs.min/ss.DNA56049
><subunit 1 of 1, 180 aa, 1 stop
><MW: 20313, pI: 8.91, NX(S/T): 1
MNTVLSRANSLFAFSLSVMAALTFGCFITTAFKDRSVPVRLHVSRIMLKNVEDFTGPRER
SDLGFITFDITADLENIFDWNVKQLFLYLSAEYSTKNNALNQVVLWDKIVLRGDNPKLLL
KDMKTKYFFFDDGNGLKGNRNVTLTLSWNVVPNAGILPLVTGSGHVSVPFPDTYEITKSY

Important features of the protein:
Signal peptide:
Amino acids 1-25

Transmembrane domain:
Amino acids 149-164

N-glycosylation site:
Amino acids 141-145

N-myristoylation sites:
Amino acids 25-31;135-141

Cell attachment sequence:
Amino acids 112-115

TonB-dependent receptor proteins signature 1:
Amino acids 1-21

FIGURE 21

AAACTTGACGCCATGAAGATCCCGGTCCTTCCTGCCGTGGTGCTCCTCTCCCTCCTGGTGCT
CCACTCTGCCCAGGGAGCCACCCTGGGTGGTCCTGAGGAAGAAAGCACCATTGAGAATTATG
CGTCACGACCCGAGGCCTTTAACACCCCGTTCCTGAACATCGACAAATTGCGATCTGCGTTT
AAGGCTGATGAGTTCCTGAACTGGCACGCCCTCTTTGAGTCTATCAAAAGGAAACTTCCTTT
CCTCAACTGGGATGCCTTTCCTAAGCTGAAAGGACTGAGGAGCGCAACTCCTGATGCCCAGT
GACCATGACCTCCACTGGAAGAGGGGGCTAGCGTGAGCGCTGATTCTCAACCTACCATAACT
CTTTCCTGCCTCAGGAACTCCAATAAAACATTTTCCATCCAAA

FIGURE 22

></usr/seqdb2/sst/DNA/Dnaseqs.min/ss.DNA57694
><subunit 1 of 1, 99 aa, 1 stop
><MW: 11050, pI: 7.47, NX(S/T): 0
MKIPVLPAVVLLSLLVLHSAQGATLGGPEEESTIENYASRPEAFNTPFLNIDKLRSAFKA
DEFLNWHALFESIKRKLPFLNWDAFPKLKGLRSATPDAQ

Important features:
Signal peptide:
Amino acids 1-22

N-myristoylation sites:
Amino acids 22-28;90-96

Homologous region to Perioxdase:
Amino acids 16-48

FIGURE 23

TCTCAGACTCTTGGAAGGGGCTATACTAGACACACAAAGACAGCCCCAAGAAGGACGGTGGA
GTAGTGTCCTCGCTAAAAGACAGTAGATATGCAACGCCTCTTGCTCCTGCCCTTTCTCCTGC
TGGGAACAGTTTCTGCTCTTCATCTGGAGAATGATGCCCCCCATCTGGAGAGCCTAGAGACA
CAGGCAGACCTAGGCCAGGATCTGGATAGTTCAAAGGAGCAGGAGAGAGACTTGGCTCTGAC
GGAGGAGGTGATTCAGGCAGAGGGAGAGGAGGTCAAGGCTTCTGCCTGTCAAGACAACTTTG
AGGATGAGGAAGCCATGGAGTCGGACCCAGCTGCCTTAGACAAGGACTTCCAGTGCCCCAGG
GAAGAAGACATTGTTGAAGTGCAGGGAAGTCCAAGGTGCAAGACCTGCCGCTACCTATTGGT
GCGGACTCCTAAAACTTTTGCAGAAGCTCAGAATGTCTGCAGCAGATGCTACGGAGGCAACC
TTGTCTCTATCCATGACTTCAACTTCAACTATCGCATTCAGTGCTGCACTAGCACAGTCAAC
CAAGCCCAGGTCTGGATTGGAGGCAACCTCAGGGGCTGGTTCCTGTGGAAGCGGTTTTGCTGG
ACTGATGGGAGCCACTGGAATTTTGCTTACTGGTCCCCAGGGCAACCTGGGAATGGGCAAGG
CTCCTGTGTGGCCCTATGCACCAAAGGAGGTTATTGGCGACGAGCTCAATGCGACAAGCAAC
TGCCCTTCGTCTGCTCCTTCTAAGCCAGCGGCACGGAGACCCTGCCAGCAGCTCCCTCCCGT
CCCCCAACCTCTCCTGCTCATAAATCCAGACTTCCCACAGCAAAAAAAAAAAAAAAAAA

FIGURE 24

</usr/seqdb2/sst/DNA/Dnaseqs.min/ss.DNA59208
<subunit 1 of 1, 225 aa, 1 stop
<MW: 25447, pI: 4.79, NX(S/T): 0
MQRLLLLPFLLLGTVSALHLENDAPHLESLETQADLGQDLDSSKEQERDLALTEEVIQAE
GEEVKASACQDNFEDEEAMESDPAALDKDFQCPREEDIVEVQGSPRCKTCRYLLVRTPKT
FAEAQNVCSRCYGGNLVSIHDFNFNYRIQCCTSTVNQAQVWIGGNLRGWFLWKRFCWTDG
SHWNFAYWSPGQPGNGQGSCVALCTKGGYWRRAQCDKQLPFVCSF

Important features:
Signal peptide:
Amino acids 1-17

N-myristoylation sites:
Amino acids 13-19;103-109;134-140;164-170;
180-186;191-197;194-200;196-202;
198-204

C-type lectin domain signature:
Amino acids 200-224

FIGURE 25

CAACAGAAGCCAAGAAGGAAGCCGTCTATCTTGTGGCGATCATGTATAAGCTGGCCTCCTGC
TGTTTGCTTTTCACAGGATTCTTAAATCCTCTCTTATCTCTTCCTCTCCTTGACTCCAGGGA
AATATCCTTTCAACTCTCAGCACCTCATGAAGACGCGCGCTTAACTCCGGAGGAGCTAGAAA
GAGCTTCCCTTCTACAGATATTGCCAGAGATGCTGGGTGCAGAAAGAGGGGATATTCTCAGG
AAAGCAGACTCAAGTACCAACATTTTTAACCCAAGAGGAAATTTGAGAAAGTTTCAGGATTT
CTCTGGACAAGATCCTAACATTTTACTGAGTCATCTTTTGGCCAGAATCTGGAAACCATACA
AGAAACGTGAGACTCCTGATTGCTTCTGGAAATACTGTGTCTGAAGTGAAATAAGCATCTGT
TAGTCAGCTCAGAAACACCCATCTTAGAATATGAAAAATAACACAATGCTTGATTTGAAAAC
AGTGTGGAGAAAAACTAGGCAAACTACACCCTGTTCATTGTTACCTGGAAAATAAATCCTCT
ATGTTTTGCACAAAAAAAAAAAAAAAA

FIGURE 26

</usr/seqdb2/sst/DNA/Dnaseqs.min/ss.DNA59214
<subunit 1 of 1, 124 aa, 1 stop
<MW: 14284, pI: 8.14, NX(S/T): 0
MYKLASCCLLFTGFLNPLLSLPLLDSREISFQLSAPHEDARLTPEELERASLLQILPEML
GAERGDILRKADSSTNIFNPRGNLRKFQDFSGQDPNILLSHLLARIWKPYKKRETPDCFW
KYCV

Important features:
Signal peptide:
Amino acids 1-20

Urotensin II signature:
Amino acids 118-124

Cell attachment sequence:
Amino acids 64-67 cAMP- and cGMP-dependent protein kinase phosphorylation site:
Amino acids 112-116

N-myristoylation sites:
Amino acids 61-67;92-98

FIGURE 27

CAAGTAAATGCAGCACTAGTGGGTGGGATTGAGGTATGCCCTGGTGCATAAATAGAGACTCA
GCTGTGCTGGCACACTCAGAAGCTTGGACCGCATCCTAGCCGCCGACTCACACAAGGCAGGT
GGGTGAGGAAATCCAGAGTTGCCATGGAGAAAATTCCAGTGTCAGCATTCTTGCTCCTTGTG
GCCCTCTCCTACACTCTGGCCAGAGATACCACAGTCAAACCTGGAGCCAAAAAGGACACAAA
GGACTCTCGACCCAAACTGCCCCAGACCCTCTCCAGAGGTTGGGGTGACCAACTCATCTGGA
CTCAGACATATGAAGAAGCTCTATATAAATCCAAGACAAGCAACAAACCCTTGATGATTATT
CATCACTTGGATGAGTGCCCACACAGTCAAGCTTTAAAGAAAGTGTTTGCTGAAAATAAAGA
AATCCAGAAATTGGCAGAGCAGTTTGTCCTCCTCAATCTGGTTTATGAAACAACTGACAAAC
ACCTTTCTCCTGATGGCCAGTATGTCCCCAGGATTATGTTTGTTGACCCATCTCTGACAGTT
AGAGCCGATATCACTGGAAGATATTCAAATCGTCTCTATGCTTACGAACCTGCAGATACAGC
TCTGTTGCTTGACAACATGAAGAAAGCTCTCAAGTTGCTGAAGACTGAATTGTAAAGAAAAA
AAATCTCCAAGCCCTTCTGTCTGTCAGGCCTTGAGACTTGAAACCAGAAGAAGTGTGAGAAG
ACTGGCTAGTGTGGAAGCATAGTGAACACACTGATTAGGTTATGGTTTAATGTTACAACAAC
TATTTTTTAAGAAAAACAAGTTTTAGAAATTTGGTTTCAAGTGTACATGTGTGAAAACAATA
TTGTATACTACCATAGTGAGCCATGATTTTCTAAAAAAAAAAATAAATGTTA

FIGURE 28

></usr/seqdb2/sst/DNA/Dnaseqs.min/ss.DNA59485
><subunit 1 of 1, 175 aa, 1 stop
><MW: 19979, pI: 9.26, NX(S/T): 0
MEKIPVSAFLLLVALSYTLARDTTVKPGAKKDTKDSRPKLPQTLSRGWGDQLIWTQTYEE
ALYKSKTSNKPLMIIHHLDECPHSQALKKVFAENKEIQKLAEQFVLLNLVYETTDKHLSP
DGQYVPRIMFVDPSLTVRADITGRYSNRLYAYEPADTALLLDNMKKALKLLKTEL

Important features:
Signal peptide:
Amino acids 1-20 cAMP- and cGMP-dependent protein kinase phosphorylation site:
Amino acids 30-34

FIGURE 29

AAGACCCTCTCTTTCGCTGTTTGAGAGTCTCTCGGCTCAAGGACCGGGAGGTAAGAGGTT
TGGGACTGCCCCGGCAACTCCAGGGTGTCTGGTCCACGACCTATCCTAGGCGCCATGGGT
GTGATAGGTATACAGCTGGTTGTTACCATGGTGATGGCCAGTGTCATGCAGAAGATTATA
CCTCACTATTCTCTTGCTCGATGGCTACTCTGTAATGGCAGTTTGAGGTGGTATCAACAT
CCTACAGAAGAAGAATTAAGAATTCTTGCAGGGAAACAACAAAAAGGGAAAACCAAAAAA
GATAGGAAATATAATGGTCACATTGAAAGTAAGCCATTAACCATTCCAAAGGATATTGAC
CTTCATCTAGAAACAAAGTCAGTTACAGAAGTGGATACTTTAGCATTGCATTACTTTCCA
GAATACCAGTGGCTGGTGGATTTCACAGTGGCTGCTACAGTTGTGTATCTAGTAACTGAA
GTCTACTACAATTTTATGAAGCCTACACAGGAAATGAATATCAGCTTAGTCTGGTGCCTA
CTTGTTTTGTCTTTTGCAATCAAAGTTCTATTTTCATTAACTACACACTATTTTAAAGTA
GAAGATGGTGGTGAAAGATCTGTTTGTGTCACCTTTGGATTTTTTTTCTTTGTCAAAGCA
ATGGCAGTGTTGATTGTAACAGAAAATTATCTGGAATTTGGACTTGAAACAGGGTTTACA
AATTTTTCAGACAGTGCGATGCAGTTTCTTGAAAAGCAAGGTTTAGAATCTCAGAGTCCT
GTTTCAAAACTTACTTTCAAATTTTTCCTGGCTATTTTCTGTTCATTCATTGGGGCTTTT
TTGACATTTCCTGGATTACGACTGGCTCAAATGCATCTGGATGCCCTGAATTTGGCAACA
GAAAAAATTACACAAACTTTACTTCATATCAACTTCTTGGCACCTTTATTTATGGTTTTG
CTCTGGGTAAAACCAATCACCAAAGACTACATTATGAACCCACCACTGGGCAAAGAAATT
TCCCCATCTGGAAGATGAAGATAATAGTATCTAACTCACAAGGTTATCATTGGAATAAAT
GAAAGAACACATGTAATGCAACCAGCTGGAATTAAGTGCTTAATAAATGTTCTTTTCACT
GCTTTGCCTCATCAGAATTAAAATAGAAATACTTGACTAGT

FIGURE 30

</usr/seqdb2/sst/DNA/Dnaseqs.full/ss.DNA64966
<subunit 1 of 1, 307 aa, 1 stop
<MW: 35098, pI: 8.11, NX(S/T): 3
MGVIGIQLVVTMVMASVMQKIIPHYSLARWLLCNGSLRWYQHPTEEELRILAGKQQKGKT
KKDRKYNGHIESKPLTIPKDIDLHLETKSVTEVDTLALHYFPEYQWLVDFTVAATVVYLV
TEVYYNFMKPTQEMNISLVWCLLVLSFAIKVLFSLTTHYFKVEDGGERSVCVTFGFFFFV
KAMAVLIVTENYLEFGLETGFTNFSDSAMQFLEKQGLESQSPVSKLTFKFFLAIFCSFIG
AFLTFPGLRLAQMHLDALNLATEKITQTLLHINFLAPLFMVLLWVKPITKDYIMNPPLGK
EISPSGR

Important features:
Signal peptide:
Amino acids 1-15

Transmembrane domains:
Amino acids 134-157;169-189;230-248;272-285

N-glycosylation sites:
Amino acids 34-38;135-139;203-207

ATP/GTP-binding site motif A (P-loop):
Amino acids 53-61

Tyrosine kinase phosphorylation site:
Amino acids 59-67

N-myristoylation sites:
Amino acids 165-171;196-202;240-246;247-253

FIGURE 31

GTAGCATAGTGTGCAGTTCACTGGACCAAAAGCTTTGGCTGCACCTCTTCTGGAAAGCTGGCC
ATGGGGCTCTTCATGATCATTGCAATTCTGCTGTTCCAGAAACCCACAGTAACCGAACAACT
TAAGAAGTGCTGGAATAACTATGTACAAGGACATTGCAGGAAAATCTGCAGAGTAAATGAAG
TGCCTGAGGCACTATGTGAAAATGGGAGATACTGTTGCCTCAATATCAAGGAACTGGAAGCA
TGTAAAAAAATTACAAAGCCACCTCGTCCAAAGCCAGCAACACTTGCACTGACTCTTCAAGA
CTATGTTACAATAATAGAAAATTTCCCAAGCCTGAAGACACAGTCTACATAAATCAAATACA
ATTTCGTTTTCACTTGCTTCTCAACCTAGTCTAATAAACTAAGGTGATGAGATATACATCTT
CTTCCTTCTGGTTTCTTGATCCTTAAAATGACCTTCGAGCATATTCTAATAAAGTGCATTGC
CAGTTAAAAAAAAAA

FIGURE 32

></usr/seqdb2/sst/DNA/Dnaseqs.min/ss.DNA82403
><subunit 1 of 1, 99 aa, 1 stop
><MW: 11343, pI: 9.17, NX(S/T): 0
MGLFMIIAILLFQKPTVTEQLKKCWNNYVQGHCRKICRVNEVPEALCENGRYCCLNIKEL
EACKKITKPPRPKPATLALTLQDYVTIIENFPSLKTQST cAMP- and cGMP-dependent protein kinase phosphorylation site:
Amino acids 64-68

FIGURE 33

CGGACGCGTGGGCGCTGAGCCCCGGAGGCCAGGGCGTCCGGGGCTGCGCCACTTCCGAGGGC
CGAGCGCTGCCGGTCCCGGCGGTGCGACACGGCCGGGAGGAGGAGAACAACGCAAGGGGCTC
AACCGTCGGTCGCTGGAGCCCCCCCCGGGGCGTGGCCTCCCGCCCCCTCAGCTGGGGAGGGC
GGGGCTCGCTGCCCCCTGCTGCCGACTGCGACCCTTACAGGGGAGGGAGGGCGCAGGCCGCG
CGGAGATGAGGAGGAGGCTGCGCCTACGCAGGGACGCATTGCTCACGCTGCTCCTTGGCGCC
TCCCTGGGCCTCTTACTCTATGCGCAGCGCGACGGCGCGGCCCCGACGGCGAGCGCGCCGCG
AGGGCGAGGGAGGGCGGCACCGAGGCCCACCCCCGGACCCCGCGCGTTCCAGTTACCCGACG
CGGGTGCAGCCCCGCCGGCCTACGAAGGGGACACACCGGCGCCGCCCACGCCTACGGGACCC
TTTGACTTCGCCCGCTATTTGCGCGCCAAGGACCAGCGGCGGTTTCCACTGCTCATTAACCA
GCCGCACAAGTGCCGCGGCGACGGCGCACCCGGTGGCCGCCCGGACCTGCTTATTGCTGTCA
AGTCGGTGGCAGAGGACTTCGAGCGGCGCCAAGCCGTGCGCCAGACGTGGGGCGCGGAGGGT
CGCGTGCAGGGGGCGCTGGTGCGCCGCGTGTTCTTGCTGGGCGTGCCCAGGGGCGCAGGCTC
GGGCGGGGCCGACGAAGTTGGGGAGGGCGCGCGAACCCACTGGCGCGCCCTGCTGCGGGCCG
AGAGCCTTGCGTATGCGGACATCCTGCTCTGGGCCTTCGACGACACCTTTTTTAACCTAACG
CTCAAGGAGATCCACTTTCTAGCCTGGGCCTCAGCTTTCTGCCCCGACGTGCGCTTCGTTTT
TAAGGGCGACGCAGATGTGTTCGTGAACGTGGGAAATCTCCTGGAGTTCCTGGCGCCGCGGGAC
CCGGCGCAAGACCTGCTTGCTGGTGACGTAATTGTGCATGCGCGGCCCATCCGCACGCGGGC
TAGCAAGTACTACATCCCCGAGGCCGTGTACGGCCTGCCCGCCTATCCGGCCTACGCGGGCG
GCGGTGGCTTTGTGCTTTCCGGGGCCACGCTGCACCGCCTGGCTGGCGCCTGTGCGCAGGTC
GAGCTCTTCCCCATCGACGACGTCTTTCTGGGCATGTGTCTGCAGCGCCTGCGGCTCACGCC
CGAGCCTCACCCTGCCTTCCGCACCTTTGGCATCCCCCAGCCTTCAGCCGCGCCGCATTTGA
GCACCTTCGACCCCTGCTTTTACCGTGAGCTGGTTGTAGTGCACGGGCTCTCGGCCGCTGAC
ATCTGGCTTATGTGGCGCCTGCTGCACGGGCCGCATGGGCCAGCCTGTGCGCATCCACAGCC
TGTCGCTGCAGGCCCCTTCCAATGGGACTCCTAGCTCCCCACTACAGCCCCAAGCTCCTAAC
TCAGACCCAGAATGGAGCCGGTTTCCCAGATTATTGCCGTGTATGTGGTTCTTCCCTGATCA
CCAGGTGCCTGTCTCCACAGGATCCCAGGGGATGGGGGTTAAGCTTGGCTCCTGGCGGTCCA
CCCTGCTGGAACCAGTTGAAACCCGTGTAATGGTGACCCTTTGAGCGAGCCAAGGCTGGGTG
GTAGATGACCATCTCTTGTCCAACAGGTCCCAGAGCAGTGGATATGTCTGGTCCTCCTAGTA
GCACAGAGGTGTGTTCTGGTGTGGTGGCAGGGACTTAGGGAATCCTACCACTCTGCTGGATT
TGGAACCCCCTAGGCTGACGCGGACGTATGCAGAGGCTCTCAAGGCCAGGCCCCACAGGGAG
GTGGAGGGGCTCCGGCCGCCACAGCCTGAATTCATGAACCTGGCAGGCACTTTGCCATAGCT
CATCTGAAAACAGATATTATGCTTCCCACAACCTCTCCTGGGCCCAGGTGTGGCTGAGCACC
AGGGATGGAGCCACACATAAGGACAAATGAGTGCACGGTCCTACCTAGTCTTTCCTCACCT
CCTGAACTCACACAACAATGCCAGTCTCCCACTGGAGGCTGTATCCCCTCAGAGGAGCCAAG
GAATGTCTTCCCCTGAGATGCCACCACTATTAATTTCCCCATATGCTTCAACCACCCCCTTG
CTCAAAAAACCAATACCCACACTTACCTTAATACAAACATCCCAGCAACAGCACATGGCAGG
CCATTGCTGAGGGCACAGGTGCTTTATTGGAGAGGGGATGTGGGCAGGGGATAAGGAAGGTTCC
CCCATTCCAGGAGGATGGGAACAGTCCTGGCTGCCCCTGACAGTGGGGATATGCAAGGGGCT
CTGGCCAGGCCACAGTCCAAATGGGAAGACACCAGTCAGTCACAAAAGTCGGGAGCGCCACA
CAAACCTGGCTATAAGGCCCAGGAACCATATAGGAGCCTGAGACAGGTCCCCTGCACATTCA
TCATTAAACTATACAGGATGAGGCTGTACATGAGTTAATTACAAAAGAGTCATATTTACAAA
AATCTGTACACACATTTGAAAAACTCACAAAATTGTCATCTATGTATCACAAGTTGCTAGAC
CCAAAATATTAAAAATGGATAAAATTNNTTTAAAAAAAAAAAAAAAAAAAAAAAAAAAAA
AAAAAAAAAAAAAA

FIGURE 34

></usr/seqdb2/sst/DNA/Dnaseqs.min/ss.DNA83505
><subunit 1 of 1, 402 aa, 1 stop
><MW: 43751, pI: 9.42, NX(S/T): 1
MRRRLRLRRDALLTLLLGASLGLLLYAQRDGAAPTASAPRGRGRAAPRPTPGPRAFQLPD
AGAAPPAYEGDTPAPPTPTGPFDFARYLRAKDQRRFPLLINQPHKCRGDGAPGGRPDLLI
AVKSVAEDFERRQAVRQTWGAEGRVQGALVRRVFLLGVPRGAGSGGADEVGEGARTHWRA
LLRAESLAYADILLWAFDDTFFNLTLKEIHFLAWASAFCPDVRFVFKGDADVFVNVGNLL
EFLAPRDPAQDLLAGDVIVHARPIRTRASKYYIPEAVYGLPAYPAYAGGGGFVLSGATLH
RLAGACAQVELFPIDDVFLGMCLQRLRLTPEPHPAFRTFGIPQPSAAPHLSTFDPCFYRE
LVVVHGLSAADIWLMWRLLHGPHGPACAHPQPVAAGPFQWDS

Important features of the protein:
Signal peptide:
Amino acids 1-27

N-glycosylation site:
Amino acids 203-207

N-myristoylation sites:
Amino acids 18-24;31-37;110-116;157-163;161-167
163-169;366-372

Cell attachment sequence:
Amino acids 107-110

FIGURE 35

AGCAGCCTCTGCCCGACCCGGCTCGTGCGGACCCCAGGACCGGGCGCGGGACGCGTGCGTCC
AGCCTCCGGCGCTGCGGAGACCCGCGGCTGGGTCCGGGGAGGCCCCAAACCCGCCCCCGCCA
GAACCCCGCCCCAAATTCCCACCTCCTCCAGAAGCCCCGCCCACTCCCGAGCCCCGAGAGCT
CCGCGCACCTGGGCGCCATCCGCCCTGGCTCCGCTGCACGAGCTCCACGCCCGTACCCCGGC
GTCACGCTCAGCCCGCGGTGCTCGCACACCTGAGACTCATCTCGCTTCGACCCCGCCGCCGC
CGCCGCCCGGCATCCTGAGCACGGAGACAGTCTCCAGCTGCCGTTCATGCTTCCTCCCCAGC
CTTCCGCAGCCCACCAGGGAAGGGGCGGTAGGAGTGGCCTTTTACCAAAGGGACCGGCGATG
CTCTGCAGGCTGTGCTGGCTGGTCTCGTACAGCTTGGCTGTGCTGTTGCTCGGCTGCCTGCT
CTTCCTGAGGAAGGCGGCCAAGCCCGCAGGAGACCCCACGGCCCACCAGCCTTTCTGGGCTCCC
CCAACACCCCGTCACAGCCGGTGTCCACCCAACCACACAGTGTCTAGCGCCTCTCTGTCCCT
GCCTAGCCGTCACCGTCTCTTCTTGACCTATCGTCACTGCCGAAATTTCTCTATCTTGCTGG
AGCCTTCAGGCTGTTCCAAGGATACCTTCTTGCTCCTGGCCATCAAGTCACAGCCTGGTCAC
GTGGAGCGACGTGCGGCTATCCGCAGCACGTGGGCAGGGTGGGGGGATGGGCTAGGGGCCG
GCAGCTGAAGCTGGTGTTCCTCCTAGGGGTGGCAGGATCCGCTCCCCCAGCCCAGCTGCTGG
CCTATGAGAGTAGGGAGTTTGATGACATCCTCCAGTGGGACTTCACTGAGGACTTCTTCAAC
CTGACGCTCAAGGAGCTGCACCTGCAGCGCTGGGTGGTGGCTGCCTGCCCCCAGGCCCATTT
CATGCTAAAGGGAGATGACGATGTCTTTGTCCACGTCCCCAACGTGTTAGAGTTCCTGGATG
GCTGGGACCCAGCCCAGGACCTCCTGGTGGGAGATGTCATCCGCCAAGCCCTGCCCAACAGG
AACACTAAGGTCAAATACTTCATCCCACCCTCAATGTACAGGGCCACCCACTACCCACCCTA
TGCTGGTGGGGGAGGATATGTCATGTCCAGAGCCACAGTGCGGCGCCTCCAGGCTATCATGG
AAGATGCTGAACTCTTCCCCATTGATGATGTCTTTGTGGGTATGTGCCTGAGGAGGCTGGGG
CTGAGCCCTATGCACCATGCTGGCTTCAAGACATTTGGAATCCGGCGGCCCCTGGACCCCTT
AGACCCCTGCCTGTATAGGGGGCTCCTGCTGGTTCACCGCCTCAGCCCCCTCGAGATGTGGA
CCATGTGGGCACTGGTGACAGATGAGGGGCTCAAGTGTGCAGCTGGCCCCATACCCCAGCGC
TGAAGGGTGGGTTGGGCAACAGCCTGAGAGTGGACTCAGTGTTGATTCTCTATCGTGATGCG
AAATTGATGCCTGCTGCTCTACAGAAAATGCCAACTTGGTTTTTTAACTCCTCTCACCCTGT
TAGCTCTGATTAAAAACACTGCAACCCAA

FIGURE 36

></usr/seqdb2/sst/DNA/Dnaseqs.min/ss.DNA84927
><subunit 1 of 1, 378 aa, 1 stop
><MW: 42310, pI: 9.58, NX(S/T): 3
MLPPQPSAAHQGRGGRSGLLPKGPAMLCRLCWLVSYSLAVLLLGCLLFLRKAAKPAGDPT
AHQPFWAPPTPRHSRCPPNHTVSSASLSLPSRHRLFLTYRHCRNFSILLEPSGCSKDTFL
LLAIKSQPGHVERRAAIRSTWGRVGGWARGRQLKLVFLLGVAGSAPPAQLLAYESREFDD
ILQWDFTEDFFNLTLKELHLQRWVVAACPQAHFMLKGDDDVFVHVPNVLEFLDGWDPAQD
LLVGDVIRQALPNRNTKVKYFIPPSMYRATHYPPYAGGGGYVMSRATVRRLQAIMEDAEL
FPIDDVFVGMCLRRLGLSPMHHAGFKTFGIRRPLDPLDPCLYRGLLLVHRLSPLEMWTMW
ALVTDEGLKCAAGPIPQR

Important features of the protein:
Signal peptide:
Amino acids 1-39

Transmembrane domain:
Amino acids 146-171

N-glycosylation sites:
Amino acids 79-83;104-108;192-196

N-myristoylation sites:
Amino acids 14-20;160-166;367-373

Prokaryotic membrane lipoprotein lipid attachment site:
Amino acids 35-46

FIGURE 37

ATGAAAGTGATAATCAGGCAGCCCAAATGATTGTTAATAAGGATCAAATGAGATCGTGTATG
TGGGTCCAATCAATTGATTCTACACAAAGGAGCCTGGGGAGGGGCCATGGTGCCAATGCACT
TACTGGGGAGACTGGAGAAGCCGCTTCTCCTCCTGTGCTGCGCCTCCTTCCTACTGGGGCTG
GCTTTGCTGGGCATAAAGACGGACATCACCCCCGTTGCTTATTTCTTTCTCACATTGGGTGG
CTTCTTCTTGTTTGCCTATCTCCTGGTCCGGTTTCTGGAATGGGGGCTTCGGTCCCAGCTCC
AATCAATGCAGACTGAGAGCCCAGGGCCCTCAGGCAATGCACGGGACAATGAAGCCTTTGAA
GTGCCAGTCTATGAAGAGGCCGTGGTGGGACTAGAATCCCAGTGCCGCCCCCAAGAGTTGGA
CCAACCACCCCCCTACAGCACTGTTGTGATACCCCCAGCACCTGAGGAGGAACAACCTAGCC
ATCCAGAGGGGTCCAGGAGAGCCAAACTGGAACAGAGGCGAATGGCCTCAGAGGGGTCCATG
GCCCAGGAAGGAAGCCCTGGAAGAGCTCCAATCAACCTTCGGCTTCGGGGACCACGGGCTGT
GTCCACTGCTCCTGATCTGCAGAGCTTGGCGGCAGTCCCCACATTAGAGCCTCTGACTCCAC
CCCCTGCCTATGATGTCTGCTTTGGTCACCCTGATGATGATAGTGTTTTTTATGAGGACAAC
TGGGCACCCCCTTAAATGACTCTCCCAAGATTTCTCTTCTCTCCACACCAGACCTCGTTCAT
TTGACTAACATTTTCCAGCGCCTACTATGTGTCAGAAACAAGTGTTTCTGCCTGGACATCAT
AAATGGGGACTTGGACCCTGAGGAGAGTCAGGCCACGGTAAGCCCTTCCCAGCTGAGATATG
GGTGGCATAATTTGAGTCTTCTGGCAACATTTGGTGACCTACCCCATATCCAATATTTCCAG
CGTTAGATTGAGGATGAGGTAGGGAGGTGATCCAGAGAAGGCGGAGAAGGAAGAAGTAACCT
CTGAGTGGCGGCTATTGCTTCTGTTCCAGGTGCTGTTCGAGCTGTTAGAACCCTTAGGCTTGAC
AGCTTTGTGAGTTATTATTGAAAAATGAGGATTCCAAGAGTCAGAGGAGTTTGATAATGTGC
ACGAGGGCACACTGCTAGTAAATAACATTAAAATAACTGGAATGAA

FIGURE 38

></usr/seqdb2/sst/DNA/Dnaseqs.min/ss.DNA92264
><subunit 1 of 1, 216 aa, 1 stop
><MW: 23729, pI: 4.73, NX(S/T): 0
MVPMHLLGRLEKPLLLLCCASFLLGLALLGIKTDITPVAYFFLTLGGFFLFAYLLVRFLE
WGLRSQLQSMQTESPGPSGNARDNEAFEVPVYEEAVVGLESQCRPQELDQPPPYSTVVIP
PAPEEEQPSHPEGSRRAKLEQRRMASEGSMAQEGSPGRAPINLRLRGPRAVSTAPDLQSL
AAVPTLEPLTPPPAYDVCFGHPDDDSVFYEDNWAPP

Important features of the protein:
Signal peptide:
Amino acids 1-25

Transmembrane domain:
Amino acids 41-59

N-myristoylation site:
Amino acids 133-139

FIGURE 39

CCCACGCGTCCGGCGGCTACACACCTAGGTGCGGTGGGCTTCGGGTGGGGGGCCTGCAGCTA
GCTGATGGCAAGGGAGGAATAGCAGGGGTGGGGATTGTGGTGTGCGAGAGGTCCCGCGGACG
GGGGGCTCGGGGGTCTCTTCAGACGAGATTCCCTTCAGGCTTGGCCGGGTCCCTTCGCACG
GAGATCCCAATGAACGCGGCCCCTGGAGGCCGGTGGTTGGGGCTTCTCCGCGTCGGGGATG
GGGCCGGTACCCTAGCCCGTTTCCAGCGCCTCAGTCGGTTCCCCATGCCCTCAGAGGTGGCC
CGGGGCAAGCGCGCCGCCCTCTTCTTCGCTGCGGTGGCCATCGTGCTGGGGCTACCGCTCTG
GTGGAAGACCACGGAGACCTACCGGGCCTCGTTGCCTTACTCCCAGATCAGTGGCCTGAATG
CCCTTCAGCTCCGCCTCATGGTGCCTGTCACTGTCGTGTTTACGCGGGAGTCAGTGCCCCTG
GACGACCAGGAGAAGCTGCCCTTCACCGTTGTGCATGAAAGAGAGATTCCTCTGAAATACAA
AATGAAAATCAAATGCCGTTTCCAGAAGGCCTATCGGAGGGCTTTGGACCATGAGGAGGAGG
CCCTGTCATCGGGCAGTGTGCAAGAGGCAGAAGCCATGTTAGATGAGCCTCAGGAACAAGCG
GAGGGCTCCCTGACTGTGTACGTGATATCTGAACACTCCTCACTTCTTCCCCAGGACATGAT
GAGCTACATTGGGCCCAAGAGGACAGCAGTGGTGCGGGGGATAATGCACCGGGAGGCCTTTA
ACATCATTGGCCGCCGCATAGTCCAGGTGGCCCAGGCCATGTCTTTGACTGAGGATGTGCTT
GCTGCTGCTCTGGCTGACCACCTTCCAGAGGACAAGTGGAGCGCTGAGAAGAGGCGGCCTCT
CAAGTCCAGCTTGGGCTATGAGATCACCTTCAGTTTACTCAACCCAGACCCCAAGTCCCATG
ATGTCTACTGGGACATTGAGGGGGCTGTCCGGCGCTATGTGCAACCTTTCCTGAATGCCCTC
GGTGCCGCTGGCAACTTCTCTGTGGACTCTCAGATTCTTTACTATGCAATGTTGGGGGTGAA
TCCCCGCTTTGACTCAGCTTCCTCCAGCTACTATTTGGACATGCACAGCCTCCCCCATGTCA
TCAACCCAGTGGAGTCCCGGCTGGGATCCAGTGCTGCCTCCTTGTACCCTGTGCTCAACTTT
CTACTCTACGTGCCTGAGCTTGCACACTCACCGCTGTACATTCAGGACAAGGATGGCGCTCC
AGTGGCCACCAATGCCTTCCATAGTCCCCGCTGGGGTGGCATTATGGTATATAATGTTGACT
CCAAAACCTATAATGCCTCAGTGCTGCCAGTGAGAGTCGAGGTGGACATGGTGCGAGTGATG
GAGGTGTTCCTGGCACAGTTGCGGTTGCTCTTTGGGATTGCTCAGCCCCAGCTGCCTCCAAA
ATGCCTGCTTTCAGGGCCTACGAGTGAAGGGCTAATGACCTGGGAGCTAGACCGGCTGCTCTGG
GCTCGGTCAGTGGAGAACCTGGCCACAGCCACCACCACCCTTACCTCCCTGGCGCAGCTTCT
GGGCAAGATCAGCAACATTGTCATTAAGGACGACGTGGCATCTGAGGTGTACAAGGCTGTAG
CTGCCGTCCAGAAGTCGGCAGAAGAGTTGGCGTCTGGGCACCTGGCATCTGCCTTTGTCGCC
AGCCAGGAAGCTGTGACATCCTCTGAGCTTGCCTTCTTTGACCCGTCACTCCTCCACCTCCT
TTATTTCCCTGATGACCAGAAGTTTGCCATCTACATCCCACTCTTCCTGCCTATGGCTGTGC
CCATCCTCCTGTCCCTGGTCAAGATCTTCCTGGAGACCCGCAAGTCCTGGAGAAAGCCTGAG
AAGACAGACTGAGCAGGGCAGCACCTCCATAGGAAGCCTTCCTTTCTGGCCAAGGTGGGCGG
TGTTAGATTGTGAGGCACGTACATGGGGCCTGCCGGAATGACTTAAATATTTGTCTCCAGTC
TCCACTGTTGGCTCTCCAGCAACCAAAGTACAACACTCCAAGATGGGTTCATCTTTTCTTCC
TTTCCCATTCACCTGGCTCAATCCTCCTCCACCACCAGGGGCCTCAAAAGGCACATCATCCG
GGTCTCCTTATCTTGTTTGATAAGGCTGCTGCCTGTCTCCCTCTGTGGCAAGGACTGTTTGT
TCTTTTGCCCCATTTCTCAACATAGCACACTTGTGCACTGAGAGGAGGGAGCATTATGGGAA
AGTCCCTGCCTTCCACACCTCTCTCTAGTCCCTGTGGGACAGCCCTAGCCCCTGCTGTCATG
AAGGGGCCAGGCATTGGTCACCTGTGGGACCTTCTCCCTCACTCCCCTCCCTCCTAGTTGGC
TTTGTCTGTCAGGTGCAGTCTGGCGGGAGTCCAGGAGGCAGCAGCTCAGGACATGGTGCTGT
GTGTGTGTGTGTGTGTGTGTGTGTGTGTGTGTGTGTGTGTCAGAGGTTCCAGAAAGTTCCAGATTT
GGAATCAAACAGTCCTGAATTCAAATCCTTGTTTTTGCACTTATTGTCTGGAGAGCTTTGGA
TAAGGTATTGAATCTCTCTGAGCCTCAGTTTTTCATTTGTTCAAATGGCACTGATGATGTCT
CCCTTACAAGATGGTTGTGAGGAGTAAATGTGATCAGCATGTAAAGTGTCTGGCGTGTAGTA
GGCTCTTAATAAACACTGGCTGAATATGAATTGGAATGAT

FIGURE 40

></usr/seqdb2/sst/DNA/Dnaseqs.min/ss.DNA94713
><subunit 1 of 1, 547 aa, 1 stop
><MW: 61005, pI: 6.34, NX(S/T): 2
MPSEVARGKRAALFFAAVAIVLGLPLWWKTTETYRASLPYSQISGLNALQLRLMVPVTVV
FTRESVPLDDQEKLPFTVVHEREIPLKYKMKIKCRFQKAYRRALDHEEEALSSGSVQEAE
AMLDEPQEQAEGSLTVYVISEHSSLLPQDMMSYIGPKRTAVVRGIMHREAFNIIGRRIVQ
VAQAMSLTEDVLAAALADHLPEDKWSAEKRRPLKSSLGYEITFSLLNPDPKSHDVYWDIE
GAVRRYVQPFLNALGAAGNFSVDSQILYYAMLGVNPRFDSASSSYYLDMHSLPHVINPVE
SRLGSSAASLYPVLNFLLYVPELAHSPLYIQDKDGAPVATNAFHSPRWGGIMVYNVDSKT
YNASVLPVRVEVDMVRVMEVFLAQLRLLFGIAQPQLPPKCLLSGPTSEGLMTWELDRLLW
ARSVENLATATTTLTSLAQLLGKISNIVIKDDVASEVYKAVAAVQKSAEELASGHLASAF
VASQEAVTSSELAFFDPSLLHLLYFPDDQKFAIYIPLFLPMAVPILLSLVKIFLETRKSW
RKPEKTD

Important features of the protein:
Signal peptide:
Amino acids 1-23

Transmembrane domain:
Amino acids 511-530

N-glycosylation sites:
Amino acids 259-263;362-366

N-myristoylation sites:
Amino acids 255-261;304-310;335-341

Amidation sites:
Amino acids 7-11;174-178

FIGURE 41

CCAGCTGCAGAGAGGAGGAGGTGAGCTGCAGAGAAGAGGAGGTTGGTGTGGAGCACAGGCAG
CACCGAGCCTGCCCCGTGAGCTGAGGGCCTGCAGTCTGCGGCTGGAATCAGGATAGACACCA
AGGCAGGACCCCCAGAGATGCTGAAGCCTCTTTGGAAAGCAGCAGTGGCCCCCACATGGCCA
TGCTCC<u>ATG</u>CCGCCCCGCCGCCCGTGGGACAGAGAGGCTGGCACGTTGCAGGTCCTGGGAGC
GCTGGCTGTGCTGTGGCTGGGCTCCGTGGCTCTTATCTGCCTCCTGTGGCAAGTGCCCCGTCCT
CCCACCTGGGGCCAGGTGCAGCCCAAGGACGTGCCCAGGTCCTGGGAGCATGGCTCCAGCCC
AGCTTGGGAGCCCCTGGAAGCAGAGGCCAGGCAGCAGAGGGACTCCTGCCAGCTTGTCCTTG
TGGAAAGCATCCCCCAGGACCTGCCATCTGCAGCCGGCAGCCCCTCTGCCCAGCCTCTGGGC
CAGGCCTGGCTGCAGCTGCTGGACACTGCCCAGGAGAGCGTCCACGTGGCTTCATACTACTG
GTCCCTCACAGGGCCTGACATCGGGGTCAACGACTCGTCTTCCCAGCTGGGAGAGGCTCTTC
TGCAGAAGCTGCAGCAGCTGCTGGGCAGGAACATTTCCCTGGCTGTGGCCACCAGCAGCCCG
ACACTGGCCAGGACATCCACCGACCTGCAGGTTCTGGCTGCCCGAGGTGCCCATGTACGACA
GGTGCCCATGGGGCGGCTCACCAGGGGTGTTTTGCACTCCAAATTCTGGGTTGTGGATGGAC
GGCACATATACATGGGCAGTGCCAACATGGACTGGCGGTCTCTGACGCAGGTGAAGGAGCTT
GGCGCTGTCATCTATAACTGCAGCCACCTGGCCCAAGACCTGGAGAAGACCTTCCAGACCTA
CTGGGTACTGGGGGTGCCCAAGGCTGTCCTCCCCAAAACCTGGCCTCAGAACTTCTCATCTC
ACTTCAACCGTTTCCAGCCCTTCCACGGCCTCTTTGATGGGGTGCCCACCACTGCCTACTTC
TCAGCGTCGCCACCAGCACTCTGTCCCCAGGGCCGCACCCGGGACCTGGAGGCGCTGCTGGC
GGTGATGGGGAGCGCCCAGGAGTTCATCTATGCCTCCGTGATGGAGTATTTCCCCACCACGC
GCTTCAGCCACCCCCCGAGGTACTGGCCGGTGCTGGACAACGCGCTGCGGGCGGCAGCCTTC
GGCAAGGGCGTGCGCGTGCGCCTGCTGGTCGGCTGCGGACTCAACACGGACCCCACCATGTT
CCCCTACCTGCGGTCCCTGCAGGCGCTCAGCAACCCCGCGGCCAACGTCTCTGTGGACGTGA
AAGTCTTCATCGTGCCGGTGGGGAACCATTCCAACATCCCATTCAGCAGGGTGAACCACAGC
AAGTTCATGGTCACGGAGAAGGCAGCCTACATAGGCACCTCCAACTGGTCGGAGGATTACTT
CAGCAGCACGGCGGGGGTGGGCTTGGTGGTCACCCAGAGCCCTGGCGCGCAGCCCGCGGGGG
CCACGGTGCAGGAGCAGCTGCGGCAGCTCTTTGAGCGGGACTGGAGTTCGCGCTACGCCGTC
GGCCTGGACGGACAGGCTCCGGGCCAGGACTGCGTTTGGCAGGGC<u>TGA</u>GGGGGGCCTCTTTT
TCTCTCGGCGACCCCGCCCCGCACGCGCCCTCCCCTCTGACCCCGGCCTGGGCTTCAGCCGC
TTCCTCCCGCAAGCAGCCCGGGTCCGCACTGCGCCAGGAGCCGCCTGCGACCGCCCGGGCGT
CGCAAACCGCCCGCCTGCTCTCTGATTTCCGAGTCCAGCCCCCCCTGAGCCCCACCTCCTCC
AGGGAGCCCTCCAGGAAGCCCCTTCCCTGACTCCTGGCCCACAGGCCAGGCCTAAAAAAAAC
TCGTGGCTTCAAAAAAAAAAAAAAAAAAAAAAAAAAAA

FIGURE 42

></usr/seqdb2/sst/DNA/Dnaseqs.min/ss.DNA96869
><subunit 1 of 1, 489 aa, 1 stop
><MW: 53745, pI: 8.36, NX(S/T): 8
MPPRRPWDREAGTLQVLGALAVLWLGSVALICLLWQVPRPPTWGQVQPKDVPRSWEHGSS
PAWEPLEAEARQQRDSCQLVLVESIPQDLPSAAGSPSAQPLGQAWLQLLDTAQESVHVAS
YYWSLTGPDIGVNDSSSQLGEALLQKLQQLLGRNISLAVATSSPTLARTSTDLQVLAARG
AHVRQVPMGRLTRGVLHSKFWVVDGRHIYMGSANMDWRSLTQVKELGAVIYNCSHLAQDL
EKTFQTYWVLGVPKAVLPKTWPQNFSSHFNRFQPFHGLFDGVPTTAYFSASPPALCPQGR
TRDLEALLAVMGSAQEFIYASVMEYFPTTRFSHPPRYWPVLDNALRAAAFGKGVRVRLLV
GCGLNTDPTMFPYLRSLQALSNPAANVSVDVKVFIVPVGNHSNIPFSRVNHSKFMVTEKA
AYIGTSNWSEDYFSSTAGVGLVVTQSPGAQPAGATVQEQLRQLFERDWSSRYAVGLDGQA
PGQDCVWQG

Important features of the protein:
Signal peptide:
Amino acids 1-29

N-glycosylation sites:
Amino acids 133-137;154-158;232-236;264-268;
386-390;400-404;410-414;427-431

N-myristoylation sites:
Amino acids 58-64;94-100;131-137;194-200;251-257;
277-283;281-287;361-367;399-405;
440-446;448-454;478-484

FIGURE 43

GGGCCTGGCGATCCGGATCCCGCAGGCGCGCTGGCTGCGCTGCCCGGCTGTCTGTCGTCATG
GTGGGGCCCTGGGTGTATCTGGTGGCGGCAGTTTTGCTCATCGGCCTGATCCTCTTCCTGAC
TCGCAGCCGGGGTCGGGCGGCAGCAGCTGACGGAGAACCACTGCACAATGAGGAAGAGAGGG
CAGGAGCAGGCCAGGTAGGCCGCTCTTTGCCCCAGGAGTCTGAAGAACAGAGAACTGGAAGC
AGACCCCGGCGTCGGAGGGACTTGGGCAGCCGTCTACAGGCCCAGCGTCGAGCCCAGCGAGT
GGCCTGGGAAGACGGGGATGAGAATGTGGGTCAAACTGTTATTCCAGCCCAGGAGGAAGAAG
GCATTGAGAAGCCAGCAGAAGTTCACCCAACAGGGAAAATTGGAGCCAAGAAACTACGGAAG
CTAGAGGAAAAACAGGCTCGAAAGGCTCAGCGAGAGGCAGAGGAGGCTGAACGTGAAGAACG
GAAACGCCTAGAGTCCCAACGTGAGGCCGAATGGAAGAAGGAAGAGGAACGGCTTCGCCTGA
AGGAAGAACAGAAGGAGGAGGAAGAGAGGAAGGCTCAGGAGGAGCAGGCCCGGCGGGATCAC
GAGGAGTACCTGAAACTGAAGGAGGCCTTCGTGGTAGAAGAAGAAGGTGTTAGCGAAACCAT
GACTGAGGAGCAGTCTCACAGCTTCCTGACAGAATTCATCAATTACATCAAGAAGTCCAAGG
TTGTGCTTTTGGAAGATCTGGCTTTCCAGATGGGCCTAAGGACTCAGGACGCCATAAACCGC
ATCCAGGACCTGCTGACGGAGGGGACTCTAACAGGTGTGATTGACGACCGGGGCAAGTTTAT
CTACATAACCCCAGAGGAACTGGCTGCCGTGGCCAATTTCATCCGACAGCGGGGCCGGGTGT
CCATCACAGAGCTTGCCCAGGCCAGCAACTCCCTCATCTCCTGGGGCCAGGACCTCCCTGCC
CAGGCTTCAGCCTGACTCCAGTCCTTCCTTGAGTGTATCCTGTGGCCTACATGTGTCTTCAT
CCTTCCCTAATGCCGTCTTGGGGCAGGGATGGAATATGACCAGAAAGTTGTGGATTAAAGGC
CTGTGAATACTGAA

FIGURE 44

></usr/seqdb2/sst/DNA/Dnaseqs.min/ss.DNA96881
><subunit 1 of 1, 315 aa, 1 stop
><MW: 35963, pI: 5.38, NX(S/T): 0
MVGPWVYLVAAVLLIGLILFLTRSRGRAAAADGEPLHNEEERAGAGQVGRSLPQESEEQR
TGSRPRRRRDLGSRLQAQRRAQRVAWEDGDENVGQTVIPAQEEEGIEKPAEVHPTGKIGA
KKLRKLEEKQARKAQREAEEAEREERKRLESQREAEWKKEEERLRLKEEQKEEEERKAQE
EQARRDHEEYLKLKEAFVVEEEGVSETMTEEQSHSFLTEFINYIKKSKVVLLEDLAFQMG
LRTQDAINRIQDLLTEGTLTGVIDDRGKFIYITPEELAAVANFIRQRGRVSITELAQASN
SLISWGQDLPAQASA

Important features of the protein:
Signal peptide:
Amino acids 1-26

N-myristoylation sites:
Amino acids 203-209;257-263

FIGURE 45

ACGGGCCGCAGCGGCAGTGACGTAGGGTTGGCGCACGGATCCGTTGCGGCTGCAGCTCTGCA
GTCGGGCCGTTCCTTCGCCGCCGCCAGGGGTAGCGGTGTAGCTGCGCAGCGTCGCGCGCGCT
ACCGCACCCAGGTTCGGCCCGTAGGCGTCTGGCAGCCCGGCGCCATCTTCATCGAGCGCCAT
GGCCGCAGCCTGCGGGCCGGGAGCGGCCGGGTACTGCTTGCTCCTCGGCTTGCATTTGTTTC
TGCTGACCGCGGGCCCTGCCCTGGGCTGGAACGACCCTGACAGAATGTTGCTGCGGGATGTA
AAAGCTCTTACCCTCCACTATGACCGCTATACCACCTCCCGCAGGCTGGATCCCATCCCACA
GTTGAAATGTGTTGGAGGCACAGCTGGTTGTGATTCTTATACCCCAAAAGTCATACAGTGTC
AGAACAAAGGCTGGGATGGGTATGATGTACAGTGGGAATGTAAGACGGACTTAGATATTGCA
TACAAATTTGGAAAAACTGTGGTGAGCTGTGAAGGCTATGAGTCCTCTGAAGACCAGTATGT
ACTAAGAGGTTCTTGTGGCTTGGAGTATAATTTAGATTATACAGAACTTGGCCTGCAGAAAC
TGAAGGAGTCTGGAAAGCAGCACGGCTTTGCCTCTTTCTCTGATTATTATTATAAGTGGTCC
TCGGCGGATTCCTGTAACATGAGTGGATTGATTACCATCGTGGTACTCCTTGGGATCGCCTT
TGTAGTCTATAAGCTGTTCCTGAGTGACGGGCAGTATTCTCCTCCACCGTACTCTGAGTATC
CTCCATTTTCCCACCGTTACCAGAGATTCACCAACTCAGCAGGACCTCCTCCCCCAGGCTTT
AAGTCTGAGTTCACAGGACCACAGAATACTGGCCATGGTGCAACTTCTGGTTTTGGCAGTGC
TTTTACAGGACAACAAGGATATGAAAATTCAGGACCAGGGTTCTGGACAGGCTTGGGAACTG
GTGGAATACTAGGATATTTGTTTGGCAGCAATAGAGCGGCAACACCCTTCTCAGACTCGTGG
TACTACCCGTCCTATCCTCCCTCCTACCCTGGCACGTGGAATAGGGCTTACTCACCCCTTCA
TGGAGGCTCGGGCAGCTATTCGGTATGTTCAAACTCAGACACGAAAACCAGAACTGCATCAG
GATATGGTGGTACCAGGAGACGATAAAGTAGAAAGTTGGAGTCAAACACTGGATGCAGAAAT
TTTGGATTTTTCATCACTTTCTCTTTAGAAAAAAAGTACTACCTGTTAACAATTGGAAAAG
GGGATATTCAAAAGTTCTGTGGTGTTATGTCCAGTGTAGCTTTTTGTATTCTATTATTTGAG
GCTAAAAGTTGATGTGTGACAAAATACTTATGTGTTGTATGTCAGTGTAACATGCAGATGTA
TATTGCAGTTTTTGAAAGTGATCATTACTGTGGAATGCTAAAAATACATTAATTTCTAAAAC
CTGTGATGCCCTAAGAAGCATTAAGAATGAAGGTGTTGTACTAATAGAAACTAAGTACAGAA
AATTTCAGTTTTAGGTGGTTGTAGCTGATGAGTTATTACCTCATAGAGACTATAATATTCTA
TTTGGTATTATATTATTTGATGTTTGCTGTTCTTCAAACATTTAAATCAAGCTTTGGACTAA
TTATGCTAATTTGTGAGTTCTGATCACTTTTGAGCTCTGAAGCTTTGAATCATTCAGTGGTG
GAGATGGCCTTCTGGTAACTGAATATTACCTTCTGTAGGAAAAGGTGGAAAATAAGCATCTA
GAAGGTTGTTGTGAATGACTCTGTGCTGGCAAAAATGCTTGAAACCTCTATATTTCTTTCGT
TCATAAGAGGTAAAGGTCAAATTTTTCAACAAAAGTCTTTTAATAACAAAAGCATGCAGTTCTC
TGTGAAATCTCAAATATTGTTGTAATAGTCTGTTTCAATCTTAAAAAGAATCA

FIGURE 46

></usr/seqdb2/sst/DNA/Dnaseqs.min/ss.DNA96889
><subunit 1 of 1, 339 aa, 1 stop
><MW: 36975, pI: 7.85, NX(S/T): 1
MAAACGPGAAGYCLLLGLHLFLLTAGPALGWNDPDRMLLRDVKALTLHYDRYTTSRRLDP
IPQLKCVGGTAGCDSYTPKVIQCQNKGWDGYDVQWECKTDLDIAYKFGKTVVSCEGYESS
EDQYVLRGSCGLEYNLDYTELGLQKLKESGKQHGFASFSDYYYKWSSADSCNMSGLITIV
VLLGIAFVVYKLFLSDGQYSPPPYSEYPPFSHRYQRFTNSAGPPPPGFKSEFTGPQNTGH
GATSGFGSAFTGQQGYENSGPGFWTGLGTGGILGYLFGSNRAATPFSDSWYYPSYPPSYP
GTWNRAYSPLHGGSGSYSVCSNSDTKTRTASGYGGTRRR

Important features of the protein:
Signal peptide:
Amino acids 1-30

Transmembrane domain:
Amino acids 171-190

N-glycosylation site:
Amino acids 172-176

Glycosaminoglycan attachment sites:
Amino acids 244-248;259-263;331-335

Tyrosine kinase phosphorylation site:
Amino acids 98-106

N-myristoylation sites:
Amino acids 68-74;69-75;131-137;241-247;
247-253;266-272;270-276;278-284;
312-318

FIGURE 47

CCCGGAGCCGGGGAGGGAGGGAGCGAGGTTCGGACACCGGCGGCGGCTGCCTGGCCTTTCCA
TGAGCCCGCGGCGGACCCTCCCGCGCCCCCTCTCGCTCTGCCTCTCCCTCTGCCTCTGCCTC
TGCCTGGCCGCGGCTCTGGGAAGTGCGCAGTCCGGGTCGTGTAGGGATAAAAAGAACTGTAA
GGTGGTCTTTTCCCAGCAGGAACTGAGGAAGCGGCTAACACCCCTGCAGTACCATGTCACTC
AGGAGAAAGGGACCGAAAGTGCCTTTGAAGGAGAATACACACATCACAAAGATCCTGGAATA
TATAAATGTGTTGTTTGTGGAACTCCATTGTTTAAGTCAGAAACCAAATTTGACTCCGGTTC
AGGTTGGCCTTCATTCCACGATGTGATCAATTCTGAGGCAATCACATTCACAGATGACTTTT
CCTATGGGATGCACAGGGTGGAAACAAGCTGCTCTCAGTGTGGTGCTCACCTTGGGCACATT
TTTGATGATGGGCCTCGTCCAACTGGGAAAAGATACTGCATAAATTCGGCTGCCTTGTCTTT
TACACCTGCGGATAGCAGTGGCACCGCCGAGGGAGGCAGTGGGGTCGCCAGCCCGGCCCAGG
CAGACAAAGCGGAGCTCTAGAGTAATGGAGAGTGATGGAAACAAAGTGTACTTAATGCACAG
CTTATTAAAAAAATCAAAATTGTTATCTTAATAGATATATTTTTTCAAAAACTATAAGGGCA
GTTTTGTGCTATTGATATTTTTTCTTCTTTTGCTTAAACAGAAGCCCTGGCCATCCATGTAT
TTTGCAATTGACTAGATCAAGAACTGTTTATAGCTTTAGCAAATGGAGACAGCTTTGTGAAA
CTTCTTCACAAGCCACTTATACCCTTTGGCATTCTTTTCTTTGAGCACATGGCTTCTTTTGC
AGTTTTTCCCCCTTTGATTCAGAAGCAGAGGGTTCATGGTCTTCAAACATGAAAATAGAGAT
CTCCTCTGCAGTGTAGAGACCAGAGCTGGGCAGTGCAGGGCATGGAGACCTGCAAGACACAT
GGCCTTGAGGCCTTTGCACAGACCCACCTAAGATAAGGTTGGAGTGATGTTTTAATGAGACT
GTTCAGCTTTGTGGAAAGTTTGAGCTAAGGTCATTTTTTTTTTTCTCACTGAAAGGGTGTGA
AGGTCTAAAGTCTTTCCTTATGTTAAATTGTTGCCAGATCCAAAGGGGCATACTGAGTGTTG
TGGCAGAGAAGTAAACATTACCACACTGTTAGGCCTTTATTTTATTTTATTTTCCATCGAAA
GCATTGGAGGCCCAGTGCAATGGCTCACGCCTGTGATCCCAGCACTTTGGGAGGCCAAGGCG
GGTGGATCACGAGGTCAGGAGATGGAGACCATCCTGGCTAACATGGTGAAACCCCGTCTCTA
CTAAAAATACGAAAAATTAGCCAGGCGTGGTGGTGGGCACCTGTAGTCCCAGCTACTCAGGAGG
CTGAGGCAGGAGAATGGCGTGAACCCGGAAGGCGGAGCTTGCAGTTAGCCGAGATCATGCCA
CTGCACTCCAGCCTACATGACAATGTGACACTCCATCTCAAAAAATAATAATAATAACAATA
TAAGAACTAGCTGGGCATGGTGGCGCATGCATGTAGTCCCAGCTACTCCTGAGGCTCAGTCA
GGAGAATCGCTTGAACTTGGGAGGCGGAGGTTGCAGTGAGCTGAGCTCATACCACTGCACTC
CAGCCTGAACAGAGTGAGATCCTGTCAA

FIGURE 48

></usr/seqdb2/sst/DNA/Dnaseqs.min/ss.DNA96898
><subunit 1 of 1, 192 aa, 1 stop
><MW: 20702, pI: 7.50, NX(S/T): 0
MSPRRTLPRPLSLCLSLCLCLCLAAALGSAQSGSCRDKKNCKVVFSQQELRKRLTPLQYH
VTQEKGTESAFEGEYTHHKDPGIYKCVVCGTPLFKSETKFDSGSGWPSFHDVINSEAITF
TDDFSYGMHRVETSCSQCGAHLGHIFDDGPRPTGKRYCINSAALSFTPADSSGTAEGGSG
VASPAQADKAEL

Important features of the protein:
Signal peptide:
Amino acids 1-24

Glycosaminoglycan attachment site:
Amino acids 102-106 cAMP- and cGMP-dependent protein kinase phosphorylation site:
Amino acids 52-56

N-myristoylation sites:
Amino acids 28-34;66-72;82-88;139-145;
173-179;178-184

Amidation site:
Amino acids 153-157

FIGURE 49

CCCAAAGAGGTGAGGAGCCGGCAGCGGGGGCGGCTGTAACTGTGAGGAAGGCTGCAGAGTGG
CGACGTCTACGCCGTAGGTTGGAGGCTGTGGGGGGTGGCCGGGCGCCAGCTCCCAGGCCGCA
GAAGTGACCTGCGGTGGAGTTCCCTCCTCGCTGCTGGAGAACGGAGGGAGAAGGTTGCTGGC
CGGGTGAAAGTGCCTCCCTCTGCTTGACGGGGCTGAGGGGCCCGAAGTCTAGGGCGTCCGTA
GTCGCCCCGGCCTCCGTGAAGCCCCAGGTCTAGAGATATGACCCGAGAGTGCCCATCTCCGG
CCCCGGGGCCTGGGGCTCCGCTGAGTGGATCGGTGCTGGCAGAGGCGGCAGTAGTGTTTGCA
GTGGTGCTGAGCATCCACGCAACCGTATGGGACCGATACTCGTGGTGCGCCGTGGCCCTCGC
AGTGCAGGCCTTCTACGTCCAATACAAGTGGGACCGGCTGCTACAGCAGGGAAGCGCCGTCT
TCCAGTTCCGAATGTCCGCAAACAGTGGCCTATTGCCCGCCTCCATGGTCATGCCTTTGCTT
GGACTAGTCATGAAGGAGCGGTGCCAGACTGCTGGGAACCCGTTCTTTGAGCGTTTTGGCAT
TGTGGTGGCAGCCACTGGCATGGCAGTGGCCCTCTTCTCATCAGTGTTGGCGCTCGGCATCA
CTCGCCCAGTGCCAACCAACACTTGTGTCATCTTGGGCTTGGCTGGAGGTGTTATCATTTAT
ATCATGAAGCACTCGTTGAGCGTGGGGGAGGTGATCGAAGTCCTGGAAGTCCTTCTGATCTT
CGTTTATCTCAACATGATCCTGCTGTACCTGCTGCCCCGCTGCTTCACCCCTGGTGAGGCAC
TGCTGGTATTGGGTGGCATTAGCTTTGTCCTCAACCAGCTCATCAAGCGCTCTCTGACACTG
GTGGAAAGTCAGGGGGACCCAGTGGACTTCTTCCTGCTGGTGGTGGTAGTAGGGATGGTACT
CATGGGCATTTTCTTCAGCACTCTGTTTGTCTTCATGGACTCAGGCACCTGGGCCTCCTCCA
TCTTCTTCCACCTCATGACCTGTGTGCTGAGCCTTGGTGTGGTCCTACCCTGGCTGCACCGG
CTCATCCGCAGGAATCCCCTGCTCTGGCTTCTTCAGTTTCTCTTCCAGACAGACACCCGCAT
CTACCTCCTAGCCTATTGGTCTCTGCTGGCCACCTTGGCCTGCCTGGTGGTGCTGTACCAGA
ATGCCAAGCGGTCATCTTCCGAGTCCAAGAAGCACCAGGCCCCCACCATCGCCCGAAAGTAT
TTCCACCTCATTGTGGTAGCCACCTACATCCCAGGTATCATCTTTGACCGGCCACTGCTCTAT
GTAGCCGCCACTGTATGCCTGGCGGTCTTCATCTTCCTGGAGTATGTGCGCTACTTCCGCAT
CAAGCCTTTGGGTCACACTCTACGGAGCTTCCTGTCCCTTTTTCTGGATGAACGAGACAGTG
GACCACTCATTCTGACACACATCTACCTGCTCCTGGGCATGTCTCTTCCCATCTGGCTGATC
CCCAGACCCTGCACACAGAAGGGTAGCCTGGGAGGAGCCAGGGCCCTCGTCCCCTATGCCGG
TGTCCTGGCTGTGGGTGTGGGTGATACTGTGGCCTCCATCTTCGGTAGCACCATGGGGGAGA
TCCGCTGGCCTGGAACCAAAAAGACTTTTGAGGGGACCATGACATCTATATTTGCGCAGATC
ATTTCTGTAGCTCTGATCTTAATCTTTGACAGTGGAGTGGACCTAAACTACAGTTATGCTTG
GATTTTGGGGTCCATCAGCACTGTGTCCCTCCTGGAAGCATACACTACACAGATAGACAATC
TCCTTCTGCCTCTCTACCTCCTGATATTGCTGATGGCCTAGCTGTTACAGTGCAGCAGCAGT
GACGGAGGAAACAGACATGGGGAGGGTGAACAGTCCCCACAGCAGACAGCTACTTGGGCATG
AAGAGCCAAGGTGTGAAAAGCAGATTTGATTTTTCAGTTGATTCAGATTTAAAATAAAAAGC
AAAGCTCTCCTAGTTCTA

FIGURE 50

></usr/seqdb2/sst/DNA/Dnaseqs.min/ss.DNA97003
><subunit 1 of 1, 538 aa, 1 stop
><MW: 59268, pI: 8.94, NX(S/T): 1
MTRECPSPAPGPGAPLSGSVLAEAAVVFAVVLSIHATVWDRYSWCAVALAVQAFYVQYKW
DRLLQQGSAVFQFRMSANSGLLPASMVMPLLGLVMKERCQTAGNPFFERFGIVVAATGMA
VALFSSVLALGITRPVPTNTCVILGLAGGVIIYIMKHSLSVGEVIEVLEVLLIFVYLNMI
LLYLLPRCFTPGEALLVLGGISFVLNQLIKRSLTLVESQGDPVDFFLLVVVVGMVLMGIF
FSTLFVFMDSGTWASSIFFHLMTCVLSLGVVLPWLHRLIRRNPLLWLLQFLFQTDTRIYL
LAYWSLLATLACLVVLYQNAKRSSSESKKHQAPTIARKYFHLIVVATYIPGIIFDRPLLY
VAATVCLAVFIFLEYVRYFRIKPLGHTLRSFLSLFLDERDSGPLILTHIYLLLGMSLPIW
LIPRPCTQKGSLGGARALVPYAGVLAVGVGDTVASIFGSTMGEIRWPGTKKTFEGTMTSI
FAQIISVALILIFDSGVDLNYSYAWILGSISTVSLLEAYTTQIDNLLLPLYLLILLMA

Important features of the protein:
Signal peptide:
Amino acids 1-36

Transmembrane domains:
Amino acids 77-95;111-133;161-184;225-248;
255-273;299-314;348-373;406-421;
435-456;480-497

N-glycosylation sites:
Amino acids 500-504 cAMP- and cGMP-dependent protein kinase phosphorylation site:
Amino acids 321-325

N-myristoylation sites:
Amino acids 13-19;18-24;80-86;111-117;
118-124;145-151;238-244;251-257;
430-436;433-439;448-454;458-464;
468-474;475-481;496-502;508-514

Prokaryotic membrane lipoprotein lipid attachment site:
Amino acids 302-313

FIGURE 51

GCTCTATGCCGCCTACCTTGCTCTCGCCGCTGCTGCCGGAGCCGAAGCAGAGAAGGCAGCGGGTCCCGTGACCG
TCCCGAGAGCCCCGCGCTCCCGACCAGGGGGCGGGGGCGGCCCCGGGGAGGGCGGGGCAGGGGCGGGGGGAAGA
AAGGGGGTTTTGTGCTGCGCCGGGAGGGCCGGCGCCCTCTTCCGAATGTCCTGCGGCCCCAGCCTCTCCTCACG
CTCGCGCAGTCTCCGCCGCAGTCTCAGCTGCAGCTGCAGGACTGAGCCGTGCACCCGGAGGAGACCCCCGGAGG
AGGCGACAAACTTCGCAGTGCCGCGACCCAACCCCAGCCCTGGGTAGCCTGCAGCATGGCCCAGCTGTTCCTGC
CCCTGCTGGCAGCCCTGGTCCTGGCCCAGGCTCCTGCAGCTTTAGCAGATGTTCTGGAAGGAGACAGCTCAGAG
GACCGCGCTTTTCGCGTGCGCATCGCGGGCGACGCGCCACTGCAGGGCGTGCTCGGCGGCGCCCTCACCATCCC
TTGCCACGTCCACTACCTGCGGCCACCGCCGAGCCGCCGGGCTGTGCTGGGCTCTCCGCGGGTCAAGTGGACTT
TCCTGTCCCGGGGCCGGGAGGCAGAGGTGCTGGTGGCGCGGGGAGTGCGCGTCAAGGTGAACGAGGCCTACCGG
TTCCGCGTGGCACTGCCTGCGTACCCAGCGTCGCTCACCGACGTCTCCCTGGCGCTGAGCGAGCTGCGCCCCAA
CGACTCAGGTATCTATCGCTGTGAGGTCCAGCACGGCATCGATGACAGCAGCGACGCTGTGGAGGTCAAGGTCA
AAGGGGTCGTCTTTCTCTACCGAGAGGGCTCTGCCCGCTATGCTTTCTCCTTTTCTGGGGCCCAGGAGGCCTGT
GCCCGCATTGGAGCCCACATCGCCACCCCGGAGCAGCTCTATGCCGCCTACCTTGGGGGCTATGAGCAATGTGA
TGCTGGCTGGCTGTCGGATCAGACCGTGAGGTATCCCATCCAGACCCCACGAGAGGCCTGTTACGGAGACATGG
ATGGCTTCCCCGGGGTCCGGAACTATGGTGTGGTGGACCCGGATGACCTCTATGATGTGTACTGTTATGCTGAA
GACCTAAATGGAGAACTGTTCCTGGGTGACCCTCCAGAGAAGCTGACATTGGAGGAAGCACGGGCGTACTGCCA
GGAGCGGGGTGCAGAGATTGCCACCACGGGCCAACTGTATGCAGCCTGGGATGGTGGCCTGGACCACTGCAGCC
CAGGGTGGCTAGCTGATGGCAGTGTGCGCTACCCCATCGTCACACCCAGCCAGCGCTGTGGTGGGGGCTTGCCT
GGTGTCAAGACTCTCTTCCTCTTCCCCAACCAGACTGGCTTCCCCAATAAGCACAGCCGCTTCAACGTCTACTG
CTTCCGAGACTCGGCCCAGCCTTCTGCCATCCCTGAGGCCTCCAACCCAGCCTCCAACCCAGCCTCTGATGGAC
TAGAGGCTATCGTCACAGTGACAGAGACCCTGGAGGAACTGCAGCTGCCTCAGGAAGCCACAGAGAGTGAATCC
CGTGGGGCCATCTACTCCATCCCCATCATGGAGGACGGAGGAGGTGGAAGCTCCACTCCAGAAGACCCAGCAGA
GGCCCCTAGGACGCTCCTAGAATTTGAAACACAATCCATGGTACCGCCCACGGGGTTCTCAGAAGAGGAAGGTA
AGGCATTGGAGGAAGAAGAGAAATATGAAGATGAAGAAGAGAAAGAGGAGGAAGAAGAAGAGGAGGAGGTGGAG
GATGAGGCTCTGTGGGCATGGCCCAGCGAGCTCAGCAGCCCGGGCCCTGAGGCCTCTCTCCCCACTGAGCCAGC
AGCCCAGGAGAAGTCACTCTCCCAGGCGCCAGCAAGGGCAGTCCTGCAGCCTGGTGCATCACCACTTCCTGATG
GAGAGTCAGAAGCTTCCAGGCCTCCAAGGGTCCATGGACCACCTACTGAGACTCTGCCCACTCCCAGGGAGAGG
AACCTAGCATCCCCATCACCTTCCACTCTGGTTGAGGCAAGAGAGGTGGGGGAGGCAACTGGTGGTCCTGAGCT
ATCTGGGGTCCCTCGAGGAGAGAGCGAGGAGACAGGAAGCTCCGAGGGTGCCCCTTCCCTGCTTCCAGCCACAC
GGGCCCCTGAGGGTACCAGGGAGCTGGAGGCCCCCTCTGAAGATAATTCTGGAAGAACTGCCCCAGCAGGGACC
TCAGTGCAGGCCCAGCCAGTGCTGCCCACTGACAGCGCCAGCCGAGGTGGAGTGGCCGTGGTCCCCGCATCAGG
TGACTGTGTCCCCAGCCCCTGCCACAATGGTGGGACATGCTTGGAGGAGGAGGAAGGGGTCCGCTGCCTATGTC
TGCCTGGCTATGGGGGGGACCTGTGCGATGTTGGCCTCCGCTTCTGCAACCCCGGCTGGGACGCCTTCCAGGGC
GCCTGCTACAAGCACTTTTCCACACGAAGGAGCTGGGAGGAGGCAGAGACCCAGTGCCGGATGTACGGCGCGCA
TCTGGCCAGCATCAGCACACCCGAGGAACAGGACTTCATCAACAACCGGTACCGGGAGTACCAGTGGATCGGAC
TCAACGACAGGACCATCGAAGGCGACTTCTTGTGGTCGGATGGCGTCCCCCTGCTCTATGAGAACTGGAACCCT
GGGCAGCCTGACAGCTACTTCCTGTCTGGAGAGAACTGCGTGGTCATGGTGTGGCATGATCAGGGACAATGGAG
TGACGTGCCCTGCAACTACCACCTGTCCTACACCTGCAAGATGGGGCTGGTGTCCTGTGGGCCGCCACCGGAGC
TGCCCCTGGCTCAAGTGTTCGGCCGCCCACGGCTGCGCTATGAGGTGGACACTGTGCTTCGCTACCGGTGCCGG
GAAGGACTGGCCCAGCGCAATCTGCCGCTGATCCGATGCCAAGAGAACGGTCGTTGGGAGGCCCCCCAGATCTC
CTGTGTGCCCAGAAGACCTGCCCGAGCTCTGCACCCAGAGGAGGACCCAGAAGGACGTCAGGGGAGGCTACTGG
GACGCTGGAAGGCGCTGTTGATCCCCCCTTCCAGCCCCATGCCAGGTCCCTAGGGGGCAAGGCCTTGAACACTGCCG
GCCACAGCACTGCCCTGTCACCCAAATTTTCCCTCACACCTTGCGCTCCCGCCACCACAGGAAGTGACAACATG
ACGAGGGGTGGTGCTGGAGTCCAGGTGACAGTTCCTGAAGGGGCTTCTGGGAAATACCTAGGAGGCTCCAGCCC
AGCCCAGGCCCTCTCCCCCTACCCTGGGCACCAGATCTTCCATCAGGGCCGGAGTAAATCCCTAAGTGCCTCAA
CTGCCCTCTCCCTGGCAGCCATCTTGTCCCCTCTATTCCTCTAGGGAGCACTGTGCCCACTCTTTCTGGGTTTT
CCAAGGGAATGGGCTTGCAGGATGGAGTGTCTGTAAAATCAACAGGAAATAAAACTGTGTATGAGCCCA

FIGURE 52

></usr/seqdb2/sst/DNA/Dnaseqs.min/ss.DNA98565
><subunit 1 of 1, 911 aa, 1 stop
><MW: 99117, pI: 4.62, NX(S/T): 2
MAQLFLPLLAALVLAQAPAALADVLEGDSSEDRAFRVRIAGDAPLQGVLGGALTIPCHVH
YLRPPPSRRAVLGSPRVKWTFLSRGREAEVLVARGVRVKVNEAYRFRVALPAYPASLTDV
SLALSELRPNDSGIYRCEVQHGIDDSSDAVEVKVKGVVFLYREGSARYAFSFSGAQEACA
RIGAHIATPEQLYAAYLGGYEQCDAGWLSDQTVRYPIQTPREACYGDMDGFPGVRNYGVV
DPDDLYDVYCYAEDLNGELFLGDPPEKLTLEEARAYCQERGAEIATTGQLYAAWDGGLDH
CSPGWLADGSVRYPIVTPSQRCGGGLPGVKTLFLFPNQTGFPNKHSRFNVYCFRDSAQPS
AIPEASNPASNPASDGLEAIVTVTETLEELQLPQEATESESRGAIYSIPIMEDGGGGSST
PEDPAEAPRTLLEFETQSMVPPTGFSEEEGKALEEEEKYEDEEEKEEEEEEEEVEDEALW
AWPSELSSPGPEASLPTEPAAQEKSLSQAPARAVLQPGASPLPDGESEASRPPRVHGPPT
ETLPTPRERNLASPSPSTLVEAREVGEATGGPELSGVPRGESEETGSSEGAPSLLPATRA
PEGTRELEAPSEDNSGRTAPAGTSVQAQPVLPTDSASRGGVAVVPASGDCVPSPCHNGGT
CLEEEEGVRCLCLPGYGGDLCDVGLRFCNPGWDAFQGACYKHFSTRRSWEEAETQCRMYG
AHLASISTPEEQDFINNRYREYQWIGLNDRTIEGDFLWSDGVPLLYENWNPGQPDSYFLS
GENCVVMVWHDQGQWSDVPCNYHLSYTCKMGLVSCGPPPELPLAQVFGRPRLRYEVDTVL
RYRCREGLAQRNLPLIRCQENGRWEAPQISCVPRRPARALHPEEDPEGRQGRLLGRWKAL
LIPPSSPMPGP

Important features of the protein:

Signal peptide:
Amino acids 1-15
N-glycosylation sites:
Amino acids 130-134;337-341
Tyrosine kinase phosphorylation sites:
Amino acids 128-136;451-460
N-myristoylation sites:
Amino acids 47-53;50-56;133-139;142-148;
174-180;183-189;281-287;288-294;
297-303;324-330;403-409;414-420;
415-421;576-582;586-592;677-683;
684-690;720-726;772-778;811-817
EGF-like domain cysteine pattern signature:
Amino acids 670-682
C-type lectin domain signature:
Amino acids 784-809
Immunoglobulins and major histocompatibility complex proteins signature:
Amino acids 135-142
Link domain proteins:
Amino acids 166-216;264-314
Calcium-binding EGF-like domain proteins pattern proteins.
Amino acids 655-676
C-type lectin domain proteins:
Amino acids 791-800

FIGURE 53

CTGCCAGGTGACAGCCGCCAAGATGGGGTCTTGGGCCCTGCTGTGGCCTCCCCTGCTGTTCACCGGGCTGCTCG
TCCGACCCCCGGGGACCATGGCCCAGGCCCAGTACTGCTCTGTGAACAAGGACATCTTTGAAGTAGAGGAGAAC
ACAAATGTCACCGAGCCGCTGGTGGACATCCACGTCCCGGAGGGCCAGGAGGTGACCCTCGGAGCCTTGTCCAC
CCCCTTTGCATTTCGGATCCAGGGAAACCAGCTGTTTCTCAACGTGACTCCTGATTACGAGCAGAAGTCACTGC
TTGAGGCTCAGCTGCTGTGTCAGAGCGGAGGCACATTGGTGACCCAGCTAAGGGTGTTCGTGTCAGTGCTGGAC
GTCAATGACAATGCCCCCGAATTCCCCTTTAAGACCAAGGAGATAAGGGTGGAGGAGGACACGAAAGTGAACTC
CACCGTCATCCCTGAGACGCAACTGCAGGCTGAGGACCGCGACAAGGACGACATTCTGTTCTACACCCTCCAGG
AAATGACAGCAGGTGCCACTGACTACTTCTCCCTGGTGAGTGTAAACCGTCCCGCCCTGAGGCTGGACCGGCCC
CTGGACTTCTACGAGCGGCCGAACATGACCTTCTGGCTGCTGGTGCGGGACACTCCAGGGGAGAATGTGGAACC
CAGCCACACTGCCACCGCCACACTAGTGCTGAACGTGGTGCCCGCCGACCTGCGGCCCCCGTGGTTCCTGCCCT
GCACCTTCTCAGATGGCTACGTCTGCATTCAAGCTCAGTACCACGGGGCTGTCCCCACGGGGCACATACTGCCA
TCTCCCCTCGTCCTGCGTCCCGGACCCATCTACGCTGAGGACGGAGACCGCGGCATCAACCAGCCCATCATCTA
CAGCATCTTTAGGGGAAACGTGAATGGTACATTCATCATCCACCCAGACTCGGGCAACCTCACCGTGGCCAGGA
GTGTCCCCAGCCCCATGACCTTCCTTCTGCTGGTGAAGGGCCAACAGGCCGACCTTGCCCGCTACTCAGTGACC
CAGGTCACCGTGGAGGCTGTGGCTGCGGCCGGGAGCCCGCCCCGCTTCCCCCAGAGCCTGTATCGTGGCACCGT
GGCGCGTGGCGCTGGAGCGGGCGTTGTGGTCAAGGATGCAGCTGCCCCTTCTCAGCCTCTGAGGATCCAGGCTC
AGGACCCGGAGTTCTCGGACCTCAACTCGGCCATCACATATCGAATTACCAACCACTCACACTTCCGGATGGAG
GGAGAGGTTGTGCTGACCACCACCACACTGGCACAGGCGGAGCCTTCTACGCAGAGGTTGAGGCCCACAACAC
GGTGACCTCTGGCACCGCAACCACAGTCATTGAGATACAAGTTTCCGAACAGGAGCCCCCCTCCACAGAGGCTG
GAGGAACAACTGGGCCCTGGACCAGCACCACTTCCGAGGTCCCCAGACCCCCTGAGCCCTCCCAGGGACCCTCC
ACGACCAGCTCTGGGGGAGGCACAGCCCCTCATCCACCCTCTGGCACAACTCTGAGGCCACCAACCTCGTCCAC
ACCCGGGGGGCCCCCGGGTGCAGAAAACAGCACCTCCCACCAACCAGCCACTCCCGGTGGGGACACAGCACAGA
CCCCAAAGCCAGGAACCTCTCAGCCGATGCCCCCCGGTGTGGGAACCAGCACCTCCCACCAACCAGCCACACCC
AGTGGGGGCACAGCACAGACCCCAGAGCCAGGAACCTCTCAGCCGATGCCCCCCAGTATGGGAACCAGCACCTC
CCACCAACCAGCCACACCCGGTGGGGGCACAGCACAGACCCCAGAGGCAGGAACCTCTCAGCCGATGCCCCCCG
GTATGGGAACCAGCACCTCCCACCAACCAACCACACCCGGTGGGGGCACAGCACAGACCCCAGAGCCAGGAACC
TCTCAGCCGATGCCCCTCAGCAAGAGCACCCCATCTTCAGGTGGCGGCCCCTCGGAGGACAAGCGCTTCTCGGT
GGTGGATATGGCGGCCCTGGGCGGGGTGCTGGGTGCGCTGCTGCTGCTGGCTCTCCTTGGCCTCGCCGTCCTTG
TCCACAAGCACTATGGCCCCCGGCTCAAGTGCTGCTCTGGCAAAGCTCCGGAGCCCCAGCCCCAAGGCTTTGAC
AACCAGGCGTTCCTCCCTGACCACAAGGCCAACTGGGCGCCCGTCCCCAGCCCCACGCACGACCCCAAGCCCGC
GGAGGCACCGATGCCCGCAGAGCCCGCACCCCCCGGCCCTGCCTCCCCAGGCGGTGCCCCTGAGCCCCCCGCAG
CGGCCCGAGCTGGCGGAAGCCCCACGGCGGTGAGGTCCATCCTGACCAAGGAGCGGCGGCCGGAGGGCGGGTAC
AAGGCCGTCTGGTTTGGCGAGGACATCGGGACGGAGGCAGACGTGGTCGTTCTCAACGCGCCCACCCTGGACGT
GGATGGCGCCAGTGACTCCGGCAGCGGCGACGAGGGCGAGGGCGCGGGGAGGGGTGGGGGTCCCTACGATGCAC
CCGGTGGTGATGACTCCTACATCTAAGTGGCCCCTCCACCCTCTCCCCCAGCCGCACGGGCACTGGAGGTCTCG
CTCCCCCAGCCTCCGACCCGAGGCAGAATAAAGCAAGGCTCCCGAAACCCAGGCCATGGCGTGGGGCAGGCGCG
TGGGTCCCTGGGGGCCCCATTCACTCAGTCCCCTGTCGTCATTAGCGCTTGAGCCCAGGTGTGCAGATGAGGCG
GTGGGTCTGGCCACGCTGTCCCCACCCCAAGGCTGCAGCACTTCCCGTAAACCACCTGCAGTGCCCGCCGCCTT
CCCGAGGCTCTGTGCCAGCTAGTCTGGGAAGTTCCTCTCCCGCTCTAACCACAGCCCGAGGGGGCTCCCCTCC
CCCGACCTGCACCAGAGATCTCAGGCACCCGGCTCAACTCAGACCTCCCGCTCCCGACCCTACACAGAGATTGC
CTGGGGAGGCTGAGGAGCCGATGCAAACCCCCAAGGCGACGCACTTGGGAGCCGGTGGTCTCAAACACCTGCCG
GGGGTCCTAGTCCCCTTCTGAAATCTACATGCTTGGGTTGGAGCGCAGCAGTAAACACCCTGCCCAGTGACCTG
GACTGAGGCGCGCTGGGGGTGGGTGCGCCGTGTGGCCTGAGCAGGAGCCAGACCAGGAGGCCTAGGGGTGAGAG
ACACATTCCCCTCGCTGCTCCCAAAGCCAGAGCCCAGGCTGGGCGCCCATGCCCAGAACCATCAAGGGATCCCT
TGCGGCTTGTCAGCACTTTCCCTAATGGAAATACACCATTAATTCCTTTCCAAATGTTTT

FIGURE 54

></usr/seqdb2/sst/DNA/Dnaseqs.min/ss.DNA102846
><subunit 1 of 1, 839 aa, 1 stop
><MW: 87546, pI: 4.84, NX(S/T): 8
MGSWALLWPPLLFTGLLVRPPGTMAQAQYCSVNKDIFEVEENTNVTEPLVDIHVPEGQEV
TLGALSTPFAFRIQGNQLFLNVTPDYEEKSLLEAQLLCQSGGTLVTQLRVFVSVLDVNDN
APEFPFKTKEIRVEEDTKVNSTVIPETQLQAEDRDKDDILFYTLQEMTAGASDYFSLVSV
NRPALRLDRPLDFYERPNMTFWLLVRDTPGENVEPSHTATATLVLNVVPADLRPPWFLPC
TFSDGYVCIQAQYHGAVPTGHILPSPLVLRPGPIYAEDGDRGINQPIIYSIFRGNVNGTF
IIHPDSGNLTVARSVPSPMTFLLLVKGQQADLARYSVTQVTVEAVAAAGSPPRFPQSLYR
GTVARGAGAGVVVKDAAAPSQPLRIQAQDPEFSDLNSAITYRITNHSHFRMEGEVVLTTT
TLAQAGAFYAEVEAHNTVTSGTATTVIEIQVSEQEPPSTEAGGTTGPWTSTTSEVPRPPE
PSQGPSTTSSGGGTGPHPPSGTTLRPPTSSTPGGPPGAENSTSHQPATPGGDTAQTPKPG
TSQPMPPGVGTSTSHQPATPSGGTAQTPEPGTSQPMPPSMGTSTSHQPATPGGGTAQTPE
AGTSQPMPPGMGTSTSHQPTTPGGGTAQTPEPGTSQPMPLSKSTPSSGGGPSEDKRFSVV
DMAALGGVLGALLLLALLGLAVLVHKHYGPRLKCCSGKAPEPQPQGFDNQAFLPDHKANW
APVPSPTHDPKPAEAPMPAEPAPPGPASPGGAPEPPAAARAGGSPTAVRSILTKERRPEG
GYKAVWFGEDIGTEADVVVLNAPTLDVDGASDSGSGDEGEGAGRGGGPYDAPGGDDSYI

Important features of the protein:

Signal peptide:
Amino acids 1-25

Transmembrane domain:
Amino acids 662-684

N-glycosylation sites:
Amino acids 44-48;140-144;198-202;297-301;
308-312;405-409;520-524

Glycosaminoglycan attachment sites:
Amino acids 490-494;647-651;813-817 cAMP- and cGMP-dependent protein kinase phosphorylation site:
Amino acids 655-659

Tyrosine kinase phosphorylation sites:
Amino acids 154-163;776-783

N-myristoylation sites:
Amino acids 57-63;102-108;255-261;294-300;
366-372;426-432;441-447;513-519;
517-523;530-536;548-554;550-556;
581-587;592-598;610-616;612-618;
623-629;648-654;666-672;667-673;
762-768;763-769;780-786;809-815;
821-827;833-839

Cadherins extracellular repeated domain signature:
Amino acids 112-123

FIGURE 55

GCAGCTGGGTTCTCCCGGTTCCCTTGGGCAGGTGCAGGGTCGGGTTCAAAGCCTCCGGAACGCGTTTTGGCCTG
ATTTGAGGAGGGGGGCGGGGAGGGACCTGCGGCTTGCGGCCCCGCCCCCTTCTCCGGCTCGCAGCCGACCGGTA
AGCCCGCCTCCTCCCTCGGCCGGCCCTGGGGCCGTGTCCGCCGGGCAACTCCAGCCGAGGCCTGGGCTTCTGCC
TGCAGGTGTCTGCGGCGAGGCCCCTAGGGTACAGCCCGATTTGGCCCCATGGTGGGTTTCGGGGCCAACCGGCG
GGCTGGCCGCCTGCCCTCTCTCGTGCTGGTGGTGCTGCTGGTGGTGATCGTCGTCCTCGCCTTCAACTACTGGA
GCATCTCCTCCCGCCACGTCCTGCTTCAGGAGGAGGTGGCCGAGCTGCAGGGCCAGGTCCAGCGCACCGAAGTG
GCCCGCGGGCGGCTGGAAAAGCGCAATTCGGACCTCTTGCTGTTGGTGGACACGCACAAGAAACAGATCGACCA
GAAGGAGGCCGACTACGGCCGCCTCAGCAGCCGGCTGCAGGCCAGAGAGGGCCTCGGGAAGAGATGCCAGGATG
ACAAGGTTAAACTACAGAACAACATATCGTATCAGATGGCAGACATACATCATTTAAAGGAGCAACTTGCTGAG
CTTCGTCAGGAATTTCTTCGACAAGAAGACCAGCTTCAGGACTATAGGAAGAACAATACTTACCTTGTGAAGAG
GTTAGAATATGAAAGTTTTCAGTGTGGACAGCAGATGAAGGAATTGAGAGCACAGCATGAAGAAAATATTAAAA
AGTTAGCAGACCAGTTTTTAGAGGAACAAAAGCAAGAGACCCAAAAGATTCAATCAAATGATGGAAAGGAATTG
GATATAAACAATCAAGTAGTACCTAAAAATATTCCAAAAGTAGCTGAGAATGTTGCAGATAAGAATGAAGAACC
CTCAAGCAATCATATTCCACATGGGAAAGAACAAATCAAAAGAGGTGGTGATGCAGGGATGCCTGGAATAGAAG
AGAATGACCTAGCAAAAGTTGATGATCTTCCCCCTGCTTTAAGGAAGCCTCCTATTTCAGTTTCTCAACATGAA
AGTCATCAAGCAATCTCCCATCTTCCAACTGGACAACCTCTCTCCCCAAATATGCCTCCAGATTCACACATAAA
CCACAATGGAAACCCCGGTACTTCAAAACAGAATCCTTCCAGTCCTCTTCAGCGTTTAATTCCAGGCTCAAACT
TGGACAGTGAACCCAGAATTCAAACAGATATACTAAAGCAGGCTACCAAGGACAGAGTCAGTGATTTCCATAAA
TTGAAGCAAAATGATGAAGAACGAGAGCTTCAAATGGATCCTGCAGACTATGGAAAGCAACATTTCAATGATGT
CCTTTAAGTCCTAAAGGAATGCTTCAGAAAACCTAAAGTGCTGTAAAATGAAATCATTCTACTTTGTCCTTTCT
GACTTTTGTTGTAAAGACGAATTGTATCAGTTGTAAAGATACATTGAGATAGAATTAAGGAAAAACTTTAATGA
AGGAATGTACCCATGTACATATGTGAACTTTTTCATATTGTATTATCAAGGTATAGACTTTTTTGGTTATGATA
CAGTTAAGCCAAAAACAGCTAATCTTTGCATCTAAAGCAAACTAATGTATATTTCACATTTTATTGAGCCGACT
TATTTCCACAAATAGATAAACAGGACAAAATAGTTGTACAGGTTATATGTGGCATAGCATAACCACAGTAAGAA
CAGAACAGATATTCAGCAGAAAACTTTTTATACTCTAATTCTTTTTTTTTTTTTTTTGAGACAGAGTTTTAGTC
TTGTTTCCCAGGCTGGAGTGCAATGGCACAATCTTGGCTCACTGCAACCTCCGCCTCCTGGGTTCAGGCAATTT
TCCTGCCTCAGCCTCCCAAGTAGCTGGGATTACAGGCACCCACCACCATGCCCAGCTAATTTTTGTATTTTTAA
TAGAGAGCTAATAATTGTATATTTAATAAAGACGGGTTTCACCATGTTGGCCAGGCTGGTCTTGAACTCCTGAC
CTCAGGTGATCCTCCTGCATTGGCCTCCCAAAGTGCTGGAATTCCAGGCATGAGCCACTGCGCCCAGTCTACAC
ACTAATTCTTGTTAGCCCAACAGCTGTTCTGTTCTATCTACCCCTCATTTCACGCTCAAGGAGTCATACCTAGA
ATAGTTACACACAAGAGGGAAACTGGAAGCCAAACACTGTACAGTATTGTGTAGAAAGTCACCTCCCTACTCCT
TTTATTTTACATGAGTGCTGATGTGTTTTGGCAGATGAGCTTTCAGCTGAGGCCTGATGGAAATTGAGATAACCTG
CAAAGACATAACAGTATTTATGAGTTATATCTTAGTTCTTGAAATTGTGGAATGCATGATTGACAATATATTTT
TAATTTTTATTTTTTCAAGTAATACCAGTACTGTTTAACTATAGCCAGAACTGGCTAAAATTTTTATATTTTCA
GAGTTGAAGTTGGTGAAGACATTCATGATTTAAACACCAGATCCTGAAAGGGGTTAAATCTACTTTGAAATGAA
TCTGCAATCAGTATTTCAAAGCTTTTCTGGTAATTTTAGTGATCTTATTTGATTAGACTTTTTCAGAAGTACTA
AATAAGGAATTTTAACAGGTTTTTATTAATGCACAGATAAATAGAAGTACAGTGAGGTCTATAGCCATTTTATT
AAAATAGCTTAAAAGTTTGTAAAAAAATGAATCTTTGTAATTACTTAATATGTTAGTTAAGAACCCGTCAAGCT
TATATTTGCTAGACTTACAAATTATTTTAAATGCATTTATCTTTTTTGACACTATTCAGTGGAATGTGTAAGCT
AGCTAATTCTTGTTTTCTGATTTAAAGCACTTTTAAATCTTATCCTGCCCCCTAAAAACAAAAGGTTTTGATCA
CAAGGGGAAATTTAAGATTGTTAACCCTGTTTTTCAGAAGGGCTACTGTTAATTGCACATAAACATGAAATGTG
TTTTCCCCTGTGTACTAACACATTCTAGGCAAAATTCAAACTTATAGTGGTAAAGAAACAGGTTGTTCACTTGC
TGAGGTGCAAAAATTCTTAAGACTTCTGTTTGAAATTGCTCAATGACTAGGAAAAGATGTAGTAGTTTACTAAA
ATTGTTTTTCTACCATATCAAATTAAACAATTCATGCCTTTATAGGGTCAGGCCTACAATGAATAGGTATGGTG
GTTTCACAGAATTTTAAAATAGAGTTAAAGGGAAGTGATGTACATTTCGGGGGCATTAGGGTAGGGAGATGAAT
CAAAAAATACCCCTAGTAATGCTTTATATTTAATACTGCAAAAGCTTTACAAATGGAAACCATGCAATTACCT
GCCTTAGTTCTTTTGTCATAAAAACAATCACTTGGTTGGTTGTATTGTAGCTATTACTTATACAGCAACATTTC
TTCAATTAGCAGTCTAGACATTTTATAAACAGAAATCTTCGACCAATTGATAATATTTCTGACTGTATTAATAT
TTTAGTGCTATAAAATACTATGTGAATCTCTTAAAAATCTGACATTTTACAGTCTGTATTAGACATACTGTTTTTA
TAATGTTTTACTTCTGCCTTAAGATTTAGGTTTTTTAAATGTATTTTTGCCCTGAATTAAGTGTTAATTTGATG
GAAACTCTGCTTTTAAAATCATCATTTACTGGGTTCTAATAAATTAAAAATTAAACTTGAAAAAAAAAAAAAAA
AAAAAAAAAAAAAAAAAAAAAAAAAAAAAAAAAAAAAAAAAAAAAAAAAAAAAAA

FIGURE 56

MVGFGANRRAGRLPSLVLVVLLVVIVVLAFNYWSISSRHVLLQEEVAELQGQVQRTEVAR
GRLEKRNSDLLLLVDTHKKQIDQKEADYGRLSSRLQAREGLGKRCEDDKVKLQNNISYQM
ADIHHLKEQLAELRQEFLRQEDQLQDYRKNNTYLVKRLEYESFQCGQQMKELRAQHEENI
KKLADQFLEEQKQETQKIQSNDGKELDINNQVVPKNIPKVAENVADKNEEPSSNHIPHGK
EQIKRGGDAGMPGIEENDLAKVDDLPPALRKPPISVSQHESHQAISHLPTGQPLSPNMPP
DSHINHNGNPGTSKQNPSSPLQRLIPGSNLDSEPRIQTDILKQATKDRVSDFHKLKQNDE
ERELQMDPADYGKQHFNDVL

Important features of the protein:
Signal peptide:
1-29

Transmembrane domain.
None

N-glycosylation site.
115-119
150-154 cAMP- and cGMP-dependent protein kinase phosphorylation site.
65-69

N-myristoylation site.
246-252
253-259
308-314

Amidation site.
101-105

FIGURE 57

GGATGGGCGAGCAGTCTGAATGCCAGAATGGATAACCGTTTTGCTACAGCATTTGTAATTGC
TTGTGTGCTTAGCCTCATTTCCACCATCTACATGGCAGCCTCCATTGGCACAGACTTCTGGT
ATGAATATCGAAGTCCAGTTCAAGAAAATTCCAGTGATTTGAATAAAAGCATCTGGGATGAA
TTCATTAGTGATGAGGCAGATGAAAAGACTTATAATGATGCACTTTTTCGATACAATGGCAC
AGTGGGATTGTGGAGACGGTGTATCACCATACCCAAAAACATGCATTGGTATAGCCCACCAG
AAAGGACAGAGTCATTTGATGTGGTCACAAAATGTGTGAGTTTCACACTAACTGAGCAGTTC
ATGGAGAAATTTGTTGATCCCGGAAACCACAATAGCGGGATTGATCTCCTTAGGACCTATCT
TTGGCGTTGCCAGTTCCTTTTACCTTTTGTGAGTTTAGGTTTGATGTGCTTTGGGGCTTTGA
TCGGACTTTGTGCTTGCATTTGCCGAAGCTTATATCCCACCATTGCCACGGGCATTCTCCAT
CTCCTTGCAGATACCATGCTGTGAAGTCCAGGCCACATGGAGGTGTCCTGTGTAGATGCTCC
AGCTGAAATCCCAAGCTAAGCTCCCAACTGACAGCCAACATCATTTCCAGCCATGTGTGGGA
GCCATCCTGGATGTCCAGCCTTAACAAGCCTTCAGAGGACTTCAGCCACAGCTATTATCTTA
CTACATCCTTGTGAGACTCTAATAAAGAACCAACTAGCTGAGCCCAATCAACCTATGGAACTG
ATAGAAATAAAATGAATTGTTGTTTTGTGCCGTT

FIGURE 58

></usr/seqdb2/sst/DNA/Dnaseqs.min/ss.DNA102880
><subunit 1 of 1, 184 aa, 1 stop
><MW: 21052, pI: 5.01, NX(S/T): 3
MDNRFATAFVIACVLSLISTIYMAASIGTDFWYEYRSPVQENSSDLNKSIWDEFISDEAD
EKTYNDALFRYNGTVGLWRRCITIPKNMHWYSPPERTESFDVVTKCVSFTLTEQFMEKFV
DPGNHNSGIDLLRTYLWRCQFLLPFVSLGLMCFGALIGLCACICRSLYPTIATGILHLLA
DTML

Important features of the protein:
Signal peptide:
Amino acids 1-20

Transmembrane domain:
Amino acids 142-163

N-glycosylation sites:
Amino acids 42-46;47-51;72-76;

N-myristoylation sites:
Amino acids 123-129;154-160;158-164

Prokaryotic membrane lipoprotein lipid attachment site:
Amino acids 152-163

FIGURE 59

GCGTGGACACCACCTCAGCCCACTGAGCAGGAGTCACAGCACGAAGACCAAGCGCAAAGCGA
CCCCTGCCCTCCATCCTGACTGCTCCTCCTAAGAGAGATGGCACCGGCCAGAGCAGGATTCT
GCCCCCTTCTGCTGCTTCTGCTGCTGGGGCTGTGGGTGGCAGAGATCCCAGTCAGTGCCAAG
CCCAAGGGCATGACCTCATCACAGTGGTTTAAAATTCAGCACATGCAGCCCAGCCCTCAAGC
ATGCAACTCAGCCATGAAAAACATTAACAAGCACACAAAACGGTGCAAAGACCTCAACACCT
TCCTGCACGAGCCTTTCTCCAGTGTGGCCGCCACCTGCCAGACCCCCAAAATAGCCTGCAAG
AATGGCGATAAAAACTGCCACCAGAGCCACGGGCCCGTGTCCCTGACCATGTGTAAGCTCAC
CTCAGGGAAGTATCCGAACTGCAGGTACAAAGAGAAGCGACAGAACAAGTCTTACGTAGTGG
CCTGTAAGCCTCCCCAGAAAAAGGACTCTCAGCAATTCCACCTGGTTCCTGTACACTTGGAC
AGAGTCCTTTAGGTTTCCAGACTGGCTTGCTCTTTGGCTGACCTTCAATTCCCTCTCCAGGA
CTCCGCACCACTCCCCTACACCCAGAGCATTCTCTTCCCCTCATCTCTTGGGGCTGTTCCTG
GTTCAGCCTCTGCTGGGAGGCTGAAGCTGACACTCTGGTGAGCTGAGCTCTAGAGGGATGGC
TTTTCATCTTTTTGTTGCTGTTTTCCCAGATGCTTATCCCCAAGAAACAGCAAGCTCAGGTC
TGTGGGTTCCCTGGTCTATGCCATTGCACATGTCTCCCCTGCCCCCTGGCATTAGGGCAGCA
TGACAAGGAGAGGAAATAAATGGAAAGGGGGCAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAA
AAAAA

FIGURE 60

></usr/seqdb2/sst/DNA/Dnaseqs.min/ss.DNA105782
><subunit 1 of 1, 156 aa, 1 stop
><MW: 17472, pI: 10.01, NX(S/T): 1
MAPARAGFCPLLLLLLLGLWVAEIPVSAKPKGMTSSQWFKIQHMQPSPQACNSAMKNINK
HTKRCKDLNTFLHEPFSSVAATCQTPKIACKNGDKNCHQSHGPVSLTMCKLTSGKYPNCR
YKEKRQNKSYVVACKPPQKKDSQQFHLVPVHLDRVL

Important features of the protein:
Signal peptide:
Amino acids 1-22

N-glycosylation site:
Amino acids 127-131 cAMP- and cGMP-dependent protein kinase phosphorylation site:
Amino acids 139-143

N-myristoylation sites:
Amino acids 18-24;32-38

Pancreatic ribonuclease family signature:
Amino acids 65-72

Pancreatic ribonuclease family proteins:
Amino acids 49-93

FIGURE 61

CGGGTCATGCGCCGCCGCCTGTGGCTGGGCCTGGCCTGGCTGCTGCTGGCGCGGGCGCCGGA
CGCCGCGGGAACCCCGAGCGCGTCGCGGGGACCGCGCAGCTACCCGCACCTGGAGGGCGACGTG
CGCTGGCGGCGCCTCTTCTCCTCCACTCACTTCTTCCTGCGCGTGGATCCCGGCGGCCGCGT
GCAGGGCACCCGCTGGCGCCACGGCCAGGACAGCATCCTGGAGATCCGCTCTGTACACGTGG
GCGTCGTGGTCATCAAAGCAGTGTCCTCAGGCTTCTACGTGGCCATGAACCGCCGGGGCCGC
CTCTACGGGTCGCGACTCTACACCGTGGACTGCAGGTTCCGGGAGCGCATCGAAGAGAACGG
CCACAACACCTACGCCTCACAGCGCTGGCGCCGCCGCGGCCAGCCCATGTTCCTGGCGCTGG
ACAGGAGGGGGGGGCCCCGGCCAGGCGGCCGGACGCGGCGGTACCACCTGTCCGCCCACTTC
CTGCCCGTCCTGGTCTCCTGAG

FIGURE 62

></usr/seqdb2/sst/DNA/Dnaseqs.min/ss.DNA108912
><subunit 1 of 1, 170 aa, 1 stop
><MW: 19663, pI: 11.81, NX(S/T): 0
MRRRLWLGLAWLLLARAPDAAGTPSASRGPRSYPHLEGDVRWRRLFSSTHFFLRVDPGGR
VQGTRWRHGQDSILEIRSVHVGVVVIKAVSSGFYVAMNRRGRLYGSRLYTVDCRFRERIE
ENGHNTYASQRWRRRGQPMFLALDRRGGPRPGGRTRRYHLSAHFLPVLVS

Important features of the protein:
Signal peptide:
Amino acids 1-17

N-myristoylation site:
Amino acids 22-28

HBGF/FGF family proteins:
Amino acids 74-125;139-166

FIGURE 63

ATCCCTCGACCTCGACCCACGCGTCCGCTGGAAGGTGGCGTGCCCTCCTCTGGCTGGTACCA
TGCAGCTCCCACTGGCCCTGTGTCTCGTCTGCCTGCTGGTACACACAGCCTTCCGTGTAGTG
GAGGGCCAGGGGTGGCAGGCGTTCAAGAATGATGCCACGGAAATCATCCCCGAGCTCGGAGA
GTACCCCGAGCCTCCACCGGAGCTGGAGAACAACAAGACCATGAACCGGGCGGAGAACGGAG
GGCGGCCTCCCCACCACCCCTTTGAGACCAAAGACGTGTCCGAGTACAGCTGCCGCGAGCTG
CACTTCACCCGCTACGTGACCGATGGGCCGTGCCGCAGCGCCAAGCCGGTCACCGAGCTGGT
GTGCTCCGGCCAGTGCGGCCCGGCGCGCCTGCTGCCCAACGCCATCGGCCGCGGCAAGTGGT
GGCGACCTAGTGGGCCCGACTTCCGCTGCATCCCCGACCGCTACCGCGCGCAGCGCGTGCAG
CTGCTGTGTCCCGGTGGTGAGGCGCCGCGCGCGCGCAAGGTGCGCCTGGTGGCCTCGTGCAA
GTGCAAGCGCCTCACCCGCTTCCACAACCAGTCGGAGCTCAAGGACTTCGGGACCGAGGCCG
CTCGGCCGCAGAAGGGCCGGAAGCCGCGGCCCCGCGCCCGGAGCGCCAAAGCCAACCAGGCC
GAGCTGGAGAACGCCTACTAGAGCCCGCCCGCGCCCCTCCCCACCGGCGGGCGCCCCGGCCC
TGAACCCGCGCCCCACATTTCTGTCCTCTGCGCGTGGTTTGATTGTTTATATTTCATTGTAA
ATGCCTGCAACCCAGGGCAGGGGGCTGAGACCTTCCAGGCCCTGAGGAATCCCGGGCGCCGG
CAAGGCCCCCCTCAGCCCGCCAGCTGAGGGGTCCCACGGGGCAGGGGAGGGAATTGAGAGTC
ACAGACACTGAGCCACGCAGCCCCGCCTCTGGGGCCGCCTACCTTTGCTGGTCCCACTTCAG
AGGAGGCAGAAATGGAAGCATTTTCACCGCCCTGGGGTTTTAAGGGAGCGGTGTGGGAGTGG
GAAAGTCCAGGGACTGGTTAAGAAAGTTGGATAAGATTCCCCCTTGCACCTCGCTGCCCATC
AGAAAGCCTGAGGCGTGCCCAGAGCACAAGACTGGGGGCAACTGTAGATGTGGTTTCTAGTCC
TGGCTCTGCCACTAACTTCCTGTGTAACCTTGAACTACACAATTCTCCTTCGGGACCTCAAT
TTCCACTTTGTAAAATGAGGGTGGAGGTGGGAATAGGATCTCGAGGAGACTATTGGCATATG
ATTCCAAGGACTCCAGTGCCTTTTGAATGGGCAGAGGTGAGAGAGAGAGAGAGAAAGAGAGA
GAATGAATGCAGTTGCATTGATTCAGTGCCAAGGTCACTTCCAGAATTCAGAGTTGTGATGC
TCTCTTCTGACAGCCAAAGATGAAAAACAAACAGAAAAAAAAAAGTAAAGAGTCTATTTATG
GCTGACATATTTACGGCTGACAAACTCCTGGAAGAAGCTATGCTGCTTCCCAGCCTGGCTTC
CCCGGATGTTTGGCTACCTCCACCCCTCCATCTCAAAGAAATAACATCATCCATTGGGGTAG
AAAAGGAGAGGGTCCGAGGGTGGTGGGAGGGATAGAAATCACATCCGCCCCAACTTCCCAAA
GAGCAGCATCCCTCCCCCGACCCATAGCCATGTTTTAAAGTCACCTTCCGAAGAGAAGTGAA
AGGTTCAAGGACACTGGCCTTGCAGGCCCGAGGGAGCAGCCATCACAAACTCACAGACCAGC
ACATCCCTTTTGAGACACCGCCTTCTGCCCACCACTCACGGACACATTTCTGCCTAGAAAAC
AGCTTCTTACTGCTCTTACATGTGATGGCATATCTTACACTAAAAGAATATTATTGGGGGAA
AAACTACAAGTGCTGTACATATGCTGAGAAACTGCAGAGCATAATAGCTGCCACCCAAAAAT
CTTTTTGAAAATCATTTCCAGACAACCTCTTACTTTCTGTGTAGTTTTTAATTGTTAAAAAA
AAAAAGTTTTAAACAGAAGCACATGACATATGAAAGCCTGCAGGACTGGTCGTTTTTTTGGC
AATTCTTCCACGTGGGACTTGTCCACAAGAATGAAAGTAGTGGTTTTTAAAGAGTTAAGTTA
CATATTTATTTTCTCACTTAAGTTATTTATGCAAAAGTTTTTCTTGTAGAGAATGACAATGT
TAATATTGCTTTATGAATTAACAGTCTGTTCTTCCAGAGTCCAGAGACATTGTTAATAAAGA
CAATGAATCATGAAAAAAAAAAAAAAAAAAAAAA

FIGURE 64

</usr/seqdb2/sst/DNA/Dnaseqs.min/ss.DNA115253
<subunit 1 of 1, 213 aa, 1 stop
<MW: 24031, pI: 9.59, NX(S/T): 2
MQLPLALCLVCLLVHTAFRVVEGQGWQAFKNDATEIIPELGEYPEPPPELENNKTMNRAE
NGGRPPHHPFETKDVSEYSCRELHFTRYVTDGPCRSAKPVTELVCSGQCGPARLLPNAIG
RGKWWRPSGPDFRCIPDRYRAQRVQLLCPGGEAPRARKVRLVASCKCKRLTRFHNQSELK
DFGTEAARPQKGRKPRPRARSAKANQAELENAY

Important features of the protein:
Signal peptide:
Amino acids 1-16

N-glycosylation sites:
Amino acids 53-57;175-179 cAMP- and cGMP-dependent protein kinase phosphorylation site:
Amino acids 168-172

N-myristoylation site:
Amino acids 183-189

Amidation site:
Amino acids 191-195

FIGURE 65

CCCACTCGGCGGTTTGGCGGGAGGGAGGGGCTTTGCGCAGGCCCCGCTCCCGCCCCGCCTCC
ATGCGGCCCGCCCCGATTGCGCTGTGGCTGCGCCTGGTCTTGGCCCTGGCCCTTGTCCGCCC
CCGGGCTGTGGGGTGGGCCCCGGTCCGAGCCCCCATCTATGTCAGCAGCTGGGCCGTCCAGG
TGTCCCAGGGTAACCGGGAGGTCGAGCGCCTGGCACGCAAATTCGGCTTCGTCAACCTGGGG
CCGATCTTCTCTGACGGGCAGTACTTTCACCTGCGGCACCGGGGCGTGGTCCAGCAGTCCCT
GACCCCGCACTGGGGCCACCGCCTGCACCTGAAGAAAAACCCCAAGGTGCAGTGGTTCCAGC
AGCAGACGCTGCAGCGGCGGGTGAAACGCTCTGTCGTGGTGCCCACGGACCCCTGGTTCTCC
AAGCAGTGGTACATGAACAGCGAGGCCCAACCAGACCTGAGCATCCTGCAGGCCTGGAGTCA
GGGGCTGTCAGGCCAGGGCATCGTGGTCTCTGTGCTGGACGATGGCATCGAGAAGGACCACC
CGGACCTCTGGGCCAACTACGACCCCCTGGCCAGCTATGACTTCAATGACTACGACCCGGAC
CCCCAGCCCCGCTACACCCCCAGCAAAGAGAACCGGCACGGGACCCGCTGTGCTGGGGAGGT
GGCCGCGATGGCCAACAATGGCTTCTGTGGTGTGGGGGTCGCTTTCAACGCCCGAATCGGAG
GCGTACGGATGCTGGACGGTACCATCACCGATGTCATCGAGGCCCAGTCGCTGAGCCTGCAG
CCGCAGCACATCCACATTTACAGCGCCAGCTGGGGTCCCGAGGACGACGGCCGCACGGTGGA
CGGCCCCGGCATCCTCACCCGCGAGGCCTTCCGGCGTGGTGTGACCAAGGGCCGCGGCGGGC
TGGGCACGCTCTTCATCTGGGCCTCGGGCAACGGCGGCCTGCACTACGACAACTGCAACTGC
GACGGCTACACCAACAGCATCCACACGCTTTCCGTGGGCAGCACCACCCAGCAGGGCCGCGT
GCCCTGGTACAGCGAAGCCTGCGCCTCCACCCTCACCACCACCTACAGCAGCGGCGTGGCCA
CCGACCCCCAGATCGTCACCACGGACCTGCATCACGGGTGCACAGACCAGCACACGGGCACC
TCGGCCTCAGCCCCACTGGCGGCCGGCATGATCGCCCTAGCGCTGGAGGCCAACCCGTTCCT
GACGTGGAGAGACATGCAGCACCTGGTGGTCCGCGCGTCCAAGCCGGCGCACCTGCAGGCCG
AGGACTGGAGGACCAACGGCGTGGGGCGCCAAGTGAGCCATCACTACGGATACGGGCTGCTG
GACGCCGGGCTGCTGGTGGACACCGCCCGCACCTGGCTGCCCACCCAGCCGCAGAGGAAGTG
CGCCGTCCGGGTCCAGAGCCGCCCCACCCCCATCCTGCCGCTGATCTACATCAGGGAAAACG
TATCGGCCTGCGCCGGCCTCCACAACTCCATCCGCTCGCTGGAGCACGTGCAGGCGCAGCTG
ACGCTGTCCTACAGCCGGCGCGGAGACCTGGAGATCTCGCTCACCAGCCCCATGGGCACGCG
CTCCACACTCGTGGCCATACGACCCTTGGACGTCAGCACTGAAGGCTACAACAACTGGGTCT
TCATGTCCACCCACTTCTGGGATGAGAACCCACAGGGCGTGTGGACCCTGGGCCTAGAGAAC
AAGGGCTACTATTTCAACACGGGGACGTTGTACCGCTACACGCTGCTGCTCTATGGGACGGC
CGAGGACATGACAGCGCGGCCTACAGGCCCCCAGGTGACCAGCAGCGCGTGTGTGCAGCGGGAC
ACAGAGGGGCTGTGCCAGGCGTGTGACGGCCCCGCCTACATCCTGGGACAGCTCTGCCTGGC
CTACTGCCCCCCGCGGTTCTTCAACCACACAAGGCTGGTGACCGCTGGGCCTGGGCACACGG
CGGCGCCCGCGCTGAGGGTCTGCTCCAGCTGCCATGCCTCCTGCTACACCTGCCGCGGCGGC
TCCCCGAGGGACTGCACCTCCTGTCCCCCATCCTCCACGCTGGACCAGCAGCAGGGCTCCTG
CATGGGACCCACCACCCCCGACAGCCGCCCCCGGCTTAGAGCTGCCGCCTGTCCCCACCACCG
CTGCCCAGCCTCGGCCATGGTGCTGAGCCTCCTGGCCGTGACCCTCGGAGGCCCCGTCCTCT
GCGGCATGTCCATGGACCTCCCACTATACGCCTGGCTCTCCCGTGCCAGGGCCACCCCCACC
AAACCCCAGGTCTGGCTGCCAGCTGGAACCTGAAGTTGTCAGCTCAGAAAGCGACCTTGCCC
CCGCCTGGGTCCCTGACAGGCACTGCTGCCATGCTGCCTCCCCAGGCTGGCCCCAGAGGAGC
GAGCACCAGCACCCGACGCCTGGCCTGCCAGGGATGGCCCCGTGGAACCCCGAAGCCTGGC
GGGAGAGAGAGAGAGAGAAGTCTCCTCTGCATTTTGGGTTTGGGCAGGAGTGGGCTGGGGGG
AGAGGCTGGAGCACCCCAAAAGCCAGGGGAAAGTGGAGGGAGAGAAACGTGACACTGTCCGT
CTCGGGCACCGCGTCCAACCTCAGAGTTTGCAAATAAAGGTTGCTTAGAAGGTGAA

FIGURE 66

></usr/seqdb2/sst/DNA/Dnaseqs.min/ss.DNA119302
><subunit 1 of 1, 755 aa, 1 stop
><MW: 82785, pI: 8.71, NX(S/T): 2

MRPAPIALWLRLVLALALVRPRAVGWAPVRAPIYVSSWAVQVSQGNREVERLARKFGFVN
LGPIFSDGQYFHLRHRGVVQQSLTPHWGHRLHLKKNPKVQWFQQQTLQRRVKRSVVVPTD
PWFSKQWYMNSEAQPDLSILQAWSQGLSGQGIVVSVLDDGIEKDHPDLWANYDPLASYDF
NDYDPDPQPRYTPSKENRHGTRCAGEVAAMANNGFCGVGVAFNARIGGVRMLDGTITDVI
EAQSLSLQPQHIHIYSASWGPEDDGRTVDGPGILTREAFRRGVTKGRGGLGTLFIWASGN
GGLHYDNCNCDGYTNSIHTLSVGSTTQQGRVPWYSEACASTLTTTYSSGVATDPQIVTTD
LHHGCTDQHTGTSASAPLAAGMIALALEANPFLTWRDMQHLVVRASKPAHLQAEDWRTNG
VGRQVSHHYGYGLLDAGLLVDTARTWLPTQPQRKCAVRVQSRPTPILPLIYIRENVSACA
GLHNSIRSLEHVQAQLTLSYSRRGDLEISLTSPMGTRSTLVAIRPLDVSTEGYNNWVFMS
THFWDENPQGVWTLGLENKGYYFNTGTLYRYTLLLYGTAEDMTARPTGPQVTSSACVQRD
TEGLCQACDGPAYILGQLCLAYCPPRFFNHTRLVTAGPGHTAAPALRVCSSCHASCYTCR
GGSPRDCTSCPPSSTLDQQQGSCMGPTTPDSRPRLRAAACPHHRCPASAMVLSLLAVTLG
GPVLCGMSMDLPLYAWLSRARATPTKPQVWLPAGT

Important features of the protein:

Signal peptide:
Amino acids 1-21

Transmembrane domain:
Amino acids 706-730

N-glycosylation sites:
Amino acids 475-479;629-633

Glycosaminoglycan attachment sites:
Amino acids 148-152;298-302

N-myristoylation sites:
Amino acids 151-157;200-206;217-223;219-225;
282-288;288-294;371-377;432-438;
481-487;515-521;603-609

Prokaryotic membrane lipoprotein lipid attachment site:
Amino acids 586-597

Cell attachment sequence:
Amino acids 503-506

Serine proteases, subtilase family, aspartic acid active site:
Amino acids 154-166

Serine proteases, subtilase family, histidine active site:
Amino acids 199-210

Serine proteases, subtilase family, serine active site:
Amino acids 371-382

Cytochrome c family heme-binding site signature:
Amino acids 649-655

FIGURE 67

ATGAGGAAGCTCCAGGGCAGGATGGTTTACCTGCCTGGACAGCAAGATGATGGCTACACTAG
CCCCCATTCTCTGGGCGCCTGGATTTGCCCACCAGATCTCCTCACCTCTTGCCCTTCACCTC
CTGCTGTACCTACAAGGTCTCCCCGATTCTCATCTGCCCATAATCATGGACACAGCCCCAGG
ATGTGCAGGACTCTCAGGGACCATCTGGAGTTCCAGCTGGAATCTGGGCCTGGTGGAGTGGG
AGTGGGGCAGGGGCCTGCATTGGGCTGACTTAGAGAGCACAGTTATTCCATCCATATGGAAA
TAAACATTTTGGATTCCTGATC

FIGURE 68

></usr/seqdb2/sst/DNA/Dnaseqs.min/ss.DNA119536
><subunit 1 of 1, 88 aa, 1 stop
><MW: 9645, pI: 5.45, NX(S/T): 0
MMATLAPILWAPGFAHQISSPLALHLLLYLQGLPDSHLPIIMDTAPGCAGLSGTIWSSSW
NLGLVEWEWGRGLHWADLESTVIPSIWK

Signal sequence:
Amino acids 1-15

N-myristoylation sites:
Amino acids 32-38;50-56;53-59;72-78

FIGURE 69

TTTGCAGTGGGGTCCTCCTCTGGCCTCCTGCCCCTCCTGCTGCTGCTGCTTCCATTGCT
GGCAGCCCAGGGTGGGGGTGGCCTGCAGGCAGCGCTGCTGGCCCTTGAGGTGGGGCTGGTGG
GTCTGGGGGCCTCCTACCTGCTCCTTTGTACAGCCCTGCACCTGCCCTCCAGTCTTTTCCTA
CTCCTGGCCCAGGGTACCGCACTGGGGGCCGTCCTGGGCCTGAGCTGGCGCCGAGGCCTCAT
GGGTGTTCCCCTGGGCCTTGGAGCTGCCTGGCTCTTAGCTTGGCCAGGCCTAGCTCTACCTC
TGGTGGCTATGGCAGCGGGGGGCAGATGGGTGCGGCAGCAGGGCCCCCGGGTGCGCCGGGGC
ATATCTCGACTCTGGTTGCGGGTTCTGCTGCGCCTGTCACCCATGGCCTTCCGGGCCCTGCA
GGGCTGTGGGGCTGTGGGGGACCGGGGTCTGTTTGCACTGTACCCCAAAACCAACAAGGATG
GCTTCCGCAGCCGCCTGCCCGTCCCTGGGCCCCGGCGGCGTAATCCCCGCACCACCCAACAC
CCATTAGCTCTGTTGGCAAGGGTCTGGGTCCTGTGCAAGGGCTGGAACTGGCGTCTGGCACG
GGCCAGCCAGGGTTTAGCATCCCACTTGCCCCCGTGGGCCATCCACACACTGGCCAGCTGGG
GCCTGCTTCGGGGTGAACGGCCCACCCGAATCCCCCGGCTACTACCACGCAGCCAGCGCCAG
CTAGGGCCCCCTGCCTCCCGCCAGCCACTGCCAGGGACTCTAGCCGGGCGGAGGTCACGCAC
CCGCCAGTCCCGGGCCCTGCCCCCCTGGAGGTAGCTGACTCCAGCCCTTCCAGCCCAAATCT
AGAGCATTGAGCACTTTATCTCCCACGACTCAGTGAAGTTTCTCCAGTCCCTAGTCCTCTCT
TTTCACCCACCTTCCTCAGTTTGCTCACTTACCCCAGGCCCAGCCCTTCGGACCTCTAGACA
GGCAGCCTCCTCAGCTGTGGAGTCCAGCAGTCACTCTGTGTTCTCCTGGCGCTCCTCCCCTA
AGTTATTGCTGTTCGCCCGCTGTGTGTGCTCATCCTCACCCTCATTGACTCAGGCCTGGGGC
CAGGGGTGGTGGAGGGTGGGAAGAGTCATGTTTTTTTTCTCCTCTTTGATTTTGTTTTTCTG
TCTCCCTTCCAACCTGTCCCCTTCCCCCCACCAAAAAAAXXXXXXXXXXXXXXXXXXXXX
XXXXXXXXXXXXAAAAAAAAAAAAAAAAAAAAAAAAAAAAAAAAAAAAAAAAAAAAAAAAA

FIGURE 70

></usr/seqdb2/sst/DNA/Dnaseqs.min/ss.DNA119542
><subunit 1 of 1, 197 aa, 1 stop
><MW: 21992, pI: 12.18, NX(S/T): 0
MGVPLGLGAAWLLAWPGLALPLVAMAAGGRWVRQQGPRVRRGISRLWLRVLLRLSPMAFR
ALQGCGAVGDRGLFALYPKTNKDGFRSRLPVPGPRRRNPRTTQHPLALLARVWVLCKGWN
WRLARASQGLASHLPPWAIHTLASWGLLRGERPTRIPRLLPRSQRQLGPPASRQPLPGTL
AGRRSRTRQSRALPPWR

Important features of the protein:
Signal peptide:
Amino acids 1-21

N-myristoylation sites:
Amino acids 2-8;6-12;146-152;178-184

Amidation site:
Amino acids 181-185

FIGURE 71

GTTTGGGGGTTGTTTGGGATTAGTGAAGCTACTGCCTTTGCCGCCAGCGCAGCCTCAGAGTT
TGATTATTTGCA<u>ATG</u>TCAGGCTTTGAAAACTTAAACACGGATTTCTACCAGACAAGTTACAG
CATCGATGATCAGTCACAGCAGTCCTATGATTATGGAGGAAGTGGAGGACCCTATAGCAAAC
AGTATGCTGGCTATGACTATTCGCAGCAAGGCAGATTTGTCCCTCCAGACATGATGCAGCCA
CAACAGCCATACACCGGGCAGATTTACCAGCCAACTCAGGCATATACTCCAGCTTCACCTCA
GCCTTTCTATGGAAACAACTTTGAGGATGAGCCACCTTTATTAGAAGAGTTAGGTATCAATTTT
GACCACATCTGGCAAAAAACACTAACAGTATTACATCCGTTAAAAGTAGCAGATGGCAGCAT
CATGAATGAAACTGATTTGGCAGGTCCAATGGTTTTTGCCTTGCTTTTGGAGCCACATTGC
TACTGGCTGGCAAAATCCAGTTTGGCTATGTATACGGGATCAGTGCAATTGGATGTCTAGGA
ATGTTTTGTTTATTAAACTTAATGAGTATGACAGGTGTTTCATTTGGTTGTGTGGCAAGTGT
CCTTGGATATTGTCTTCTGCCCATGATCCTACTTTCCAGCTTTGCAGTGATATTTTCTTTGC
AAGGAATGGTAGGAATCATTCTCACTGCTGGGATTATTGGATGGTGTAGTTTTTCTGCTTCC
AAAATATTTATTTCTGCATTAGCCATGGAAGGACAGCAACTTTTAGTAGCATATCCTTGCGC
TTTGTTATATGGAGTCTTTGCCCTGATTTCCGTCTTT<u>TGA</u>AAATTTATCTGGGATGTGGACA
TCAGTGGGCCAGATGTACAAAAAGGACCTTGAACTCTTAAATTGGACCAGCAAACTGCTGCA
GCGCAACTCTCATGCAGATTTACATTTGACTGTTGGAGCAATGAAAGTAAACGTGTATCTCT
TGTTCATTTTTATAGAACTTTTGCATACTATATTGGATTTACCTGCGGTGTGACTAGCTTTA
AATGTTTGTGTTTATACAGATAAGAAATGCTATTTCTTTCTGGTTCCTGCAGCCATTGAAAA
ACCTTTTTCCTTGCAAATTATAATGTTTTTGATAGATTTTTATCAACTGTGGGAAACCAAAC
ACAAAGCTGATAACCTTTCTTAAAAACGACCCAGTCACAGTAAAGAAGACACAAGACGGCCG
GGCGTGGTAGCTCACGCCTGTAATCCCAGCACTTTGGGAGGCCGAGGCGGGCGGATCACAAG
GGCAGGAGATCGAGACCATCCTGGTTAACACGGTGAAACCCCGACTCTACTAAAACTACAAA
AAAAATTAGCTGGGCGTGGTGGCGGGCGCCTGTAGTCCCAGCTACTCAGGAGGCTGAGGCAG
GAGAAGTGTGAACCCAGGAGGCGGAGCTTGCAGTGAGCCGAGATCACACCACTGCACTCCAT
CCAGCCTGGGTGACAGGGTGAGACTCTGTCTCAAAAAAAAAAAAAAAAGGAGACACAAGACT
TACTGCAAAAATATTTTTCCAAGGATTTAGGAAAGAAAAATTGCCTTGTATTCTCAAGTCAG
GTAACTCAAAGCAAAAAAGTGATCCAAATGTAGAGTATGAGTTTGCACTCCAAAAATTTGAC
ATTACTGTAAATTATCTCATGGAATTTTTGCTAAAATTCAGAGATACGGGAAGTTCACAATC
TACCTCATTGTAGACATGAAATGCGAACACTTACTTACATATTAATGTTAACTCAACCTTAG
GGACCTGGAATGGTTGCATTAATGCTATAATCGTTGGATCGCCACATTTCCCAAAAATAATA
AAAAAATCACTAACCTTTTTTAAGGAAAATATTTAAAGTTTTACAAAATTCAATATTGCAAT
TATCAATGTAAAGTACATTTGAATGCTTATTAAAACTTTCCCAATTAATTTT

FIGURE 72

></usr/seqdb2/sst/DNA/Dnaseqs.min/ss.DNA143498
><subunit 1 of 1, 257 aa, 1 stop
><MW: 27989, pI: 4.16, NX(S/T): 1
MSGFENLNTDFYQTSYSIDDQSQQSYDYGGSGGPYSKQYAGYDYSQQGRFVPPDMMQPQQ
PYTGQIYQPTQAYTPASPQPFYGNNFEDEPPLLEELGINFDHIWQKTLTVLHPLKVADGS
IMNETDLAGPMVFCLAFGATLLLAGKIQFGYVYGISAIGCLGMFCLLNLMSMTGVSFGCV
ASVLGYCLLPMILLSSFAVIFSLQGMVGIILTAGIIGWCSFSASKIFISALAMEGQQLLV
AYPCALLYGVFALISVF

Transmembrane domain:
Amino acids 129-145;184-203

N-glycosylation sites:
Amino acids 123-127

N-myristoylation sites:
Amino acids 32-38;119-125;174-180;178-184;208-214

Prokaryotic membrane lipoprotein lipid attachment site:
Amino acids 150-161;169-180

FIGURE 73

ACACTGGCCAAAACGCGGCTCGCCCTCGGCTGCGCTCGGCTCCCGCGGGCGCTCGGCCCCGA
GCCCCTCCTCCCCCTACCCGCCGGCCGGACAGGGAGGAGCCAATGGCTGGGCCTGCCATCCA
CACCGCTCCCATGCTGTTCCTCGTCCTCCTGCTGCCCCAGCTGAGCCTGGCAGGCGCCCTTG
CACCTGGGACCCCTGCCCGGAACCTCCCTGAGAATCACATTGACCTCCCAGGCCCAGCGCTG
TGGACGCCTCAGGCCAGCCACCACCGCCGGCGGGGCCCGGGCAAGAAGGAGTGGGGCCCAGG
CCTGCCCAGCCAGGCCCAGGATGGGGCTGTGGTCACCGCCACCAGGCAGGCCTCCAGGCTGC
CAGAGGCTGAGGGGCTGCTGCCTGAGCAGAGTCCTGCAGGCCTGCTGCAGGACAAGGACCTG
CTCCTGGGACTGGCATTGCCCTACCCCGAGAAGGAGAACAGACCTCCAGGTTGGGAGAGGAC
CAGGAAACGCAGCAGGGAGCACAAGAGACGCAGGGACAGGTTGAGGCTGCACCAAGGCCGAG
CCTTGGTCCGAGGTCCCAGCTCCCTGATGAAGAAGGCAGAGCTCTCCGAAGCCCAGGTGCTG
GATGCAGCCATGGAGGAATCCTCCACCAGCCTGGCGCCCACCATGTTCTTTCTCACCACCTT
TGAGGCAGCACCTGCCACAGAAGAGTCCCTGATCCTGCCCGTCACCTCCCTGCGGCCCCAGC
AGGCACAGCCCAGGTCTGACGGGGAGGTGATGCCCACGCTGGACATGGCCTTGTTCGACTGG
ACCGATTATGAAGACTTAAAACCTGATGGTTGGCCCTCTGCAAAGAAGAAAGAGAAACACCG
CGGTAAACTCTCCAGTGATGGTAACGAAACATCACCAGCCGAAGGGGAACCATGCGACCATC
ACCAAGACTGCCTGCCAGGGACTTGCTGCGACCTGCGGGAGCATCTCTGCACACCCCACAAC
CGAGGCCTCAACAACAAATGCTTCGATGACTGCATGTGTGTGGAAGGGCTGCGCTGCTATGC
CAAATTCCACCGGAACCGCAGGGTTACACGGAGGAAAGGGCGCTGTGTGGAGCCCGAGACGG
CCAACGGCGACCAGGGATCCTTCATCAACGTCTAGCGGCCCCGCGGGACTGGGGACTGAGCC
CAGGAGGTTTGCACAAGCCGGGCGATTTGTTTGTAACTAGCAGTGGGAGATCAAGTTGGGGA
ACAGATGGCTGAGGCTGCAGACTCAGGCCCAGGACACTCAACCCC

FIGURE 74

></usr/seqdb2/sst/DNA/Dnaseqs.min/ss.DNA145583
><subunit 1 of 1, 348 aa, 1 stop
><MW: 38536, pI: 8.24, NX(S/T): 1
MAGPAIHTAPMLFLVLLLPQLSLAGALAPGTPARNLPENHIDLPGPALWTPQASHHRRRG
PGKKEWGPGLPSQAQDGAVVTATRQASRLPEAEGLLPEQSPAGLLQDKDLLLGLALPYPE
KENRPPGWERTRKRSREHKRRRDRLRLHQGRALVRGPSSLMKKAELSEAQVLDAAMEESS
TSLAPTMFFLTTFEAAPATEESLILPVTSLRPQQAQPRSDGEVMPTLDMALFDWTDYEDL
KPDGWPSAKKKEKHRGKLSSDGNETSPAEGEPCDHHQDCLPGTCCDLREHLCTPHNRGLN
NKCFDDCMCVEGLRCYAKFHRNRRVTRRKGRCVEPETANGDQGSFINV

Important features of the protein:

Signal peptide:

Amino acids 1-24

N-glycosylation site:

Amino acids 263-267 cAMP- and cGMP-dependent protein kinase phosphorylation site:

Amino acids 132-136;323-327

N-myristoylation sites:

Amino acids 77-83;343-349

Amidation site:

Amino acids 61-65

FIGURE 75

CAGAAGGGCAAAAACATTGACTGCCTCAAGGTCTCAAGCACCAGTCTTCACCGCGGAAAGCA
TGTTGTGGCTGTTCCAATCGCTCCTGTTTGTCTTCTGCTTTGGCCCAGGGAATGTAGTTTCA
CAAAGCAGCTTAACCCCATTGATGGTGAACGGGATTCTGGGGGAGTCAGTAACTCTTCCCCT
GGAGTTTCCTGCAGGAGAGAAGGTCAACTTCATCACTTGGCTTTTCAATGAAACATCTCTTG
CCTTCATAGTACCCCATGAAACCAAAAGTCCAGAAATCCACGTGACTAATCCGAAACAGGGA
AAGCGACTGAACTTCACCCAGTCCTACTCCCTGCAACTCAGCAACCTGAAGATGGAAGACAC
AGGCTCTTACAGAGCCCAGATATCCACAAAGACCTCTGCAAAGCTGTCCAGTTACACTCTGA
GGATATTAAGACAACTGAGGAACATACAAGTTACCAATCACAGTCAGCTATTTCAGAATATG
ACCTGTGAGCTCCATCTGACTTGCTCTGTGGAGGATGCAGATGACAATGTCTCATTCAGATG
GGAGGCCTTGGGAAACACACTTTCAAGTCAGCCAAACCTCACTGTCTCCTGGGACCCCAGGA
TTTCCAGTGAACAGGACTACACCTGCATAGCAGAGAATGCTGTCAGTAATTTATCCTTCTCT
GTCTCTGCCCAGAAGCTTTGCGAAGATGTTAAAATTCAATATACAGATACCAAAATGATTCT
GTTTATGGTTTCTGGGATATGCATAGTCTTCGGTTTCATCATACTGCTGTTACTTGTTTTGA
GGAAAAGAAGAGATTCCCTATCTTTGTCTACTCAGCGAACACAGGGCCCCGCAGAGTCCGCA
AGGAACCTAGAGTATGTTTCAGTGTCTCCAACGAACAACACTGTGTATGCTTCAGTCACTCA
TTCAAACAGGGAAACAGAAATCTGGACACCTAGAGAAAATGATACTATCACAATTTACTCCA
CAATTAATCATTCCAAAGAGAGTAAACCCACTTTTTCCAGGGCAACTGCCCTTGACAATGTC
GTGTAAGTTGCTGAAAGGCCTCAGAGGAATTCGGGAATGACACGTCTTCTGATCCCATGAGA
CAGAACAAAGAACAGGAAGCTTGGTTCCTGTTGTTCCTGGCAACAGAATTTGAATATCTAGG
ATAGGATGATCACCTCCAGTCCTTCGGACTTAAACCTGCCTACCTGAGTCAAACACCTAAGG
ATAACATCATTTCCAGCATGTGGTTCAAATAATATTTTCCAATCCACTTCAGGCCAAAACAT
GCTAAAGATAACACACCAGCACATTGACTCTCTCTTTGATAACTAAGCAAATGGAATTATGG
TTGACAGAGAGTTTATGATCCAGAAGACAACCACTTCTCTCCTTTTAGAAAGCAGCAGGATT
GACTTATTGAGAAATAATGCAGTGTGTTGGTTACATGTGTAGTCTCTGGAGTTGGATGGGCC
CATCCTGATACAAGTTGAGCATCCCTTGTCTGAAATGCTTGGGATTAGAAATGTTTCAGATT
TCAATTTTTTTTCAGATTTTGGAATATTTGCATTATATTTAGCGGTTGAGTATCCAAATCCA
AAAATCCAAAATTCAAAATGCTCCAATAAGCATTTCCCTTGAGTTTCATTGATGTCGATGCA
GTGCTCAAAATCTCAGATTTTGGAGCAATTTGGATATTGGATTTTTGGATTTGGGATGCTCA
ACTTGTACAATGTTTATTAGACACATCTCCTGGGACATACTGCCTAACCTTTTGGAGCCTTA
GTCTCCCAGACTGAAAAAGGAAGAGGATGGTATTACATCAGCTCCATTGTTTGAGCCAAGAA
TCTAAGTC

FIGURE 76

></usr/seqdb2/sst/DNA/Dnaseqs.min/ss.DNA161000
><subunit 1 of 1, 332 aa, 1 stop
><MW: 37345, pI: 6.72, NX(S/T): 10
MLWLFQSLLFVFCFGPGNVVSQSSLTPLMVNGILGESVTLPLEFPAGEKVNFITWLFNET
SLAFIVPHETKSPEIHVTNPKQGKRLNFTQSYSLQLSNLKMEDTGSYRAQISTKTSAKLS
SYTLRILRQLRNIQVTNHSQLFQNMTCELHLTCSVEDADDNVSFRWEALGNTLSSQPNLT
VSWDPRISSEQDYTCIAENAVSNLSFSVSAQKLCEDVKIQYTDTKMILFMVSGICIVFGF
IILLLLVLRKRRDSLSLSTQRTQGPAESARNLEYVSVSPTNNTVYASVTHSNRETEIWTP
RENDTITIYSTINHSKESKPTFSRATALDNVV

Important features of the protein:

Signal peptide:
Amino acids 1-13

Transmembrane domain:
Amino acids 228-247

N-glycosylation sites:
Amino acids 58-62;87-91;137-141;144-148;161-165;
178-182;203-207;281-285;303-307;
313-317 cAMP- and cGMP-dependent protein kinase phosphorylation site:
Amino acids 251-255

Tyrosine kinase phosphorylation sites:
Amino acids 100-108;186-194

N-myristoylation sites:
Amino acids 17-23;105-111;170-176

Amidation site:
Amino acids 82-86

Immunoglobulin domain:
Amino acids 35-111

FIGURE 77

GATCCCTCGACCTCGACCCACGCGTCCGCTCTTTAATGCTTTCTTTTTAAGAGATCACCTTC
TGACTTCTCACAGAAGAGGTTAACTATTACCTGTGGGAAGTCAGAAGGTGATCTCTTTAATG
CTTTCTTTTTAAGAATTTTTCAAATTGAGACTAATTGCAGAGGTTCCAGTTGACCAGCATTC
ATAGGAATGAAGACAAACACAGAGATGGTGTGTCTAAGAAACTTCAAAAGGTGTAGACCTCC
TGACTGAAGCATATTGGATTTATTTAATTTTTTTCACTGTATTTCTGTCCTCCTACAAGGGA
AAGTCATGATTACACTAACTGAGCTAAAATGCTTAGCAGATGCCCAGTCATCTTATCACATC
TTAAAACCATGGTGGGACGTCTTCTGGTATTACATCACACTGATCATGCTGCTGGTGGCCGTG
CTGGCCGGAGCTCTCCAGCTGACGCAGAGCAGGGTTCTGTGCTGTCTTCCATGCAAAGTGGA
ATTTGACAATCACTGTGCCGTGCCTTGGGACATCCTGAAAGCCAGCATGAACACATCCTCTA
ATCCTGGGACACCGCTTCCGCTCCCCCTCCGAATTCAGAATGACCTCCACCGACAGCAGTAC
TCCTATATTGATGCCGTCTGTTACGAGAAACAGCTCCATTGGTTTGCAAAGTTTTTCCCCTA
TCTGGTGCTCTTGCACACGCTCATCTTTGCAGCCTGCAGCAACTTTTGGCTTCACTACCCCA
GTACCAGTTCCAGGCTCGAGCATTTTGTGGCCATCCTTCACAAGTGCTTCGATTCTCCATGG
ACCACCCGCGCCCTTTCAGAAACAGTGGCTGAGCAGTCAGTGAGGCCTCTGAAACTCTCCAA
GTCCAAGATTTTGCTTTCGTCCTCAGGGTGTTCAGCTGACATAGATTCCGGCAAACAGTCAT
TGCCCTACCCACAGCCAGGTTTGGAGTCAGCTGGTATAGAAAGCCCAACTTCCAGTGGCCTG
GACAAGAAGGAGGGTGAACAGGCCAAAGCCATCTTTGAAAAAGTGAAAAGATTCCGCATGCA
TGTGGAGCAGAAGGACATCATTTATAGAGTATATCTGAAACAGATAATAGTCAAAGTCATTT
TGTTTGTGCTCATCATAACTTATGTTCCATATTTTTTAACCCACATCACTCTTGAAATCGAC
TGTTCAGTTGATGTGCAGGCTTTTACAGGATATAAGCGCTACCAGTGTGTCTATTCCTTGGC
AGAAATCTTTAAGGTCCTGGCTTCATTTTATGTCATTTTGGTTATACTTTATGGTCTGACCT
CTTCCTACAGCCTGTGGTGGATGCTGAGGAGTTCCCTGAAGCAATATTCCTTTGAGGCGTTA
AGAGAAAAAAGCAACTACAGTGACATCCCTGATGTCAAGAATGACTTTGCCTTCATCCTTCA
TCTGGCTGATCAGTATGATCCTCTTTATTCCAAACGCTTCTCCATATTCCTATCAGAGGTCA
GTGAGAACAAACTGAAACAGATCAACCTCAATAATGAATGGACAGTTGAGAAACTGAAAAGT
AAGCTTGTGAAAAATGCCCAGGACAAGATAGAACTGCATCTTTTTATGCTCAACGGTCTTCC
AGACAATGTCTTTGAGTTAACTGAAATGGAAGTGCTAAGCCTGGAGCTTATCCCAGAGGTGA
AGCTGCCCTCTGCAGTCTCACAGCTGGTCAACCTCAAGGAGCTTCGTGTGTACCATTCATCT
CTGGTCGTAGACCATCCTGCACTGGCCTTTCTAGAGGAGAATTTAAAAATCCTCCGCCTGAA
ATTTACTGAAATGGGAAAAATCCCACGCTGGGTATTTCACCTCAAGAATCTCAAGGAACTTT
ATCTTTCGGGCTGTGTTCTCCCTGAACAGTTGAGTACTATGCAGTTGGAGGGCTTTCAGGAC
TTAAAAAATCTAAGGACCCTGTACTTGAAGAGCAGCCTCTCCCGGATCCCACAAGTTGTTACA
GACCTCCTGCCTTCATTGCAGAAACTGTCCCTTGATAATGAGGGAAGCAAACTGGTTGTGTT
GAACAACTTGAAAAAGATGGTCAATCTGAAAAGCCTAGAACTGATCAGCTGTGACCTGGAAC
GCATCCCACATTCCATTTTCAGCCTGAATAATTTGCATGAGTTAGACCTAAGGGAAAATAAC
CTTAAAACTGTGGAAGAGATTAGCTTTCAGCATCTTCAGAATCTTTCCTGCTTAAAGTTGTG
GCACAATAACATTGCTTATATTCCTGCACAGATTGGGGCATTATCTAACCTAGAGCAGCTCT
CTTTGGACCATAATAATATTGAGAATCTGCCCTTGCAGCTTTTCCTATGCACTAAACTACAT
TATTTGGATCTAAGCTATAACCACTTGACCTTCATTCCAGAAGAAATCCAGTATCTGAGTAA
TTTGCAGTACTTTGCTGTGACCAACAACAATATTGAGATGCTACCAGATGGGCTGTTTCAGT
GCAAAAAGCTGCAGTGTTTACTTTTGGGGAAAAATAGCTTGATGAATTTGTCCCCTCATGTG
GGTGAGCTGTCAAACCTTACTCATCTGGAGCTCATTGGTAATTACCTGGAAACACTTCCTCC
TGAACTAGAAGGATGTCAGTCCCTAAAACGGAACTGTCTGATTGTTGAGGAGAACTTGCTCA
ATACTCTTCCTCTCCCTGTAACAGAACGTTTACAGACGTGCTTAGACAAATGTTGACTTAAA
GAAAAGAGACCCGTGTTTCAAAATCATTTTTAAAAGTATGCTCGGCCGGGCGTGGTGGCTCA
TGCCTATAATCCCAGCACTTTGGGAGGCCAAGATGGGCGGATTGCTTGAGGTCAGGAGTTCG
AGACCAGTCTGGCCAACCTGGTGAAACCCCATCTCTGCTAAAACTACAAAAAAATTAGCCAG
GCGTGGTGGCGTGCGCCTGTAATCCCAGCTACTTGGGAGGCTGACGCAGGGGAATTGCTTGA
ACCAGGGAGGTGGAGGTTGCAGTGAGCCGAGATTGTGCCACTGTACACCAGCCTGGGTGACA
GAGCAAGACTCTTATCTCAAAAAAAAAAAAAAA

FIGURE 78

></usr/seqdb2/sst/DNA/Dnaseqs.min/ss.DNA161005
><subunit 1 of 1, 802 aa, 1 stop
><MW: 92235, pI: 6.80, NX(S/T): 5
MITLTELKCLADAQSSYHILKPWWDVFWYYITLIMLLVAVLAGALQLTQSRVLCCLPCKV
EFDNHCAVPWDILKASMNTSSNPGTPLPLPLRIQNDLHRQQYSYIDAVCYEKQLHWFAKF
FPYLVLLHTLIFAACSNFWLHYPSTSSRLEHFVAILHKCFDSPWTTRALSETVAEQSVRP
LKLSKSKILLSSSGCSADIDSGKQSLPYPQPGLESAGIESPTSSGLDKKEGEQAKAIFEK
VKRFRMHVEQKDIIYRVYLKQIIVKVILFVLIITYVPYFLTHITLEIDCSVDVQAFTGYK
RYQCVYSLAEIFKVLASFYVILVILYGLTSSYSLWWMLRSSLKQYSFEALREKSNYSDIP
DVKNDFAFILHLADQYDPLYSKRFSIFLSEVSENKLKQINLNNEWTVEKLKSKLVKNAQD
KIELHLFMLNGLPDNVFELTEMEVLSLELIPEVKLPSAVSQLVNLKELRVYHSSLVVDHP
ALAFLEENLKILRLKFTEMGKIPRWVFHLKNLKELYLSGCVLPEQLSTMQLEGFQDLKNL
RTLYLKSSLSRIPQVVTDLLPSLQKLSLDNEGSKLVVLNNLKKMVNLKSLELISCDLERI
PHSIFSLNNLHELDLRENNLKTVEEISFQHLQNLSCLKLWHNNIAYIPAQIGALSNLEQL
SLDHNNIENLPLQLFLCTKLHYLDLSYNHLTFIPEEIQYLSNLQYFAVTNNNIEMLPDGL
FQCKKLQCLLLGKNSLMNLSPHVGELSNLTHLELIGNYLETLPPELEGCQSLKRNCLIVE
ENLLNTLPLPVTERLQTCLDKC

Important features of the protein:
Signal peptide:
Amino acids 1-46

Transmembrane domains:
Amino acids 118-138;261-281;311-332

N-glycosylation sites:
Amino acids 78-82;355-359;633-637;748-752 cAMP- and cGMP-dependent protein kinase phosphorylation site:
Amino acids 382-386

Tyrosine kinase phosphorylation site:
Amino acids 21-30

N-myristoylation sites:
Amino acids 212-218;327-333;431-437;652-658; 719-725

Prokaryotic membrane lipoprotein lipid attachment site:
Amino acids 125-136

Leucine zipper pattern:
Amino acids 468-490

Leucine Rich Repeat:
Amino acids 609-632; 748-770

FIGURE 79

CGGACGCGTGGGCCGCGCTCCCTCACGGCCCCTCGGCGGCGCCCGTCGGATCCGGCCTCTCT
CTGCGCCCCGGGGCGCGCCACCTCCCCGCCGGAGGTGTCCACGCGTCCGGCCGTCCATCCGT
CCGTCCCTCCTGGGGCCGGCGCTGACCATGCCCAGCGGCTGCCGCTGCCTGCATCTCGTGTG
CCTGTTGTGCATTCTGGGGGCTCCCGGTCAGCCTGTCCGAGCCGATGACTGCAGCTCCCACT
GTGACCTGGCCCACGGCTGCTGTGCACCTGACGGCTCCTGCAGGTGTGACCCGGGCTGGGAG
GGGCTGCACTGTGAGCGCTGTGTGAGGATGCCTGGCTGCCAGCACGGTACCTGCCACCAGCC
ATGGCAGTGCATCTGCCACAGTGGCTGGGCAGGCAAGTTCTGTGACAAAGATGAACATATCT
GTACCACGCAGTCCCCCTGCCAGAATGGAGGCCAGTGCATGTATGACGGGGGCGGTGAGTAC
CATTGTGTGTGCTTACCAGGCTTCCATGGGCGTGACTGCGAGCGCAAGGCTGGACCCTGTGA
ACAGGCAGGCTCCCCATGCCGCAATGGCGGGCAGTGCCAGGACGACCAGGGCTTTGCTCTCA
ACTTCACGTGCCGCTGCTTGGTGGGCTTTGTGGGTGCCCGCTGTGAGGTAAATGTGGATGAC
TGCCTGATGCGGCCTTGTGCTAACGGTGCCACCTGCCTTGACGGCATAAACCGCTTCTCCTG
CCTCTGTCCTGAGGGCTTTGCTGGACGCTTCTGCACCATCAACCTGGATGACTGTGCCAGCC
GCCCATGCCAGAGAGGGGCCCGCTGTCGGGACCGTGTCCACGACTTCGACTGCCTCTGCCCC
AGTGGCTATGGTGGCAAGACCTGTGAGCTTGTCTTACCTGTCCCAGACCCCCCAACCACAGTG
GACACCCCTCTAGGGCCCACCTCAGCTGTAGTGGTACCTGCTACGGGGCCAGCCCCCCACAG
CGCAGGGGCTGGTCTGCTGCGGATCTCAGTGAAGGAGGTGGTGCGGAGGCAAGAGGCTGGGC
TAGGTGAGCCTAGCTTGGTGGCCCTGGTGGTGTTTGGGGCCCTCACTGCTGCCCTGGTTCTG
GCTACTGTGTTGCTGACCCTGAGGGCCTGGCGCCGGGGTGTCTGCCCCCCTGGACCCTGTTG
CTACCCTGCCCCACACTATGCTCCAGCGTGCCAGGACCAGGAGTGTCAGGTTAGCATGCTGC
CAGCAGGGCTCCCCCTGCCACGTGACTTGCCCCCTGAGCCTGGAAAGACCACAGCACTGTGA
TGGAGGTGGGGGCTTTCTGGCCCCCTTCCTCACCTCTTCCACCCCTCAGACTGGAGTGGTCC
GTTCTCACCACCCTTCAGCTTGGGTACACACACAGAGGAGACCTCAGCCTCACACCAGAAAT
ATTATTTTTTAATACACAGAATGTAAGATGGAATTTTATCAAATAAAACTATGAAAATGCA
AAAAAAAAAAAAAAA

FIGURE 80

```
></usr/seqdb2/sst/DNA/Dnaseqs.min/ss.DNA170245
><subunit 1 of 1, 383 aa, 1 stop
><MW: 40548, pI: 6.48, NX(S/T): 1
MPSGCRCLHLVCLLCILGAPGQPVRADDCSSHCDLAHGCCAPDGSCRCDPGWEGLHCERC
VRMPGCQHGTCHQPWQCICHSGWAGKFCDKDEHICTTQSPCQNGGQCMYDGGGEYHCVCL
PGFHGRDCERKAGPCEQAGSPCRNGGQCQDDQGFALNFTCRCLVGFVGARCEVNVDDCLM
RPCANGATCLDGINRFSCLCPEGFAGRFCTINLDDCASRPCQRGARCRDRVHDFDCLCPS
GYGGKTCELVLPVPDPPTTVDTPLGPTSAVVVPATGPAPHSAGAGLLRISVKEVVRRQEA
GLGEPSLVALVVFGALTAALVLATVLLTLRAWRRGVCPPGPCCYPAPHYAPACQDQECQV
SMLPAGLPLPRDLPPEPGKTTAL
```

Important features of the protein:

Signal peptide:
Amino acids 1-21

Transmembrane domain:
Amino acids 306-331

N-glycosylation site:
Amino acids 157-160

Glycosaminoglycan attachment site:
Amino acids 240-243

N-myristoylation sites:
Amino acids 44-49;65-70;243-248;314-319

Aspartic acid and asparagine hydroxylation sites:
Amino acids 189-200;227-238

EGF-like domain cysteine pattern signature:
Amino acids 46-57;77-88;117-128;160-171;198-209;
236-247

Zinc finger, C3HC4 type, signature:
Amino acids 7-16

EGF-like domain proteins:
Amino acids 46-58;77-89;117-129;160-172;198-210;
216-228;236-248

FIGURE 81

GTTTGTTGCTCAAACCGAGTTCTGGAGAACGCCATCAGCTCGCTGCTTAAAATTAAACCACA
GGTTCCATTATGGGTCGACTTGATGGGAAAGTCATCATCCTGACGGCCGCTGCTCAGGGGAT
TGGCCAAGCAGCTGCCTTAGCTTTTGCAAGAGAAGGTGCCAAAGTCATAGCCACAGACATTA
ATGAGTCCAAACTTCAGGAACTGGAAAAGTACCCGGGTATTCAAACTCGTGTCCTTGATGTC
ACAAAGAAGAAACAAATTGATCAGTTTGCCAGTGAAGTTGAGAGACTTGATGTTCTCTTTAAT
GTTGCTGGTTTTGTCCATCATGGAACTGTCCTGGATTGTGAGGAGAAAGACTGGGACTTCTC
GATGAATCTCAATGTGCGCAGCATGTACCTGATGATCAAGGCATTCCTTCCTAAAATGCTTG
CTCAGAAATCTGGCAATATTATCAACATGTCTTCTGTGGCTTCCAGCGTCAAAGGAGTTGTG
AACAGATGTGTGTACAGCACAACCAAGGCAGCCGTGATTGGCCTCACAAAATCTCTGGCTGC
AGATTTCATCCAGCAGGGCATCAGGTGCAACTGTGTGTGCCCAGGAACAGTTGATACGCCAT
CTCTACAAGAAAGAATACAAGCCAGAGGAAATCCTGAAGAGGCACGGAATGATTTCCTGAAG
AGACAAAAGACGGGAAGATTCGCAACTGCAGAAGAAATAGCCATGCTCTGCGTGTATTTGGC
TTCTGATGAATCTGCTTATGTAACTGGTAACCCTGTCATCATTGATGGAGGCTGGAGCTTGT
GATTTTAGGATCTCCATGGTGGGAAGGAAGGCAGGCCCTTCCTATCCACAGTGAACCTGGTT
ACGAAGAAAACTCACCAATCATCTCCTTCCTGTTAATCACATGTTAATGAAAATAAGCTCTT
TTTAATGATGTCACTGTTTGCAAGAGTCTGATTCTTTAAGTATATTAATCTCTTTGTAATCT
CTTCTGAAATCATTGTAAAGAAATAAAAATATTGAACTCAT

FIGURE 82

></usr/seqdb2/sst/DNA/Dnaseqs.min/ss.DNA171771
><subunit 1 of 1, 245 aa, 1 stop
><MW: 26711, pI: 8.00, NX(S/T): 2
MGRLDGKVIILTAAAQGIGQAAALAFAREGAKVIATDINESKLQELEKYPGIQTRVLDVT
KKKQIDQFASEVERLDVLFNVAGFVHHGTVLDCEEKDWDFSMNLNVRSMYLMIKAFLPKM
LAQKSGNIINMSSVASSVKGVVNRCVYSTTKAAVIGLTKSLAADFIQQGIRCNCVCPGTV
DTPSLQERIQARGNPEEARNDFLKRQKTGRFATAEEIAMLCVYLASDESAYVTGNPVIID
GGWSL

Important features of the protein:
Signal peptide:
Amino acids 1-20

N-glycosylation sites:
Amino acids 39-43;130-134

Tyrosine kinase phosphorylation site:
Amino acids 42-50

N-myristoylation sites:
Amino acids 17-23;19-25;126-132;156-162;169-175

Short-chain dehydrogenases/reductases family proteins:
Amino acids 7-19;73-83;127-164; 169-178

Short chain dehydrogenase:
Amino acids 7-183

FIGURE 83

GGGCGGCGGCGGCAGCGGTTGGAGGTTGTAGGACCGGCGAGGAATAGGAATCATGGCGGCTG
CGCTGTTCGTGCTGCTGGGATTCGCGCTGCTGGGCACCCACGGAGCCTCCGGGGCTGCCGGC
TTCGTCCAGGCGCCGCTGTCCCAGCAGAGGTGGGTGGGGGCAGTGTGGAGCTGCACTGCGA
GGCCGTGGGCAGCCCGGTGCCCGAGATCCAGTGGTGGTTTGAAGGGCAGGGTCCCAACGACA
CCTGCTCCCAGCTCTGGGACGGCGCCCGGCTGGACCGCGTCCACATCCACGCCACCTACCAC
CAGCACGCGGCCAGCACCATCTCCATCGACACGCTCGTGGAGGAGGACACGGGCACTTACGA
GTGCCGGGCCAGCAACGACCCGGATCGCAACCACCTGACCCGGGCGCCCAGGGTCAAGTGGG
TCCGCGCCCAGGCAGTCGTGCTAGTCCTGGAACCCGGCACAGTCTTCACTACCGTAGAAGAC
CTTGGCTCCAAGATACTCCTCACCTGCTCCTTGAATGACAGCGCCACAGAGGTCACAGGGCA
CCGCTGGCTGAAGGGGGGCGTGGTGCTGAAGGAGGACGCGCTGCCCGGCCAGAAAACGGAGT
TCAAGGTGGACTCCGACGACCAGTGGGGAGAGTACTCCTGCGTCTTCCTCCCCGAGCCCATG
GGCACGGCCAACATCCAGCTCCACGGGCCTCCCAGAGTGAAGGCTGTGAAGTCGTCAGAACA
CATCAACGAGGGGGAGACGGCCATGCTGGTCTGCAAGTCAGAGTCCGTGCCACCTGTCACTG
ACTGGGCCTGGTACAAGATCACTGACTCTGAGGACAAGGCCCTCATGAACGGCTCCGAGAGC
AGGTTCTTCGTGAGTTCCTCGCAGGGCCGGTCAGAGCTACACATTGAGAACCTGAACATGGA
GGCCGACCCCGGCCAGTACCGGTGCAACGGCACCAGCTCCAAGGGCTCCGACCAGGCCATCA
TCACGCTCCGCGTGCGCAGCCACCTGGCCGCCCTCTGGCCCTTCCTGGGCATCGTGGCTGAG
GTGCTGGTGCTGGTCACCATCATCTTCATCTACGAGAAGCGCCGGAAGCCCGAGGACGTCCT
GGATGATGACGACGCCGGCTCTGCACCCCTGAAGAGCAGCGGGCAGCACCAGAATGACAAAG
GCAAGAACGTCCGCCAGAGGAACTCTTCCTGAGGCAGGTGGCCCGAGGACGCTCCCTGCTCC
ACGTCTGCGCCGCCGCCGGAGTCCACTCCCAGTGCTTGCAAGATTCCAAGTTCTCACCTCTT
AAAGAAAACCCACCCCGTAGATTCCCATCATACACTTCCTTCTTTTTTAAAAAAGTTGGGTT
TTCTCCATTCAGGATTCTGTTCCTTAGGTTTTTTTCCTTCTGAAGTGTTTCACGAGAGCCCG
GGAGCTGCTGCCCTGCGGCCCCGTCTGTGGCTTTCAGCCTCTGGGTCTGAGTCATGGCCGGG
TGGGCGGCACAGCCTTCTCCACTGGCCGGAGTCAGTGCCAGGTCCTTGCCCTTTGTGGAAAGTC
ACAGGTCACACGAGGGGCCCCGTGTCCTGCCTGTCTGAAGCCAATGCTGTCTGGTTGCGCCA
TTTTTGTGCTTTTATGTTTAATTTTATGAGGGCCACGGGTCTGTGTTCGACTCAGCCTCAGG
GACGACTCTGACCTCTTGGCCACAGAGGACTCACTTGCCCACACCGAGGGCGACCCCGTCAC
AGCCTCAAGTCACTCCCAAGCCCCCTCCTTGTCTGTGCATCCGGGGGCAGCTCTGGAGGGGG
TTTGCTGGGGAACTGGCGCCATCGCCGGGACTCCAGAACCGCAGAAGCCTCCCCAGCTCACC
CCTGGAGGACGGCCGGCTCTCTATAGCACCAGGGCTCACGTGGGAACCCCCCTCCCACCCAC
CGCCACAATAAAGATCGCCCCCACCTCCACCCAAAAA

FIGURE 84

></usr/seqdb2/sst/DNA/Dnaseqs.min/ss.DNA173157
><subunit 1 of 1, 385 aa, 1 stop
><MW: 42200, pI: 5.57, NX(S/T): 5
MAAALFVLLGFALLGTHGASGAAGFVQAPLSQQRWVGGSVELHCEAVGSPVPEIQWWFEG
QGPNDTCSQLWDGARLDRVHIHATYHQHAASTISIDTLVEEDTGTYECRASNDPDRNHLT
RAPRVKWVRAQAVVLVLEPGTVFTTVEDLGSKILLTCSLNDSATEVTGHRWLKGGVVLKE
DALPGQKTEFKVDSDDQWGEYSCVFLPEPMGTANIQLHGPPRVKAVKSSEHINEGETAML
VCKSESVPPVTDWAWYKITDSEDKALMNGSESRFFVSSSQGRSELHIENLNMEADPGQYR
CNGTSSKGSDQAIITLRVRSHLAALWPFLGIVAEVLVLVTIIFIYEKRRKPEDVLDDDDA
GSAPLKSSGQHQNDKGKNVRQRNSS

Important features of the protein:
Signal peptide:
Amino acids 1-18

Transmembrane domain:
Amino acids 320-343

N-glycosylation sites:
Amino acids 64-68;160-164;268-272;302-306

N-myristoylation sites:
Amino acids 15-21;18-24;60-66;104-110;140-146;
297-303;308-314;369-375

Immunoglobulin domain:
Amino acids 37-110;150-205;235-303

FIGURE 85

GGCTCGAGCAAAGACATACGAACAGGGAGGAAGGCCGACTGAAAGAAAGACGGAGAAGAGGA
GAGAGAAGCCAGGGCCGAGCGTGCCAGCAGGCGGATGGAGGGCGGCCTGGTGGAGGAGGAGA
CGTAGTGGCCTGGGCTGAGCTGGGTGGGCCGGGAGAAGCGGGTGCCTCAGAGTGGGGGTGGG
GGCATGGGAGGGGCAGGCATTCTGCTGCTGCTGCTGGCTGGGGCGGGGGTGGTGGTGGCCTGG
AGACCCCCAAAGGGAAAGTGTCCCCTGCGCTGCTCCTGCTCTAAAGACAGCGCCCTGTGTGA
GGGCTCCCCGGACCTGCCCGTCAGCTTCTCTCCGACCCTGCTGTCACTCTCACTCGTCAGGA
CGGGAGTCACCCAGCTGAAGGCCGGCAGCTTCCTGAGAATTCCGTCTCTGCACCTGCTCCTC
TTCACCTCCAACTCCTTCTCCGTGATTGAGGACGATGCATTTGCGGGCCTGTCCCACCTGCA
GTACCTCTTCATCGAGGACAATGAGATTGGCTCCATCTCTAAGAATGCCCTCAGAGGACTTC
GCTCGCTTACACACCTAAGCCTGGCCAATAACCATCTGGAGACCCTCCCCAGATTCCTGTTC
CGAGGCCTGGACACCCTTACTCACGTGGACCTCCGCGGGAACCCGTTCCAGTGTGACTGCCG
CGTCCTCTGGCTCCTGCAGTGGATGCCCACCGTGAATGCCAGCGTGGGGACCGGCGCCTGTG
CGGGCCCCGCCTCCCTGAGCCACATGCAGCTCCACCACCTCGACCCCAAGACTTTCAAGTGC
AGAGCCATAGGTGGGGGGCTTTCCCGATGGGGTGGGAGGCGGGAGATCTGGGGGAAAGGCTG
CCAGGGCCAAGAGGCTCGTCTCACTCCCTGCCCTGCCATTTCCCGGAGTGGGAAGACCCTGA
GCAAGCAGCACTGCCTTCCTGAGCCCCAGTTTTCTCATCTGTAAAGTGGGGGTAATAAACAG
TGATATAGG

FIGURE 86

></usr/seqdb2/sst/DNA/Dnaseqs.min/ss.DNA175734
><subunit 1 of 1, 261 aa, 1 stop
><MW: 28231, pI: 9.28, NX(S/T): 1
MGGAGILLLLLAGAGVVVAWRPPKGKCPLRCSCSKDSALCEGSPDLPVSFSPTLLSLSLV
RTGVTQLKAGSFLRIPSLHLLLFTSNSFSVIEDDAFAGLSHLQYLFIEDNEIGSISKNAL
RGLRSLTHLSLANNHLETLPRFLFRGLDTLTHVDLRGNPFQCDCRVLWLLQWMPTVNASV
GTGACAGPASLSHMQLHHLDPKTFKCRAIGGGLSRWGGRREIWGKGCQGQEARLTPCPAI
SRSGKTLSKQHCLPEPQFSHL

Important features of the protein:
Signal peptide:
Amino acids 1-19

N-glycosylation site:
Amino acids 177-181

N-myristoylation sites:
Amino acids 15-21;181-186;210-215

Amidation site:
Amino acids 217-220

Microbodies C-terminal targeting signal:
Amino acids 259-262

ATP/GTP-binding site motif A (P-loop):
Amino acids 239-246

Leucine zipper pattern:
Amino acids 129-150

Leucine Rich Repeat:
Amino acids 53-76; 149-171

Leucine rich repeat C-terminal domain:
Amino acids 158-207

FIGURE 87

CGGACGCGTGGGGCGGCGAGAGCAGCTGCAGTTCGCATCTCAGGCAGTACCTAGAGGAGCTG
CCGGTGCCTCCTCAGAACATCTCCTGATCGCTACCCAGGACCAGGCACCAAGGACAGGGAGT
CCCAGGCGCACACCCCCCATTCTGGGTCCCCCAGGCCCAGACCCCCACTCTGCCACAGGTTG
CATCTTGACCTGGTCCTCCTGCAGAAGTGGCCCCTGTGGTCCTGCTCTGAGACTCGTCCCTG
GGCGCCCCTGCAGCCCCTTTCTATGACTCCATCTGGATTTGGCTGGCTGTGGGGACGCGGTC
CGAGGGGCGGCCTGGCTCTCAGCGTGGTGGCAGCCAGCTCTCTGGCCACCATGGCAAATGCT
GAGATCTGAGGGGACAAGGCTCTACAGCCTCAGCCAGGGGCACTCAGCTGTTGCAGGGTGTG
ATGGAGAACAAAGCTATGTACCTACACACCGTCAGCGACTGTGACACCAGCTCCATCTGTGA
GGATTCCTTTGATGGCAGGAGCCTGTCCAAGCTGAACCTGTGTGAGGATGGTCCATGTCACA
AACGGCGGGCAAGCATCTGCTGTACCCAGCTGGGGTCCCTGTCGGCCCTGAAGCATGCTGTC
CTGGGGCTCTACCTGCTGGTCTTCCTGATTCTTGTGGGCATCTTCATCTTAGCAGGGCCACC
GGGACCCAAAGGTGATCAGGGGGATGAAGGAAAGGAAGGCAGGCCTGGCATCCCTGGATTGC
CTGGACTTCGAGGTCTGCCCGGGGAGAGAGGTACCCCAGGATTGCCCGGGCCCAAGGGCGAT
GATGGGAAGCTGGGGGCCACAGGACCAATGGGCATGCGTGGGTTCAAAGGTGACCGAGGCCC
AAAAGGAGAGAAAGGAGAGAAAGGAGACAGAGCTGGGGATGCCAGTGGCGTGGAGGCCCCGA
TGATGATCCGCCTGGTGAATGGCTCAGGTCCGCACGAGGGCCGCGTGGAAGTGTACCACGAC
CGGCGCTGGGGCACCGTGTGTGACGACGGCTGGGACAAGAAGGACGGAGACGTGGTGTGCCG
CATGCTCGGCTTCCGCGGTGTGGAGGAGGTGTACCGCACAGCTCGATTCGGGCAAGGCACTG
GGAGGATCTGGATGGATGACGTTGCCTGCAAGGGCACAGAGGAAACCATCTTCCGCTGCAGC
TTCTCCAAATGGGGGGTGACAAACTGTGGACATGCCGAAGATGCCAGCGTGACATGCAACAG
ACACTGAAAGTGGGCAGAGCCCAAGTTCGGGGTCCTGCACAGAGCACCCTTGCTGCATCCCT
GGGGTGGGGCACAGCTCGGGGCCACCCTGACCATGCCTCGACCACACCCCGTCCAGCATTCT
CAGTCCTCACACCTGCATCCCAGGACCGTGGGGGCCGGTCGTCATTTCCCTCTTGAACATGT
GCTCCGAAGTATAACTCTGGGACCTACTGCCCGTCTCTCTCTTCCACCAGGTTCCTGCATGA
GGAGCCCTGATCAACTGGATCACCACTTTGCCCAGCCTCTGAACACCATGCACCAGGCCTCA
ATATCCCAGTTCCCTTTGGCCTTTTAGTTACAGGTGAATGCTGAGAATGTGTCAGAGACAAG
TGCAGCAGCAGCGATGGTTGGTAGTATAGATCATTTACTCTTCAGACAATTCCCAAACCTCC
ATTAGTCCAAGAGTTTCTACATCTTCCTCCCCAGCAAGAGGCAACGTCAAGTGATGAATTTC
CCCCCTTTACTCTGCCTCTGCTCCCCATTTGCTAGTTTGAGGAAGTGACATAGAGGAGAAGC
CAGCTGTAGGGGCAAGAGGGAAATGCAAGTCACCTGCAGGAATCCAGCTAGATTTGGAGAAG
GGAATGAAACTAACATTGAATGACTACCATGGCACGCTAAATAGTATCTTGGGTGCCAAATTCA
TGTATCCACTTAGCTGCATTGGTCCAGGGCATGTCAGTCTGGATACAGCCTTACCTTCAGGT
AGCACTTAACTGGTCCATTCACCTAGACTGCAAGTAAGAAGACAAAATGACTGAGACCGTGT
GCCCACCTGAACTTATTGTCTTTACTTGGCCTGAGCTAAAAGCTTGGGTGCAGGACCTGTGT
AACTAGAAAGTTGCCTACTTCAGAACCTCCAGGGCGTGAGTGCAAGGTCAAACATGACTGGC
TTCCAGGCCGACCATCAATGTAGGAGGAGAGCTGATGTGGAGGGTGACATGGGGGCTGCCCA
TGTTAAACCTGAGTCCAGTGCTCTGGCATTGGGCAGTCACGGTTAAAGCCAAGTCATGTGTG
TCTCAGCTGTTTGGAGGTGATGATTTTGCATCTTCCAAGCCTCTTCAGGTGTGAATCTGTGG
TCAGGAAAACACAAGTCCTAATGGAACCCTTAGGGGGGAAGGAAATGAAGATTCCCTATAAC
CTCTGGGGGTGGGGAGTAGGAATAAGGGGCCTTGGGCCTCCATAAATCTGCAATCTGCACCC
TCCTCCTAGAGACAGGGAGATCGTGTTCTGCTTTTTACATGAGGAGCAGAACTGGGCCATAC
ACGTGTTCAAGAACTAGGGGAGCTACCTGGTAGCAAGTGAGTGCAGACCCACCTCACCTTGG
GGGAATCTCAAACTCATAGGCCTCAGATACACGATCACCTGTCATATCAGGTGAGCACTGGC
CTGCTTGGGGAGAGACCTGGGCCCCTCCAGGTGTAGGAACAGCAACACTCCTGGCTGACAAC
TAAGCCAATATGGCCCTAGGTCATTCTTGCTTCCAATATGCTTGCCACTCCTTAAATGTCCT
AATGATGAGAAACTCTCTTTCTGACCAATTGCTATGTTTACATAACACGCATGTACTCATGC
ATCCCTTGCCAGAGCCCATATATGTATGCATATATAAACATAGCACTTTTTACTACATAGCT
CAGCACATTGCAAGGTTTGCATTTAAGTT

FIGURE 88

></usr/seqdb2/sst/DNA/Dnaseqs.min/ss.DNA176108
><subunit 1 of 1, 270 aa, 1 stop
><MW: 28871, pI: 7.09, NX(S/T): 1
MENKAMYLHTVSDCDTSSICEDSFDGRSLSKLNLCEDGPCHKRRASICCTQLGSLSALKH
AVLGLYLLVFLILVGIFILAGPPGPKGDQGDEGKEGRPGIPGLPGLRGLPGERGTPGLPG
PKGDDGKLGATGPMGMRGFKGDRGPKGEKGEKGDRAGDASGVEAPMMIRLVNGSGPHEGR
VEVYHDRRWGTVCDDGWDKKDGDVVCRMLGFRGVEEVYRTARFGQGTGRIWMDDVACKGT
EETIFRCSFSKWGVTNCGHAEDASVTCNRH

Transmembrane domain:
Amino acids 55-80

N-glycosylation site:
Amino acids 172-175 cAMP- and cGMP-dependent protein kinase phosphorylation site:
Amino acids 43-46

Tyrosine kinase phosphorylation site:
Amino acids 212-218

N-myristoylation sites:
Amino acids 53-58;224-229;239-244;253-258

Speract receptor repeated domain signature:
Amino acids 173-211

Scavenger receptor cysteine-rich domain:
Amino acids 171-268

Collagen Collagen triple helix repeat:
Amino acids 90-149

FIGURE 89

GTCGCCGCGAGGGACGCAGAGAGCACCCTCCACGCCCAGATGCCTGCGTAGTTTTTGTGACC
AGTCCGCTCCTGCCTCCCCCTGGGGCAGTAGAGGGGGAGCGATGGAGAACTGGACTGGCAGG
CCCTGGCTGTATCTGCTGCTGCTTCTGTCCCTCCCTCAGCTCTGCTTGGATCAGGAGGTGTT
GTCCGGACACTCTCTTCAGACACCTACAGAGGAGGGCCAGGGCCCCGAAGGTGTCTGGGGAC
CTTGGGTCCAGTGGGCCTCTTGCTCCCAGCCCTGCGGGGTGGGGGTGCAGCGCAGGAGCCGG
ACATGTCAGCTCCCTACAGTGCAGCTCCACCCGAGTCTGCCCCTCCCTCCCCGGCCCCCAAG
ACATCCAGAAGCCCTCCTCCCCCGGGGCCAGGGTCCCAGACCCCAGACTTCTCCAGAAACCC
TCCCCTTGTACAGGACACAGTCTCGGGGAAGGGGTGGCCCACTTCGAGGTCCCGCTTCCCAC
CTAGGGAGAGAGGAGACCCAGGAGATTCGAGCGGCCAGGAGGTCCCGGCTTCGAGACCCCAT
CAAGCCAGGAATGTTCGGTTATGGGAGAGTGCCCTTTGCATTGCCACTGCACCGGAACCGCA
GGCACCCTCGGAGCCCACCCAGATCTGAGCTGTCCCTGATCTCTTCTAGAGGGGAAGAGGCT
ATTCCGTCCCCTACTCCAAGAGCAGAGCCATTCTCCGCAAACGGCAGCCCCCAAACTGAGCT
CCCTCCCACAGAACTGTCTGTCCACACCCCATCCCCCCAAGCAGAACCTCTAAGCCCTGAAA
CTGCTCAGACAGAGGTGGCCCCCAGAACCAGGCCTGCCCCCCTACGGCATCACCCCAGAGCC
CAGGCCTCTGGCACAGAGCCCCCCTCACCCACGCACTCCTTAGGAGAAGGTGGCTTCTTCCG
TGCATCCCCTCAGCCACGAAGGCCAAGTTCCCAGGGTTGGGCCAGTCCCCAGGTAGCAGGGA
GACGCCCTGATCCTTTTCCTTCGGTCCCTCGGGGCCGAGGCCAGCAGGGCCAAGGGCCTTGG
GGAACGGGGGGGACTCCTCACGGGCCCCGCCTGGAGCCTGACCCTCAGCACCCGGGCGCCTG
GCTGCCCCTGCTGAGCAACGGCCCCCATGCCAGCTCCCTCTGGAGCCTCTTTGCTCCCAGTA
GCCCTATTCCAAGATGTTCTGGGGAGAGTGAACAGCTAAGAGCCTGCAGCCAAGCGCCCTGC
CCCCCTGAGCAGCCAGACCCCCGGGCCCTGCAGTGCGCAGCCTTTAACTCCCAGGAATTCATG
GGCCAGCTGTATCAGTGGGAGCCCTTCACTGAAGTCCAGGGCTCCCAGCGCTGTGAACTGAA
CTGCCGGCCCCGTGGCTTCCGCTTCTATGTCCGTCACACTGAAAAGGTCCAGGATGGGACCC
TGTGTCAGCCTGGAGCCCCTGACATCTGTGTGGCTGGACGCTGTCTGAGCCCCGGCTGTGAT
GGGATCCTTGGCTCTGGCAGGCGTCCTGATGGCTGTGGAGTCTGTGGGGGTGATGATTCTAC
CTGTCGCCTTGTTTCGGGGAACCTCACTGACCGAGGGGGCCCCCTGGGCTATCAGAAGATCT
TGTGGATTCCAGCGGGAGCCTTGCGGCTCCAGATTGCCCAGCTCCGGCCTAGCTCCAACTAC
CTGGCACTTCGTGGCCCTGGGGGCCGGTCCATCATCAATGGGAACTGGGCTGTGGATCCCCC
TGGGTCCTACAGGGCCGGCGGGACCGTCTTTCGATATAACCGTCCTCCCAGGGAGGAGGGCA
AAGGGGAGAGTCTGTCGGCTGAAGGCCCCACCACCCAGCCTGTGGATGTCTATATGATCTTT
CAGGAGGAAAACCCAGGCGTTTTTTATCAGTATGTCATCTCTTCACCTCCTCCAATCCTTGA
GAACCCCACCCCAGAGCCCCCTGTCCCCCAGCTTCAGCCGGAGATTCTGAGGGTGGAGCCCC
CACTTGCTCCGGCACCCCGCCCAGCCCGGACCCCAGGCACCCTCCAGCGTCAGGTGCGGATC
CCCCAGATGCCCGCCCCGCCCCATCCCAGGACACCCCTGGGGTCTCCAGCTGCGTACTGGAA
ACGAGTGGGACACTCTGCATGCTCAGCGTCCTGCGGGAAAGGTGTCTGGCGCCCCATTTTCC
TCTGCATCTCCCGTGAGTCGGGAGAGGAACTGGATGAACGCAGCTGTGCCGCGGGTGCCAGG
CCCCCAGCCTCCCCTGAACCCTGCCACGGCACCCCATGCCCCCCATACTGGGAGGCTGGCGA
GTGGACATCCTGCAGCCGCTCCTGTGGCCCCGGCACCCAGCACCGCCAGCTGCAGTGCCGGC
AGGAATTTGGGGGGGGTGGCTCCTCGGTGCCCCCGGAGCGCTGTGGACATCTCCCCCGGCCC
AACATCACCCAGTCTTGCCAGCTGCGCCTCTGTGGCCATTGGGAAGTTGGCTCTCCTTGGAG
CCAGTGCTCCGTGCGGTGCGGCCGGGGCCAGAGAAGCCGGCAGGTTCGCTGTGTTGGGAACA
ACGGTGATGAAGTGAGCGAGCAGGAGTGTGCGTCAGGCCCCCCACAGCCCCCCAGCAGAGAG
GCCTGTGACATGGGGCCCTGTACTACTGCCTGGTTCCACAGCGACTGGAGCTCCAAGGTGAG
CCCGGAACCCCCAGCCATATCCTGCATCCTGGGTAACCATGCCCAGGACACCTCAGCCTTTC
CAGCATAGCTCAATAAACTTGTATTGATC

FIGURE 90

></usr/seqdb2/sst/DNA/Dnaseqs.min/ss.DNA190710
><subunit 1 of 1, 877 aa, 1 stop
><MW: 95132, pI: 8.77, NX(S/T): 5
MENWTGRPWLYLLLLLSLPQLCLDQEVLSGHSLQTPTEEGQGPEGVWGPWVQWASCSQPC
GVGVQRRSRTCQLPTVQLHPSLPLPPRPPRHPEALLPRGQGPRPQTSPETLPLYRTQSRG
RGGPLRGPASHLGREETQEIRAARRSRLRDPIKPGMFGYGRVPFALPLHRNRRHPRSPPR
SELSLISSRGEEAIPSPTPRAEPFSANGSPQTELPPTELSVHTPSPQAEPLSPETAQTEV
APRTRPAPLRHHPRAQASGTEPPSPTHSLGEGGFFRASPQPRRPSSQGWASPQVAGRRPD
PFPSVPRGRGQQGQGPWGTGGTPHGPRLEPDPQHPGAWLPLLSNGPHASSLWSLFAPSSP
IPRCSGESEQLRACSQAPCPPEQPDPRALQCAAFNSQEFMGQLYQWEPFTEVQGSQRCEL
NCRPRGFRFYVRHTEKVQDGTLCQPGAPDICVAGRCLSPGCDGILGSGRRPDGCGVCGGD
DSTCRLVSGNLTDRGGPLGYQKILWIPAGALRLQIAQLRPSSNYLALRGPGGRSIINGNW
AVDPPGSYRAGGTVFRYNRPPREEGKGESLSAEGPTTQPVDVYMIFQEENPGVFYQYVIS
SPPPILENPTPEPPVPQLQPEILRVEPPLAPAPRPARTPGTLQRQVRIPQMPAPPHPRTP
LGSPAAYWKRVGHSACSASCGKGVWRPIFLCISRESGEELDERSCAAGARPPASPEPCHG
TPCPPYWEAGEWTSCSRSCGPGTQHRQLQCRQEFGGGGSSVPPERCGHLPRPNITQSCQL
RLCGHWEVGSPWSQCSVRCGRGQRSRQVRCVGNNGDEVSEQECASGPPQPPSREACDMGP
CTTAWFHSDWSSKVSPEPPAISCILGNHAQDTSAFPA

Important features of the protein:
Signal peptide:
Amino acids 1-24

N-glycosylation sites:
Amino acids 3-6;490-493;773-776 cAMP- and cGMP-dependent protein kinase phosphorylation site:
Amino acids 282-285

N-myristoylation sites:
Amino acids 208-213;414-419;463-468;473-478;475-480;
478-483;495-500;546-551;662-667;755-760;
756-761;789-794

Amidation sites:
Amino acids 295-298;467-470

Leucine zipper pattern:
Amino acids 504-526

VWFC domain proteins:
Amino acids 53-67;732-746;792-806

Thrombospondin type 1 domain:
Amino acids 48-87;727-783;787-841

FIGURE 91

CGAGTATTTTCCCACCATCTCCAGCCGGAAACTGACCAAGAACTCTGAGGCGGATGGCATGT
TCGCGTACGTCTTCCATGATGAGTTCGTGGCCTCGATGATTAAGATCCCTTCGGACACCTTC
ACCATCATCCCTGACTTTGATATCTACTATGTCTATGGTTTTAGCAGTGGCAACTTTGTCTA
CTTTTTGACCCTCCAACCTGAGATGGTGTCTCCACCAGGCTCCACCACCAAGGAGCAGGTGT
ATACATCCAAGCTCGTGAGGCTTTGCAAGGAGGACACAGCCTTCAACTCCTATGTAGAGGTG
CCCATTGGCTGTGAGCGCAGTGGGGTGGAGTACCGCCTGCTGCAGGCTGCCTACCTGTCCAA
AGCGGGGGCCGTGCTTGGCAGGACCCTTGGAGTCCATCCAGATGATGACCTGCTCTTCACCG
TCTTCTCCAAGGGCCAGAAGCGGAAAATGAAATCCCTGGATGAGTCGGCCCTGTGCATCTTC
ATCTTGAAGCAGATAAATGACCGCATTAAGGAGCGGCTGCAGTCTTGTTACCGGGGCGAGGG
CACGCTGGACCTGGCCTGGCTCAAGGTGAAGGACATCCCCTGCAGCAGTGCGCTCTTAACCA
TTGACGATAACTTCTGTGGCCTGGACATGAATGCTCCCCTGGGAGTGTCCGACATGGTGCGT
GGAATTCCCGTCTTCACGGAGGACAGGGACCGCATGACGTCTGTCATCGCATATGTCTACAA
GAACCACTCTCTGGCCTTTGTGGGCACCAAAAGTGGCAAGCTGAAGAAGGTGCCTGGTACCA
GCCTCTGCCCTACCCTTGAGCTACAGACGGGACCCCGATCCCACAGAGCAACAGTGACTCTG
GAACTCCTGTTCTCCAGCTGTTCATCAAACTGAGAAAAACTTCAGAGCTGTGTAGGCTTATT
TAGTGTGTTGTCAGCCTTGGATATTGGAAAATGGAAACAGATGAGACACATCTACCTCCCTG
TGACCCCAGCCATACATCATAGCTCATGTCCTGCCACCCCAAGTCCTTAGGGAAAAAGACT
TTGGAGAATGTGTCTCTGCTTAGCTTGGCTAGGTAGTTGGTCTCTTTTCTCTGCCCCAAGCG
TCCCCTGGGTAATTTTGGACAATGGAGTGTAGGCATGTTTGACTCTTGTGGTGTTATCACTT
GTATATGTCAGTGAAACTAACTGATTCTCCCATCGGAATATAGTTATCTCTTGGGCCTGATA
TATGGTAGGATAACCTTATGCTCATCTGTCCACTTCTGCAGCCAAGTCGCCTGGCCAGTGTG
TGTGTGTGTGTGTGTGTGTGTGTGTGTGTGTGTGTATGCTTATCTGTGTTTAAAGGTGTGTG
TGCATACACAGGGCAGAGAGGATGGAGCCCACCGTACTGCAGCATCATGTAATTAACTCAGT
GCTCAGAACCATCCCAGCCTCTGCGGGAAAGAGAAAAGTAAGCCAACAGTGCCTGATGAGCT
GATCATATGTGCAAAAGCTCTGTTGGCATCTGGTCCAGGAGAGCACCCAAAAAAAGTTAATT
GGTGTTGTCCAGTCTCCTTTCCTTAAGACTATGGTTACAACAAAGCGTGAGCAGTGTCTCCT
GCATGGCCACTATCCAGCACAATTCCATAATTCCCCCATAGAGCCGGTGGGGAGGAGGAGGT
GAGTGGCGAAGGAAGTGGAAACACTTGGTGTCATGTGCTCCTATCATTTCTACTAGCTTACT
GGGAAATAAAGTGTAGTCAAGAGTGTATGAAGGCAAGATGTAAAATTAGCGACTGGTGCTAA
TCTGGTTACTTGAAAACAAGTGAAAGTGCTGTAGATTTGTTCTGTTGCTAAGAACCACCACA
CTAAACCTCGTATAGTTCCTGGAGGATATACAACAGTGTAATTCTCTTTAGGGTGTGCCACA
GGTTCCTGGCCTGTGGGAGGGAATGAATCAGGAGGGCTCTTGAGAACCTTCATCTGTGTGCT
TGCACTGAAAGTGAGTCCCAAAGCTGGAGATTTAGTGAGAGCAGGCAACCCCTCTGTGTCTC
ACTGTCCATATTCTGGAGGCAGAGGTTTGTAACAGGCCATGTGCACCTGCATAGGGATGGGT
AAAGCAAGGACTTTGAAAGAGTTGAAAAGCATTATAAACAGTTGTTCAGAAATACGTCCCAG
GAGTTCCATGTGAAACTGGCTCTGTGTGCATTGAAGCATGGCTGTTGGGAATTCTAACTGGT
CCAACACTCCTGCAAAACAATGTGTAAATATTTAGGAAGAAACTTGAAAATAGTCAAATCCT
TTGAACTGGTGACAATTTTTTAAAGAATCAATTCTAATTTGTTTCAAGGGTAATAATCACCA
AGATACACATTTCAGCATTTATTTAGTCTATCAAAAATTGGAATTGATATATACACTCATTT
ATAGGAGAATGGTTAGGTAGATTTGGTATATTTATGTAGTCATTGAAAACTTAGTTTATAAA
GGCCAATCTTGTAACTGATTCTTGTGTGATAACATTCAGTGAAAAAGCATGAGACAATTAGA
AAGCATGATACAATGAATAAAATAAAAACTGGAAAGAGAACCATCAAAATGCTAA

FIGURE 92

></usr/seqdb2/sst/DNA/Dnaseqs.min/ss.DNA190803
><subunit 1 of 1, 280 aa, 1 stop
><MW: 31222, pI: 7.40, NX(S/T): 1
MFAYVFHDEFVASMIKIPSDTFTIIPDFDIYYVYGFSSGNFVYFLTLQPEMVSPPGSTTK
EQVYTSKLVRLCKEDTAFNSYVEVPIGCERSGVEYRLLQAAYLSKAGAVLGRTLGVHPDD
DLLFTVFSKGQKRKMKSLDESALCIFILKQINDRIKERLQSCYRGEGTLDLAWLKVKDIP
CSSALLTIDDNFCGLDMNAPLGVSDMVRGIPVFTEDRDRMTSVIAYVYKNHSLAFVGTKS
GKLKKVPGTSLCPTLELQTGPRSHRATVTLELLFSSCSSN

Important features of the protein:

N-glycosylation site:
Amino acids 230-233

N-myristoylation sites:
Amino acids 87-92;107-112;194-199;237-242

FIGURE 93

CCTTATCAGACAAAGGACGAGATGGAAAATACAAGATAATTTACAGTGGAGAAGAATTAGAA
TGTAACCTGAAAGATCTTAGACCAGCAACAGATTATCATGTGAGGGTGTATGCCATGTACAA
TTCCGTAAAGGGATCCTGCTCCGAGCCTGTTAGCTTCACCACCCACAGCTGTGCACCCGAGT
GTCCTTTCCCCCCTAAGCTGGCACATAGGAGCAAAAGTTCACTAACCCTGCAGTGGAAGGCA
CCAATTGACAACGGTTCAAAAATCACCAACTACCTTTTAGAGTGGGATGAGGGAAAAAGAAA
TAGTGGTTTCAGACAGTGCTTCTTCGGGAGCCAGAAGCACTGCAAGTTGACAAAGCTTTGTC
CGGCAATGGGGTACACATTCAGGCTGGCCGCTCGAAACGACATTGGCACCAGTGGTTATAGC
CAAGAGGTGGTGTGCTACACATTAGGAAATATCCCTCAGATGCCTTCTGCACTAAGGCTGGT
TCGAGCTGGCATCACATGGGTCACGTTGCAGTGGAGTAAGCCAGAAGGCTGTTCACCCGAGG
AAGTGATCACCTACACCTTGGAAATTCAGGAGGATGAAAATGATAACCTTTTCCACCCAAAA
TACACTGGAGAGGATTTAACCTGTACTGTGAAAAATCTCAAAAGAAGCACACAGTATAAATT
CAGGCTGACTGCTTCTAATACGGAAGGAAAAAGCTGTCCAAGCGAAGTTCTTGTTTGTACGA
CGAGTCCTGACAGGCCTGGACCTCCTACCAGACCGCTTGTCAAAGGCCCAGTTACATCTCAT
GGCTTTAGTGTCAAATGGGATCCCCCTAAGGACAATGGTGGTTCAGAAATCCTCAAGTACTT
GCTAGAGATTACTGATGGAAATTCTGAAGCGAATCAGTGGGAAGTGGCCTACAGTGGGTCGG
CTACCGAATACACCTTCACCCACTTGAAACCAGGCACTTTGTACAAACTCCGAGCATGCTGC
ATCAGTACCGGCGGACACAGCCAGTGTTCTGAAAGTCTCCCTGTTCGCACACTAAGCATTGC
ACCAGGTCAATGTCGACCACCGAGGGTTTTGGGTAGACCAAAGCACAAAGAAGTCCACTTAG
AGTGGGATGTTCCTGCATCGGAAAGTGGCTGTGAGGTCTCAGAGTACAGCGTGGAGATGACG
GAGCCCGAAGACGTAGCCTCGGAAGTGTACCATGGCCCAGAGCTGGAGTGCACCGTCGGCAA
CCTGCTTCCTGGAACCGTGTATCGCTTCCGGGTGAGGGCTCTGAATGATGGAGGGTATGGTC
CCTATTCTGATGTCTCAGAAATTACCACTGCTGCAGGGCCTCCTGGACAATGCAAAGCACCT
TGTATTTCTTGTACACCTGATGGATGTGTCTTAGTGGGTTGGGAGAGTCCTGATAGTTCTGG
TGCTGACATCTCAGAGTACAGGTTGGAATGGGGAGAAGATGAAGAATCCTTAGAACTCATTT
ATCATGGGACAGACACCCGTTTTGAAATAAGAGACCTGTTGCCTGCTGCACAGTATTGCTGT
AGACTACAGGCCTTCAATCAAGCAGGGGCAGGGCCGTACAGTGAACTTGTCCTTTGCCAGAC
GCCAGCGTCTGCCCCTGACCCCGTCTCCACTCTCTGTGTCCTGGAGGAGGAGCCCCTTGATGCC
TACCCTGATTCACCTTCTGCGTGCCTTGTACTGAACTGGGAAGAGCCGTGCAATAACGGATC
TGAAATCCTTGCTTACACCATTGATCTAGGAGACACTAGCATTACCGTGGGCAACACCACCA
TGCATGTTATGAAAGATCTCCTTCCAGAAACCACCTACCGGATCAGAATTCAGGCTATAAAT
GAAATTGGAGCTGGACCATTTAGTCAGTTCATTAAAGCAAAAACTCGGCCATTACCACCCTT
GCCTCCTAGGCTAGAATGTGCTGCTGCTGGTCCTCAGAGCCTGAAGCTAAAATGGGGAGACA
GTAACTCCAAGACACATGCTGCTGAGGACATTGTGTACACACTACAGCTGGAGGACAGAAAC
AAGAGGTTTATTTCAATCTACAGAGGACCCAGCCACACCTACAAGGTCCAGAGACTGACGGA
ATTCACATGCTACTCCTTCAGAATCCAGGCAGCAAGCGAGGCTGGAGAAGGGCCCTTCTCAG
AAACCTATACCTTCAGCACAACCAAAAGTGTCCCCCCCACCATCAAAGCACCTCGAGTAACA
CAGTTAGAAGTAAATTCATGTGAAATTTTATGGAGACGGTACCATCAATGAAAGGTGACCC
TGTTAACTACATTCTGCAGGTATTGGTTGGAAGAGAATCTGAGTACAAACAGGTGTACAAGG
GAGAAGAAGCCACATTCCAAATCTCAGGCCTCCAGACCAACACAGACTACAGGTTCCGCGTA
TGTGCGTGTCGTCGCTGTTTAGACACCTCTCAGGAGCTAAGCGGAGCCTTCAGCCCCTCTGC
GGCTTTTGTATTACAACGAAGTGAGGTCATGCTTACAGGGGACATGGGGAGCTTAGATGATC
CCAAAATGAAGAGCATGATGCCTACTGATGAACAGTTTGCAGCCATCATTGTGCTTGGCTTT
GCAACTTTGTCCATTTTATTTGCCTTTATATTACAGTACTTCTTAATGAAGTAAACCCAACA
AAACTAGAGGTATGAATTAATGCTACACATTTTAATACACACATTTATTCAGATACTCCCCT
TTTTAAAGCCCTTTTGTTTTTTGATTTATATACTCTGTTTTACAGATTTAGCTAGAAAAAAA
ATGTCAGTGTTTTGGTGCACCTTTTTGAAATGCAAAACTAGGAAAAGGTTAAACTGGATTTT
TTTTTAAAAAAAAAAAAAAAAAAAAAAAA

FIGURE 94

></usr/seqdb2/sst/DNA/Dnaseqs.min/ss.DNA191064
><subunit 1 of 1, 847 aa, 1 stop
><MW: 93607, pI: 5.33, NX(S/T): 3

MYNSVKGSCSEPVSFTTHSCAPECPFPPKLAHRSKSSLTLQWKAPIDNGSKITNYLLEWD
EGKRNSGFRQCFFGSQKHCKLTKLCPAMGYTFRLAARNDIGTSGYSQEVVCYTLGNIPQM
PSALRLVRAGITWVTLQWSKPEGCSPEEVITYTLEIQEDENDNLFHPKYTGEDLTCTVKN
LKRSTQYKFRLTASNTEGKSCPSEVLVCTTSPDRPGPPTRPLVKGPVTSHGFSVKWDPPK
DNGGSEILKYLLEITDGNSEANQWEVAYSGSATEYTFTHLKPGTLYKLRACCISTGGHSQ
CSESLPVRTLSIAPGQCRPPRVLGRPKHKEVHLEWDVPASESGCEVSEYSVEMTEPEDVA
SEVYHGPELECTVGNLLPGTVYRFRVRALNDGGYGPYSDVSEITTAAGPPGQCKAPCISC
TPDGCVLVGWESPDSSGADISEYRLEWGEDEESLELIYHGTDTRFEIRDLLPAAQYCCRL
QAFNQAGAGPYSELVLCQTPASAPDPVSTLCVLEEEPLDAYPDSPSACLVLNWEEPCNNG
SEILAYTIDLGDTSITVGNTTMHVMKDLLPETTYRIRIQAINEIGAGPFSQFIKAKTRPL
PPLPPRLECAAAGPQSLKLKWGDSNSKTHAAEDIVYTLQLEDRNKRFISIYRGPSHTYKV
QRLTEFTCYSFRIQAASEAGEGPFSETYTFSTTKSVPPTIKAPRVTQLEVNSCEILWETV
PSMKGDPVNYILQVLVGRESEYKQVYKGEEATFQISGLQTNTDYRFRVCACRRCLDTSQE
LSGAFSPSAAFVLQRSEVMLTGDMGSLDDPKMKSMMPTDEQFAAIIVLGFATLSILFAFI
LQYFLMK

Important features of the protein:

Transmembrane domain:
Amino acids 823-843

N-glycosylation sites:
Amino acids 48-51;539-542;559-562 cAMP- and cGMP-dependent protein kinase phosphorylation site:
Amino acids 63-66;182-185

Tyrosine kinase phosphorylation sites:
Amino acids 387-394;662-669

N-myristoylation sites:
Amino acids 49-54;257-262;343-348;437-442;757-762

Amidation site:
Amino acids 61-64

ATP/GTP-binding site motif A (P-loop):
Amino acids 193-200

Fibronectin type III domain:
Amino acids 22-106;118-203;215-302;314-398;
410-492;504-590;601-685;697-778

FIGURE 95A

CAATTCGGCCTCGCTCCTTGTGATTGCGCTAAACCTTCCGTCCTCAGCTGAGAACGCTCCACCACCTCCCCGGA
TCGCTCATCTCTTGGCTGCCCTCCCACTGTTCCTGATGTTATTTACTCCCCGTATCCCCTACTCGTTCTTCAC
AATTCTGTAGGTGAGTGGTTCCAGCTGGTGCCTGGCCTGTGTCTCTTGGATGCCCTGTGGCTTCAGTCCGTCTC
CTGTTGCCCACCACCTCGTCCCTGGGCCGCCTGATACCCCAGCCCAACAGCTAAGGTGTGGATGGACAGTAGGG
GGCTGGCTTCTCTCACTGGTCAGGGGTCTTCTCCCCTGTCTGCCTCCCGGAGCTAGGACTGCAGAGGGGCCTAT
CATGGTGCTTGCAGGCCCCCTGGCTGTCTCGCTGTTGCTGCCCAGCCTCACACTGCTGGTGTCCCACCTCTCCA
GCTCCCAGGATGTCTCCAGTGAGCCCAGCAGTGAGCAGCAGCTGTGCGCCCTTAGCAAGCACCCCACCGTGGCC
TTTGAAGACCTGCAGCCGTGGGTCTCTAACTTCACCTACCCTGGAGCCCGGGATTTCTCCCAGCTGGCTTTGGA
CCCCTCCGGGAACCAGCTCATCGTGGGAGCCAGGAACTACCTCTTCAGACTCAGCCTTGCCAATGTCTCTCTTC
TTCAGGCCACAGAGTGGGCCTCCAGTGAGGACACGCGCCGCTCCTGCCAAAGCAAAGGGAAGACTGAGGAGGAG
TGTCAGAACTACGTGCGAGTCCTGATCGTCGCCGGCCGGAAGGTGTTCATGTGTGGAACCAATGCCTTTTCCCC
CATGTGCACCAGCAGACAGGTGGGGAACCTCAGCCGGACTATTGAGAAGATCAATGGTGTGGCCCGCTGCCCCT
ATGACCCACGCCACAACTCCACAGCTGTCATCTCCTCCCAGGGGGAGCTCTATGCAGCCACGGTCATCGACTTC
TCAGGTCGGGACCCTGCCATCTACCGCAGCCTGGGCAGTGGGCCACCGCTTCGCACTGCCCAATATAACTCCAAG
TGGCTTAATGAGCCAAACTTCGTGGCAGCCTATGATATTGGGCTGTTTGCATACTTCTTCCTGCGGGAGAACGC
AGTGGAGCACGACTGTGGACGCACCGTGTACTCTCGCGTGGCCCGCGTGTGCAAGAATGACGTGGGGGGCCGAT
TCCTGCTGGAGGACACATGGACCACATTCATGAAGGCCCGGCTCAACTGCTCCCGCCCGGGCGAGGTCCCCTTC
TACTATAACGAGCTGCAGAGTGCCTTCCACTTGCCGGAGCAGGACCTCATCTATGGAGTTTTCACAACCAACGT
AAACAGCATCGCGGCTTCTGCTGTCTGCGCCTTCAACCTCAGTGCTATCTCCCAGGCTTTCAATGGCCCATTTC
GCTACCAGGAGAACCCCAGGGCTGCCTGGCTCCCCATAGCCAACCCCATCCCCAATTTCCAGTGTGGCACCCTG
CCTGAGACCGGTCCCAACGAGAACCTGACGGAGCGCAGCCTGCAGGACGCGCAGCGCCTCTTCCTGATGAGCGA
GGCCGTGCAGCCGGTGACACCCGAGCCCTGTGTCACCCAGGACAGCGTGCGCTTCTCACACCTCGTGGTGGACC
TGGTGCAGGCTAAAGACACGCTCTACCATGTACTCTACATTGGCACCGAGTCGGGCACCATCCTGAAGGCGCTG
TCCACGGCGAGCCGCAGCCTCCACGGCTGCTACCTGGAGGAGCTGCACGTGCTGCCCCCCGGGCGCCGCGAGCC
CCTGCGCAGCCTGCGCATCCTGCACAGCGCCCGCGCGCTCTTCGTGGGGCTGAGAGACGGCGTCCTGCGGGTCC
CACTGGAGAGGTGCGCCGCCTACCGCAGCCAGGGGGCATGCCTGGGGGCCCGGGACCCGTACTGTGGCTGGGAC
GGGAAGCAGCAACGTTGCAGCACACTCGAGGACAGCTCCAACATGAGCCTCTGGACCCAGAACATCACCGCCTG
TCCTGTGCGGAATGTGACACGGGATGGGGGCTTCGGCCCATGGTCACCATGGCAACCATGTGAGCACTTGGATC
GGGACAACTCAGGCTCTTGCCTGTGTCGAGCTCGATCCTGTGATTCCCCTCGACCCCGCTGTGGGGGCCTTGAC
TGCCTGGGGCCAGCCATCCACATCGCCAACTGCTCCAGGAATGGGGCGTGGACCCCGTGGTCATCGTGGGCGCT
GTGCAGCACGTCCTGTGGCATCGGCTTCCAGGTCCGCCAGCGAAGTTGCAGCAACCCTGCTCCCCGCCACGGGGGC
CGCATCTTCGTGGGCAAGAGCCGGGAGGAACGGTTCTGTAATGAGAACACGCCTTGCCCGGTGCCCATCTTCTG
GGCTTCCTGGGGCTCCTGGAGCAAGTGCAGCAGCAACTGTGGAGGGGGCATGCAGTCGCGGCGTCGGGCCTGCG
AGAACGGCAACTCCTGCCTGGGCTGCGGCGAGTTCAAGACGTGCAACCCCGAGGGCTGCCCCGAAGTGCGGCGC
AACACCCCCTGGACGCCGTGGCTGCCCGTGAACGTGACGCAGGGCGGGGCACGGCAGGAGCAGCGGTTCCGCTT
CACCTGCCGCGCGCCCCTTGCAGACCCGCACGGCCTGCAGTTCGGCAGGAGAAGGACCGAGACGAGGACCTGTC
CCGCGGACGGCTCCGGCTCCTGCGACACCGACGCCCTGGTGGAGGTCCTCCTGCGCAGCGGGAGCACCTCCCCG
CACACGGTGAGCGGGGGCTGGGCCGCCTGGGGCCCGTGGTCGTCCTGCTCCCGGGACTGCGAGCTGGGCTTCCG
CGTCCGCAAGAGAACGTGCACTAACCCGGAGCCCCGCAACGGGGGCCTGCCCTGCGTGGGCGATGCTGCCGAGT
ACCAGGACTGCAACCCCCAGGCTTGCCCAGTTCGGGGTGCTTGGTCCTGCTGGACCTCATGGTCTCCATGCTCA
GCTTCCTGTGGTGGGGGTCACTATCAACGCACCCGTTCCTGCACCAGCCCCGCACCCTCCCCAGGTGAGGACAT
CTGTCTCGGGCTGCACACGGAGGAGGCACTATGTGCCACACAGGCCTGCCCAGGCTGGTCGCCCTGGTCTGAGT
GGAGTAAGTGCACTGACGACGGAGCCCAGAGCCGAAGCCGGCACTGTGAGGAGCTCCTCCCAGGGTCCAGCGCC
TGTGCTGGAAACAGCAGCCAGAGCCGCCCCTGCCCCTACAGCGAGATTCCCGTCATCCTGCCAGCCTCCAGCAT
GGAGGAGGCCACCGACTGTGCAGGTAAAAGAAACCGGACCTACCTCATGCTGCGGTCCTCCCAGCCCTCCAGCA
CCCCACTCCAAAGTCTGGACTCTTTCCACATCCTGCTCCAGACAGCCAAGCTTTGTTGGGGTCCCCACTGCTTT
GAGATGGGTTCAATCTCATCCACTTGGTGGCCACGGGCATCTCCTGCTTCTTGGGCTCTGGGCTCCTGACCCTA
GCAGTGTACCTGTCTTGCCAGCACTGCCAGCGTCAGTCCCAGGAGTCCACACTGGTCCATCCTGCCACCCCCAACC
ATTTGCACTACAAGGGCGGAGGCACCCCGAAGAATGAAAAGTACACACCCATGGAATTCAAGACCCTGAACAAG
AATAACTTGATCCCTGATGACAGAGCCAACTTCTACCCATTGCAGCAGACCAATGTGTACACCACTACTTACTA
CCCAAGCCCCCTGAACAAACACAGCTTCCGGCCCGAGGCCTCACCTGGACAACGGTGCTTCCCCAACAGCTGAT
ACCGCCGTCCTGGGGACTTGGGCTTCTTGCCTTCATAAGGCACAGAGCAGATGGAGATGGGACAGTGGAGCCAG
TTTGGTTTTCTCCCTCTGCACTAGGCCAAGAACTTGCTGCCTTGCCTGTGGGGGTCCCATCCGGCTTCAGAGA
GCTCTGGCTGGCATTGACCATGGGGGAAAGGGCTGGTTTCAGGCTGACATATGGCCGCAGGTCCAGTTCAGCCC
AGGTCTCTCATGGTTATCTTCCAACCCACTGTCACGCTGACACTATGCTGCCATGCCTGGGCTGTGGACCTACT
GGGCATTTGAGGAATTGGAGAATGGAGATGGCAAGAGGGCAGGCTTTTAAGTTTGGGTTGGAGACAACTTCCTG
TGGCCCCCACAAGCTGAGTCTGGCCTTCTCCAGCTGGCCCCAAAAAAGGCCTTTGCTACATCCTGATTATCTCT
GAAAGTAATCAATCAAGTGGCTCCAGTAGCTCTGGATTTTCTGCCAGGGCTGGGCCATTGTGGTGCTGCCCCAG
TATGACATGGGACCAAGGCCAGCGCAGGTTATCCACCTCTGCCTGGAAGTCTATACTCTACCCAGGGCATCCCT
CTGGTCAGAGGCAGTGAGTACTGGGAACTGGAGGCTGACCTGTGCTTAGAAGTCCTTTAATCTGGGCTGGTACA
GGCCTCAGCCTTGCCCTCAATGCACGAAAGGTGGCCCAGGAGAGAGGATCAATGCCATAGGAGGCAGAAGTCTG
GCCTCTGTGCCTCTATGGAGACTATCTTCCAGTTGCTGCTCAACAGAGTTGTTGGCTGAGACCTGCTTGGGAGT

FIGURE 95B

CTCTGCTGGCCCTTCATCTGTTCAGGAACACACACACACACACACTCACACACGCACACACAATCACAATTTGC
TACAGCAACAAAAAAGACATTGGGCTGTGGCATTATTAATTAAAGATGATATCCAGTC

FIGURE 96

></usr/seqdb2/sst/DNA/Dnaseqs.min/ss.DNA194909
><subunit 1 of 1, 1092 aa, 1 stop
><MW: 119324, pI: 8.13, NX(S/T): 14

```
MPCGFSPSPVAHHLVPGPPDTPAQQLRCGWTVGGWLLSLVRGLLPCLPPGARTAEGPIMV
LAGPLAVSLLLPSLTLLVSHLSSSQDVSSEPSSEQQLCALSKHPTVAFEDLQPWVSNFTY
PGARDFSQLALDPSGNQLIVGARNYLFRLSLANVSLLQATEWASSEDTRRSCQSKGKTEE
ECQNYVRVLTVAGRKVFMCGTNAFSPMCTSRQVGNLSRTIEKINGVARCPYDPRHNSTAV
ISSQGELYAATVIDFSGRDPAIYRSLGSGPPLRTAQYNSKWLNEPNFVAAYDIGLFAYFF
LRENAVEHDCGRTVYSRVARVCKNDVGGRFLLEDTWTTFMKARLNCSRPGEVPFYYNELQ
SAFHLPEQDLIYGVFTTNVNSIAASAVCAFNLSAISQAFNGPFRYQENPRAAWLPIANPI
PNFQCGTLPETGPNENLTERSLQDAQRLFLMSEAVQPVTPEPCVTQDSVRFSHLVVDLVQ
AKDTLYHVLYIGTESGTILKALSTASRSLHGCYLEELHVLPPGRREPLRSLRILHSARAL
FVGLRDGVLRVPLERCAAYRSQGACLGARDPYCGWDGKQQRCSTLEDSSNMSLWTQNITA
CPVRNVTRDGGFGPWSPWQPCEHLDGDNSGSCLCRARSCDSPRPRCGGLDCLGPAIHIAN
CSRNGAWTPWSSWALCSTSCGIGFQVRQRSCSNPAPRHGGRIFVGKSREERFCNENTPCP
VPIFWASWGSWSKCSSNCGGGMQSRRRACENGNSCLGCGEFKTCNPEGCPEVRRNTPWTP
WLPVNVTQGGARQEQRFRFTCRAPLADPHGLQFGRRRTETRTCPADGSGSCDTDALVEVL
LRSGSTSPHTVSGGWAAWGPWSSCSRDCELGFRVRKRTCTNPEPRNGGLPCVGDAAEYQD
CNPQACPVRGAWSCWTSWSPCSASCGGGHYQRTRSCTSPAPSPGEDICLGLHTEEALCAT
QACPGWSPWSEWSKCTDDGAQSRSRHCEELLPGSSACAGNSSQSRPCPYSEIPVILPASS
MEEATDCAGKRNRTYLMLRSSQPSSTPLQSLDSFHILLQTAKLCWGPHCFEMGSISSTWW
PRASPASWALGS
```

Important features of the protein:

Signal peptide:
Amino acids 1-42

Transmembrane domain:
Amino acids 56-79;373-395

N-glycosylation sites:
Amino acids 117-120;153-156;215-218;236-239;345-348;391-394;436-439;590-593;597-600;605-608;660-663;785-788;1000-1003;1032-1035 cAMP- and cGMP-dependent protein kinase phosphorylation sites:
Amino acids 773-776;815-818;875-878

Tyrosine kinase phosphorylation site:
Amino acids 177-185;348-355

N-myristoylation sites:
Amino acids 42-47;50-55;373-378;492-497;543-548;563-568;630-635;647-652;740-745;810-815;827-832;829-834;853-858;887-892;910-915;993-998;1073-1078

Amidation sites:
Amino acids 192-195;522-525;813-816;1028-1031

ATP/GTP-binding site motif A (P-loop):
Amino acids 700-707

Cytochrome c oxidase subunit II, copper A binding region signature:
Amino acids 921-929

Growth factor and cytokines receptors family signature 2:
Amino acids 967-973

Sema domain:
Amino acids 126-537

Plexin repeat:
Amino acids 555-602

Thrombospondin type 1 domain:
Amino acids 613-661;668-719;726-769;856-906;913-963;967-1007

FIGURE 97

CAAGCCCTCCCAGCATCCCCTCTCCTGTGTTCCTCCCCAGTTCTCTACTCAGAGTTGACTGACCAGAGATTTAT
CAGCTTGGAGGGCTGGAGGTGTGGATCCATGGGGTAGCCTCAACGCATCTGCCCCTCCACCCCAGCCAGCTCAT
GGGCCACGTGGCCTGGCCCAGCCTCAGCACCCAGGGCCAGTGAACAGAGCCCTGGCTGGAGTCCAAACATGTGG
GGCCTGGTGAGGCTCCTGCTGGCCTGGCTGGGTGGCTGGGGCTGCATGGGGCGTCTGGCAGCCCCAGCCCGGGC
CTGGGCAGGGTCCCGGGAACACCCAGGGCCTGCTCTGCTGCGGACTCGAAGGAGCTGGGTCTGGAACCAGTTCT
TTGTCATTGAGGAATATGCTGGTCCAGAGCCTGTTCTCATTGGCAAGCTGCACTCGGATGTTGACCGGGGAGAG
GGCCGCACCAAGTACCTGTTGACCGGGGAGGGGGCAGGCACCGTATTTGTGATTGATGAGGCCACAGGCAATAT
TCATGTTACCAAGAGCCTTGACCGGGAGGAAAAGGCGCAATATGTGCTACTGGCCCAAGCCGTGGACCGAGCCT
CCAACCGGCCCCTGGAGCCCCCATCAGAGTTCATCATCAAAGTGCAAGACATCAACGACAATCCACCCATTTTT
CCCCTTGGGCCCTACCATGCCACCGTGCCCGAGATGTCCAATGTCGGGACATCAGTGATCCAGGTGACTGCTCA
CGATGCTGATGACCCCAGCTATGGGAACAGTGCCAAGCTGGTGTACACTGTTCTGGATGGACTGCCTTTCTTCT
CTGTGGACCCCCAGACTGGAGTGGTGCGTACAGCCATCCCCAACATGGACCGGGAGACACAGGAGGAGTTCTTG
GTGGTGATCCAGGCCAAGGACATGGGCGGCCACATGGGGGGCTGTCAGGCAGCACTACGGTGACTGTCACGCT
CAGCGATGTCAACGACAACCCCCCCAAGTTCCCACAGAGCCTATACCAGTTCTCCGTGGTGGAGACAGCTGGAC
CTGGCACACTGGTGGGCCGGCTCCGGGCCCAGGACCCAGACCTGGGGCACAACGCCCTGATGGCATACAGCATC
CTGGATGGGGAGGGGTCTGAGGCCTTCAGCATCAGCACAGACTTGCAGGGTCGAGACGGGCTCCTCACTGTCCG
CAAGCCCCTAGACTTTGAGAGCCAGCGCTCCTACTCCTTCCGTGTCGAGGCCACCAACACGCTCATTGACCCAGCC
TATCTGCGGCGAGGGCCCTTCAAGGATGTGGCCTCTGTGCGTGTGGCAGTGCAAGATGCCCCAGAGCCACCTGC
CTTCACCCAGGCTGCCTACCACCTGACAGTGCCTGAGAACAAGGCCCCGGGGACCCTGGTAGGCCAGATCTCCG
CGGCTGACCTGGACTCCCCTGCCAGCCCAATCAGATACTCCATCCTCCCCCACTCAGATCCGGAGCGTTGCTTC
TCTATCCAGCCCGAGGAAGGCACCATCCATACAGCAGCACCCCTGGATCGCGAGGCTCGCGCCTGGCACAACCT
CACTGTGCTGGCTACAGAGCTCGACAGTTCTGCACAGGCCTCGCGCGTGCAAGTGGCCATCCAGACCCTGGATG
AGAATGACAATGCTCCCCAGCTGGCTGAGCCCTACGATACTTTTGTGTGTGACTCTGCAGCTCCTGGCCAGCTG
ATTCAGGTCATCCGGGCCCTGGACAGAGATGAAGTTGGCAACAGTAGCCATGTCTCCTTTCAAGGTCCTCTGGG
CCCTGATGCCAACTTTACTGTCCAGGACAACCGAGATGGCTCCGCCAGCCTGCTGCTGCCCTCCCGCCCTGCTC
CACCCCGCCATGCCCCCTACTTGGTTCCCATAGAACTGTGGGACTGGGGGCAGCCGGCGCTGAGCAGCACTGCC
ACAGTGACTGTTAGTGTGTGCCGCTGCCAGCCTGACGGCTCTGTGGCATCCTGCTGGCCTGAGGCTCACCTCTC
AGCTGCTGGGCTCAGCACCGGCGCCCTGCTTGCCATCATCACCTGTGTGGGTGCCCTGCTTGCCCTGGTGGTGC
TCTTCGTGGCCCTGCGGCGGCAGAAGCAAGAAGCACTGATGGTACTGGAGGAGGAGGACGTCCGAGAGAACATC
ATCACCTACGACGACGAGGGCGGCGGCGAGGAGGACACCGAGGCCTTCGACATCACGGCCTTGCAGAACCCGGA
CGGGGCGGCCCCCCCGGCGCCCGGCCCTCCCGCGCGCCGAGACGTGTTGCCCCGGGCCCGGGTGTCGCGCCAGC
CCAGACCCCCCGGCCCCGCCGACGTGGCGCAGCTCCTGGCGCTGCGGCTCCGCGAGGCGGACGAGGACCCCGGC
GTACCCCCGTACGACTCGGTGCAGGTGTACGGCTACGAGGGCCGCGGCTCCTCTTGCGGCTCCCTCAGCTCCCT
GGGCTCCGGCAGCGAAGCCGGCGGCGCCCCCGGCCCCGCGGAGCCGCTGGACGACTGGGGTCCGCTCTTCCGCACC
CTGGCCGAGCTGTATGGGGCCAAGGAGCCCCCGGCCCCCTGAGCGCCCGGGCTGGCCCGGCCCACCGCGGGGG
GGGGCAGCGGGCACAGGCCCTCTGAGTGAGCCCCACGGGGTCCAGGCGGGCGGCAGCAGCCCAGGGGCCCCAGG
CCTCCTCCCTGTCCTTGTGTCCCTCCTTGCTTCCCCGGGGCACCCTCGCTCTCACCTCCCTCCTCCTGAGTCGG
TGTGTGTGTCTCTCTCCAGGAATCTTTGTCTCTATCTGTGACACGCTCCTCTGTCCGGGCCTGGGTTTCCTGCC
CTGGCCCTGGCCCTGCGATCTCTCACTGTGATTCCTCTCCTTCCTCCGTGGCGTTTTGTCTCTGCAGTTCTGAA
GCTCACACATAGTCTCCCTGCGTCTTCCTTGCCCATACACATGCTCTGTGTCTGTCTCCTGCCCACATCTCCCT
TCCTTCTCTCTGGGTCCCTGTGACTGGCTTTTTGTTTTTTTCTGTTGTCCATCCCAAAATCAAGAGAAACTTCC
AGCCACTGCTGCCCACCCTCCTGCAGGGGATGTTGTGCCCCAGACCTGCCTGCATGGTTCCATCCATTACTCAT
GGCCTCAGCCTCATCCTGGCTCCACTGGCCTCCAGCTGAGAGAGGGAACCAGCCTGCCTCCCAGGGCAAGAGCT
CCAGCCTCCCGTGTGGCCGCCTCCCTGGAGCTCTGCCCAGCTGCCAGCTTCCCCTGGGCATCCCAGCCCTGGGC
ATTGTCTTGTGTGCTTCCTGAGGGAGTAGGGAAAGGAAAGGGGGAGGCGGCTGGGAAGGGGAAAGAGGGAGGA
AGGGGAGGGGCCTCCATCTCTAATTTCATAATAAACAAACACTTTATTTTGTAAAAC

FIGURE 98

MWGLVRLLLAWLGGWGCMGRLAAPARAWAGSREHPGPALLRTRRSWVWNQFFVIEEYAGP
EPVLIGKLHSDVDRGEGRTKYLLTGEGAGTVFVIDEATGNIHVTKSLDREEKAQYVLLAQ
AVDRASNRPLEPPSEFIIKVQDINDNPPIFPLGPYHATVPEMSNVGTSVIQVTAHDADDP
SYGNSAKLVYTVLDGLPFFSVDPQTGVVRTAIPNMDRETQEEFLVVIQAKDMGGHMGGLS
GSTTVTVTLSDVNDNPPKFPQSLYQFSVVETAGPGTLVGRLRAQDPDLGDNALMAYSILD
GEGSEAFSISTDLQGRDGLLTVRKPLDFESQRSYSFRVEATNTLIDPAYLRRGPFKDVAS
VRVAVQDAPEPPAFTQAAYHLTVPENKAPGTLVGQISAADLDSPASPIRYSILPHSDPER
CFSIQPEEGTIHTAAPLDREARAWHNLTVLATELDSSAQASRVQVAIQTLDENDNAPQLA
EPYDTFVCDSAAPGQLIQVIRALDRDEVGNSSHVSFQGPLGPDANFTVQDNRDGSASLLL
PSRPAPPRHAPYLVPIELWDWGQPALSSTATVTVSVCRCQPDGSVASCWPEAHLSAAGLS
TGALLAIITCVGALLALVVLFVALRRQKQEALMVLEEEDVRENIITYDDEGGGEEDTEAF
DITALQNPDGAAPPAPGPPARRDVLPRARVSRQPRPPGPADVAQLLALRLREADEDPGVP
PYDSVQVYGYEGRGSSCGSLSSLGSGSEAGGAPGPAEPLDDWGPLFRTLAELYGAKEPPA
P

Signal peptide:
Amino acids 1-16

Transmembrane domain:
Amino acids 597-624

N-glycosylation sites:
Amino acids 446-449;510-513;525-528

N-myristoylation sites:
Amino acids 13-18;206-211;233-238;237-242;238-243;275-280;390-395;
394-399;429-434;583-588;598-603;602-607;612-617;
734-739;738-743;746-751

ATP synthase c subunit signature:
Amino acids 691-712

Cadherins extracellular repeated domain signature:
Amino acids 138-148;247-257

Cadherin domain:
Amino acids 50-141;155-250;264-366;379-470;483-577

Cadherin cytoplasmic region:
Amino acids 625-776

FIGURE 99

GCCAACACTGGCCAAACATATGGGGCTGGAATCTCAACATCGGTCACTGGGACCTCAATATT
TGGAGCCGGAACCCCACAATTTGGAACACAGACCCCAATATTTGGAGCAGAACCCCAAGATT
TGACATCTAAAACCTCAAGCCTGGAGCTGAACTCTGAATTCTGGGCCTGGGACCTTGAAATC
TGGGACTGGATTTCCAGTACTGTACCCTGGAACCCACTCTTGGGGACCTGAACCCTGGGATT
CAGGCCTCAAATTCCAAGATCTGGACTGTGGGATTCCAAGGGGCCTGAACCCGAGTTTGGGC
CTGAAGTCCTTGCTGCAGACCTGAGTGCTTAAATCTGGGGCTTGAGACCTCCCAATCTTGAC
TCAGCACCCCAATATCTGAATGCAGAACCCCGGGATCGGATCTCAGACTCTAAACCCCACCG
TTTGGCTGCTTAGCATCCCAAGACTGGACCTGGGAGACCCTGACCCTGAACAACCCAAACTG
GACCCGTAAAACTGGACCCTAGAGGCCCAATATTTAGGGGTCTGGAACCCCGAGTATTAAGG
TCTGGAGACTCCGTTGCCACAGATTTGAGCCGAGTCAGGACACAGTCCCTCTACAGAAGCCT
TGGGGACAGGAAAAGCATGACCAGATGCTCCCTCCAGAGCCCTGACCTCTGACTCCCCTGGA
GCTAGGACTCTGCTCCCTGGGGCTGCTTCTAGCTCAGGACACCCCTGCCCGCGATGGCCATC
CTCCCGTTGCTCCTGTGCCTGCTGCCGCTGGCCCCTGCCTCATCCCCACCCCAGTCAGCCAC
ACCCAGCCCATGTCCCCGCCGCTGCCGCTGCCAGACACAGTCGCTGCCCCTAAGCGTGCTGT
GCCCAGGGGCAGGCCTCCTGTTCGTGCCACCCTCGCTGGACCGCCGGGCAGCCGAGCTGCGG
CTGGCAGACAACTTCATCGCCTCCGTGCGCCGCCGCGACCTGGCCAACATGACAGGCCTGCT
GCATCTGAGCCTGTCGCGGAACACCATCCGCCACGTGGCTGCCGGCGCCTTCGCCGACCTGC
GGGCCCTGCGTGCCCTGCACCTGGATGGCAACCGGCTGACCTCACTGGGCGAGGGCCAGCTG
CGCGGCCTGGTCAACTTGCGCCACCTCATCCTCAGCAACAACCAGCTGGCAGCGCTGGCGGC
CGGCGCCCTGGATGATTGTGCCGAGACACTGGAGGACCTCGACCTCTCCTACAACAACCTCG
AGCAGCTGCCCTGGGAGGCCCTGGGCCGCCTGGGCAACGTCAACACGTTGGGCCTCGACCAC
AACCTGCTGGCTTCTGTGCCCGGCGCTTTTTCCCGCCTGCACAAGCTGGCCCGGCTGGACAT
GACCTCCAACCGCCTGACCACAATCCCACCCGACCCACTCTTCTCCCGCCTGCCCCTGCTCG
CCAGGCCCCGGGGCTCGCCCGCCTCTGCCCTGGTGCTGGCCTTTGGCGGGAACCCCCTGCAC
TGCAACTGCGAGCTGGTGTGGCTGCGTCGCCTGGCGCGGGAGGACGACCTCGAGGCCTGCGC
GTCCCCACCTGCTCTGGGCGGCCGCTACTTCTGGGCGGTGGGCGAGGAGGAGTTTGTCTGCG
AGCCGCCCGTGGTGACTCACCGCTCACCACCTCTGGCTGTGCCCGCAGGTCGGCCGGCTGCC
CTGCGCTGCCGGGCAGTGGGGGACCCAGAGCCCCGTGTGCGTTGGGTGTCACCCCAGGGCCG
GCTGCTAGGCAACTCAAGCCGTGCCCGCGCCTTCCCCAATGGGACGCTGGAGCTGCTGGTCA
CCGAGCCGGGTGATGGTGGCATCTTCACCTGCATTGCGGCCAATGCAGCTGGCGAGGCCACA
GCTGCTGTGGAGCTGACTGTGGGTCCCCCACCACCTCCTCAGCTAGCCAACAGCACCAGCTG
TGACCCCCCGCGGGACGGGGATCCTGATGCTCTCACCCCACCCTCCGCTGCCTCTGCTTCTG
CCAAGGTGGCCGACACTGGGCCCCCTACCGACCGTGGCGTCCAGGTGACTGAGCACGGGGCC
ACAGCTGCTCTTGTCCAGTGGCCGGATCAGCGGCCTATCCCGGGCATCCGCATGTACCAGAT
CCAGTACAACAGCTCGGCTGATGACATCCTCGTCTACAGGATGATCCCGGCGGAGAGCCGCT
CGTTCCTGCTGACGGACCTGGCGTCAGGCCGGACCTACGATCTGTGCGTGCTCGCCGTGTAT
GAGGACAGCGCCACGGGGCTCACGGCCACGCGGCCTGTGGGCTGCGCCCGCTTCTCCACCGAA
CCTGCGCTGCGGCCATGCGGGGCGCCGCACGCTCCCTTCCTGGGCGGCACGATGATCATCGC
GCTGGGCGGCGTCATCGTAGCCTCGGTACTGGTCTTCATCTTCGTGCTGCTAATGCGCTACA
AGGTGCACGGCGGCCAGCCCCCCGGCAAGGCCAAGATTCCCGCGCCTGTTAGCAGCGTTTGC
TCCCAGACCAACGGCGCCCTGGGCCCCACGCCCACGCCCGCCCCGCCCGCCCCGGAGCCCGC
GGCGCTCAGGGCCCACACCGTGGTCCAGCTGGACTGCGAGCCCTGGGGGCCCGGCCACGAAC
CTGTGGGACCCTAGCCAGGCGCCCCCCCCTCTAAGGGTCCTCTGGCCCCACGGACAGCAGGA
CCCGGACACCCTGTGGGACCTGGCCTCAAACTCACCAAATCGCTCATGGTTTTTAAAACTCT
GATGGGGAGGGTGTCGGGGACACCGGGGCAAAACAAGAAAGTCCTATTTTTCCAAAAAAAAA
AAAAAAAAAAAAAAAAAAAAAAAAAAAAAAAAAAAAAAAAAAAAAAAAAAAAAAAAAAAA

FIGURE 100

></usr/seqdb2/sst/DNA/Dnaseqs.min/ss.DNA213858
><subunit 1 of 1, 627 aa, 1 stop
><MW: 66189, pI: 7.31, NX(S/T): 5
MAILPLLLCLLPLAPASSPPQSATPSPCPRRCRCQTQSLPLSVLCPGAGLLFVPPSLDRR
AAELRLADNFIASVRRRDLANMTGLLHLSLSRNTIRHVAAGAFADLRALRALHLDGNRLT
SLGEGQLRGLVNLRHLILSNNQLAALAAGALDDCAETLEDLDLSYNNLEQLPWEALGRLG
NVNTLGLDHNLLASVPGAFSRLHKLARLDMTSNRLTTIPPDPLFSRLPLLARPRGSPASA
LVLAFGGNPLHCNCELVWLRRLAREDDLEACASPPALGGRYFWAVGEEEFVCEPPVVTHR
SPPLAVPAGRPAALRCRAVGDPEPRVRWVSPQGRLLGNSSRARAFPNGTLELLVTEPGDG
GIFTCIAANAAGEATAAVELTVGPPPPPQLANSTSCDPPRDGDPDALTPPSAASASAKVA
DTGPPTDRGVQVTEHGATAALVQWPDQRPIPGIRMYQIQYNSSADDILVYRMIPAESRSF
LLTDLASGRTYDLCVLAVYEDSATGLTATRPVGCARFSTEPALRPCGAPHAPFLGGTMII
ALGGVIVASVLVFIFVLLMRYKVHGGQPPGKAKIPAPVSSVCSQTNGALGPTPTPAPPAP
EPAALRAHTVVQLDCEPWGPGHEPVGP

Important features of the protein:

Signal peptide:
Amino acids 1-16

Transmembrane domain:
Amino acids 35-55; 536-556

N-glycosylation sites:
Amino acids 81-84;338-341;347-350;392-395;461-464

N-myristoylation sites:
Amino acids 116-121;125-130;180-185;186-191;235-240;
360-365;361-366;429-434;436-441;505-510;
544-549;566-571

Leucine Rich Repeat:
Amino acids 60-83;84-107;108-131;132-155;157-180;
181-203;204-227

Leucine rich repeat C-terminal domain:
Amino acids 248-293

Immunoglobulin domain:
Amino acids 309-367

Fibronectin type III domain:
Amino acids 424-504

FIGURE 101

CGACTCCATAACCGTGGCCTTGGCCCCAGTCCCCCTGACTTCCGGACTTCAGACCAGATACTGCCCATATCCCC
TTATGAAGTCTTGGCCAGGCAACCCCTAGGGTGTACGTTTTCTAAAGATTAAAGAGGCGGTGCTAAGCTGCAGA
CGGACTTGCGACTCAGCCACTGGTGTAAGTCAGGCGGGAGGTGGCGCCCAATAAGCTCAAGAGAGGAGGCGGGT
TCTGGAAAAAGGCCAATAGCCTGTGAAGGCGAGTCTAGCAGCAACCAATAGCTATGAGCGAGAGGCGGGACTCT
GAGGGAAGTCAATCGCTGCCGCAGGTACCGCCAATGGCTTTTGGCGGGGGCGTTCCCCAACCCTGCCCTCTCTC
ATGACCCCGCTCCGGGATTATGGCCGGGACTGGGCTGCTGGCGCTGCGGACGCTGCCAGGGCCCAGCTGGGTGC
GAGGCTCGGGCCCTTCCGTGCTGAGCCGCCTGCAGGACGCGGCCGTGGTGCGGCCTGGCTTCCTGAGCACGGCA
GAGGAGGAGACGCTGAGCCGAGAACTGGAGCCCGAGCTGCGCCGCCGCCGCTACGAATACGATCACTGGGACGC
GGCCATCCACGGCTTCCGAGAGACAGAGAAGTCGCGCTGGTCAGAAGCCAGCCGGGCCATCCTGCAGCGCGTGC
AGGCGGCCGCCTTTGGCCCCGGCCAGACCCTGCTCTCCTCCGTGCACGTGCTGGACCTGGAAGCCCGCGGCTAC
ATCAAGCCCCACGTGGACAGCATCAAGTTCTGCGGGGCCACCATCGCCGGCCTGTCTCTCCTGTCTCCCAGCGT
TATGCGGCTGGTGCACACCCAGGAGCCGGGGGAGTGGCTGGAACTCTTGCTGGAGCCGGGCTCCCTCTACATCC
TTAGGGGCTCAGCCCGTTATGACTTCTCCCATGAGATCCTTCGGGATGAAGAGTCCTTCTTTGGGGAACGCCGG
ATTCCCCGGGGCCGGCGCATCTCCGTGATCTGCCGCTCCCTCCCTGAGGGCATGGGGCCAGGGGAGTCTGGACA
GCCGCCCCCAGCCTGCTGACCCCCAGCTTTCTACAGACACCAGATTTGTGAATAAAGTTGGGGAATGGACAGCCT

FIGURE 102

MAGTGLLALRTLPGPSWVRGSGPSVLSRLQDAAVVRPGFLSTAEEETLSRELEPELRRRRYEYDHWDAAIHGFR
ETEKSRWSEASRAILQRVQAAAFGPGQTLLSSVHVLDLEARGYIKPHVDSIKFCGATIAGLSLLSPSVMRLVHT
QEPGEWLELLLEPGSLYILRGSARYDFSHEILRDEESFFGERRIPRGRRISVICRSLPEGMGPGESGQPPPAC

Important features of the protein:

Signal peptide:
1-18

Transmembrane domain:
None cAMP- and cGMP-dependent protein kinase phosphorylation site.
196-199

N-myristoylation site.
20-25
129-134
208-213

Amidation site.
194-197

FIGURE 103

CTCCCCGGCGCCGCAGGCAGCGTCCTCCTCCGAAGCAGCTGCACCTGCAACTGGGCAGCCTGGACCCTCGTGCC
CTGTTCCCGGGACCTCGCGCAGGGGGCGCCCCGGGACACCCCCTGCGGGCCGGGTGGAGGAGGAAGAGGAGGAG
GAGGAAGAAGACGTGGACAAGGACCCCCATCCTACCCAGAACACCTGCCTGCGCTGCCGCCACTTCTCTTTAAG
GGAGAGGAAAAGAGAGCCTAGGAGAACCATGGGGGGCTGCGAAGTCCGGGAATTTCTTTTGCAATTTGGTTTCT
TCTTGCCTCTGCTGACAGCGTGGCCAGGCGACTGCAGTCACGTCTCCAACAACCAAGTTGTGTTGCTTGATACA
ACAACTGTACTGGGAGAGCTAGGATGGAAAACATATCCATTAAATGGGTGGGATGCCATCACTGAAATGGATGA
ACATAATAGGCCCATTCACACATACCAGGTATGTAATGTAATGGAACCAAACCAAAACAACTGGCTTCGTACAA
ACTGGATCTCCCGTGATGCAGCTCAGAAAATTTATGTGGAAATGAAATTCACACTAAGGGATTGTAACAGCATC
CCATGGGTCTTGGGGACTTGCAAAGAAACATTTAATCTGTTTTATATGGAATCAGATGAGTCCCACGGAATTAA
ATTCAAGCCAAACCAGTATACAAAGATCGACACAATTGCTGCTGATGAGAGTTTTACCCAGATGGATTTGGGTG
ATCGCATCCTCAAACTCAACACTGAAATTCGTGAGGTGGGGCCTATAGAAAGGAAAGGATTTTATCTGGCTTTT
CAAGACATTGGGGCGTGCATTGCCCTGGTTTCAGTCCGTGTTTTCTACAAGAAATGCCCCTTCACTGTTCGTAA
CTTGGCCATGTTTCCTGATACCATTCCAAGCGTTGATTCCTCCTCTTTGGTTGAAGTACGGGGTTCTTGTGTGA
AGAGTGCTGAAGAGCGTGACACTCCTAAACTGTATTGTGGAGCTGATGGAGATTGGCTGGTTCCTCTTGGAAGG
TGCATCTGCAGTACAGGATATGAAGAAATTGAGGGTTCTTGCCATGCTTGCAGACCAGGATTCTATAAAGCTTT
TGCTGGGAACACAAAATGTTCTAAATGTCCTCCACACAGTTTAACATACATGGAAGCAACTTCTGTCTGTCAGT
GTGAAAAGGGTTATTTCCGAGCTGAAAAAGACCCACCTTCTATGGCATGTACCAGGCCACCTTCAGCTCCTAGG
AATGTGGTTTTTAACATCAATGAAACAGCCCTTATTTTGGAATGGAGCCCACCAAGTGACACAGGAGGGAGAAA
AGATCTCACATACAGTGTAATCTGTAAGAAATGTGGCTTAGACACCAGCCAGTGTGAGGACTGTGGTGGAGGAC
TCCGCTTCATCCCAAGACATACAGGCCTGATCAACAATTCCGTGATAGTACTTGACTTTGTGTCTCACGTGAAT
TACACCTTTGAAATAGAAGCAATGAATGGAGTTTCTGAGTTGAGTTTTTCTCCCAAGCCATTCACAGCTATTAC
AGTGACCACGGATCAAGATGCACCTTCCCTGATAGGTGTGGTAAGGAAGGACTGGGCATCCCAAAATAGCATTGCC
CTATCATGGCAAGCACCTGCTTTTTCCAATGGAGCCATTCTGGACTACGAGATCAAGTACTATGAGAAAGAACA
TGAGCAGCTGACCTACTCTTCCACAAGGTCCAAAGCCCCCAGTGTCATCATCACAGGTCTTAAGCCAGCCACCA
AATATGTATTTCACATCCGAGTGAGAACTGCGACAGGATACAGTGGCTACAGTCAGAAATTTGAATTTGAAACA
GGAGATGAAACTTCTGACATGGCAGCAGAACAAGGACAGATTCTCGTGATAGCCACCGCCGCTGTTGGCGGATT
CACTCTCCTCGTCATCCTCACTTTATTCTTCTTGATCACTGGGAGATGTCAGTGGTACATAAAAGCCAAGATGA
AGTCAGAAGAGAAGAGAAGAAACCACTTACAGAATGGGCATTTGCGCTTCCCGGGAATTAAAACTTACATTGAT
CCAGATACATATGAAGACCCATCCCTAGCAGTCCATGAATTTGCAAAGGAGATTGATCCCTCAAGAATTCGTAT
TGAGAGAGTCATTGGGGCAGGTGAATTTGGAGAAGTCTGTAGTGGGCGTTTGAAGACACCAGGGAAAAGAGAGA
TCCCAGTTGCCATTAAAACTTTGAAAGGTGGCCACATGGATCGGCAAAGAAGAGATTTTCTAAGAGAAGCTAGT
ATCATGGGCCAGTTTGACCATCCAAACATCATTCGCCTAGAAGGGGTTGTCACCAAAAGATCCTTCCCGGCCAT
TGGGGTGGAGGCGTTTTGCCCCAGCTTCCTGAGGGCAGGGTTTTTAAATAGCATCCAGGCCCCGCATCCAGTGC
CAGGGGGAGGATCTTTGCCCCCCAGGATTCCTGCTGGCAGACCAGTAATGATTGTGGTGGAATATATGGAGAAT
GGATCCCTAGACTCCTTTTTGCGGAAGCATGATGGCCACTTCACAGTCATCCAGTTGGTCGGAATGCTCCGAGG
CATTGCATCAGGCATGAAGTATCTTTCTGATATGGGTTATGTTCATCGAGACCTAGCGGCTCGGAATATACTGG
TCAATAGCAACTTAGTATGCAAAGTTTCTGATTTTGGTCTCTCCAGAGTGCTGGAAGATGATCCAGAAGCTGCT
TATACAACAACTGGTGGAAAAATCCCCATAAGGTGGACAGCCCCAGAAGCCATCGCCTACAGAAAATTCTCCTC
AGCAAGCGATGCATGGAGCTATGGCATTGTCATGTGGGAGGTCATGTCCTATGGAGAGAGACCTTATTGGGAAATG
TCTAACCAAGATGTCATTCTGTCCATTGAAGAAGGGTACAGACTTCCAGCTCCCATGGGCTGTCCAGCATCTCT
ACACCAGCTGATGCTCCACTGCTGGCAGAAGGAGAGAAATCACAGACCAAAATTTACTGACATTGTCAGCTTCC
TTGACAAACTGATCCGAAATCCCAGTGCCCTTCACACCCTGGTGGAGGACATCCTTGTAATGCCAGAGTCCCCT
GGTGAAGTTCCGGAATATCCTTTGTTTGTCACAGTTGGTGACTGGCTAGATTCTATAAAGATGGGGCAATACAA
GAATAACTTCGTGGCAGCAGGGTTTACAACATTTGACCTGATTTCAAGAATGAGCATTGATGACATTAGAAGAA
TTGGAGTCATACTTATTGGACACCAGAGACGAATAGTCAGCAGCATACAGACTTTACGTTTACACATGATGCAC
ATACAGGAGAAGGGATTTCATGTATGAAAGTACCACAAGCACCTGTGTTTTGTGCCTCAGCATTTCTAAAATGA
ACGATATCCTCTCTACTACTCTCTCTTCTGATTCTCCAAACATCACTTCACAAACTGCAGTCTTCTGTTCAGAC
TATAGGCACACACCTTATGTTTATGCTTCCAACCAGGATTTTAAAATCATGCTACATAAATCCGTTCTGAATAA
CCTGCAACTAAAAAAAAAAAAAAAAAA

FIGURE 104

></usr/seqdb2/sst/DNA/Dnaseqs.min/ss.DNA222653
><subunit 1 of 1, 1036 aa, 1 stop
><MW: 116379, pI: 6.94, NX(S/T): 5
MGGCEVREFLLQFGFFLPLLTAWPGDCSHVSNNQVVLLDTTTVLGELGWKTYPLNGWDAI
TEMDEHNRPIHTYQVCNVMEPNQNNWLRTNWISRDAAQKIYVEMKFTLRDCNSIPWVLGT
CKETFNLFYMESDESHGIKFKPNQYTKIDTIAADESFTQMDLGDRILKLNTEIREVGPIE
RKGFYLAFQDIGACIALVSVRVFYKKCPFTVRNLAMFPDTIPRVDSSSLVEVRGSCVKSA
EERDTPKLYCGADGDWLVPLGRCICSTGYEEIEGSCHACRPGFYKAFAGNTKCSKCPPHS
LTYMEATSVCQCEKGYFRAEKDPPSMACTRPPSAPRNVVFNINETALILEWSPPSDTGGR
KDLTYSVICKKCGLDTSQCEDCGGGLRFIPRHTGLINNSVIVLDFVSHVNYTFEIEAMNG
VSELSFSPKPFTAITVTTDQDAPSLIGVVRKDWASQNSIALSWQAPAFSNGAILDYEIKY
YEKEHEQLTYSSTRSKAPSVIITGLKPATKYVFHIRVRTATGYSGYSQKFEFETGDETSD
MAAEQGQILVIATAAVGGFTLLVILTLFFLITGRCQWYIKAKMKSEEKRRNHLQNGHLRF
PGIKTYIDPDTYEDPSLAVHEFAKEIDPSRIRIERVIGAGEFGEVCSGRLKTPGKREIPV
AIKTLKGGHMDRQRRDFLREASIMGQFDHPNIIRLEGVVTKRSFPAIGVEAFCPSFLRAG
FLNSIQAPHPVPGGGSLPPRIPAGRPVMIVVEYMENGSLDSFLRKHDGHFTVIQLVGMLR
GIASGMKYLSDMGYVHRDLAARNILVNSNLVCKVSDFGLSRVLEDDPEAAYTTTGGKIPI
RWTAPEAIAYRKFSSASDAWSYGIVMWEVMSYGERPYWEMSNQDVILSIEEGYRLPAPMG
CPASLHQLMLHCWQKERNHRPKFTDIVSFLDKLIRNPSALHTLVEDILVMPESPGEVPEY
PLFVTVGDWLDSIKMGQYKNNFVAAGFTTFDLISRMSIDDIRRIGVILIGHQRRIVSSIQ
TLRLHMMHIQEKGFHV

Important features of the protein:

Signal peptide:
Amino acids 1-22

Transmembrane domain:
Amino acids 551-571

N-glycosylation sites:
Amino acids 343-346;397-400;410-413;756-759 cAMP- and cGMP-dependent protein kinase phosphorylation site:
Amino acids 851-854

Tyrosine kinase phosphorylation sites:
Amino acids 483-490;604-612;787-794

N-myristoylation sites:
Amino acids 192-197;274-279;289-294;373-378;394-399;504-509;
757-762;777-782;781-786;900-905;976-981

Amidation site:
Amino acids 358-361;653-656

Tyrosine protein kinases specific active-site signature:
Amino acids 794-806

Receptor tyrosine kinase class V signature 1:
Amino acids 192-208

Ephrin receptor ligand binding domain:
Amino acids 34-207 pkinase Protein kinase domain:
Amino acids 631-927

Fibronectin type III domain:
Amino acids 332-425;440-527

SAM domain (Sterile alpha motif):
Amino acids 959-1023

FIGURE 105

```
GGCGGCGGGCTGCGCGGAGCGGCGTCCCCTGCAGCCGCGGACCGAGGCAGCGGCGGCACCTGCCGGCCGAGCAA
TGCCAAGTGAGTACACCTATGTGAAACTGAGAAGTGATTGCTCGAGGCCTTCCCTGCAATGGTACACCCGAGCT
CAAAGCAAGATGAGAAGGCCCAGCTTGTTATTAAAAGACATCCTCAAATGTACATTGCTTGTGTTTGGAGTGTG
GATCCTTTATATCCTCAAGTTAAATTATACTACTGAAGAATGTGACATGAAAAAAATGCATTATGTGGACCCTG
ACCATGTAAAGAGAGCTCAGAAATATGCTCAGCAAGTCTTGCAGAAGGAATGTCGTCCCAAGTTTGCCAAGACA
TCAATGGCGCTGTTATTTGAGCACAGGTATAGCGTGGACTTACTCCCTTTTGTGCAGAAGGCCCCCAAAGACAG
TGAAGCTGAGTCCAAGTACGATCCTCCTTTTGGGTTCCGGAAGTTCTCCAGTAAAGTCCAGACCCTCTTGGAAC
TCTTGCCAGAGCACGACCTCCCTGAACACTTGAAAGCCAAGACCTGTCGGCGCTGTGTGGTTATTGGAAGCGGA
GGAATACTGCACGGATTAGAACTGGGCCACACCCTGAACCAGTTCGATGTTGTGATAAGGTTAAACAGTGCACC
AGTTGAGGGATATTCAGAACATGTTGGAAATAAAACTACTATAAGGATGACTTATCCAGAGGGCGCACCACTGT
CTGACCTTGAATATTATTCCAATGACTTATTTGTTGCTGTTTTATTTAAGAGTGTTGATTTCAACTGGCTTCAA
GCAATGGTAAAAAAGGAAACCCTGCCATTCTGGGTACGACTCTTCTTTTGGAAGCAGGTGGCAGAAAAAATCCC
ACTGCAGCCAAAACATTTCAGGATTTTGAATCCAGTTATCATCAAAGAGACTGCCTTTGACATCCTTCAGTACT
CAGAGCCTCAGTCAAGGTTCTGGGGCCGAGATAAGAACGTCCCCACAATCGGTGTCATTGCCGTTGTCTTAGCC
ACACATCTGTGCGATGAAGTCAGTTTGGCGGGTTTTGGATATGACCTCAATCAACCCAGAACACCTTTGCACTA
CTTCGACAGTCAATGCATGGCTGCTATGAACTTTCAGACCATGCATAATGTGACAACGGAAACCAAGTTCCTCT
TAAAGCTGGTCAAAGAGGGAGTGGTGAAAGATCTCAGTGGAGGCATTGATCGTGAATTTTGAACACAGAAAACC
TCAGTTGAAAATGCAACTCTAACTCTGAGAGCTGTTTTTGACAGCCTTCTTGATGTATTTCTCCATCCTGCAGA
TACTTTGAAGTGCAGCTCATGTTTTTAACTTTTAATTTAAAAACACAAAAAAAATTTTAGCTCTTCCCACTTTT
TTTTTCCTATTTATTTGAGGTCAGTGTTTGTTTTTGCACACCATTTTGTAAATGAAACTTAAGAATTGAATTGG
AAAGACTTCTCAAAGAGAATTCTATGTAACGATGTTGTATTGATTTTTAAGAAAGTAATTTAATTTGTAAAACT
TCTGCTCGTTTACACTGCACATTGAATACACGTAACTAATTGGAAGGAGAGGGGGAGGTCACTCTTTTGATGGTG
GCCCTGAACCTCATTCTGGTTCCCTGCTGCGCTGCTTGGTGTGACCCACGGAGGATCCACTCCCAGGATGACGT
GCTCCGTAGCTCTGCTGCTGATACTGGGTCTGCGATGCAGCGGCGTGAGGCCTGGGCTGGTTGGAGAAGGTCAC
AACCCTTCTCTGTTGGTCTGCCTTCTGCTGAAAGACTCGAGAACCAACCAGGGAAGCTGTCCTGGAGGTCCCTG
GTCGGAGAGGGACATAGAATCTGTGACCTCTGACAACTGTGAAGCCACCCTGGGCTACAGAACCACAGTCTTC
CCAGCAATTATTACAATTCTTGAATTCCTTGGGGATTTTTTACTGCCCTTTCAAAGCACTTAAGTGTTAGATCT
AACGTGTTCCAGTGTCTGTCTGAGGTGACTTAAAAAATCAGAACAAAACTTCTATTATCCAGAGTCATGGGAGA
GTACACCCTTTCCAGGAATAATGTTTTGGGAAACACTGAAATGAAATCTTCCCAGTATTATAAATTGTGTATTTAA
```

FIGURE 106

></usr/seqdb2/sst/DNA/Dnaseqs.min/ss.DNA96897
><subunit 1 of 1, 362 aa, 1 stop
><MW: 41736, pI: 8.80, NX(S/T): 3
MRRPSLLLKDILKCTLLVFGVWILYILKLNYTTEECDMKKMHYVDPDHVKRAQKYAQQVLQK
ECRPKFAKTSMALLFEHRYSVDLLPFVQKAPKDSEAESKYDPPFGFRKFSSKVQTLLELLPE
HDLPEHLKAKTCRRCVVIGSGGILHGLELGHTLNQFDVVIRLNSAPVEGYSEHVGNKTTIRM
TYPEGAPLSDLEYYSNDLFVAVLFKSVDFNWLQAMVKKETLPFWVRLFFWKQVAEKIPLQPK
HFRILNPVIIKETAFDILQYSEPQSRFWGRDKNVPTIGVIAVVLATHLCDEVSLAGFGYDLN
QPRTPLHYFDSQCMAAMNFQTMHNVTTETKFLLKLVKEGVVKDLSGGIDREF

Important features of the protein:

Transmembrane domain:
Amino acids 11-27;281-297

N-glycosylation sites:
Amino acids 30-34;180-184;334-338 cAMP- and cGMP-dependent protein kinase phosphorylation site:
Amino acids 2-6;109-113;223-227

N-myristoylation sites:
Amino acids 146-152;150-156;179-185;191-197

FIGURE 107

TGACGCGGGGCGCCAGCTGCCAACTTCGCGCGCGGAGCTCCCCGGCGGTGCAGTCCCGTCCCGGCGGCGCGG
GCGGCATGAAGACTAGCCGCCGCGGCCGAGCGCTCCTGGCCGTGGCCCTGAACCTGCTGGCGCTGCTGTTCG
CCACCACCGCTTTCCTCACCACGCACTGGTGCCAGGGCACGCAGCGGGTCCCCAAGCCGGGCTGCGGCCAGG
GCGGGCGCGCCAACTGCCCCAACTCGGGCGCCAACGCCACGGCCAACGGCACCGCCGCCCCCGCCGCCGCCG
CCGCCGCCGCCACCGCCTCGGGGAACGGCCCCCCTGGCGGCGCGCTCTACAGCTGGGAGACCGGCGACGACC
GCTTCCTCTTCAGGAATTTCCACACCGGCATCTGGTACTCGTGCGAGGAGGAGCTCAGCGGGCTTGGTGAAA
AATGTCGCAGCTTCATTGACCTGGCCCCGGCGTCGGAGAAAGGCCTCCTGGGAATGGTCGCCCACATGATGT
ACACGCAGGTGTTCCAGGTCACCGTGAGCCTCGGTCCTGAGGACTGGAGACCCCATTCCTGGGACTACGGGT
GGTCCTTCTGCCTGGCGTGGGGCTCCTTTACCTGCTGCATGGCAGCCTCTGTCACCACGCTCAACTCCTACA
CCAAGACGGTCATTGAGTTCCGGCACAAGCGCAAGGTCTTTGAGCAGGGCTACCGGGAAGAGCCGACCTTCA
TAGACCCTGAGGCCATCAAGTACTTCCGGGAGAGGATGGAGAAGAGGGACGGGAGCGAGGAGGACTTTCACT
TAGACTGCCGCCACGAGAGATACCCTGCCCGACACCAGCCACACATGGCGGATTCCTGGCCCCGGAGCTCCG
CACAGGAAGCACCAGAGCTGAACCGACAGTGCTGGGTCTTGGGGCACTGGGTGTGACCAAGACCTCAACCTG
GCCCGCGGACCTCAGGCCATCGCTGGCACCAGCCCCTGCTGCAAGACCACCAGAGTGGTGCCCCCAGAACCC
TGGCCTGTGTGCCGTGAACTCAGTCAGCCTGCGTGGGAGATGCCAGGCCTGTCCTGCCCATCGCTGCCTGGG
TCCCATGGCCTTGGAAATGGGGCCAGGGCAGGCCCAAGGGAATGCACAGGGCTGCACAGAGTGACTTTGGGA
CAGCAGCCCCGGACTCTTGCCATCATCACATGAGCCCTGCTGGGCACAGCTGCGATGCCAGGAGACACATGG
CCACTGGCCACTGAATGGCTGGCACCCACAAGCCAGTCAGGTGCCCAGAGGGGCAGAGCCCTTTGGGGGGCA
GAGAGTGGCTTCCTGAAGGAGGGGGCAGTGGCGCAGGCACTGCAGGGGTGTCACACAGCAGGCACACAGCAG
GGGCTCAATAAATGCTTGTTGAACTTGTTTT

FIGURE 108

MKTSRRGRALLAVALNLLALLFATTAFLTTHWCQGTQRVPKPGCGQGGRANCPNSGANATANGTAAPAAAA
AAATASGNGPPGGALYSWETGDDRFLFRNFHTGIWYSCEEELSGLGEKCRSFIDLAPASEKGLLGMVAHMM
YTQVFQVTVSLGPEDWRPHSWDYGWSFCLAWGSFTCCMAASVTTLNSYTKTVIEFRHKRKVFEQGYREEPT
FIDPEAIKYFRERMEKRDGSEEDFHLDCRHERYPARHQPHMADSWPRSSAQEAPELNRQCWVLGHWV

Important features of the protein:

Signal peptide:
1-26

Transmembrane domain:
169-189

N-glycosylation site.
58-61
62-65

Glycosaminoglycan attachment site.
77-80
114-117

Tyrosine kinase phosphorylation site.
202-208

N-myristoylation site.
43-48
47-52
56-61
84-89
104-109
174-179

FIGURE 109

GATTACCAAGCAAGAACAGCTAAAATGAAAGCCATCATTCATCTTACTCTTCTTGCTCTCCT
TTCTGTAAACACAGCCACCAACCAAGGCAACTCAGCTGATGCTGTAACAACCCACAGAAACTG
CGACTAGTGGTCCTACAGTAGCTGCAGCTGATACCACTGAAACTAATTTCCCTGAAACTGCT
AGCACCACAGCAAATACACCTTCTTTCCCAACAGCTACTTCACCTGCTCCCCCCATAATTAG
TACACATAGTTCCTCCACAATTCCTACACCTGCTCCCCCCATAATTAGTACACATAGTTCCT
CCACAATTCCTATACCTACTGCTGCAGACAGTGAGTCAACCACAAATGTAAATTCATTAGCT
ACCTCTGACATAATCACCGCTTCATCTCCAAATGATGGATTAATCACAATGGTTCCTTCTGA
AACACAAAGTAACAATGAAATGTCCCCCACCACAGAAGACAATCAATCATCAGGGCCTCCCA
CTGGCACCGCTTTATTGGAGACCAGCACCCTAAACAGCACAGGTCCCAGCAATCCTTGCCAA
GATGATCCCTGTGCAGATAATTCGTTATGTGTTAAGCTGCATAATACAAGTTTTTGCCTGTG
TTTAGAAGGGTATTACTACAACTCTTCTACATGTAAGAAAGGAAAGGTATTCCCTGGGAAGATT
TCAGTGACAGTATCAGAAACATTTGACCCAGAAGAGAAACATTCCATGGCCTATCAAGACTT
GCATAGTGAAATTACTAGCTTGTTTAAAGATGTATTTGGCACATCTGTTTATGGACAGACTG
TAATTCTTACTGTAAGCACATCTCTGTCACCAAGATCTGAAATGCGTGCTGATGACAAGTTT
GTTAATGTAACAATAGTAACAATTTTGGCAGAAACCACAAGTGACAATGAGAAGACTGTGAC
TGAGAAAATTAATAAAGCAATTAGAAGTAGCTCAAGCAACTTTCTAAACTATGATTTGACCC
TTCGGTGTGATTATTATGGCTGTAACCAGACTGCGGATGACTGCCTCAATGGTTTAGCATGC
GATTGCAAATCTGACCTGCAAAGGCCTAACCCACAGAGCCCTTTCTGCGTTGCTTCCAGTCT
CAAGTGTCCTGATGCCTGCAACGCACAGCACAAGCAATGCTTAATAAAGAAGAGTGGTGGGG
CCCCTGAGTGTGCGTGCGTGCCCGGCTACCAGGAAGATGCTAATGGGAACTGCCAAAAGTGT
GCATTTGGCTACAGTGGACTCGACTGTAAGGACAAATTTCAGCTGATCCTCACTATTGTGGG
CACCATCGCTGGCATTGTCATTCTCAGCATGATAATTGCATTGATTGTCACAGCAAGATCAA
ATAACAAAACGAAGCATATTGAAGAAGAGAACTTGATTGACGAAGACTTTCAAAATCTAAAA
CTGCGGTCGACAGGCTTCACCAATCTTGGAGCAGAAGGGAGCGTCTTTCCTAAGGTCAGGAT
AACGGCCTCCAGAGACAGCCAGATGCAAAATCCCTATTCAAGCCACAGCAGCATGCCCCGCC
CTGACTATTAGAATCATAAGAATGTGGAACCCGCCATGGCCCCCAACCAATGTACAAGCTAT
TATTTAGAGTGTTTAGAAAGACTGATGGAGAAGTGAGCACCAGTAAAGATCTGGCCTCCGGG
GTTTTTCTTCCATCTGACATCTGCCAGCCTCTCTGAATGGAAGTTGTGAATGTTTGCAACGA
ATCCAGCTCACTTGCTAAATAAGAATCTATGACATTAAATGTAGTAGATGCTATTAGCGCTT
GTCAGAGAGGTGGTTTTCTTCAATCAGTACAAAGTACTGAGACAATGGTTAGGGTTGTTTTC
TTAATTCTTTTCCTGGTAGGGCAACAAGAACCATTTCCAATCTAGAGGAAAGCTCCCCAGCA
TTGCTTGCTCCTGGGCAAACATTGCTCTTGAGTTAAGTGACCTAATTCCCCTGGGAGACATA
CGCATCAACTGTGGAGGTCCGAGGGGATGAGAAGGGATACCCACCATCTTTCAAGGGTCACA
AGCTCACTCTCTGACAAGTCAGAATAGGGACACTGCTTCTATCCCTCCAATGGAGAGATTCT
GGCAACCTTTGAACAGCCCAGAGCTTGCAACCTAGCCTCACCCAAGAAGACTGGAAAGAGAC
ATATCTCTCAGCTTTTTCAGGAGGCGTGCCTGGGAATCCAGGAACTTTTTGATGCTAATTAG
AAGGCCTGGACTAAAAATGTCCACTATGGGGTGCACTCTACAGTTTTTGAAATGCTAGGAGG
CAGAAGGGGCAGAGAGTAAAAAACATGACCTGGTAGAAGGAAGAGAGGCAAAGGAAACTGGG
TGGGGAGGATCAATTAGAGAGGAGGCACCTGGGATCCACCTTCTTCCTTAGGTCCCCTCCTC
CATCAGCAAAGGAGCACTTCTCTAATCATGCCCTCCCGAAGACTGGCTGGGAGAAGGTTTAAAA
ACAAAAAATCCAGGAGTAAGAGCCTTAGGTCAGTTTGAAATTGGAGACAAACTGTCTGGCAA
AGGGTGCGAGAGGGAGCTTGTGCTCAGGAGTCCAGCCGCCCAGCCTCGGGGTGTAGGTTTCT
GAGGTGTGCCATTGGGGCCTCAGCCTTCTCTGGTGACAGAGGCTCAGCTGTGGCCACCAACA
CACAACCACACACACACAACCACACACACAAATGGGGGCAACCACATCCAGTACAAGCTTTT
ACAAATGTTATTAGTGTCCTTTTTTATTTCTAATGCCTTGTCCTCTTAAAAGTTATTTTATT
TGTTATTATTATTTGTTCTTGACTGTTAATTGTGAATGGTAATGCAATAAAGTGCCTTTGTT
AGATGGTGAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAA

FIGURE 110

></usr/seqdb2/sst/DNA/Dnaseqs.min/ss.DNA142930
><subunit 1 of 1, 512 aa, 1 stop
><MW: 54535, pI: 4.89, NX(S/T): 7
MKAIIHLTLLALLSVNTATNQGNSADAVTTTETATSGPTVAAADTTETNFPETASTTANT
PSFPTATSPAPPIISTHSSSTIPTPAPPIISTHSSSTIPIPTAADSESTTNVNSLATSDI
ITASSPNDGLITMVPSETQSNNEMSPTTEDNQSSGPPTGTALLETSTLNSTGPSNPCQDD
PCADNSLCVKLHNTSFCLCLEGYYYNSSTCKKGKVFPGKISVTVSETFDPEEKHSMAYQD
LHSEITSLFKDVFGTSVYGQTVILTVSTSLSPRSEMRADDKFVNVTIVTILAETTSDNEK
TVTEKINKAIRSSSSNFLNYDLTLRCDYYGCNQTADDCLNGLACDCKSDLQRPNPQSPFC
VASSLKCPDACNAQHKQCLIKKSGGAPECACVPGYQEDANGNCQKCAFGYSGLDCKDKFQ
LILTIVGTIAGIVILSMIIALIVTARSNNKTKHIEEENLIDEDFQNLKLRSTGFTNLGAE
GSVFPKVRITASRDSQMQNPYSSHSSMPRPDY

Important features of the protein:

Signal peptide:
Amino acids 1-17

Transmembrane domain:
Amino acids 421-442

N-glycosylation sites:
Amino acids 151-155;169-173;193-197;206-210;284-288;
332-336;449-453

N-myristoylation sites:
Amino acids 330-336;385-391;427-433;478-484

SEA domain:
Amino acids 212-328

FIGURE 111

CTGGGACTTGGCTTTCTCCGGATAAGCGGCGGCACCGGCGTCAGCGATGACCGTGCAGAGAC
TCGTGGCCGCGGCCGTGCTGGTGGCCCTGGTCTCACTCATCCTCAACAACGTGGCGGCCTTC
ACCTCCAACTGGGTGTGCCAGACGCTGGAGGATGGGCGCAGGCGCAGCGTGGGGCTGTGGAG
GTCCTGCTGGCTGGTGGACAGGACCCGGGGAGGGCCGAGCCCTGGGGCCAGAGCCGGCCAGG
TGGACGCACATGACTGTGAGGCGCTGGGCTGGGGCTCCGAGGCAGCCGGCTTCCAGGAGTCC
CGAGGCACCGTCAAACTGCAGTTCGACATGATGCGCGCCTGCAACCTGGTGGCCACGGCCGC
GCTCACCGCAGGCCAGCTCACCTTCCTCCTGGGGCTGGTGGGCCTGCCCCTGCTGTCACCCG
ACGCCCCGTGCTGGGAGGAGGCCATGGCCGCTGCATTCCAACTGGCGAGTTTTGTCCTGGTC
ATCGGGCTCGTGACTTTCTACAGAATTGGCCCATACACCAACCTGTCCTGGTCCTGCTACCT
GAACATTGGCGCCTGCCTTCTGGCCACGCTGGCGGCAGCCATGCTCATCTGGAACATTCTCC
ACAAGAGGGAGGACTGCATGGCCCCCCGGGTGATTGTCATCAGCCGCTCCCTGACAGCGCGC
TTTCGCCGTGGGCTGGACAATGACTACGTGGAGTCACCATGCTGAGTCGCCCTTCTCAGCGC
TCCATCAACGCACACCTGCTATCGTGGAACAGCCTAGAAACCAAGGGACTCCACCACCAAGT
CACTTCCCCTGCTCGTGCAGAGGCACGGGATGAGTCTGGGTGACCTCTGCGCCATGCGTGCG
AGACACGTGTGCGTTTACTGTTATGTCGGTCATATGTCTGTACGTGTCGTGGGCCAACCTCG
TTCTGCCTCCAGC

FIGURE 112

></usr/seqdb2/sst/DNA/Dnaseqs.min/ss.DNA147253
><subunit 1 of 1, 226 aa, 1 stop
><MW: 24540, pI: 8.27, NX(S/T): 1
MTVQRLVAAAVLVALVSLILNNVAAFTSNWVCQTLEDGRRRSVGLWRSCWLVDRTRGGPS
PGARAGQVDAHDCEALGWGSEAAGFQESRGTVKLQFDMMRACNLVATAALTAGQLTFLLG
LVGLPLLSPDAPCWEEAMAAAFQLASFVLVIGLVTFYRIGPYTNLSWSCYLNIGACLLAT
LAAAMLIWNILHKREDCMAPRVIVISRSLTARFRRGLDNDYVESPC

Important features of the protein:
Signal peptide:
Amino acids 1-25

Transmembrane domains:
Amino acids 105-125;139-157;169-188

N-glycosylation site:
Amino acids 164-168 cAMP- and cGMP-dependent protein kinase phosphorylation site:
Amino acids 39-43

Tyrosine kinase phosphorylation site:
Amino acids 214-222

N-myristoylation sites:
Amino acids 44-50;62-68;66-72;79-85

Amidation site:
Amino acids 37-41

FIGURE 113

GACTTTACCACTACTCGCTATAGAGCCCTGGTCAAGTTCTCTCCACCTCTCTATCTATGTCT
CAGTTTCTTCATCTGTAACATCAAATGAATAATAATACCAATCTCCTAGACTTCATAAGAGG
ATTAACAAAGACAAAATATGGGAAAAACATAACATGGCGTCCCATAATTATTAGATCTTATT
ATTGACACTAAAATGGCATTAAAATTACCAAAAGGAAGACAGCATCTGTTTCCTCTTTGGTC
CTGAGCTGGTTAAAAGGAACACTGGTTGCCTGAACAGTCACACTTGCAACCATGATGCCTAA
ACATTGCTTTCTAGGCTTCCTCATCAGTTTCTTCCTTACTGGTGTAGCAGGAACTCAGTCAA
CGCATGAGTCTCTGAAGCCTCAGAGGGTACAATTTCAGTCCCGAAATTTTCACAACATTTTG
CAATGGCAGCCTGGGAGGGCACTTACTGGCAACAGCAGTGTCTATTTTGTGCAGTACAAAAT
ATATGGACAGAGACAATGGAAAAATAAAGAAGACTGTTGGGGTACTCAAGAACTCTCTTGTG
ACCTTACCAGTGAAACCTCAGACATACAGGAACCTTATTACGGGAGGGTGAGGGCGGCCTCG
GCTGGGAGCTACTCAGAATGGAGCATGACGCCGCGGTTCACTCCCTGGTGGGAAACAAAAAT
AGATCCTCCAGTCATGAATATAACCCAAGTCAATGGCTCTTTGTTGGTAATTCTCCATGCTC
CAAATTTACCATATAGATACCAAAAGGAAAAAAATGTATCTATAGAAGATTACTATGAACTA
CTATACCGAGTTTTTATAATTAACAATTCACTAGAAAAGGAGCAAAAGGTTTATGAAGGGGC
TCACAGAGCGGTTGAAATTGAAGCTCTAACACCACACTCCAGCTACTGTGTAGTGGCTGAAA
TATATCAGCCCATGTTAGACAGAAGAAGTCAGAGAAGTGAAGAGAGATGTGTGGAAATTCCA
TGACTTGTGGAATTTGGCATTCAGCAATGTGGAAATTCTAAAGCTCCCTGAGAACAGGATGA
CTCGTGTTTGAAGGATCTTATTTAAAATTGTTTTTGTATTTTCTTAAAGCAATATTCACTGT
TACACCTTGGGGACTTCTTTGTTTACCCATTCTTTTATCCTTTATATTTCATTTGTAAACTA
TATTTGAACGACATTCCCCCCGAAAAATTGAAATGTAAAGATGAGGCAGAGAATAAAGTGTT
CTATGAAATTCAGAACTTTATTTCTGAATGTAACATCCCTAATAACAACCTTCATTCTTCTA
ATACAGCAAAATAAAAATTTAACAACCAAGGAATAGTATTTAAGAAAATGTTGAAATAATTT
TTTTAAAATAGCATTACAGACTGAG

FIGURE 114

></usr/seqdb2/sst/DNA/Dnaseqs.min/ss.DNA149927
><subunit 1 of 1, 231 aa, 1 stop
><MW: 26980, pI: 7.06, NX(S/T): 5
MMPKHCFLGFLISFFLTGVAGTQSTHESLKPQRVQFQSRNFHNILQWQPGRALTGNSSVY
FVQYKIYGQRQWKNKEDCWGTQELSCDLTSETSDIQEPYYGRVRAASAGSYSEWSMTPRF
TPWWETKIDPPVMNITQVNGSLLVILHAPNLPYRYQKEKNVSIEDYYELLYRVFIINNSL
EKEQKVYEGAHRAVEIEALTPHSSYCVVAEIYQPMLDRRSQRSEERCVEIP

Important features of the protein:
Signal peptide:
Amino acids 1-21

N-glycosylation sites:
Amino acids 56-60;134-138;139-143;160-164;177-181

N-myristoylation sites:
Amino acids 18-24;21-27;189-195

PRO10268 POLYPEPTIDES

RELATED APPLICATIONS

This application is a continuation of, and claims priority under 35 USC § 120 to, U.S. application Ser. No. 10/197,942 filed Jul. 18, 2002, now abandoned, which is a continuation of, and claims priority under 35 USC § 120 to, PCT Application PCT/US01/27099 filed Aug. 29, 2001, which is a continuation-in-part of, and claims priority under 35 USC § 120 to, PCT Application PCT/US00/30873 filed Nov. 10, 2000, which claims priority under 35 USC § 119 to U.S. provisional application 60/177,118 filed Jan. 20, 2000.

FIELD OF THE INVENTION

The present invention relates generally to the identification and isolation of novel DNA and to the recombinant production of novel polypeptides.

BACKGROUND OF THE INVENTION

Extracellular proteins play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. These secreted polypeptides or signaling molecules normally pass through the cellular secretory pathway to reach their site of action in the extracellular environment.

Secreted proteins have various industrial applications, including as pharmaceuticals, diagnostics, biosensors and bioreactors. Most protein drugs available at present, such as thrombolytic agents, interferons, interleukins, erythropoietins, colony stimulating factors, and various other cytokines, are secretory proteins. Their receptors, which are membrane proteins, also have potential as therapeutic or diagnostic agents. Efforts are being undertaken by both industry and academia to identify new, native secreted proteins. Many efforts are focused on the screening of mammalian recombinant DNA libraries to identify the coding sequences for novel secreted proteins. Examples of screening methods and techniques are described in the literature [see, for example, Klein et al., *Proc. Natl. Acad. Sci*. 93:7108-7113 (1996); U.S. Pat. No. 5,536,637)].

Membrane-bound proteins and receptors can play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. Such membrane-bound proteins and cell receptors include, but are not limited to, cytokine receptors, receptor kinases, receptor phosphatases, receptors involved in cell-cell interactions, and cellular adhesin molecules like selectins and integrins. For instance, transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Membrane-bound proteins and receptor molecules have various industrial applications, including as pharmaceutical and diagnostic agents. Receptor immunoadhesins, for instance, can be employed as therapeutic agents to block receptor-ligand interactions. The membrane-bound proteins can also be employed for screening of potential peptide or small molecule inhibitors of the relevant receptor/ligand interaction.

Efforts are being undertaken by both industry and academia to identify new, native receptor or membrane-bound proteins. Many efforts are focused on the screening of mammalian recombinant DNA libraries to identify the coding sequences for novel receptor or membrane-bound proteins.

SUMMARY OF THE INVENTION

In one embodiment, the invention provides an isolated nucleic acid molecule comprising a nucleotide sequence that encodes a PRO polypeptide.

In one aspect, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule encoding a PRO polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule comprising the coding sequence of a full-length PRO polypeptide cDNA as disclosed herein, the coding sequence of a PRO polypeptide lacking the signal peptide as disclosed herein, the coding sequence of an extracellular domain of a transmembrane PRO polypeptide, with or without the signal peptide, as disclosed herein or the coding sequence of any other specifically defined fragment of the full-length amino acid sequence as disclosed herein, or (b) the complement of the DNA molecule of (a).

In a further aspect, the invention concerns an isolated nucleic acid molecule comprising a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule that encodes the same mature polypeptide encoded by any of the human protein cDNAs deposited with the ATCC as disclosed herein, or (b) the complement of the DNA molecule of (a).

Another aspect the invention provides an isolated nucleic acid molecule comprising a nucleotide sequence encoding a PRO polypeptide which is either transmembrane domain-deleted or transmembrane domain-inactivated, or is complementary to such encoding nucleotide sequence, wherein the transmembrane domain(s) of such polypeptide are disclosed herein. Therefore, soluble extracellular domains of the herein described PRO polypeptides are contemplated.

Another embodiment is directed to fragments of a PRO polypeptide coding sequence, or the complement thereof, that may find use as, for example, hybridization probes, for encoding fragments of a PRO polypeptide that may optionally encode a polypeptide comprising a binding site for an anti-PRO antibody or as antisense oligonucleotide probes. Such nucleic acid fragments are usually at least about 10 nucleotides in length, alternatively at least about 15 nucleotides in length, alternatively at least about 20 nucleotides in length, alternatively at least about 30 nucleotides in length, alternatively at least about 40 nucleotides in length, alternatively at least about 50 nucleotides in length, alternatively at least about 60 nucleotides in length, alternatively at least about 70 nucleotides in length, alternatively at least about 80 nucleotides in length, alternatively at least about 90 nucleotides in length, alternatively at least about 100 nucleotides in length, alternatively at least about 110 nucleotides in length, alternatively at least about 120 nucleotides in length, alternatively at least about 130 nucleotides in length, alternatively at least about 140 nucleotides in length, alternatively at least about 150 nucleotides in length, alternatively at least about 160 nucleotides in length, alternatively at least about 170 nucleotides in length, alternatively at least about 180 nucleotides in length, alternatively at least about 190 nucleotides in length, alternatively at least about 200 nucleotides in length, alternatively at least about 250 nucleotides in length, alternatively at least about 300 nucleotides in length, alternatively at least about 350 nucleotides in length, alternatively at least about 400 nucleotides in length, alternatively at least about 450 nucleotides in length, alternatively at least about 500 nucleotides in length, alternatively at least about 600 nucleotides in length, alternatively at least about 700 nucleotides in length, alternatively at least about 800 nucleotides in length, alternatively at least about 900 nucleotides in length and alternatively at least about 1000 nucleotides in length, wherein in this context the term "about" means the referenced nucleotide sequence length plus or minus 10% of that referenced length. It is noted that novel fragments of a PRO polypeptide-encoding nucleotide sequence may be determined in a routine manner by aligning the PRO polypeptide-encoding nucleotide sequence with other known nucleotide sequences using any of a number of well known sequence alignment programs and determining which PRO polypeptide-encoding nucleotide sequence fragment(s) are novel. All of such PRO polypeptide-encoding nucleotide sequences are contemplated herein. Also contemplated are the PRO polypeptide fragments encoded by these nucleotide molecule fragments, preferably those PRO polypeptide fragments that comprise a binding site for an anti-PRO antibody.

In another embodiment, the invention provides isolated PRO polypeptide encoded by any of the isolated nucleic acid sequences hereinabove identified.

In a certain aspect, the invention concerns an isolated PRO polypeptide, comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a PRO polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein.

In a further aspect, the invention concerns an isolated PRO polypeptide comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to an amino acid sequence encoded by any of the human protein cDNAs deposited with the ATCC as disclosed herein.

In a specific aspect, the invention provides an isolated PRO polypeptide without the N-terminal signal sequence and/or the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

Another aspect the invention provides an isolated PRO polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

In yet another embodiment, the invention concerns agonists and antagonists of a native PRO polypeptide as defined herein. In a particular embodiment, the agonist or antagonist is an anti-PRO antibody or a small molecule.

In a further embodiment, the invention concerns a method of identifying agonists or antagonists to a PRO polypeptide which comprise contacting the PRO polypeptide with a candidate molecule and monitoring a biological activity mediated by said PRO polypeptide. Preferably, the PRO polypeptide is a native PRO polypeptide.

In a still further embodiment, the invention concerns a composition of matter comprising a PRO polypeptide, or an agonist or antagonist of a PRO polypeptide as herein described, or an anti-PRO antibody, in combination with a carrier. Optionally, the carrier is a pharmaceutically acceptable carrier.

Another embodiment of the present invention is directed to the use of a PRO polypeptide, or an agonist or antagonist thereof as hereinbefore described, or an anti-PRO antibody, for the preparation of a medicament useful in the treatment of a condition which is responsive to the PRO polypeptide, an agonist or antagonist thereof or an anti-PRO antibody.

In other embodiments of the present invention, the invention provides vectors comprising DNA encoding any of the herein described polypeptides. Host cell comprising any such vector are also provided. By way of example, the host cells may be CHO cells, *E. coli*, or yeast. A process for producing any of the herein described polypeptides is further provided and comprises culturing host cells under conditions suitable for expression of the desired polypeptide and recovering the desired polypeptide from the cell culture.

In other embodiments, the invention provides chimeric molecules comprising any of the herein described polypeptides fused to a heterologous polypeptide or amino acid sequence. Example of such chimeric molecules comprise any of the herein described polypeptides fused to an epitope tag sequence or a Fc region of an immunoglobulin.

In another embodiment, the invention provides an antibody which binds, preferably specifically, to any of the above or below described polypeptides. Optionally, the antibody is a monoclonal antibody, humanized antibody, antibody fragment or single-chain antibody.

In yet other embodiments, the invention provides oligonucleotide probes which may be useful for isolating genomic and cDNA nucleotide sequences, measuring or detecting expression of an associated gene or as antisense probes, wherein those probes may be derived from any of the above or below described nucleotide sequences. Preferred probe lengths are described above.

In yet other embodiments, the present invention is directed to methods of using the PRO polypeptides of the present invention for a variety of uses based upon the functional biological assay data presented in the Examples below.

BRIEF DESCRIPTION OF THE DRAWINGS

FIG. 1 shows a nucleotide sequence (SEQ ID NO:1) of a native sequence PRO281 cDNA, wherein SEQ ID NO:1 is a clone designated herein as "DNA16422-1209".

FIG. 2 shows the amino acid sequence (SEQ ID NO:2) derived from the coding sequence of SEQ ID NO:1 shown in FIG. 1.

FIG. 3 shows a nucleotide sequence (SEQ ID NO:3) of a native sequence PRO1560 cDNA, wherein SEQ ID NO:3 is a clone designated herein as "DNA19902-1669".

FIG. 4 shows the amino acid sequence (SEQ ID NO:4) derived from the coding sequence of SEQ ID NO:3 shown in FIG. 3.

FIG. 5 shows a nucleotide sequence (SEQ ID NO:5) of a native sequence PRO189 cDNA, wherein SEQ ID NO:5 is a clone designated herein as "DNA21624-1391".

FIG. 6 shows the amino acid sequence (SEQ ID NO:6) derived from the coding sequence of SEQ ID NO:5 shown in FIG. 5.

FIG. 7 shows a nucleotide sequence (SEQ ID NO:7) of a native sequence PRO240 cDNA, wherein SEQ ID NO:7 is a clone designated herein as "DNA34387-1138".

FIG. 8 shows the amino acid sequence (SEQ ID NO:8) derived from the coding sequence of SEQ ID NO:7 shown in FIG. 7.

FIG. 9 shows a nucleotide sequence (SEQ ID NO:9) of a native sequence PRO256 cDNA, wherein SEQ ID NO:9 is a clone designated herein as "DNA35880-1160".

FIG. 10 shows the amino acid sequence (SEQ ID NO:10) derived from the coding sequence of SEQ ID NO:9 shown in FIG. 9.

FIG. 11 shows a nucleotide sequence (SEQ ID NO:11) of a native sequence PRO306 cDNA, wherein SEQ ID NO:11 is a clone designated herein as "DNA39984-1221".

FIG. 12 shows the amino acid sequence (SEQ ID NO:12) derived from the coding sequence of SEQ ID NO:11 shown in FIG. 11.

FIG. 13 shows a nucleotide sequence (SEQ ID NO:13) of a native sequence PRO540 cDNA, wherein SEQ ID NO:13 is a clone designated herein as "DNA44189-1322".

FIG. 14 shows the amino acid sequence (SEQ ID NO:14) derived from the coding sequence of SEQ ID NO:13 shown in FIG. 13.

FIG. 15 shows a nucleotide sequence (SEQ ID NO:15) of a native sequence PRO773 cDNA, wherein SEQ ID NO:15 is a clone designated herein as "DNA48303-2829".

FIG. 16 shows the amino acid sequence (SEQ ID NO:16) derived from the coding sequence of SEQ ID NO:15 shown in FIG. 15.

FIG. 17 shows a nucleotide sequence (SEQ ID NO:17) of a native sequence PRO698 cDNA, wherein SEQ ID NO:17 is a clone designated herein as "DNA48320-1433".

FIG. 18 shows the amino acid sequence (SEQ ID NO:18) derived from the coding sequence of SEQ ID NO:17 shown in FIG. 17.

FIG. 19 shows a nucleotide sequence (SEQ ID NO:19) of a native sequence PRO3567 cDNA, wherein SEQ ID NO:19 is a clone designated herein as "DNA56049-2543".

FIG. 20 shows the amino acid sequence (SEQ ID NO:20) derived from the coding sequence of SEQ ID NO:19 shown in FIG. 19.

FIG. 21 shows a nucleotide sequence (SEQ ID NO:21) of a native sequence PRO826 cDNA, wherein SEQ ID NO:21 is a clone designated herein as "DNA57694-1341".

FIG. 22 shows the amino acid sequence (SEQ ID NO:22) derived from the coding sequence of SEQ ID NO:21 shown in FIG. 21.

FIG. 23 shows a nucleotide sequence (SEQ ID NO:23) of a native sequence PRO1002 cDNA, wherein SEQ ID NO:23 is a clone designated herein as "DNA59208-1373".

FIG. 24 shows the amino acid sequence (SEQ ID NO:24) derived from the coding sequence of SEQ ID NO:23 shown in FIG. 23.

FIG. 25 shows a nucleotide sequence (SEQ ID NO:25) of a native sequence PRO1068 cDNA, wherein SEQ ID NO:25 is a clone designated herein as "DNA59214-1449".

FIG. 26 shows the amino acid sequence (SEQ ID NO:26) derived from the coding sequence of SEQ ID NO:25 shown in FIG. 25.

FIG. 27 shows a nucleotide sequence (SEQ ID NO:27) of a native sequence PRO1030 cDNA, wherein SEQ ID NO:27 is a clone designated herein as "DNA59485-1336".

FIG. 28 shows the amino acid sequence (SEQ ID NO:28) derived from the coding sequence of SEQ ID NO:27 shown in FIG. 27.

FIG. 29 shows a nucleotide sequence (SEQ ID NO:29) of a native sequence PRO1313 cDNA, wherein SEQ ID NO:29 is a clone designated herein as "DNA64966-1575".

FIG. 30 shows the amino acid sequence (SEQ ID NO:30) derived from the coding sequence of SEQ ID NO:29 shown in FIG. 29.

FIG. 31 shows a nucleotide sequence (SEQ ID NO:31) of a native sequence PRO6071 cDNA, wherein SEQ ID NO:31 is a clone designated herein as "DNA82403-2959".

FIG. 32 shows the amino acid sequence (SEQ ID NO:32) derived from the coding sequence of SEQ ID NO:31 shown in FIG. 31.

FIG. 33 shows a nucleotide sequence (SEQ ID NO:33) of a native sequence PRO4397 cDNA, wherein SEQ ID NO:33 is a clone designated herein as "DNA83505-2606".

FIG. 34 shows the amino acid sequence (SEQ ID NO:34) derived from the coding sequence of SEQ ID NO:33 shown in FIG. 33.

FIG. 35 shows a nucleotide sequence (SEQ ID NO:35) of a native sequence PRO4344 cDNA, wherein SEQ ID NO:35 is a clone designated herein as "DNA84927-2585".

FIG. 36 shows the amino acid sequence (SEQ ID NO:36) derived from the coding sequence of SEQ ID NO:35 shown in FIG. 35.

FIG. 37 shows a nucleotide sequence (SEQ ID NO:37) of a native sequence PRO4407 cDNA, wherein SEQ ID NO:37 is a clone designated herein as "DNA92264-2616".

FIG. 38 shows the amino acid sequence (SEQ ID NO:38) derived from the coding sequence of SEQ ID NO:37 shown in FIG. 37.

FIG. 39 shows a nucleotide sequence (SEQ ID NO:39) of a native sequence PRO4316 cDNA, wherein SEQ ID NO:39 is a clone designated herein as "DNA94713-2561".

FIG. 40 shows the amino acid sequence (SEQ ID NO:40) derived from the coding sequence of SEQ ID NO:39 shown in FIG. 39.

FIG. 41 shows a nucleotide sequence (SEQ ID NO:41) of a native sequence PRO5775 cDNA, wherein SEQ ID NO:41 is a clone designated herein as "DNA96869-2673".

FIG. 42 shows the amino acid sequence (SEQ ID NO:42) derived from the coding sequence of SEQ ID NO:41 shown in FIG. 41.

FIG. 43 shows a nucleotide sequence (SEQ ID NO:43) of a native sequence PRO6016 cDNA, wherein SEQ ID NO:43 is a clone designated herein as "DNA96881-2699".

FIG. 44 shows the amino acid sequence (SEQ ID NO:44) derived from the coding sequence of SEQ ID NO:43 shown in FIG. 43.

FIG. 45 shows a nucleotide sequence (SEQ ID NO:45) of a native sequence PRO4499 cDNA, wherein SEQ ID NO:45 is a clone designated herein as "DNA96889-2641".

FIG. 46 shows the amino acid sequence (SEQ ID NO:46) derived from the coding sequence of SEQ ID NO:45 shown in FIG. 45.

FIG. 47 shows a nucleotide sequence (SEQ ID NO:47) of a native sequence PRO4487 cDNA, wherein SEQ ID NO:47 is a clone designated herein as "DNA96898-2640".

FIG. 48 shows the amino acid sequence (SEQ ID NO:48) derived from the coding sequence of SEQ ID NO:47 shown in FIG. 47.

FIG. 49 shows a nucleotide sequence (SEQ ID NO:49) of a native sequence PRO4980 cDNA, wherein SEQ ID NO:49 is a clone designated herein as "DNA97003-2649".

FIG. 50 shows the amino acid sequence (SEQ ID NO:50) derived from the coding sequence of SEQ ID NO:49 shown in FIG. 49.

FIG. 51 shows a nucleotide sequence (SEQ ID NO:51) of a native sequence PRO6018 cDNA, wherein SEQ ID NO:51 is a clone designated herein as "DNA98565-2701".

FIG. 52 shows the amino acid sequence (SEQ ID NO:52) derived from the coding sequence of SEQ ID NO:51 shown in FIG. 51.

FIG. 53 shows a nucleotide sequence (SEQ ID NO:53) of a native sequence PRO7168 cDNA, wherein SEQ ID NO:53 is a clone designated herein as "DNA102846-2742".

FIG. 54 shows the amino acid sequence (SEQ ID NO:54) derived from the coding sequence of SEQ ID NO:53 shown in FIG. 53.

FIG. 55 shows a nucleotide sequence (SEQ ID NO:55) of a native sequence PRO6308 cDNA, wherein SEQ ID NO:55 is a clone designated herein as "DNA102847-2726".

FIG. 56 shows the amino acid sequence (SEQ ID NO:56) derived from the coding sequence of SEQ ID NO:55 shown in FIG. 55.

FIG. 57 shows a nucleotide sequence (SEQ ID NO:57) of a native sequence PRO6000 cDNA, wherein SEQ ID NO:57 is a clone designated herein as "DNA102880-2689".

FIG. 58 shows the amino acid sequence (SEQ ID NO:58) derived from the coding sequence of SEQ ID NO:57 shown in FIG. 57.

FIG. 59 shows a nucleotide sequence (SEQ ID NO:59) of a native sequence PRO6006 cDNA, wherein SEQ ID NO:59 is a clone designated herein as "DNA105782-2693".

FIG. 60 shows the amino acid sequence (SEQ ID NO:60) derived from the coding sequence of SEQ ID NO:59 shown in FIG. 59.

FIG. 61 shows a nucleotide sequence (SEQ ID NO:61) of a native sequence PRO5800 cDNA, wherein SEQ ID NO:61 is a clone designated herein as "DNA108912-2680".

FIG. 62 shows the amino acid sequence (SEQ ID NO:62) derived from the coding sequence of SEQ ID NO:61 shown in FIG. 61.

FIG. 63 shows a nucleotide sequence (SEQ ID NO:63) of a native sequence PRO7476 cDNA, wherein SEQ ID NO:63 is a clone designated herein as "DNA115253-2757".

FIG. 64 shows the amino acid sequence (SEQ ID NO:64) derived from the coding sequence of SEQ ID NO:63 shown in FIG. 63.

FIG. 65 shows a nucleotide sequence (SEQ ID NO:65) of a native sequence PRO6496 cDNA, wherein SEQ ID NO:65 is a clone designated herein as "DNA119302-2737".

FIG. 66 shows the amino acid sequence (SEQ ID NO:66) derived from the coding sequence of SEQ ID NO:65 shown in FIG. 65.

FIG. 67 shows a nucleotide sequence (SEQ ID NO:67) of a native sequence PRO7422 cDNA, wherein SEQ ID NO:67 is a clone designated herein as "DNA119536-2752".

FIG. 68 shows the amino acid sequence (SEQ ID NO:68) derived from the coding sequence of SEQ ID NO:67 shown in FIG. 67.

FIG. 69 shows a nucleotide sequence (SEQ ID NO:69) of a native sequence PRO7431cDNA, wherein SEQ ID NO:69 is a clone designated herein as "DNA119542-2754".

FIG. 70 shows the amino acid sequence (SEQ ID NO:70) derived from the coding sequence of SEQ ID NO:69 shown in FIG. 69.

FIG. 71 shows a nucleotide sequence (SEQ ID NO:71) of a native sequence PRO10275 cDNA, wherein SEQ ID NO:71 is a clone designated herein as "DNA143498-2824".

FIG. 72 shows the amino acid sequence (SEQ ID NO:72) derived from the coding sequence of SEQ ID NO:71 shown in FIG. 71.

FIG. 73 shows a nucleotide sequence (SEQ ID NO:73) of a native sequence PRO10268 cDNA, wherein SEQ ID NO:73 is a clone designated herein as "DNA145583-2820".

FIG. 74 shows the amino acid sequence (SEQ ID NO:74) derived from the coding sequence of SEQ ID NO:73 shown in FIG. 73.

FIG. 75 shows a nucleotide sequence (SEQ ID NO:75) of a native sequence PRO20080 cDNA, wherein SEQ ID NO:75 is a clone designated herein as "DNA161000-2896".

FIG. 76 shows the amino acid sequence (SEQ ID NO:76) derived from the coding sequence of SEQ ID NO:75 shown in FIG. 75.

FIG. 77 shows a nucleotide sequence (SEQ ID NO:77) of a native sequence PRO21207 cDNA, wherein SEQ ID NO:77 is a clone designated herein as "DNA161005-2943".

FIG. 78 shows the amino acid sequence (SEQ ID NO:78) derived from the coding sequence of SEQ ID NO:77 shown in FIG. 77.

FIG. 79 shows a nucleotide sequence (SEQ ID NO:79) of a native sequence PRO28633 cDNA, wherein SEQ ID NO:79 is a clone designated herein as "DNA170245-3053".

FIG. 80 shows the amino acid sequence (SEQ ID NO:80) derived from the coding sequence of SEQ ID NO:79 shown in FIG. 79.

FIG. 81 shows a nucleotide sequence (SEQ ID NO:81) of a native sequence PRO20933 cDNA, wherein SEQ ID NO:81 is a clone designated herein as "DNA171771-2919".

FIG. 82 shows the amino acid sequence (SEQ ID NO:82) derived from the coding sequence of SEQ ID NO:81 shown in FIG. 81.

FIG. 83 shows a nucleotide sequence (SEQ ID NO:83) of a native sequence PRO21383 cDNA, wherein SEQ ID NO:83 is a clone designated herein as "DNA173157-2981".

FIG. 84 shows the amino acid sequence (SEQ ID NO:84) derived from the coding sequence of SEQ ID NO:83 shown in FIG. 83.

FIG. 85 shows a nucleotide sequence (SEQ ID NO:85) of a native sequence PRO21485 cDNA, wherein SEQ ID NO:85 is a clone designated herein as "DNA175734-2985".

FIG. 86 shows the amino acid sequence (SEQ ID NO:86) derived from the coding sequence of SEQ ID NO:85 shown in FIG. 85.

FIG. 87 shows a nucleotide sequence (SEQ ID NO:87) of a native sequence PRO28700 cDNA, wherein SEQ ID NO:87 is a clone designated herein as "DNA176108-3040".

FIG. 88 shows the amino acid sequence (SEQ ID NO:88) derived from the coding sequence of SEQ ID NO:87 shown in FIG. 87.

FIG. 89 shows a nucleotide sequence (SEQ ID NO:89) of a native sequence PRO34012 cDNA, wherein SEQ ID NO:89 is a clone designated herein as "DNA190710-3028".

FIG. 90 shows the amino acid sequence (SEQ ID NO:90) derived from the coding sequence of SEQ ID NO:89 shown in FIG. 89.

FIG. 91 shows a nucleotide sequence (SEQ ID NO:91) of a native sequence PRO34003 cDNA, wherein SEQ ID NO:91 is a clone designated herein as "DNA190803-3019".

FIG. 92 shows the amino acid sequence (SEQ ID NO:92) derived from the coding sequence of SEQ ID NO:91 shown in FIG. 91.

FIG. 93 shows a nucleotide sequence (SEQ ID NO:93) of a native sequence PRO34274 cDNA, wherein SEQ ID NO:93 is a clone designated herein as "DNA191064-3069".

FIG. 94 shows the amino acid sequence (SEQ ID NO:94) derived from the coding sequence of SEQ ID NO:93 shown in FIG. 93.

FIGS. 95A-95B shows a nucleotide sequence (SEQ ID NO:95) of a native sequence PRO34001 cDNA, wherein SEQ ID NO:95 is a clone designated herein as "DNA194909-3013".

FIG. 96 shows the amino acid sequence (SEQ ID NO:96) derived from the coding sequence of SEQ ID NO:95 shown in FIGS. 95A-95B.

FIG. 97 shows a nucleotide sequence (SEQ ID NO:97) of a native sequence PRO34009 cDNA, wherein SEQ ID NO:97 is a clone designated herein as "DNA203532-3029".

FIG. 98 shows the amino acid sequence (SEQ ID NO:98) derived from the coding sequence of SEQ ID NO:97 shown in FIG. 97.

FIG. 99 shows a nucleotide sequence (SEQ ID NO:99) of a native sequence PRO34192 cDNA, wherein SEQ ID NO:99 is a clone designated herein as "DNA213858-3060".

FIG. 100 shows the amino acid sequence (SEQ ID NO:100) derived from the coding sequence of SEQ ID NO:99 shown in FIG. 99.

FIG. 101 shows a nucleotide sequence (SEQ ID NO:101) of a native sequence PRO34564 cDNA, wherein SEQ ID NO:101 is a clone designated herein as "DNA216676-3083".

FIG. 102 shows the amino acid sequence (SEQ ID NO:102) derived from the coding sequence of SEQ ID NO:101 shown in FIG. 101.

FIG. 103 shows a nucleotide sequence (SEQ ID NO:103) of a native sequence PRO35444 cDNA, wherein SEQ ID NO:103 is a clone designated herein as "DNA222653-3104".

FIG. 104 shows the amino acid sequence (SEQ ID NO:104) derived from the coding sequence of SEQ ID NO:103 shown in FIG. 103.

FIG. 105 shows a nucleotide sequence (SEQ ID NO:105) of a native sequence PRO5998 cDNA, wherein SEQ ID NO:105 is a clone designated herein as "DNA96897-2688".

FIG. 106 shows the amino acid sequence (SEQ ID NO:106) derived from the coding sequence of SEQ ID NO:105 shown in FIG. 105.

FIG. 107 shows a nucleotide sequence (SEQ ID NO:107) of a native sequence PRO19651 cDNA, wherein SEQ ID NO:107 is a clone designated herein as "DNA142917-3081".

FIG. 108 shows the amino acid sequence (SEQ ID NO:108) derived from the coding sequence of SEQ ID NO:107 shown in FIG. 107.

FIG. 109 shows a nucleotide sequence (SEQ ID NO:109) of a native sequence PRO20221 cDNA, wherein SEQ ID NO:109 is a clone designated herein as "DNA142930-2914".

FIG. 110 shows the amino acid sequence (SEQ ID NO:110) derived from the coding sequence of SEQ ID NO:109 shown in FIG. 109.

FIG. 111 shows a nucleotide sequence (SEQ ID NO:111) of a native sequence PRO21434 cDNA, wherein SEQ ID NO:111 is a clone designated herein as "DNA147253-2983".

FIG. 112 shows the amino acid sequence (SEQ ID NO:112) derived from the coding sequence of SEQ ID NO:111 shown in FIG. 111.

FIG. 113 shows a nucleotide sequence (SEQ ID NO:113) of a native sequence PRO19822 cDNA, wherein SEQ ID NO:113 is a clone designated herein as "DNA149927-2887".

FIG. 114 shows the amino acid sequence (SEQ ID NO:114) derived from the coding sequence of SEQ ID NO:113 shown in FIG. 113.

DETAILED DESCRIPTION OF THE PREFERRED EMBODIMENTS

I. Definitions

The terms "PRO polypeptide" and "PRO" as used herein and when immediately followed by a numerical designation refer to various polypeptides, wherein the complete designation (i.e., PRO/number) refers to specific polypeptide sequences as described herein. The terms "PRO/number polypeptide" and "PRO/number" wherein the term "number" is provided as an actual numerical designation as used herein encompass native sequence polypeptides and polypeptide variants (which are further defined herein). The PRO polypeptides described herein may be isolated from a variety of sources, such as from human tissue types or from another source, or prepared by recombinant or synthetic methods. The term "PRO polypeptide" refers to each individual PRO/number polypeptide disclosed herein. All disclosures in this specification which refer to the "PRO polypeptide" refer to each of the polypeptides individually as well as jointly. For example, descriptions of the preparation of, purification of, derivation of, formation of antibodies to or against, administration of, compositions containing, treatment of a disease with, etc., pertain to each polypeptide of the invention individually. The term "PRO polypeptide" also includes variants of the PRO/number polypeptides disclosed herein.

A "native sequence PRO polypeptide" comprises a polypeptide having the same amino acid sequence as the corresponding PRO polypeptide derived from nature. Such native sequence PRO polypeptides can be isolated from nature or can be produced by recombinant or synthetic means. The term "native sequence PRO polypeptide" specifically encompasses naturally-occurring truncated or secreted forms of the specific PRO polypeptide (e.g., an extracellular domain sequence), naturally-occurring variant forms (e.g., alternatively spliced forms) and naturally-occurring allelic variants of the polypeptide. In various embodiments of the invention, the native sequence PRO polypeptides disclosed herein are mature or full-length native sequence polypeptides comprising the full-length amino acids sequences shown in the accompanying figures. Start and stop codons are shown in bold font and underlined in the figures. However, while the PRO polypeptide disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the PRO polypeptides.

The PRO polypeptide "extracellular domain" or "ECD" refers to a form of the PRO polypeptide which is essentially free of the transmembrane and cytoplasmic domains. Ordinarily, a PRO polypeptide ECD will have less than 1% of such transmembrane and/or cytoplasmic domains and preferably, will have less than 0.5% of such domains. It will be understood that any transmembrane domains identified for the PRO polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a PRO polypeptide may contain from about 5 or fewer amino acids on either side of the transmembrane domain/extracellular domain boundary as identified in the Examples or specification and such polypeptides, with or without the associated signal peptide, and nucleic acid encoding them, are comtemplated by the present invention.

The approximate location of the "signal peptides" of the various PRO polypeptides disclosed herein are shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Eng.* 10:1-6 (1997) and von Heinje et al., *Nucl. Acids. Res.* 14:4683-4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"PRO polypeptide variant" means an active PRO polypeptide as defined above or below having at least about 80% amino acid sequence identity with a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Such PRO polypeptide variants include, for instance, PRO polypeptides wherein one or more amino acid residues are added, or deleted, at the N- or C-terminus of the full-length native amino acid sequence. Ordinarily, a PRO polypeptide variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other specifically defined fragment of a full-length PRO polypeptide sequence as disclosed herein. Ordinarily, PRO variant polypeptides are at least about 10 amino acids in length, alternatively at least about 20 amino acids in length, alternatively at least about 30 amino acids in length, alternatively at least about 40 amino acids in length, alternatively at least about 50 amino acids in length, alternatively at least about 60 amino acids in length, alternatively at least about 70 amino acids in length, alternatively at least about 80 amino acids in length, alternatively at least about 90 amino acids in length, alternatively at least about 100 amino acids in length, alternatively at least about 150 amino acids in length, alternatively at least about 200 amino acids in length, alternatively at least about 300 amino acids in length, or more.

"Percent (%) amino acid sequence identity" with respect to the PRO polypeptide sequences identified herein is defined as the percentage of amino acid residues in a candidate sequence that are identical with the amino acid residues in the specific PRO polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "PRO", wherein "PRO" represents the amino acid sequence of a hypothetical PRO polypeptide of interest, "Comparison Protein" represents the amino acid sequence of a polypeptide against which the "PRO" polypeptide of interest is being compared, and "X, "Y" and "Z" each represent different hypothetical amino acid residues.

Unless specifically stated otherwise, all % amino acid sequence identity values used herein are obtained as described in the immediately preceding paragraph using the ALIGN-2 computer program. However, % amino acid sequence identity values may also be obtained as described below by using the WU-BLAST-2 computer program (Altschul et al., *Methods in Enzymology* 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % amino acid sequence identity value is determined by dividing (a) the number of matching identical amino acid residues between the amino acid sequence of the PRO polypeptide of interest having a sequence derived from the native PRO polypeptide and the comparison amino acid sequence of interest (i.e., the sequence against which the PRO polypeptide of interest is being compared which may be a PRO variant polypeptide) as determined by WU-BLAST-2 by (b) the total number of amino acid residues of the PRO polypeptide of interest. For example, in the statement "a polypeptide comprising an the amino acid sequence A which has or having at least 80% amino acid sequence identity to the amino acid sequence B", the amino acid sequence A is the comparison amino acid sequence of interest and the amino acid sequence B is the amino acid sequence of the PRO polypeptide of interest.

Percent amino acid sequence identity may also be determined using the sequence comparison program NCBI-BLAST2 (Altschul et al., *Nucleic Acids Res*. 25:3389-3402 (1997)). The NCBI-BLAST2 sequence comparison program may be obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"PRO variant polynucleotide" or "PRO variant nucleic acid sequence" means a nucleic acid molecule which encodes an active PRO polypeptide as defined below and which has at least about 80% nucleic acid sequence identity with a nucleotide acid sequence encoding a full-length native sequence PRO polypeptide sequence as disclosed herein, a full-length native sequence PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Ordinarily, a PRO variant polynucleotide will have at least about 80% nucleic acid sequence identity, alternatively at least about 81%/nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity with a nucleic acid sequence encoding a full-length native sequence PRO polypeptide sequence as disclosed herein, a full-length native sequence PRO polypeptide sequence lacking the signal peptide as disclosed herein, an extracellular domain of a PRO polypeptide, with or without the signal sequence, as disclosed herein or any other fragment of a full-length PRO polypeptide sequence as disclosed herein. Variants do not encompass the native nucleotide sequence.

Ordinarily, PRO variant polynucleotides are at least about 30 nucleotides in length, alternatively at least about 60 nucleotides in length, alternatively at least about 90 nucleotides in length, alternatively at least about 120 nucleotides in length, alternatively at least about 150 nucleotides in length, alternatively at least about 180 nucleotides in length, alternatively at least about 210 nucleotides in length, alternatively at least about 240 nucleotides in length, alternatively at least about 270 nucleotides in length, alternatively at least about 300 nucleotides in length, alternatively at least about 450 nucleotides in length, alternatively at least about 600 nucleotides in length, alternatively at least about 900 nucleotides in length, or more.

"Percent (%) nucleic acid sequence identity" with respect to PRO-encoding nucleic acid sequences identified herein is defined as the percentage of nucleotides in a candidate sequence that are identical with the nucleotides in the PRO nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "PRO-DNA", wherein "PRO-DNA" represents a hypothetical PRO-encoding nucleic acid sequence of interest, "Comparison DNA" represents the nucleotide sequence of a nucleic acid molecule against which the "PRO-DNA" nucleic acid molecule of interest is being compared, and "N", "L" and "V" each represent different hypothetical nucleotides.

Unless specifically stated otherwise, all % nucleic acid sequence identity values used herein are obtained as described in the immediately preceding paragraph using the ALIGN-2 computer program. However, % nucleic acid sequence identity values may also be obtained as described below by using the WU-BLAST-2 computer program (Altschul et al., *Methods in Enzymology* 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % nucleic acid sequence identity value is determined by dividing (a) the number of matching identical nucleotides between the nucleic acid sequence of the PRO polypeptide-encoding nucleic acid molecule of interest having a sequence derived from the native sequence PRO polypeptide-encoding nucleic acid and the comparison nucleic acid molecule of interest (i.e., the sequence against which the PRO polypeptide-encoding nucleic acid molecule of interest is being compared which may be a variant PRO polynucleotide) as determined by WU-BLAST-2 by (b) the total number of nucleotides of the PRO polypeptide-encoding nucleic acid molecule of interest. For example, in the statement "an isolated nucleic acid molecule comprising a nucleic acid sequence A which has or having at least 80% nucleic acid sequence identity to the nucleic acid sequence B", the nucleic acid sequence A is the comparison nucleic acid molecule of interest and the nucleic acid sequence B is the nucleic acid sequence of the PRO polypeptide-encoding nucleic acid molecule of interest.

Percent nucleic acid sequence identity may also be determined using the sequence comparison program NCBI-BLAST2 (Altschul et al., *Nucleic Acids Res.* 25:3389-3402 (1997)). The NCBI-BLAST2 sequence comparison program may be obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, PRO variant polynucleotides are nucleic acid molecules that encode an active PRO polypeptide and which are capable of hybridizing, preferably under stringent hybridization and wash conditions, to nucleotide sequences encoding a full-length PRO polypeptide as disclosed herein. PRO variant polypeptides may be those that are encoded by a PRO variant polynucleotide.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO polypeptide natural environment will not be present. Ordinarily, however, isolated polypeptide will be prepared by at least one purification step.

An "isolated" PRO polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers, for example, single anti-PRO monoclonal antibodies (including agonist, antagonist, and neutralizing antibodies), anti-PRO antibody compositions with polyepitopic specificity, single chain anti-PRO antibodies, and fragments of anti-PRO antibodies (see below). The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that:

(1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a PRO polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Active" or "activity" for the purposes herein refers to form(s) of a PRO polypeptide which retain a biological and/or an immunological activity of native or naturally-occurring PRO, wherein "biological" activity refers to a biological function (either inhibitory or stimulatory) caused by a native or naturally-occurring PRO other than the ability to induce the production of an antibody against an antigenic epitope possessed by a native or naturally-occurring PRO and an "immunological" activity refers to the ability to induce the production of an antibody against an antigenic epitope possessed by a native or naturally-occurring PRO.

The term "antagonist" is used in the broadest sense, and includes any molecule that partially or fully blocks, inhibits, or neutralizes a biological activity of a native PRO polypeptide disclosed herein. In a similar manner, the term "agonist" is used in the broadest sense and includes any molecule that mimics a biological activity of a native PRO polypeptide disclosed herein. Suitable agonist or antagonist molecules specifically include agonist or antagonist antibodies or antibody fragments, fragments or amino acid sequence variants of native PRO polypeptides, peptides, antisense oligonucleotides, small organic molecules, etc. Methods for identifying agonists or antagonists of a PRO polypeptide may comprise contacting a PRO polypeptide with a candidate agonist or antagonist molecule and measuring a detectable change in one or more biological activities normally associated with the PRO polypeptide.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

"Antibody fragments" comprise a portion of an intact antibody, preferably the antigen binding or variable region of the intact antibody. Examples of antibody fragments include Fab, Fab', $F(ab')_2$, and Fv fragments; diabodies; linear antibodies (Zapata et al., *Protein Eng*. 8(10): 1057-1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an $F(ab')_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a PRO polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

An "effective amount" of a polypeptide disclosed herein or an agonist or antagonist thereof is an amount sufficient to carry out a specifically stated purpose. An "effective amount" may be determined empirically and in a routine manner, in relation to the stated purpose.

TABLE 2

| | | |
|---|---|---|
| PRO | XXXXXXXXXXXXXXX | (Length = 15 amino acids) |
| Comparison Protein | XXXXXYYYYYYY | (Length = 12 amino acids) |

% amino acid sequence identity =
(the number of identically matching amino acid residues between the two polypeptide sequences as determined by ALIGN-2) divided by (the total number of amino acid residues of the PRO (polypeptide) =

5 divided by 15 = 33.3%

TABLE 3

| | | |
|---|---|---|
| PRO | XXXXXXXXXX | (Length = 10 amino acids) |
| Comparison Protein | XXXXXYYYYYYZZYZ | (Length = 15 amino acids) |

TABLE 3-continued

% amino acid sequence identity =
(the number of identically matching amino acid residues between the two polypeptide sequences as determined by ALIGN-2) divided by (the total number of amino acid residues of the PRO polypeptide) =

5 divided by 10 = 50%

TABLE 4

| | | |
|---|---|---|
| PRO-DNA | NNNNNNNNNNNNNN | (Length = 14 nucleotides) |
| Comparison DNA | NNNNNNLLLLLLLLLL | (Length = 16 nucleotides) |

% nucleic acid sequence identity =
(the number of identically matching nucleotides between the two nucleic acid sequences as determined by ALIGN-2) divided by (the total number of nucleotides of the PRO-DNA nucleic acid sequence) =

6 divided by 14 = 42.9%

TABLE 5

| | | |
|---|---|---|
| PRO-DNA | NNNNNNNNNNNN | (Length = 12 nucleotides) |
| Comparison DNA | NNNNLLLVV | (Length = 9 nucleotides) |

% nucleic acid sequence identity =
(the number of identically matching nucleotides between the two nucleic acid sequences as determined by ALIGN-2) divided by (the total number of nucleotides of the PRO-DNA nucleic acid sequence) =

4 divided by 12 = 33.3%

II. Compositions and Methods of the Invention

A. Full-Length PRO Polypeptides

The present invention provides newly identified and isolated nucleotide sequences encoding polypeptides referred to in the present application as PRO polypeptides. In particular, cDNAs encoding various PRO polypeptides have been identified and isolated, as disclosed in further detail in the Examples below. It is noted that proteins produced in separate expression rounds may be given different PRO numbers but the UNQ number is unique for any given DNA and the encoded protein, and will not be changed. However, for sake of simplicity, in the present specification the protein encoded by the full length native nucleic acid molecules disclosed herein as well as all further native homologues and variants included in the foregoing definition of PRO, will be referred to as "PRO/number", regardless of their origin or mode of preparation.

As disclosed in the Examples below, various cDNA clones have been deposited with the ATCC. The actual nucleotide sequences of those clones can readily be determined by the skilled artisan by sequencing of the deposited clone using routine methods in the art. The predicted amino acid sequence can be determined from the nucleotide sequence using routine skill. For the PRO polypeptides and encoding nucleic acids described herein, Applicants have identified what is believed to be the reading frame best identifiable with the sequence information available at the time.

B. PRO Polypeptide Variants

In addition to the full-length native sequence PRO polypeptides described herein, it is contemplated that PRO variants can be prepared. PRO variants can be prepared by introducing appropriate nucleotide changes into the PRO DNA, and/or by synthesis of the desired PRO polypeptide. Those skilled in the art will appreciate that amino acid changes may alter post-translational processes of the PRO, such as changing the number or position of glycosylation sites or altering the membrane anchoring characteristics.

Variations in the native full-length sequence PRO or in various domains of the PRO described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO that results in a change in the amino acid sequence of the PRO as compared with the native sequence PRO. Optionally the variation is by substitution of at least one amino acid with any other amino acid in one or more of the domains of the PRO. Guidance in determining which amino acid residue may be inserted, substituted or deleted without adversely affecting the desired activity may be found by comparing the sequence of the PRO with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

PRO polypeptide fragments are provided herein. Such fragments may be truncated at the N-terminus or C-terminus, or may lack internal residues, for example, when compared with a full length native protein. Certain fragments lack amino acid residues that are not essential for a desired biological activity of the PRO polypeptide.

PRO fragments may be prepared by any of a number of conventional techniques. Desired peptide fragments may be chemically synthesized. An alternative approach involves generating PRO fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, PRO polypeptide fragments share at least one biological and/or immunological activity with the native PRO polypeptide disclosed herein.

In particular embodiments, conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are introduced and the products screened.

TABLE 6

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the PRO polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gin, his, lys, arg;

(5) residues that influence chain orientation: gly, pro; and (6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al. *Gene*, 34:315 (1985)], restriction selection mutagenesis [Wells et al., *Philos. Trans. R. Soc. London SerA*, 317:415 (1986)] or other known techniques can be performed on the cloned DNA to produce the PRO variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science*, 244: 1081-1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol*., 150:1 (1976)]. If alanine substitution does not yield adequate amounts of variant, an isoteric amino acid can be used.

C. Modifications of PRO

Covalent modifications of PRO are included within the scope of this invention. One type of covalent modification includes reacting targeted amino acid residues of a PRO polypeptide with an organic derivatizing agent that is capable of reacting with selected side chains or the N- or C-terminal residues of the PRO. Derivatization with bifunctional agents is useful, for instance, for crosslinking PRO to a water-insoluble support matrix or surface for use in the method for purifying anti-PRO antibodies, and vice-versa. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the PRO polypeptide included within the scope of this invention comprises altering the native glycosylation pattern of the polypeptide. "Altering the native glycosylation pattern" is intended for purposes herein to mean deleting one or more carbohydrate moieties found in native sequence PRO (either by removing the underlying glycosylation site or by deleting the glycosylation by chemical and/or enzymatic means), and/or adding one or more glycosylation sites that are not present in the native sequence PRO. In addition, the phrase includes qualitative changes in the glycosylation of the native proteins, involving a change in the nature and proportions of the various carbohydrate moieties present.

Addition of glycosylation sites to the PRO polypeptide may be accomplished by altering the amino acid sequence. The alteration may be made, for example, by the addition of, or substitution by, one or more serine or threonine residues to the native sequence PRO (for O-linked glycosylation sites). The PRO amino acid sequence may optionally be altered through changes at the DNA level, particularly by mutating the DNA encoding the PRO polypeptide at preselected bases such that codons are generated that will translate into the desired amino acids.

Another means of increasing the number of carbohydrate moieties on the PRO polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem., pp.* 259-306 (1981).

Removal of carbohydrate moieties present on the PRO polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.,* 259:52 (1987) and by Edge et al., *Anal. Biochem*., 118:131 (1981). Enzymatic cleavage of carbohydrate moieties on polypeptides can be achieved by the use of a variety of endo- and exo-glycosidases as described by Thotakura et al., *Meth. Enzymol*., 138:350 (1987).

Another type of covalent modification of PRO comprises linking the PRO polypeptide to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337.

The PRO of the present invention may also be modified in a way to form a chimeric molecule comprising PRO fused to another, heterologous polypeptide or amino acid sequence.

In one embodiment, such a chimeric molecule comprises a fusion of the PRO with a tag polypeptide which provides an epitope to which an anti-tag antibody can selectively bind. The epitope tag is generally placed at the amino- or carboxyl-terminus of the PRO. The presence of such epitope-tagged forms of the PRO can be detected using an antibody against the tag polypeptide. Also, provision of the epitope tag enables the PRO to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol*., 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology,* 6:1204-1210 (1988)]; the KT3 epitope peptide [Martin et al., *Science,* 255:192-194 (1992)]; an α-tubulin epitope peptide [Skinner et al., *J. Biol. Chem*., 266:15163-15166 (1991)]; and the T7 gene 10 protein peptide tag [Lutz-Freyermuth et al., *Proc. Natl. Acad. Sci. USA*, 87:6393-6397 (1990)].

In an alternative embodiment, the chimeric molecule may comprise a fusion of the PRO with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a PRO polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of PRO

The description below relates primarily to production of PRO by culturing cells transformed or transfected with a vector containing PRO nucleic acid. It is, of course, contemplated that alternative methods, which are well known in the art, may be employed to prepare PRO. For instance, the PRO sequence, or portions thereof, may be produced by direct peptide synthesis using solid-phase techniques [see, e.g., Stewart et al., *Solid-Phase Peptide Synthesis*, W. H. Freeman Co., San Francisco, Calif. (1969); Merrifield, *J. Am. Chem. Soc*., 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the PRO may be chemically synthesized separately and combined using chemical or enzymatic methods to produce the full-length PRO.

1. Isolation of DNA Encoding PRO

DNA encoding PRO may be obtained from a cDNA library prepared from tissue believed to possess the PRO mRNA and to express it at a detectable level. Accordingly, human PRO DNA can be conveniently obtained from a cDNA library prepared from human tissue, such as described in the Examples. The PRO-encoding gene may also be obtained from a genomic library or by known synthetic procedures (e.g., automated nucleic acid synthesis).

Libraries can be screened with probes (such as antibodies to the PRO or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding PRO is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}P$-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for PRO production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci.* (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT $kan^r$; *E. coli* W3110 strain 37D6, which has the complete genotype tonA ptr3 phoA E15 (argF-lac)169 degP ompT rbs7 ilvG $kan^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for PRO-encoding vectors. *Saccharomyces cerevisiae* is a commonly used lower eukaryotic host microorganism. Others include *Schizosaccharomyces pombe* (Beach and Nurse, *Nature,* 290: 140 [1981]; EP 139,383 published 2 May 1985); *Kluyveromyces* hosts (U.S. Pat. No. 4,943,529; Fleer et al., *Bio/Technology*, 9:968-975 (1991)) such as, e.g., *K. lactis* (MW98-8C, CBS683, CBS4574; Louvencourt et al., *J. Bacteriol*., 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology,* 8:135 (1990)), *K. thermotolerans*, and *K. marxianus; yarrowia* (EP 402,226); *Pichia pastoris* (EP 183,070; Sreekrishna et al., *J. Basic Microbiol*., 28:265-278 [1988]); *Candida; Trichoderma reesia* (EP 244,234); *Neurospora crassa* (Case et al., *Proc. Natl. Acad. Sci. USA*, 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun*., 112:284-289 [1983]; Tilburn et al., *Gene*, 26:205-221 [1983]; Yelton et al., *Proc. Natl. Acad. Sci. USA,* 81: 1470-1474 [1984]) and *A. niger* (Kelly and Hynes, *EMBO J*., 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, *The Biochemistry of Methylotrophs,* 269 (1982).

Suitable host cells for the expression of glycosylated PRO are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol*., 36:59 (1977)); Chinese hamster ovary cells/-DHFR(CHO, Urlaub and Chasin, *Proc. Natl. Acad. Sci. USA*, 77:4216 (1980)); mouse sertoli cells (TM4, Mather, *Biol. Reprod.,* 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding PRO may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010, 182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli.*

An example of suitable selectable markers for mammalian cells are those that enable the identification of cells competent to take up the PRO-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene,* 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the PRO-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature,* 281:544 (1979)], alkaline phosphatase, a tryptophan (trp) promoter system [Goeddel, *Nucleic Acids Res*., 8:4057 (1980); EP 36,776], and hybrid promoters such as the tac promoter [deBoer et al., *Proc. Natl. Acad. Sci. USA*, 80:21-25 (1983)].

Promoters for use in bacterial systems also will contain a Shine-Dalgarno (S.D.) sequence operably linked to the DNA encoding PRO.

Examples of suitable promoting sequences for use with yeast hosts include the promoters for 3-phosphoglycerate kinase [Hitzeman et al., *J. Biol. Chem*., 255:2073 (1980)] or other glycolytic enzymes [Hess et al., *J. Adv. Enzyme Reg*., 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the PRO coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO.

Still other methods, vectors, and host cells suitable for adaptation to the synthesis of PRO in recombinant vertebrate cell culture are described in Gething et al., *Nature,* 293:620-625 (1981); Mantei et al., *Nature,* 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO polypeptide or against a synthetic peptide based on the DNA sequences provided herein or against exogenous sequence fused to PRO DNA and encoding a specific antibody epitope.

5. Purification of Polypeptide

Forms of PRO may be recovered from culture medium or from host cell lysates. If membrane-bound, it can be released from the membrane using a suitable detergent solution (e.g. Triton-X 100) or by enzymatic cleavage. Cells employed in expression of PRO can be disrupted by various physical or chemical means, such as freeze-thaw cycling, sonication, mechanical disruption, or cell lysing agents.

It may be desired to purify PRO from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the PRO. Various methods of protein purification may be employed and such methods are known in the art and described for example in Deutscher, *Methods in Enzymology,* 182 (1990); Scopes, *Protein Purification: Principles and Practice*, Springer-Verlag, New York (1982). The purification step(s) selected will depend, for example, on the nature of the production process used and the particular PRO produced.

E. Uses for PRO

Nucleotide sequences (or their complement) encoding PRO have various applications in the art of molecular biology, including uses as hybridization probes, in chromosome and gene mapping and in the generation of anti-sense RNA and DNA. PRO nucleic acid will also be useful for the preparation of PRO polypeptides by the recombinant techniques described herein.

The full-length native sequence PRO gene, or portions thereof, may be used as hybridization probes for a cDNA library to isolate the full-length PRO cDNA or to isolate still other cDNAs (for instance, those encoding naturally-occurring variants of PRO or PRO from other species) which have a desired sequence identity to the native PRO sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence PRO. By way of example, a screening method will comprise isolating the coding region of the PRO gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the PRO gene of the present invention can be used to screen libraries of human cDNA, genomic DNA or mRNA to determine which members of such libraries the probe hybridizes to. Hybridization techniques are described in further detail in the Examples below.

Any EST sequences disclosed in the present application may similarly be employed as probes, using the methods disclosed herein.

Other useful fragments of the PRO nucleic acids include antisense or sense oligonucleotides comprising a singe-stranded nucleic acid sequence (either RNA or DNA) capable of binding to target PRO mRNA (sense) or PRO DNA (antisense) sequences. Antisense or sense oligonucleotides, according to the present invention, comprise a fragment of the coding region of PRO DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res*, 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of PRO proteins. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 bases in length, about 10 bases in length, about 15 bases in length, about 20 bases in length, about 25 bases in length, about 30 bases in length, about 35 bases in length, about 40 bases in length, about 45 bases in length, about 50 bases in length, about 55 bases in length, about 60 bases in length, about 65 bases in length, about 70 bases in length, about 75 bases in length, about 80 bases in length, about 85 bases in length, about 90 bases in length, about 95 bases in length, about 100 bases in length, or more.

The probes may also be employed in PCR techniques to generate a pool of sequences for identification of closely related PRO coding sequences.

Nucleotide sequences encoding a PRO can also be used to construct hybridization probes for mapping the gene which encodes that PRO and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for PRO encode a protein which binds to another protein (example, where the PRO is a receptor), the PRO can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor PRO can be used to isolate correlative ligand(s). Screening assays can be designed to find lead compounds that mimic the biological activity of a native PRO or a receptor for PRO. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode PRO or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding PRO can be used to clone genomic DNA encoding PRO in accordance with established techniques and the genomic sequences used to generate transgenic animals that contain cells which express DNA encoding PRO. Methods for generating transgenic animals, particularly animals such as mice or rats, have become conventional in the art and are described, for example, in U.S. Pat. Nos. 4,736,866 and 4,870,009. Typically, particular cells would be targeted for PRO transgene incorporation with tissue-specific enhancers. Transgenic animals that include a copy of a transgene encoding PRO introduced into the germ line of the animal at an embryonic stage can be used to examine the effect of increased expression of DNA encoding PRO. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of PRO can be used to construct a PRO "knock out" animal which has a defective or altered gene encoding PRO as a result of homologous recombination between the endogenous gene encoding PRO and altered genomic DNA encoding PRO introduced into an embryonic stem cell of the animal. For example, cDNA encoding PRO can be used to clone genomic DNA encoding PRO in accordance with established techniques. A portion of the genomic DNA encoding PRO can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell*, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the PRO polypeptide.

Nucleic acid encoding the PRO polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429-4432 (1987); and Wagner et al., *Proc. Natl. Acad. Sci. USA* 87, 3410-3414 (1990). For review of gene marking and gene therapy protocols see Anderson et al., *Science* 256, 808-813 (1992).

The PRO polypeptides described herein may also be employed as molecular weight markers for protein electrophoresis purposes and the isolated nucleic acid sequences may be used for recombinantly expressing those markers.

The nucleic acid molecules encoding the PRO polypeptides or fragments thereof described herein are useful for chromosome identification. In this regard, there exists an ongoing need to identify new chromosome markers, since relatively few chromosome marking reagents, based upon actual sequence data are presently available. Each PRO nucleic acid molecule of the present invention can be used as a chromosome marker.

The PRO polypeptides and nucleic acid molecules of the present invention may also be used diagnostically for tissue typing, wherein the PRO polypeptides of the present invention may be differentially expressed in one tissue as compared to another, preferably in a diseased tissue as compared to a normal tissue of the same tissue type. PRO nucleic acid molecules will find use for generating probes for PCR, Northern analysis, Southern analysis and Western analysis.

The PRO polypeptides described herein may also be employed as therapeutic agents. The PRO polypeptides of the present invention can be formulated according to known methods to prepare pharmaceutically useful compositions, whereby the PRO product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

When in vivo administration of a PRO polypeptide or agonist or antagonist thereof is employed, normal dosage amounts may vary from about 10 ng/kg to up to 100 mg/kg of mammal body weight or more per day, preferably about 1 μg/kg/day to 10 mg/kg/day, depending upon the route of administration. Guidance as to particular dosages and methods of delivery is provided in the literature; see, for example, U.S. Pat. No. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a PRO polypeptide is desired in a formulation with release characteristics suitable for the treatment of any disease or disorder requiring administration of the PRO polypeptide, microencapsulation of the PRO polypeptide is contemplated. Microencapsulation of recombinant proteins for sustained release has been successfully performed with human growth hormone (rhGH), interferon-(rhIFN−), interleukin-2, and MN rgp120. Johnson et al., *Nat. Med.*, 2:795-799 (1996); Yasuda, *Biomed. Ther.*, 27:1221-1223 (1993); Hora et al., *Bio/Technology*, 8:755-758 (1990); Cleland, "Design and Production of Single Immunization Vaccines Using Polylactide Polyglycolide Microsphere Systems," in *Vaccine Design: The Subunit and Adjuvant Approach*, Powell and Newman, eds, (Plenum Press: New York, 1995), pp. 439-462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), *Biodegradable Polymers as Drug Delivery Systems* (Marcel Dekker: New York, 1990), pp. 1-41.

This invention encompasses methods of screening compounds to identify those that mimic the PRO polypeptide (agonists) or prevent the effect of the PRO polypeptide (antagonists). Screening assays for antagonist drug candidates are designed to identify compounds that bind or complex with the PRO polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a PRO polypeptide encoded by a nucleic acid identified herein under conditions and for a time sufficient to allow these two components to interact.

In binding assays, the interaction is binding and the complex formed can be isolated or detected in the reaction mixture. In a particular embodiment, the PRO polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the PRO polypeptide and drying. Alternatively, an immobilized antibody, e.g., a monoclonal antibody, specific for the PRO polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular PRO polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature* (*London*), 340:245-246 (1989); Chien et al., *Proc. Natl. Acad. Sci. USA*, 88:9578-9582 (1991)) as disclosed by Chevray and Nathans, *Proc. Natl. Acad. Sci. USA*, 89: 5789-5793 (1991). Many transcriptional activators, such as yeast GALA, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a PRO polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the PRO polypeptide may be added to a cell along with the compound to be screened for a particular activity and the ability of the compound to inhibit the activity of interest in the presence of the PRO polypeptide indicates that the compound is an antagonist to the PRO polypeptide. Alternatively, antagonists may be detected by combining the PRO polypeptide and a potential antagonist with membrane-bound PRO polypeptide receptors or recombinant receptors under appropriate conditions for a competitive inhibition assay. The PRO polypeptide can be labeled, such as by radioactivity, such that the number of PRO polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.*, 1(2): Chapter 5 (1991). Preferably, expression cloning is employed wherein polyadenylated RNA is prepared from a cell responsive to the PRO polypeptide and a cDNA library created from this RNA is divided into pools and used to transfect COS cells or other cells that are not responsive to the PRO polypeptide. Transfected cells that are grown on glass slides are exposed to labeled PRO polypeptide. The PRO polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled PRO polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled PRO polypeptide in the presence of the candidate compound. The ability of the compound to enhance or block this interaction could then be measured.

More specific examples of potential antagonists include an oligonucleotide that binds to the fusions of immunoglobulin with PRO polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the PRO polypeptide that recognizes the receptor but imparts no effect, thereby competitively inhibiting the action of the PRO polypeptide.

Another potential PRO polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature PRO polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.*, 6:3073 (1979); Cooney et al., *Science*, 241: 456 (1988); Dervan et al., *Science*, 251:1360 (1991)), thereby preventing transcription and the production of the PRO polypeptide. The antisense RNA oligonucleotide hybridizes to the mRNA in vivo and blocks translation of the mRNA molecule into the PRO polypeptide (antisense—Okano, *Neurochem.*, 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the PRO polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the PRO polypeptide, thereby blocking the normal biological activity of the PRO polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology*, 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

Diagnostic and therapeutic uses of the herein disclosed molecules may also be based upon the positive functional assay hits disclosed and described below.

F. Anti-PRO Antibodies

The present invention further provides anti-PRO antibodies. Exemplary antibodies include polyclonal, monoclonal, humanized, bispecific, and heteroconjugate antibodies.

1. Polyclonal Antibodies

The anti-PRO antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the PRO polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-PRO antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the PRO polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against PRO. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-PRO antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522-525 (1986); Riechmann et al., *Nature*, 332:323-329 (1988); and Presta, *Curr. Op. Struct. Biol.*, 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779-783 (1992); Lonberg et al., *Nature* 368 856-859 (1994); Morrison, *Nature* 368, 812-13 (1994); Fishwild et al., *Nature Biotechnology* 14, 845-51 (1996); Neuberger, *Nature Biotechnology* 14, 826 (1996); Lonberg and Huszar, *Intern. Rev. Immunol.* 13 65-93 (1995).

The antibodies may also be affinity matured using known selection and/or mutagenesis methods as described above. Preferred affinity matured antibodies have an affinity which is five times, more preferably 10 limes, even more preferably 20 or 30 times greater than the starting antibody (generally murine, humanized or human) from which the matured antibody is prepared.

4. Bispecific Antibodies

Bispecific antibodies are monoclonal, preferably human or humanized, antibodies that have binding specificities for at least two different antigens. In the present case, one of the binding specificities is for the PRO, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature*, 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.*, 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. $F(ab')_2$ bispecific antibodies). Techniques for generating bispecific antibodies from antibody fragments have been described in the literature. For example, bispecific antibodies can be prepared can be prepared using chemical linkage. Brennan et al., *Science* 229:81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175:217-225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antibody fragments directly from recombinant cell culture have also been described. For example, bispecific antibodies have been produced using leucine zippers. Kostelny et al., *J. Immunol.* 148(5): 1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152:5368 (1994).

Antibodies with more than two valencies are contemplated. For example, trispecific antibodies can be prepared. Tutt et al., *J. Immunol.* 147:60 (1991).

Exemplary bispecific antibodies may bind to two different epitopes on a given PRO polypeptide herein. Alternatively, an anti-PRO polypeptide arm may be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD 16) so as to focus cellular defense mechanisms to the cell expressing the particular PRO polypeptide. Bispecific antibodies may also be used to localize cytotoxic agents to cells which express a particular PRO polypeptide. These antibodies possess a PRO-binding arm and an arm which binds a cytotoxic agent or a radionuclide chelator, such as EOTUBE, DPTA, DOTA, or TETA. Another bispecific antibody of interest binds the PRO polypeptide and further binds tissue factor (TF).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

6. Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.*, 176: 1191-1195 (1992) and Shopes, *J. Immunol.*, 148: 2918-2922 (1992). Homodimeric antibodies with enhanced anti-rumor activity may also be prepared using heterobifunctional cross-linkers as described in Wolff et al. *Cancer Research*, 53: 2560-2565 (1993). Alternatively, an antibody can be engineered that has dual Fc regions and may thereby have enhanced complement lysis and ADCC capabilities. See Stevenson et al., *Anti-Cancer Drug Design*, 3: 219-230 (1989).

7. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

8. Immunoliposomes

The antibodies disclosed herein may also be formulated as immunoliposomes. Liposomes containing the antibody are prepared by methods known in the art, such as described in Epstein et al., *Proc. Natl. Acad. Sci. USA*, 82: 3688 (1985); Hwang et al., *Proc. Natl. Acad. Sci. USA*, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.*, 257: 286-288 (1982) via a disulfide-interchange reaction. A chemotherapeutic agent (such as Doxorubicin) is optionally contained within the liposome. See Gabizon et al., *J. National Cancer Inst.*, 81(19): 1484 (1989).

9. Pharmaceutical Compositions of Antibodies

Antibodies specifically binding a PRO polypeptide identified herein, as well as other molecules identified by the screening assays disclosed hereinbefore, can be administered for the treatment of various disorders in the form of pharmaceutical compositions.

If the PRO polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA*, 90: 7889-7893 (1993). The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's *Pharmaceutical Sciences*, supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and $\gamma$ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

G. Uses for Anti-PRO Antibodies

The anti-PRO antibodies of the invention have various utilities. For example, anti-PRO antibodies may be used in diagnostic assays for PRO, e.g., detecting its expression (and in some cases, differential expression) in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^{3}H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth*., 40:219 (1981); and Nygren, *J. Histochem. and Cytochem*., 30:407 (1982).

Anti-PRO antibodies also are useful for the affinity purification of PRO from recombinant cell culture or natural sources. In this process, the antibodies against PRO are immobilized on a suitable support, such a Sephadex resin or filter paper, using methods well known in the art. The immobilized antibody then is contacted with a sample containing the PRO to be purified, and thereafter the support is washed with a suitable solvent that will remove substantially all the material in the sample except the PRO, which is bound to the immobilized antibody. Finally, the support is washed with another suitable solvent that will release the PRO from the antibody.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Extracellular Domain Homology Screening to Identify Novel Polypeptides and cDNA Encoding Therefor The extracellular domain (ECD) sequences (including the secretion signal sequence, if any) from about 950 known secreted proteins from the Swiss-Prot public database were used to search EST databases. The EST databases included public databases (e.g., Dayhoff, GenBank), and proprietary databases (e.g. LIFESEQ™, Incyte Pharmaceuticals, Palo Alto, Calif.). The search was performed using the computer program BLAST or BLAST-2 (Altschul et al., *Methods in Enzymology*, 266:460-480 (1996)) as a comparison of the ECD protein sequences to a 6 frame translation of the EST sequences. Those comparisons with a BLAST score of 70 (or in some cases 90) or greater that did not encode known proteins were clustered and assembled into consensus DNA sequences with the program "phrap" (Phil Green, University of Washington, Seattle, Wash.).

Using this extracellular domain homology screen, consensus DNA sequences were assembled relative to the other identified EST sequences using phrap. In addition, the consensus DNA sequences obtained were often (but not always) extended using repeated cycles of BLAST or BLAST-2 and phrap to extend the consensus sequence as far as possible using the sources of EST sequences discussed above.

Based upon the consensus sequences obtained as described above, oligonucleotides were then synthesized and used to identify by PCR a cDNA library that contained the sequence of interest and for use as probes to isolate a clone of the full-length coding sequence for a PRO polypeptide. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, with the PCR primer pair. A positive library was then used to isolate clones encoding the gene of interest using the probe oligonucleotide and one of the primer pairs.

The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science*, 253:1278-1280 (1991)) in the unique XhoI and NotI sites.

Example 2

Isolation of cDNA Clones by Amylase Screening

1. Preparation of Oligo dT Primed cDNA Library mRNA was isolated from a human tissue of interest using reagents and protocols from Invitrogen, San Diego, Calif. (Fast Track 2). This RNA was used to generate an oligo dT primed cDNA library in the vector pRK5D using reagents and protocols from Life Technologies, Gaithersburg, Md. (Super Script Plasmid System). In this procedure, the double stranded cDNA was sized to greater than 1000 bp and the SalI/NotI linkered cDNA was cloned into XhoI/NotI cleaved vector. pRK5D is a cloning vector that has an sp6 transcription initiation site followed by an SfiI restriction enzyme site preceding the XhoI/NotI cDNA cloning sites.

2. Preparation of Random Primed cDNA Library

A secondary cDNA library was generated in order to preferentially represent the 5' ends of the primary cDNA clones. Sp6 RNA was generated from the primary library (described above), and this RNA was used to generate a random primed cDNA library in the vector pSST-AMY.0 using reagents and protocols from Life Technologies (Super Script Plasmid System, referenced above). In this procedure the double stranded cDNA was sized to 500-1000 bp, linkered with blunt to NotI adaptors, cleaved with SfiI, and cloned into SfiI/NotI cleaved vector. pSST-AMY.0 is a cloning vector that has a yeast alcohol dehydrogenase promoter preceding the cDNA cloning sites and the mouse amylase sequence (the mature sequence without the secretion signal) followed by the yeast alcohol dehydrogenase terminator, after the cloning sites. Thus, cDNAs cloned into this vector that are fused in frame with amylase sequence will lead to the secretion of amylase from appropriately transfected yeast colonies.

3. Transformation and Detection

DNA from the library described in paragraph 2 above was chilled on ice to which was added electrocompetent DH10B bacteria (Life Technologies, 20 ml). The bacteria and vector mixture was then electroporated as recommended by the manufacturer. Subsequently, SOC media (Life Technologies, 1 ml) was added and the mixture was incubated at 37° C. for 30 minutes. The transformants were then plated onto 20 standard 150 mm LB plates containing ampicillin and incubated for 16 hours (37° C.). Positive colonies were scraped off the plates and the DNA was isolated from the bacterial pellet using standard protocols, e.g. CsCl-gradient. The purified DNA was then carried on to the yeast protocols below.

The yeast methods were divided into three categories: (1) Transformation of yeast with the plasmid/cDNA combined vector; (2) Detection and isolation of yeast clones secreting amylase; and (3) PCR amplification of the insert directly from the yeast colony and purification of the DNA for sequencing and further analysis.

The yeast strain used was HD56-5A (ATCC-90785). This strain has the following genotype: MAT alpha, ura3-52, leu2-3, leu2-112, his3-11, his3-15, $MAL^+$, $SUC^+$, $GAL^+$. Preferably, yeast mutants can be in sec71, sec72, sec62, with truncated sec71 being most preferred. Alternatively, antagonists (including antisense nucleotides and/or ligands) which interfere with the normal operation of these genes, other proteins implicated in this post translationpathway (e.g., SEC61p, SEC72p, SEC62p, SEC63p, TDJ1p or SSA1p-4p) or the complex formation of these proteins may also be preferably employed in combination with the amylase-expressing yeast.

Transformation was performed based on the protocol outlined by Gietz et al., *Nucl. Acid. Res*., 20:1425 (1992). Transformed cells were then inoculated from agar into YEPD complex media broth (100 ml) and grown overnight at 30° C. The YEPD broth was prepared as described in Kaiser et al., *Methods in Yeast Genetics*, Cold Spring Harbor Press, Cold Spring Harbor, N.Y., p. 207 (1994). The overnight culture was then diluted to about $2\times10^6$ cells/ml (approx. $OD_{600}$=0.1) into fresh YEPD broth (500 ml) and regrown to $1\times10^7$ cells/ml (approx. $OD_{600}$=0.4-0.5).

The cells were then harvested and prepared for transformation by transfer into GS3 rotor bottles in a Sorval GS3 rotor at 5,000 rpm for 5 minutes, the supernatant discarded, and then resuspended into sterile water, and centrifuged again in 50 ml falcon tubes at 3,500 rpm in a Beckman GS-6KR centrifuge. The supernatant was discarded and the cells were subsequently washed with LiAc/TE (10 ml, 10 mM Tris-HCl, 1 mM EDTA pH 7.5, 100 mM $Li_2OOCCH_3$), and resuspended into LiAc/TE (2.5 ml).

Transformation took place by mixing the prepared cells (100 µl) with freshly denatured single stranded salmon testes DNA (Lofstrand Labs, Gaithersburg, Md.) and transforming DNA (1 µg, vol. <10 µl) in microfuge tubes. The mixture was mixed briefly by vortexing, then 40% PEG/TE (600 µl, 40% polyethylene glycol-4000, 10 mM Tris-HCl, 1 mM EDTA, 100 mM $Li_2OOCCH_3$, pH 7.5) was added. This mixture was gently mixed and incubated at 30° C. while agitating for 30 minutes. The cells were then heat shocked at 42° C. for 15 minutes, and the reaction vessel centrifuged in a microfuge at 12,000 rpm for 5-10 seconds, decanted and resuspended into TE (500 µl, 10 mM Tris-HCl, 1 mM EDTA pH 7.5) followed by recentrifugation. The cells were then diluted into TE (1 ml) and aliquots (200 µl) were spread onto the selective media previously prepared in 150 mm growth plates (VWR).

Alternatively, instead of multiple small reactions, the transformation was performed using a single, large scale reaction, wherein reagent amounts were scaled up accordingly.

The selective media used was a synthetic complete dextrose agar lacking uracil (SCD-Ura) prepared as described in Kaiser et al., *Methods in Yeast Genetics*, Cold Spring Harbor Press, Cold Spring Harbor, N.Y., p. 208-210 (1994). Transformants were grown at 30° C. for 2-3 days.

The detection of colonies secreting amylase was performed by including red starch in the selective growth media. Starch was coupled to the red dye (Reactive Red-120, Sigma) as per the procedure described by Biely et al., *Anal. Biochem*., 172:176-179 (1988). The coupled starch was incorporated into the SCD-Ura agar plates at a final concentration of 0.15% (w/v), and was buffered with potassium phosphate to a pH of 7.0 (50-100 mM final concentration).

The positive colonies were picked and streaked across fresh selective media (onto 150 mm plates) in order to obtain well isolated and identifiable single colonies. Well isolated single colonies positive for amylase secretion were detected by direct incorporation of red starch into buffered SCD-Ura agar. Positive colonies were determined by their ability to break down starch resulting in a clear halo around the positive colony visualized directly.

4. Isolation of DNA by PCR Amplification

When a positive colony was isolated, a portion of it was picked by a toothpick and diluted into sterile water (30 µl) in a 96 well plate. At this time, the positive colonies were either frozen and stored for subsequent analysis or immediately amplified. An aliquot of cells (5 µl) was used as a template for the PCR reaction in a 25 µl volume containing: 0.5 µl Klentaq (Clontech, Palo Alto, Calif.); 4.0 µl 10 mM dNTP's (Perkin Elmer-Cetus); 2.5 µl Kentaq buffer (Clontech); 0.25 µl forward oligo 1; 0.25 µl reverse oligo 2; 12.5 µl distilled water. The sequence of the forward oligonucleotide 1 was:

5'-TGTAAAACGACGGCCAGT
TAAATAGACCTGCAATTATTAATCT-3' (SEQ ID NO:115)

The sequence of reverse oligonucleotide 2 was:

5'-CAGGAAACAGCTATGACC
ACCTGCACACCTGCAAATCCATT-3' (SEQ ID NO:116)

PCR was then performed as follows:

| | | | |
|---|---|---|---|
| a. | | Denature | 92° C., 5 minutes |
| b. | 3 cycles of: | Denature | 92° C., 30 seconds |
| | | Anneal | 59° C., 30 seconds |
| | | Extend | 72° C., 60 seconds |

-continued

| | | | |
|---|---|---|---|
| c. | 3 cycles of: | Denature | 92° C., 30 seconds |
| | | Anneal | 57° C., 30 seconds |
| | | Extend | 72° C., 60 seconds |
| d. | 25 cycles of: | Denature | 92° C., 30 seconds |
| | | Anneal | 55° C., 30 seconds |
| | | Extend | 72° C., 60 seconds |
| e. | | Hold | 4° C. |

The underlined regions of the oligonucleotides annealed to the ADH promoter region and the amylase region, respectively, and amplified a 307 bp region from vector pSST-AMY.0 when no insert was present. Typically, the first 18 nucleotides of the 5' end of these oligonucleotides contained annealing sites for the sequencing primers. Thus, the total product of the PCR reaction from an empty vector was 343 bp. However, signal sequence-fused cDNA resulted in considerably longer nucleotide sequences.

Following the PCR, an aliquot of the reaction (5 μl) was examined by agarose gel electrophoresis in a 1% agarose gel using a Tris-Borate-EDTA (TBE) buffering system as described by Sambrook et al., supra. Clones resulting in a single strong PCR product larger than 400 bp were further analyzed by DNA sequencing after purification with a 96 Qiaquick PCR clean-up column (Qiagen Inc., Chatsworth, Calif.).

Example 3

Isolation of cDNA Clones Using Signal Algorithm Analysis

Various polypeptide-encoding nucleic acid sequences were identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals. Use of this algorithm resulted in the identification of numerous polypeptide-encoding nucleic acid sequences.

Example 4

Isolation of cDNA Clones Encoding Human PRO Polypeptides

Using the techniques described in Examples 1 to 3 above, numerous full-length cDNA clones were identified as encoding PRO polypeptides as disclosed herein. These cDNAs were then deposited under the terms of the Budapest Treaty with the American Type Culture Collection, 10801 University Blvd., Manassas, Va. 20110-2209, USA (ATCC) as shown in Table 7 below.

TABLE 7

| Material | ATCC Dep. No. | Deposit Date |
|---|---|---|
| DNA16422-1209 | 209929 | Jun. 2, 1998 |
| DNA19902-1669 | 203454 | Nov. 3, 1998 |
| DNA21624-1391 | 209917 | Jun. 2, 1998 |
| DNA34387-1138 | 209260 | Sep. 16, 1997 |
| DNA35880-1160 | 209379 | Oct. 16, 1997 |
| DNA39984-1221 | 209435 | Nov. 7, 1997 |
| DNA44189-1322 | 209699 | Mar. 26, 1998 |
| DNA48303-2829 | PTA-1342 | Feb. 8, 2000 |
| DNA48320-1433 | 209904 | May 27, 1998 |
| DNA56049-2543 | 203662 | Feb. 9, 1999 |
| DNA57694-1341 | 203017 | Jun. 23, 1998 |
| DNA59208-1373 | 209881 | May 20, 1998 |
| DNA59214-1449 | 203046 | Jul. 1, 1998 |
| DNA59485-1336 | 203015 | Jun. 23, 1998 |
| DNA64966-1575 | 203575 | Jan. 12, 1999 |
| DNA 82403-2959 | PTA-2317 | Aug. 1, 2000 |
| DNA83505-2606 | PTA-132 | May 25, 1999 |
| DNA84927-2585 | 203865 | Mar. 23, 1999 |
| DNA92264-2616 | 203969 | Apr. 27, 1999 |
| DNA94713-2561 | 203835 | Mar. 9, 1999 |
| DNA96869-2673 | PTA-255 | Jun. 22, 1999 |
| DNA96881-2699 | PTA-553 | Aug. 17, 1999 |
| DNA96889-2641 | PTA-119 | May 25, 1999 |
| DNA96898-2640 | PTA-122 | May 25, 1999 |
| DNA97003-2649 | PTA-43 | May 11, 1999 |
| DNA98565-2701 | PTA-481 | Aug. 3, 1999 |
| DNA102846-2742 | PTA-545 | Aug. 17, 1999 |
| DNA102847-2726 | PTA-517 | Aug. 10, 1999 |
| DNA102880-2689 | PTA-383 | Jul. 20, 1999 |
| DNA105782-2683 | PTA-387 | Jul. 20, 1999 |
| DNA108912-2680 | PTA-124 | May, 25, 1999 |
| DNA115253-2757 | PTA-612 | Aug. 31, 1999 |
| DNA119302-2737 | PTA-520 | Aug. 10, 1999 |
| DNA119536-2752 | PTA-551 | Aug. 17, 1999 |
| DNA119542-2754 | PTA-619 | Aug. 31, 1999 |
| DNA143498-2824 | PTA-1263 | Feb. 2, 2000 |
| DNA145583-2820 | PTA-1179 | Jan. 11, 2000 |
| DNA161000-2896 | PTA-1731 | Apr. 18, 2000 |
| DNA161005-2943 | PTA-2243 | Jun. 27, 2000 |
| DNA170245-3053 | PTA-2952 | Jan. 23, 2001 |
| DNA171771-2919 | PTA-1902 | May 23, 2000 |
| DNA173157-2981 | PTA-2388 | Aug. 8, 2000 |
| DNA175734-2985 | PTA-2455 | Sep. 12, 2000 |
| DNA176108-3040 | PTA-2824 | Dec. 19, 2000 |
| DNA190710-3028 | PTA-2822 | Dec. 19, 2000 |
| DNA190803-3019 | PTA-2785 | Dec. 12, 2000 |
| DNA191064-3069 | PTA-3016 | Feb. 6, 2001 |
| DNA194909-3013 | PTA-2779 | Dec. 12, 2000 |
| DNA203532-3029 | PTA-2823 | Dec. 19, 2000 |
| DNA213858-3060 | PTA-2958 | Jan. 23, 2001 |
| DNA216676-3083 | PTA-3157 | Mar. 6, 2001 |
| DNA222653-3104 | PTA-3330 | Apr. 24, 2001 |
| DNA96897-2688 | PTA-379 | Jul. 20, 1999 |
| DNA142917-3081 | PTA-3155 | Mar. 6, 2001 |
| DNA142930-2914 | PTA-1901 | May 23, 2000 |
| DNA147253-2983 | PTA-2405 | Aug. 22, 2000 |
| DNA149927-2887 | PTA-1782 | Apr. 25, 2000 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit and for at least five (5) years after the most recent request for the furnishing of a sample of the deposit received by the depository. The deposits will be made available by ATCC under the terms of the Budapest Treaty, and subject to an agreement between Genentech, Inc. and ATCC, which assures that all restrictions imposed by the depositor on the availability to the public of the deposited material will be irrevocably removed upon the granting of the pertinent U.S. patent, assures availability of the progeny of one determined by the U.S. Commissioner of Patents and Trademarks to be entitled thereto according to 35 USC § 122 and the Commissioner's rules pursuant thereto (including 37 CFR § 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Example 5

Use of PRO as a Hybridization Probe

The following method describes use of a nucleotide sequence encoding PRO as a hybridization probe.

DNA comprising the coding sequence of full-length or mature PRO as disclosed herein is employed as a probe to screen for homologous DNAs (such as those encoding naturally-occurring variants of PRO) in human tissue cDNA libraries or human tissue genomic libraries.

Hybridization and washing of filters containing either library DNAs is performed under the following high stringency conditions. Hybridization of radiolabeled PRO-derived probe to the filters is performed in a solution of 50% formamide, 5×SSC, 0.1% SDS, 0.1% sodium pyrophosphate, 50 mM sodium phosphate, pH 6.8, 2× Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence PRO can then be identified using standard techniques known in the art.

Example 6

Expression of PRO in *E. coli*

This example illustrates preparation of an unglycosylated form of PRO by recombinant expression in *E. coli*.

The DNA sequence encoding PRO is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene,* 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO protein can then be purified using a metal chelating column under conditions that allow tight binding of the protein.

PRO may be expressed in *E. coli* in a poly-His tagged form, using the following procedure. The DNA encoding PRO is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. coli* host based on strain 52 (W3110 fhA(tonA) lon galE rpoHts(htpRts) clpP(lacIq). Transformants are first grown in LB containing 50 mg/ml carbenicillin at 30° C. with shaking until an O.D.600 of 3-5 is reached. Cultures are then diluted 50-100 fold into CRAP media (prepared by mixing 3.57 g $(NH_4)_2SO_4$, 0.71 g sodium citrate.$2H_2O$, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

*E. coli* paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration.

The refolded protein is chromatographed on a Poros R1/H reversed phase column using a mobile buffer of 0.1% TFA with elution with a gradient of acetonitrile from 10 to 80%. Aliquots of fractions with $A_{280}$ absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded PRO polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Many of the PRO polypeptides disclosed herein were successfully expressed as described above.

Example 7

Expression of PRO in Mammalian Cells

This example illustrates preparation of a potentially glycosylated form of PRO by recombinant expression in mammalian cells.

The vector, pRK5 (see EP 307,247, published Mar. 15, 1989), is employed as the expression vector. Optionally, the PRO DNA is ligated into pRK5 with selected restriction enzymes to allow insertion of the PRO DNA using ligation methods such as described in Sambrook et al., supra. The resulting vector is called pRK5-PRO.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-PRO DNA is mixed with about 1 μg DNA encoding the VA RNA gene [Thimmappaya et al., *Cell*, 31:543 (1982)] and dissolved in 500 μl of 1 mM Tris-HCl 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of PRO polypeptide. The cultures containing transfected cells may undergo further incubation (in serum free medium) and the medium is tested in selected bioassays.

In an alternative technique, PRO may be introduced into 293 cells transiently using the dextran sulfate method described by Somparyrac et al., *Proc. Natl. Acad. Sci.*, 12:7575 (1981). 293 cells are grown to maximal density in a spinner flask and 700 μg pRK5-PRO DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed PRO can then be concentrated and purified by any selected method, such as dialysis and/or column chromatography.

In another embodiment, PRO can be expressed in CHO cells. The pRK5-PRO can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of PRO polypeptide, the culture medium may be replaced with serum free medium. Preferably, the cultures are incubated for about 6 days, and then the conditioned medium is harvested. The medium containing the expressed PRO can then be concentrated and purified by any selected method.

Epitope-tagged PRO may also be expressed in host CHO cells. The PRO may be subcloned out of the pRK5 vector. The subclone insert can undergo PCR to fuse in frame with a selected epitope tag such as a poly-his tag into a Baculovirus expression vector. The poly-his tagged PRO insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PRO can then be concentrated and purified by any selected method, such as by $Ni^{2+}$-chelate affinity chromatography.

PRO may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., *Nucl. Acids Res.* 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect® (Qiagen), Dosper® or Fugene® (Boehringer Mannheim). The cells are grown as described in Lucas et al., supra.

Approximately $3\times10^7$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 μm filtered PS20 with 5% 0.2 μm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3\times10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3 L production spinner is seeded at $1.2\times10^6$ cells/mL. On day 0, the cell number pH ie determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 μm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 μL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Many of the PRO polypeptides disclosed herein were successfully expressed as described above.

Example 8

Expression of PRO in Yeast

The following method describes recombinant expression of PRO in yeast.

First, yeast expression vectors are constructed for intracellular production or secretion of PRO from the ADH2/GAPDH promoter. DNA encoding PRO and the promoter is inserted into suitable restriction enzyme sites in the selected plasmid to direct intracellular expression of PRO. For secretion, DNA encoding PRO can be cloned into the selected plasmid, together with DNA encoding the ADH2/GAPDH promoter, a native PRO signal peptide or other mammalian signal peptide, or, for example, a yeast alpha-factor or invertase secretory signal/leader sequence, and linker sequences (if needed) for expression of PRO.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO can subsequently be isolated and purified by removing the yeast cells from the fermentation medium by centrifugation and then concentrating the medium using selected cartridge filters. The concentrate containing PRO may further be purified using selected column chromatography resins.

Many of the PRO polypeptides disclosed herein were successfully expressed as described above.

Example 9

Expression of PRO in Baculovirus-Infected Insect Cells

The following method describes recombinant expression of PRO in Baculovirus-infected insect cells.

The sequence coding for PRO is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding PRO or the desired portion of the coding sequence of PRO such as the sequence encoding the extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged PRO can then be purified, for example, by $Ni^{2+}$-chelate affinity chromatography as follows. Extracts are prepared from recombinant virus-infected Sf9 cells as described by Rupert et al., *Nature*, 362:175-179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged PRO are pooled and dialyzed against loading buffer.

Alternatively, purification of the IgG tagged (or Fc tagged) PRO can be performed using known chromatography techniques, including for instance, Protein A or protein G column chromatography.

Many of the PRO polypeptides disclosed herein were successfully expressed as described above.

Example 10

Preparation of Antibodies that Bind PRO

This example illustrates preparation of monoclonal antibodies which can specifically bind PRO.

Techniques for producing the monoclonal antibodies are known in the art and are described, for instance, in Goding, supra. Immunogens that may be employed include purified PRO, fusion proteins containing PRO, and cells expressing recombinant PRO on the cell surface. Selection of the immunogen can be made by the skilled artisan without undue experimentation.

Mice, such as Balb/c, are immunized with the PRO immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-PRO antibodies.

After a suitable antibody titer has been detected, the animals "positive" for antibodies can be injected with a final intravenous injection of PRO. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against PRO. Determination of "positive" hybridoma cells secreting the desired monoclonal antibodies against PRO is within the skill in the art.

The positive hybridoma cells can be injected intraperitoneally into syngeneic Balb/c mice to produce ascites containing the anti-PRO monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 11

Purification of PRO Polypeptides Using Specific Antibodies

Native or recombinant PRO polypeptides may be purified by a variety of standard techniques in the art of protein purification. For example, pro-PRO polypeptide, mature PRO polypeptide, or pre-PRO polypeptide is purified by immunoaffinity chromatography using antibodies specific for the PRO polypeptide of interest. In general, an immunoaffinity column is constructed by covalently coupling the anti-PRO polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of PRO polypeptide by preparing a fraction from cells containing PRO polypeptide in a soluble form. This preparation is derived by solubilization of the whole cell or of a subcellular fraction obtained via differential centrifugation by the addition of detergent or by other methods well known in the art. Alternatively, soluble PRO polypeptide containing a signal sequence may be secreted in useful quantity into the medium in which the cells are grown.

A soluble PRO polypeptide-containing preparation is passed over the immunoaffinity column, and the column is washed under conditions that allow the preferential absorbance of PRO polypeptide (e.g., high ionic strength buffers in the presence of detergent). Then, the column is eluted under conditions that disrupt antibody/PRO polypeptide binding (e.g., a low pH buffer such as approximately pH 2-3, or a high concentration of a chaotrope such as urea or thiocyanate ion), and PRO polypeptide is collected.

Example 12

Drug Screening

This invention is particularly useful for screening compounds by using PRO polypeptides or binding fragment thereof in any of a variety of drug screening techniques. The PRO polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the PRO polypeptide or fragment. Drugs are screened against such transformed cells in competitive binding assays. Such cells, either in viable or fixed form, can be used for standard binding assays. One may measure, for example, the formation of complexes between PRO polypeptide or a fragment and the agent being tested. Alternatively, one can examine the diminution in complex formation between the PRO polypeptide and its target cell or target receptors caused by the agent being tested.

Thus, the present invention provides methods of screening for drugs or any other agents which can affect a PRO polypeptide-associated disease or disorder. These methods comprise contacting such an agent with an PRO polypeptide or fragment thereof and assaying (I) for the presence of a complex between the agent and the PRO polypeptide or fragment, or (ii) for the presence of a complex between the PRO polypeptide or fragment and the cell, by methods well known in the art. In such competitive binding assays, the PRO polypeptide or fragment is typically labeled. After suitable incubation, free PRO polypeptide or fragment is separated from that present in bound form, and the amount of free or uncomplexed label is a measure of the ability of the particular agent to bind to PRO polypeptide or to interfere with the PRO polypeptide/cell complex.

Another technique for drug screening provides high throughput screening for compounds having suitable binding affinity to a polypeptide and is described in detail in WO 84/03564, published on Sep. 13, 1984. Briefly stated, large numbers of different small peptide test compounds are synthesized on a solid substrate, such as plastic pins or some other surface. As applied to a PRO polypeptide, the peptide test compounds are reacted with PRO polypeptide and washed. Bound PRO polypeptide is detected by methods well known in the art. Purified PRO polypeptide can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding PRO polypeptide specifically compete with a test compound for binding to PRO polypeptide or fragments thereof. In this manner, the antibodies can be used to detect the presence of any peptide which shares one or more antigenic determinants with PRO polypeptide.

Example 13

Rational Drug Design

The goal of rational drug design is to produce structural analogs of biologically active polypeptide of interest (i.e., a PRO polypeptide) or of small molecules with which they interact, e.g., agonists, antagonists, or inhibitors. Any of these examples can be used to fashion drugs which are more active or stable forms of the PRO polypeptide or which enhance or interfere with the function of the PRO polypeptide in vivo (cf., Hodgson, *Bio/Technology*, 9: 19-21 (1991)).

In one approach, the three-dimensional structure of the PRO polypeptide, or of an PRO polypeptide-inhibitor complex, is determined by x-ray crystallography, by computer modeling or, most typically, by a combination of the two approaches. Both the shape and charges of the PRO polypeptide must be ascertained to elucidate the structure and to determine active site(s) of the molecule. Less often, useful information regarding the structure of the PRO polypeptide may be gained by modeling based on the structure of homologous proteins. In both cases, relevant structural information is used to design analogous PRO polypeptide-like molecules or to identify efficient inhibitors. Useful examples of rational drug design may include molecules which have improved activity or stability as shown by Braxton and Wells, *Biochemistry*, 31:7796-7801 (1992) or which act as inhibitors, agonists, or antagonists of native peptides as shown by Athauda et al., *J. Biochem.*, 113:742-746 (1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the PRO polypeptide may be made available to perform such analytical studies as X-ray crystallography. In addition, knowledge of the PRO polypeptide amino acid sequence provided herein will provide guidance to those employing computer modeling techniques in place of or in addition to x-ray crystallography.

Example 14

Ability of PRO Polypeptides to Stimulate the Release of Proteoglycans from Cartilage (Assay 97)

The ability of various PRO polypeptides to stimulate the release of proteoglycans from cartilage tissue was tested as follows.

The metacarphophalangeal joint of 4-6 month old pigs was aseptically dissected, and articular cartilage was removed by free hand slicing being careful to avoid the underlying bone. The cartilage was minced and cultured in bulk for 24 hours in a humidified atmosphere of 95% air, 5% $CO_2$ in serum free (SF) media (DME/F12 1:1) with 0.1% BSA and 100 U/ml penicillin and 100 μg/ml streptomycin. After washing three times, approximately 100 mg of articular cartilage was aliquoted into micronics tubes and incubated for an additional 24 hours in the above SF media. PRO polypeptides were then added at 1% either alone or in combination with 18 ng/ml interleukin-1α, a known stimulator of proteoglycan release from cartilage tissue. The supernatant was then harvested and assayed for the amount of proteoglycans using the 1,9-dimethyl-methylene blue (DMB) colorimetric assay (Farndale and Buttle, *Biochem. Biophys. Acta* 883:173-177 (1985)). A positive result in this assay indicates that the test polypeptide will find use, for example, in the treatment of sports-related joint problems, articular cartilage defects, osteoarthritis or rheumatoid arthritis.

When various PRO polypeptides were tested in the above assay, the polypeptides demonstrated a marked ability to stimulate release of proteoglycans from cartilage tissue both basally and after stimulation with interleukin-1α and at 24 and 72 hours after treatment, thereby indicating that these PRO polypeptides are useful for stimulating proteoglycan release from cartilage tissue. As such, these PRO polypeptides are useful for the treatment of sports-related joint problems, articular cartilage defects, osteoarthritis or rheumatoid arthritis. PRO6018 polypeptide testing positive in this assay.

Example 15

Human Microvascular Endothelial Cell Proliferation (Assay 146)

This assay is designed to determine whether PRO polypeptides of the present invention show the ability to induce proliferation of human microvascular endothelial cells in culture and, therefore, function as useful growth factors.

On day 0, human microvascular endothelial cells were plated in 96-well plates at 1000 cells/well per 100 microliter and incubated overnight in complete media [EBM-2 growth media, plus supplements: IGF-1; ascorbic acid; VEGF; hEGF; hFGF; hydrocortisone, gentamicin (GA-1000), and fetal bovine serum (FBS, Clonetics)]. On day 1, complete media was replaced by basal media [EBM-2 plus 1% FBS] and addition of PRO polypeptides at 1%, 0.1% and 0.01%. On day 7, an assessment of cell proliferation was performed using the ViaLight HS kit [ATP/luciferase Lumitech]. Results are expressed as % of the cell growth observed with control buffer.

The following PRO polypeptides stimulated human microvascular endothelial cell proliferation in this assay: PRO1313, PRO20080, and PRO21383.

The following PRO polypeptides inhibited human microvascular endothelial cell proliferation in this assay: PRO6071, PRO4487, and PRO6006.

Example 16

Microarray Analysis to Detect Overexpression of PRO Polypeptides in Cancerous Tumors Nucleic acid microarrays, often containing thousands of gene sequences, are useful for identifying differentially expressed genes in diseased tissues as compared to their normal counterparts. Using nucleic acid microarrays, test and control mRNA samples from test and control tissue samples are reverse transcribed and labeled to generate cDNA probes. The cDNA probes are then hybridized to an array of nucleic acids immobilized on a solid support. The array is configured such that the sequence and position of each member of the array is known. For example, a selection of genes known to be expressed in certain disease states may be arrayed on a solid support. Hybridization of a labeled probe with a particular array member indicates that the sample from which the probe was derived expresses that gene. If the hybridization signal of a probe from a test (disease tissue) sample is greater than hybridization signal of a probe from a control (normal tissue) sample, the gene or genes overexpressed in the disease tissue are identified. The implication of this result is that an overexpressed protein in a diseased tissue is useful not only as a diagnostic marker for the presence of the disease condition, but also as a therapeutic target for treatment of the disease condition.

The methodology of hybridization of nucleic acids and microarray technology is well known in the art. In the present example, the specific preparation of nucleic acids for hybridization and probes, slides, and hybridization conditions are all detailed in U.S. Provisional Patent Application Ser. No. 60/193,767, filed on Mar. 31, 2000 and which is herein incorporated by reference.

In the present example, cancerous tumors derived from various human tissues were studied for PRO polypeptide-encoding gene expression relative to non-cancerous human tissue in an attempt to identify those PRO polypeptides which are overexpressed in cancerous tumors. Cancerous human tumor tissue from any of a variety of different human tumors was obtained and compared to a "universal" epithelial control sample which was prepared by pooling non-cancerous human tissues of epithelial origin, including liver, kidney, and lung. mRNA isolated from the pooled tissues represents a mixture of expressed gene products from these different tissues. Microarray hybridization experiments using the pooled control samples generated a linear plot in a 2-color analysis. The slope of the line generated in a 2-color analysis was then used to normalize the ratios of (test:control detection) within each experiment. The normalized ratios from various experiments were then compared and used to identify clustering of gene expression. Thus, the pooled "universal control" sample not only allowed effective relative gene expression determinations in a simple 2-sample comparison, it also allowed multi-sample comparisons across several experiments.

In the present experiments, nucleic acid probes derived from the herein described PRO polypeptide-encoding nucleic acid sequences were used in the creation of the microarray and RNA from a panel of nine different tumor tissues (listed below) were used for the hybridization thereto. A value based upon the normalized ratio:experimental ratio was designated as a "cutoff ratio". Only values that were above this cutoff ratio were determined to be significant. Table 8 below shows the results of these experiments, demonstrating that various PRO polypeptides of the present invention are significantly overexpressed in various human tumor tissues, as compared to a non-cancerous human tissue control or other human tumor tissues. As described above, these data demonstrate that the PRO polypeptides of the present invention are useful not only as diagnostic markers for the presence of one or more cancerous tumors, but also serve as therapeutic targets for the treatment of those tumors.

TABLE 8

| Molecule | is overexpressed in: | as compared to normal control: |
|---|---|---|
| PRO240 | breast tumor | universal normal control |
| PRO240 | lung tumor | universal normal control |
| PRO256 | colon tumor | universal normal control |
| PRO256 | lung tumor | universal normal control |
| PRO256 | breast tumor | universal normal control |
| PRO306 | colon tumor | universal normal control |
| PRO306 | lung tumor | universal normal control |
| PRO540 | lung tumor | universal normal control |
| PRO540 | colon tumor | universal normal control |
| PRO773 | breast tumor | universal normal control |
| PRO773 | colon tumor | universal normal control |
| PRO698 | colon tumor | universal normal control |
| PRO698 | breast tumor | universal normal control |
| PRO698 | lung tumor | universal normal control |
| PRO698 | prostate tumor | universal normal control |
| PRO698 | rectal tumor | universal normal control |
| PRO3567 | colon tumor | universal normal control |
| PRO3567 | breast tumor | universal normal control |
| PRO3567 | lung tumor | universal normal control |
| PRO826 | colon tumor | universal normal control |
| PRO826 | lung tumor | universal normal control |
| PRO826 | breast tumor | universal normal control |
| PRO826 | rectal tumor | universal normal control |
| PRO826 | liver tumor | universal normal control |
| PRO1002 | colon tumor | universal normal control |

TABLE 8-continued

| Molecule | is overexpressed in: | as compared to normal control: |
|---|---|---|
| PRO1002 | lung tumor | universal normal control |
| PRO1068 | colon tumor | universal normal control |
| PRO1068 | breast tumor | universal normal control |
| PRO1030 | colon tumor | universal normal control |
| PRO1030 | breast tumor | universal normal control |
| PRO1030 | lung tumor | universal normal control |
| PRO1030 | prostate tumor | universal normal control |
| PRO1030 | rectal tumor | universal normal control |
| PRO4397 | colon tumor | universal normal control |
| PRO4397 | breast tumor | universal normal control |
| PRO4344 | colon tumor | universal normal control |
| PRO4344 | lung tumor | universal normal control |
| PRO4344 | rectal tumor | universal normal control |
| PRO4407 | colon tumor | universal normal control |
| PRO4407 | breast tumor | universal normal control |
| PRO4407 | lung tumor | universal normal control |
| PRO4407 | liver tumor | universal normal control |
| PRO4407 | rectal tumor | universal normal control |
| PRO4316 | colon tumor | universal normal control |
| PRO4316 | prostate tumor | universal normal control |
| PRO5775 | colon tumor | universal normal control |
| PRO6016 | colon tumor | universal normal control |
| PRO4980 | breast tumor | universal normal control |
| PRO4980 | colon tumor | universal normal control |
| PRO4980 | lung tumor | universal normal control |
| PRO6018 | colon tumor | universal normal control |
| PRO7168 | colon tumor | universal normal control |
| PRO6000 | colon tumor | universal normal control |
| PRO6006 | colon tumor | universal normal control |
| PRO5800 | colon tumor | universal normal control |
| PRO5800 | breast tumor | universal normal control |
| PRO5800 | lung tumor | universal normal control |
| PRO5800 | rectal tumor | universal normal control |
| PRO7476 | colon tumor | universal normal control |
| PRO10268 | colon tumor | universal normal control |
| PRO6496 | colon tumor | universal normal control |
| PRO6496 | breast tumor | universal normal control |
| PRO6496 | lung tumor | universal normal control |
| PRO7422 | colon tumor | universal normal control |
| PRO7431 | colon tumor | universal normal control |
| PRO28633 | colon tumor | universal normal control |
| PRO28633 | lung tumor | universal normal control |
| PRO28633 | liver tumor | universal normal control |
| PRO21485 | colon tumor | universal normal control |
| PRO28700 | breast tumor | universal normal control |
| PRO28700 | lung tumor | universal normal control |
| PRO28700 | colon tumor | universal normal control |
| PRO34012 | colon tumor | universal normal control |
| PRO34012 | lung tumor | universal normal control |
| PRO34003 | colon tumor | universal normal control |
| PRO34003 | lung tumor | universal normal control |
| PRO34001 | colon tumor | universal normal control |
| PRO34009 | colon tumor | universal normal control |
| PRO34009 | breast tumor | universal normal control |
| PRO34009 | lung tumor | universal normal control |
| PRO34009 | rectal tumor | universal normal control |
| PRO34192 | colon tumor | universal normal control |
| PRO34564 | colon tumor | universal normal control |
| PRO35444 | colon tumor | universal normal control |
| PRO5998 | colon tumor | universal normal control |
| PRO5998 | lung tumor | universal normal control |
| PRO5998 | kidney tumor | universal normal control |
| PRO19651 | colon tumor | universal normal control |
| PRO20221 | liver tumor | universal normal control |
| PRO21434 | liver tumor | universal normal control |

Example 17

Fetal Hemoglobin Induction in an Erythroblastic Cell Line (Assay 107)

This assay is useful for screening PRO polypeptides for the ability to induce the switch from adult hemoglobin to fetal hemoglobin in an erythroblastic cell line. Molecules testing positive in this assay are expected to be useful for therapeutically treating various mammalian hemoglobin-associated disorders such as the various thalassemias. The assay is performed as follows. Erythroblastic cells are plated in standard growth medium at 1000 cells/well in a 96 well format. PRO polypeptides are added to the growth medium at a concentration of 0.2% or 2% and the cells are incubated for 5 days at 37° C. As a positive control, cells are treated with 100 μM hemin and as a negative control, the cells are untreated. After 5 days, cell lysates are prepared and analyzed for the expression of gamma globin (a fetal marker). A positive in the assay is a gamma globin level at least 2-fold above the negative control.

PRO20080 polypeptide tested positive in this assay.

Example 18

Microarray Analysis to Detect Overexpression of PRO Polypeptides in HUVEC Cells Treated with Growth Factors This assay is designed to determine whether PRO polypeptides of the present invention show the ability to induce angiogenesis by stimulating endothelial cell tube formation in HUVEC cells.

Nucleic acid microarrays, often containing thousands of gene sequences, are useful for identifying differentially expressed genes in tissues exposed to various stimuli (e.g., growth factors) as compared to their normal, unexposed counterparts. Using nucleic acid microarrays, test and control mRNA samples from test and control tissue samples are reverse transcribed and labeled to generate cDNA probes. The cDNA probes are then hybridized to an array of nucleic acids immobilized on a solid support. The array is configured such that the sequence and position of each member of the array is known. Hybridization of a labeled probe with a particular array member indicates that the sample from which the probe was derived expresses that gene. If the hybridization signal of a probe from a test (exposed tissue) sample is greater than hybridization signal of a probe from a control (normal, unexposed tissue) sample, the gene or genes overexpressed in the exposed tissue are identified. The implication of this result is that an overexpressed protein in an exposed tissue may be involved in the functional changes within the tissue following exposure to the stimuli (e.g., tube formation).

The methodology of hybridization of nucleic acids and microarray technology is well known in the art. In the present example, the specific preparation of nucleic acids for hybridization and probes, slides, and hybridization conditions are all detailed in U.S. Provisional Patent Application Ser. No. 60/193,767, filed on Mar. 31, 2000 and which is herein incorporated by reference.

In the present example, HUVEC cells grown in either collagen gels or fibrin gels were induced to form tubes by the addition of various growth factors. Specifically, collagen gels were prepared as described previously in Yang et al., *American J. Pathology*, 1999, 155(3):887-895 and Xin et al., *American J. Pathology*, 2001, 158(3):1111-1120. Following gelation of the HUVEC cells, 1× basal medium containing M199 supplemented with 1% FBS, 1× ITS, 2 mM L-glutamine, 50 μg/ml ascorbic acid, 26.5 mM $NaHCO_3$, 100 U/ml penicillin and 100 U/ml streptomycin was added. Tube formation was elicited by the inclusion in the culture media of either a mixture of phorbol myrsitate acetate (50 nM), vascular endothelial cell growth factor (40 ng/ml) and basic fibroblast growth factor (40 ng/ml) ("PMA growth factor mix") or hepatocyte growth factor (40 ng/ml) and vascular endothelial cell growth factor (40 ng/ml) (HGF/VEGF mix) for the indicated period of time. Fibrin Gels were prepared by suspending Huvec ($4\times10^5$ cells/ml) in M199 containing 1% fetal bovine serum (Hyclone) and human fibrinogen (2.5 mg/ml). Thrombin (50 U/ml) was then added to the fibrinogen suspension at a ratio of 1 part thrombin solution: 30 parts fibrinogen suspension. The solution was then layered onto 10 cm tissue culture plates (total volume: 15 ml/plate) and allowed to solidify at 37° C. for 20 min. Tissue culture media (10 ml of BM containing PMA (50 nM), bFGF (40 ng/ml) and VEGF (40 ng/ml)) was then added and the cells incubated at 37° C. in 5% $CO_2$ in air for the indicated period of time.

Total RNA was extracted from the HUVEC cells incubated for 0, 4, 8, 24, 40 and 50 hours in the different matrix and media combinations using a TRIzol extraction followed by a second purification using RNAeasy Mini Kit (Qiagen). The total RNA was used to prepare cRNA which was then hybridized to the microarrays.

In the present experiments, nucleic acid probes derived from the herein described PRO polypeptide-encoding nucleic acid sequences were used in the creation of the microarray and RNA from the HUVEC cells described above were used for the hybridization thereto. Pairwise comparisons were made using time 0 chips as a baseline. Three replicate samples were analyzed for each experimental condition and time. Hence there were 3 time 0 samples for each treatment and 3 replicates of each successive time point. Therefore, a 3 by 3 comparison was performed for each time point compared against each time 0 point. This resulted in 9 comparisons per time point. Only those genes that had increased expression in all three non-time-0 replicates in each of the different matrix and media combinations as compared to any of the three time zero replicates were considered positive. Although this stringent method of data analysis does allow for false negatives, it minimizes false positives.

PRO281, PRO1560, PRO189, PRO4499, PRO6308, PRO6000, PRO10275, PRO21207, PRO20933, and PRO34274 tested positive in this assay.

Example 19

Tumor Versus Normal Differential Tissue Expression Distribution

Oligonucleotide probes were constructed from some of the PRO polypeptide-encoding nucleotide sequences shown in the accompanying figures for use in quantitative PCR amplification reactions. The oligonucleotide probes were chosen so as to give an approximately 200-600 base pair amplified fragment from the 3' end of its associated template in a standard PCR reaction. The oligonucleotide probes were employed in standard quantitative PCR amplification reactions with cDNA libraries isolated from different human tumor and normal human tissue samples and analyzed by agarose gel electrophoresis so as to obtain a quantitative determination of the level of expression of the PRO polypeptide-encoding nucleic acid in the various tumor and normal tissues tested. β-actin was used as a control to assure that equivalent amounts of nucleic acid was used in each reaction. Identification of the differential expression of the PRO polypeptide-encoding nucleic acid in one or more tumor tissues as compared to one or more normal tissues of the same tissue type renders the molecule useful diagnostically for the determination of the presence or absence of tumor in a subject suspected of possessing a tumor as well as therapeutically as a target for the treatment of a tumor in a subject possessing such a tumor. These assays provided the following results:

(1) DNA161005-2943 molecule is very highly expressed in human umblilical vein endothelial cells (HUVEC), substantia niagra, hippocampus and dendrocytes; highly expressed in lymphoblasts; expressed in spleen, prostate, uterus and macrophages; and is weakly expressed in cartilage and heart. Among a panel of normal and tumor tissues examined, it is expressed in esophageal tumor, and is not expressed in normal esophagus, normal stomach, stomach tumor, normal kidney, kidney tumor, normal lung, lung tumor, normal rectum, rectal tumor, normal liver and liver tumor.

(2) DNA170245-3053 molecule is highly expressed in cartilage, testis, adrenal gland, and uterus, and not expressed in HUVEC, colon tumor, heart, placenta, bone marrow, spleen and aortic endothelial cells. In a panel of tumor and normal tissue samples examined, the DNA170245-3053 molecule was found to be expressed in normal esophagus and esophagial tumor, expressed in normal stomach and in stomach tumor, not expressed in normal kidney, but expressed in kidney tumor, not expressed in normal lung, but expressed in lung tumor, not expressed in normal rectum nor in rectal tumor, and not expressed in normal liver, but is expressed in liver tumor.

(3) DNA173157-2981 molecule is significantly expressed in the following tissues: cartilage, testis, HUVEC, heart, placenta, bone marrow, adrenal gland, prostate, spleen, aortic endothelial cells, and uterus. When these assays were conducted on a tumor tissue panel, it was found that the DNA173157-2981 molecule is significantly expressed in the following tissues: normal esophagus and esophagial tumor, normal stomach and stomach tumor, normal kidney and kidney tumor, normal lung and lung tumor, normal rectum and rectal tumor, normal liver and liver tumor, and colon tumor.

(4) DNA175734-2985 molecule is significantly expressed in the adrenal gland and the uterus. The DNA175734-2985 molecule is not significantly expressed in the following tissues: cartilage, testis, HUVEC, colon tumor, heart, placenta, bone marrow, prostate, spleen and aortic endothelial cells. Screening of a tumor panel revealed that DNA175734-2985 is significantly expressed in normal esophagus but not in esophagial tumor. Similarly, while highly expressed in normal rectum, DNA175734-2985 is expressed to a lesser extent in rectal tumor. DNA175734-2985 is expressed equally in normal stomach and stomach tumor as well as normal liver and liver tumor. While not expressed in normal kidney, DNA175734-2985 is highly expressed in kidney tumor.

(5) DNA176108-3040 molecule is highly expressed in prostate and uterus, expressed in cartilage, testis, heart, placenta, bone marrow, adrenal gland and spleen, and not significantly expressed in HUVEC, colon tumor, and aortic endothelial cells. In a panel of tumor and normal tissue samples examined, the DNA176108-3040 molecule was found to be highly expressed in normal esophagus, but expressed at lower levels in esophagial tumor, highly expressed in normal stomach, and expressed at a lower level in stomach tumor, expressed in kidney and in kidney tumor, expressed in normal rectum and at a lower level in rectal tumor, and expressed in normal liver and not expressed in liver tumor.

(6) DNA191064-3069 molecule is significantly expressed in the following tissues: cartilage, testis, HUVEC, heart, placenta, bone marrow, adrenal gland, prostate, spleen, aortic endothelial cells, and uterus and not significantly expressed in colon tumor. In a panel of tumor and normal tissue samples, the DNA191064-3069 molecule was found to be expressed in normal esophagus and in esophagial tumors, expressed in normal stomach and in stomach tumors, expressed in normal kidney and in kidney tumors, expressed in normal lung and in lung tumors, expressed in normal rectum and in rectal tumors, expressed in normal liver and in liver tumors.

(7) DNA194909-3013 molecule is highly expressed in placenta, and expressed in cartilage, testis, HUVEC, colon tumor, heart, bone marrow, adrenal gland, prostate, spleen, aortic endothelial cells and uterus. In a panel of tumor and normal tissue samples examined, the DNA194909-3013 molecule was found to be expressed in normal esophagus and expressed at a lower level in esophagial tumor, not expressed in normal stomach nor stomach tumor, expressed in normal kidney and kidney tumor, expressed in normal lung and lung tumor, expressed in normal rectum and rectal tumor, and not expressed in normal liver, but is expressed in liver tumor.

(8) The PRO34009 encoding genes of the invention (DNA203532-3029) were screened in normal tissues and the following primary tumors and the resulting values are reported below.

Tumor Panel:

PRO34009 encoding genes were expressed 39.3 fold higher in lung tumor than normal lung. It is expressed 9.5 fold higher in esophagial tumors than normal esophagus. It is expressed 6.7 fold higher in kidney tumor than normal kidney. It is expressed 4.0 fold higher in colon tumor than normal colon. It is expressed 2.7 fold higher in stomach tumor than normal stomach. It is expressed at similar levels in normal rectum and rectal tumor, normal liver and liver tumor, normal uterus and uterine tumor.

Normal Panel:

For the normal tissue values, the normal tissue with the highest expression, in this case normal thymus, was given a value of 1 and all other normal tissues were given a value of less than 1, and described as expressed, weakly expressed or not expressed, based on their expression relative to thymus. PRO34009 encoding genes were expressed in normal thymus. It is weakly expressed in lymphoblast, spleen, heart, fetal limb, fetal lung, placenta, HUVEC, testis, fetal kidney, uterus, prostate, macrophage, substantia nigra, hippocampus, liver, skin, esophagus, stomach, rectum, kidney, thyroid, skeletal muscle, or fetal articular cartilage.

It is not expressed in bone marrow, fetal liver, colon, lung or dendrocytes.

(9) DNA213858-3060 molecule is not significantly expressed in cartilage, testis, HUVEC, colon tumor, heart, placenta, bone marrow, adrenal gland, prostate, spleen, aortic endothelial cells or uterus. In a panel of tumor and normal tissue samples examined, the DNA213858-3060 molecule was found to be expressed in normal esophagus and esophagial tumor, expressed in normal stomach and in stomach tumor, expressed in normal kidney and and kidney tumor, expressed in normal lung and in lung tumor, expressed in normal rectum and in rectal tumor, and expressed in normal liver and in liver tumor.

(10) DNA216676-3083 molecule is significantly expressed in the following tissues: testis, heart, bone marrow, and uterus, and not significantly expressed in the following tissues: cartilage, HUVEC, colon tumor, placenta, adrenal gland, prostate, spleen, or aortic endothelial cells In a panel of tumor and normal tissues samples examined, the DNA216676-3083 molecule was found to be expressed in normal esophagus and esophagial tumor, not expressed in normal stomach, but is expressed in stomach tumor, not expressed in normal kidney nor in kidney tumor, not expressed in normal lung, but is expressed in lung tumor, not expressed in normal rectum, but is expressed in rectal tumor, and not expressed in normal liver nor in liver tumor.

(11) DNA222653-3104 molecule is significantly expressed testis, and not significantly expressed in cartilage, HUVEC, colon tumor, heart, placenta, bone marrow, adrenal gland, prostate, spleen, aortic endothelial cells and uterus. In a panel of tumor and normal tissue samples examined, the DNA22653-3104 molecule was not expressed in normal esophagus, esophagial tumor, normal stomach, stomach tumor, normal kidney, kidney tumor, normal lung, lung tumor, normal rectum, rectal tumor, normal liver and liver tumor.

Example 20

Guinea Pig Vascular Leak (Assay 51)

This assay is designed to determine whether PRO polypeptides of the present invention show the ability to induce vascular permeability. Polypeptides testing positive in this assay are expected to be useful for the therapeutic treatment of conditions which would benefit from enhanced vascular permeability including, for example, conditions which may benefit from enhanced local immune system cell infiltration.

Hairless guinea pigs weighing 350 grams or more were anesthetized with Ketamine (75-80 mg/kg) and 5 mg/kg Xylazine intramuscularly. Test samples containing the PRO polypeptide or a physiological buffer without the test polypeptide are injected into skin on the back of the test animals with 100 μl per injection site intradermally. There were approximately 16-24 injection sites per animal. One ml of Evans blue dye (1% in PBS) is then injected intracardially. Skin vascular permeability responses to the compounds (i.e., blemishes at the injection sites of injection) are visually scored by measuring the diameter (in mm) of blue-colored leaks from the site of injection at 1 and 6 hours post administration of the test materials. The mm diameter of blueness at the site of injection is observed and recorded as well as the severity of the vascular leakage. Blemishes of at least 5 mm in diameter are considered positive for the assay when testing purified proteins, being indicative of the ability to induce vascular leakage or permeability. A response greater than 7 mm diameter is considered positive for conditioned media samples. Human VEGF at 0.1 μg/100 μl is used as a positive control, inducing a response of 15-23 mm diameter.

PRO19822 polypeptides tested positive in this assay.

Example 21

Skin Vascular Permeability Assay (Assay 64)

This assay shows that certain polypeptides of the invention stimulate an immune response and induce inflammation by inducing mononuclear cell, eosinophil and PMN infiltration at the site of injection of the animal. Compounds which stimulate an immune response are useful therapeutically where stimulation of an immune response is beneficial. This skin vascular permeability assay is conducted as follows. Hairless guinea pigs weighing 350 grams or more are anesthetized with ketamine (75-80 mg/Kg) and 5 mg/Kg xylazine intramuscularly (IM). A sample of purified polypeptide of the invention or a conditioned media test sample is injected intradermally onto the backs of the test animals with 100 μl per injection site: It is possible to have about 10-30, preferably about 16-24, injection sites per animal. One μl of Evans blue dye (1% in physiologic buffered saline) is injected intracardially. Blemishes at the injection sites are then measured (mm diameter) at 1 hr and 6 hr post injection. Animals were sacrificed at 6 hrs after injection. Each skin injection site is biopsied and fixed in formalin. The skins are then prepared for histopathologic evaluation. Each site is evaluated for inflammatory cell infiltration into the skin. Sites with visible inflammatory cell inflammation are scored as positive. Inflammatory cells may be neutrophilic, eosinophilic, monocytic or lymphocytic. At least a minimal perivascular infiltrate at the injection site is scored as positive, no infiltrate at the site of injection is scored as negative.

PRO19822 polypeptide tested positive in this assay.

What is claimed is:

1. An isolated polypeptide comprising:

(a) the amino acid sequence of the polypeptide of SEQ ID NO: 74;

(b) the amino acid sequence of the polypeptide of SEQ ID NO: 74, lacking its associated signal peptide; or (c) the amino acid sequence of the polypeptide encoded by the full-length coding sequence of the cDNA deposited under ATCC accession number PTA-1179.

2. The isolated polypeptide of claim 1 comprising the amino acid sequence of the polypeptide of SEQ ID NO: 74.

3. The isolated polypeptide of claim 1 comprising the amino acid sequence of the polypeptide of SEQ ID NO: 74, lacking its associated signal peptide.

4. The isolated polypeptide of claim 1 comprising the amino acid sequence of the polypeptide encoded by the full-length coding sequence of the cDNA deposited under ATCC accession number PTA-1179.

5. A chimeric polypeptide comprising a polypeptide according to claim 1 fused to a heterologous polypeptide.

6. The chimeric polypeptide of claim 5, wherein said heterologous polypeptide is an epitope tag on an Fc region of an immunoglobulin.

* * * * *

SEQUENCE LISTING

<160> NUMBER OF SEQ ID NOS: 116

<210> SEQ ID NO 1
<211> LENGTH: 1943
<212> TYPE: DNA
<213> ORGANISM: Homo Sapien

<400> SEQUENCE: 1

```
cggacgcgtg ggtgcgaggc gaaggtgacc ggggaccgag catttcagat      50

ctgctcggta gacctggtgc accaccacca tgttggctgc aaggctggtg     100

tgtctccgga cactaccttc tagggttttc cacccagctt tcaccaaggc     150

ctcccctgtt gtgaagaatt ccatcacgaa gaatcaatgg ctgttaacac     200

ctagcaggga atatgccacc aaaacaagaa ttgggatccg gcgtgggaga     250

actggccaag aactcaaaga ggcagcattg gaaccatcga tggaaaaaat     300

atttaaaatt gatcagatgg gaagatggtt tgttgctgga ggggctgctg     350

ttggtcttgg agcattgtgc tactatggct tgggactgtc taatgagatt     400

ggagctattg aaaaggctgt aatttggcct cagtatgtca aggatagaat     450

tcattccacc tatatgtact tagcagggag tattggttta acagctttgt     500

ctgccatagc aatcagcaga acgcctgttc tcatgaactt catgatgaga     550

ggctcttggg tgacaattgg tgtgaccttt gcagccatgg ttggagctgg     600

aatgctggta cgatcaatac catatgacca gagcccaggc ccaaagcatc     650

ttgcttggtt gctacattct ggtgtgatgg gtgcagtggt ggctcctctg     700

acaatattag gggtcctctt tctcatcaga gctgcatggt acacagctgg     750

cattgtggga ggcctctcca ctgtggccat gtgtgcgccc agtgaaaagt     800

ttctgaacat gggtgcaccc ctgggagtgg gcctgggtct cgtctttgtg     850

tcctcattgg gatctatgtt tcttccacct accaccgtgg ctggtgccac     900

tctttactca gtggcaatgt acggtggatt agttcttttc agcatgttcc     950

ttctgtatga tacccagaaa gtaatcaagc gtgcagaagt atcaccaatg    1000

tatggagttc aaaaatatga tcccattaac tcgatgctga gtatctacat    1050

ggatacatta aatatattta tgcgagttgc aactatgctg gcaactggag    1100

gcaacagaaa gaaatgaagt gactcagctt ctggcttctc tgctacatca    1150

aatatcttgt ttaatggggc agatatgcat taaatagttt gtacaagcag    1200

ctttcgttga agtttagaag ataagaaaca tgtcatcata tttaaatgtt    1250

ccggtaatgt gatgcctcag gtctgccttt ttttctggag aataaatgca    1300
```

-continued

```
gtaatcctct cccaaataag cacacacatt ttcaattctc atgtttgagt        1350

gattttaaaa tgttttggtg aatgtgaaaa ctaaagtttg tgtcatgaga        1400

atgtaagtct tttttctact ttaaaattta gtaggttcac tgagtaacta        1450

aaatttagca aacctgtgtt tgcatatttt tttggagtgc agaatattgt        1500

aattaatgtc ataagtgatt tggagctttg gtaaagggac cagagagaag        1550

gagtcacctg cagtcttttg tttttttaaa tacttagaac ttagcacttg        1600

tgttattgat tagtgaggag ccagtaagaa acatctgggt atttggaaac        1650

aagtggtcat tgttacattc atttgctgaa cttaacaaaa ctgttcatcc        1700

tgaaacaggc acaggtgatg cattctcctg ctgttgcttc tcagtgctct        1750

ctttccaata tagatgtggt catgtttgac ttgtacagaa tgttaatcat        1800

acagagaatc cttgatggaa ttatatatgt gtgttttact tttgaatgtt        1850

acaaaaggaa ataactttaa aactattctc aagagaaaat attcaaagca        1900

tgaaatatgt tgctttttcc agaatacaaa cagtatactc atg               1943
```

<210> SEQ ID NO 2
<211> LENGTH: 345
<212> TYPE: PRT
<213> ORGANISM: Homo Sapien

<400> SEQUENCE: 2

```
Met Leu Ala Ala Arg Leu Val Cys Leu Arg Thr Leu Pro Ser Arg
  1               5                  10                  15

Val Phe His Pro Ala Phe Thr Lys Ala Ser Pro Val Val Lys Asn
                 20                  25                  30

Ser Ile Thr Lys Asn Gln Trp Leu Leu Thr Pro Ser Arg Glu Tyr
                 35                  40                  45

Ala Thr Lys Thr Arg Ile Gly Ile Arg Arg Gly Arg Thr Gly Gln
                 50                  55                  60

Glu Leu Lys Glu Ala Ala Leu Glu Pro Ser Met Glu Lys Ile Phe
                 65                  70                  75

Lys Ile Asp Gln Met Gly Arg Trp Phe Val Ala Gly Gly Ala Ala
                 80                  85                  90

Val Gly Leu Gly Ala Leu Cys Tyr Tyr Gly Leu Gly Leu Ser Asn
                 95                 100                 105

Glu Ile Gly Ala Ile Glu Lys Ala Val Ile Trp Pro Gln Tyr Val
                110                 115                 120

Lys Asp Arg Ile His Ser Thr Tyr Met Tyr Leu Ala Gly Ser Ile
                125                 130                 135

Gly Leu Thr Ala Leu Ser Ala Ile Ala Ile Ser Arg Thr Pro Val
                140                 145                 150

Leu Met Asn Phe Met Met Arg Gly Ser Trp Val Thr Ile Gly Val
                155                 160                 165

Thr Phe Ala Ala Met Val Gly Ala Gly Met Leu Val Arg Ser Ile
                170                 175                 180

Pro Tyr Asp Gln Ser Pro Gly Pro Lys His Leu Ala Trp Leu Leu
                185                 190                 195

His Ser Gly Val Met Gly Ala Val Val Ala Pro Leu Thr Ile Leu
                200                 205                 210

Gly Gly Pro Leu Leu Ile Arg Ala Ala Trp Tyr Thr Ala Gly Ile
                215                 220                 225
```

-continued

```
Val Gly Gly Leu Ser Thr Val Ala Met Cys Ala Pro Ser Glu Lys
                230                 235                 240

Phe Leu Asn Met Gly Ala Pro Leu Gly Val Gly Leu Gly Leu Val
                245                 250                 255

Phe Val Ser Ser Leu Gly Ser Met Phe Leu Pro Pro Thr Thr Val
                260                 265                 270

Ala Gly Ala Thr Leu Tyr Ser Val Ala Met Tyr Gly Gly Leu Val
                275                 280                 285

Leu Phe Ser Met Phe Leu Leu Tyr Asp Thr Gln Lys Val Ile Lys
                290                 295                 300

Arg Ala Glu Val Ser Pro Met Tyr Gly Val Gln Lys Tyr Asp Pro
                305                 310                 315

Ile Asn Ser Met Leu Ser Ile Tyr Met Asp Thr Leu Asn Ile Phe
                320                 325                 330

Met Arg Val Ala Thr Met Leu Ala Thr Gly Gly Asn Arg Lys Lys
                335                 340                 345


<210> SEQ ID NO 3
<211> LENGTH: 1110
<212> TYPE: DNA
<213> ORGANISM: Homo Sapien

<400> SEQUENCE: 3

ccaatcgccc ggtgcggtgg tgcagggtct cgggctagtc atggcgtccc          50

cgtctcggag actgcagact aaaccagtca ttacttgttt caagagcgtt         100

ctgctaatct acacttttat tttctggatc actggcgtta tccttcttgc         150

agttggcatt tggggcaagg tgagcctgga gaattacttt tctcttttaa         200

atgagaaggc caccaatgtc cccttcgtgc tcattgctac tggtaccgtc         250

attattcttt tgggcacctt tggttgtttt gctacctgcc gagcttctgc         300

atggatgcta aaactgtatg caatgtttct gactctcgtt tttttggtcg         350

aactggtcgc tgccatcgta ggatttgttt tcagacatga gattaagaac         400

agctttaaga ataattatga gaaggctttg aagcagtata actctacagg         450

agattataga agccatgcag tagacaagat ccaaaatacg ttgcattgtt         500

gtggtgtcac cgattataga gattggacag atactaatta ttactcagaa         550

aaaggatttc ctaagagttg ctgtaaactt gaagattgta ctccacagag         600

agatgcagac aaagtaaaca atgaaggttg ttttataaag gtgatgacca         650

ttatagagtc agaaatggga gtcgttgcag gaatttcctt tggagttgct         700

tgcttccaac tgattggaat ctttctcgcc tactgccwct ctcgtgccat         750

aacaaataac cagtatgaga tagtgtaacc caatgtatct gtgggcctat         800

tcctctctac ctttaaggac atttagggtc ccccctgtga attagaaagt         850

tgcttggctg gagaactgac aacactactt actgatagac caaaaaacta         900

caccagtagg ttgattcaat caagatgtat gtagacctaa aactacacca         950

ataggctgat tcaatcaaga tccgtgctcg cagtgggctg attcaatcaa        1000

gatgtatgtt tgctatgttc taagtccacc ttctatccca ttcatgttag        1050

atcgttgaaa ccctgtatcc ctctgaaaca ctggaagagc tagtaaattg        1100

taaatgaagt                                                    1110
```

-continued

<210> SEQ ID NO 4
<211> LENGTH: 245
<212> TYPE: PRT
<213> ORGANISM: Homo Sapien
<220> FEATURE:
<221> NAME/KEY: unsure
<222> LOCATION: 233
<223> OTHER INFORMATION: unknown amino acid

<400> SEQUENCE: 4

```
Met Ala Ser Pro Ser Arg Arg Leu Gln Thr Lys Pro Val Ile Thr
  1               5                  10                  15

Cys Phe Lys Ser Val Leu Leu Ile Tyr Thr Phe Ile Phe Trp Ile
                 20                  25                  30

Thr Gly Val Ile Leu Leu Ala Val Gly Ile Trp Gly Lys Val Ser
                 35                  40                  45

Leu Glu Asn Tyr Phe Ser Leu Leu Asn Glu Lys Ala Thr Asn Val
                 50                  55                  60

Pro Phe Val Leu Ile Ala Thr Gly Thr Val Ile Ile Leu Leu Gly
                 65                  70                  75

Thr Phe Gly Cys Phe Ala Thr Cys Arg Ala Ser Ala Trp Met Leu
                 80                  85                  90

Lys Leu Tyr Ala Met Phe Leu Thr Leu Val Phe Leu Val Glu Leu
                 95                 100                 105

Val Ala Ala Ile Val Gly Phe Val Phe Arg His Glu Ile Lys Asn
                110                 115                 120

Ser Phe Lys Asn Asn Tyr Glu Lys Ala Leu Lys Gln Tyr Asn Ser
                125                 130                 135

Thr Gly Asp Tyr Arg Ser His Ala Val Asp Lys Ile Gln Asn Thr
                140                 145                 150

Leu His Cys Cys Gly Val Thr Asp Tyr Arg Asp Trp Thr Asp Thr
                155                 160                 165

Asn Tyr Tyr Ser Glu Lys Gly Phe Pro Lys Ser Cys Cys Lys Leu
                170                 175                 180

Glu Asp Cys Thr Pro Gln Arg Asp Ala Asp Lys Val Asn Asn Glu
                185                 190                 195

Gly Cys Phe Ile Lys Val Met Thr Ile Ile Glu Ser Glu Met Gly
                200                 205                 210

Val Val Ala Gly Ile Ser Phe Gly Val Ala Cys Phe Gln Leu Ile
                215                 220                 225

Gly Ile Phe Leu Ala Tyr Cys Xaa Ser Arg Ala Ile Thr Asn Asn
                230                 235                 240

Gln Tyr Glu Ile Val
                245
```

<210> SEQ ID NO 5
<211> LENGTH: 1373
<212> TYPE: DNA
<213> ORGANISM: Homo Sapien

<400> SEQUENCE: 5

```
ggggccgcgg tctagggcgg ctacgtgtgt tgccatagcg accattttgc               50

attaactggt tggtagcttc tatcctgggg gctgagcgac tgcgggccag              100

ctcttcccct actccctctc ggctccttgt ggcccaaagg cctaaccggg              150

gtccggcggt ctggcctagg gatcttcccc gttgcccctt tggggcggga              200

tggctgcgga agaagaagac gaggtggagt gggtagtgga gagcatcgcg              250
```

-continued

```
gggttcctgc gaggcccaga ctggtccatc cccatcttgg actttgtgga            300

acagaaatgt gaagttaact gcaaaggagg gcatgtgata actccaggaa            350

gcccagagcc ggtgattttg gtggcctgtg ttccccttgt ttttgatgat            400

gaagaagaaa gcaaattgac ctatacagag attcatcagg aatacaaaga            450

actagttgaa aagctgttag aaggttacct caaagaaatt ggaattaatg            500

aagatcaatt tcaagaagca tgcacttctc ctcttgcaaa gacccataca            550

tcacaggcca ttttgcaacc tgtgttggca gcagaagatt ttactatctt            600

taaagcaatg atggtccaga aaaacattga aatgcagctg caagccattc            650

gaataattca agagagaaat ggtgtattac ctgactgctt aaccgatggc            700

tctgatgtgg tcagtgacct tgaacacgaa gagatgaaaa tcctgaggga            750

agttcttaga aaatcaaaag aggaatatga ccaggaagaa gaaaggaaga            800

ggaaaaaaca gttatcagag gctaaaacag aagagcccac agtgcattcc            850

agtgaagctg caataatgaa taattcccaa ggggatggtg aacattttgc            900

acacccaccc tcagaagtta aaatgcattt tgctaatcag tcaatagaac            950

ctttgggaag aaaagtggaa aggtctgaaa cttcctccct cccacaaaaa           1000

ggcctgaaga ttcctggctt agagcatgcg agcattgaag gaccaatagc           1050

aaacttatca gtacttggaa cagaagaact tcggcaacga gaacactatc           1100

tcaagcagaa gagagataag ttgatgtcca tgagaaagga tatgaggact           1150

aaacagatac aaaatatgga gcagaaagga aaacccactg gggaggtaga           1200

ggaaatgaca gagaaaccag aaatgacagc agaggagaag caaacattac           1250

taaagaggag attgcttgca gagaaactca aagaagaagt tattaataag           1300

taataattaa gaacaattta acaaaatgga agttcaaatt gtcttaaaaa           1350

taaattattt agtccttaca ctg                                        1373
```

```
<210> SEQ ID NO 6
<211> LENGTH: 367
<212> TYPE: PRT
<213> ORGANISM: Homo Sapien

<400> SEQUENCE: 6

Met Ala Ala Glu Glu Glu Asp Glu Val Glu Trp Val Val Glu Ser
  1               5                  10                  15

Ile Ala Gly Phe Leu Arg Gly Pro Asp Trp Ser Ile Pro Ile Leu
                 20                  25                  30

Asp Phe Val Glu Gln Lys Cys Glu Val Asn Cys Lys Gly Gly His
                 35                  40                  45

Val Ile Thr Pro Gly Ser Pro Glu Pro Val Ile Leu Val Ala Cys
                 50                  55                  60

Val Pro Leu Val Phe Asp Asp Glu Glu Glu Ser Lys Leu Thr Tyr
                 65                  70                  75

Thr Glu Ile His Gln Glu Tyr Lys Glu Leu Val Glu Lys Leu Leu
                 80                  85                  90

Glu Gly Tyr Leu Lys Glu Ile Gly Ile Asn Glu Asp Gln Phe Gln
                 95                 100                 105

Glu Ala Cys Thr Ser Pro Leu Ala Lys Thr His Thr Ser Gln Ala
                110                 115                 120
```

-continued

```
Ile Leu Gln Pro Val Leu Ala Ala Glu Asp Phe Thr Ile Phe Lys
                125                 130                 135

Ala Met Met Val Gln Lys Asn Ile Glu Met Gln Leu Gln Ala Ile
                140                 145                 150

Arg Ile Ile Gln Glu Arg Asn Gly Val Leu Pro Asp Cys Leu Thr
                155                 160                 165

Asp Gly Ser Asp Val Val Ser Asp Leu Glu His Glu Glu Met Lys
                170                 175                 180

Ile Leu Arg Glu Val Leu Arg Lys Ser Lys Glu Glu Tyr Asp Gln
                185                 190                 195

Glu Glu Glu Arg Lys Arg Lys Lys Gln Leu Ser Glu Ala Lys Thr
                200                 205                 210

Glu Glu Pro Thr Val His Ser Ser Glu Ala Ala Ile Met Asn Asn
                215                 220                 225

Ser Gln Gly Asp Gly Glu His Phe Ala His Pro Pro Ser Glu Val
                230                 235                 240

Lys Met His Phe Ala Asn Gln Ser Ile Glu Pro Leu Gly Arg Lys
                245                 250                 255

Val Glu Arg Ser Glu Thr Ser Ser Leu Pro Gln Lys Gly Leu Lys
                260                 265                 270

Ile Pro Gly Leu Glu His Ala Ser Ile Glu Gly Pro Ile Ala Asn
                275                 280                 285

Leu Ser Val Leu Gly Thr Glu Glu Leu Arg Gln Arg Glu His Tyr
                290                 295                 300

Leu Lys Gln Lys Arg Asp Lys Leu Met Ser Met Arg Lys Asp Met
                305                 310                 315

Arg Thr Lys Gln Ile Gln Asn Met Glu Gln Lys Gly Lys Pro Thr
                320                 325                 330

Gly Glu Val Glu Glu Met Thr Glu Lys Pro Glu Met Thr Ala Glu
                335                 340                 345

Glu Lys Gln Thr Leu Leu Lys Arg Arg Leu Leu Ala Glu Lys Leu
                350                 355                 360

Lys Glu Glu Val Ile Asn Lys
                365
```

<210> SEQ ID NO 7
<211> LENGTH: 932
<212> TYPE: DNA
<213> ORGANISM: Homo Sapien
<220> FEATURE:
<221> NAME/KEY: unsure
<222> LOCATION: 911
<223> OTHER INFORMATION: unknown base

<400> SEQUENCE: 7

```
gggaacggaa aatggcgcct cacggcccgg gtagtcttac gaccctggtg          50

ccctgggctg ccgccctgct cctcgctctg ggcgtggaaa gggctctggc         100

gctacccgag atatgcaccc aatgtccagg gagcgtgcaa aatttgtcaa         150

aagtggcctt ttattgtaaa acgacacgag agctaatgct gcatgcccgt         200

tgctgcctga atcagaaggg caccatcttg ggctggatct tccagaactg         250

ttctctggag gaccctggtc caaactttca tcaggcacat accactgtca         300

tcatagacct gcaagcaaac cccctcaaag gtgacttggc caacaccttc         350

cgtggcttta ctcagctcca gactctgata ctgccacaac atgtcaactg         400
```

-continued

```
tcctggagga attaatgcct ggaatactat cacctcttat atagacaacc        450

aaatctgtca agggcaaaag aacctttgca ataacactgg ggacccagaa        500

atgtgtcctg agaatggatc ttgtgtacct gatggtccag gtcttttgca        550

gtgtgtttgt gctgatggtt tccatggata caagtgtatg cgccagggct        600

cgttctcact gcttatgttc ttcgggattc tgggagccac cactctatcc        650

gtctccattc tgctttgggc gacccagcgc cgaaaagcca agacttcatg        700

aactacatag gtcttaccat tgacctaaga tcaatctgaa ctatcttagc        750

ccagtcaggg agctctgctt cctagaaagg catctttcgc cagtggattc        800

gcctcaaggt tgaggccgcc attggaagat gaaaaattgc actcccttgg        850

tgtagacaaa taccagttcc cattggtgtt gttgcctata ataaacactt        900

tttcttttt naaaaaaaaa aaaaaaaaaa aa                            932
```

<210> SEQ ID NO 8
<211> LENGTH: 229
<212> TYPE: PRT
<213> ORGANISM: Homo Sapien

<400> SEQUENCE: 8

```
Met Ala Pro His Gly Pro Gly Ser Leu Thr Thr Leu Val Pro Trp
  1               5                  10                  15

Ala Ala Ala Leu Leu Leu Ala Leu Gly Val Glu Arg Ala Leu Ala
                 20                  25                  30

Leu Pro Glu Ile Cys Thr Gln Cys Pro Gly Ser Val Gln Asn Leu
                 35                  40                  45

Ser Lys Val Ala Phe Tyr Cys Lys Thr Thr Arg Glu Leu Met Leu
                 50                  55                  60

His Ala Arg Cys Cys Leu Asn Gln Lys Gly Thr Ile Leu Gly Leu
                 65                  70                  75

Asp Leu Gln Asn Cys Ser Leu Glu Asp Pro Gly Pro Asn Phe His
                 80                  85                  90

Gln Ala His Thr Thr Val Ile Ile Asp Leu Gln Ala Asn Pro Leu
                 95                 100                 105

Lys Gly Asp Leu Ala Asn Thr Phe Arg Gly Phe Thr Gln Leu Gln
                110                 115                 120

Thr Leu Ile Leu Pro Gln His Val Asn Cys Pro Gly Gly Ile Asn
                125                 130                 135

Ala Trp Asn Thr Ile Thr Ser Tyr Ile Asp Asn Gln Ile Cys Gln
                140                 145                 150

Gly Gln Lys Asn Leu Cys Asn Asn Thr Gly Asp Pro Glu Met Cys
                155                 160                 165

Pro Glu Asn Gly Ser Cys Val Pro Asp Gly Pro Gly Leu Leu Gln
                170                 175                 180

Cys Val Cys Ala Asp Gly Phe His Gly Tyr Lys Cys Met Arg Gln
                185                 190                 195

Gly Ser Phe Ser Leu Leu Met Phe Phe Gly Ile Leu Gly Ala Thr
                200                 205                 210

Thr Leu Ser Val Ser Ile Leu Leu Trp Ala Thr Gln Arg Arg Lys
                215                 220                 225

Ala Lys Thr Ser
```

<210> SEQ ID NO 9

-continued

<211> LENGTH: 2482
<212> TYPE: DNA
<213> ORGANISM: Homo Sapien

<400> SEQUENCE: 9
gggggagaag gcggccgagc cccagctctc cgagcaccgg gtcggaagcc 50
gcgacccgag ccgcgcagga agctgggacc ggaacctcgg cggacccggc 100
cccacccaac tcacctgcgc aggtcaccag caccctcgga acccagaggc 150
ccgcgctctg aaggtgaccc ccctggggag gaaggcgatg gcccctgcga 200
ggacgatggc ccgcgcccgc ctcgccccgg ccggcatccc tgccgtcgcc 250
ttgtggcttc tgtgcacgct cggcctccag ggcacccagg ccgggccacc 300
gcccgcgccc cctgggctgc ccgcgggagc cgactgcctg aacagcttta 350
ccgccggggt gcctggcttc gtgctggaca ccaacgcctc ggtcagcaac 400
ggagctacct tcctggagtc ccccaccgtg cgccggggct gggactgcgt 450
gcgcgcctgc tgcaccaccc agaactgcaa cttggcgcta gtggagctgc 500
agcccgaccg cggggaggac gccatcgccg cctgcttcct catcaactgc 550
ctctacgagc agaacttcgt gtgcaagttc gcgcccaggg agggcttcat 600
caactacctc acgagggaag tgtaccgctc ctaccgccag ctgcggaccc 650
agggctttgg agggtctggg atccccaagg cctgggcagg catagacttg 700
aaggtacaac cccaggaacc cctggtgctg aaggatgtgg aaaacacaga 750
ttggcgccta ctgcggggtg acacggatgt cagggtagag aggaaagacc 800
caaaccaggt ggaactgtgg ggactcaagg aaggcaccta cctgttccag 850
ctgacagtga ctagctcaga ccacccagag gacacggcca acgtcacagt 900
cactgtgctg tccaccaagc agacagaaga ctactgcctc gcatccaaca 950
aggtgggtcg ctgccggggc tctttcccac gctggtacta tgaccccacg 1000
gagcagatct gcaagagttt cgtttatgga ggctgcttgg gcaacaagaa 1050
caactacctt cgggaagaag agtgcattct agcctgtcgg ggtgtgcaag 1100
gtgggccttt gagaggcagc tctggggctc aggcgacttt cccccagggc 1150
ccctccatgg aaaggcgcca tccagtgtgc tctggcacct gtcagcccac 1200
ccagttccgc tgcagcaatg gctgctgcat cgacagtttc ctggagtgtg 1250
acgacacccc caactgcccc gacgcctccg acgaggctgc ctgtgaaaaa 1300
tacacgagtg gctttgacga gctccagcgc atccatttcc ccagtgacaa 1350
agggcactgc gtggacctgc cagacacagg actctgcaag gagagcatcc 1400
cgcgctggta ctacaacccc ttcagcgaac actgcgcccg ctttacctat 1450
ggtggttgtt atggcaacaa gaacaacttt gaggaagagc agcagtgcct 1500
cgagtcttgt cgcggcatct ccaagaagga tgtgtttggc ctgaggcggg 1550
aaatccccat tcccagcaca ggctctgtgg agatggctgt cacagtgttc 1600
ctggtcatct gcattgtggt ggtggtagcc atcttgggtt actgcttctt 1650
caagaaccag agaaaggact tccacggaca ccaccaccac ccaccaccca 1700
cccctgccag ctccactgtc tccactaccg aggacacgga gcacctggtc 1750
tataaccaca ccacccggcc cctctgagcc tgggtctcac cggctctcac 1800
ctggccctgc ttcctgcttg ccaaggcaga ggcctgggct gggaaaaact 1850

-continued

```
ttggaaccag actcttgcct gtttcccagg cccactgtgc ctcagagacc        1900
agggctccag cccctcttgg agaagtctca gctaagctca cgtcctgaga        1950
aagctcaaag gtttggaagg agcagaaaac ccttgggcca gaagtaccag        2000
actagatgga cctgcctgca taggagtttg gaggaagttg gagttttgtt        2050
tcctctgttc aaagctgcct gtccctaccc catggtgcta ggaagaggag        2100
tggggtggtg tcagaccctg gaggccccaa ccctgtcctc ccgagctcct        2150
cttccatgct gtgcgcccag ggctgggagg aaggacttcc ctgtgtagtt        2200
tgtgctgtaa agagttgctt tttgtttatt taatgctgtg gcatgggtga        2250
agaggagggg aagaggcctg tttggcctct ctgtcctctc ttcctcttcc        2300
cccaagattg agctctctgc ccttgatcag ccccaccctg gcctagacca        2350
gcagacagag ccaggagagg ctcagctgca ttccgcagcc cccacccccca       2400
aggttctcca acatcacagc ccagcccacc cactgggtaa taaaagtggt        2450
ttgtggaaaa aaaaaaaaaa aaaaaaaaaa aa                           2482
```

<210> SEQ ID NO 10
<211> LENGTH: 529
<212> TYPE: PRT
<213> ORGANISM: Homo Sapien

<400> SEQUENCE: 10

```
Met Ala Pro Ala Arg Thr Met Ala Arg Ala Arg Leu Ala Pro Ala
  1               5                  10                  15

Gly Ile Pro Ala Val Ala Leu Trp Leu Leu Cys Thr Leu Gly Leu
                 20                  25                  30

Gln Gly Thr Gln Ala Gly Pro Pro Pro Ala Pro Pro Gly Leu Pro
                 35                  40                  45

Ala Gly Ala Asp Cys Leu Asn Ser Phe Thr Ala Gly Val Pro Gly
                 50                  55                  60

Phe Val Leu Asp Thr Asn Ala Ser Val Ser Asn Gly Ala Thr Phe
                 65                  70                  75

Leu Glu Ser Pro Thr Val Arg Arg Gly Trp Asp Cys Val Arg Ala
                 80                  85                  90

Cys Cys Thr Thr Gln Asn Cys Asn Leu Ala Leu Val Glu Leu Gln
                 95                 100                 105

Pro Asp Arg Gly Glu Asp Ala Ile Ala Ala Cys Phe Leu Ile Asn
                110                 115                 120

Cys Leu Tyr Glu Gln Asn Phe Val Cys Lys Phe Ala Pro Arg Glu
                125                 130                 135

Gly Phe Ile Asn Tyr Leu Thr Arg Glu Val Tyr Arg Ser Tyr Arg
                140                 145                 150

Gln Leu Arg Thr Gln Gly Phe Gly Gly Ser Gly Ile Pro Lys Ala
                155                 160                 165

Trp Ala Gly Ile Asp Leu Lys Val Gln Pro Gln Glu Pro Leu Val
                170                 175                 180

Leu Lys Asp Val Glu Asn Thr Asp Trp Arg Leu Leu Arg Gly Asp
                185                 190                 195

Thr Asp Val Arg Val Glu Arg Lys Asp Pro Asn Gln Val Glu Leu
                200                 205                 210

Trp Gly Leu Lys Glu Gly Thr Tyr Leu Phe Gln Leu Thr Val Thr
                215                 220                 225
```

-continued

```
Ser Ser Asp His Pro Glu Asp Thr Ala Asn Val Thr Val Thr Val
                230                 235                 240

Leu Ser Thr Lys Gln Thr Glu Asp Tyr Cys Leu Ala Ser Asn Lys
                245                 250                 255

Val Gly Arg Cys Arg Gly Ser Phe Pro Arg Trp Tyr Tyr Asp Pro
                260                 265                 270

Thr Glu Gln Ile Cys Lys Ser Phe Val Tyr Gly Gly Cys Leu Gly
                275                 280                 285

Asn Lys Asn Asn Tyr Leu Arg Glu Glu Glu Cys Ile Leu Ala Cys
                290                 295                 300

Arg Gly Val Gln Gly Gly Pro Leu Arg Gly Ser Ser Gly Ala Gln
                305                 310                 315

Ala Thr Phe Pro Gln Gly Pro Ser Met Glu Arg Arg His Pro Val
                320                 325                 330

Cys Ser Gly Thr Cys Gln Pro Thr Gln Phe Arg Cys Ser Asn Gly
                335                 340                 345

Cys Cys Ile Asp Ser Phe Leu Glu Cys Asp Asp Thr Pro Asn Cys
                350                 355                 360

Pro Asp Ala Ser Asp Glu Ala Ala Cys Glu Lys Tyr Thr Ser Gly
                365                 370                 375

Phe Asp Glu Leu Gln Arg Ile His Phe Pro Ser Asp Lys Gly His
                380                 385                 390

Cys Val Asp Leu Pro Asp Thr Gly Leu Cys Lys Glu Ser Ile Pro
                395                 400                 405

Arg Trp Tyr Tyr Asn Pro Phe Ser Glu His Cys Ala Arg Phe Thr
                410                 415                 420

Tyr Gly Gly Cys Tyr Gly Asn Lys Asn Asn Phe Glu Glu Glu Gln
                425                 430                 435

Gln Cys Leu Glu Ser Cys Arg Gly Ile Ser Lys Lys Asp Val Phe
                440                 445                 450

Gly Leu Arg Arg Glu Ile Pro Ile Pro Ser Thr Gly Ser Val Glu
                455                 460                 465

Met Ala Val Thr Val Phe Leu Val Ile Cys Ile Val Val Val Val
                470                 475                 480

Ala Ile Leu Gly Tyr Cys Phe Phe Lys Asn Gln Arg Lys Asp Phe
                485                 490                 495

His Gly His His His His Pro Pro Pro Thr Pro Ala Ser Ser Thr
                500                 505                 510

Val Ser Thr Thr Glu Asp Thr Glu His Leu Val Tyr Asn His Thr
                515                 520                 525

Thr Arg Pro Leu


<210> SEQ ID NO 11
<211> LENGTH: 1899
<212> TYPE: DNA
<213> ORGANISM: Homo Sapien

<400> SEQUENCE: 11

gtgctgggct ttttcagaca agtgcatctc ctaaccaggt cacatttcag              50

ccgcgaccca ctctccgcca gtcaccggag gcagaccgcg ggaggagagc             100

tgaggacagc cgcgtgcgct tcgccagcag cggggtggga ggaaggacat             150

taaaatactg cagaagtcaa gacccccca ggtcgaaccc agaccacgat              200
```

-continued

```
gcgcgccccg ggctgcgggc ggctggtgct gccgctgctg ctcctggccg          250

cggcagccct ggccgaaggc gacgccaagg ggctcaagga gggcgagacc          300

cccggcaatt tcatggagga cgagcaatgg ctgtcgtcca tctcgcagta          350

cagcggcaag atcaagcact ggaaccgctt ccgagacgaa gtggaggatg          400

actatatcaa gagctgggag gacaatcagc aaggagatga agccctggat          450

accaccaagg acccctgcca gaaggtgaag tgcagccgcc acaaggtgtg          500

cattgcccag ggctaccagc gggccatgtg catcagtcgc aagaagctgg          550

agcacaggat caagcagccg accgtgaaac tccatggaaa caaagactcc          600

atctgcaagc cctgccacat ggcccagctt gcctctgtct gcggctcaga          650

tggccacact tacagctctg tgtgtaagct ggagcaacag gcgtgcctga          700

gcagcaagca gctggcggtg cgatgcgagg gcccctgccc ctgccccacg          750

gagcaggctg ccacctccac cgccgatggc aaaccagaga cttgcaccgg          800

tcaggacctg gctgacctgg gagatcggct gcgggactgg ttccagctcc          850

ttcatgagaa ctccaagcag aatggctcag ccagcagtgt agccggcccg          900

gccagcgggc tggacaagag cctgggggcc agctgcaagg actccattgg          950

ctggatgttc tccaagctgg acaccagtgc tgacctcttc ctggaccaga         1000

cggagctggc cgccatcaac ctggacaagt acgaggtctg catccgtccc         1050

ttcttcaact cctgtgacac ctacaaggat ggccgggtct ctactgctga         1100

gtggtgcttc tgcttctgga gggagaagcc cccctgcctg gcagagctgg         1150

agcgcatcca gatccaggag gccgccaaga agaagccagg catcttcatc         1200

ccgagctgcg acgaggatgg ctactaccgg aagatgcagt gtgaccagag         1250

cagcggtgac tgctggcgtg tggaccagct gggcctggag ctgactggca         1300

cgcgcacgca tgggagcccc gactgcgatg acatcgtggg cttctcgggg         1350

gactttggaa gcggtgtcgg ctgggaggat gaggaggaga aggagacgga         1400

ggaagcaggc gaggaggccg aggaggagga gggcgaggca ggcgaggctg         1450

acgacggggg ctacatctgg tagacgccct caggagccgg ctgccggggg         1500

ggactcaaca gcagagctct gagcagcagc aggcaacttc gagaacggat         1550

ccagaaatgc agtcagaagg accctgctcc acctgggggg actgggagtg         1600

tgagtgtgca tggcatgtgt gtggcacaga tggctgggac gggtgacagt         1650

gtgagtgcat gtgtgcatgc atgtgtgtat gtgtgtgtgt gtgtggcatg         1700

cgctgacaaa tgtgtccttg atccacactg ctcctggcag agtgagtcac         1750

ccaaaggccc cttcggcctc cttgtagctg ttttctttcc ttttgttgtt         1800

ggttttaaaa tacattcaca cacaaataca aaaaaaaaaa aaaaaaaaaa         1850

aaaaaaaaaa aaaaaaaaaa aaaaaaaaaa aaaaaaaaaa aaaaaaaaa          1899
```

<210> SEQ ID NO 12
<211> LENGTH: 424
<212> TYPE: PRT
<213> ORGANISM: Homo Sapien

<400> SEQUENCE: 12

```
Met Arg Ala Pro Gly Cys Gly Arg Leu Val Leu Pro Leu Leu Leu
  1               5                  10                  15
```

-continued

```
Leu Ala Ala Ala Ala Leu Ala Glu Gly Asp Ala Lys Gly Leu Lys
                20                  25                  30

Glu Gly Glu Thr Pro Gly Asn Phe Met Glu Asp Glu Gln Trp Leu
                35                  40                  45

Ser Ser Ile Ser Gln Tyr Ser Gly Lys Ile Lys His Trp Asn Arg
                50                  55                  60

Phe Arg Asp Glu Val Glu Asp Asp Tyr Ile Lys Ser Trp Glu Asp
                65                  70                  75

Asn Gln Gln Gly Asp Glu Ala Leu Asp Thr Thr Lys Asp Pro Cys
                80                  85                  90

Gln Lys Val Lys Cys Ser Arg His Lys Val Cys Ile Ala Gln Gly
                95                 100                 105

Tyr Gln Arg Ala Met Cys Ile Ser Arg Lys Lys Leu Glu His Arg
               110                 115                 120

Ile Lys Gln Pro Thr Val Lys Leu His Gly Asn Lys Asp Ser Ile
               125                 130                 135

Cys Lys Pro Cys His Met Ala Gln Leu Ala Ser Val Cys Gly Ser
               140                 145                 150

Asp Gly His Thr Tyr Ser Ser Val Cys Lys Leu Glu Gln Gln Ala
               155                 160                 165

Cys Leu Ser Ser Lys Gln Leu Ala Val Arg Cys Glu Gly Pro Cys
               170                 175                 180

Pro Cys Pro Thr Glu Gln Ala Ala Thr Ser Thr Ala Asp Gly Lys
               185                 190                 195

Pro Glu Thr Cys Thr Gly Gln Asp Leu Ala Asp Leu Gly Asp Arg
               200                 205                 210

Leu Arg Asp Trp Phe Gln Leu Leu His Glu Asn Ser Lys Gln Asn
               215                 220                 225

Gly Ser Ala Ser Ser Val Ala Gly Pro Ala Ser Gly Leu Asp Lys
               230                 235                 240

Ser Leu Gly Ala Ser Cys Lys Asp Ser Ile Gly Trp Met Phe Ser
               245                 250                 255

Lys Leu Asp Thr Ser Ala Asp Leu Phe Leu Asp Gln Thr Glu Leu
               260                 265                 270

Ala Ala Ile Asn Leu Asp Lys Tyr Glu Val Cys Ile Arg Pro Phe
               275                 280                 285

Phe Asn Ser Cys Asp Thr Tyr Lys Asp Gly Arg Val Ser Thr Ala
               290                 295                 300

Glu Trp Cys Phe Cys Phe Trp Arg Glu Lys Pro Pro Cys Leu Ala
               305                 310                 315

Glu Leu Glu Arg Ile Gln Ile Gln Glu Ala Ala Lys Lys Lys Pro
               320                 325                 330

Gly Ile Phe Ile Pro Ser Cys Asp Glu Asp Gly Tyr Tyr Arg Lys
               335                 340                 345

Met Gln Cys Asp Gln Ser Ser Gly Asp Cys Trp Arg Val Asp Gln
               350                 355                 360

Leu Gly Leu Glu Leu Thr Gly Thr Arg Thr His Gly Ser Pro Asp
               365                 370                 375

Cys Asp Asp Ile Val Gly Phe Ser Gly Asp Phe Gly Ser Gly Val
               380                 385                 390

Gly Trp Glu Asp Glu Glu Glu Lys Glu Thr Glu Glu Ala Gly Glu
               395                 400                 405

Glu Ala Glu Glu Glu Glu Gly Glu Ala Gly Glu Ala Asp Asp Gly
```

-continued 410 415 420

Gly Tyr Ile Trp

<210> SEQ ID NO 13
<211> LENGTH: 2680
<212> TYPE: DNA
<213> ORGANISM: Homo Sapien

<400> SEQUENCE: 13
tgcggcgacc gtcgtacacc atgggcctcc acctccgccc ctaccgtgtg 50
gggctgctcc cggatggcct cctgttcctc ttgctgctgc taatgctgct 100
cgcggaccca gcgctcccgg ccggacgtca ccccccagtg gtgctggtcc 150
ctggtgattt gggtaaccaa ctggaagcca agctggacaa gccgacagtg 200
gtgcactacc tctgctccaa gaagaccgaa agctacttca caatctggct 250
gaacctggaa ctgctgctgc ctgtcatcat tgactgctgg attgacaata 300
tcaggctggt ttacaacaaa acatccaggg ccacccagtt tcctgatggt 350
gtggatgtac gtgtccctgg ctttgggaag accttctcac tggagttcct 400
ggaccccagc aaaagcagcg tgggttccta tttccacacc atggtggaga 450
gccttgtggg ctggggctac acacggggtg aggatgtccg aggggctccc 500
tatgactggc gccgagcccc aaatgaaaac gggccctact tcctggccct 550
ccgcgagatg atcgaggaga tgtaccagct gtatgggggc cccgtggtgc 600
tggttgccca cagtatgggc aacatgtaca cgctctactt tctgcagcgg 650
cagccgcagg cctggaagga caagtatatc cgggccttcg tgtcactggg 700
tgcgccctgg gggggcgtgg ccaagaccct gcgcgtcctg gcttcaggag 750
acaacaaccg gatcccagtc atcgggcccc tgaagatccg ggagcagcag 800
cggtcagctg tctccaccag ctggctgctg ccctacaact acacatggtc 850
acctgagaag gtgttcgtgc agacacccac aatcaactac acactgcggg 900
actaccgcaa gttcttccag gacatcggct ttgaagatgg ctggctcatg 950
cggcaggaca cagaagggct ggtggaagcc acgatgccac ctggcgtgca 1000
gctgcactgc ctctatggta ctggcgtccc cacaccagac tccttctact 1050
atgagagctt ccctgaccgt gaccctaaaa tctgctttgg tgacggcgat 1100
ggtactgtga acttgaagag tgccctgcag tgccaggcct ggcagagccg 1150
ccaggagcac caagtgttgc tgcaggagct gccaggcagc gagcacatcg 1200
agatgctggc caacgccacc accctggcct atctgaaacg tgtgctcctt 1250
gggccctgac tcctgtgcca caggactcct gtggctcggc cgtggacctg 1300
ctgttggcct ctggggctgt catggcccac gcgttttgca aagtttgtga 1350
ctcaccattc aaggccccga gtcttggact gtgaagcatc tgccatgggg 1400
aagtgctgtt tgttatcctt tctctgtggc agtgaagaag gaagaaatga 1450
gagtctagac tcaagggaca ctggatggca agaatgctgc tgatggtgga 1500
actgctgtga ccttaggact ggctccacag ggtggactgg ctgggccctg 1550
gtcccagtcc ctgcctgggg ccatgtgtcc ccctattcct gtgggctttt 1600
catacttgcc tactgggccc tggccccgca gccttcctat gagggatgtt 1650
actgggctgt ggtcctgtac ccagaggtcc cagggatcgg ctcctggccc 1700

-continued

```
ctcgggtgac ccttcccaca caccagccac agataggcct gccactggtc          1750

atgggtagct agagctgctg gcttccctgt ggcttagctg gtggccagcc          1800

tgactggctt cctgggcgag cctagtagct cctgcaggca ggggcagttt          1850

gttgcgttct tcgtggttcc caggccctgg gacatctcac tccactccta          1900

cctcccttac caccaggagc attcaagctc tggattgggc agcagatgtg          1950

cccccagtcc cgcaggctgt gttccagggg ccctgatttc ctcggatgtg          2000

ctattggccc caggactgaa gctgcctccc ttcaccctgg gactgtggtt          2050

ccaaggatga gagcaggggt tggagccatg gccttctggg aacctatgga          2100

gaaagggaat ccaaggaagc agccaaggct gctcgcagct tccctgagct          2150

gcacctcttg ctaaccccac catcacactg ccaccctgcc ctagggtctc          2200

actagtacca agtgggtcag cacagggctg aggatggggc tcctatccac          2250

cctggccagc acccagctta gtgctgggac tagcccagaa acttgaatgg          2300

gaccctgaga gagccagggg tcccctgagg ccccccctagg ggctttctgt         2350

ctgccccagg gtgctccatg gatctccctg tggcagcagg catggagagt          2400

cagggctgcc ttcatggcag taggctctaa gtgggtgact ggccacaggc          2450

cgagaaaagg gtacagcctc taggtggggt tcccaaagac gccttcaggc          2500

tggactgagc tgctctccca cagggtttct gtgcagctgg attttctctg          2550

ttgcatacat gcctggcatc tgtctcccct tgttcctgag tggccccaca          2600

tggggctctg agcaggctgt atctggattc tggcaataaa agtactctgg          2650

atgctgtaaa aaaaaaaaaa aaaaaaaaaa                                2680
```

<210> SEQ ID NO 14
<211> LENGTH: 412
<212> TYPE: PRT
<213> ORGANISM: Homo Sapien

<400> SEQUENCE: 14

```
Met Gly Leu His Leu Arg Pro Tyr Arg Val Gly Leu Leu Pro Asp
  1               5                  10                  15

Gly Leu Leu Phe Leu Leu Leu Leu Leu Met Leu Leu Ala Asp Pro
                 20                  25                  30

Ala Leu Pro Ala Gly Arg His Pro Pro Val Val Leu Val Pro Gly
                 35                  40                  45

Asp Leu Gly Asn Gln Leu Glu Ala Lys Leu Asp Lys Pro Thr Val
                 50                  55                  60

Val His Tyr Leu Cys Ser Lys Lys Thr Glu Ser Tyr Phe Thr Ile
                 65                  70                  75

Trp Leu Asn Leu Glu Leu Leu Leu Pro Val Ile Ile Asp Cys Trp
                 80                  85                  90

Ile Asp Asn Ile Arg Leu Val Tyr Asn Lys Thr Ser Arg Ala Thr
                 95                 100                 105

Gln Phe Pro Asp Gly Val Asp Val Arg Val Pro Gly Phe Gly Lys
                110                 115                 120

Thr Phe Ser Leu Glu Phe Leu Asp Pro Ser Lys Ser Ser Val Gly
                125                 130                 135

Ser Tyr Phe His Thr Met Val Glu Ser Leu Val Gly Trp Gly Tyr
                140                 145                 150
```

-continued

```
Thr Arg Gly Glu Asp Val Arg Gly Ala Pro Tyr Asp Trp Arg Arg
                155                 160                 165

Ala Pro Asn Glu Asn Gly Pro Tyr Phe Leu Ala Leu Arg Glu Met
                170                 175                 180

Ile Glu Glu Met Tyr Gln Leu Tyr Gly Gly Pro Val Val Leu Val
                185                 190                 195

Ala His Ser Met Gly Asn Met Tyr Thr Leu Tyr Phe Leu Gln Arg
                200                 205                 210

Gln Pro Gln Ala Trp Lys Asp Lys Tyr Ile Arg Ala Phe Val Ser
                215                 220                 225

Leu Gly Ala Pro Trp Gly Gly Val Ala Lys Thr Leu Arg Val Leu
                230                 235                 240

Ala Ser Gly Asp Asn Asn Arg Ile Pro Val Ile Gly Pro Leu Lys
                245                 250                 255

Ile Arg Glu Gln Gln Arg Ser Ala Val Ser Thr Ser Trp Leu Leu
                260                 265                 270

Pro Tyr Asn Tyr Thr Trp Ser Pro Glu Lys Val Phe Val Gln Thr
                275                 280                 285

Pro Thr Ile Asn Tyr Thr Leu Arg Asp Tyr Arg Lys Phe Phe Gln
                290                 295                 300

Asp Ile Gly Phe Glu Asp Gly Trp Leu Met Arg Gln Asp Thr Glu
                305                 310                 315

Gly Leu Val Glu Ala Thr Met Pro Pro Gly Val Gln Leu His Cys
                320                 325                 330

Leu Tyr Gly Thr Gly Val Pro Thr Pro Asp Ser Phe Tyr Tyr Glu
                335                 340                 345

Ser Phe Pro Asp Arg Asp Pro Lys Ile Cys Phe Gly Asp Gly Asp
                350                 355                 360

Gly Thr Val Asn Leu Lys Ser Ala Leu Gln Cys Gln Ala Trp Gln
                365                 370                 375

Ser Arg Gln Glu His Gln Val Leu Leu Gln Glu Leu Pro Gly Ser
                380                 385                 390

Glu His Ile Glu Met Leu Ala Asn Ala Thr Thr Leu Ala Tyr Leu
                395                 400                 405

Lys Arg Val Leu Leu Gly Pro
                410
```

<210> SEQ ID NO 15
<211> LENGTH: 1371
<212> TYPE: DNA
<213> ORGANISM: Homo Sapien

<400> SEQUENCE: 15

```
cagagcagat aatggcaagc atggctgccg tgctcacctg ggctctggct         50

cttctttcag cgttttcggc cacccaggca cggaaaggct tctgggacta        100

cttcagccag accagcgggg acaaaggcag ggtggagcag atccatcagc        150

agaagatggc tcgcgagccc gcgaccctga aagacagcct tgagcaagac        200

ctcaacaata tgaacaagtt cctggaaaag ctgaggcctc tgagtgggag        250

cgaggctcct cggctcccac aggacccggt gggcatgcgg cggcagctgc        300

aggaggagtt ggaggaggtg aaggctcgcc tccagcccta catggcagag        350

gcgcacgagc tggtgggctg gaatttggag ggcttgcggc agcaactgaa        400

gccctacacg atggatctga tggagcaggt ggccctgcgc gtgcaggagc        450
```

-continued

```
tgcaggagca gttgcgcgtg gtgggggaag acaccaaggc ccagttgctg     500
gggggcgtgg acgaggcttg ggctttgctg cagggactgc agagccgcgt     550
ggtgcaccac accggccgct tcaaagagct cttccaccca tacgccgaga     600
gcctggtgag cggcatcggg cgccacgtgc aggagctgca ccgcagtgtg     650
gctccgcacg cccccgccag ccccgcgcgc ctcagtcgct gcgtgcaggt     700
gctctcccgg aagctcacgc tcaaggccaa ggccctgcac gcacgcatcc     750
agcagaacct ggaccagctg cgcgaagagc tcagcagagc ctttgcaggc     800
actgggactg aggaaggggc cggcccggac ccctagatgc tctccgagga     850
ggtgcgccag cgacttcagg ctttccgcca ggacacctac ctgcagatag     900
ctgccttcac tcgcgccatc gaccaggaga ctgaggaggt ccagcagcag     950
ctggcgccac ctccaccagg ccacagtgcc ttcgccccag agtttcaaca    1000
aacagacagt ggcaaggttc tgagcaagct gcaggcccgt ctggatgacc    1050
tgtgggaaga catcactcac agccttcatg accagggcca cagccatctg    1100
ggggacccct gaggatctac ctgcccaggc ccattcccag cttcttgtct    1150
ggggagcctt ggctctgagc ctctagcatg gttcagtcct tgaaagtggc    1200
ctgttgggtg gagggtggaa ggtcctgtgc aggacaggga ggccaccaaa    1250
ggggctgctg tctcctgcat atccagcctc ctgcgactcc ccaatctgga    1300
tgcattacat tcaccaggct ttgcaaaaaa aaaaaaaaaa aaaaaaaaaa    1350
aaaaaaaaaa aaaaaaaaaa a                                   1371
```

<210> SEQ ID NO 16
<211> LENGTH: 274
<212> TYPE: PRT
<213> ORGANISM: Homo Sapien

<400> SEQUENCE: 16

```
Met Ala Ser Met Ala Ala Val Leu Thr Trp Ala Leu Ala Leu Leu
  1               5                  10                  15

Ser Ala Phe Ser Ala Thr Gln Ala Arg Lys Gly Phe Trp Asp Tyr
                 20                  25                  30

Phe Ser Gln Thr Ser Gly Asp Lys Gly Arg Val Glu Gln Ile His
                 35                  40                  45

Gln Gln Lys Met Ala Arg Glu Pro Ala Thr Leu Lys Asp Ser Leu
                 50                  55                  60

Glu Gln Asp Leu Asn Asn Met Asn Lys Phe Leu Glu Lys Leu Arg
                 65                  70                  75

Pro Leu Ser Gly Ser Glu Ala Pro Arg Leu Pro Gln Asp Pro Val
                 80                  85                  90

Gly Met Arg Arg Gln Leu Gln Glu Glu Leu Glu Glu Val Lys Ala
                 95                 100                 105

Arg Leu Gln Pro Tyr Met Ala Glu Ala His Glu Leu Val Gly Trp
                110                 115                 120

Asn Leu Glu Gly Leu Arg Gln Gln Leu Lys Pro Tyr Thr Met Asp
                125                 130                 135

Leu Met Glu Gln Val Ala Leu Arg Val Gln Glu Leu Gln Glu Gln
                140                 145                 150

Leu Arg Val Val Gly Glu Asp Thr Lys Ala Gln Leu Leu Gly Gly
                155                 160                 165
```

-continued

```
Val Asp Glu Ala Trp Ala Leu Leu Gln Gly Leu Gln Ser Arg Val
                170                 175                 180

Val His His Thr Gly Arg Phe Lys Glu Leu Phe His Pro Tyr Ala
                185                 190                 195

Glu Ser Leu Val Ser Gly Ile Gly Arg His Val Gln Glu Leu His
                200                 205                 210

Arg Ser Val Ala Pro His Ala Pro Ala Ser Pro Ala Arg Leu Ser
                215                 220                 225

Arg Cys Val Gln Val Leu Ser Arg Lys Leu Thr Leu Lys Ala Lys
                230                 235                 240

Ala Leu His Ala Arg Ile Gln Gln Asn Leu Asp Gln Leu Arg Glu
                245                 250                 255

Glu Leu Ser Arg Ala Phe Ala Gly Thr Gly Thr Glu Glu Gly Ala
                260                 265                 270

Gly Pro Asp Pro


<210> SEQ ID NO 17
<211> LENGTH: 2854
<212> TYPE: DNA
<213> ORGANISM: Homo Sapien

<400> SEQUENCE: 17

ctaagaggac aagatgaggc ccggcctctc atttctccta gcccttctgt          50

tcttccttgg ccaagctgca ggggatttgg gggatgtggg acctccaatt         100

cccagccccg gcttcagctc tttcccaggt gttgactcca gctccagctt         150

cagctccagc tccaggtcgg gctccagctc cagccgcagc ttaggcagcg         200

gaggttctgt gtcccagttg ttttccaatt tcaccggctc cgtggatgac         250

cgtgggacct gccagtgctc tgtttccctg ccagacacca cctttcccgt         300

ggacagagtg gaacgcttgg aattcacagc tcatgttctt tctcagaagt         350

ttgagaaaga actttctaaa gtgagggaat atgtccaatt aattagtgtg         400

tatgaaaaga aactgttaaa cctaactgtc cgaattgaca tcatggagaa         450

ggataccatt tcttacactg aactggactt cgagctgatc aaggtagaag         500

tgaaggagat ggaaaaactg gtcatacagc tgaaggagag ttttggtgga         550

agctcagaaa ttgttgacca gctggaggtg gagataagaa atatgactct         600

cttggtagag aagcttgaga cactagacaa aaacaatgtc cttgccattc         650

gccgagaaat cgtggctctg aagaccaagc tgaaagagtg tgaggcctct         700

aaagatcaaa acacccctgt cgtccaccct cctcccactc cagggagctg         750

tggtcatggt ggtgtggtga acatcagcaa accgtctgtg gttcagctca         800

actggagagg gttttcttat ctatatggtg cttggggtag ggattactct         850

ccccagcatc caaacaaagg actgtattgg gtggcgccat tgaatacaga         900

tgggagactg ttggagtatt atagactgta caacacactg gatgatttgc         950

tattgtatat aaatgctcga gagttgcgga tcacctatgg ccaaggtagt        1000

ggtacagcag tttacaacaa caacatgtac gtcaacatgt acaacaccgg        1050

gaatattgcc agagttaacc tgaccaccaa cacgattgct gtgactcaaa        1100

ctctccctaa tgctgcctat aataaccgct tttcatatgc taatgttgct        1150

tggcaagata ttgactttgc tgtggatgag aatggattgt gggttattta        1200
```

-continued

```
ttcaactgaa gccagcactg gtaacatggt gattagtaaa ctcaatgaca        1250

ccacacttca ggtgctaaac acttggtata ccaagcagta taaaccatct        1300

gcttctaacg ccttcatggt atgtggggtt ctgtatgcca cccgtactat        1350

gaacaccaga acagaagaga ttttttacta ttatgacaca aacacaggga        1400

aagagggcaa actagacatt gtaatgcata agatgcagga aaaagtgcag        1450

agcattaact ataacccttt tgaccagaaa ctttatgtct ataacgatgg        1500

ttaccttctg aattatgatc tttctgtctt gcagaagccc cagtaagctg        1550

tttaggagtt agggtgaaag agaaaatgtt tgttgaaaaa atagtcttct        1600

ccacttactt agatatctgc aggggtgtct aaaagtgtgt tcattttgca        1650

gcaatgttta ggtgcatagt tctaccacac tagagatcta ggacatttgt        1700

cttgatttgg tgagttctct tgggaatcat ctgcctcttc aggcgcattt        1750

tgcaataaag tctgtctagg gtgggattgt cagaggtcta ggggcactgt        1800

gggcctagtg aagcctactg tgaggaggct tcactagaag ccttaaatta        1850

ggaattaagg aacttaaaac tcagtatggc gtctagggat tctttgtaca        1900

ggaaatattg cccaatgact agtcctcatc catgtagcac cactaattct        1950

tccatgcctg gaagaaacct ggggacttag ttaggtagat taatatctgg        2000

agctcctcga gggaccaaat ctccaacttt tttttcccct cactagcacc        2050

tggaatgatg ctttgtatgt ggcagataag taaatttggc atgcttatat        2100

attctacatc tgtaaagtgc tgagttttat ggagagaggc ctttttatgc        2150

attaaattgt acatggcaaa taaatcccag aaggatctgt agatgaggca        2200

cctgcttttt cttttctctc attgtccacc ttactaaaag tcagtagaat        2250

cttctacctc ataacttcct tccaaaggca gctcagaaga ttagaaccag        2300

acttactaac caattccacc ccccaccaac cccc ttctac tgcctacttt        2350

aaaaaaatta atagttttct atggaactga tctaagatta gaaaaattaa        2400

ttttctttaa tttcattatg gacttttatt tacatgactc taagactata        2450

agaaaatctg atggcagtga caaagtgcta gcatttattg ttatctaata        2500

aagaccttgg agcatatgtg caacttatga gtgtatcagt tgttgcatgt        2550

aatttttgcc tttgtttaag cctggaactt gtaagaaaat gaaaatttaa        2600

tttttttttc taggacgagc tatagaaaag ctattgagag tatctagtta        2650

atcagtgcag tagttggaaa ccttgctggt gtatgtgatg tgcttctgtg        2700

cttttgaatg actttatcat ctagtctttg tctatttttc ctttgatgtt        2750

caagtcctag tctataggat tggcagttta aatgctttac tccccctttt        2800

aaaataaatg attaaaatgt gctttgaaaa aaaaaaaaaa aaaaaaaaaa        2850

aaaa                                                          2854
```

<210> SEQ ID NO 18
<211> LENGTH: 510
<212> TYPE: PRT
<213> ORGANISM: Homo Sapien

<400> SEQUENCE: 18

```
Met Arg Pro Gly Leu Ser Phe Leu Leu Ala Leu Leu Phe Phe Leu
  1               5                  10                  15
```

-continued

```
Gly Gln Ala Ala Gly Asp Leu Gly Asp Val Gly Pro Pro Ile Pro
                20                  25                  30

Ser Pro Gly Phe Ser Ser Phe Pro Gly Val Asp Ser Ser Ser Ser
                35                  40                  45

Phe Ser Ser Ser Ser Arg Ser Gly Ser Ser Ser Ser Arg Ser Leu
                50                  55                  60

Gly Ser Gly Gly Ser Val Ser Gln Leu Phe Ser Asn Phe Thr Gly
                65                  70                  75

Ser Val Asp Asp Arg Gly Thr Cys Gln Cys Ser Val Ser Leu Pro
                80                  85                  90

Asp Thr Thr Phe Pro Val Asp Arg Val Glu Arg Leu Glu Phe Thr
                95                 100                 105

Ala His Val Leu Ser Gln Lys Phe Glu Lys Glu Leu Ser Lys Val
               110                 115                 120

Arg Glu Tyr Val Gln Leu Ile Ser Val Tyr Glu Lys Lys Leu Leu
               125                 130                 135

Asn Leu Thr Val Arg Ile Asp Ile Met Glu Lys Asp Thr Ile Ser
               140                 145                 150

Tyr Thr Glu Leu Asp Phe Glu Leu Ile Lys Val Glu Val Lys Glu
               155                 160                 165

Met Glu Lys Leu Val Ile Gln Leu Lys Glu Ser Phe Gly Gly Ser
               170                 175                 180

Ser Glu Ile Val Asp Gln Leu Glu Val Glu Ile Arg Asn Met Thr
               185                 190                 195

Leu Leu Val Glu Lys Leu Glu Thr Leu Asp Lys Asn Asn Val Leu
               200                 205                 210

Ala Ile Arg Arg Glu Ile Val Ala Leu Lys Thr Lys Leu Lys Glu
               215                 220                 225

Cys Glu Ala Ser Lys Asp Gln Asn Thr Pro Val Val His Pro Pro
               230                 235                 240

Pro Thr Pro Gly Ser Cys Gly His Gly Gly Val Val Asn Ile Ser
               245                 250                 255

Lys Pro Ser Val Val Gln Leu Asn Trp Arg Gly Phe Ser Tyr Leu
               260                 265                 270

Tyr Gly Ala Trp Gly Arg Asp Tyr Ser Pro Gln His Pro Asn Lys
               275                 280                 285

Gly Leu Tyr Trp Val Ala Pro Leu Asn Thr Asp Gly Arg Leu Leu
               290                 295                 300

Glu Tyr Tyr Arg Leu Tyr Asn Thr Leu Asp Asp Leu Leu Leu Tyr
               305                 310                 315

Ile Asn Ala Arg Glu Leu Arg Ile Thr Tyr Gly Gln Gly Ser Gly
               320                 325                 330

Thr Ala Val Tyr Asn Asn Asn Met Tyr Val Asn Met Tyr Asn Thr
               335                 340                 345

Gly Asn Ile Ala Arg Val Asn Leu Thr Thr Asn Thr Ile Ala Val
               350                 355                 360

Thr Gln Thr Leu Pro Asn Ala Ala Tyr Asn Asn Arg Phe Ser Tyr
               365                 370                 375

Ala Asn Val Ala Trp Gln Asp Ile Asp Phe Ala Val Asp Glu Asn
               380                 385                 390

Gly Leu Trp Val Ile Tyr Ser Thr Glu Ala Ser Thr Gly Asn Met
               395                 400                 405
```

-continued

```
Val Ile Ser Lys Leu Asn Asp Thr Thr Leu Gln Val Leu Asn Thr
                410                 415                 420

Trp Tyr Thr Lys Gln Tyr Lys Pro Ser Ala Ser Asn Ala Phe Met
                425                 430                 435

Val Cys Gly Val Leu Tyr Ala Thr Arg Thr Met Asn Thr Arg Thr
                440                 445                 450

Glu Glu Ile Phe Tyr Tyr Tyr Asp Thr Asn Thr Gly Lys Glu Gly
                455                 460                 465

Lys Leu Asp Ile Val Met His Lys Met Gln Glu Lys Val Gln Ser
                470                 475                 480

Ile Asn Tyr Asn Pro Phe Asp Gln Lys Leu Tyr Val Tyr Asn Asp
                485                 490                 495

Gly Tyr Leu Leu Asn Tyr Asp Leu Ser Val Leu Gln Lys Pro Gln
                500                 505                 510
```

<210> SEQ ID NO 19
<211> LENGTH: 663
<212> TYPE: DNA
<213> ORGANISM: Homo Sapien

<400> SEQUENCE: 19

```
gcaccgcaga cggcgcggat cgcagggagc cggtccgccg ccggaacggg              50

agcctgggtg tgcgtgtgga gtccggactc gtgggagacg atcgcgatga             100

acacggtgct gtcgcgggcg aactcactgt tcgccttctc gctgagcgtg             150

atggcggcgc tcaccttcgg ctgcttcatc accaccgcct tcaaagacag             200

gagcgtcccg gtgcggctgc acgtctcgcg gatcatgcta aaaaatgtag             250

aagatttcac tggacctaga gaaagaagtg atctgggatt tatcacattt             300

gatataactg ctgatctaga gaatatattt gattggaatg ttaagcagtt             350

gtttctttat ttatcagcag aatattcaac aaaaaataat gctctgaacc             400

aagttgtcct atgggacaag attgttttga gaggtgataa tccgaagctg             450

ctgctgaaag atatgaaaac aaaatatttt ttctttgacg atggaaatgg             500

tctcaaggga aacaggaatg tcactttgac cctgtcttgg aacgtcgtac             550

caaatgctgg aattctacct cttgtgacag gatcaggaca cgtatctgtc             600

ccatttccag atacatatga aataacgaag agttattaaa ttattctgaa             650

tttgaaacaa aaa                                                     663
```

<210> SEQ ID NO 20
<211> LENGTH: 180
<212> TYPE: PRT
<213> ORGANISM: Homo Sapien

<400> SEQUENCE: 20

```
Met Asn Thr Val Leu Ser Arg Ala Asn Ser Leu Phe Ala Phe Ser
  1               5                  10                  15

Leu Ser Val Met Ala Ala Leu Thr Phe Gly Cys Phe Ile Thr Thr
                 20                  25                  30

Ala Phe Lys Asp Arg Ser Val Pro Val Arg Leu His Val Ser Arg
                 35                  40                  45

Ile Met Leu Lys Asn Val Glu Asp Phe Thr Gly Pro Arg Glu Arg
                 50                  55                  60

Ser Asp Leu Gly Phe Ile Thr Phe Asp Ile Thr Ala Asp Leu Glu
                 65                  70                  75
```

-continued

```
Asn Ile Phe Asp Trp Asn Val Lys Gln Leu Phe Leu Tyr Leu Ser
                80                  85                  90

Ala Glu Tyr Ser Thr Lys Asn Asn Ala Leu Asn Gln Val Val Leu
                95                  100                 105

Trp Asp Lys Ile Val Leu Arg Gly Asp Asn Pro Lys Leu Leu Leu
                110                 115                 120

Lys Asp Met Lys Thr Lys Tyr Phe Phe Phe Asp Asp Gly Asn Gly
                125                 130                 135

Leu Lys Gly Asn Arg Asn Val Thr Leu Thr Leu Ser Trp Asn Val
                140                 145                 150

Val Pro Asn Ala Gly Ile Leu Pro Leu Val Thr Gly Ser Gly His
                155                 160                 165

Val Ser Val Pro Phe Pro Asp Thr Tyr Glu Ile Thr Lys Ser Tyr
                170                 175                 180


<210> SEQ ID NO 21
<211> LENGTH: 415
<212> TYPE: DNA
<213> ORGANISM: Homo Sapien

<400> SEQUENCE: 21

aaacttgacg ccatgaagat cccggtcctt cctgccgtgg tgctcctctc             50

cctcctggtg ctccactctg cccagggagc caccctgggt ggtcctgagg            100

aagaaagcac cattgagaat tatgcgtcac gacccgaggc ctttaacacc            150

ccgttcctga acatcgacaa attgcgatct gcgtttaagg ctgatgagtt            200

cctgaactgg cacgccctct ttgagtctat caaaaggaaa cttcctttcc            250

tcaactggga tgcctttcct aagctgaaag gactgaggag cgcaactcct            300

gatgcccagt gaccatgacc tccactggaa gagggggcta gcgtgagcgc            350

tgattctcaa cctaccataa ctctttcctg cctcaggaac tccaataaaa            400

cattttccat ccaaa                                                  415


<210> SEQ ID NO 22
<211> LENGTH: 99
<212> TYPE: PRT
<213> ORGANISM: Homo Sapien

<400> SEQUENCE: 22

Met Lys Ile Pro Val Leu Pro Ala Val Val Leu Leu Ser Leu Leu
  1               5                  10                  15

Val Leu His Ser Ala Gln Gly Ala Thr Leu Gly Gly Pro Glu Glu
                20                  25                  30

Glu Ser Thr Ile Glu Asn Tyr Ala Ser Arg Pro Glu Ala Phe Asn
                35                  40                  45

Thr Pro Phe Leu Asn Ile Asp Lys Leu Arg Ser Ala Phe Lys Ala
                50                  55                  60

Asp Glu Phe Leu Asn Trp His Ala Leu Phe Glu Ser Ile Lys Arg
                65                  70                  75

Lys Leu Pro Phe Leu Asn Trp Asp Ala Phe Pro Lys Leu Lys Gly
                80                  85                  90

Leu Arg Ser Ala Thr Pro Asp Ala Gln
                95


<210> SEQ ID NO 23
```

-continued

<211> LENGTH: 866
<212> TYPE: DNA
<213> ORGANISM: Homo Sapien

<400> SEQUENCE: 23
tctcagactc ttggaagggg ctatactaga cacacaaaga cagccccaag 50
aaggacggtg gagtagtgtc ctcgctaaaa gacagtagat atgcaacgcc 100
tcttgctcct gccctttctc ctgctgggaa cagtttctgc tcttcatctg 150
gagaatgatg ccccccatct ggagagccta gagacacagg cagacctagg 200
ccaggatctg gatagttcaa aggagcagga gagagacttg gctctgacgg 250
aggaggtgat tcaggcagag ggagaggagg tcaaggcttc tgcctgtcaa 300
gacaactttg aggatgagga agccatggag tcggacccag ctgccttaga 350
caaggacttc cagtgcccca gggaagaaga cattgttgaa gtgcagggaa 400
gtccaaggtg caagacctgc cgctacctat tggtgcggac tcctaaaact 450
tttgcagaag ctcagaatgt ctgcagcaga tgctacggag gcaaccttgt 500
ctctatccat gacttcaact tcaactatcg cattcagtgc tgcactagca 550
cagtcaacca agcccaggtc tggattggag gcaacctcag ggctggttc 600 ctgtggaagc ggttttgctg gactgatggg agccactgga attttgctta 650
ctggtcccca gggcaacctg ggaatgggca aggctcctgt gtggccctat 700
gcaccaaagg aggttattgg cgacgagctc aatgcgacaa gcaactgccc 750
ttcgtctgct ccttctaagc cagcggcacg gagaccctgc cagcagctcc 800
ctcccgtccc ccaacctctc ctgctcataa atccagactt cccacagcaa 850
aaaaaaaaaa aaaaaa 866

<210> SEQ ID NO 24
<211> LENGTH: 225
<212> TYPE: PRT
<213> ORGANISM: Homo Sapien

<400> SEQUENCE: 24

Met Gln Arg Leu Leu Leu Leu Pro Phe Leu Leu Leu Gly Thr Val
1 5 10 15

Ser Ala Leu His Leu Glu Asn Asp Ala Pro His Leu Glu Ser Leu
20 25 30

Glu Thr Gln Ala Asp Leu Gly Gln Asp Leu Asp Ser Ser Lys Glu
35 40 45

Gln Glu Arg Asp Leu Ala Leu Thr Glu Glu Val Ile Gln Ala Glu
50 55 60

Gly Glu Glu Val Lys Ala Ser Ala Cys Gln Asp Asn Phe Glu Asp
65 70 75

Glu Glu Ala Met Glu Ser Asp Pro Ala Ala Leu Asp Lys Asp Phe
80 85 90

Gln Cys Pro Arg Glu Glu Asp Ile Val Glu Val Gln Gly Ser Pro
95 100 105

Arg Cys Lys Thr Cys Arg Tyr Leu Leu Val Arg Thr Pro Lys Thr
110 115 120

Phe Ala Glu Ala Gln Asn Val Cys Ser Arg Cys Tyr Gly Gly Asn
125 130 135

Leu Val Ser Ile His Asp Phe Asn Phe Asn Tyr Arg Ile Gln Cys
140 145 150

-continued

```
Cys Thr Ser Thr Val Asn Gln Ala Gln Val Trp Ile Gly Gly Asn
                155                 160                 165

Leu Arg Gly Trp Phe Leu Trp Lys Arg Phe Cys Trp Thr Asp Gly
                170                 175                 180

Ser His Trp Asn Phe Ala Tyr Trp Ser Pro Gly Gln Pro Gly Asn
                185                 190                 195

Gly Gln Gly Ser Cys Val Ala Leu Cys Thr Lys Gly Gly Tyr Trp
                200                 205                 210

Arg Arg Ala Gln Cys Asp Lys Gln Leu Pro Phe Val Cys Ser Phe
                215                 220                 225


<210> SEQ ID NO 25
<211> LENGTH: 584
<212> TYPE: DNA
<213> ORGANISM: Homo Sapien

<400> SEQUENCE: 25

caacagaagc caagaaggaa gccgtctatc ttgtggcgat catgtataag                50

ctggcctcct gctgtttgct tttcacagga ttcttaaatc ctctcttatc               100

tcttcctctc cttgactcca gggaaatatc ctttcaactc tcagcacctc               150

atgaagacgc gcgcttaact ccggaggagc tagaaagagc ttcccttcta               200

cagatattgc cagagatgct gggtgcagaa agaggggata ttctcaggaa               250

agcagactca agtaccaaca tttttaaccc aagaggaaat ttgagaaagt               300

ttcaggattt ctctggacaa gatcctaaca ttttactgag tcatcttttg               350

gccagaatct ggaaaccata caagaaacgt gagactcctg attgcttctg               400

gaaatactgt gtctgaagtg aaataagcat ctgttagtca gctcagaaac               450

acccatctta gaatatgaaa aataacacaa tgcttgattt gaaaacagtg               500

tggagaaaaa ctaggcaaac tacaccctgt tcattgttac ctggaaaata               550

aatcctctat gttttgcaca aaaaaaaaaa aaaa                                584


<210> SEQ ID NO 26
<211> LENGTH: 124
<212> TYPE: PRT
<213> ORGANISM: Homo Sapien

<400> SEQUENCE: 26

Met Tyr Lys Leu Ala Ser Cys Cys Leu Leu Phe Thr Gly Phe Leu
  1               5                  10                  15

Asn Pro Leu Leu Ser Leu Pro Leu Leu Asp Ser Arg Glu Ile Ser
                 20                  25                  30

Phe Gln Leu Ser Ala Pro His Glu Asp Ala Arg Leu Thr Pro Glu
                 35                  40                  45

Glu Leu Glu Arg Ala Ser Leu Leu Gln Ile Leu Pro Glu Met Leu
                 50                  55                  60

Gly Ala Glu Arg Gly Asp Ile Leu Arg Lys Ala Asp Ser Ser Thr
                 65                  70                  75

Asn Ile Phe Asn Pro Arg Gly Asn Leu Arg Lys Phe Gln Asp Phe
                 80                  85                  90

Ser Gly Gln Asp Pro Asn Ile Leu Leu Ser His Leu Leu Ala Arg
                 95                 100                 105

Ile Trp Lys Pro Tyr Lys Lys Arg Glu Thr Pro Asp Cys Phe Trp
                110                 115                 120
```

-continued

Lys Tyr Cys Val

<210> SEQ ID NO 27
<211> LENGTH: 920
<212> TYPE: DNA
<213> ORGANISM: Homo Sapien

<400> SEQUENCE: 27
caagtaaatg cagcactagt gggtgggatt gaggtatgcc ctggtgcata 50
aatagagact cagctgtgct ggcacactca gaagcttgga ccgcatccta 100
gccgccgact cacacaaggc aggtgggtga ggaaatccag agttgccatg 150
gagaaaattc cagtgtcagc attcttgctc cttgtggccc tctcctacac 200
tctggccaga gataccacag tcaaacctgg agccaaaaag gacacaaagg 250
actctcgacc caaactgccc cagaccctct ccagaggttg gggtgaccaa 300
ctcatctgga ctcagacata tgaagaagct ctatataaat ccaagacaag 350
caacaaaccc ttgatgatta ttcatcactt ggatgagtgc ccacacagtc 400
aagctttaaa gaaagtgttt gctgaaaata aagaaatcca gaaattggca 450
gagcagtttg tcctcctcaa tctggtttat gaaacaactg acaaacacct 500
ttctcctgat ggccagtatg tccccaggat tatgtttgtt gacccatctc 550
tgacagttag agccgatatc actggaagat attcaaatcg tctctatgct 600
tacgaacctg cagatacagc tctgttgctt gacaacatga agaaagctct 650
caagttgctg aagactgaat tgtaaagaaa aaaaatctcc aagcccttct 700
gtctgtcagg ccttgagact tgaaaccaga agaagtgtga gaagactggc 750
tagtgtggaa gcatagtgaa cacactgatt aggttatggt ttaatgttac 800
aacaactatt ttttaagaaa aacaagtttt agaaatttgg tttcaagtgt 850
acatgtgtga aaacaatatt gtatactacc atagtgagcc atgattttct 900
aaaaaaaaaa ataaatgtta 920

<210> SEQ ID NO 28
<211> LENGTH: 175
<212> TYPE: PRT
<213> ORGANISM: Homo Sapien

<400> SEQUENCE: 28

Met Glu Lys Ile Pro Val Ser Ala Phe Leu Leu Leu Val Ala Leu
1 5 10 15

Ser Tyr Thr Leu Ala Arg Asp Thr Thr Val Lys Pro Gly Ala Lys
20 25 30

Lys Asp Thr Lys Asp Ser Arg Pro Lys Leu Pro Gln Thr Leu Ser
35 40 45

Arg Gly Trp Gly Asp Gln Leu Ile Trp Thr Gln Thr Tyr Glu Glu
50 55 60

Ala Leu Tyr Lys Ser Lys Thr Ser Asn Lys Pro Leu Met Ile Ile
65 70 75

His His Leu Asp Glu Cys Pro His Ser Gln Ala Leu Lys Lys Val
80 85 90

Phe Ala Glu Asn Lys Glu Ile Gln Lys Leu Ala Glu Gln Phe Val
95 100 105

Leu Leu Asn Leu Val Tyr Glu Thr Thr Asp Lys His Leu Ser Pro

-continued

```
                110                 115                 120

Asp Gly Gln Tyr Val Pro Arg Ile Met Phe Val Asp Pro Ser Leu
                125                 130                 135

Thr Val Arg Ala Asp Ile Thr Gly Arg Tyr Ser Asn Arg Leu Tyr
                140                 145                 150

Ala Tyr Glu Pro Ala Asp Thr Ala Leu Leu Leu Asp Asn Met Lys
                155                 160                 165

Lys Ala Leu Lys Leu Leu Lys Thr Glu Leu
                170                 175
```

<210> SEQ ID NO 29
<211> LENGTH: 1181
<212> TYPE: DNA
<213> ORGANISM: Homo Sapien

<400> SEQUENCE: 29

```
aagaccctct ctttcgctgt ttgagagtct ctcggctcaa ggaccgggag            50

gtaagaggtt tgggactgcc ccggcaactc cagggtgtct ggtccacgac           100

ctatcctagg cgccatgggt gtgataggta tacagctggt tgttaccatg           150

gtgatggcca gtgtcatgca gaagattata cctcactatt ctcttgctcg           200

atggctactc tgtaatggca gtttgaggtg gtatcaacat cctacagaag           250

aagaattaag aattcttgca gggaaacaac aaaaagggaa aaccaaaaaa           300

gataggaaat ataatggtca cattgaaagt aagccattaa ccattccaaa           350

ggatattgac cttcatctag aaacaaagtc agttacagaa gtggatactt           400

tagcattgca ttactttcca gaataccagt ggctggtgga tttcacagtg           450

gctgctacag ttgtgtatct agtaactgaa gtctactaca attttatgaa           500

gcctacacag gaaatgaata tcagcttagt ctggtgccta cttgttttgt           550

cttttgcaat caaagttcta ttttcattaa ctacacacta ttttaaagta           600

gaagatggtg gtgaaagatc tgtttgtgtc acctttggat tttttttctt           650

tgtcaaagca atggcagtgt tgattgtaac agaaaattat ctggaatttg           700

gacttgaaac agggtttaca aatttttcag acagtgcgat gcagtttctt           750

gaaaagcaag gtttagaatc tcagagtcct gtttcaaaac ttactttcaa           800

atttttcctg gctattttct gttcattcat tggggctttt ttgacatttc           850

ctggattacg actggctcaa atgcatctgg atgccctgaa tttggcaaca           900

gaaaaaatta cacaaacttt acttcatatc aacttcttgg cacctttatt           950

tatggttttg ctctgggtaa aaccaatcac caaagactac attatgaacc          1000

caccactggg caaagaaatt tccccatctg gaagatgaag ataatagtat          1050

ctaactcaca aggttatcat tggaataaat gaaagaacac atgtaatgca          1100

accagctgga attaagtgct taataaatgt tcttttcact gctttgcctc          1150

atcagaatta aaatagaaat acttgactag t                              1181
```

<210> SEQ ID NO 30
<211> LENGTH: 307
<212> TYPE: PRT
<213> ORGANISM: Homo Sapien

<400> SEQUENCE: 30

```
Met Gly Val Ile Gly Ile Gln Leu Val Val Thr Met Val Met Ala
```

-continued

```
1               5                   10                  15

Ser Val Met Gln Lys Ile Ile Pro His Tyr Ser Leu Ala Arg Trp
                20                  25                  30

Leu Leu Cys Asn Gly Ser Leu Arg Trp Tyr Gln His Pro Thr Glu
                35                  40                  45

Glu Glu Leu Arg Ile Leu Ala Gly Lys Gln Gln Lys Gly Lys Thr
                50                  55                  60

Lys Lys Asp Arg Lys Tyr Asn Gly His Ile Glu Ser Lys Pro Leu
                65                  70                  75

Thr Ile Pro Lys Asp Ile Asp Leu His Leu Glu Thr Lys Ser Val
                80                  85                  90

Thr Glu Val Asp Thr Leu Ala Leu His Tyr Phe Pro Glu Tyr Gln
                95                  100                 105

Trp Leu Val Asp Phe Thr Val Ala Ala Thr Val Val Tyr Leu Val
                110                 115                 120

Thr Glu Val Tyr Tyr Asn Phe Met Lys Pro Thr Gln Glu Met Asn
                125                 130                 135

Ile Ser Leu Val Trp Cys Leu Leu Val Leu Ser Phe Ala Ile Lys
                140                 145                 150

Val Leu Phe Ser Leu Thr Thr His Tyr Phe Lys Val Glu Asp Gly
                155                 160                 165

Gly Glu Arg Ser Val Cys Val Thr Phe Gly Phe Phe Phe Phe Val
                170                 175                 180

Lys Ala Met Ala Val Leu Ile Val Thr Glu Asn Tyr Leu Glu Phe
                185                 190                 195

Gly Leu Glu Thr Gly Phe Thr Asn Phe Ser Asp Ser Ala Met Gln
                200                 205                 210

Phe Leu Glu Lys Gln Gly Leu Glu Ser Gln Ser Pro Val Ser Lys
                215                 220                 225

Leu Thr Phe Lys Phe Phe Leu Ala Ile Phe Cys Ser Phe Ile Gly
                230                 235                 240

Ala Phe Leu Thr Phe Pro Gly Leu Arg Leu Ala Gln Met His Leu
                245                 250                 255

Asp Ala Leu Asn Leu Ala Thr Glu Lys Ile Thr Gln Thr Leu Leu
                260                 265                 270

His Ile Asn Phe Leu Ala Pro Leu Phe Met Val Leu Leu Trp Val
                275                 280                 285

Lys Pro Ile Thr Lys Asp Tyr Ile Met Asn Pro Pro Leu Gly Lys
                290                 295                 300

Glu Ile Ser Pro Ser Gly Arg
                305
```

<210> SEQ ID NO 31
<211> LENGTH: 513
<212> TYPE: DNA
<213> ORGANISM: Homo Sapien

<400> SEQUENCE: 31

```
gtagcatagt gtgcagttca ctggaccaaa agctttggct gcacctcttc          50

tggaaagctg gccatggggc tcttcatgat cattgcaatt ctgctgttcc         100

agaaacccac agtaaccgaa caacttaaga agtgctggaa taactatgta         150

caaggacatt gcaggaaaat ctgcagagta aatgaagtgc ctgaggcact         200

atgtgaaaat gggagatact gttgcctcaa tatcaaggaa ctggaagcat         250
```

-continued

```
gtaaaaaaat tacaaagcca cctcgtccaa agccagcaac acttgcactg     300

actcttcaag actatgttac aataatagaa aatttcccaa gcctgaagac     350

acagtctaca taaatcaaat acaatttcgt tttcacttgc ttctcaacct     400

agtctaataa actaaggtga tgagatatac atcttcttcc ttctggtttc     450

ttgatcctta aaatgacctt cgagcatatt ctaataaagt gcattgccag     500

ttaaaaaaaa aaa                                             513
```

<210> SEQ ID NO 32
<211> LENGTH: 99
<212> TYPE: PRT
<213> ORGANISM: Homo Sapien

<400> SEQUENCE: 32

```
Met Gly Leu Phe Met Ile Ile Ala Ile Leu Leu Phe Gln Lys Pro
  1               5                  10                  15

Thr Val Thr Glu Gln Leu Lys Lys Cys Trp Asn Asn Tyr Val Gln
                 20                  25                  30

Gly His Cys Arg Lys Ile Cys Arg Val Asn Glu Val Pro Glu Ala
                 35                  40                  45

Leu Cys Glu Asn Gly Arg Tyr Cys Cys Leu Asn Ile Lys Glu Leu
                 50                  55                  60

Glu Ala Cys Lys Lys Ile Thr Lys Pro Pro Arg Pro Lys Pro Ala
                 65                  70                  75

Thr Leu Ala Leu Thr Leu Gln Asp Tyr Val Thr Ile Ile Glu Asn
                 80                  85                  90

Phe Pro Ser Leu Lys Thr Gln Ser Thr
                 95
```

<210> SEQ ID NO 33
<211> LENGTH: 2684
<212> TYPE: DNA
<213> ORGANISM: Homo Sapien
<220> FEATURE:
<221> NAME/KEY: unsure
<222> LOCATION: 2636-2637
<223> OTHER INFORMATION: unknown base

<400> SEQUENCE: 33

```
cggacgcgtg ggcgctgagc cccggaggcc agggcgtccg gggctgcgcc      50

acttccgagg gccgagcgct gccggtcccg gcggtgcgac acggccggga     100

ggaggagaac aacgcaaggg gctcaaccgt cggtcgctgg agcccccccc     150

ggggcgtggc ctcccgcccc ctcagctggg gagggcgggg ctcgctgccc     200

cctgctgccg actgcgaccc ttacagggga gggagggcgc aggccgcgcg     250

gagatgagga ggaggctgcg cctacgcagg gacgcattgc tcacgctgct     300

ccttggcgcc tccctgggcc tcttactcta tgcgcagcgc gacggcgcgg     350

ccccgacggc gagcgcgccg cgagggcgag ggagggcggc accgaggccc     400

acccccggac cccgcgcgtt ccagttaccc gacgcgggtg cagccccgcc     450

ggcctacgaa ggggacacac cggcgccgcc cacgcctacg ggaccctttg     500

acttcgcccg ctatttgcgc gccaaggacc agcggcggtt tccactgctc     550

attaaccagc cgcacaagtg ccgcggcgac ggcgcacccg gtggccgccc     600

ggacctgctt attgctgtca agtcggtggc agaggacttc gagcggcgcc     650
```

-continued

```
aagccgtgcg ccagacgtgg ggcgcggagg gtcgcgtgca gggggcgctg        700
gtgcgccgcg tgttcttgct gggcgtgccc aggggcgcag gctcgggcgg        750
ggccgacgaa gttggggagg gcgcgcgaac ccactggcgc gccctgctgc        800
gggccgagag ccttgcgtat gcggacatcc tgctctgggc cttcgacgac        850
acctttttta acctaacgct caaggagatc cactttctag cctgggcctc        900
agctttctgc cccgacgtgc gcttcgtttt taagggcgac gcagatgtgt        950
tcgtgaacgt gggaaatctc ctggagttcc tggcgccgcg ggacccggcg       1000
caagacctgc ttgctggtga cgtaattgtg catgcgcggc ccatccgcac       1050
gcgggctagc aagtactaca tccccgaggc cgtgtacggc ctgcccgcct       1100
atccggccta cgcgggcggc ggtggctttg tgctttccgg ggccacgctg       1150
caccgcctgg ctggcgcctg tgcgcaggtc gagctcttcc ccatcgacga       1200
cgtctttctg ggcatgtgtc tgcagcgcct gcggctcacg cccgagcctc       1250
accctgcctt ccgcaccttt ggcatccccc agccttcagc cgcgccgcat       1300
ttgagcacct tcgacccctg cttttaccgt gagctggttg tagtgcacgg       1350
gctctcggcc gctgacatct ggcttatgtg gcgcctgctg cacgggccgc       1400
atgggccagc ctgtgcgcat ccacagcctg tcgctgcagg ccccttccaa       1450
tgggactcct agctccccac tacagcccca agctcctaac tcagacccag       1500
aatggagccg gtttcccaga ttattgccgt gtatgtggtt cttccctgat       1550
caccaggtgc ctgtctccac aggatcccag gggatggggg ttaagcttgg       1600
ctcctggcgg tccaccctgc tggaaccagt tgaaacccgt gtaatggtga       1650
ccctttgagc gagccaaggc tgggtggtag atgaccatct cttgtccaac       1700
aggtcccaga gcagtggata tgtctggtcc tcctagtagc acagaggtgt       1750
gttctggtgt ggtggcaggg acttagggaa tcctaccact ctgctggatt       1800
tggaaccccc taggctgacg cggacgtatg cagaggctct caaggccagg       1850
ccccacaggg aggtggaggg gctccggccg ccacagcctg aattcatgaa       1900
cctggcaggc actttgccat agctcatctg aaaacagata ttatgcttcc       1950
cacaacctct cctgggccca ggtgtggctg agcaccaggg atggagccac       2000
acataaggga caaatgagtg cacggtccta cctagtcttt cctcacctcc       2050
tgaactcaca caacaatgcc agtctcccac tggaggctgt atcccctcag       2100
aggagccaag gaatgtcttc ccctgagatg ccaccactat taatttcccc       2150
atatgcttca accacccct tgctcaaaaa accaataccc acacttacct       2200
taatacaaac atcccagcaa cagcacatgg caggccattg ctgagggcac       2250
aggtgcttta ttggagaggg gatgtgggca ggggataagg aaggttcccc       2300
cattccagga ggatgggaac agtcctggct gcccctgaca gtggggatat       2350
gcaaggggct ctggccaggc cacagtccaa atgggaagac accagtcagt       2400
cacaaaagtc gggagcgcca cacaaacctg gctataaggc ccaggaacca       2450
tataggagcc tgagacaggt cccctgcaca ttcatcatta aactatacag       2500
gatgaggctg tacatgagtt aattacaaaa gagtcatatt tacaaaaatc       2550
tgtacacaca tttgaaaaac tcacaaaatt gtcatctatg tatcacaagt       2600
```

-continued

```
tgctagaccc aaaatattaa aaatgggata aaattnnttt aaaaaaaaaa           2650

aaaaaaaaaa aaaaaaaaaa aaaaaaaaaa aaaa                            2684


<210> SEQ ID NO 34
<211> LENGTH: 402
<212> TYPE: PRT
<213> ORGANISM: Homo Sapien

<400> SEQUENCE: 34

Met Arg Arg Arg Leu Arg Leu Arg Arg Asp Ala Leu Leu Thr Leu
  1               5                  10                  15

Leu Leu Gly Ala Ser Leu Gly Leu Leu Leu Tyr Ala Gln Arg Asp
                 20                  25                  30

Gly Ala Ala Pro Thr Ala Ser Ala Pro Arg Gly Arg Gly Arg Ala
                 35                  40                  45

Ala Pro Arg Pro Thr Pro Gly Pro Arg Ala Phe Gln Leu Pro Asp
                 50                  55                  60

Ala Gly Ala Ala Pro Pro Ala Tyr Glu Gly Asp Thr Pro Ala Pro
                 65                  70                  75

Pro Thr Pro Thr Gly Pro Phe Asp Phe Ala Arg Tyr Leu Arg Ala
                 80                  85                  90

Lys Asp Gln Arg Arg Phe Pro Leu Leu Ile Asn Gln Pro His Lys
                 95                 100                 105

Cys Arg Gly Asp Gly Ala Pro Gly Gly Arg Pro Asp Leu Leu Ile
                110                 115                 120

Ala Val Lys Ser Val Ala Glu Asp Phe Glu Arg Arg Gln Ala Val
                125                 130                 135

Arg Gln Thr Trp Gly Ala Glu Gly Arg Val Gln Gly Ala Leu Val
                140                 145                 150

Arg Arg Val Phe Leu Leu Gly Val Pro Arg Gly Ala Gly Ser Gly
                155                 160                 165

Gly Ala Asp Glu Val Gly Glu Gly Ala Arg Thr His Trp Arg Ala
                170                 175                 180

Leu Leu Arg Ala Glu Ser Leu Ala Tyr Ala Asp Ile Leu Leu Trp
                185                 190                 195

Ala Phe Asp Asp Thr Phe Phe Asn Leu Thr Leu Lys Glu Ile His
                200                 205                 210

Phe Leu Ala Trp Ala Ser Ala Phe Cys Pro Asp Val Arg Phe Val
                215                 220                 225

Phe Lys Gly Asp Ala Asp Val Phe Val Asn Val Gly Asn Leu Leu
                230                 235                 240

Glu Phe Leu Ala Pro Arg Asp Pro Ala Gln Asp Leu Leu Ala Gly
                245                 250                 255

Asp Val Ile Val His Ala Arg Pro Ile Arg Thr Arg Ala Ser Lys
                260                 265                 270

Tyr Tyr Ile Pro Glu Ala Val Tyr Gly Leu Pro Ala Tyr Pro Ala
                275                 280                 285

Tyr Ala Gly Gly Gly Gly Phe Val Leu Ser Gly Ala Thr Leu His
                290                 295                 300

Arg Leu Ala Gly Ala Cys Ala Gln Val Glu Leu Phe Pro Ile Asp
                305                 310                 315

Asp Val Phe Leu Gly Met Cys Leu Gln Arg Leu Arg Leu Thr Pro
                320                 325                 330

Glu Pro His Pro Ala Phe Arg Thr Phe Gly Ile Pro Gln Pro Ser
```

-continued

```
                335                 340                 345

Ala Ala Pro His Leu Ser Thr Phe Asp Pro Cys Phe Tyr Arg Glu
                350                 355                 360

Leu Val Val Val His Gly Leu Ser Ala Ala Asp Ile Trp Leu Met
                365                 370                 375

Trp Arg Leu Leu His Gly Pro His Gly Pro Ala Cys Ala His Pro
                380                 385                 390

Gln Pro Val Ala Ala Gly Pro Phe Gln Trp Asp Ser
                395                 400


<210> SEQ ID NO 35
<211> LENGTH: 1643
<212> TYPE: DNA
<213> ORGANISM: Homo Sapien

<400> SEQUENCE: 35

agcagcctct gcccgacccg gctcgtgcgg accccaggac cgggcgcggg          50

acgcgtgcgt ccagcctccg gcgctgcgga gacccgcggc tgggtccggg         100

gaggccccaa acccgccccc gccagaaccc cgccccaaat tcccacctcc         150

tccagaagcc ccgcccactc ccgagccccg agagctccgc gcacctgggc         200

gccatccgcc ctggctccgc tgcacgagct ccacgcccgt accccggcgt         250

cacgctcagc ccgcggtgct cgcacacctg agactcatct cgcttcgacc         300

ccgccgccgc cgccgcccgg catcctgagc acggagacag tctccagctg         350

ccgttcatgc ttcctcccca gccttccgca gcccaccagg gaaggggcgg         400

taggagtggc cttttaccaa agggaccggc gatgctctgc aggctgtgct         450

ggctggtctc gtacagcttg gctgtgctgt tgctcggctg cctgctcttc         500

ctgaggaagg cggccaagcc cgcaggagac cccacggccc accagccttt         550

ctgggctccc ccaacacccc gtcacagccg gtgtccaccc aaccacacag         600

tgtctagcgc ctctctgtcc ctgcctagcc gtcaccgtct cttcttgacc         650

tatcgtcact gccgaaattt ctctatcttg ctggagcctt caggctgttc         700

caaggatacc ttcttgctcc tggccatcaa gtcacagcct ggtcacgtgg         750

agcgacgtgc ggctatccgc agcacgtggg gcagggtggg gggatgggct         800

aggggccggc agctgaagct ggtgttcctc ctaggggtgg caggatccgc         850

tcccccagcc cagctgctgg cctatgagag tagggagttt gatgacatcc         900

tccagtggga cttcactgag gacttcttca acctgacgct caaggagctg         950

cacctgcagc gctgggtggt ggctgcctgc ccccaggccc atttcatgct        1000

aaagggagat gacgatgtct ttgtccacgt ccccaacgtg ttagagttcc        1050

tggatggctg ggacccagcc caggacctcc tggtgggaga tgtcatccgc        1100

caagccctgc ccaacaggaa cactaaggtc aaatacttca tcccaccctc        1150

aatgtacagg gccacccact acccacccta tgctggtggg ggaggatatg        1200

tcatgtccag agccacagtg cggcgcctcc aggctatcat ggaagatgct        1250

gaactcttcc ccattgatga tgtctttgtg ggtatgtgcc tgaggaggct        1300

ggggctgagc cctatgcacc atgctggctt caagacattt ggaatccggc        1350

ggcccctgga ccccttagac ccctgcctgt ataggggggct cctgctggtt        1400

caccgcctca gcccccctcga gatgtggacc atgtgggcac tggtgacaga        1450
```

-continued

```
tgaggggctc aagtgtgcag ctggccccat accccagcgc tgaagggtgg            1500

gttgggcaac agcctgagag tggactcagt gttgattctc tatcgtgatg            1550

cgaaattgat gcctgctgct ctacagaaaa tgccaacttg gtttttttaac           1600

tcctctcacc ctgttagctc tgattaaaaa cactgcaacc caa                   1643
```

<210> SEQ ID NO 36
<211> LENGTH: 378
<212> TYPE: PRT
<213> ORGANISM: Homo Sapien

<400> SEQUENCE: 36

```
Met Leu Pro Pro Gln Pro Ser Ala Ala His Gln Gly Arg Gly Gly
  1               5                  10                  15

Arg Ser Gly Leu Leu Pro Lys Gly Pro Ala Met Leu Cys Arg Leu
                 20                  25                  30

Cys Trp Leu Val Ser Tyr Ser Leu Ala Val Leu Leu Leu Gly Cys
                 35                  40                  45

Leu Leu Phe Leu Arg Lys Ala Ala Lys Pro Ala Gly Asp Pro Thr
                 50                  55                  60

Ala His Gln Pro Phe Trp Ala Pro Pro Thr Pro Arg His Ser Arg
                 65                  70                  75

Cys Pro Pro Asn His Thr Val Ser Ser Ala Ser Leu Ser Leu Pro
                 80                  85                  90

Ser Arg His Arg Leu Phe Leu Thr Tyr Arg His Cys Arg Asn Phe
                 95                 100                 105

Ser Ile Leu Leu Glu Pro Ser Gly Cys Ser Lys Asp Thr Phe Leu
                110                 115                 120

Leu Leu Ala Ile Lys Ser Gln Pro Gly His Val Glu Arg Arg Ala
                125                 130                 135

Ala Ile Arg Ser Thr Trp Gly Arg Val Gly Gly Trp Ala Arg Gly
                140                 145                 150

Arg Gln Leu Lys Leu Val Phe Leu Leu Gly Val Ala Gly Ser Ala
                155                 160                 165

Pro Pro Ala Gln Leu Leu Ala Tyr Glu Ser Arg Glu Phe Asp Asp
                170                 175                 180

Ile Leu Gln Trp Asp Phe Thr Glu Asp Phe Phe Asn Leu Thr Leu
                185                 190                 195

Lys Glu Leu His Leu Gln Arg Trp Val Val Ala Ala Cys Pro Gln
                200                 205                 210

Ala His Phe Met Leu Lys Gly Asp Asp Asp Val Phe Val His Val
                215                 220                 225

Pro Asn Val Leu Glu Phe Leu Asp Gly Trp Asp Pro Ala Gln Asp
                230                 235                 240

Leu Leu Val Gly Asp Val Ile Arg Gln Ala Leu Pro Asn Arg Asn
                245                 250                 255

Thr Lys Val Lys Tyr Phe Ile Pro Pro Ser Met Tyr Arg Ala Thr
                260                 265                 270

His Tyr Pro Pro Tyr Ala Gly Gly Gly Gly Tyr Val Met Ser Arg
                275                 280                 285

Ala Thr Val Arg Arg Leu Gln Ala Ile Met Glu Asp Ala Glu Leu
                290                 295                 300

Phe Pro Ile Asp Asp Val Phe Val Gly Met Cys Leu Arg Arg Leu
                305                 310                 315
```

-continued

Gly Leu Ser Pro Met His His Ala Gly Phe Lys Thr Phe Gly Ile
320 325 330

Arg Arg Pro Leu Asp Pro Leu Asp Pro Cys Leu Tyr Arg Gly Leu
335 340 345

Leu Leu Val His Arg Leu Ser Pro Leu Glu Met Trp Thr Met Trp
350 355 360

Ala Leu Val Thr Asp Glu Gly Leu Lys Cys Ala Ala Gly Pro Ile
365 370 375

Pro Gln Arg

<210> SEQ ID NO 37
<211> LENGTH: 1226
<212> TYPE: DNA
<213> ORGANISM: Homo Sapien

<400> SEQUENCE: 37
atgaaagtga taatcaggca gcccaaatga ttgttaataa ggatcaaatg 50
agatcgtgta tgtgggtcca atcaattgat tctacacaaa ggagcctggg 100
gaggggccat ggtgccaatg cacttactgg ggagactgga gaagccgctt 150
ctcctcctgt gctgcgcctc cttcctactg gggctggctt tgctgggcat 200
aaagacggac atcacccccg ttgcttattt ctttctcaca ttgggtggct 250
tcttcttgtt tgcctatctc ctggtccggt ttctggaatg gggcttcgg 300 tcccagctcc aatcaatgca gactgagagc ccagggccct caggcaatgc 350
acgggacaat gaagcctttg aagtgccagt ctatgaagag gccgtggtgg 400
gactagaatc ccagtgccgc ccccaagagt tggaccaacc acccccctac 450
agcactgttg tgataccccc agcacctgag gaggaacaac ctagccatcc 500
agaggggtcc aggagagcca aactggaaca gaggcgaatg gcctcagagg 550
ggtccatggc ccaggaagga agccctggaa gagctccaat caaccttcgg 600
cttcggggac cacgggctgt gtccactgct cctgatctgc agagcttggc 650
ggcagtcccc acattagagc ctctgactcc acccccctgcc tatgatgtct 700 gctttggtca ccctgatgat gatagtgttt tttatgagga caactgggca 750 ccccccttaaa tgactctccc aagatttctc ttctctccac accagacctc 800
gttcatttga ctaacatttt ccagcgccta ctatgtgtca gaaacaagtg 850
tttctgcctg gacatcataa atggggactt ggaccctgag gagagtcagg 900
ccacggtaag cccttcccag ctgagatatg ggtggcataa tttgagtctt 950
ctggcaacat ttggtgacct accccatatc caatatttcc agcgttagat 1000
tgaggatgag gtagggaggt gatccagaga aggcggagaa ggaagaagta 1050
acctctgagt ggcggctatt gcttctgttc caggtgctgt tcgagctgtt 1100
agaaccctta ggcttgacag ctttgtgagt tattattgaa aaatgaggat 1150
tccaagagtc agaggagttt gataatgtgc acgagggcac actgctagta 1200
aataacatta aaataactgg aatgaa 1226

<210> SEQ ID NO 38
<211> LENGTH: 216
<212> TYPE: PRT
<213> ORGANISM: Homo Sapien -continued

<400> SEQUENCE: 38

```
Met Val Pro Met His Leu Leu Gly Arg Leu Glu Lys Pro Leu Leu
  1               5                  10                  15

Leu Leu Cys Cys Ala Ser Phe Leu Leu Gly Leu Ala Leu Leu Gly
                 20                  25                  30

Ile Lys Thr Asp Ile Thr Pro Val Ala Tyr Phe Phe Leu Thr Leu
                 35                  40                  45

Gly Gly Phe Phe Leu Phe Ala Tyr Leu Leu Val Arg Phe Leu Glu
                 50                  55                  60

Trp Gly Leu Arg Ser Gln Leu Gln Ser Met Gln Thr Glu Ser Pro
                 65                  70                  75

Gly Pro Ser Gly Asn Ala Arg Asp Asn Glu Ala Phe Glu Val Pro
                 80                  85                  90

Val Tyr Glu Glu Ala Val Val Gly Leu Glu Ser Gln Cys Arg Pro
                 95                 100                 105

Gln Glu Leu Asp Gln Pro Pro Pro Tyr Ser Thr Val Val Ile Pro
                110                 115                 120

Pro Ala Pro Glu Glu Glu Gln Pro Ser His Pro Glu Gly Ser Arg
                125                 130                 135

Arg Ala Lys Leu Glu Gln Arg Arg Met Ala Ser Glu Gly Ser Met
                140                 145                 150

Ala Gln Glu Gly Ser Pro Gly Arg Ala Pro Ile Asn Leu Arg Leu
                155                 160                 165

Arg Gly Pro Arg Ala Val Ser Thr Ala Pro Asp Leu Gln Ser Leu
                170                 175                 180

Ala Ala Val Pro Thr Leu Glu Pro Leu Thr Pro Pro Pro Ala Tyr
                185                 190                 195

Asp Val Cys Phe Gly His Pro Asp Asp Asp Ser Val Phe Tyr Glu
                200                 205                 210

Asp Asn Trp Ala Pro Pro
                215
```

<210> SEQ ID NO 39
<211> LENGTH: 2770
<212> TYPE: DNA
<213> ORGANISM: Homo Sapien

<400> SEQUENCE: 39

```
cccacgcgtc cggcggctac acacctaggt gcggtgggct tcgggtgggg      50

ggcctgcagc tagctgatgg caagggagga atagcagggg tggggattgt     100

ggtgtgcgag aggtcccgcg gacggggggc tcgggggtct cttcagacga     150

gattcccttc aggcttgggc cgggtccctt cgcacggaga tcccaatgaa     200

cgcgggcccc tggaggccgg tggttggggc ttctccgcgt cggggatggg     250

gccggtaccc tagcccgttt ccagcgcctc agtcggttcc ccatgccctc     300

agaggtggcc cggggcaagc gcgccgccct cttcttcgct gcggtggcca     350

tcgtgctggg gctaccgctc tggtggaaga ccacggagac ctaccgggcc     400

tcgttgcctt actcccagat cagtggcctg aatgcccttc agctccgcct     450

catggtgcct gtcactgtcg tgtttacgcg ggagtcagtg cccctggacg     500

accaggagaa gctgcccttc accgttgtgc atgaaagaga gattcctctg     550

aaatacaaaa tgaaaatcaa atgccgtttc cagaaggcct atcggagggc     600
```

-continued

```
tttggaccat gaggaggagg ccctgtcatc gggcagtgtg caagaggcag      650
aagccatgtt agatgagcct caggaacaag cggagggctc cctgactgtg      700
tacgtgatat ctgaacactc ctcacttctt ccccaggaca tgatgagcta      750
cattgggccc aagaggacag cagtggtgcg ggggataatg caccgggagg      800
cctttaacat cattggccgc cgcatagtcc aggtggccca ggccatgtct      850
ttgactgagg atgtgcttgc tgctgctctg gctgaccacc ttccagagga      900
caagtggagc gctgagaaga ggcggcctct caagtccagc ttgggctatg      950
agatcacctt cagtttactc aacccagacc ccaagtccca tgatgtctac     1000
tgggacattg agggggctgt ccggcgctat gtgcaacctt tcctgaatgc     1050
cctcggtgcc gctggcaact tctctgtgga ctctcagatt ctttactatg     1100
caatgttggg ggtgaatccc cgctttgact cagcttcctc cagctactat     1150
ttggacatgc acagcctccc ccatgtcatc aacccagtgg agtcccggct     1200
gggatccagt gctgcctcct tgtaccctgt gctcaacttt ctactctacg     1250
tgcctgagct tgcacactca ccgctgtaca ttcaggacaa ggatggcgct     1300
ccagtggcca ccaatgcctt ccatagtccc cgctggggtg gcattatggt     1350
atataatgtt gactccaaaa cctataatgc ctcagtgctg ccagtgagag     1400
tcgaggtgga catggtgcga gtgatggagg tgttcctggc acagttgcgg     1450
ttgctctttg ggattgctca gccccagctg cctccaaaat gcctgctttc     1500
agggcctacg agtgaagggc taatgacctg ggagctagac cggctgctct     1550
gggctcggtc agtggagaac ctggccacag ccaccaccac ccttacctcc     1600
ctggcgcagc ttctgggcaa gatcagcaac attgtcatta aggacgacgt     1650
ggcatctgag gtgtacaagg ctgtagctgc cgtccagaag tcggcagaag     1700
agttggcgtc tgggcacctg gcatctgcct ttgtcgccag ccaggaagct     1750
gtgacatcct ctgagcttgc cttctttgac ccgtcactcc tccacctcct     1800
ttatttccct gatgaccaga agtttgccat ctacatccca ctcttcctgc     1850
ctatggctgt gcccatcctc ctgtccctgg tcaagatctt cctggagacc     1900
cgcaagtcct ggagaaagcc tgagaagaca gactgagcag ggcagcacct     1950
ccataggaag ccttcctttc tggccaaggt gggcggtgtt agattgtgag     2000
gcacgtacat ggggcctgcc ggaatgactt aaatatttgt ctccagtctc     2050
cactgttggc tctccagcaa ccaaagtaca acactccaag atgggttcat     2100
cttttcttcc tttcccattc acctggctca atcctcctcc accaccaggg     2150
gcctcaaaag gcacatcatc cgggtctcct tatcttgttt gataaggctg     2200
ctgcctgtct ccctctgtgg caaggactgt ttgttctttt gccccatttc     2250
tcaacatagc acacttgtgc actgagagga gggagcatta tgggaaagtc     2300
cctgccttcc acacctctct ctagtccctg tgggacagcc ctagcccctg     2350
ctgtcatgaa ggggccaggc attggtcacc tgtgggacct tctccctcac     2400
tcccctccct cctagttggc tttgtctgtc aggtgcagtc tggcgggagt     2450
ccaggaggca gcagctcagg acatggtgct gtgtgtgtgt gtgtgtgtgt     2500
gtgtgtgtgt gtgtgtgtca gaggttccag aaagttccag atttggaatc     2550
aaacagtcct gaattcaaat ccttgttttt gcacttattg tctggagagc     2600
```

-continued

```
tttggataag gtattgaatc tctctgagcc tcagtttttc atttgttcaa           2650

atggcactga tgatgtctcc cttacaagat ggttgtgagg agtaaatgtg           2700

atcagcatgt aaagtgtctg gcgtgtagta ggctcttaat aaacactggc           2750

tgaatatgaa ttggaatgat                                            2770


<210> SEQ ID NO 40
<211> LENGTH: 547
<212> TYPE: PRT
<213> ORGANISM: Homo Sapien

<400> SEQUENCE: 40

Met Pro Ser Glu Val Ala Arg Gly Lys Arg Ala Ala Leu Phe Phe
  1               5                  10                  15

Ala Ala Val Ala Ile Val Leu Gly Leu Pro Leu Trp Trp Lys Thr
                 20                  25                  30

Thr Glu Thr Tyr Arg Ala Ser Leu Pro Tyr Ser Gln Ile Ser Gly
                 35                  40                  45

Leu Asn Ala Leu Gln Leu Arg Leu Met Val Pro Val Thr Val Val
                 50                  55                  60

Phe Thr Arg Glu Ser Val Pro Leu Asp Asp Gln Glu Lys Leu Pro
                 65                  70                  75

Phe Thr Val Val His Glu Arg Glu Ile Pro Leu Lys Tyr Lys Met
                 80                  85                  90

Lys Ile Lys Cys Arg Phe Gln Lys Ala Tyr Arg Arg Ala Leu Asp
                 95                 100                 105

His Glu Glu Glu Ala Leu Ser Ser Gly Ser Val Gln Glu Ala Glu
                110                 115                 120

Ala Met Leu Asp Glu Pro Gln Glu Gln Ala Glu Gly Ser Leu Thr
                125                 130                 135

Val Tyr Val Ile Ser Glu His Ser Ser Leu Leu Pro Gln Asp Met
                140                 145                 150

Met Ser Tyr Ile Gly Pro Lys Arg Thr Ala Val Val Arg Gly Ile
                155                 160                 165

Met His Arg Glu Ala Phe Asn Ile Ile Gly Arg Arg Ile Val Gln
                170                 175                 180

Val Ala Gln Ala Met Ser Leu Thr Glu Asp Val Leu Ala Ala Ala
                185                 190                 195

Leu Ala Asp His Leu Pro Glu Asp Lys Trp Ser Ala Glu Lys Arg
                200                 205                 210

Arg Pro Leu Lys Ser Ser Leu Gly Tyr Glu Ile Thr Phe Ser Leu
                215                 220                 225

Leu Asn Pro Asp Pro Lys Ser His Asp Val Tyr Trp Asp Ile Glu
                230                 235                 240

Gly Ala Val Arg Arg Tyr Val Gln Pro Phe Leu Asn Ala Leu Gly
                245                 250                 255

Ala Ala Gly Asn Phe Ser Val Asp Ser Gln Ile Leu Tyr Tyr Ala
                260                 265                 270

Met Leu Gly Val Asn Pro Arg Phe Asp Ser Ala Ser Ser Ser Tyr
                275                 280                 285

Tyr Leu Asp Met His Ser Leu Pro His Val Ile Asn Pro Val Glu
                290                 295                 300

Ser Arg Leu Gly Ser Ser Ala Ala Ser Leu Tyr Pro Val Leu Asn
                305                 310                 315
```

-continued

```
Phe Leu Leu Tyr Val Pro Glu Leu Ala His Ser Pro Leu Tyr Ile
                320                 325                 330

Gln Asp Lys Asp Gly Ala Pro Val Ala Thr Asn Ala Phe His Ser
                335                 340                 345

Pro Arg Trp Gly Gly Ile Met Val Tyr Asn Val Asp Ser Lys Thr
                350                 355                 360

Tyr Asn Ala Ser Val Leu Pro Val Arg Val Glu Val Asp Met Val
                365                 370                 375

Arg Val Met Glu Val Phe Leu Ala Gln Leu Arg Leu Leu Phe Gly
                380                 385                 390

Ile Ala Gln Pro Gln Leu Pro Pro Lys Cys Leu Leu Ser Gly Pro
                395                 400                 405

Thr Ser Glu Gly Leu Met Thr Trp Glu Leu Asp Arg Leu Leu Trp
                410                 415                 420

Ala Arg Ser Val Glu Asn Leu Ala Thr Ala Thr Thr Thr Leu Thr
                425                 430                 435

Ser Leu Ala Gln Leu Leu Gly Lys Ile Ser Asn Ile Val Ile Lys
                440                 445                 450

Asp Asp Val Ala Ser Glu Val Tyr Lys Ala Val Ala Ala Val Gln
                455                 460                 465

Lys Ser Ala Glu Glu Leu Ala Ser Gly His Leu Ala Ser Ala Phe
                470                 475                 480

Val Ala Ser Gln Glu Ala Val Thr Ser Ser Glu Leu Ala Phe Phe
                485                 490                 495

Asp Pro Ser Leu Leu His Leu Leu Tyr Phe Pro Asp Asp Gln Lys
                500                 505                 510

Phe Ala Ile Tyr Ile Pro Leu Phe Leu Pro Met Ala Val Pro Ile
                515                 520                 525

Leu Leu Ser Leu Val Lys Ile Phe Leu Glu Thr Arg Lys Ser Trp
                530                 535                 540

Arg Lys Pro Glu Lys Thr Asp
                545
```

<210> SEQ ID NO 41
<211> LENGTH: 1964
<212> TYPE: DNA
<213> ORGANISM: Homo Sapien

<400> SEQUENCE: 41

```
ccagctgcag agaggaggag gtgagctgca gagaagagga ggttggtgtg           50

gagcacaggc agcaccgagc ctgccccgtg agctgagggc ctgcagtctg          100

cggctggaat caggatagac accaaggcag gacccccaga gatgctgaag          150

cctctttgga aagcagcagt ggcccccaca tggccatgct ccatgccgcc          200

ccgccgcccg tgggacagag aggctggcac gttgcaggtc ctgggagcgc          250

tggctgtgct gtggctgggc tccgtggctc ttatctgcct cctgtggcaa          300

gtgccccgtc ctcccacctg ggccaggtg cagcccaagg acgtgcccag           350

gtcctgggag catggctcca gcccagcttg ggagcccctg gaagcagagg          400

ccaggcagca gagggactcc tgccagcttg tccttgtgga aagcatcccc          450

caggacctgc catctgcagc cggcagcccc tctgcccagc ctctgggcca          500

ggcctggctg cagctgctgg acactgccca ggagagcgtc cacgtggctt          550
```

-continued

```
catactactg gtccctcaca gggcctgaca tcggggtcaa cgactcgtct    600

tcccagctgg gagaggctct tctgcagaag ctgcagcagc tgctgggcag    650

gaacatttcc ctggctgtgg ccaccagcag cccgacactg gccaggacat    700

ccaccgacct gcaggttctg gctgcccgag gtgcccatgt acgacaggtg    750

cccatggggc ggctcaccag ggtgttttg cactccaaat tctgggttgt     800

ggatggacgg cacatataca tgggcagtgc caacatggac tggcggtctc    850

tgacgcaggt gaaggagctt ggcgctgtca tctataactg cagccacctg    900

gcccaagacc tggagaagac cttccagacc tactgggtac tgggggtgcc    950

caaggctgtc ctccccaaaa cctggcctca gaacttctca tctcacttca   1000

accgtttcca gcccttccac ggcctctttg atggggtgcc caccactgcc   1050

tacttctcag cgtcgccacc agcactctgt ccccagggcc gcacccggga   1100

cctggaggcg ctgctggcgg tgatggggag cgcccaggag ttcatctatg   1150

cctccgtgat ggagtatttc cccaccacgc gcttcagcca ccccccgagg   1200

tactggccgg tgctggacaa cgcgctgcgg gcggcagcct tcggcaaggg   1250

cgtgcgcgtg cgcctgctgg tcggctgcgg actcaacacg gaccccacca   1300

tgttccccta cctgcggtcc ctgcaggcgc tcagcaaccc cgcggccaac   1350

gtctctgtgg acgtgaaagt cttcatcgtg ccggtgggga accattccaa   1400

catcccattc agcagggtga accacagcaa gttcatggtc acggagaagg   1450

cagcctacat aggcacctcc aactggtcgg aggattactt cagcagcacg   1500

gcgggggtgg gcttggtggt cacccagagc cctggcgcgc agcccgcggg   1550

ggccacggtg caggagcagc tgcggcagct ctttgagcgg gactggagtt   1600

cgcgctacgc cgtcggcctg gacggacagg ctccgggcca ggactgcgtt   1650

tggcagggct gagggggcc tctttttctc tcggcgaccc cgccccgcac    1700

gcgccctccc ctctgacccc ggcctgggct tcagccgctt cctcccgcaa   1750

gcagcccggg tccgcactgc gccaggagcc gcctgcgacc gcccgggcgt   1800

cgcaaaccgc ccgcctgctc tctgatttcc gagtccagcc ccccctgagc   1850

cccacctcct ccagggagcc ctccaggaag ccccttccct gactcctggc   1900

ccacaggcca ggcctaaaaa aaactcgtgg cttcaaaaaa aaaaaaaaaa   1950

aaaaaaaaaa aaaa                                          1964
```

<210> SEQ ID NO 42
<211> LENGTH: 489
<212> TYPE: PRT
<213> ORGANISM: Homo Sapien

<400> SEQUENCE: 42

```
Met Pro Pro Arg Arg Pro Trp Asp Arg Glu Ala Gly Thr Leu Gln
  1               5                  10                  15

Val Leu Gly Ala Leu Ala Val Leu Trp Leu Gly Ser Val Ala Leu
                 20                  25                  30

Ile Cys Leu Leu Trp Gln Val Pro Arg Pro Pro Thr Trp Gly Gln
                 35                  40                  45

Val Gln Pro Lys Asp Val Pro Arg Ser Trp Glu His Gly Ser Ser
                 50                  55                  60

Pro Ala Trp Glu Pro Leu Glu Ala Glu Ala Arg Gln Gln Arg Asp
```

-continued

```
                65                  70                  75

Ser Cys Gln Leu Val Leu Val Glu Ser Ile Pro Gln Asp Leu Pro
                80                  85                  90

Ser Ala Ala Gly Ser Pro Ser Ala Gln Pro Leu Gly Gln Ala Trp
                95                  100                 105

Leu Gln Leu Leu Asp Thr Ala Gln Glu Ser Val His Val Ala Ser
                110                 115                 120

Tyr Tyr Trp Ser Leu Thr Gly Pro Asp Ile Gly Val Asn Asp Ser
                125                 130                 135

Ser Ser Gln Leu Gly Glu Ala Leu Leu Gln Lys Leu Gln Gln Leu
                140                 145                 150

Leu Gly Arg Asn Ile Ser Leu Ala Val Ala Thr Ser Ser Pro Thr
                155                 160                 165

Leu Ala Arg Thr Ser Thr Asp Leu Gln Val Leu Ala Ala Arg Gly
                170                 175                 180

Ala His Val Arg Gln Val Pro Met Gly Arg Leu Thr Arg Gly Val
                185                 190                 195

Leu His Ser Lys Phe Trp Val Val Asp Gly Arg His Ile Tyr Met
                200                 205                 210

Gly Ser Ala Asn Met Asp Trp Arg Ser Leu Thr Gln Val Lys Glu
                215                 220                 225

Leu Gly Ala Val Ile Tyr Asn Cys Ser His Leu Ala Gln Asp Leu
                230                 235                 240

Glu Lys Thr Phe Gln Thr Tyr Trp Val Leu Gly Val Pro Lys Ala
                245                 250                 255

Val Leu Pro Lys Thr Trp Pro Gln Asn Phe Ser Ser His Phe Asn
                260                 265                 270

Arg Phe Gln Pro Phe His Gly Leu Phe Asp Gly Val Pro Thr Thr
                275                 280                 285

Ala Tyr Phe Ser Ala Ser Pro Pro Ala Leu Cys Pro Gln Gly Arg
                290                 295                 300

Thr Arg Asp Leu Glu Ala Leu Leu Ala Val Met Gly Ser Ala Gln
                305                 310                 315

Glu Phe Ile Tyr Ala Ser Val Met Glu Tyr Phe Pro Thr Thr Arg
                320                 325                 330

Phe Ser His Pro Pro Arg Tyr Trp Pro Val Leu Asp Asn Ala Leu
                335                 340                 345

Arg Ala Ala Ala Phe Gly Lys Gly Val Arg Val Arg Leu Leu Val
                350                 355                 360

Gly Cys Gly Leu Asn Thr Asp Pro Thr Met Phe Pro Tyr Leu Arg
                365                 370                 375

Ser Leu Gln Ala Leu Ser Asn Pro Ala Ala Asn Val Ser Val Asp
                380                 385                 390

Val Lys Val Phe Ile Val Pro Val Gly Asn His Ser Asn Ile Pro
                395                 400                 405

Phe Ser Arg Val Asn His Ser Lys Phe Met Val Thr Glu Lys Ala
                410                 415                 420

Ala Tyr Ile Gly Thr Ser Asn Trp Ser Glu Asp Tyr Phe Ser Ser
                425                 430                 435

Thr Ala Gly Val Gly Leu Val Val Thr Gln Ser Pro Gly Ala Gln
                440                 445                 450

Pro Ala Gly Ala Thr Val Gln Glu Gln Leu Arg Gln Leu Phe Glu
                455                 460                 465
```

-continued

```
Arg Asp Trp Ser Ser Arg Tyr Ala Val Gly Leu Asp Gly Gln Ala
              470                 475                 480

Pro Gly Gln Asp Cys Val Trp Gln Gly
              485


<210> SEQ ID NO 43
<211> LENGTH: 1130
<212> TYPE: DNA
<213> ORGANISM: Homo Sapien

<400> SEQUENCE: 43

gggcctggcg atccggatcc cgcaggcgcg ctggctgcgc tgcccggctg              50

tctgtcgtca tggtggggcc ctgggtgtat ctggtggcgg cagttttgct             100

catcggcctg atcctcttcc tgactcgcag ccggggtcgg gcggcagcag             150

ctgacggaga accactgcac aatgaggaag agagggcagg agcaggccag             200

gtaggccgct ctttgcccca ggagtctgaa gaacagagaa ctggaagcag             250

accccggcgt cggagggact tgggcagccg tctacaggcc cagcgtcgag             300

cccagcgagt ggcctgggaa gacggggatg agaatgtggg tcaaactgtt             350

attccagccc aggaggaaga aggcattgag aagccagcag aagttcaccc             400

aacagggaaa attggagcca agaaactacg gaagctagag gaaaaacagg             450

ctcgaaaggc tcagcgagag gcagaggagg ctgaacgtga agaacggaaa             500

cgcctagagt cccaacgtga ggccgaatgg aagaaggaag aggaacggct             550

tcgcctgaag gaagaacaga aggaggagga agagaggaag gctcaggagg             600

agcaggcccg gcgggatcac gaggagtacc tgaaactgaa ggaggccttc             650

gtggtagaag aagaaggtgt tagcgaaacc atgactgagg agcagtctca             700

cagcttcctg acagaattca tcaattacat caagaagtcc aaggttgtgc             750

ttttggaaga tctggctttc cagatgggcc taaggactca ggacgccata             800

aaccgcatcc aggacctgct gacggagggg actctaacag gtgtgattga             850

cgaccggggc aagtttatct acataacccc agaggaactg gctgccgtgg             900

ccaatttcat ccgacagcgg ggccgggtgt ccatcacaga gcttgcccag             950

gccagcaact ccctcatctc ctggggccag gacctccctg cccaggcttc            1000

agcctgactc cagtccttcc ttgagtgtat cctgtggcct acatgtgtct            1050

tcatccttcc ctaatgccgt cttggggcag ggatggaata tgaccagaaa            1100

gttgtggatt aaaggcctgt gaatactgaa                                  1130


<210> SEQ ID NO 44
<211> LENGTH: 315
<212> TYPE: PRT
<213> ORGANISM: Homo Sapien

<400> SEQUENCE: 44

Met Val Gly Pro Trp Val Tyr Leu Val Ala Ala Val Leu Leu Ile
  1               5                  10                  15

Gly Leu Ile Leu Phe Leu Thr Arg Ser Arg Gly Arg Ala Ala Ala
               20                  25                  30

Ala Asp Gly Glu Pro Leu His Asn Glu Glu Glu Arg Ala Gly Ala
               35                  40                  45

Gly Gln Val Gly Arg Ser Leu Pro Gln Glu Ser Glu Glu Gln Arg
```

-continued

```
                50                  55                  60

Thr Gly Ser Arg Pro Arg Arg Arg Arg Asp Leu Gly Ser Arg Leu
                65                  70                  75

Gln Ala Gln Arg Arg Ala Gln Arg Val Ala Trp Glu Asp Gly Asp
                80                  85                  90

Glu Asn Val Gly Gln Thr Val Ile Pro Ala Gln Glu Glu Glu Gly
                95                  100                 105

Ile Glu Lys Pro Ala Glu Val His Pro Thr Gly Lys Ile Gly Ala
                110                 115                 120

Lys Lys Leu Arg Lys Leu Glu Glu Lys Gln Ala Arg Lys Ala Gln
                125                 130                 135

Arg Glu Ala Glu Glu Ala Glu Arg Glu Glu Arg Lys Arg Leu Glu
                140                 145                 150

Ser Gln Arg Glu Ala Glu Trp Lys Lys Glu Glu Glu Arg Leu Arg
                155                 160                 165

Leu Lys Glu Glu Gln Lys Glu Glu Glu Glu Arg Lys Ala Gln Glu
                170                 175                 180

Glu Gln Ala Arg Arg Asp His Glu Glu Tyr Leu Lys Leu Lys Glu
                185                 190                 195

Ala Phe Val Val Glu Glu Glu Gly Val Ser Glu Thr Met Thr Glu
                200                 205                 210

Glu Gln Ser His Ser Phe Leu Thr Glu Phe Ile Asn Tyr Ile Lys
                215                 220                 225

Lys Ser Lys Val Val Leu Leu Glu Asp Leu Ala Phe Gln Met Gly
                230                 235                 240

Leu Arg Thr Gln Asp Ala Ile Asn Arg Ile Gln Asp Leu Leu Thr
                245                 250                 255

Glu Gly Thr Leu Thr Gly Val Ile Asp Asp Arg Gly Lys Phe Ile
                260                 265                 270

Tyr Ile Thr Pro Glu Glu Leu Ala Ala Val Ala Asn Phe Ile Arg
                275                 280                 285

Gln Arg Gly Arg Val Ser Ile Thr Glu Leu Ala Gln Ala Ser Asn
                290                 295                 300

Ser Leu Ile Ser Trp Gly Gln Asp Leu Pro Ala Gln Ala Ser Ala
                305                 310                 315
```

<210> SEQ ID NO 45
<211> LENGTH: 1977
<212> TYPE: DNA
<213> ORGANISM: Homo Sapien

<400> SEQUENCE: 45

```
acgggccgca gcggcagtga cgtagggttg gcgcacggat ccgttgcggc          50

tgcagctctg cagtcgggcc gttccttcgc cgccgccagg ggtagcggtg         100

tagctgcgca gcgtcgcgcg cgctaccgca cccaggttcg gcccgtaggc         150

gtctggcagc ccggcgccat cttcatcgag cgccatggcc gcagcctgcg         200

ggccgggagc ggccgggtac tgcttgctcc tcggcttgca tttgtttctg         250

ctgaccgcgg gccctgccct gggctggaac gaccctgaca gaatgttgct         300

gcgggatgta aaagctctta ccctccacta tgaccgctat accacctccc         350

gcaggctgga tcccatccca cagttgaaat gtgttggagg cacagctggt         400

tgtgattctt ataccccaaa agtcatacag tgtcagaaca aaggctggga         450
```

-continued

```
tgggtatgat gtacagtggg aatgtaagac ggacttagat attgcataca        500

aatttggaaa aactgtggtg agctgtgaag gctatgagtc ctctgaagac        550

cagtatgtac taagaggttc ttgtggcttg gagtataatt tagattatac        600

agaacttggc ctgcagaaac tgaaggagtc tggaaagcag cacggctttg        650

cctctttctc tgattattat tataagtggt cctcggcgga ttcctgtaac        700

atgagtggat tgattaccat cgtggtactc cttgggatcg cctttgtagt        750

ctataagctg ttcctgagtg acgggcagta ttctcctcca ccgtactctg        800

agtatcctcc attttcccac cgttaccaga gattcaccaa ctcagcagga        850

cctcctcccc caggctttaa gtctgagttc acaggaccac agaatactgg        900

ccatggtgca acttctggtt ttggcagtgc ttttacagga caacaaggat        950

atgaaaattc aggaccaggg ttctggacag gcttgggaac tggtggaata       1000

ctaggatatt tgtttggcag caatagagcg gcaacaccct tctcagactc       1050

gtggtactac ccgtcctatc ctccctccta ccctggcacg tggaataggg       1100

cttactcacc ccttcatgga ggctcgggca gctattcggt atgttcaaac       1150

tcagacacga aaaccagaac tgcatcagga tatggtggta ccaggagacg       1200

ataaagtaga aagttggagt caaacactgg atgcagaaat tttggatttt       1250

tcatcacttt ctctttagaa aaaaagtact acctgttaac aattgggaaa       1300

aggggatatt caaaagttct gtggtgttat gtccagtgta gctttttgta       1350

ttctattatt tgaggctaaa agttgatgtg tgacaaaata cttatgtgtt       1400

gtatgtcagt gtaacatgca gatgtatatt gcagtttttg aaagtgatca       1450

ttactgtgga atgctaaaaa tacattaatt tctaaaacct gtgatgccct       1500

aagaagcatt aagaatgaag gtgttgtact aatagaaact aagtacagaa       1550

aatttcagtt ttaggtggtt gtagctgatg agttattacc tcatagagac       1600

tataatattc tatttggtat tatattattt gatgtttgct gttcttcaaa       1650

catttaaatc aagctttgga ctaattatgc taatttgtga gttctgatca       1700

cttttgagct ctgaagcttt gaatcattca gtggtggaga tggccttctg       1750

gtaactgaat attaccttct gtaggaaaag gtggaaaata agcatctaga       1800

aggttgttgt gaatgactct gtgctggcaa aaatgcttga aacctctata       1850

tttctttcgt tcataagagg taaaggtcaa atttttcaac aaaagtcttt       1900

taataacaaa agcatgcagt tctctgtgaa atctcaaata ttgttgtaat       1950

agtctgtttc aatcttaaaa agaatca                                1977
```

<210> SEQ ID NO 46
<211> LENGTH: 339
<212> TYPE: PRT
<213> ORGANISM: Homo Sapien

<400> SEQUENCE: 46

```
Met Ala Ala Ala Cys Gly Pro Gly Ala Ala Gly Tyr Cys Leu Leu
  1               5                  10                  15

Leu Gly Leu His Leu Phe Leu Leu Thr Ala Gly Pro Ala Leu Gly
                 20                  25                  30

Trp Asn Asp Pro Asp Arg Met Leu Leu Arg Asp Val Lys Ala Leu
                 35                  40                  45
```

-continued

```
Thr Leu His Tyr Asp Arg Tyr Thr Thr Ser Arg Arg Leu Asp Pro
                50                  55                  60

Ile Pro Gln Leu Lys Cys Val Gly Gly Thr Ala Gly Cys Asp Ser
                65                  70                  75

Tyr Thr Pro Lys Val Ile Gln Cys Gln Asn Lys Gly Trp Asp Gly
                80                  85                  90

Tyr Asp Val Gln Trp Glu Cys Lys Thr Asp Leu Asp Ile Ala Tyr
                95                  100                 105

Lys Phe Gly Lys Thr Val Val Ser Cys Glu Gly Tyr Glu Ser Ser
                110                 115                 120

Glu Asp Gln Tyr Val Leu Arg Gly Ser Cys Gly Leu Glu Tyr Asn
                125                 130                 135

Leu Asp Tyr Thr Glu Leu Gly Leu Gln Lys Leu Lys Glu Ser Gly
                140                 145                 150

Lys Gln His Gly Phe Ala Ser Phe Ser Asp Tyr Tyr Tyr Lys Trp
                155                 160                 165

Ser Ser Ala Asp Ser Cys Asn Met Ser Gly Leu Ile Thr Ile Val
                170                 175                 180

Val Leu Leu Gly Ile Ala Phe Val Val Tyr Lys Leu Phe Leu Ser
                185                 190                 195

Asp Gly Gln Tyr Ser Pro Pro Pro Tyr Ser Glu Tyr Pro Pro Phe
                200                 205                 210

Ser His Arg Tyr Gln Arg Phe Thr Asn Ser Ala Gly Pro Pro Pro
                215                 220                 225

Pro Gly Phe Lys Ser Glu Phe Thr Gly Pro Gln Asn Thr Gly His
                230                 235                 240

Gly Ala Thr Ser Gly Phe Gly Ser Ala Phe Thr Gly Gln Gln Gly
                245                 250                 255

Tyr Glu Asn Ser Gly Pro Gly Phe Trp Thr Gly Leu Gly Thr Gly
                260                 265                 270

Gly Ile Leu Gly Tyr Leu Phe Gly Ser Asn Arg Ala Ala Thr Pro
                275                 280                 285

Phe Ser Asp Ser Trp Tyr Tyr Pro Ser Tyr Pro Pro Ser Tyr Pro
                290                 295                 300

Gly Thr Trp Asn Arg Ala Tyr Ser Pro Leu His Gly Gly Ser Gly
                305                 310                 315

Ser Tyr Ser Val Cys Ser Asn Ser Asp Thr Lys Thr Arg Thr Ala
                320                 325                 330

Ser Gly Tyr Gly Gly Thr Arg Arg Arg
                335
```

<210> SEQ ID NO 47
<211> LENGTH: 1766
<212> TYPE: DNA
<213> ORGANISM: Homo Sapien

<400> SEQUENCE: 47

```
cccggagccg gggagggagg gagcgaggtt cggacaccgg cggcggctgc        50

ctggcctttc catgagcccg cggcggaccc tcccgcgccc cctctcgctc       100

tgcctctccc tctgcctctg cctctgcctg gccgcggctc tgggaagtgc       150

gcagtccggg tcgtgtaggg ataaaaagaa ctgtaaggtg gtcttttccc       200

agcaggaact gaggaagcgg ctaacacccc tgcagtacca tgtcactcag       250

gagaaaggga ccgaaagtgc ctttgaagga gaatacacac atcacaaaga       300
```

-continued

```
tcctggaata tataaatgtg ttgtttgtgg aactccattg tttaagtcag          350
aaaccaaatt tgactccggt tcaggttggc cttcattcca cgatgtgatc          400
aattctgagg caatcacatt cacagatgac ttttcctatg ggatgcacag          450
ggtggaaaca agctgctctc agtgtggtgc tcaccttggg cacatttttg          500
atgatgggcc tcgtccaact gggaaaagat actgcataaa ttcggctgcc          550
ttgtctttta cacctgcgga tagcagtggc accgccgagg gaggcagtgg          600
ggtcgccagc ccggcccagg cagacaaagc ggagctctag agtaatggag          650
agtgatggaa acaaagtgta cttaatgcac agcttattaa aaaaatcaaa          700
attgttatct taatagatat attttttcaa aaactataag ggcagttttg          750
tgctattgat atttttttctt cttttgctta aacagaagcc ctggccatcc          800
atgtattttg caattgacta gatcaagaac tgtttatagc tttagcaaat          850
ggagacagct ttgtgaaact tcttcacaag ccacttatac cctttggcat          900
tcttttcttt gagcacatgg cttcttttgc agtttttccc cctttgattc          950
agaagcagag ggttcatggt cttcaaacat gaaaatagag atctcctctg         1000
cagtgtagag accagagctg ggcagtgcag ggcatggaga cctgcaagac         1050
acatggcctt gaggcctttg cacagaccca cctaagataa ggttggagtg         1100
atgttttaat gagactgttc agctttgtgg aaagtttgag ctaaggtcat         1150
tttttttttt ctcactgaaa gggtgtgaag gtctaaagtc tttccttatg         1200
ttaaattgtt gccagatcca aaggggcata ctgagtgttg tggcagagaa         1250
gtaaacatta ccacactgtt aggcctttat tttattttat tttccatcga         1300
aagcattgga ggcccagtgc aatggctcac gcctgtgatc ccagcacttt         1350
gggaggccaa ggcgggtgga tcacgaggtc aggagatgga gaccatcctg         1400
gctaacatgg tgaaaccccg tctctactaa aaatacgaaa aattagccag         1450
gcgtggtggt gggcacctgt agtcccagct actcaggagg ctgaggcagg         1500
agaatggcgt gaacccggaa ggcggagctt gcagttagcc gagatcatgc         1550
cactgcactc cagcctacat gacaatgtga cactccatct caaaaaataa         1600
taataataac aatataagaa ctagctgggc atggtggcgc atgcatgtag         1650
tcccagctac tcctgaggct cagtcaggag aatcgcttga acttgggagg         1700
cggaggttgc agtgagctga gctcatacca ctgcactcca gcctgaacag         1750
agtgagatcc tgtcaa                                              1766
```

<210> SEQ ID NO 48
<211> LENGTH: 192
<212> TYPE: PRT
<213> ORGANISM: Homo Sapien

<400> SEQUENCE: 48

```
Met Ser Pro Arg Arg Thr Leu Pro Arg Pro Leu Ser Leu Cys Leu
  1               5                  10                  15

Ser Leu Cys Leu Cys Leu Cys Leu Ala Ala Ala Leu Gly Ser Ala
                 20                  25                  30

Gln Ser Gly Ser Cys Arg Asp Lys Lys Asn Cys Lys Val Val Phe
                 35                  40                  45

Ser Gln Gln Glu Leu Arg Lys Arg Leu Thr Pro Leu Gln Tyr His
```

-continued

```
                50                  55                  60

Val Thr Gln Glu Lys Gly Thr Glu Ser Ala Phe Glu Gly Glu Tyr
                65                  70                  75

Thr His His Lys Asp Pro Gly Ile Tyr Lys Cys Val Val Cys Gly
                80                  85                  90

Thr Pro Leu Phe Lys Ser Glu Thr Lys Phe Asp Ser Gly Ser Gly
                95                  100                 105

Trp Pro Ser Phe His Asp Val Ile Asn Ser Glu Ala Ile Thr Phe
                110                 115                 120

Thr Asp Asp Phe Ser Tyr Gly Met His Arg Val Glu Thr Ser Cys
                125                 130                 135

Ser Gln Cys Gly Ala His Leu Gly His Ile Phe Asp Asp Gly Pro
                140                 145                 150

Arg Pro Thr Gly Lys Arg Tyr Cys Ile Asn Ser Ala Ala Leu Ser
                155                 160                 165

Phe Thr Pro Ala Asp Ser Ser Gly Thr Ala Glu Gly Gly Ser Gly
                170                 175                 180

Val Ala Ser Pro Ala Gln Ala Asp Lys Ala Glu Leu
                185                 190
```

<210> SEQ ID NO 49
<211> LENGTH: 2065
<212> TYPE: DNA
<213> ORGANISM: Homo Sapien

<400> SEQUENCE: 49

```
cccaaagagg tgaggagccg gcagcggggg cggctgtaac tgtgaggaag        50

gctgcagagt ggcgacgtct acgccgtagg ttggaggctg tggggggtgg       100

ccgggcgcca gctcccaggc cgcagaagtg acctgcggtg gagttccctc       150

ctcgctgctg gagaacggag ggagaaggtt gctggccggg tgaaagtgcc       200

tccctctgct tgacggggct gaggggcccg aagtctaggg cgtccgtagt       250

cgccccggcc tccgtgaagc cccaggtcta gagatatgac ccgagagtgc       300

ccatctccgg ccccggggcc tggggctccg ctgagtggat cggtgctggc       350

agaggcggca gtagtgtttg cagtggtgct gagcatccac gcaaccgtat       400

gggaccgata ctcgtggtgc gccgtggccc tcgcagtgca ggccttctac       450

gtccaataca agtgggaccg gctgctacag cagggaagcg ccgtcttcca       500

gttccgaatg tccgcaaaca gtggcctatt gcccgcctcc atggtcatgc       550

ctttgcttgg actagtcatg aaggagcggt gccagactgc tgggaacccg       600

ttctttgagc gttttggcat tgtggtggca gccactggca tggcagtggc       650

cctcttctca tcagtgttgg cgctcggcat cactcgccca gtgccaacca       700

acacttgtgt catcttgggc ttggctggag gtgttatcat ttatatcatg       750

aagcactcgt tgagcgtggg ggaggtgatc gaagtcctgg aagtccttct       800

gatcttcgtt tatctcaaca tgatcctgct gtacctgctg ccccgctgct       850

tcacccctgg tgaggcactg ctggtattgg gtggcattag ctttgtcctc       900

aaccagctca tcaagcgctc tctgacactg gtggaaagtc agggggaccc       950

agtggacttc ttcctgctgg tggtggtagt agggatggta ctcatgggca      1000

ttttcttcag cactctgttt gtcttcatgg actcaggcac ctgggcctcc      1050
```

-continued

```
tccatcttct tccacctcat gacctgtgtg ctgagccttg gtgtggtcct         1100

accctggctg caccggctca tccgcaggaa tcccctgctc tggcttcttc         1150

agtttctctt ccagacagac acccgcatct acctcctagc ctattggtct         1200

ctgctggcca ccttggcctg cctggtggtg ctgtaccaga atgccaagcg         1250

gtcatcttcc gagtccaaga agcaccaggc ccccaccatc gcccgaaagt         1300

atttccacct cattgtggta gccacctaca tcccaggtat catctttgac         1350

cggccactgc tctatgtagc cgccactgta tgcctggcgg tcttcatctt         1400

cctggagtat gtgcgctact tccgcatcaa gcctttgggt cacactctac         1450

ggagcttcct gtcccttttt ctggatgaac gagacagtgg accactcatt         1500

ctgacacaca tctacctgct cctgggcatg tctcttccca tctggctgat         1550

ccccagaccc tgcacacaga agggtagcct gggaggagcc agggccctcg         1600

tcccctatgc cggtgtcctg gctgtgggtg tgggtgatac tgtggcctcc         1650

atcttcggta gcaccatggg ggagatccgc tggcctggaa ccaaaaagac         1700

ttttgagggg accatgacat ctatatttgc gcagatcatt tctgtagctc         1750

tgatcttaat ctttgacagt ggagtggacc taaactacag ttatgcttgg         1800

attttggggt ccatcagcac tgtgtccctc ctggaagcat acactacaca         1850

gatagacaat ctccttctgc ctctctacct cctgatattg ctgatggcct         1900

agctgttaca gtgcagcagc agtgacggag gaaacagaca tggggagggt         1950

gaacagtccc cacagcagac agctacttgg gcatgaagag ccaaggtgtg         2000

aaaagcagat ttgatttttc agttgattca gatttaaaat aaaaagcaaa         2050

gctctcctag ttcta                                               2065


<210> SEQ ID NO 50
<211> LENGTH: 538
<212> TYPE: PRT
<213> ORGANISM: Homo Sapien

<400> SEQUENCE: 50

Met Thr Arg Glu Cys Pro Ser Pro Ala Pro Gly Pro Gly Ala Pro
  1               5                  10                  15

Leu Ser Gly Ser Val Leu Ala Glu Ala Ala Val Val Phe Ala Val
                 20                  25                  30

Val Leu Ser Ile His Ala Thr Val Trp Asp Arg Tyr Ser Trp Cys
                 35                  40                  45

Ala Val Ala Leu Ala Val Gln Ala Phe Tyr Val Gln Tyr Lys Trp
                 50                  55                  60

Asp Arg Leu Leu Gln Gln Gly Ser Ala Val Phe Gln Phe Arg Met
                 65                  70                  75

Ser Ala Asn Ser Gly Leu Leu Pro Ala Ser Met Val Met Pro Leu
                 80                  85                  90

Leu Gly Leu Val Met Lys Glu Arg Cys Gln Thr Ala Gly Asn Pro
                 95                 100                 105

Phe Phe Glu Arg Phe Gly Ile Val Val Ala Ala Thr Gly Met Ala
                110                 115                 120

Val Ala Leu Phe Ser Ser Val Leu Ala Leu Gly Ile Thr Arg Pro
                125                 130                 135

Val Pro Thr Asn Thr Cys Val Ile Leu Gly Leu Ala Gly Gly Val
                140                 145                 150
```

-continued

```
Ile Ile Tyr Ile Met Lys His Ser Leu Ser Val Gly Glu Val Ile
                155                 160                 165

Glu Val Leu Glu Val Leu Leu Ile Phe Val Tyr Leu Asn Met Ile
                170                 175                 180

Leu Leu Tyr Leu Leu Pro Arg Cys Phe Thr Pro Gly Glu Ala Leu
                185                 190                 195

Leu Val Leu Gly Gly Ile Ser Phe Val Leu Asn Gln Leu Ile Lys
                200                 205                 210

Arg Ser Leu Thr Leu Val Glu Ser Gln Gly Asp Pro Val Asp Phe
                215                 220                 225

Phe Leu Leu Val Val Val Val Gly Met Val Leu Met Gly Ile Phe
                230                 235                 240

Phe Ser Thr Leu Phe Val Phe Met Asp Ser Gly Thr Trp Ala Ser
                245                 250                 255

Ser Ile Phe Phe His Leu Met Thr Cys Val Leu Ser Leu Gly Val
                260                 265                 270

Val Leu Pro Trp Leu His Arg Leu Ile Arg Arg Asn Pro Leu Leu
                275                 280                 285

Trp Leu Leu Gln Phe Leu Phe Gln Thr Asp Thr Arg Ile Tyr Leu
                290                 295                 300

Leu Ala Tyr Trp Ser Leu Leu Ala Thr Leu Ala Cys Leu Val Val
                305                 310                 315

Leu Tyr Gln Asn Ala Lys Arg Ser Ser Ser Glu Ser Lys Lys His
                320                 325                 330

Gln Ala Pro Thr Ile Ala Arg Lys Tyr Phe His Leu Ile Val Val
                335                 340                 345

Ala Thr Tyr Ile Pro Gly Ile Ile Phe Asp Arg Pro Leu Leu Tyr
                350                 355                 360

Val Ala Ala Thr Val Cys Leu Ala Val Phe Ile Phe Leu Glu Tyr
                365                 370                 375

Val Arg Tyr Phe Arg Ile Lys Pro Leu Gly His Thr Leu Arg Ser
                380                 385                 390

Phe Leu Ser Leu Phe Leu Asp Glu Arg Asp Ser Gly Pro Leu Ile
                395                 400                 405

Leu Thr His Ile Tyr Leu Leu Leu Gly Met Ser Leu Pro Ile Trp
                410                 415                 420

Leu Ile Pro Arg Pro Cys Thr Gln Lys Gly Ser Leu Gly Gly Ala
                425                 430                 435

Arg Ala Leu Val Pro Tyr Ala Gly Val Leu Ala Val Gly Val Gly
                440                 445                 450

Asp Thr Val Ala Ser Ile Phe Gly Ser Thr Met Gly Glu Ile Arg
                455                 460                 465

Trp Pro Gly Thr Lys Lys Thr Phe Glu Gly Thr Met Thr Ser Ile
                470                 475                 480

Phe Ala Gln Ile Ile Ser Val Ala Leu Ile Leu Ile Phe Asp Ser
                485                 490                 495

Gly Val Asp Leu Asn Tyr Ser Tyr Ala Trp Ile Leu Gly Ser Ile
                500                 505                 510

Ser Thr Val Ser Leu Leu Glu Ala Tyr Thr Thr Gln Ile Asp Asn
                515                 520                 525

Leu Leu Leu Pro Leu Tyr Leu Leu Ile Leu Leu Met Ala
                530                 535
```

-continued

<210> SEQ ID NO 51
<211> LENGTH: 3476
<212> TYPE: DNA
<213> ORGANISM: Homo Sapien

<400> SEQUENCE: 51

```
gctctatgcc gcctaccttg ctctcgccgc tgctgccgga gccgaagcag      50
agaaggcagc gggtcccgtg accgtcccga gagccccgcg ctcccgacca     100
gggggcgggg gcggccccgg ggagggcggg gcaggggcgg ggggaagaaa     150
gggggttttg tgctgcgccg ggagggccgg cgccctcttc cgaatgtcct     200
gcggccccag cctctcctca cgctcgcgca gtctccgccg cagtctcagc     250
tgcagctgca ggactgagcc gtgcacccgg aggagacccc cggaggaggc     300
gacaaacttc gcagtgccgc gacccaaccc cagccctggg tagcctgcag     350
catggcccag ctgttcctgc ccctgctggc agccctggtc ctggcccagg     400
ctcctgcagc tttagcagat gttctggaag gagacagctc agaggaccgc     450
gcttttcgcg tgcgcatcgc gggcgacgcg ccactgcagg gcgtgctcgg     500
cggcgccctc accatccctt gccacgtcca ctacctgcgg ccaccgccga     550
gccgccgggc tgtgctgggc tctccgcggg tcaagtggac tttcctgtcc     600
cggggccggg aggcagaggt gctggtggcg cggggagtgc gcgtcaaggt     650
gaacgaggcc taccggttcc gcgtggcact gcctgcgtac ccagcgtcgc     700
tcaccgacgt ctccctggcg ctgagcgagc tgcgccccaa cgactcaggt     750
atctatcgct gtgaggtcca gcacggcatc gatgacagca gcgacgctgt     800
ggaggtcaag gtcaaagggg tcgtctttct ctaccgagag ggctctgccc     850
gctatgcttt ctccttttct ggggcccagg aggcctgtgc ccgcattgga     900
gcccacatcg ccaccccgga gcagctctat gccgcctacc ttgggggcta     950
tgagcaatgt gatgctggct ggctgtcgga tcagaccgtg aggtatccca    1000
tccagacccc acgagaggcc tgttacggag acatggatgg cttccccggg    1050
gtccggaact atggtgtggt ggacccggat gacctctatg atgtgtactg    1100
ttatgctgaa gacctaaatg gagaactgtt cctgggtgac cctccagaga    1150
agctgacatt ggaggaagca cgggcgtact gccaggagcg gggtgcagag    1200
attgccacca cgggccaact gtatgcagcc tgggatggtg gcctggacca    1250
ctgcagccca gggtggctag ctgatggcag tgtgcgctac cccatcgtca    1300
cacccagcca gcgctgtggt gggggcttgc ctggtgtcaa gactctcttc    1350
ctcttcccca accagactgg cttccccaat aagcacagcc gcttcaacgt    1400
ctactgcttc cgagactcgg cccagccttc tgccatccct gaggcctcca    1450
acccagcctc caacccagcc tctgatggac tagaggctat cgtcacagtg    1500
acagagaccc tggaggaact gcagctgcct caggaagcca cagagagtga    1550
atcccgtggg gccatctact ccatccccat catggaggac ggaggaggtg    1600
gaagctccac tccagaagac ccagcagagg cccctaggac gctcctagaa    1650
tttgaaacac aatccatggt accgcccacg gggttctcag aagaggaagg    1700
taaggcattg gaggaagaag agaaatatga agatgaagaa gagaaagagg    1750
aggaagaaga agaggaggag gtggaggatg aggctctgtg ggcatggccc    1800
```

-continued

```
agcgagctca gcagcccggg ccctgaggcc tctctcccca ctgagccagc      1850

agcccaggag aagtcactct cccaggcgcc agcaagggca gtcctgcagc      1900

ctggtgcatc accacttcct gatggagagt cagaagcttc caggcctcca      1950

agggtccatg gaccacctac tgagactctg cccactccca gggagaggaa      2000

cctagcatcc ccatcacctt ccactctggt tgaggcaaga gaggtggggg      2050

aggcaactgg tggtcctgag ctatctgggg tccctcgagg agagagcgag      2100

gagacaggaa gctccgaggg tgccccttcc ctgcttccag ccacacgggc      2150

ccctgagggt accagggagc tggaggcccc ctctgaagat aattctggaa      2200

gaactgcccc agcagggacc tcagtgcagg cccagccagt gctgcccact      2250

gacagcgcca gccgaggtgg agtggccgtg gtccccgcat caggtgactg      2300

tgtccccagc ccctgccaca atggtgggac atgcttggag gaggaggaag      2350

gggtccgctg cctatgtctg cctggctatg ggggggacct gtgcgatgtt      2400

ggcctccgct tctgcaaccc cggctgggac gccttccagg gcgcctgcta      2450

caagcacttt tccacacgaa ggagctggga ggaggcagag acccagtgcc      2500

ggatgtacgg cgcgcatctg gccagcatca gcacacccga ggaacaggac      2550

ttcatcaaca accggtaccg ggagtaccag tggatcggac tcaacgacag      2600

gaccatcgaa ggcgacttct tgtggtcgga tggcgtcccc ctgctctatg      2650

agaactggaa ccctgggcag cctgacagct acttcctgtc tggagagaac      2700

tgcgtggtca tggtgtggca tgatcaggga caatggagtg acgtgccctg      2750

caactaccac ctgtcctaca cctgcaagat ggggctggtg tcctgtgggc      2800

cgccaccgga gctgcccctg gctcaagtgt tcggccgccc acggctgcgc      2850

tatgaggtgg acactgtgct tcgctaccgg tgccgggaag gactggccca      2900

gcgcaatctg ccgctgatcc gatgccaaga gaacggtcgt tgggaggccc      2950

cccagatctc ctgtgtgccc agaagacctg cccgagctct gcacccagag      3000

gaggacccag aaggacgtca ggggaggcta ctgggacgct ggaaggcgct      3050

gttgatcccc ccttccagcc ccatgccagg tccctagggg gcaaggcctt      3100

gaacactgcc ggccacagca ctgccctgtc acccaaattt tccctcacac      3150

cttgcgctcc cgccaccaca ggaagtgaca acatgacgag ggtggtgct      3200

ggagtccagg tgacagttcc tgaaggggct tctgggaaat acctaggagg      3250

ctccagccca gcccaggccc tctcccccta ccctgggcac cagatcttcc      3300

atcagggccg gagtaaatcc ctaagtgcct caactgccct ctccctggca      3350

gccatcttgt cccctctatt cctctaggga gcactgtgcc cactctttct      3400

gggttttcca agggaatggg cttgcaggat ggagtgtctg taaaatcaac      3450

aggaaataaa actgtgtatg agccca                                3476
```

<210> SEQ ID NO 52
<211> LENGTH: 911
<212> TYPE: PRT
<213> ORGANISM: Homo Sapien

<400> SEQUENCE: 52

```
Met Ala Gln Leu Phe Leu Pro Leu Leu Ala Ala Leu Val Leu Ala
  1               5                  10                  15
```

-continued

```
Gln Ala Pro Ala Ala Leu Ala Asp Val Leu Glu Gly Asp Ser Ser
                20                  25                  30

Glu Asp Arg Ala Phe Arg Val Arg Ile Ala Gly Asp Ala Pro Leu
                35                  40                  45

Gln Gly Val Leu Gly Gly Ala Leu Thr Ile Pro Cys His Val His
                50                  55                  60

Tyr Leu Arg Pro Pro Pro Ser Arg Arg Ala Val Leu Gly Ser Pro
                65                  70                  75

Arg Val Lys Trp Thr Phe Leu Ser Arg Gly Arg Glu Ala Glu Val
                80                  85                  90

Leu Val Ala Arg Gly Val Arg Val Lys Val Asn Glu Ala Tyr Arg
                95                 100                 105

Phe Arg Val Ala Leu Pro Ala Tyr Pro Ala Ser Leu Thr Asp Val
               110                 115                 120

Ser Leu Ala Leu Ser Glu Leu Arg Pro Asn Asp Ser Gly Ile Tyr
               125                 130                 135

Arg Cys Glu Val Gln His Gly Ile Asp Asp Ser Ser Asp Ala Val
               140                 145                 150

Glu Val Lys Val Lys Gly Val Val Phe Leu Tyr Arg Glu Gly Ser
               155                 160                 165

Ala Arg Tyr Ala Phe Ser Phe Ser Gly Ala Gln Glu Ala Cys Ala
               170                 175                 180

Arg Ile Gly Ala His Ile Ala Thr Pro Glu Gln Leu Tyr Ala Ala
               185                 190                 195

Tyr Leu Gly Gly Tyr Glu Gln Cys Asp Ala Gly Trp Leu Ser Asp
               200                 205                 210

Gln Thr Val Arg Tyr Pro Ile Gln Thr Pro Arg Glu Ala Cys Tyr
               215                 220                 225

Gly Asp Met Asp Gly Phe Pro Gly Val Arg Asn Tyr Gly Val Val
               230                 235                 240

Asp Pro Asp Asp Leu Tyr Asp Val Tyr Cys Tyr Ala Glu Asp Leu
               245                 250                 255

Asn Gly Glu Leu Phe Leu Gly Asp Pro Pro Glu Lys Leu Thr Leu
               260                 265                 270

Glu Glu Ala Arg Ala Tyr Cys Gln Glu Arg Gly Ala Glu Ile Ala
               275                 280                 285

Thr Thr Gly Gln Leu Tyr Ala Ala Trp Asp Gly Gly Leu Asp His
               290                 295                 300

Cys Ser Pro Gly Trp Leu Ala Asp Gly Ser Val Arg Tyr Pro Ile
               305                 310                 315

Val Thr Pro Ser Gln Arg Cys Gly Gly Gly Leu Pro Gly Val Lys
               320                 325                 330

Thr Leu Phe Leu Phe Pro Asn Gln Thr Gly Phe Pro Asn Lys His
               335                 340                 345

Ser Arg Phe Asn Val Tyr Cys Phe Arg Asp Ser Ala Gln Pro Ser
               350                 355                 360

Ala Ile Pro Glu Ala Ser Asn Pro Ala Ser Asn Pro Ala Ser Asp
               365                 370                 375

Gly Leu Glu Ala Ile Val Thr Val Thr Glu Thr Leu Glu Glu Leu
               380                 385                 390

Gln Leu Pro Gln Glu Ala Thr Glu Ser Glu Ser Arg Gly Ala Ile
               395                 400                 405
```

-continued

```
Tyr Ser Ile Pro Ile Met Glu Asp Gly Gly Gly Gly Ser Ser Thr
                410                 415                 420

Pro Glu Asp Pro Ala Glu Ala Pro Arg Thr Leu Leu Glu Phe Glu
                425                 430                 435

Thr Gln Ser Met Val Pro Pro Thr Gly Phe Ser Glu Glu Glu Gly
                440                 445                 450

Lys Ala Leu Glu Glu Glu Glu Lys Tyr Glu Asp Glu Glu Glu Lys
                455                 460                 465

Glu Glu Glu Glu Glu Glu Glu Glu Val Glu Asp Glu Ala Leu Trp
                470                 475                 480

Ala Trp Pro Ser Glu Leu Ser Ser Pro Gly Pro Glu Ala Ser Leu
                485                 490                 495

Pro Thr Glu Pro Ala Ala Gln Glu Lys Ser Leu Ser Gln Ala Pro
                500                 505                 510

Ala Arg Ala Val Leu Gln Pro Gly Ala Ser Pro Leu Pro Asp Gly
                515                 520                 525

Glu Ser Glu Ala Ser Arg Pro Pro Arg Val His Gly Pro Pro Thr
                530                 535                 540

Glu Thr Leu Pro Thr Pro Arg Glu Arg Asn Leu Ala Ser Pro Ser
                545                 550                 555

Pro Ser Thr Leu Val Glu Ala Arg Glu Val Gly Glu Ala Thr Gly
                560                 565                 570

Gly Pro Glu Leu Ser Gly Val Pro Arg Gly Glu Ser Glu Glu Thr
                575                 580                 585

Gly Ser Ser Glu Gly Ala Pro Ser Leu Leu Pro Ala Thr Arg Ala
                590                 595                 600

Pro Glu Gly Thr Arg Glu Leu Glu Ala Pro Ser Glu Asp Asn Ser
                605                 610                 615

Gly Arg Thr Ala Pro Ala Gly Thr Ser Val Gln Ala Gln Pro Val
                620                 625                 630

Leu Pro Thr Asp Ser Ala Ser Arg Gly Gly Val Ala Val Val Pro
                635                 640                 645

Ala Ser Gly Asp Cys Val Pro Ser Pro Cys His Asn Gly Gly Thr
                650                 655                 660

Cys Leu Glu Glu Glu Glu Gly Val Arg Cys Leu Cys Leu Pro Gly
                665                 670                 675

Tyr Gly Gly Asp Leu Cys Asp Val Gly Leu Arg Phe Cys Asn Pro
                680                 685                 690

Gly Trp Asp Ala Phe Gln Gly Ala Cys Tyr Lys His Phe Ser Thr
                695                 700                 705

Arg Arg Ser Trp Glu Glu Ala Glu Thr Gln Cys Arg Met Tyr Gly
                710                 715                 720

Ala His Leu Ala Ser Ile Ser Thr Pro Glu Glu Gln Asp Phe Ile
                725                 730                 735

Asn Asn Arg Tyr Arg Glu Tyr Gln Trp Ile Gly Leu Asn Asp Arg
                740                 745                 750

Thr Ile Glu Gly Asp Phe Leu Trp Ser Asp Gly Val Pro Leu Leu
                755                 760                 765

Tyr Glu Asn Trp Asn Pro Gly Gln Pro Asp Ser Tyr Phe Leu Ser
                770                 775                 780

Gly Glu Asn Cys Val Val Met Val Trp His Asp Gln Gly Gln Trp
                785                 790                 795

Ser Asp Val Pro Cys Asn Tyr His Leu Ser Tyr Thr Cys Lys Met
```

-continued

```
                800                 805                 810

Gly Leu Val Ser Cys Gly Pro Pro Pro Glu Leu Pro Leu Ala Gln
                815                 820                 825

Val Phe Gly Arg Pro Arg Leu Arg Tyr Glu Val Asp Thr Val Leu
                830                 835                 840

Arg Tyr Arg Cys Arg Glu Gly Leu Ala Gln Arg Asn Leu Pro Leu
                845                 850                 855

Ile Arg Cys Gln Glu Asn Gly Arg Trp Glu Ala Pro Gln Ile Ser
                860                 865                 870

Cys Val Pro Arg Arg Pro Ala Arg Ala Leu His Pro Glu Glu Asp
                875                 880                 885

Pro Glu Gly Arg Gln Gly Arg Leu Leu Gly Arg Trp Lys Ala Leu
                890                 895                 900

Leu Ile Pro Pro Ser Ser Pro Met Pro Gly Pro
                905                 910
```

<210> SEQ ID NO 53
<211> LENGTH: 3316
<212> TYPE: DNA
<213> ORGANISM: Homo Sapien

<400> SEQUENCE: 53

```
ctgccaggtg acagccgcca agatggggtc ttgggccctg ctgtggcctc      50

ccctgctgtt caccgggctg ctcgtccgac ccccggggac catggcccag     100

gcccagtact gctctgtgaa caaggacatc tttgaagtag aggagaacac     150

aaatgtcacc gagccgctgg tggacatcca cgtcccggag ggccaggagg     200

tgaccctcgg agccttgtcc accccctttg catttcggat ccagggaaac     250

cagctgtttc tcaacgtgac tcctgattac gaggagaagt cactgcttga     300

ggctcagctg ctgtgtcaga gcggaggcac attggtgacc cagctaaggg     350

tgttcgtgtc agtgctggac gtcaatgaca atgcccccga attccccttt     400

aagaccaagg agataagggt ggaggaggac acgaaagtga actccaccgt     450

catccctgag acgcaactgc aggctgagga ccgcgacaag gacgacattc     500

tgttctacac cctccaggaa atgacagcag gtgccagtga ctacttctcc     550

ctggtgagtg taaaccgtcc cgccctgagg ctggaccggc ccctggactt     600

ctacgagcgg ccgaacatga ccttctggct gctggtgcgg gacactccag     650

gggagaatgt ggaacccagc cacactgcca ccgccacact agtgctgaac     700

gtggtgcccg ccgacctgcg gcccccgtgg ttcctgccct gcaccttctc     750

agatggctac gtctgcattc aagctcagta ccacggggct gtccccacgg     800

ggcacatact gccatctccc ctcgtcctgc gtcccggacc catctacgct     850

gaggacggag accgcggcat caaccagccc atcatctaca gcatctttag     900

gggaaacgtg aatggtacat tcatcatcca cccagactcg ggcaacctca     950

ccgtggccag gagtgtcccc agccccatga ccttccttct gctggtgaag    1000

ggccaacagg ccgaccttgc ccgctactca gtgacccagg tcaccgtgga    1050

ggctgtggct gcggccggga gcccgccccg cttcccccag agcctgtatc    1100

gtggcaccgt ggcgcgtggc gctggagcgg gcgttgtggt caaggatgca    1150

gctgcccctt ctcagcctct gaggatccag gctcaggacc cggagttctc    1200
```

-continued

```
ggacctcaac tcggccatca catatcgaat taccaaccac tcacacttcc      1250
ggatggaggg agaggttgtg ctgaccacca ccacactggc acaggcggga      1300
gccttctacg cagaggttga ggcccacaac acggtgacct ctggcaccgc      1350
aaccacagtc attgagatac aagtttccga acaggagccc ccctccacag      1400
aggctggagg aacaactggg ccctggacca gcaccacttc cgaggtcccc      1450
agacccccctg agccctccca gggaccctcc acgaccagct ctgggggagg     1500
cacaggccct catccaccct ctggcacaac tctgaggcca ccaacctcgt      1550
ccacacccgg ggggcccccg ggtgcagaaa acagcacctc ccaccaacca      1600
gccactcccg gtggggacac agcacagacc ccaaagccag gaacctctca      1650
gccgatgccc cccggtgtgg gaaccagcac ctcccaccaa ccagccacac      1700
ccagtggggg cacagcacag accccagagc caggaacctc tcagccgatg      1750
ccccccagta tgggaaccag cacctcccac caaccagcca cacccggtgg      1800
gggcacagca cagaccccag aggcaggaac ctctcagccg atgccccccg      1850
gtatgggaac cagcacctcc caccaaccaa ccacacccgg tgggggcaca      1900
gcacagaccc cagagccagg aacctctcag ccgatgcccc tcagcaagag      1950
caccccatct tcaggtggcg gcccctcgga ggacaagcgc ttctcggtgg      2000
tggatatggc ggccctgggc ggggtgctgg gtgcgctgct gctgctggct      2050
ctccttggcc tcgccgtcct tgtccacaag cactatggcc cccggctcaa      2100
gtgctgctct ggcaaagctc cggagcccca gccccaaggc tttgacaacc      2150
aggcgttcct ccctgaccac aaggccaact gggcgcccgt ccccagcccc      2200
acgcacgacc ccaagcccgc ggaggcaccg atgcccgcag agcccgcacc      2250
ccccggccct gcctccccag gcggtgcccc tgagcccccc gcagcggccc      2300
gagctggcgg aagccccacg gcggtgaggt ccatcctgac caaggagcgg      2350
cggccggagg gcgggtacaa ggccgtctgg tttggcgagg acatcgggac      2400
ggaggcagac gtggtcgttc tcaacgcgcc caccctggac gtggatggcg      2450
ccagtgactc cggcagcggc gacgagggcg agggcgcggg gaggggtggg      2500
ggtccctacg atgcacccgg tggtgatgac tcctacatct aagtggcccc      2550
tccaccctct cccccagccg cacgggcact ggaggtctcg ctcccccagc      2600
ctccgacccg aggcagaata aagcaaggct cccgaaaccc aggccatggc      2650
gtggggcagg cgcgtgggtc cctgggggcc ccattcactc agtcccctgt      2700
cgtcattagc gcttgagccc aggtgtgcag atgaggcggt gggtctggcc      2750
acgctgtccc caccccaagg ctgcagcact tcccgtaaac cacctgcagt      2800
gcccgccgcc ttcccgaggc tctgtgccag ctagtctggg aagttcctct      2850
cccgctctaa ccacagcccg aggggggctc ccctccccccg acctgcacca     2900
gagatctcag gcacccggct caactcagac ctcccgctcc cgaccctaca      2950
cagagattgc ctggggaggc tgaggagccg atgcaaaccc ccaaggcgac      3000
gcacttggga gccggtggtc tcaaacacct gccgggggtc ctagtcccct      3050
tctgaaatct acatgcttgg gttggagcgc agcagtaaac accctgccca      3100
gtgacctgga ctgaggcgcg ctgggggtgg gtgcgccgtg tggcctgagc      3150
aggagccaga ccaggaggcc taggggtgag agacacattc cctcgctgc       3200
```

-continued

```
tcccaaagcc agagcccagg ctgggcgccc atgcccagaa ccatcaaggg           3250

atcccttgcg gcttgtcagc actttcccta atggaaatac accattaatt           3300

cctttccaaa tgtttt                                                3316


<210> SEQ ID NO 54
<211> LENGTH: 839
<212> TYPE: PRT
<213> ORGANISM: Homo Sapien

<400> SEQUENCE: 54

Met Gly Ser Trp Ala Leu Leu Trp Pro Pro Leu Leu Phe Thr Gly
  1               5                  10                  15

Leu Leu Val Arg Pro Pro Gly Thr Met Ala Gln Ala Gln Tyr Cys
                 20                  25                  30

Ser Val Asn Lys Asp Ile Phe Glu Val Glu Glu Asn Thr Asn Val
                 35                  40                  45

Thr Glu Pro Leu Val Asp Ile His Val Pro Glu Gly Gln Glu Val
                 50                  55                  60

Thr Leu Gly Ala Leu Ser Thr Pro Phe Ala Phe Arg Ile Gln Gly
                 65                  70                  75

Asn Gln Leu Phe Leu Asn Val Thr Pro Asp Tyr Glu Glu Lys Ser
                 80                  85                  90

Leu Leu Glu Ala Gln Leu Leu Cys Gln Ser Gly Gly Thr Leu Val
                 95                 100                 105

Thr Gln Leu Arg Val Phe Val Ser Val Leu Asp Val Asn Asp Asn
                110                 115                 120

Ala Pro Glu Phe Pro Phe Lys Thr Lys Glu Ile Arg Val Glu Glu
                125                 130                 135

Asp Thr Lys Val Asn Ser Thr Val Ile Pro Glu Thr Gln Leu Gln
                140                 145                 150

Ala Glu Asp Arg Asp Lys Asp Asp Ile Leu Phe Tyr Thr Leu Gln
                155                 160                 165

Glu Met Thr Ala Gly Ala Ser Asp Tyr Phe Ser Leu Val Ser Val
                170                 175                 180

Asn Arg Pro Ala Leu Arg Leu Asp Arg Pro Leu Asp Phe Tyr Glu
                185                 190                 195

Arg Pro Asn Met Thr Phe Trp Leu Leu Val Arg Asp Thr Pro Gly
                200                 205                 210

Glu Asn Val Glu Pro Ser His Thr Ala Thr Ala Thr Leu Val Leu
                215                 220                 225

Asn Val Val Pro Ala Asp Leu Arg Pro Pro Trp Phe Leu Pro Cys
                230                 235                 240

Thr Phe Ser Asp Gly Tyr Val Cys Ile Gln Ala Gln Tyr His Gly
                245                 250                 255

Ala Val Pro Thr Gly His Ile Leu Pro Ser Pro Leu Val Leu Arg
                260                 265                 270

Pro Gly Pro Ile Tyr Ala Glu Asp Gly Asp Arg Gly Ile Asn Gln
                275                 280                 285

Pro Ile Ile Tyr Ser Ile Phe Arg Gly Asn Val Asn Gly Thr Phe
                290                 295                 300

Ile Ile His Pro Asp Ser Gly Asn Leu Thr Val Ala Arg Ser Val
                305                 310                 315

Pro Ser Pro Met Thr Phe Leu Leu Leu Val Lys Gly Gln Gln Ala
```

-continued

```
                320                 325                 330

Asp Leu Ala Arg Tyr Ser Val Thr Gln Val Thr Val Glu Ala Val
                335                 340                 345

Ala Ala Ala Gly Ser Pro Pro Arg Phe Pro Gln Ser Leu Tyr Arg
                350                 355                 360

Gly Thr Val Ala Arg Gly Ala Gly Ala Gly Val Val Val Lys Asp
                365                 370                 375

Ala Ala Ala Pro Ser Gln Pro Leu Arg Ile Gln Ala Gln Asp Pro
                380                 385                 390

Glu Phe Ser Asp Leu Asn Ser Ala Ile Thr Tyr Arg Ile Thr Asn
                395                 400                 405

His Ser His Phe Arg Met Glu Gly Glu Val Val Leu Thr Thr Thr
                410                 415                 420

Thr Leu Ala Gln Ala Gly Ala Phe Tyr Ala Glu Val Glu Ala His
                425                 430                 435

Asn Thr Val Thr Ser Gly Thr Ala Thr Thr Val Ile Glu Ile Gln
                440                 445                 450

Val Ser Glu Gln Glu Pro Pro Ser Thr Glu Ala Gly Gly Thr Thr
                455                 460                 465

Gly Pro Trp Thr Ser Thr Thr Ser Glu Val Pro Arg Pro Pro Glu
                470                 475                 480

Pro Ser Gln Gly Pro Ser Thr Thr Ser Ser Gly Gly Gly Thr Gly
                485                 490                 495

Pro His Pro Pro Ser Gly Thr Thr Leu Arg Pro Pro Thr Ser Ser
                500                 505                 510

Thr Pro Gly Gly Pro Pro Gly Ala Glu Asn Ser Thr Ser His Gln
                515                 520                 525

Pro Ala Thr Pro Gly Gly Asp Thr Ala Gln Thr Pro Lys Pro Gly
                530                 535                 540

Thr Ser Gln Pro Met Pro Pro Gly Val Gly Thr Ser Thr Ser His
                545                 550                 555

Gln Pro Ala Thr Pro Ser Gly Gly Thr Ala Gln Thr Pro Glu Pro
                560                 565                 570

Gly Thr Ser Gln Pro Met Pro Pro Ser Met Gly Thr Ser Thr Ser
                575                 580                 585

His Gln Pro Ala Thr Pro Gly Gly Gly Thr Ala Gln Thr Pro Glu
                590                 595                 600

Ala Gly Thr Ser Gln Pro Met Pro Pro Gly Met Gly Thr Ser Thr
                605                 610                 615

Ser His Gln Pro Thr Thr Pro Gly Gly Gly Thr Ala Gln Thr Pro
                620                 625                 630

Glu Pro Gly Thr Ser Gln Pro Met Pro Leu Ser Lys Ser Thr Pro
                635                 640                 645

Ser Ser Gly Gly Gly Pro Ser Glu Asp Lys Arg Phe Ser Val Val
                650                 655                 660

Asp Met Ala Ala Leu Gly Gly Val Leu Gly Ala Leu Leu Leu Leu
                665                 670                 675

Ala Leu Leu Gly Leu Ala Val Leu Val His Lys His Tyr Gly Pro
                680                 685                 690

Arg Leu Lys Cys Cys Ser Gly Lys Ala Pro Glu Pro Gln Pro Gln
                695                 700                 705

Gly Phe Asp Asn Gln Ala Phe Leu Pro Asp His Lys Ala Asn Trp
                710                 715                 720
```

-continued

```
Ala Pro Val Pro Ser Pro Thr His Asp Pro Lys Pro Ala Glu Ala
                725                 730                 735

Pro Met Pro Ala Glu Pro Ala Pro Pro Gly Pro Ala Ser Pro Gly
                740                 745                 750

Gly Ala Pro Glu Pro Pro Ala Ala Ala Arg Ala Gly Gly Ser Pro
                755                 760                 765

Thr Ala Val Arg Ser Ile Leu Thr Lys Glu Arg Arg Pro Glu Gly
                770                 775                 780

Gly Tyr Lys Ala Val Trp Phe Gly Glu Asp Ile Gly Thr Glu Ala
                785                 790                 795

Asp Val Val Val Leu Asn Ala Pro Thr Leu Asp Val Asp Gly Ala
                800                 805                 810

Ser Asp Ser Gly Ser Gly Asp Glu Gly Glu Gly Ala Gly Arg Gly
                815                 820                 825

Gly Gly Pro Tyr Asp Ala Pro Gly Gly Asp Asp Ser Tyr Ile
                830                 835
```

<210> SEQ ID NO 55
<211> LENGTH: 3846
<212> TYPE: DNA
<213> ORGANISM: Homo Sapien

<400> SEQUENCE: 55

```
gcagctgggt tctcccggtt cccttgggca ggtgcagggt cgggttcaaa          50
gcctccggaa cgcgttttgg cctgatttga ggagggggc ggggagggac          100
ctgcggcttg cggccccgcc cccttctccg gctcgcagcc gaccggtaag          150
cccgcctcct ccctcggccg gccctggggc cgtgtccgcc gggcaactcc          200
agccgaggcc tgggcttctg cctgcaggtg tctgcggcga ggcccctagg          250
gtacagcccg atttggcccc atggtgggtt tcggggccaa ccggcgggct          300
ggccgcctgc cctctctcgt gctggtggtg ctgctggtgg tgatcgtcgt          350
cctcgccttc aactactgga gcatctcctc ccgccacgtc ctgcttcagg          400
aggaggtggc cgagctgcag ggccaggtcc agcgcaccga agtggcccgc          450
gggcggctgg aaaagcgcaa ttcggacctc ttgctgttgg tggacacgca          500
caagaaacag atcgaccaga aggaggccga ctacggccgc ctcagcagcc          550
ggctgcaggc cagagagggc ctcgggaaga gatgcgagga tgacaaggtt          600
aaactacaga acaacatatc gtatcagatg gcagacatac atcatttaaa          650
ggagcaactt gctgagcttc gtcaggaatt tcttcgacaa gaagaccagc          700
ttcaggacta taggaagaac aatacttacc ttgtgaagag gttagaatat          750
gaaagttttc agtgtggaca gcagatgaag gaattgagag cacagcatga          800
agaaaatatt aaaaagttag cagaccagtt tttagaggaa caaaagcaag          850
agacccaaaa gattcaatca aatgatggaa aggaattgga tataaacaat          900
caagtagtac ctaaaaatat tccaaaagta gctgagaatg ttgcagataa          950
gaatgaagaa ccctcaagca atcatattcc acatgggaaa gaacaaatca         1000
aaagaggtgg tgatgcaggg atgcctggaa tagaagagaa tgacctagca         1050
aaagttgatg atcttccccc tgctttaagg aagcctccta tttcagtttc         1100
tcaacatgaa agtcatcaag caatctccca tcttccaact ggacaacctc         1150
```

-continued

```
tctccccaaa tatgcctcca gattcacaca taaaccacaa tggaaacccc        1200
ggtacttcaa aacagaatcc ttccagtcct cttcagcgtt taattccagg        1250
ctcaaacttg gacagtgaac ccagaattca aacagatata ctaaagcagg        1300
ctaccaagga cagagtcagt gatttccata aattgaagca aaatgatgaa        1350
gaacgagagc ttcaaatgga tcctgcagac tatggaaagc aacatttcaa        1400
tgatgtcctt taagtcctaa aggaatgctt cagaaaacct aaagtgctgt        1450
aaaatgaaat cattctactt tgtcctttct gacttttgtt gtaaagacga        1500
attgtatcag ttgtaaagat acattgagat agaattaagg aaaaacttta        1550
atgaaggaat gtacccatgt acatatgtga actttttcat attgtattat        1600
caaggtatag actttttttgg ttatgataca gttaagccaa aaacagctaa       1650
tctttgcatc taaagcaaac taatgtatat ttcacatttt attgagccga        1700
cttatttcca caaatagata aacaggacaa aatagttgta caggttatat        1750
gtggcatagc ataaccacag taagaacaga acagatattc agcagaaaac        1800
tttttatact ctaattcttt tttttttttt tttgagacag agttttagtc        1850
ttgtttccca ggctggagtg caatggcaca atcttggctc actgcaacct        1900
ccgcctcctg ggttcaggca attttcctgc ctcagcctcc caagtagctg        1950
ggattacagg cacccaccac catgcccagc taatttttgt atttttaata        2000
gagagctaat aattgtatat ttaataaaga cgggtttcac catgttggcc        2050
aggctggtct tgaactcctg acctcaggtg atcctcctgc attggcctcc        2100
caaagtgctg gaattccagg catgagccac tgcgcccagt ctacacacta        2150
attcttgtta gcccaacagc tgttctgttc tatctacccc tcatttcacg        2200
ctcaaggagt catacctaga atagttacac acaagaggga aactggaagc        2250
caaacactgt acagtattgt gtagaaagtc acctccctac tccttttatt        2300
ttacatgagt gctgatgtgt tttggcagat gagctttcag ctgaggcctg        2350
atggaaattg agataacctg caaagacata acagtattta tgagttatat        2400
cttagttctt gaaattgtgg aatgcatgat tgacaatata tttttaattt        2450
ttattttttc aagtaatacc agtactgttt aactatagcc agaactggct        2500
aaaattttta tattttcaga gttgaagttg gtgaagacat tcatgattta        2550
aacaccagat cctgaaaggg gttaaatcta ctttgaaatg aatctgcaat        2600
cagtatttca aagcttttct ggtaatttta gtgatcttat ttgattagac        2650
tttttcagaa gtactaaata aggaatttta acaggttttt attaatgcac        2700
agataaatag aagtacagtg aggtctatag ccattttatt aaaatagctt        2750
aaaagtttgt aaaaaaatga atctttgtaa ttacttaata tgttagttaa        2800
gaacccgtca agcttatatt tgctagactt acaaattatt ttaaatgcat        2850
ttatcttttt tgacactatt cagtggaatg tgtaagctag ctaattcttg        2900
ttttctgatt taaagcactt ttaaatctta tcctgccccc taaaaacaaa        2950
aggttttgat cacaagggga aatttaagat tgttaaccct gtttttcaga        3000
agggctactg ttaattgcac ataaacatga aatgtgtttt cccctgtgta        3050
ctaacacatt ctaggcaaaa ttcaaactta tagtggtaaa gaaacaggtt        3100
gttcacttgc tgaggtgcaa aaattcttaa gacttctgtt tgaaattgct        3150
```

-continued

```
caatgactag gaaaagatgt agtagtttac taaaattgtt tttctaccat       3200

atcaaattaa acaattcatg cctttatagg gtcaggccta caatgaatag       3250

gtatggtggt ttcacagaat tttaaaatag agttaaaggg aagtgatgta       3300

catttcgggg gcattagggt agggagatga atcaaaaaat acccctagta       3350

atgctttata ttttaatact gcaaaagctt tacaaatgga aaccatgcaa       3400

ttacctgcct tagttctttt gtcataaaaa caatcacttg gttggttgta       3450

ttgtagctat tacttataca gcaacatttc ttcaattagc agtctagaca       3500

ttttataaac agaaatcttg gaccaattga taatatttct gactgtatta       3550

atattttagt gctataaaat actatgtgaa tctcttaaaa atctgacatt       3600

ttacagtctg tattagacat actgttttta taatgtttta cttctgcctt       3650

aagatttagg ttttttaaat gtatttttgc cctgaattaa gtgttaattt       3700

gatggaaact ctgcttttaa aatcatcatt tactgggttc taataaatta       3750

aaaattaaac ttgaaaaaaa aaaaaaaaaa aaaaaaaaaa aaaaaaaaaa       3800

aaaaaaaaaa aaaaaaaaaa aaaaaaaaaa aaaaaaaaaa aaaaaa           3846
```

```
<210> SEQ ID NO 56
<211> LENGTH: 380
<212> TYPE: PRT
<213> ORGANISM: Homo Sapien

<400> SEQUENCE: 56

Met Val Gly Phe Gly Ala Asn Arg Arg Ala Gly Arg Leu Pro Ser
  1               5                  10                  15

Leu Val Leu Val Val Leu Leu Val Val Ile Val Val Leu Ala Phe
                 20                  25                  30

Asn Tyr Trp Ser Ile Ser Ser Arg His Val Leu Leu Gln Glu Glu
                 35                  40                  45

Val Ala Glu Leu Gln Gly Gln Val Gln Arg Thr Glu Val Ala Arg
                 50                  55                  60

Gly Arg Leu Glu Lys Arg Asn Ser Asp Leu Leu Leu Leu Val Asp
                 65                  70                  75

Thr His Lys Lys Gln Ile Asp Gln Lys Glu Ala Asp Tyr Gly Arg
                 80                  85                  90

Leu Ser Ser Arg Leu Gln Ala Arg Glu Gly Leu Gly Lys Arg Cys
                 95                 100                 105

Glu Asp Asp Lys Val Lys Leu Gln Asn Asn Ile Ser Tyr Gln Met
                110                 115                 120

Ala Asp Ile His His Leu Lys Glu Gln Leu Ala Glu Leu Arg Gln
                125                 130                 135

Glu Phe Leu Arg Gln Glu Asp Gln Leu Gln Asp Tyr Arg Lys Asn
                140                 145                 150

Asn Thr Tyr Leu Val Lys Arg Leu Glu Tyr Glu Ser Phe Gln Cys
                155                 160                 165

Gly Gln Gln Met Lys Glu Leu Arg Ala Gln His Glu Glu Asn Ile
                170                 175                 180

Lys Lys Leu Ala Asp Gln Phe Leu Glu Glu Gln Lys Gln Glu Thr
                185                 190                 195

Gln Lys Ile Gln Ser Asn Asp Gly Lys Glu Leu Asp Ile Asn Asn
                200                 205                 210
```

-continued

```
Gln Val Val Pro Lys Asn Ile Pro Lys Val Ala Glu Asn Val Ala
                215                 220                 225

Asp Lys Asn Glu Glu Pro Ser Ser Asn His Ile Pro His Gly Lys
                230                 235                 240

Glu Gln Ile Lys Arg Gly Gly Asp Ala Gly Met Pro Gly Ile Glu
                245                 250                 255

Glu Asn Asp Leu Ala Lys Val Asp Asp Leu Pro Pro Ala Leu Arg
                260                 265                 270

Lys Pro Pro Ile Ser Val Ser Gln His Glu Ser His Gln Ala Ile
                275                 280                 285

Ser His Leu Pro Thr Gly Gln Pro Leu Ser Pro Asn Met Pro Pro
                290                 295                 300

Asp Ser His Ile Asn His Asn Gly Asn Pro Gly Thr Ser Lys Gln
                305                 310                 315

Asn Pro Ser Ser Pro Leu Gln Arg Leu Ile Pro Gly Ser Asn Leu
                320                 325                 330

Asp Ser Glu Pro Arg Ile Gln Thr Asp Ile Leu Lys Gln Ala Thr
                335                 340                 345

Lys Asp Arg Val Ser Asp Phe His Lys Leu Lys Gln Asn Asp Glu
                350                 355                 360

Glu Arg Glu Leu Gln Met Asp Pro Ala Asp Tyr Gly Lys Gln His
                365                 370                 375

Phe Asn Asp Val Leu
                380
```

<210> SEQ ID NO 57
<211> LENGTH: 841
<212> TYPE: DNA
<213> ORGANISM: Homo Sapien

<400> SEQUENCE: 57

```
ggatgggcga gcagtctgaa tgccagaatg gataaccgtt ttgctacagc        50

atttgtaatt gcttgtgtgc ttagcctcat ttccaccatc tacatggcag       100

cctccattgg cacagacttc tggtatgaat atcgaagtcc agttcaagaa       150

aattccagtg atttgaataa aagcatctgg gatgaattca ttagtgatga       200

ggcagatgaa aagacttata atgatgcact tttcgatac aatggcacag        250

tgggattgtg gagacggtgt atcaccatac ccaaaaacat gcattggtat       300

agcccaccag aaaggacaga gtcatttgat gtggtcacaa aatgtgtgag       350

tttcacacta actgagcagt tcatggagaa atttgttgat cccggaaacc       400

acaatagcgg gattgatctc cttaggacct atctttggcg ttgccagttc       450

cttttacctt ttgtgagttt aggtttgatg tgctttgggg ctttgatcgg       500

actttgtgct tgcatttgcc gaagcttata tcccaccatt gccacgggca       550

ttctccatct ccttgcagat accatgctgt gaagtccagg ccacatggag       600

gtgtcctgtg tagatgctcc agctgaaatc ccaagctaag ctcccaactg       650

acagccaaca tcatttccag ccatgtgtgg gagccatcct ggatgtccag       700

ccttaacaag ccttcagagg acttcagcca cagctattat cttactacat       750

ccttgtgaga ctctaataaa gaaccaacta gctgagccca atcaacctat       800

ggaactgata gaaataaaat gaattgttgt tttgtgccgt t                841
```

-continued

<210> SEQ ID NO 58
<211> LENGTH: 184
<212> TYPE: PRT
<213> ORGANISM: Homo Sapien

<400> SEQUENCE: 58

```
Met Asp Asn Arg Phe Ala Thr Ala Phe Val Ile Ala Cys Val Leu
  1               5                  10                  15

Ser Leu Ile Ser Thr Ile Tyr Met Ala Ala Ser Ile Gly Thr Asp
                 20                  25                  30

Phe Trp Tyr Glu Tyr Arg Ser Pro Val Gln Glu Asn Ser Ser Asp
                 35                  40                  45

Leu Asn Lys Ser Ile Trp Asp Glu Phe Ile Ser Asp Glu Ala Asp
                 50                  55                  60

Glu Lys Thr Tyr Asn Asp Ala Leu Phe Arg Tyr Asn Gly Thr Val
                 65                  70                  75

Gly Leu Trp Arg Arg Cys Ile Thr Ile Pro Lys Asn Met His Trp
                 80                  85                  90

Tyr Ser Pro Pro Glu Arg Thr Glu Ser Phe Asp Val Val Thr Lys
                 95                 100                 105

Cys Val Ser Phe Thr Leu Thr Glu Gln Phe Met Glu Lys Phe Val
                110                 115                 120

Asp Pro Gly Asn His Asn Ser Gly Ile Asp Leu Leu Arg Thr Tyr
                125                 130                 135

Leu Trp Arg Cys Gln Phe Leu Leu Pro Phe Val Ser Leu Gly Leu
                140                 145                 150

Met Cys Phe Gly Ala Leu Ile Gly Leu Cys Ala Cys Ile Cys Arg
                155                 160                 165

Ser Leu Tyr Pro Thr Ile Ala Thr Gly Ile Leu His Leu Leu Ala
                170                 175                 180

Asp Thr Met Leu
```

<210> SEQ ID NO 59
<211> LENGTH: 997
<212> TYPE: DNA
<213> ORGANISM: Homo Sapien

<400> SEQUENCE: 59

```
gcgtggacac cacctcagcc cactgagcag gagtcacagc acgaagacca         50

agcgcaaagc gacccctgcc ctccatcctg actgctcctc ctaagagaga        100

tggcaccggc cagagcagga ttctgccccc ttctgctgct tctgctgctg        150

gggctgtggg tggcagagat cccagtcagt gccaagccca agggcatgac        200

ctcatcacag tggtttaaaa ttcagcacat gcagcccagc cctcaagcat        250

gcaactcagc catgaaaaac attaacaagc acacaaaacg gtgcaaagac        300

ctcaacacct tcctgcacga gcctttctcc agtgtggccg ccacctgcca        350

gacccccaaa atagcctgca agaatggcga taaaaactgc caccagagcc        400

acgggcccgt gtccctgacc atgtgtaagc tcacctcagg gaagtatccg        450

aactgcaggt acaaagagaa gcgacagaac aagtcttacg tagtggcctg        500

taagcctccc cagaaaaagg actctcagca attccacctg gttcctgtac        550

acttggacag agtcctttag gtttccagac tggcttgctc tttggctgac        600

cttcaattcc ctctccagga ctccgcacca ctcccctaca cccagagcat        650
```

-continued

```
tctcttcccc tcatctcttg gggctgttcc tggttcagcc tctgctggga         700

ggctgaagct gacactctgg tgagctgagc tctagaggga tggcttttca         750

tctttttgtt gctgttttcc cagatgctta tccccaagaa acagcaagct         800

caggtctgtg ggttccctgg tctatgccat tgcacatgtc tcccctgccc         850

cctggcatta gggcagcatg acaaggagag gaaataaatg gaaagggggc         900

aaaaaaaaaa aaaaaaaaaa aaaaaaaaaa aaaaaaaaaa aaaaaaaaaa         950

aaaaaaaaaa aaaaaaaaaa aaaaaaaaaa aaaaaaaaaa aaaaaaa            997
```

<210> SEQ ID NO 60
<211> LENGTH: 156
<212> TYPE: PRT
<213> ORGANISM: Homo Sapien

<400> SEQUENCE: 60

```
Met Ala Pro Ala Arg Ala Gly Phe Cys Pro Leu Leu Leu Leu Leu
  1               5                  10                  15

Leu Leu Gly Leu Trp Val Ala Glu Ile Pro Val Ser Ala Lys Pro
                 20                  25                  30

Lys Gly Met Thr Ser Ser Gln Trp Phe Lys Ile Gln His Met Gln
                 35                  40                  45

Pro Ser Pro Gln Ala Cys Asn Ser Ala Met Lys Asn Ile Asn Lys
                 50                  55                  60

His Thr Lys Arg Cys Lys Asp Leu Asn Thr Phe Leu His Glu Pro
                 65                  70                  75

Phe Ser Ser Val Ala Ala Thr Cys Gln Thr Pro Lys Ile Ala Cys
                 80                  85                  90

Lys Asn Gly Asp Lys Asn Cys His Gln Ser His Gly Pro Val Ser
                 95                 100                 105

Leu Thr Met Cys Lys Leu Thr Ser Gly Lys Tyr Pro Asn Cys Arg
                110                 115                 120

Tyr Lys Glu Lys Arg Gln Asn Lys Ser Tyr Val Val Ala Cys Lys
                125                 130                 135

Pro Pro Gln Lys Lys Asp Ser Gln Gln Phe His Leu Val Pro Val
                140                 145                 150

His Leu Asp Arg Val Leu
                155
```

<210> SEQ ID NO 61
<211> LENGTH: 520
<212> TYPE: DNA
<213> ORGANISM: Homo Sapien

<400> SEQUENCE: 61

```
cgggtcatgc gccgccgcct gtggctgggc ctggcctggc tgctgctggc          50

gcgggcgccg gacgccgcgg gaaccccgag cgcgtcgcgg ggaccgcgca         100

gctacccgca cctggagggc gacgtgcgct ggcggcgcct cttctcctcc         150

actcacttct tcctgcgcgt ggatcccggc ggccgcgtgc agggcacccg         200

ctggcgccac ggccaggaca gcatcctgga gatccgctct gtacacgtgg         250

gcgtcgtggt catcaaagca gtgtcctcag gcttctacgt ggccatgaac         300

cgccggggcc gcctctacgg gtcgcgactc tacaccgtgg actgcaggtt         350

ccgggagcgc atcgaagaga acggccacaa cacctacgcc tcacagcgct         400
```

-continued

```
ggcgccgccg cggccagccc atgttcctgg cgctggacag gaggggggg          450

ccccggccag gcggccggac gcggcggtac cacctgtccg cccacttcct         500

gcccgtcctg gtctcctgag                                          520
```

```
<210> SEQ ID NO 62
<211> LENGTH: 170
<212> TYPE: PRT
<213> ORGANISM: Homo Sapien

<400> SEQUENCE: 62

Met Arg Arg Arg Leu Trp Leu Gly Leu Ala Trp Leu Leu Leu Ala
  1               5                  10                  15

Arg Ala Pro Asp Ala Ala Gly Thr Pro Ser Ala Ser Arg Gly Pro
                 20                  25                  30

Arg Ser Tyr Pro His Leu Glu Gly Asp Val Arg Trp Arg Arg Leu
                 35                  40                  45

Phe Ser Ser Thr His Phe Phe Leu Arg Val Asp Pro Gly Gly Arg
                 50                  55                  60

Val Gln Gly Thr Arg Trp Arg His Gly Gln Asp Ser Ile Leu Glu
                 65                  70                  75

Ile Arg Ser Val His Val Gly Val Val Val Ile Lys Ala Val Ser
                 80                  85                  90

Ser Gly Phe Tyr Val Ala Met Asn Arg Arg Gly Arg Leu Tyr Gly
                 95                 100                 105

Ser Arg Leu Tyr Thr Val Asp Cys Arg Phe Arg Glu Arg Ile Glu
                110                 115                 120

Glu Asn Gly His Asn Thr Tyr Ala Ser Gln Arg Trp Arg Arg Arg
                125                 130                 135

Gly Gln Pro Met Phe Leu Ala Leu Asp Arg Arg Gly Gly Pro Arg
                140                 145                 150

Pro Gly Gly Arg Thr Arg Arg Tyr His Leu Ser Ala His Phe Leu
                155                 160                 165

Pro Val Leu Val Ser
                170
```

```
<210> SEQ ID NO 63
<211> LENGTH: 2329
<212> TYPE: DNA
<213> ORGANISM: Homo Sapien

<400> SEQUENCE: 63

atccctcgac ctcgacccac gcgtccgctg gaaggtggcg tgccctcctc          50

tggctggtac catgcagctc ccactggccc tgtgtctcgt ctgcctgctg         100

gtacacacag ccttccgtgt agtggagggc caggggtggc aggcgttcaa         150

gaatgatgcc acggaaatca tccccgagct cggagagtac cccgagcctc         200

caccggagct ggagaacaac aagaccatga accgggcgga gaacggaggg         250

cggcctcccc accacccctt tgagaccaaa gacgtgtccg agtacagctg         300

ccgcgagctg cacttcaccc gctacgtgac cgatgggccg tgccgcagcg         350

ccaagccggt caccgagctg gtgtgctccg gccagtgcgg cccggcgcgc         400

ctgctgccca acgccatcgg ccgcggcaag tggtggcgac ctagtgggcc         450

cgacttccgc tgcatccccg accgctaccg cgcgcagcgc gtgcagctgc         500

tgtgtcccgg tggtgaggcg ccgcgcgcgc gcaaggtgcg cctggtggcc         550
```

-continued

```
tcgtgcaagt gcaagcgcct cacccgcttc cacaaccagt cggagctcaa       600
ggacttcggg accgaggccg ctcggccgca gaagggccgg aagccgcggc       650
cccgcgcccg gagcgccaaa gccaaccagg ccgagctgga gaacgcctac       700
tagagcccgc ccgcgcccct ccccaccggc gggcgccccg gccctgaacc       750
cgcgccccac atttctgtcc tctgcgcgtg gtttgattgt ttatatttca       800
ttgtaaatgc ctgcaaccca gggcaggggg ctgagacctt ccaggccctg       850
aggaatcccg ggcgccggca aggccccct cagcccgcca gctgaggggt        900
cccacggggc aggggaggga attgagagtc acagacactg agccacgcag       950
ccccgcctct ggggccgcct acctttgctg gtcccacttc agaggaggca      1000
gaaatggaag cattttcacc gccctggggt tttaagggag cggtgtggga      1050
gtgggaaagt ccagggactg gttaagaaag ttggataaga ttccccccttg     1100
cacctcgctg cccatcagaa agcctgaggc gtgcccagag cacaagactg      1150
ggggcaactg tagatgtggt ttctagtcct ggctctgcca ctaacttcct      1200
gtgtaacctt gaactacaca attctccttc gggacctcaa tttccacttt      1250
gtaaaatgag ggtggaggtg ggaataggat ctcgaggaga ctattggcat      1300
atgattccaa ggactccagt gccttttgaa tgggcagagg tgagagagag      1350
agagagaaag agagagaatg aatgcagttg cattgattca gtgccaaggt      1400
cacttccaga attcagagtt gtgatgctct cttctgacag ccaaagatga      1450
aaaacaaaca gaaaaaaaaa agtaaagagt ctatttatgg ctgacatatt      1500
tacggctgac aaactcctgg aagaagctat gctgcttccc agcctggctt      1550
ccccggatgt ttggctacct ccacccctcc atctcaaaga aataacatca      1600
tccattgggg tagaaaagga gagggtccga gggtggtggg agggatagaa      1650
atcacatccg ccccaacttc ccaaagagca gcatccctcc cccgacccat      1700
agccatgttt taaagtcacc ttccgaagag aagtgaaagg ttcaaggaca      1750
ctggccttgc aggcccgagg gagcagccat cacaaactca cagaccagca      1800
catccctttt gagacaccgc cttctgccca ccactcacgg acacatttct      1850
gcctagaaaa cagcttctta ctgctcttac atgtgatggc atatcttaca      1900
ctaaaagaat attattgggg gaaaaactac aagtgctgta catatgctga      1950
gaaactgcag agcataatag ctgccaccca aaaatctttt tgaaaatcat      2000
ttccagacaa cctcttactt tctgtgtagt ttttaattgt taaaaaaaaa      2050
aagttttaaa cagaagcaca tgacatatga aagcctgcag gactggtcgt      2100
tttttggca attcttccac gtgggacttg tccacaagaa tgaaagtagt       2150
ggtttttaaa gagttaagtt acatatttat tttctcactt aagttattta      2200
tgcaaaagtt tttcttgtag agaatgacaa tgttaatatt gctttatgaa      2250
ttaacagtct gttcttccag agtccagaga cattgttaat aaagacaatg      2300
aatcatgaaa aaaaaaaaaa aaaaaaaaa                             2329
```

<210> SEQ ID NO 64
<211> LENGTH: 213
<212> TYPE: PRT
<213> ORGANISM: Homo Sapien -continued

<400> SEQUENCE: 64

```
Met Gln Leu Pro Leu Ala Leu Cys Leu Val Cys Leu Leu Val His
  1               5                  10                  15

Thr Ala Phe Arg Val Val Glu Gly Gln Gly Trp Gln Ala Phe Lys
                 20                  25                  30

Asn Asp Ala Thr Glu Ile Ile Pro Glu Leu Gly Glu Tyr Pro Glu
                 35                  40                  45

Pro Pro Pro Glu Leu Glu Asn Asn Lys Thr Met Asn Arg Ala Glu
                 50                  55                  60

Asn Gly Gly Arg Pro Pro His His Pro Phe Glu Thr Lys Asp Val
                 65                  70                  75

Ser Glu Tyr Ser Cys Arg Glu Leu His Phe Thr Arg Tyr Val Thr
                 80                  85                  90

Asp Gly Pro Cys Arg Ser Ala Lys Pro Val Thr Glu Leu Val Cys
                 95                 100                 105

Ser Gly Gln Cys Gly Pro Ala Arg Leu Leu Pro Asn Ala Ile Gly
                110                 115                 120

Arg Gly Lys Trp Trp Arg Pro Ser Gly Pro Asp Phe Arg Cys Ile
                125                 130                 135

Pro Asp Arg Tyr Arg Ala Gln Arg Val Gln Leu Leu Cys Pro Gly
                140                 145                 150

Gly Glu Ala Pro Arg Ala Arg Lys Val Arg Leu Val Ala Ser Cys
                155                 160                 165

Lys Cys Lys Arg Leu Thr Arg Phe His Asn Gln Ser Glu Leu Lys
                170                 175                 180

Asp Phe Gly Thr Glu Ala Ala Arg Pro Gln Lys Gly Arg Lys Pro
                185                 190                 195

Arg Pro Arg Ala Arg Ser Ala Lys Ala Asn Gln Ala Glu Leu Glu
                200                 205                 210

Asn Ala Tyr
```

<210> SEQ ID NO 65
<211> LENGTH: 2663
<212> TYPE: DNA
<213> ORGANISM: Homo Sapien

<400> SEQUENCE: 65

```
cccactcggc ggtttggcgg gagggagggg ctttgcgcag gccccgctcc        50
cgccccgcct ccatgcggcc cgccccgatt gcgctgtggc tgcgcctggt       100
cttggccctg gcccttgtcc gccccgggc tgtggggtgg gccccggtcc        150
gagcccccat ctatgtcagc agctgggccg tccaggtgtc ccagggtaac       200
cgggaggtcg agcgcctggc acgcaaattc ggcttcgtca acctggggcc       250
gatcttctct gacgggcagt actttcacct gcggcaccgg ggcgtggtcc       300
agcagtccct gaccccgcac tggggccacc gcctgcacct gaagaaaaac       350
cccaaggtgc agtggttcca gcagcagacg ctgcagcggc gggtgaaacg       400
ctctgtcgtg gtgcccacgg acccctggtt ctccaagcag tggtacatga       450
acagcgaggc ccaaccagac ctgagcatcc tgcaggcctg gagtcagggg       500
ctgtcaggcc agggcatcgt ggtctctgtg ctggacgatg gcatcgagaa       550
ggaccacccg gacctctggg ccaactacga ccccctggcc agctatgact       600
tcaatgacta cgacccggac ccccagcccc gctacacccc cagcaaagag       650
```

-continued

```
aaccggcacg ggacccgctg tgctggggag gtggccgcga tggccaacaa     700
tggcttctgt ggtgtggggg tcgctttcaa cgcccgaatc ggaggcgtac     750
ggatgctgga cggtaccatc accgatgtca tcgaggccca gtcgctgagc     800
ctgcagccgc agcacatcca catttacagc gccagctggg gtcccgagga     850
cgacggccgc acggtggacg gccccggcat cctcacccgc gaggccttcc     900
ggcgtggtgt gaccaagggc cgcggcgggc tgggcacgct cttcatctgg     950
gcctcgggca acggcggcct gcactacgac aactgcaact gcgacggcta    1000
caccaacagc atccacacgc tttccgtggg cagcaccacc cagcagggcc    1050
gcgtgccctg gtacagcgaa gcctgcgcct ccaccctcac caccacctac    1100
agcagcggcg tggccaccga cccccagatc gtcaccacgg acctgcatca    1150
cgggtgcaca gaccagcaca cgggcacctc ggcctcagcc ccactggcgg    1200
ccggcatgat cgccctagcg ctggaggcca acccgttcct gacgtggaga    1250
gacatgcagc acctggtggt ccgcgcgtcc aagccggcgc acctgcaggc    1300
cgaggactgg aggaccaacg gcgtggggcg ccaagtgagc catcactacg    1350
gatacgggct gctggacgcc gggctgctgg tggacaccgc ccgcacctgg    1400
ctgcccaccc agccgcagag gaagtgcgcc gtccgggtcc agagccgccc    1450
cacccccatc ctgccgctga tctacatcag ggaaaacgta tcggcctgcg    1500
ccggcctcca caactccatc cgctcgctgg agcacgtgca ggcgcagctg    1550
acgctgtcct acagccggcg cggagacctg gagatctcgc tcaccagccc    1600
catgggcacg cgctccacac tcgtggccat acgacccttg gacgtcagca    1650
ctgaaggcta caacaactgg gtcttcatgt ccacccactt ctgggatgag    1700
aacccacagg gcgtgtggac cctgggccta gagaacaagg gctactattt    1750
caacacgggg acgttgtacc gctacacgct gctgctctat gggacggccg    1800
aggacatgac agcgcggcct acaggccccc aggtgaccag cagcgcgtgt    1850
gtgcagcggg acacagaggg gctgtgccag gcgtgtgacg gccccgccta    1900
catcctggga cagctctgcc tggcctactg ccccccgcgg ttcttcaacc    1950
acacaaggct ggtgaccgct gggcctgggc acacggcggc gcccgcgctg    2000
agggtctgct ccagctgcca tgcctcctgc tacacctgcc gcggcggctc    2050
cccgagggac tgcacctcct gtcccccatc ctccacgctg gaccagcagc    2100
agggctcctg catgggaccc accacccccg acagccgccc ccggcttaga    2150
gctgccgcct gtccccacca ccgctgccca gcctcggcca tggtgctgag    2200
cctcctggcc gtgaccctcg gaggccccgt cctctgcggc atgtccatgg    2250
acctcccact atacgcctgg ctctcccgtg ccagggccac ccccaccaaa    2300
ccccaggtct ggctgccagc tggaacctga agttgtcagc tcagaaagcg    2350
accttgcccc cgcctgggtc cctgacaggc actgctgcca tgctgcctcc    2400
ccaggctggc cccagaggag cgagcaccag caccccgacgc ctggcctgcc   2450
agggatgggc cccgtggaac cccgaagcct ggcgggagag agagagagag    2500
aagtctcctc tgcattttgg gtttgggcag gagtgggctg gggggagagg    2550
ctggagcacc ccaaaagcca ggggaaagtg gagggagaga aacgtgacac    2600
```

-continued tgtccgtctc gggcaccgcg tccaacctca gagtttgcaa ataaaggttg 2650
cttagaaggt gaa 2663

<210> SEQ ID NO 66
<211> LENGTH: 755
<212> TYPE: PRT
<213> ORGANISM: Homo Sapien

<400> SEQUENCE: 66

Met Arg Pro Ala Pro Ile Ala Leu Trp Leu Arg Leu Val Leu Ala
1 5 10 15

Leu Ala Leu Val Arg Pro Arg Ala Val Gly Trp Ala Pro Val Arg
20 25 30

Ala Pro Ile Tyr Val Ser Ser Trp Ala Val Gln Val Ser Gln Gly
35 40 45

Asn Arg Glu Val Glu Arg Leu Ala Arg Lys Phe Gly Phe Val Asn
50 55 60

Leu Gly Pro Ile Phe Ser Asp Gly Gln Tyr Phe His Leu Arg His
65 70 75

Arg Gly Val Val Gln Gln Ser Leu Thr Pro His Trp Gly His Arg
80 85 90

Leu His Leu Lys Lys Asn Pro Lys Val Gln Trp Phe Gln Gln Gln
95 100 105

Thr Leu Gln Arg Arg Val Lys Arg Ser Val Val Val Pro Thr Asp
110 115 120

Pro Trp Phe Ser Lys Gln Trp Tyr Met Asn Ser Glu Ala Gln Pro
125 130 135

Asp Leu Ser Ile Leu Gln Ala Trp Ser Gln Gly Leu Ser Gly Gln
140 145 150

Gly Ile Val Val Ser Val Leu Asp Asp Gly Ile Glu Lys Asp His
155 160 165

Pro Asp Leu Trp Ala Asn Tyr Asp Pro Leu Ala Ser Tyr Asp Phe
170 175 180

Asn Asp Tyr Asp Pro Asp Pro Gln Pro Arg Tyr Thr Pro Ser Lys
185 190 195

Glu Asn Arg His Gly Thr Arg Cys Ala Gly Glu Val Ala Ala Met
200 205 210

Ala Asn Asn Gly Phe Cys Gly Val Gly Val Ala Phe Asn Ala Arg
215 220 225

Ile Gly Gly Val Arg Met Leu Asp Gly Thr Ile Thr Asp Val Ile
230 235 240

Glu Ala Gln Ser Leu Ser Leu Gln Pro Gln His Ile His Ile Tyr
245 250 255

Ser Ala Ser Trp Gly Pro Glu Asp Asp Gly Arg Thr Val Asp Gly
260 265 270

Pro Gly Ile Leu Thr Arg Glu Ala Phe Arg Arg Gly Val Thr Lys
275 280 285

Gly Arg Gly Gly Leu Gly Thr Leu Phe Ile Trp Ala Ser Gly Asn
290 295 300

Gly Gly Leu His Tyr Asp Asn Cys Asn Cys Asp Gly Tyr Thr Asn
305 310 315

Ser Ile His Thr Leu Ser Val Gly Ser Thr Thr Gln Gln Gly Arg
320 325 330

Val Pro Trp Tyr Ser Glu Ala Cys Ala Ser Thr Leu Thr Thr Thr

-continued

```
                335                 340                 345

Tyr Ser Ser Gly Val Ala Thr Asp Pro Gln Ile Val Thr Thr Asp
                350                 355                 360

Leu His His Gly Cys Thr Asp Gln His Thr Gly Thr Ser Ala Ser
                365                 370                 375

Ala Pro Leu Ala Ala Gly Met Ile Ala Leu Ala Leu Glu Ala Asn
                380                 385                 390

Pro Phe Leu Thr Trp Arg Asp Met Gln His Leu Val Val Arg Ala
                395                 400                 405

Ser Lys Pro Ala His Leu Gln Ala Glu Asp Trp Arg Thr Asn Gly
                410                 415                 420

Val Gly Arg Gln Val Ser His His Tyr Gly Tyr Gly Leu Leu Asp
                425                 430                 435

Ala Gly Leu Leu Val Asp Thr Ala Arg Thr Trp Leu Pro Thr Gln
                440                 445                 450

Pro Gln Arg Lys Cys Ala Val Arg Val Gln Ser Arg Pro Thr Pro
                455                 460                 465

Ile Leu Pro Leu Ile Tyr Ile Arg Glu Asn Val Ser Ala Cys Ala
                470                 475                 480

Gly Leu His Asn Ser Ile Arg Ser Leu Glu His Val Gln Ala Gln
                485                 490                 495

Leu Thr Leu Ser Tyr Ser Arg Arg Gly Asp Leu Glu Ile Ser Leu
                500                 505                 510

Thr Ser Pro Met Gly Thr Arg Ser Thr Leu Val Ala Ile Arg Pro
                515                 520                 525

Leu Asp Val Ser Thr Glu Gly Tyr Asn Asn Trp Val Phe Met Ser
                530                 535                 540

Thr His Phe Trp Asp Glu Asn Pro Gln Gly Val Trp Thr Leu Gly
                545                 550                 555

Leu Glu Asn Lys Gly Tyr Tyr Phe Asn Thr Gly Thr Leu Tyr Arg
                560                 565                 570

Tyr Thr Leu Leu Leu Tyr Gly Thr Ala Glu Asp Met Thr Ala Arg
                575                 580                 585

Pro Thr Gly Pro Gln Val Thr Ser Ser Ala Cys Val Gln Arg Asp
                590                 595                 600

Thr Glu Gly Leu Cys Gln Ala Cys Asp Gly Pro Ala Tyr Ile Leu
                605                 610                 615

Gly Gln Leu Cys Leu Ala Tyr Cys Pro Pro Arg Phe Phe Asn His
                620                 625                 630

Thr Arg Leu Val Thr Ala Gly Pro Gly His Thr Ala Ala Pro Ala
                635                 640                 645

Leu Arg Val Cys Ser Ser Cys His Ala Ser Cys Tyr Thr Cys Arg
                650                 655                 660

Gly Gly Ser Pro Arg Asp Cys Thr Ser Cys Pro Pro Ser Ser Thr
                665                 670                 675

Leu Asp Gln Gln Gln Gly Ser Cys Met Gly Pro Thr Thr Pro Asp
                680                 685                 690

Ser Arg Pro Arg Leu Arg Ala Ala Ala Cys Pro His His Arg Cys
                695                 700                 705

Pro Ala Ser Ala Met Val Leu Ser Leu Leu Ala Val Thr Leu Gly
                710                 715                 720

Gly Pro Val Leu Cys Gly Met Ser Met Asp Leu Pro Leu Tyr Ala
                725                 730                 735
```

-continued

Trp Leu Ser Arg Ala Arg Ala Thr Pro Thr Lys Pro Gln Val Trp
740 745 750

Leu Pro Ala Gly Thr
755

<210> SEQ ID NO 67
<211> LENGTH: 332
<212> TYPE: DNA
<213> ORGANISM: Homo Sapien

<400> SEQUENCE: 67
atgaggaagc tccagggcag gatggtttac ctgcctggac agcaagatga 50
tggctacact agcccccatt ctctgggcgc ctggatttgc ccaccagatc 100
tcctcacctc ttgcccttca cctcctgctg tacctacaag gtctccccga 150
ttctcatctg cccataatca tggacacagc cccaggatgt gcaggactct 200
cagggaccat ctggagttcc agctggaatc tgggcctggt ggagtgggag 250
tggggcaggg gcctgcattg ggctgactta gagagcacag ttattccatc 300
catatggaaa taaacatttt ggattcctga tc 332

<210> SEQ ID NO 68
<211> LENGTH: 88
<212> TYPE: PRT
<213> ORGANISM: Homo Sapien

<400> SEQUENCE: 68

Met Met Ala Thr Leu Ala Pro Ile Leu Trp Ala Pro Gly Phe Ala
1 5 10 15

His Gln Ile Ser Ser Pro Leu Ala Leu His Leu Leu Leu Tyr Leu
20 25 30

Gln Gly Leu Pro Asp Ser His Leu Pro Ile Ile Met Asp Thr Ala
35 40 45

Pro Gly Cys Ala Gly Leu Ser Gly Thr Ile Trp Ser Ser Ser Trp
50 55 60

Asn Leu Gly Leu Val Glu Trp Glu Trp Gly Arg Gly Leu His Trp
65 70 75

Ala Asp Leu Glu Ser Thr Val Ile Pro Ser Ile Trp Lys
80 85

<210> SEQ ID NO 69
<211> LENGTH: 1302
<212> TYPE: DNA
<213> ORGANISM: Homo Sapien
<220> FEATURE:
<221> NAME/KEY: unsure
<222> LOCATION: 1218-1253
<223> OTHER INFORMATION: unknown base

<400> SEQUENCE: 69
tttgcagtgg ggtcctcctc tggcctcctg cccctcctgc tgctgctgct 50
gcttccattg ctggcagccc agggtggggg tggcctgcag gcagcgctgc 100
tggcccttga ggtggggctg gtgggtctgg gggcctccta cctgctcctt 150
tgtacagccc tgcacctgcc ctccagtctt ttcctactcc tggcccaggg 200
taccgcactg gggggccgtcc tgggcctgag ctggcgccga ggcctcatgg 250
gtgttcccct gggccttgga gctgcctggc tcttagcttg gccaggccta 300

-continued

```
gctctacctc tggtggctat ggcagcgggg ggcagatggg tgcggcagca          350

gggcccccgg gtgcgccggg gcatatctcg actctggttg cgggttctgc          400

tgcgcctgtc acccatggcc ttccgggccc tgcagggctg tggggctgtg          450

ggggaccggg gtctgtttgc actgtacccc aaaaccaaca aggatggctt          500

ccgcagccgc ctgcccgtcc ctgggccccg gcggcgtaat ccccgcacca          550

cccaacaccc attagctctg ttggcaaggg tctgggtcct gtgcaagggc          600

tggaactggc gtctggcacg ggccagccag ggtttagcat cccacttgcc          650

cccgtgggcc atccacacac tggccagctg ggcctgctt cggggtgaac           700

ggcccacccg aatcccccgg ctactaccac gcagccagcg ccagctaggg          750

ccccctgcct cccgccagcc actgccaggg actctagccg ggcggaggtc          800

acgcacccgc cagtcccggg ccctgccccc ctggaggtag ctgactccag          850

cccttccagc ccaaatctag agcattgagc actttatctc ccacgactca          900

gtgaagtttc tccagtccct agtcctctct tttcacccac cttcctcagt          950

ttgctcactt accccaggcc cagcccttcg gacctctaga caggcagcct         1000

cctcagctgt ggagtccagc agtcactctg tgttctcctg gcgctcctcc         1050

cctaagttat tgctgttcgc ccgctgtgtg tgctcatcct caccctcatt         1100

gactcaggcc tggggccagg ggtggtggag ggtgggaaga gtcatgtttt         1150

ttttctcctc tttgattttg tttttctgtc tcccttccaa cctgtcccct         1200

tccccccacc aaaaaaannn nnnnnnnnnn nnnnnnnnnn nnnnnnnnnn         1250

nnnaaaaaaa aaaaaaaaaa aaaaaaaaaa aaaaaaaaaa aaaaaaaaaa         1300

aa                                                             1302
```

<210> SEQ ID NO 70
<211> LENGTH: 197
<212> TYPE: PRT
<213> ORGANISM: Homo Sapien

<400> SEQUENCE: 70

```
Met Gly Val Pro Leu Gly Leu Gly Ala Ala Trp Leu Leu Ala Trp
  1               5                  10                  15

Pro Gly Leu Ala Leu Pro Leu Val Ala Met Ala Ala Gly Gly Arg
                 20                  25                  30

Trp Val Arg Gln Gln Gly Pro Arg Val Arg Arg Gly Ile Ser Arg
                 35                  40                  45

Leu Trp Leu Arg Val Leu Leu Arg Leu Ser Pro Met Ala Phe Arg
                 50                  55                  60

Ala Leu Gln Gly Cys Gly Ala Val Gly Asp Arg Gly Leu Phe Ala
                 65                  70                  75

Leu Tyr Pro Lys Thr Asn Lys Asp Gly Phe Arg Ser Arg Leu Pro
                 80                  85                  90

Val Pro Gly Pro Arg Arg Arg Asn Pro Arg Thr Thr Gln His Pro
                 95                 100                 105

Leu Ala Leu Leu Ala Arg Val Trp Val Leu Cys Lys Gly Trp Asn
                110                 115                 120

Trp Arg Leu Ala Arg Ala Ser Gln Gly Leu Ala Ser His Leu Pro
                125                 130                 135

Pro Trp Ala Ile His Thr Leu Ala Ser Trp Gly Leu Leu Arg Gly
                140                 145                 150
```

-continued

Glu Arg Pro Thr Arg Ile Pro Arg Leu Leu Pro Arg Ser Gln Arg
155 160 165

Gln Leu Gly Pro Pro Ala Ser Arg Gln Pro Leu Pro Gly Thr Leu
170 175 180

Ala Gly Arg Arg Ser Arg Thr Arg Gln Ser Arg Ala Leu Pro Pro
185 190 195

Trp Arg

<210> SEQ ID NO 71
<211> LENGTH: 1976
<212> TYPE: DNA
<213> ORGANISM: Homo Sapien

<400> SEQUENCE: 71
gtttgggggt tgtttgggat tagtgaagct actgcctttg ccgccagcgc 50
agcctcagag tttgattatt tgcaatgtca ggctttgaaa acttaaacac 100
ggatttctac cagacaagtt acagcatcga tgatcagtca cagcagtcct 150
atgattatgg aggaagtgga ggaccctata gcaaacagta tgctggctat 200
gactattcgc agcaaggcag atttgtccct ccagacatga tgcagccaca 250
acagccatac accgggcaga tttaccagcc aactcaggca tatactccag 300
cttcacctca gcctttctat ggaaacaact ttgaggatga gccaccttta 350
ttagaagagt taggtatcaa ttttgaccac atctggcaaa aaacactaac 400
agtattacat ccgttaaaag tagcagatgg cagcatcatg aatgaaactg 450
atttggcagg tccaatggtt ttttgccttg cttttggagc cacattgcta 500
ctggctggca aaatccagtt tggctatgta tacgggatca gtgcaattgg 550
atgtctagga atgttttgtt tattaaactt aatgagtatg acaggtgttt 600
catttggttg tgtggcaagt gtccttggat attgtcttct gcccatgatc 650
ctactttcca gctttgcagt gatattttct ttgcaaggaa tggtaggaat 700
cattctcact gctgggatta ttggatggtg tagtttttct gcttccaaaa 750
tatttatttc tgcattagcc atggaaggac agcaactttt agtagcatat 800
ccttgcgctt tgttatatgg agtctttgcc ctgatttccg tcttttgaaa 850
atttatctgg gatgtggaca tcagtgggcc agatgtacaa aaaggacctt 900
gaactcttaa attggaccag caaactgctg cagcgcaact ctcatgcaga 950
tttacatttg actgttggag caatgaaagt aaacgtgtat ctcttgttca 1000
tttttataga actttttgcat actatattgg atttacctgc ggtgtgacta 1050
gctttaaatg tttgtgttta tacagataag aaatgctatt tctttctggt 1100
tcctgcagcc attgaaaaac ctttttcctt gcaaattata atgtttttga 1150
tagattttta tcaactgtgg gaaaccaaac acaaagctga taacctttct 1200
taaaaacgac ccagtcacag taaagaagac acaagacggc cgggcgtggt 1250
agctcacgcc tgtaatccca gcactttggg aggccgaggc gggcggatca 1300
caagggcagg agatcgagac catcctggtt aacacggtga aaccccgact 1350
ctactaaaac tacaaaaaaa attagctggg cgtggtggcg ggcgcctgta 1400
gtcccagcta ctcaggaggc tgaggcagga gaagtgtgaa cccaggaggc 1450
ggagcttgca gtgagccgag atcacaccac tgcactccat ccagcctggg 1500

-continued

```
tgacagggtg agactctgtc tcaaaaaaaa aaaaaaaagg agacacaaga          1550

cttactgcaa aaatattttt ccaaggattt aggaaagaaa aattgccttg          1600

tattctcaag tcaggtaact caaagcaaaa aagtgatcca aatgtagagt          1650

atgagtttgc actccaaaaa tttgacatta ctgtaaatta tctcatggaa          1700

tttttgctaa aattcagaga tacgggaagt tcacaatcta cctcattgta          1750

gacatgaaat gcgaacactt acttacatat taatgttaac tcaaccttag          1800

ggacctggaa tggttgcatt aatgctataa tcgttggatc gccacatttc          1850

ccaaaaataa taaaaaaatc actaaccttt tttaaggaaa atatttaaag          1900

ttttacaaaa ttcaatattg caattatcaa tgtaaagtac atttgaatgc          1950

ttattaaaac tttcccaatt aatttt                                    1976
```

```
<210> SEQ ID NO 72
<211> LENGTH: 257
<212> TYPE: PRT
<213> ORGANISM: Homo Sapien

<400> SEQUENCE: 72

Met Ser Gly Phe Glu Asn Leu Asn Thr Asp Phe Tyr Gln Thr Ser
  1               5                  10                  15

Tyr Ser Ile Asp Asp Gln Ser Gln Gln Ser Tyr Asp Tyr Gly Gly
                 20                  25                  30

Ser Gly Gly Pro Tyr Ser Lys Gln Tyr Ala Gly Tyr Asp Tyr Ser
                 35                  40                  45

Gln Gln Gly Arg Phe Val Pro Pro Asp Met Met Gln Pro Gln Gln
                 50                  55                  60

Pro Tyr Thr Gly Gln Ile Tyr Gln Pro Thr Gln Ala Tyr Thr Pro
                 65                  70                  75

Ala Ser Pro Gln Pro Phe Tyr Gly Asn Asn Phe Glu Asp Glu Pro
                 80                  85                  90

Pro Leu Leu Glu Glu Leu Gly Ile Asn Phe Asp His Ile Trp Gln
                 95                 100                 105

Lys Thr Leu Thr Val Leu His Pro Leu Lys Val Ala Asp Gly Ser
                110                 115                 120

Ile Met Asn Glu Thr Asp Leu Ala Gly Pro Met Val Phe Cys Leu
                125                 130                 135

Ala Phe Gly Ala Thr Leu Leu Leu Ala Gly Lys Ile Gln Phe Gly
                140                 145                 150

Tyr Val Tyr Gly Ile Ser Ala Ile Gly Cys Leu Gly Met Phe Cys
                155                 160                 165

Leu Leu Asn Leu Met Ser Met Thr Gly Val Ser Phe Gly Cys Val
                170                 175                 180

Ala Ser Val Leu Gly Tyr Cys Leu Leu Pro Met Ile Leu Leu Ser
                185                 190                 195

Ser Phe Ala Val Ile Phe Ser Leu Gln Gly Met Val Gly Ile Ile
                200                 205                 210

Leu Thr Ala Gly Ile Ile Gly Trp Cys Ser Phe Ser Ala Ser Lys
                215                 220                 225

Ile Phe Ile Ser Ala Leu Ala Met Glu Gly Gln Gln Leu Leu Val
                230                 235                 240

Ala Tyr Pro Cys Ala Leu Leu Tyr Gly Val Phe Ala Leu Ile Ser
                245                 250                 255
```

-continued

Val Phe

<210> SEQ ID NO 73
<211> LENGTH: 1285
<212> TYPE: DNA
<213> ORGANISM: Homo Sapien

<400> SEQUENCE: 73
acactggcca aaacgcggct cgccctcggc tgcgctcggc tcccgcgggc 50
gctcggcccc gagcccctcc tccccctacc cgccggccgg acagggagga 100
gccaatggct gggcctgcca tccacaccgc tcccatgctg ttcctcgtcc 150
tcctgctgcc ccagctgagc ctggcaggcg cccttgcacc tgggacccct 200
gcccggaacc tccctgagaa tcacattgac ctcccaggcc cagcgctgtg 250
gacgcctcag gccagccacc accgccggcg gggcccgggc aagaaggagt 300
ggggcccagg cctgcccagc caggcccagg atggggctgt ggtcaccgcc 350
accaggcagg cctccaggct gccagaggct gaggggctgc tgcctgagca 400
gagtcctgca ggcctgctgc aggacaagga cctgctcctg ggactggcat 450
tgccctaccc cgagaaggag aacagacctc caggttggga gaggaccagg 500
aaacgcagca gggagcacaa gagacgcagg gacaggttga ggctgcacca 550
aggccgagcc ttggtccgag gtcccagctc cctgatgaag aaggcagagc 600
tctccgaagc ccaggtgctg gatgcagcca tggaggaatc ctccaccagc 650
ctggcgccca ccatgttctt tctcaccacc tttgaggcag cacctgccac 700
agaagagtcc ctgatcctgc ccgtcacctc cctgcggccc cagcaggcac 750
agcccaggtc tgacggggag gtgatgccca cgctggacat ggccttgttc 800
gactggaccg attatgaaga cttaaaacct gatggttggc cctctgcaaa 850
gaagaaagag aaacaccgcg gtaaactctc cagtgatggt aacgaaacat 900
caccagccga aggggaacca tgcgaccatc accaagactg cctgccaggg 950
acttgctgcg acctgcggga gcatctctgc acaccccaca accgaggcct 1000
caacaacaaa tgcttcgatg actgcatgtg tgtggaaggg ctgcgctgct 1050
atgccaaatt ccaccggaac cgcagggtta cacggaggaa agggcgctgt 1100
gtggagcccg agacggccaa cggcgaccag ggatccttca tcaacgtcta 1150
gcggccccgc gggactgggg actgagccca ggaggtttgc acaagccggg 1200
cgatttgttt gtaactagca gtgggagatc aagttgggga acagatggct 1250
gaggctgcag actcaggccc aggacactca acccc 1285

<210> SEQ ID NO 74
<211> LENGTH: 348
<212> TYPE: PRT
<213> ORGANISM: Homo Sapien

<400> SEQUENCE: 74

Met Ala Gly Pro Ala Ile His Thr Ala Pro Met Leu Phe Leu Val
1 5 10 15

Leu Leu Leu Pro Gln Leu Ser Leu Ala Gly Ala Leu Ala Pro Gly
20 25 30

Thr Pro Ala Arg Asn Leu Pro Glu Asn His Ile Asp Leu Pro Gly
35 40 45

-continued

```
Pro Ala Leu Trp Thr Pro Gln Ala Ser His His Arg Arg Arg Gly
                50                  55                  60

Pro Gly Lys Lys Glu Trp Gly Pro Gly Leu Pro Ser Gln Ala Gln
                65                  70                  75

Asp Gly Ala Val Val Thr Ala Thr Arg Gln Ala Ser Arg Leu Pro
                80                  85                  90

Glu Ala Glu Gly Leu Leu Pro Glu Gln Ser Pro Ala Gly Leu Leu
                95                 100                 105

Gln Asp Lys Asp Leu Leu Leu Gly Leu Ala Leu Pro Tyr Pro Glu
               110                 115                 120

Lys Glu Asn Arg Pro Pro Gly Trp Glu Arg Thr Arg Lys Arg Ser
               125                 130                 135

Arg Glu His Lys Arg Arg Arg Asp Arg Leu Arg Leu His Gln Gly
               140                 145                 150

Arg Ala Leu Val Arg Gly Pro Ser Ser Leu Met Lys Lys Ala Glu
               155                 160                 165

Leu Ser Glu Ala Gln Val Leu Asp Ala Ala Met Glu Glu Ser Ser
               170                 175                 180

Thr Ser Leu Ala Pro Thr Met Phe Phe Leu Thr Thr Phe Glu Ala
               185                 190                 195

Ala Pro Ala Thr Glu Glu Ser Leu Ile Leu Pro Val Thr Ser Leu
               200                 205                 210

Arg Pro Gln Gln Ala Gln Pro Arg Ser Asp Gly Glu Val Met Pro
               215                 220                 225

Thr Leu Asp Met Ala Leu Phe Asp Trp Thr Asp Tyr Glu Asp Leu
               230                 235                 240

Lys Pro Asp Gly Trp Pro Ser Ala Lys Lys Lys Glu Lys His Arg
               245                 250                 255

Gly Lys Leu Ser Ser Asp Gly Asn Glu Thr Ser Pro Ala Glu Gly
               260                 265                 270

Glu Pro Cys Asp His His Gln Asp Cys Leu Pro Gly Thr Cys Cys
               275                 280                 285

Asp Leu Arg Glu His Leu Cys Thr Pro His Asn Arg Gly Leu Asn
               290                 295                 300

Asn Lys Cys Phe Asp Asp Cys Met Cys Val Glu Gly Leu Arg Cys
               305                 310                 315

Tyr Ala Lys Phe His Arg Asn Arg Arg Val Thr Arg Arg Lys Gly
               320                 325                 330

Arg Cys Val Glu Pro Glu Thr Ala Asn Gly Asp Gln Gly Ser Phe
               335                 340                 345

Ile Asn Val
```

<210> SEQ ID NO 75
<211> LENGTH: 1868
<212> TYPE: DNA
<213> ORGANISM: Homo Sapien

<400> SEQUENCE: 75

```
cagaagggca aaaacattga ctgcctcaag gtctcaagca ccagtcttca        50

ccgcggaaag catgttgtgg ctgttccaat cgctcctgtt tgtcttctgc       100

tttggcccag ggaatgtagt ttcacaaagc agcttaaccc cattgatggt       150

gaacgggatt ctgggggagt cagtaactct tcccctggag tttcctgcag       200
```

-continued

```
gagagaaggt caacttcatc acttggcttt tcaatgaaac atctcttgcc          250

ttcatagtac cccatgaaac caaaagtcca gaaatccacg tgactaatcc          300

gaaacaggga aagcgactga acttcaccca gtcctactcc ctgcaactca          350

gcaacctgaa gatggaagac acaggctctt acagagccca gatatccaca          400

aagacctctg caaagctgtc cagttacact ctgaggatat taagacaact          450

gaggaacata caagttacca atcacagtca gctatttcag aatatgacct          500

gtgagctcca tctgacttgc tctgtggagg atgcagatga caatgtctca          550

ttcagatggg aggccttggg aaacacactt tcaagtcagc caaacctcac          600

tgtctcctgg gaccccagga tttccagtga acaggactac acctgcatag          650

cagagaatgc tgtcagtaat ttatccttct ctgtctctgc ccagaagctt          700

tgcgaagatg ttaaaattca atatacagat accaaaatga ttctgtttat          750

ggtttctggg atatgcatag tcttcggttt catcatactg ctgttacttg          800

ttttgaggaa aagaagagat tccctatctt tgtctactca gcgaacacag          850

ggccccgcag agtccgcaag gaacctagag tatgtttcag tgtctccaac          900

gaacaacact gtgtatgctt cagtcactca ttcaaacagg gaaacagaaa          950

tctggacacc tagagaaaat gatactatca caatttactc cacaattaat         1000

cattccaaag agagtaaacc cactttttcc agggcaactg cccttgacaa         1050

tgtcgtgtaa gttgctgaaa ggcctcagag gaattcggga atgacacgtc         1100

ttctgatccc atgagacaga acaaagaaca ggaagcttgg ttcctgttgt         1150

tcctggcaac agaatttgaa tatctaggat aggatgatca cctccagtcc         1200

ttcggactta aacctgccta cctgagtcaa acacctaagg ataacatcat         1250

ttccagcatg tggttcaaat aatattttcc aatccacttc aggccaaaac         1300

atgctaaaga taacacacca gcacattgac tctctctttg ataactaagc         1350

aaatggaatt atggttgaca gagagtttat gatccagaag acaaccactt         1400

ctctcctttt agaaagcagc aggattgact tattgagaaa taatgcagtg         1450

tgttggttac atgtgtagtc tctggagttg gatgggccca tcctgataca         1500

agttgagcat ccccttgtctg aaatgcttgg gattagaaat gtttcagatt        1550

tcaatttttt ttcagatttt ggaatatttg cattatattt agcggttgag         1600

tatccaaatc caaaaatcca aaattcaaaa tgctccaata agcatttccc         1650

ttgagtttca ttgatgtcga tgcagtgctc aaaatctcag attttggagc         1700

aatttggata ttggattttt ggatttggga tgctcaactt gtacaatgtt         1750

tattagacac atctcctggg acatactgcc taaccttttg gagccttagt         1800

ctcccagact gaaaaaggaa gaggatggta ttacatcagc tccattgttt         1850

gagccaagaa tctaagtc                                            1868
```

<210> SEQ ID NO 76
<211> LENGTH: 332
<212> TYPE: PRT
<213> ORGANISM: Homo Sapien

<400> SEQUENCE: 76

```
Met Leu Trp Leu Phe Gln Ser Leu Leu Phe Val Phe Cys Phe Gly
  1               5                  10                  15
```

-continued

```
Pro Gly Asn Val Val Ser Gln Ser Ser Leu Thr Pro Leu Met Val
                 20                  25                  30

Asn Gly Ile Leu Gly Glu Ser Val Thr Leu Pro Leu Glu Phe Pro
                 35                  40                  45

Ala Gly Glu Lys Val Asn Phe Ile Thr Trp Leu Phe Asn Glu Thr
                 50                  55                  60

Ser Leu Ala Phe Ile Val Pro His Glu Thr Lys Ser Pro Glu Ile
                 65                  70                  75

His Val Thr Asn Pro Lys Gln Gly Lys Arg Leu Asn Phe Thr Gln
                 80                  85                  90

Ser Tyr Ser Leu Gln Leu Ser Asn Leu Lys Met Glu Asp Thr Gly
                 95                 100                 105

Ser Tyr Arg Ala Gln Ile Ser Thr Lys Thr Ser Ala Lys Leu Ser
                110                 115                 120

Ser Tyr Thr Leu Arg Ile Leu Arg Gln Leu Arg Asn Ile Gln Val
                125                 130                 135

Thr Asn His Ser Gln Leu Phe Gln Asn Met Thr Cys Glu Leu His
                140                 145                 150

Leu Thr Cys Ser Val Glu Asp Ala Asp Asp Asn Val Ser Phe Arg
                155                 160                 165

Trp Glu Ala Leu Gly Asn Thr Leu Ser Ser Gln Pro Asn Leu Thr
                170                 175                 180

Val Ser Trp Asp Pro Arg Ile Ser Ser Glu Gln Asp Tyr Thr Cys
                185                 190                 195

Ile Ala Glu Asn Ala Val Ser Asn Leu Ser Phe Ser Val Ser Ala
                200                 205                 210

Gln Lys Leu Cys Glu Asp Val Lys Ile Gln Tyr Thr Asp Thr Lys
                215                 220                 225

Met Ile Leu Phe Met Val Ser Gly Ile Cys Ile Val Phe Gly Phe
                230                 235                 240

Ile Ile Leu Leu Leu Leu Val Leu Arg Lys Arg Arg Asp Ser Leu
                245                 250                 255

Ser Leu Ser Thr Gln Arg Thr Gln Gly Pro Ala Glu Ser Ala Arg
                260                 265                 270

Asn Leu Glu Tyr Val Ser Val Ser Pro Thr Asn Asn Thr Val Tyr
                275                 280                 285

Ala Ser Val Thr His Ser Asn Arg Glu Thr Glu Ile Trp Thr Pro
                290                 295                 300

Arg Glu Asn Asp Thr Ile Thr Ile Tyr Ser Thr Ile Asn His Ser
                305                 310                 315

Lys Glu Ser Lys Pro Thr Phe Ser Arg Ala Thr Ala Leu Asp Asn
                320                 325                 330

Val Val
```

<210> SEQ ID NO 77
<211> LENGTH: 3073
<212> TYPE: DNA
<213> ORGANISM: Homo Sapien

<400> SEQUENCE: 77

```
gatccctcga cctcgaccca cgcgtccgct ctttaatgct ttctttttaa          50

gagatcacct tctgacttct cacagaagag gttaactatt acctgtggga         100

agtcagaagg tgatctcttt aatgctttct ttttaagaat ttttcaaatt         150
```

-continued

```
gagactaatt gcagaggttc cagttgacca gcattcatag gaatgaagac 200
aaacacagag atggtgtgtc taagaaactt caaaaggtgt agacctcctg 250
actgaagcat attggattta tttaattttt ttcactgtat ttctgtcctc 300
ctacaaggga aagtcatgat tacactaact gagctaaaat gcttagcaga 350
tgcccagtca tcttatcaca tcttaaaacc atggtgggac gtcttctggt 400
attacatcac actgatcatg ctgctggtgg ccgtgctggc cggagctctc 450
cagctgacgc agagcagggt tctgtgctgt cttccatgca aagtggaatt 500
tgacaatcac tgtgccgtgc cttgggacat cctgaaagcc agcatgaaca 550
catcctctaa tcctgggaca ccgcttccgc tccccctccg aattcagaat 600
gacctccacc gacagcagta ctcctatatt gatgccgtct gttacgagaa 650
acagctccat tggtttgcaa agtttttccc ctatctggtg ctcttgcaca 700
cgctcatctt tgcagcctgc agcaactttt ggcttcacta ccccagtacc 750
agttccaggc tcgagcattt tgtggccatc cttcacaagt gcttcgattc 800
tccatggacc acccgcgccc tttcagaaac agtggctgag cagtcagtga 850
ggcctctgaa actctccaag tccaagattt tgctttcgtc ctcagggtgt 900
tcagctgaca tagattccgg caaacagtca ttgccctacc cacagccagg 950
tttggagtca gctggtatag aaagcccaac ttccagtggc ctggacaaga 1000
aggagggtga acaggccaaa gccatctttg aaaaagtgaa aagattccgc 1050
atgcatgtgg agcagaagga catcatttat agagtatatc tgaaacagat 1100
aatagtcaaa gtcattttgt ttgtgctcat cataacttat gttccatatt 1150
ttttaaccca catcactctt gaaatcgact gttcagttga tgtgcaggct 1200
tttacaggat ataagcgcta ccagtgtgtc tattccttgg cagaaatctt 1250
taaggtcctg gcttcatttt atgtcatttt ggttatactt tatggtctga 1300
cctcttccta cagcctgtgg tggatgctga ggagttccct gaagcaatat 1350
tcctttgagg cgttaagaga aaaaagcaac tacagtgaca tccctgatgt 1400
caagaatgac tttgccttca tccttcatct ggctgatcag tatgatcctc 1450
tttattccaa acgcttctcc atattcctat cagaggtcag tgagaacaaa 1500
ctgaaacaga tcaacctcaa taatgaatgg acagttgaga aactgaaaag 1550
taagcttgtg aaaaatgccc aggacaagat agaactgcat ctttttatgc 1600
tcaacggtct tccagacaat gtctttgagt taactgaaat ggaagtgcta 1650
agcctggagc ttatcccaga ggtgaagctg ccctctgcag tctcacagct 1700
ggtcaacctc aaggagcttc gtgtgtacca ttcatctctg gtcgtagacc 1750
atcctgcact ggcctttcta gaggagaatt taaaaatcct ccgcctgaaa 1800
tttactgaaa tgggaaaaat cccacgctgg gtatttcacc tcaagaatct 1850
caaggaactt tatctttcgg gctgtgttct ccctgaacag ttgagtacta 1900
tgcagttgga gggctttcag gacttaaaaa atctaaggac cctgtacttg 1950
aagagcagcc tctcccggat cccacaagtt gttacagacc tcctgccttc 2000
attgcagaaa ctgtcccttg ataatgaggg aagcaaactg gttgtgttga 2050
acaacttgaa aaagatggtc aatctgaaaa gcctagaact gatcagctgt 2100
gacctggaac gcatcccaca ttccattttc agcctgaata atttgcatga 2150
```

-continued

```
gttagaccta agggaaaata accttaaaac tgtggaagag attagctttc        2200
agcatcttca gaatctttcc tgcttaaagt tgtggcacaa taacattgct        2250
tatattcctg cacagattgg ggcattatct aacctagagc agctctcttt        2300
ggaccataat aatattgaga atctgccctt gcagcttttc ctatgcacta        2350
aactacatta tttggatcta agctataacc acttgacctt cattccagaa        2400
gaaatccagt atctgagtaa tttgcagtac tttgctgtga ccaacaacaa        2450
tattgagatg ctaccagatg ggctgtttca gtgcaaaaag ctgcagtgtt        2500
acttttgggg gaaaaatagc ttgatgaatt tgtcccctca tgtgggtgag        2550
ctgtcaaacc ttactcatct ggagctcatt ggtaattacc tggaaacact        2600
tcctcctgaa ctagaaggat gtcagtccct aaaacggaac tgtctgattg        2650
ttgaggagaa cttgctcaat actcttcctc tccctgtaac agaacgttta        2700
cagacgtgct tagacaaatg ttgacttaaa gaaaagagac ccgtgtttca        2750
aaatcatttt taaaagtatg ctcggccggg cgtggtggct catgcctata        2800
atcccagcac tttgggaggc caagatgggc ggattgcttg aggtcaggag        2850
ttcgagacca gtctggccaa cctggtgaaa ccccatctct gctaaaacta        2900
caaaaaaatt agccaggcgt ggtggcgtgc gcctgtaatc ccagctactt        2950
gggaggctga cgcaggggaa ttgcttgaac cagggaggtg gaggttgcag        3000
tgagccgaga ttgtgccact gtacaccagc ctgggtgaca gagcaagact        3050
cttatctcaa aaaaaaaaaa aaa                                     3073
```

<210> SEQ ID NO 78
<211> LENGTH: 802
<212> TYPE: PRT
<213> ORGANISM: Homo Sapien

<400> SEQUENCE: 78

```
Met Ile Thr Leu Thr Glu Leu Lys Cys Leu Ala Asp Ala Gln Ser
  1               5                  10                  15

Ser Tyr His Ile Leu Lys Pro Trp Trp Asp Val Phe Trp Tyr Tyr
                 20                  25                  30

Ile Thr Leu Ile Met Leu Leu Val Ala Val Leu Ala Gly Ala Leu
                 35                  40                  45

Gln Leu Thr Gln Ser Arg Val Leu Cys Cys Leu Pro Cys Lys Val
                 50                  55                  60

Glu Phe Asp Asn His Cys Ala Val Pro Trp Asp Ile Leu Lys Ala
                 65                  70                  75

Ser Met Asn Thr Ser Ser Asn Pro Gly Thr Pro Leu Pro Leu Pro
                 80                  85                  90

Leu Arg Ile Gln Asn Asp Leu His Arg Gln Gln Tyr Ser Tyr Ile
                 95                 100                 105

Asp Ala Val Cys Tyr Glu Lys Gln Leu His Trp Phe Ala Lys Phe
                110                 115                 120

Phe Pro Tyr Leu Val Leu Leu His Thr Leu Ile Phe Ala Ala Cys
                125                 130                 135

Ser Asn Phe Trp Leu His Tyr Pro Ser Thr Ser Ser Arg Leu Glu
                140                 145                 150

His Phe Val Ala Ile Leu His Lys Cys Phe Asp Ser Pro Trp Thr
                155                 160                 165
```

-continued

```
Thr Arg Ala Leu Ser Glu Thr Val Ala Glu Gln Ser Val Arg Pro
                170                 175                 180

Leu Lys Leu Ser Lys Ser Lys Ile Leu Leu Ser Ser Ser Gly Cys
                185                 190                 195

Ser Ala Asp Ile Asp Ser Gly Lys Gln Ser Leu Pro Tyr Pro Gln
                200                 205                 210

Pro Gly Leu Glu Ser Ala Gly Ile Glu Ser Pro Thr Ser Ser Gly
                215                 220                 225

Leu Asp Lys Lys Glu Gly Glu Gln Ala Lys Ala Ile Phe Glu Lys
                230                 235                 240

Val Lys Arg Phe Arg Met His Val Glu Gln Lys Asp Ile Ile Tyr
                245                 250                 255

Arg Val Tyr Leu Lys Gln Ile Ile Val Lys Val Ile Leu Phe Val
                260                 265                 270

Leu Ile Ile Thr Tyr Val Pro Tyr Phe Leu Thr His Ile Thr Leu
                275                 280                 285

Glu Ile Asp Cys Ser Val Asp Val Gln Ala Phe Thr Gly Tyr Lys
                290                 295                 300

Arg Tyr Gln Cys Val Tyr Ser Leu Ala Glu Ile Phe Lys Val Leu
                305                 310                 315

Ala Ser Phe Tyr Val Ile Leu Val Ile Leu Tyr Gly Leu Thr Ser
                320                 325                 330

Ser Tyr Ser Leu Trp Trp Met Leu Arg Ser Ser Leu Lys Gln Tyr
                335                 340                 345

Ser Phe Glu Ala Leu Arg Glu Lys Ser Asn Tyr Ser Asp Ile Pro
                350                 355                 360

Asp Val Lys Asn Asp Phe Ala Phe Ile Leu His Leu Ala Asp Gln
                365                 370                 375

Tyr Asp Pro Leu Tyr Ser Lys Arg Phe Ser Ile Phe Leu Ser Glu
                380                 385                 390

Val Ser Glu Asn Lys Leu Lys Gln Ile Asn Leu Asn Asn Glu Trp
                395                 400                 405

Thr Val Glu Lys Leu Lys Ser Lys Leu Val Lys Asn Ala Gln Asp
                410                 415                 420

Lys Ile Glu Leu His Leu Phe Met Leu Asn Gly Leu Pro Asp Asn
                425                 430                 435

Val Phe Glu Leu Thr Glu Met Glu Val Leu Ser Leu Glu Leu Ile
                440                 445                 450

Pro Glu Val Lys Leu Pro Ser Ala Val Ser Gln Leu Val Asn Leu
                455                 460                 465

Lys Glu Leu Arg Val Tyr His Ser Ser Leu Val Val Asp His Pro
                470                 475                 480

Ala Leu Ala Phe Leu Glu Glu Asn Leu Lys Ile Leu Arg Leu Lys
                485                 490                 495

Phe Thr Glu Met Gly Lys Ile Pro Arg Trp Val Phe His Leu Lys
                500                 505                 510

Asn Leu Lys Glu Leu Tyr Leu Ser Gly Cys Val Leu Pro Glu Gln
                515                 520                 525

Leu Ser Thr Met Gln Leu Glu Gly Phe Gln Asp Leu Lys Asn Leu
                530                 535                 540

Arg Thr Leu Tyr Leu Lys Ser Ser Leu Ser Arg Ile Pro Gln Val
                545                 550                 555
```

-continued

```
Val Thr Asp Leu Leu Pro Ser Leu Gln Lys Leu Ser Leu Asp Asn
                560                 565                 570

Glu Gly Ser Lys Leu Val Val Leu Asn Asn Leu Lys Lys Met Val
                575                 580                 585

Asn Leu Lys Ser Leu Glu Leu Ile Ser Cys Asp Leu Glu Arg Ile
                590                 595                 600

Pro His Ser Ile Phe Ser Leu Asn Asn Leu His Glu Leu Asp Leu
                605                 610                 615

Arg Glu Asn Asn Leu Lys Thr Val Glu Glu Ile Ser Phe Gln His
                620                 625                 630

Leu Gln Asn Leu Ser Cys Leu Lys Leu Trp His Asn Asn Ile Ala
                635                 640                 645

Tyr Ile Pro Ala Gln Ile Gly Ala Leu Ser Asn Leu Glu Gln Leu
                650                 655                 660

Ser Leu Asp His Asn Asn Ile Glu Asn Leu Pro Leu Gln Leu Phe
                665                 670                 675

Leu Cys Thr Lys Leu His Tyr Leu Asp Leu Ser Tyr Asn His Leu
                680                 685                 690

Thr Phe Ile Pro Glu Glu Ile Gln Tyr Leu Ser Asn Leu Gln Tyr
                695                 700                 705

Phe Ala Val Thr Asn Asn Asn Ile Glu Met Leu Pro Asp Gly Leu
                710                 715                 720

Phe Gln Cys Lys Lys Leu Gln Cys Leu Leu Leu Gly Lys Asn Ser
                725                 730                 735

Leu Met Asn Leu Ser Pro His Val Gly Glu Leu Ser Asn Leu Thr
                740                 745                 750

His Leu Glu Leu Ile Gly Asn Tyr Leu Glu Thr Leu Pro Pro Glu
                755                 760                 765

Leu Glu Gly Cys Gln Ser Leu Lys Arg Asn Cys Leu Ile Val Glu
                770                 775                 780

Glu Asn Leu Leu Asn Thr Leu Pro Leu Pro Val Thr Glu Arg Leu
                785                 790                 795

Gln Thr Cys Leu Asp Lys Cys
                800
```

<210> SEQ ID NO 79
<211> LENGTH: 1504
<212> TYPE: DNA
<213> ORGANISM: Homo Sapien

<400> SEQUENCE: 79

```
cggacgcgtg ggccgcgctc cctcacggcc cctcggcggc gcccgtcgga          50

tccggcctct ctctgcgccc cggggcgcgc cacctccccg ccggaggtgt         100

ccacgcgtcc ggccgtccat ccgtccgtcc ctcctggggc cggcgctgac         150

catgcccagc ggctgccgct gcctgcatct cgtgtgcctg ttgtgcattc         200

tgggggctcc cggtcagcct gtccgagccg atgactgcag ctcccactgt         250

gacctggccc acggctgctg tgcacctgac ggctcctgca ggtgtgaccc         300

gggctgggag gggctgcact gtgagcgctg tgtgaggatg cctggctgcc         350

agcacggtac ctgccaccag ccatggcagt gcatctgcca cagtggctgg         400

gcaggcaagt tctgtgacaa agatgaacat atctgtacca cgcagtcccc         450

ctgccagaat ggaggccagt gcatgtatga cgggggcggt gagtaccatt         500
```

-continued

```
gtgtgtgctt accaggcttc catgggcgtg actgcgagcg caaggctgga        550
ccctgtgaac aggcaggctc cccatgccgc aatggcgggc agtgccagga        600
cgaccagggc tttgctctca acttcacgtg ccgctgcttg gtgggctttg        650
tgggtgcccg ctgtgaggta aatgtggatg actgcctgat gcggccttgt        700
gctaacggtg ccacctgcct tgacggcata aaccgcttct cctgcctctg        750
tcctgagggc tttgctggac gcttctgcac catcaacctg gatgactgtg        800
ccagccgccc atgccagaga ggggcccgct gtcgggaccg tgtccacgac        850
ttcgactgcc tctgccccag tggctatggt ggcaagacct gtgagcttgt        900
cttacctgtc ccagaccccc caaccacagt ggacacccct ctagggccca        950
cctcagctgt agtggtacct gctacggggc cagcccccca cagcgcaggg       1000
gctggtctgc tgcggatctc agtgaaggag gtggtgcgga ggcaagaggc       1050
tgggctaggt gagcctagct tggtggccct ggtggtgttt ggggccctca       1100
ctgctgccct ggttctggct actgtgttgc tgaccctgag ggcctggcgc       1150
cggggtgtct gcccccctgg accctgttgc taccctgccc cacactatgc       1200
tccagcgtgc caggaccagg agtgtcaggt tagcatgctg ccagcagggc       1250
tcccccctgcc acgtgacttg ccccctgagc ctggaaagac cacagcactg       1300
tgatggaggt gggggctttc tggccccctt cctcacctct tccacccctc       1350
agactggagt ggtccgttct caccaccctt cagcttgggt acacacacag       1400
aggagacctc agcctcacac cagaaatatt attttttttaa tacacagaat       1450
gtaagatgga attttatcaa ataaaactat gaaaatgcaa aaaaaaaaaa       1500
aaaa                                                          1504
```

```
<210> SEQ ID NO 80
<211> LENGTH: 383
<212> TYPE: PRT
<213> ORGANISM: Homo Sapien

<400> SEQUENCE: 80

Met Pro Ser Gly Cys Arg Cys Leu His Leu Val Cys Leu Leu Cys
  1               5                  10                  15

Ile Leu Gly Ala Pro Gly Gln Pro Val Arg Ala Asp Asp Cys Ser
                 20                  25                  30

Ser His Cys Asp Leu Ala His Gly Cys Cys Ala Pro Asp Gly Ser
                 35                  40                  45

Cys Arg Cys Asp Pro Gly Trp Glu Gly Leu His Cys Glu Arg Cys
                 50                  55                  60

Val Arg Met Pro Gly Cys Gln His Gly Thr Cys His Gln Pro Trp
                 65                  70                  75

Gln Cys Ile Cys His Ser Gly Trp Ala Gly Lys Phe Cys Asp Lys
                 80                  85                  90

Asp Glu His Ile Cys Thr Thr Gln Ser Pro Cys Gln Asn Gly Gly
                 95                 100                 105

Gln Cys Met Tyr Asp Gly Gly Gly Glu Tyr His Cys Val Cys Leu
                110                 115                 120

Pro Gly Phe His Gly Arg Asp Cys Glu Arg Lys Ala Gly Pro Cys
                125                 130                 135

Glu Gln Ala Gly Ser Pro Cys Arg Asn Gly Gly Gln Cys Gln Asp
                140                 145                 150
```

-continued

Asp Gln Gly Phe Ala Leu Asn Phe Thr Cys Arg Cys Leu Val Gly
155 160 165

Phe Val Gly Ala Arg Cys Glu Val Asn Val Asp Asp Cys Leu Met
170 175 180

Arg Pro Cys Ala Asn Gly Ala Thr Cys Leu Asp Gly Ile Asn Arg
185 190 195

Phe Ser Cys Leu Cys Pro Glu Gly Phe Ala Gly Arg Phe Cys Thr
200 205 210

Ile Asn Leu Asp Asp Cys Ala Ser Arg Pro Cys Gln Arg Gly Ala
215 220 225

Arg Cys Arg Asp Arg Val His Asp Phe Asp Cys Leu Cys Pro Ser
230 235 240

Gly Tyr Gly Gly Lys Thr Cys Glu Leu Val Leu Pro Val Pro Asp
245 250 255

Pro Pro Thr Thr Val Asp Thr Pro Leu Gly Pro Thr Ser Ala Val
260 265 270

Val Val Pro Ala Thr Gly Pro Ala Pro His Ser Ala Gly Ala Gly
275 280 285

Leu Leu Arg Ile Ser Val Lys Glu Val Val Arg Arg Gln Glu Ala
290 295 300

Gly Leu Gly Glu Pro Ser Leu Val Ala Leu Val Val Phe Gly Ala
305 310 315

Leu Thr Ala Ala Leu Val Leu Ala Thr Val Leu Leu Thr Leu Arg
320 325 330

Ala Trp Arg Arg Gly Val Cys Pro Pro Gly Pro Cys Cys Tyr Pro
335 340 345

Ala Pro His Tyr Ala Pro Ala Cys Gln Asp Gln Glu Cys Gln Val
350 355 360

Ser Met Leu Pro Ala Gly Leu Pro Leu Pro Arg Asp Leu Pro Pro
365 370 375

Glu Pro Gly Lys Thr Thr Ala Leu
380

<210> SEQ ID NO 81
<211> LENGTH: 1034
<212> TYPE: DNA
<213> ORGANISM: Homo Sapien

<400> SEQUENCE: 81
gtttgttgct caaaccgagt tctggagaac gccatcagct cgctgcttaa 50
aattaaacca caggttccat tatgggtcga cttgatggga aagtcatcat 100
cctgacggcc gctgctcagg ggattggcca agcagctgcc ttagcttttg 150
caagagaagg tgccaaagtc atagccacag acattaatga gtccaaactt 200
caggaactgg aaaagtaccc gggtattcaa actcgtgtcc ttgatgtcac 250
aaagaagaaa caaattgatc agtttgccag tgaagttgag agacttgatg 300
ttctctttaa tgttgctggt tttgtccatc atggaactgt cctggattgt 350
gaggagaaag actgggactt ctcgatgaat ctcaatgtgc gcagcatgta 400
cctgatgatc aaggcattcc ttcctaaaat gcttgctcag aaatctggca 450
atattatcaa catgtcttct gtggcttcca gcgtcaaagg agttgtgaac 500
agatgtgtgt acagcacaac caaggcagcc gtgattggcc tcacaaaatc 550

-continued

```
tctggctgca gatttcatcc agcagggcat caggtgcaac tgtgtgtgcc         600

caggaacagt tgatacgcca tctctacaag aaagaataca agccagagga         650

aatcctgaag aggcacggaa tgatttcctg aagagacaaa agacgggaag         700

attcgcaact gcagaagaaa tagccatgct ctgcgtgtat ttggcttctg         750

atgaatctgc ttatgtaact ggtaaccctg tcatcattga tggaggctgg         800

agcttgtgat tttaggatct ccatggtggg aaggaaggca ggcccttcct         850

atccacagtg aacctggtta cgaagaaaac tcaccaatca tctccttcct         900

gttaatcaca tgttaatgaa aataagctct ttttaatgat gtcactgttt         950

gcaagagtct gattctttaa gtatattaat ctctttgtaa tctcttctga        1000

aatcattgta aagaaataaa aatattgaac tcat                         1034
```

<210> SEQ ID NO 82
<211> LENGTH: 245
<212> TYPE: PRT
<213> ORGANISM: Homo Sapien

<400> SEQUENCE: 82

```
Met Gly Arg Leu Asp Gly Lys Val Ile Ile Leu Thr Ala Ala Ala
  1               5                  10                  15

Gln Gly Ile Gly Gln Ala Ala Ala Leu Ala Phe Ala Arg Glu Gly
                 20                  25                  30

Ala Lys Val Ile Ala Thr Asp Ile Asn Glu Ser Lys Leu Gln Glu
                 35                  40                  45

Leu Glu Lys Tyr Pro Gly Ile Gln Thr Arg Val Leu Asp Val Thr
                 50                  55                  60

Lys Lys Lys Gln Ile Asp Gln Phe Ala Ser Glu Val Glu Arg Leu
                 65                  70                  75

Asp Val Leu Phe Asn Val Ala Gly Phe Val His His Gly Thr Val
                 80                  85                  90

Leu Asp Cys Glu Glu Lys Asp Trp Asp Phe Ser Met Asn Leu Asn
                 95                 100                 105

Val Arg Ser Met Tyr Leu Met Ile Lys Ala Phe Leu Pro Lys Met
                110                 115                 120

Leu Ala Gln Lys Ser Gly Asn Ile Ile Asn Met Ser Ser Val Ala
                125                 130                 135

Ser Ser Val Lys Gly Val Val Asn Arg Cys Val Tyr Ser Thr Thr
                140                 145                 150

Lys Ala Ala Val Ile Gly Leu Thr Lys Ser Leu Ala Ala Asp Phe
                155                 160                 165

Ile Gln Gln Gly Ile Arg Cys Asn Cys Val Cys Pro Gly Thr Val
                170                 175                 180

Asp Thr Pro Ser Leu Gln Glu Arg Ile Gln Ala Arg Gly Asn Pro
                185                 190                 195

Glu Glu Ala Arg Asn Asp Phe Leu Lys Arg Gln Lys Thr Gly Arg
                200                 205                 210

Phe Ala Thr Ala Glu Glu Ile Ala Met Leu Cys Val Tyr Leu Ala
                215                 220                 225

Ser Asp Glu Ser Ala Tyr Val Thr Gly Asn Pro Val Ile Ile Asp
                230                 235                 240

Gly Gly Trp Ser Leu
                245
```

-continued

<210> SEQ ID NO 83
<211> LENGTH: 1961
<212> TYPE: DNA
<213> ORGANISM: Homo Sapien

<400> SEQUENCE: 83
gggcggcggc ggcagcggtt ggaggttgta ggaccggcga ggaataggaa 50
tcatggcggc tgcgctgttc gtgctgctgg gattcgcgct gctgggcacc 100
cacggagcct ccggggctgc cggcttcgtc caggcgccgc tgtcccagca 150
gaggtgggtg gggggcagtg tggagctgca ctgcgaggcc gtgggcagcc 200
cggtgcccga gatccagtgg tggtttgaag ggcagggtcc caacgacacc 250
tgctcccagc tctgggacgg cgcccggctg gaccgcgtcc acatccacgc 300
cacctaccac cagcacgcgg ccagcaccat ctccatcgac acgctcgtgg 350
aggaggacac gggcacttac gagtgccggg ccagcaacga cccggatcgc 400
aaccacctga cccgggcgcc cagggtcaag tgggtccgcg cccaggcagt 450
cgtgctagtc ctggaacccg gcacagtctt cactaccgta gaagaccttg 500
gctccaagat actcctcacc tgctccttga atgacagcgc cacagaggtc 550
acagggcacc gctggctgaa gggggcgtg gtgctgaagg aggacgcgct 600
gcccggccag aaaacggagt tcaaggtgga ctccgacgac cagtggggag 650
agtactcctg cgtcttcctc cccgagccca tgggcacggc caacatccag 700
ctccacgggc ctcccagagt gaaggctgtg aagtcgtcag aacacatcaa 750
cgagggggag acggccatgc tggtctgcaa gtcagagtcc gtgccacctg 800
tcactgactg ggcctggtac aagatcactg actctgagga caaggccctc 850
atgaacggct ccgagagcag gttcttcgtg agttcctcgc agggccggtc 900
agagctacac attgagaacc tgaacatgga ggccgacccc ggccagtacc 950
ggtgcaacgg caccagctcc aagggctccg accaggccat catcacgctc 1000
cgcgtgcgca gccacctggc cgccctctgg cccttcctgg gcatcgtggc 1050
tgaggtgctg gtgctggtca ccatcatctt catctacgag aagcgccgga 1100
agcccgagga cgtcctggat gatgacgacg ccggctctgc accccctgaag 1150 agcagcgggc agcaccagaa tgacaaaggc aagaacgtcc gccagaggaa 1200
ctcttcctga ggcaggtggc ccgaggacgc tccctgctcc acgtctgcgc 1250
cgccgccgga gtccactccc agtgcttgca agattccaag ttctcacctc 1300
ttaaagaaaa cccaccccgt agattcccat catacacttc cttctttttt 1350
aaaaaagttg ggttttctcc attcaggatt ctgttcctta ggttttttttc 1400 cttctgaagt gtttcacgag agcccgggag ctgctgccct gcggccccgt 1450
ctgtggcttt cagcctctgg gtctgagtca tggccgggtg ggcggcacag 1500
ccttctccac tggccggagt cagtgccagg tccttgccct ttgtggaaag 1550
tcacaggtca cacgaggggc cccgtgtcct gcctgtctga agccaatgct 1600
gtctggttgc gccatttttg tgcttttatg tttaatttta tgagggccac 1650
gggtctgtgt tcgactcagc ctcagggacg actctgacct cttggccaca 1700
gaggactcac ttgcccacac cgagggcgac cccgtcacag cctcaagtca 1750
ctcccaagcc ccctccttgt ctgtgcatcc gggggcagct ctggaggggg 1800

-continued

```
tttgctgggg aactggcgcc atcgccggga ctccagaacc gcagaagcct          1850

ccccagctca cccctggagg acggccggct ctctatagca ccagggctca          1900

cgtgggaacc cccctcccac ccaccgccac aataaagatc gcccccacct          1950

ccacccaaaa a                                                    1961
```

```
<210> SEQ ID NO 84
<211> LENGTH: 385
<212> TYPE: PRT
<213> ORGANISM: Homo Sapien

<400> SEQUENCE: 84

Met Ala Ala Ala Leu Phe Val Leu Leu Gly Phe Ala Leu Leu Gly
  1               5                  10                  15

Thr His Gly Ala Ser Gly Ala Ala Gly Phe Val Gln Ala Pro Leu
                 20                  25                  30

Ser Gln Gln Arg Trp Val Gly Gly Ser Val Glu Leu His Cys Glu
                 35                  40                  45

Ala Val Gly Ser Pro Val Pro Glu Ile Gln Trp Trp Phe Glu Gly
                 50                  55                  60

Gln Gly Pro Asn Asp Thr Cys Ser Gln Leu Trp Asp Gly Ala Arg
                 65                  70                  75

Leu Asp Arg Val His Ile His Ala Thr Tyr His Gln His Ala Ala
                 80                  85                  90

Ser Thr Ile Ser Ile Asp Thr Leu Val Glu Glu Asp Thr Gly Thr
                 95                 100                 105

Tyr Glu Cys Arg Ala Ser Asn Asp Pro Asp Arg Asn His Leu Thr
                110                 115                 120

Arg Ala Pro Arg Val Lys Trp Val Arg Ala Gln Ala Val Val Leu
                125                 130                 135

Val Leu Glu Pro Gly Thr Val Phe Thr Thr Val Glu Asp Leu Gly
                140                 145                 150

Ser Lys Ile Leu Leu Thr Cys Ser Leu Asn Asp Ser Ala Thr Glu
                155                 160                 165

Val Thr Gly His Arg Trp Leu Lys Gly Gly Val Val Leu Lys Glu
                170                 175                 180

Asp Ala Leu Pro Gly Gln Lys Thr Glu Phe Lys Val Asp Ser Asp
                185                 190                 195

Asp Gln Trp Gly Glu Tyr Ser Cys Val Phe Leu Pro Glu Pro Met
                200                 205                 210

Gly Thr Ala Asn Ile Gln Leu His Gly Pro Pro Arg Val Lys Ala
                215                 220                 225

Val Lys Ser Ser Glu His Ile Asn Glu Gly Glu Thr Ala Met Leu
                230                 235                 240

Val Cys Lys Ser Glu Ser Val Pro Pro Val Thr Asp Trp Ala Trp
                245                 250                 255

Tyr Lys Ile Thr Asp Ser Glu Asp Lys Ala Leu Met Asn Gly Ser
                260                 265                 270

Glu Ser Arg Phe Phe Val Ser Ser Ser Gln Gly Arg Ser Glu Leu
                275                 280                 285

His Ile Glu Asn Leu Asn Met Glu Ala Asp Pro Gly Gln Tyr Arg
                290                 295                 300

Cys Asn Gly Thr Ser Ser Lys Gly Ser Asp Gln Ala Ile Ile Thr
                305                 310                 315
```

-continued

```
Leu Arg Val Arg Ser His Leu Ala Ala Leu Trp Pro Phe Leu Gly
                320                 325                 330

Ile Val Ala Glu Val Leu Val Leu Val Thr Ile Ile Phe Ile Tyr
                335                 340                 345

Glu Lys Arg Arg Lys Pro Glu Asp Val Leu Asp Asp Asp Asp Ala
                350                 355                 360

Gly Ser Ala Pro Leu Lys Ser Ser Gly Gln His Gln Asn Asp Lys
                365                 370                 375

Gly Lys Asn Val Arg Gln Arg Asn Ser Ser
                380                 385


<210> SEQ ID NO 85
<211> LENGTH: 1002
<212> TYPE: DNA
<213> ORGANISM: Homo Sapien

<400> SEQUENCE: 85

ggctcgagca aagacatacg aacagggagg aaggccgact gaaagaaaga          50

cggagaagag gagagagaag ccagggccga gcgtgccagc aggcggatgg         100

agggcggcct ggtggaggag gagacgtagt ggcctgggct gagctgggtg         150

ggccgggaga agcgggtgcc tcagagtggg ggtgggggca tgggaggggc         200

aggcattctg ctgctgctgc tggctggggc gggggtggtg gtggcctgga         250

gacccccaaa gggaaagtgt cccctgcgct gctcctgctc taaagacagc         300

gccctgtgtg agggctcccc ggacctgccc gtcagcttct ctccgaccct         350

gctgtcactc tcactcgtca ggacgggagt cacccagctg aaggccggca         400

gcttcctgag aattccgtct ctgcacctgc tcctcttcac ctccaactcc         450

ttctccgtga ttgaggacga tgcatttgcg ggcctgtccc acctgcagta         500

cctcttcatc gaggacaatg agattggctc catctctaag aatgccctca         550

gaggacttcg ctcgcttaca cacctaagcc tggccaataa ccatctggag         600

accctcccca gattcctgtt ccgaggcctg gacaccctta ctcacgtgga         650

cctccgcggg aacccgttcc agtgtgactg ccgcgtcctc tggctcctgc         700

agtggatgcc caccgtgaat gccagcgtgg ggaccggcgc ctgtgcgggc         750

cccgcctccc tgagccacat gcagctccac cacctcgacc ccaagacttt         800

caagtgcaga gccataggtg gggggctttc ccgatggggt gggaggcggg         850

agatctgggg gaaaggctgc cagggccaag aggctcgtct cactccctgc         900

cctgccattt cccggagtgg gaagaccctg agcaagcagc actgccttcc         950

tgagccccag ttttctcatc tgtaaagtgg gggtaataaa cagtgatata        1000

gg                                                            1002


<210> SEQ ID NO 86
<211> LENGTH: 261
<212> TYPE: PRT
<213> ORGANISM: Homo Sapien

<400> SEQUENCE: 86

Met Gly Gly Ala Gly Ile Leu Leu Leu Leu Leu Ala Gly Ala Gly
  1               5                  10                  15

Val Val Val Ala Trp Arg Pro Pro Lys Gly Lys Cys Pro Leu Arg
                 20                  25                  30
```

-continued

Cys Ser Cys Ser Lys Asp Ser Ala Leu Cys Glu Gly Ser Pro Asp
35 40 45

Leu Pro Val Ser Phe Ser Pro Thr Leu Leu Ser Leu Ser Leu Val
50 55 60

Arg Thr Gly Val Thr Gln Leu Lys Ala Gly Ser Phe Leu Arg Ile
65 70 75

Pro Ser Leu His Leu Leu Leu Phe Thr Ser Asn Ser Phe Ser Val
80 85 90

Ile Glu Asp Asp Ala Phe Ala Gly Leu Ser His Leu Gln Tyr Leu
95 100 105

Phe Ile Glu Asp Asn Glu Ile Gly Ser Ile Ser Lys Asn Ala Leu
110 115 120

Arg Gly Leu Arg Ser Leu Thr His Leu Ser Leu Ala Asn Asn His
125 130 135

Leu Glu Thr Leu Pro Arg Phe Leu Phe Arg Gly Leu Asp Thr Leu
140 145 150

Thr His Val Asp Leu Arg Gly Asn Pro Phe Gln Cys Asp Cys Arg
155 160 165

Val Leu Trp Leu Leu Gln Trp Met Pro Thr Val Asn Ala Ser Val
170 175 180

Gly Thr Gly Ala Cys Ala Gly Pro Ala Ser Leu Ser His Met Gln
185 190 195

Leu His His Leu Asp Pro Lys Thr Phe Lys Cys Arg Ala Ile Gly
200 205 210

Gly Gly Leu Ser Arg Trp Gly Gly Arg Arg Glu Ile Trp Gly Lys
215 220 225

Gly Cys Gln Gly Gln Glu Ala Arg Leu Thr Pro Cys Pro Ala Ile
230 235 240

Ser Arg Ser Gly Lys Thr Leu Ser Lys Gln His Cys Leu Pro Glu
245 250 255

Pro Gln Phe Ser His Leu
260

<210> SEQ ID NO 87
<211> LENGTH: 2945
<212> TYPE: DNA
<213> ORGANISM: Homo Sapien

<400> SEQUENCE: 87
cggacgcgtg gggcggcgag agcagctgca gttcgcatct caggcagtac 50
ctagaggagc tgccggtgcc tcctcagaac atctcctgat cgctacccag 100
gaccaggcac caaggacagg gagtcccagg cgcacacccc ccattctggg 150
tcccccaggc ccagaccccc actctgccac aggttgcatc ttgacctggt 200
cctcctgcag aagtggcccc tgtggtcctg ctctgagact cgtccctggg 250
cgcccctgca gcccctttct atgactccat ctggatttgg ctggctgtgg 300
ggacgcggtc cgaggggcgg cctggctctc agcgtggtgg cagccagctc 350
tctggccacc atggcaaatg ctgagatctg aggggacaag gctctacagc 400
ctcagccagg ggcactcagc tgttgcaggg tgtgatggag aacaaagcta 450
tgtacctaca caccgtcagc gactgtgaca ccagctccat ctgtgaggat 500
tcctttgatg gcaggagcct gtccaagctg aacctgtgtg aggatggtcc 550

-continued

```
atgtcacaaa cggcgggcaa gcatctgctg tacccagctg gggtccctgt        600
cggccctgaa gcatgctgtc ctggggctct acctgctggt cttcctgatt        650
cttgtgggca tcttcatctt agcagggcca ccgggaccca aaggtgatca        700
gggggatgaa ggaaaggaag gcaggcctgg catccctgga ttgcctggac        750
ttcgaggtct gcccggggag agaggtaccc caggattgcc cgggcccaag        800
ggcgatgatg ggaagctggg ggccacagga ccaatgggca tgcgtgggtt        850
caaaggtgac cgaggcccaa aaggagagaa aggagagaaa ggagacagag        900
ctggggatgc cagtggcgtg gaggccccga tgatgatccg cctggtgaat        950
ggctcaggtc cgcacgaggg ccgcgtggaa gtgtaccacg accggcgctg       1000
gggcaccgtg tgtgacgacg gctgggacaa gaaggacgga gacgtggtgt       1050
gccgcatgct cggcttccgc ggtgtggagg aggtgtaccg cacagctcga       1100
ttcgggcaag gcactgggag gatctggatg gatgacgttg cctgcaaggg       1150
cacagaggaa accatcttcc gctgcagctt ctccaaatgg ggggtgacaa       1200
actgtggaca tgccgaagat gccagcgtga catgcaacag acactgaaag       1250
tgggcagagc ccaagttcgg ggtcctgcac agagcaccct tgctgcatcc       1300
ctggggtggg gcacagctcg gggccaccct gaccatgcct cgaccacacc       1350
ccgtccagca ttctcagtcc tcacacctgc atcccaggac cgtgggggcc       1400
ggtcgtcatt tccctcttga acatgtgctc cgaagtataa ctctgggacc       1450
tactgcccgt ctctctcttc caccaggttc ctgcatgagg agccctgatc       1500
aactggatca ccactttgcc cagcctctga acaccatgca ccaggcctca       1550
atatcccagt tccctttggc cttttagtta caggtgaatg ctgagaatgt       1600
gtcagagaca agtgcagcag cagcgatggt tggtagtata gatcatttac       1650
tcttcagaca attcccaaac ctccattagt ccaagagttt ctacatcttc       1700
ctccccagca agaggcaacg tcaagtgatg aatttccccc ctttactctg       1750
cctctgctcc ccatttgcta gtttgaggaa gtgacataga ggagaagcca       1800
gctgtagggg caagagggaa atgcaagtca cctgcaggaa tccagctaga       1850
tttggagaag ggaatgaaac taacattgaa tgactaccat ggcacgctaa       1900
atagtatctt gggtgccaaa ttcatgtatc cacttagctg cattggtcca       1950
gggcatgtca gtctggatac agccttacct tcaggtagca cttaactggt       2000
ccattcacct agactgcaag taagaagaca aaatgactga gaccgtgtgc       2050
ccacctgaac ttattgtctt tacttggcct gagctaaaag cttgggtgca       2100
ggacctgtgt aactagaaag ttgcctactt cagaacctcc agggcgtgag       2150
tgcaaggtca aacatgactg gcttccaggc cgaccatcaa tgtaggagga       2200
gagctgatgt ggagggtgac atgggggctg cccatgttaa acctgagtcc       2250
agtgctctgg cattgggcag tcacggttaa agccaagtca tgtgtgtctc       2300
agctgtttgg aggtgatgat tttgcatctt ccaagcctct tcaggtgtga       2350
atctgtggtc aggaaaacac aagtcctaat ggaaccctta ggggggaagg       2400
aaatgaagat tccctataac ctctggggt  ggggagtagg aataaggggc       2450
cttgggcctc cataaatctg caatctgcac cctcctccta gagacaggga       2500
gatcgtgttc tgctttttac atgaggagca gaactgggcc atacacgtgt       2550
```

-continued

```
tcaagaacta ggggagctac ctggtagcaa gtgagtgcag acccacctca          2600

ccttggggga atctcaaact cataggcctc agatacacga tcacctgtca          2650

tatcaggtga gcactggcct gcttggggag agacctgggc cctccaggt           2700

gtaggaacag caacactcct ggctgacaac taagccaata tggccctagg          2750

tcattcttgc ttccaatatg cttgccactc cttaaatgtc ctaatgatga          2800

gaaactctct ttctgaccaa ttgctatgtt tacataacac gcatgtactc          2850

atgcatccct tgccagagcc catatatgta tgcatatata aacatagcac          2900

tttttactac atagctcagc acattgcaag gtttgcattt aagtt               2945
```

<210> SEQ ID NO 88
<211> LENGTH: 270
<212> TYPE: PRT
<213> ORGANISM: Homo Sapien

<400> SEQUENCE: 88

```
Met Glu Asn Lys Ala Met Tyr Leu His Thr Val Ser Asp Cys Asp
  1               5                  10                  15

Thr Ser Ser Ile Cys Glu Asp Ser Phe Asp Gly Arg Ser Leu Ser
                 20                  25                  30

Lys Leu Asn Leu Cys Glu Asp Gly Pro Cys His Lys Arg Arg Ala
                 35                  40                  45

Ser Ile Cys Cys Thr Gln Leu Gly Ser Leu Ser Ala Leu Lys His
                 50                  55                  60

Ala Val Leu Gly Leu Tyr Leu Leu Val Phe Leu Ile Leu Val Gly
                 65                  70                  75

Ile Phe Ile Leu Ala Gly Pro Pro Gly Pro Lys Gly Asp Gln Gly
                 80                  85                  90

Asp Glu Gly Lys Glu Gly Arg Pro Gly Ile Pro Gly Leu Pro Gly
                 95                 100                 105

Leu Arg Gly Leu Pro Gly Glu Arg Gly Thr Pro Gly Leu Pro Gly
                110                 115                 120

Pro Lys Gly Asp Asp Gly Lys Leu Gly Ala Thr Gly Pro Met Gly
                125                 130                 135

Met Arg Gly Phe Lys Gly Asp Arg Gly Pro Lys Gly Glu Lys Gly
                140                 145                 150

Glu Lys Gly Asp Arg Ala Gly Asp Ala Ser Gly Val Glu Ala Pro
                155                 160                 165

Met Met Ile Arg Leu Val Asn Gly Ser Gly Pro His Glu Gly Arg
                170                 175                 180

Val Glu Val Tyr His Asp Arg Arg Trp Gly Thr Val Cys Asp Asp
                185                 190                 195

Gly Trp Asp Lys Lys Asp Gly Asp Val Val Cys Arg Met Leu Gly
                200                 205                 210

Phe Arg Gly Val Glu Glu Val Tyr Arg Thr Ala Arg Phe Gly Gln
                215                 220                 225

Gly Thr Gly Arg Ile Trp Met Asp Asp Val Ala Cys Lys Gly Thr
                230                 235                 240

Glu Glu Thr Ile Phe Arg Cys Ser Phe Ser Lys Trp Gly Val Thr
                245                 250                 255

Asn Cys Gly His Ala Glu Asp Ala Ser Val Thr Cys Asn Arg His
                260                 265                 270
```

-continued

<210> SEQ ID NO 89
<211> LENGTH: 2758
<212> TYPE: DNA
<213> ORGANISM: Homo Sapien

<400> SEQUENCE: 89
gtcgccgcga gggacgcaga gagcaccctc cacgcccaga tgcctgcgta 50
gtttttgtga ccagtccgct cctgcctccc cctggggcag tagaggggga 100
gcgatggaga actggactgg caggccctgg ctgtatctgc tgctgcttct 150
gtccctccct cagctctgct tggatcagga ggtgttgtcc ggacactctc 200
ttcagacacc tacagaggag ggccagggcc ccgaaggtgt ctggggacct 250
tgggtccagt gggcctcttg ctcccagccc tgcggggtgg gggtgcagcg 300
caggagccgg acatgtcagc tccctacagt gcagctccac ccgagtctgc 350
ccctccctcc ccggccccca agacatccag aagccctcct cccccggggc 400
cagggtccca gaccccagac ttctccagaa accctcccct tgtacaggac 450
acagtctcgg ggaaggggtg gcccacttcg aggtcccgct tcccacctag 500
ggagagagga gacccaggag attcgagcgg ccaggaggtc ccggcttcga 550
gaccccatca agccaggaat gttcggttat gggagagtgc cctttgcatt 600
gccactgcac cggaaccgca ggcaccctcg gagcccaccc agatctgagc 650
tgtccctgat ctcttctaga ggggaagagg ctattccgtc ccctactcca 700
agagcagagc cattctccgc aaacggcagc ccccaaactg agctccctcc 750
cacagaactg tctgtccaca ccccatcccc ccaagcagaa cctctaagcc 800
ctgaaactgc tcagacagag gtggccccca gaaccaggcc tgccccccta 850
cggcatcacc ccagagccca ggcctctggc acagagcccc cctcacccac 900
gcactcctta ggagaaggtg gcttcttccg tgcatcccct cagccacgaa 950
ggccaagttc ccagggttgg gccagtcccc aggtagcagg gagacgccct 1000
gatccttttc cttcggtccc tcggggccga ggccagcagg gccaagggcc 1050
ttggggaacg ggggggactc ctcacgggcc ccgcctggag cctgaccctc 1100
agcacccggg cgcctggctg cccctgctga gcaacggccc ccatgccagc 1150
tccctctgga gcctctttgc tcccagtagc cctattccaa gatgttctgg 1200
ggagagtgaa cagctaagag cctgcagcca agcgccctgc ccccctgagc 1250
agccagaccc ccgggccctg cagtgcgcag cctttaactc ccaggaattc 1300
atgggccagc tgtatcagtg ggagcccttc actgaagtcc agggctccca 1350
gcgctgtgaa ctgaactgcc ggccccgtgg cttccgcttc tatgtccgtc 1400
acactgaaaa ggtccaggat gggaccctgt gtcagcctgg agcccctgac 1450
atctgtgtgg ctggacgctg tctgagcccc ggctgtgatg ggatccttgg 1500
ctctggcagg cgtcctgatg gctgtggagt ctgtgggggt gatgattcta 1550
cctgtcgcct tgtttcgggg aacctcactg accgaggggg cccccctgggc 1600 tatcagaaga tcttgtggat tccagcggga gccttgcggc tccagattgc 1650
ccagctccgg cctagctcca actacctggc acttcgtggc cctgggggcc 1700
ggtccatcat caatgggaac tgggctgtgg atcccccctgg gtcctacagg 1750 gccggcggga ccgtctttcg atataaccgt cctcccaggg aggagggcaa 1800

-continued

```
aggggagagt ctgtcggctg aaggccccac cacccagcct gtggatgtct       1850

atatgatctt tcaggaggaa aacccaggcg tttttatca gtatgtcatc        1900

tcttcacctc ctccaatcct tgagaacccc accccagagc cccctgtccc       1950

ccagcttcag ccggagattc tgagggtgga gcccccactt gctccggcac       2000

cccgcccagc ccggacccca ggcaccctcc agcgtcaggt gcggatcccc       2050

cagatgcccg ccccgcccca tcccaggaca cccctggggt ctccagctgc       2100

gtactggaaa cgagtgggac actctgcatg ctcagcgtcc tgcgggaaag       2150

gtgtctggcg ccccattttc ctctgcatct cccgtgagtc gggagaggaa       2200

ctggatgaac gcagctgtgc cgcgggtgcc aggcccccag cctcccctga       2250

accctgccac ggcaccccat gcccccata ctgggaggct ggcgagtgga        2300

catcctgcag ccgctcctgt ggccccggca cccagcaccg ccagctgcag       2350

tgccggcagg aatttggggg gggtggctcc tcggtgcccc cggagcgctg       2400

tggacatctc ccccggccca acatcaccca gtcttgccag ctgcgcctct       2450

gtggccattg ggaagttggc tctccttgga gccagtgctc cgtgcggtgc       2500

ggccggggcc agagaagccg gcaggttcgc tgtgttggga acaacggtga       2550

tgaagtgagc gagcaggagt gtgcgtcagg ccccccacag ccccccagca       2600

gagaggcctg tgacatgggg ccctgtacta ctgcctggtt ccacagcgac       2650

tggagctcca aggtgagccc ggaacccccca gccatatcct gcatcctggg      2700

taaccatgcc caggacacct cagcctttcc agcatagctc aataaacttg       2750

tattgatc                                                     2758
```

<210> SEQ ID NO 90
<211> LENGTH: 877
<212> TYPE: PRT
<213> ORGANISM: Homo Sapien

<400> SEQUENCE: 90

```
Met Glu Asn Trp Thr Gly Arg Pro Trp Leu Tyr Leu Leu Leu Leu
  1               5                  10                  15

Leu Ser Leu Pro Gln Leu Cys Leu Asp Gln Glu Val Leu Ser Gly
                 20                  25                  30

His Ser Leu Gln Thr Pro Thr Glu Glu Gly Gln Gly Pro Glu Gly
                 35                  40                  45

Val Trp Gly Pro Trp Val Gln Trp Ala Ser Cys Ser Gln Pro Cys
                 50                  55                  60

Gly Val Gly Val Gln Arg Arg Ser Arg Thr Cys Gln Leu Pro Thr
                 65                  70                  75

Val Gln Leu His Pro Ser Leu Pro Leu Pro Pro Arg Pro Pro Arg
                 80                  85                  90

His Pro Glu Ala Leu Leu Pro Arg Gly Gln Gly Pro Arg Pro Gln
                 95                 100                 105

Thr Ser Pro Glu Thr Leu Pro Leu Tyr Arg Thr Gln Ser Arg Gly
                110                 115                 120

Arg Gly Gly Pro Leu Arg Gly Pro Ala Ser His Leu Gly Arg Glu
                125                 130                 135

Glu Thr Gln Glu Ile Arg Ala Ala Arg Arg Ser Arg Leu Arg Asp
                140                 145                 150
```

-continued

```
Pro Ile Lys Pro Gly Met Phe Gly Tyr Gly Arg Val Pro Phe Ala
                155                 160                 165

Leu Pro Leu His Arg Asn Arg Arg His Pro Arg Ser Pro Pro Arg
                170                 175                 180

Ser Glu Leu Ser Leu Ile Ser Ser Arg Gly Glu Glu Ala Ile Pro
                185                 190                 195

Ser Pro Thr Pro Arg Ala Glu Pro Phe Ser Ala Asn Gly Ser Pro
                200                 205                 210

Gln Thr Glu Leu Pro Pro Thr Glu Leu Ser Val His Thr Pro Ser
                215                 220                 225

Pro Gln Ala Glu Pro Leu Ser Pro Glu Thr Ala Gln Thr Glu Val
                230                 235                 240

Ala Pro Arg Thr Arg Pro Ala Pro Leu Arg His His Pro Arg Ala
                245                 250                 255

Gln Ala Ser Gly Thr Glu Pro Pro Ser Pro Thr His Ser Leu Gly
                260                 265                 270

Glu Gly Gly Phe Phe Arg Ala Ser Pro Gln Pro Arg Arg Pro Ser
                275                 280                 285

Ser Gln Gly Trp Ala Ser Pro Gln Val Ala Gly Arg Arg Pro Asp
                290                 295                 300

Pro Phe Pro Ser Val Pro Arg Gly Arg Gly Gln Gln Gly Gln Gly
                305                 310                 315

Pro Trp Gly Thr Gly Gly Thr Pro His Gly Pro Arg Leu Glu Pro
                320                 325                 330

Asp Pro Gln His Pro Gly Ala Trp Leu Pro Leu Leu Ser Asn Gly
                335                 340                 345

Pro His Ala Ser Ser Leu Trp Ser Leu Phe Ala Pro Ser Ser Pro
                350                 355                 360

Ile Pro Arg Cys Ser Gly Glu Ser Glu Gln Leu Arg Ala Cys Ser
                365                 370                 375

Gln Ala Pro Cys Pro Pro Glu Gln Pro Asp Pro Arg Ala Leu Gln
                380                 385                 390

Cys Ala Ala Phe Asn Ser Gln Glu Phe Met Gly Gln Leu Tyr Gln
                395                 400                 405

Trp Glu Pro Phe Thr Glu Val Gln Gly Ser Gln Arg Cys Glu Leu
                410                 415                 420

Asn Cys Arg Pro Arg Gly Phe Arg Phe Tyr Val Arg His Thr Glu
                425                 430                 435

Lys Val Gln Asp Gly Thr Leu Cys Gln Pro Gly Ala Pro Asp Ile
                440                 445                 450

Cys Val Ala Gly Arg Cys Leu Ser Pro Gly Cys Asp Gly Ile Leu
                455                 460                 465

Gly Ser Gly Arg Arg Pro Asp Gly Cys Gly Val Cys Gly Gly Asp
                470                 475                 480

Asp Ser Thr Cys Arg Leu Val Ser Gly Asn Leu Thr Asp Arg Gly
                485                 490                 495

Gly Pro Leu Gly Tyr Gln Lys Ile Leu Trp Ile Pro Ala Gly Ala
                500                 505                 510

Leu Arg Leu Gln Ile Ala Gln Leu Arg Pro Ser Ser Asn Tyr Leu
                515                 520                 525

Ala Leu Arg Gly Pro Gly Gly Arg Ser Ile Ile Asn Gly Asn Trp
                530                 535                 540

Ala Val Asp Pro Pro Gly Ser Tyr Arg Ala Gly Gly Thr Val Phe
```

-continued

```
                545                 550                 555

Arg Tyr Asn Arg Pro Pro Arg Glu Glu Gly Lys Gly Glu Ser Leu
                560                 565                 570

Ser Ala Glu Gly Pro Thr Thr Gln Pro Val Asp Val Tyr Met Ile
                575                 580                 585

Phe Gln Glu Glu Asn Pro Gly Val Phe Tyr Gln Tyr Val Ile Ser
                590                 595                 600

Ser Pro Pro Pro Ile Leu Glu Asn Pro Thr Pro Glu Pro Pro Val
                605                 610                 615

Pro Gln Leu Gln Pro Glu Ile Leu Arg Val Glu Pro Pro Leu Ala
                620                 625                 630

Pro Ala Pro Arg Pro Ala Arg Thr Pro Gly Thr Leu Gln Arg Gln
                635                 640                 645

Val Arg Ile Pro Gln Met Pro Ala Pro Pro His Pro Arg Thr Pro
                650                 655                 660

Leu Gly Ser Pro Ala Ala Tyr Trp Lys Arg Val Gly His Ser Ala
                665                 670                 675

Cys Ser Ala Ser Cys Gly Lys Gly Val Trp Arg Pro Ile Phe Leu
                680                 685                 690

Cys Ile Ser Arg Glu Ser Gly Glu Glu Leu Asp Glu Arg Ser Cys
                695                 700                 705

Ala Ala Gly Ala Arg Pro Pro Ala Ser Pro Glu Pro Cys His Gly
                710                 715                 720

Thr Pro Cys Pro Pro Tyr Trp Glu Ala Gly Glu Trp Thr Ser Cys
                725                 730                 735

Ser Arg Ser Cys Gly Pro Gly Thr Gln His Arg Gln Leu Gln Cys
                740                 745                 750

Arg Gln Glu Phe Gly Gly Gly Gly Ser Ser Val Pro Pro Glu Arg
                755                 760                 765

Cys Gly His Leu Pro Arg Pro Asn Ile Thr Gln Ser Cys Gln Leu
                770                 775                 780

Arg Leu Cys Gly His Trp Glu Val Gly Ser Pro Trp Ser Gln Cys
                785                 790                 795

Ser Val Arg Cys Gly Arg Gly Gln Arg Ser Arg Gln Val Arg Cys
                800                 805                 810

Val Gly Asn Asn Gly Asp Glu Val Ser Glu Gln Glu Cys Ala Ser
                815                 820                 825

Gly Pro Pro Gln Pro Pro Ser Arg Glu Ala Cys Asp Met Gly Pro
                830                 835                 840

Cys Thr Thr Ala Trp Phe His Ser Asp Trp Ser Ser Lys Val Ser
                845                 850                 855

Pro Glu Pro Pro Ala Ile Ser Cys Ile Leu Gly Asn His Ala Gln
                860                 865                 870

Asp Thr Ser Ala Phe Pro Ala
                875
```

<210> SEQ ID NO 91
<211> LENGTH: 2597
<212> TYPE: DNA
<213> ORGANISM: Homo Sapien

<400> SEQUENCE: 91

```
cgagtatttt cccaccatct ccagccggaa actgaccaag aactctgagg            50

cggatggcat gttcgcgtac gtcttccatg atgagttcgt ggcctcgatg           100
```

-continued

```
attaagatcc cttcggacac cttcaccatc atccctgact ttgatatcta        150
ctatgtctat ggttttagca gtggcaactt tgtctacttt ttgaccctcc        200
aacctgagat ggtgtctcca ccaggctcca ccaccaagga gcaggtgtat        250
acatccaagc tcgtgaggct ttgcaaggag gacacagcct tcaactccta        300
tgtagaggtg cccattggct gtgagcgcag tggggtggag taccgcctgc        350
tgcaggctgc ctacctgtcc aaagcggggg ccgtgcttgg caggaccctt        400
ggagtccatc cagatgatga cctgctcttc accgtcttct ccaagggcca        450
gaagcggaaa atgaaatccc tggatgagtc ggccctgtgc atcttcatct        500
tgaagcagat aaatgaccgc attaaggagc ggctgcagtc ttgttaccgg        550
ggcgagggca cgctggacct ggcctggctc aaggtgaagg acatcccctg        600
cagcagtgcg ctcttaacca ttgacgataa cttctgtggc ctggacatga        650
atgctcccct gggagtgtcc gacatggtgc gtggaattcc cgtcttcacg        700
gaggacaggg accgcatgac gtctgtcatc gcatatgtct acaagaacca        750
ctctctggcc tttgtgggca ccaaaagtgg caagctgaag aaggtgcctg        800
gtaccagcct ctgccctacc cttgagctac agacgggacc ccgatcccac        850
agagcaacag tgactctgga actcctgttc tccagctgtt catcaaactg        900
agaaaaactt cagagctgtg taggcttatt tagtgtgttg tcagccttgg        950
atattggaaa atggaaacag atgagacaca tctacctccc tgtgacccca       1000
gccatacatc atagctcatg tcctgccacc ccaagtcctt agggaaaaaa       1050
gactttggag aatgtgtctc tgcttagctt ggctaggtag ttggtctctt       1100
ttctctgccc caagcgtccc ctgggtaatt ttggacaatg gagtgtaggc       1150
atgtttgact cttgtggtgt tatcacttgt atatgtcagt gaaactaact       1200
gattctccca tcggaatata gttatctctt gggcctgata tatggtagga       1250
taaccttatg ctcatctgtc cacttctgca gccaagtcgc ctggccagtg       1300
tgtgtgtgtg tgtgtgtgtg tgtgtgtgtg tgtgtgtatg cttatctgtg       1350
tttaaaggtg tgtgtgcata cacagggcag agaggatgga gcccaccgta       1400
ctgcagcatc atgtaattaa ctcagtgctc agaaccatcc cagcctctgc       1450
gggaaagaga aaagtaagcc aacagtgcct gatgagctga tcatatgtgc       1500
aaaagctctg ttggcatctg gtccaggaga gcacccaaaa aaagttaatt       1550
ggtgttgtcc agtctccttt ccttaagact atggttacaa caaagcgtga       1600
gcagtgtctc ctgcatggcc actatccagc acaattccat aattccccca       1650
tagagccggt ggggaggagg aggtgagtgg cgaaggaagt ggaaacactt       1700
ggtgtcatgt gctcctatca tttctactag cttactggga aataaagtgt       1750
agtcaagagt gtatgaaggc aagatgtaaa attagcgact ggtgctaatc       1800
tggttacttg aaaacaagtg aaagtgctgt agatttgttc tgttgctaag       1850
aaccaccaca ctaaacctcg tatagttcct ggaggatata caacagtgta       1900
attctcttta gggtgtgcca caggttcctg gcctgtggga gggaatgaat       1950
caggagggct cttgagaacc ttcatctgtg tgcttgcact gaaagtgagt       2000
cccaaagctg gagatttagt gagagcaggc aacccctctg tgtctcactg       2050
```

-continued

```
tccatattct ggaggcagag gtttgtaaca ggccatgtgc acctgcatag          2100

ggatgggtaa agcaaggact ttgaaagagt tgaaaagcat tataaacagt          2150

tgttcagaaa tacgtcccag gagttccatg tgaaactggc tctgtgtgca          2200

ttgaagcatg gctgttggga attctaactg gtccaacact cctgcaaaac          2250

aatgtgtaaa tatttaggaa gaaacttgaa aatagtcaaa tcctttgaac          2300

tggtgacaat tttttaaaga atcaattcta atttgtttca agggtaataa          2350

tcaccaagat acacatttca gcatttattt agtctatcaa aaattggaat          2400

tgatatatac actcatttat aggagaatgg ttaggtagat ttggtatatt          2450

tatgtagtca ttgaaaactt agtttataaa ggccaatctt gtaactgatt          2500

cttgtgtgat aacattcagt gaaaaagcat gagacaatta gaaagcatga          2550

tacaatgaat aaaataaaaa ctggaaagag aaccatcaaa atgctaa             2597


<210> SEQ ID NO 92
<211> LENGTH: 280
<212> TYPE: PRT
<213> ORGANISM: Homo Sapien

<400> SEQUENCE: 92

Met Phe Ala Tyr Val Phe His Asp Glu Phe Val Ala Ser Met Ile
  1               5                  10                  15

Lys Ile Pro Ser Asp Thr Phe Thr Ile Ile Pro Asp Phe Asp Ile
                 20                  25                  30

Tyr Tyr Val Tyr Gly Phe Ser Ser Gly Asn Phe Val Tyr Phe Leu
                 35                  40                  45

Thr Leu Gln Pro Glu Met Val Ser Pro Pro Gly Ser Thr Thr Lys
                 50                  55                  60

Glu Gln Val Tyr Thr Ser Lys Leu Val Arg Leu Cys Lys Glu Asp
                 65                  70                  75

Thr Ala Phe Asn Ser Tyr Val Glu Val Pro Ile Gly Cys Glu Arg
                 80                  85                  90

Ser Gly Val Glu Tyr Arg Leu Leu Gln Ala Ala Tyr Leu Ser Lys
                 95                 100                 105

Ala Gly Ala Val Leu Gly Arg Thr Leu Gly Val His Pro Asp Asp
                110                 115                 120

Asp Leu Leu Phe Thr Val Phe Ser Lys Gly Gln Lys Arg Lys Met
                125                 130                 135

Lys Ser Leu Asp Glu Ser Ala Leu Cys Ile Phe Ile Leu Lys Gln
                140                 145                 150

Ile Asn Asp Arg Ile Lys Glu Arg Leu Gln Ser Cys Tyr Arg Gly
                155                 160                 165

Glu Gly Thr Leu Asp Leu Ala Trp Leu Lys Val Lys Asp Ile Pro
                170                 175                 180

Cys Ser Ser Ala Leu Leu Thr Ile Asp Asp Asn Phe Cys Gly Leu
                185                 190                 195

Asp Met Asn Ala Pro Leu Gly Val Ser Asp Met Val Arg Gly Ile
                200                 205                 210

Pro Val Phe Thr Glu Asp Arg Asp Arg Met Thr Ser Val Ile Ala
                215                 220                 225

Tyr Val Tyr Lys Asn His Ser Leu Ala Phe Val Gly Thr Lys Ser
                230                 235                 240

Gly Lys Leu Lys Lys Val Pro Gly Thr Ser Leu Cys Pro Thr Leu
```

-continued

```
                245                 250                 255

Glu Leu Gln Thr Gly Pro Arg Ser His Arg Ala Thr Val Thr Leu
                260                 265                 270

Glu Leu Leu Phe Ser Ser Cys Ser Ser Asn
                275                 280


<210> SEQ ID NO 93
<211> LENGTH: 2883
<212> TYPE: DNA
<213> ORGANISM: Homo Sapien

<400> SEQUENCE: 93

ccttatcaga caaaggacga gatggaaaat acaagataat ttacagtgga        50

gaagaattag aatgtaacct gaaagatctt agaccagcaa cagattatca       100

tgtgagggtg tatgccatgt acaattccgt aaagggatcc tgctccgagc       150

ctgttagctt caccacccac agctgtgcac ccgagtgtcc tttcccccct       200

aagctggcac ataggagcaa aagttcacta accctgcagt ggaaggcacc       250

aattgacaac ggttcaaaaa tcaccaacta ccttttagag tgggatgagg       300

gaaaaagaaa tagtggtttc agacagtgct tcttcgggag ccagaagcac       350

tgcaagttga caaagctttg tccggcaatg ggtacacat tcaggctggc       400

cgctcgaaac gacattggca ccagtggtta tagccaagag gtggtgtgct       450

acacattagg aaatatccct cagatgcctt ctgcactaag gctggttcga       500

gctggcatca catgggtcac gttgcagtgg agtaagccag aaggctgttc       550

acccgaggaa gtgatcacct acaccttgga aattcaggag gatgaaaatg       600

ataacctttt ccacccaaaa tacactggag aggatttaac ctgtactgtg       650

aaaaatctca aaagaagcac acagtataaa ttcaggctga ctgcttctaa       700

tacggaagga aaaagctgtc caagcgaagt tcttgtttgt acgacgagtc       750

ctgacaggcc tggacctcct accagaccgc ttgtcaaagg cccagttaca       800

tctcatggct ttagtgtcaa atgggatccc cctaaggaca atggtggttc       850

agaaatcctc aagtacttgc tagagattac tgatggaaat tctgaagcga       900

atcagtggga agtggcctac agtgggtcgg ctaccgaata caccttcacc       950

cacttgaaac caggcacttt gtacaaactc cgagcatgct gcatcagtac      1000

cggcggacac agccagtgtt ctgaaagtct ccctgttcgc acactaagca      1050

ttgcaccagg tcaatgtcga ccaccgaggg ttttgggtag accaaagcac      1100

aaagaagtcc acttagagtg ggatgttcct gcatcggaaa gtggctgtga      1150

ggtctcagag tacagcgtgg agatgacgga gcccgaagac gtagcctcgg      1200

aagtgtacca tggcccagag ctggagtgca ccgtcggcaa cctgcttcct      1250

ggaaccgtgt atcgcttccg ggtgagggct ctgaatgatg gagggtatgg      1300

tccctattct gatgtctcag aaattaccac tgctgcaggg cctcctggac      1350

aatgcaaagc accttgtatt tcttgtacac ctgatggatg tgtcttagtg      1400

ggttgggaga gtcctgatag ttctggtgct gacatctcag agtacaggtt      1450

ggaatgggga gaagatgaag aatccttaga actcatttat catgggacag      1500

acacccgttt tgaaataaga gacctgttgc ctgctgcaca gtattgctgt      1550

agactacagg ccttcaatca agcaggggca gggccgtaca gtgaacttgt      1600
```

-continued

```
cctttgccag acgccagcgt ctgcccctga ccccgtctcc actctctgtg        1650
tcctggagga ggagcccctt gatgcctacc ctgattcacc ttctgcgtgc        1700
cttgtactga actgggaaga gccgtgcaat aacggatctg aaatccttgc        1750
ttacaccatt gatctaggag acactagcat taccgtgggc aacaccacca        1800
tgcatgttat gaaagatctc cttccagaaa ccacctaccg gatcagaatt        1850
caggctataa atgaaattgg agctggacca tttagtcagt tcattaaagc        1900
aaaaactcgg ccattaccac ccttgcctcc taggctagaa tgtgctgctg        1950
ctggtcctca gagcctgaag ctaaaatggg gagacagtaa ctccaagaca        2000
catgctgctg aggacattgt gtacacacta cagctggagg acagaaacaa        2050
gaggtttatt tcaatctaca gaggacccag ccacacctac aaggtccaga        2100
gactgacgga attcacatgc tactccttca gaatccaggc agcaagcgag        2150
gctggagaag ggcccttctc agaaacctat accttcagca caaccaaaag        2200
tgtccccccc accatcaaag cacctcgagt aacacagtta gaagtaaatt        2250
catgtgaaat tttatgggag acggtaccat caatgaaagg tgaccctgtt        2300
aactacattc tgcaggtatt ggttggaaga gaatctgagt acaaacaggt        2350
gtacaaggga gaagaagcca cattccaaat ctcaggcctc cagaccaaca        2400
cagactacag gttccgcgta tgtgcgtgtc gtcgctgttt agacacctct        2450
caggagctaa gcggagcctt cagcccctct gcggcttttg tattacaacg        2500
aagtgaggtc atgcttacag gggacatggg gagcttagat gatcccaaaa        2550
tgaagagcat gatgcctact gatgaacagt ttgcagccat cattgtgctt        2600
ggctttgcaa ctttgtccat tttatttgcc tttatattac agtacttctt        2650
aatgaagtaa acccaacaaa actagaggta tgaattaatg ctacacattt        2700
taatacacac atttattcag atactcccct ttttaaagcc cttttgtttt        2750
ttgatttata tactctgttt tacagattta gctagaaaaa aaatgtcagt        2800
gttttggtgc accttttga aatgcaaaac taggaaaagg ttaaactgga        2850
ttttttttta aaaaaaaaaa aaaaaaaaaa aaa                          2883
```

<210> SEQ ID NO 94
<211> LENGTH: 847
<212> TYPE: PRT
<213> ORGANISM: Homo Sapien

<400> SEQUENCE: 94

```
Met Tyr Asn Ser Val Lys Gly Ser Cys Ser Glu Pro Val Ser Phe
  1               5                  10                  15

Thr Thr His Ser Cys Ala Pro Glu Cys Pro Phe Pro Pro Lys Leu
                 20                  25                  30

Ala His Arg Ser Lys Ser Ser Leu Thr Leu Gln Trp Lys Ala Pro
                 35                  40                  45

Ile Asp Asn Gly Ser Lys Ile Thr Asn Tyr Leu Leu Glu Trp Asp
                 50                  55                  60

Glu Gly Lys Arg Asn Ser Gly Phe Arg Gln Cys Phe Phe Gly Ser
                 65                  70                  75

Gln Lys His Cys Lys Leu Thr Lys Leu Cys Pro Ala Met Gly Tyr
                 80                  85                  90
```

-continued

Thr Phe Arg Leu Ala Ala Arg Asn Asp Ile Gly Thr Ser Gly Tyr
95 100 105

Ser Gln Glu Val Val Cys Tyr Thr Leu Gly Asn Ile Pro Gln Met
110 115 120

Pro Ser Ala Leu Arg Leu Val Arg Ala Gly Ile Thr Trp Val Thr
125 130 135

Leu Gln Trp Ser Lys Pro Glu Gly Cys Ser Pro Glu Glu Val Ile
140 145 150

Thr Tyr Thr Leu Glu Ile Gln Glu Asp Glu Asn Asp Asn Leu Phe
155 160 165

His Pro Lys Tyr Thr Gly Glu Asp Leu Thr Cys Thr Val Lys Asn
170 175 180

Leu Lys Arg Ser Thr Gln Tyr Lys Phe Arg Leu Thr Ala Ser Asn
185 190 195

Thr Glu Gly Lys Ser Cys Pro Ser Glu Val Leu Val Cys Thr Thr
200 205 210

Ser Pro Asp Arg Pro Gly Pro Pro Thr Arg Pro Leu Val Lys Gly
215 220 225

Pro Val Thr Ser His Gly Phe Ser Val Lys Trp Asp Pro Pro Lys
230 235 240

Asp Asn Gly Gly Ser Glu Ile Leu Lys Tyr Leu Leu Glu Ile Thr
245 250 255

Asp Gly Asn Ser Glu Ala Asn Gln Trp Glu Val Ala Tyr Ser Gly
260 265 270

Ser Ala Thr Glu Tyr Thr Phe Thr His Leu Lys Pro Gly Thr Leu
275 280 285

Tyr Lys Leu Arg Ala Cys Cys Ile Ser Thr Gly Gly His Ser Gln
290 295 300

Cys Ser Glu Ser Leu Pro Val Arg Thr Leu Ser Ile Ala Pro Gly
305 310 315

Gln Cys Arg Pro Pro Arg Val Leu Gly Arg Pro Lys His Lys Glu
320 325 330

Val His Leu Glu Trp Asp Val Pro Ala Ser Glu Ser Gly Cys Glu
335 340 345

Val Ser Glu Tyr Ser Val Glu Met Thr Glu Pro Glu Asp Val Ala
350 355 360

Ser Glu Val Tyr His Gly Pro Glu Leu Glu Cys Thr Val Gly Asn
365 370 375

Leu Leu Pro Gly Thr Val Tyr Arg Phe Arg Val Arg Ala Leu Asn
380 385 390

Asp Gly Gly Tyr Gly Pro Tyr Ser Asp Val Ser Glu Ile Thr Thr
395 400 405

Ala Ala Gly Pro Pro Gly Gln Cys Lys Ala Pro Cys Ile Ser Cys
410 415 420

Thr Pro Asp Gly Cys Val Leu Val Gly Trp Glu Ser Pro Asp Ser
425 430 435

Ser Gly Ala Asp Ile Ser Glu Tyr Arg Leu Glu Trp Gly Glu Asp
440 445 450

Glu Glu Ser Leu Glu Leu Ile Tyr His Gly Thr Asp Thr Arg Phe
455 460 465

Glu Ile Arg Asp Leu Leu Pro Ala Ala Gln Tyr Cys Cys Arg Leu
470 475 480

Gln Ala Phe Asn Gln Ala Gly Ala Gly Pro Tyr Ser Glu Leu Val

-continued

```
                485                 490                 495

Leu Cys Gln Thr Pro Ala Ser Ala Pro Asp Pro Val Ser Thr Leu
                500                 505                 510

Cys Val Leu Glu Glu Glu Pro Leu Asp Ala Tyr Pro Asp Ser Pro
                515                 520                 525

Ser Ala Cys Leu Val Leu Asn Trp Glu Glu Pro Cys Asn Asn Gly
                530                 535                 540

Ser Glu Ile Leu Ala Tyr Thr Ile Asp Leu Gly Asp Thr Ser Ile
                545                 550                 555

Thr Val Gly Asn Thr Thr Met His Val Met Lys Asp Leu Leu Pro
                560                 565                 570

Glu Thr Thr Tyr Arg Ile Arg Ile Gln Ala Ile Asn Glu Ile Gly
                575                 580                 585

Ala Gly Pro Phe Ser Gln Phe Ile Lys Ala Lys Thr Arg Pro Leu
                590                 595                 600

Pro Pro Leu Pro Pro Arg Leu Glu Cys Ala Ala Ala Gly Pro Gln
                605                 610                 615

Ser Leu Lys Leu Lys Trp Gly Asp Ser Asn Ser Lys Thr His Ala
                620                 625                 630

Ala Glu Asp Ile Val Tyr Thr Leu Gln Leu Glu Asp Arg Asn Lys
                635                 640                 645

Arg Phe Ile Ser Ile Tyr Arg Gly Pro Ser His Thr Tyr Lys Val
                650                 655                 660

Gln Arg Leu Thr Glu Phe Thr Cys Tyr Ser Phe Arg Ile Gln Ala
                665                 670                 675

Ala Ser Glu Ala Gly Glu Gly Pro Phe Ser Glu Thr Tyr Thr Phe
                680                 685                 690

Ser Thr Thr Lys Ser Val Pro Pro Thr Ile Lys Ala Pro Arg Val
                695                 700                 705

Thr Gln Leu Glu Val Asn Ser Cys Glu Ile Leu Trp Glu Thr Val
                710                 715                 720

Pro Ser Met Lys Gly Asp Pro Val Asn Tyr Ile Leu Gln Val Leu
                725                 730                 735

Val Gly Arg Glu Ser Glu Tyr Lys Gln Val Tyr Lys Gly Glu Glu
                740                 745                 750

Ala Thr Phe Gln Ile Ser Gly Leu Gln Thr Asn Thr Asp Tyr Arg
                755                 760                 765

Phe Arg Val Cys Ala Cys Arg Arg Cys Leu Asp Thr Ser Gln Glu
                770                 775                 780

Leu Ser Gly Ala Phe Ser Pro Ser Ala Ala Phe Val Leu Gln Arg
                785                 790                 795

Ser Glu Val Met Leu Thr Gly Asp Met Gly Ser Leu Asp Asp Pro
                800                 805                 810

Lys Met Lys Ser Met Met Pro Thr Asp Glu Gln Phe Ala Ala Ile
                815                 820                 825

Ile Val Leu Gly Phe Ala Thr Leu Ser Ile Leu Phe Ala Phe Ile
                830                 835                 840

Leu Gln Tyr Phe Leu Met Lys
                845
```

<210> SEQ ID NO 95
<211> LENGTH: 4725
<212> TYPE: DNA
<213> ORGANISM: Homo Sapien -continued

<400> SEQUENCE: 95

```
caattcggcc tcgctccttg tgattgcgct aaaccttccg tcctcagctg        50
agaacgctcc accacctccc cggatcgctc atctcttggc tgccctccca       100
ctgttcctga tgttatttta ctccccgtat cccctactcg ttcttcacaa       150
ttctgtaggt gagtggttcc agctggtgcc tggcctgtgt ctcttggatg       200
ccctgtggct tcagtccgtc tcctgttgcc caccacctcg tccctgggcc       250
gcctgatacc ccagcccaac agctaaggtg tggatggaca gtagggggct       300
ggcttctctc actggtcagg ggtcttctcc cctgtctgcc tcccggagct       350
aggactgcag aggggcctat catggtgctt gcaggccccc tggctgtctc       400
gctgttgctg cccagcctca cactgctggt gtcccacctc tccagctccc       450
aggatgtctc cagtgagccc agcagtgagc agcagctgtg cgcccttagc       500
aagcacccca ccgtggcctt tgaagacctg cagccgtggg tctctaactt       550
cacctaccct ggagcccggg atttctccca gctggctttg gacccctccg       600
ggaaccagct catcgtggga gccaggaact acctcttcag actcagcctt       650
gccaatgtct ctcttcttca ggccacagag tgggcctcca gtgaggacac       700
gcgccgctcc tgccaaagca aagggaagac tgaggaggag tgtcagaact       750
acgtgcgagt cctgatcgtc gccggccgga aggtgttcat gtgtggaacc       800
aatgcctttt cccccatgtg caccagcaga caggtgggga acctcagccg       850
gactattgag aagatcaatg gtgtggcccg ctgcccctat gacccacgcc       900
acaactccac agctgtcatc tcctcccagg gggagctcta tgcagccacg       950
gtcatcgact tctcaggtcg ggaccctgcc atctaccgca gcctgggcag      1000
tgggccaccg cttcgcactg cccaatataa ctccaagtgg cttaatgagc      1050
caaacttcgt ggcagcctat gatattgggc tgtttgcata cttcttcctg      1100
cgggagaacg cagtggagca cgactgtgga cgcaccgtgt actctcgcgt      1150
ggcccgcgtg tgcaagaatg acgtgggggg ccgattcctg ctggaggaca      1200
catggaccac attcatgaag gcccggctca actgctcccg cccgggcgag      1250
gtccccttct actataacga gctgcagagt gccttccact tgccggagca      1300
ggacctcatc tatggagttt tcacaaccaa cgtaaacagc atcgcggctt      1350
ctgctgtctg cgccttcaac ctcagtgcta tctcccaggc tttcaatggc      1400
ccatttcgct accaggagaa ccccagggct gcctggctcc ccatagccaa      1450
ccccatcccc aatttccagt gtggcaccct gcctgagacc ggtcccaacg      1500
agaacctgac ggagcgcagc ctgcaggacg cgcagcgcct cttcctgatg      1550
agcgaggccg tgcagccggt gacacccgag ccctgtgtca cccaggacag      1600
cgtgcgcttc tcacacctcg tggtggacct ggtgcaggct aaagacacgc      1650
tctaccatgt actctacatt ggcaccgagt cgggcaccat cctgaaggcg      1700
ctgtccacgg cgagccgcag cctccacggc tgctacctgg aggagctgca      1750
cgtgctgccc cccgggcgcc gcgagcccct gcgcagcctg cgcatcctgc      1800
acagcgcccg cgcgctcttc gtggggctga gagacggcgt cctgcgggtc      1850
ccactggaga ggtgcgccgc ctaccgcagc caggggggcat gcctgggggc     1900
```

-continued

```
ccgggacccg tactgtggct gggacgggaa gcagcaacgt tgcagcacac    1950
tcgaggacag ctccaacatg agcctctgga cccagaacat caccgcctgt    2000
cctgtgcgga atgtgacacg ggatgggggc ttcggcccat ggtcaccatg    2050
gcaaccatgt gagcacttgg atggggacaa ctcaggctct tgcctgtgtc    2100
gagctcgatc ctgtgattcc cctcgacccc gctgtggggg ccttgactgc    2150
ctggggccag ccatccacat cgccaactgc tccaggaatg gggcgtggac    2200
cccgtggtca tcgtgggcgc tgtgcagcac gtcctgtggc atcggcttcc    2250
aggtccgcca gcgaagttgc agcaaccctg ctccccgcca cgggggccgc    2300
atcttcgtgg gcaagagccg ggaggaacgg ttctgtaatg agaacacgcc    2350
ttgcccggtg cccatcttct gggcttcctg ggctcctgg agcaagtgca    2400
gcagcaactg tggagggggc atgcagtcgc ggcgtcgggc ctgcgagaac    2450
ggcaactcct gcctgggctg cggcgagttc aagacgtgca accccgaggg    2500
ctgccccgaa gtgcggcgca acaccccctg gacgccgtgg ctgcccgtga    2550
acgtgacgca gggcggggca cggcaggagc agcggttccg cttcacctgc    2600
cgcgcgcccc ttgcagaccc gcacggcctg cagttcggca ggagaaggac    2650
cgagacgagg acctgtcccg cggacggctc cggctcctgc gacaccgacg    2700
ccctggtgga ggtcctcctg cgcagcggga gcacctcccc gcacacggtg    2750
agcgggggct gggccgcctg ggcccgtgg tcgtcctgct cccgggactg    2800
cgagctgggc ttccgcgtcc gcaagagaac gtgcactaac ccggagcccc    2850
gcaacggggg cctgccctgc gtgggcgatg ctgccgagta ccaggactgc    2900
aacccccagg cttgcccagt tcggggtgct tggtcctgct ggacctcatg    2950
gtctccatgc tcagcttcct gtggtggggg tcactatcaa cgcacccgtt    3000
cctgcaccag ccccgcaccc tccccaggtg aggacatctg tctcgggctg    3050
cacacggagg aggcactatg tgccacacag gcctgcccag gctggtcgcc    3100
ctggtctgag tggagtaagt gcactgacga cggagcccag agccgaagcc    3150
ggcactgtga ggagctcctc ccagggtcca gcgcctgtgc tggaaacagc    3200
agccagagcc gcccctgccc ctacagcgag attcccgtca tcctgccagc    3250
ctccagcatg gaggaggcca ccgactgtgc aggtaaaaga aaccggacct    3300
acctcatgct gcggtcctcc cagccctcca gcaccccact ccaaagtctg    3350
gactctttcc acatcctgct ccagacagcc aagctttgtt ggggtcccca    3400
ctgctttgag atgggttcaa tctcatccac ttggtggcca cgggcatctc    3450
ctgcttcttg ggctctgggc tcctgaccct agcagtgtac ctgtcttgcc    3500
agcactgcca gcgtcagtcc caggagtcca cactggtcca tcctgccacc    3550
cccaaccatt tgcactacaa gggcggaggc accccgaaga atgaaaagta    3600
cacacccatg gaattcaaga ccctgaacaa gaataacttg atccctgatg    3650
acagagccaa cttctaccca ttgcagcaga ccaatgtgta cacgactact    3700
tactacccaa gccccctgaa caaacacagc ttccggcccg aggcctcacc    3750
tggacaacgg tgcttcccca acagctgata ccgccgtcct ggggacttgg    3800
gcttcttgcc ttcataaggc acagagcaga tggagatggg acagtggagc    3850
cagtttggtt ttctccctct gcactaggcc aagaacttgc tgccttgcct    3900
```

-continued

```
gtggggggtc ccatccggct tcagagagct ctggctggca ttgaccatgg            3950

gggaaagggc tggtttcagg ctgacatatg gccgcaggtc cagttcagcc            4000

caggtctctc atggttatct tccaacccac tgtcacgctg acactatgct            4050

gccatgcctg ggctgtggac ctactgggca tttgaggaat tggagaatgg            4100

agatggcaag agggcaggct tttaagtttg ggttggagac aacttcctgt            4150

ggcccccaca agctgagtct ggccttctcc agctggcccc aaaaaaggcc            4200

tttgctacat cctgattatc tctgaaagta atcaatcaag tggctccagt            4250

agctctggat tttctgccag ggctgggcca ttgtggtgct gccccagtat            4300

gacatgggac caaggccagc gcaggttatc cacctctgcc tggaagtcta            4350

tactctaccc agggcatccc tctggtcaga ggcagtgagt actgggaact            4400

ggaggctgac ctgtgcttag aagtccttta atctgggctg gtacaggcct            4450

cagccttgcc ctcaatgcac gaaaggtggc ccaggagaga ggatcaatgc            4500

cataggaggc agaagtctgg cctctgtgcc tctatggaga ctatcttcca            4550

gttgctgctc aacagagttg ttggctgaga cctgcttggg agtctctgct            4600

ggcccttcat ctgttcagga acacacacac acacacactc acacacgcac            4650

acacaatcac aatttgctac agcaacaaaa aagacattgg gctgtggcat            4700

tattaattaa agatgatatc cagtc                                       4725
```

```
<210> SEQ ID NO 96
<211> LENGTH: 1092
<212> TYPE: PRT
<213> ORGANISM: Homo Sapien

<400> SEQUENCE: 96

Met Pro Cys Gly Phe Ser Pro Ser Pro Val Ala His His Leu Val
  1               5                  10                  15

Pro Gly Pro Pro Asp Thr Pro Ala Gln Gln Leu Arg Cys Gly Trp
                 20                  25                  30

Thr Val Gly Gly Trp Leu Leu Ser Leu Val Arg Gly Leu Leu Pro
                 35                  40                  45

Cys Leu Pro Pro Gly Ala Arg Thr Ala Glu Gly Pro Ile Met Val
                 50                  55                  60

Leu Ala Gly Pro Leu Ala Val Ser Leu Leu Leu Pro Ser Leu Thr
                 65                  70                  75

Leu Leu Val Ser His Leu Ser Ser Ser Gln Asp Val Ser Ser Glu
                 80                  85                  90

Pro Ser Ser Glu Gln Gln Leu Cys Ala Leu Ser Lys His Pro Thr
                 95                 100                 105

Val Ala Phe Glu Asp Leu Gln Pro Trp Val Ser Asn Phe Thr Tyr
                110                 115                 120

Pro Gly Ala Arg Asp Phe Ser Gln Leu Ala Leu Asp Pro Ser Gly
                125                 130                 135

Asn Gln Leu Ile Val Gly Ala Arg Asn Tyr Leu Phe Arg Leu Ser
                140                 145                 150

Leu Ala Asn Val Ser Leu Leu Gln Ala Thr Glu Trp Ala Ser Ser
                155                 160                 165

Glu Asp Thr Arg Arg Ser Cys Gln Ser Lys Gly Lys Thr Glu Glu
                170                 175                 180
```

-continued

```
Glu Cys Gln Asn Tyr Val Arg Val Leu Ile Val Ala Gly Arg Lys
                185                 190                 195

Val Phe Met Cys Gly Thr Asn Ala Phe Ser Pro Met Cys Thr Ser
                200                 205                 210

Arg Gln Val Gly Asn Leu Ser Arg Thr Ile Glu Lys Ile Asn Gly
                215                 220                 225

Val Ala Arg Cys Pro Tyr Asp Pro Arg His Asn Ser Thr Ala Val
                230                 235                 240

Ile Ser Ser Gln Gly Glu Leu Tyr Ala Ala Thr Val Ile Asp Phe
                245                 250                 255

Ser Gly Arg Asp Pro Ala Ile Tyr Arg Ser Leu Gly Ser Gly Pro
                260                 265                 270

Pro Leu Arg Thr Ala Gln Tyr Asn Ser Lys Trp Leu Asn Glu Pro
                275                 280                 285

Asn Phe Val Ala Ala Tyr Asp Ile Gly Leu Phe Ala Tyr Phe Phe
                290                 295                 300

Leu Arg Glu Asn Ala Val Glu His Asp Cys Gly Arg Thr Val Tyr
                305                 310                 315

Ser Arg Val Ala Arg Val Cys Lys Asn Asp Val Gly Gly Arg Phe
                320                 325                 330

Leu Leu Glu Asp Thr Trp Thr Thr Phe Met Lys Ala Arg Leu Asn
                335                 340                 345

Cys Ser Arg Pro Gly Glu Val Pro Phe Tyr Tyr Asn Glu Leu Gln
                350                 355                 360

Ser Ala Phe His Leu Pro Glu Gln Asp Leu Ile Tyr Gly Val Phe
                365                 370                 375

Thr Thr Asn Val Asn Ser Ile Ala Ala Ser Ala Val Cys Ala Phe
                380                 385                 390

Asn Leu Ser Ala Ile Ser Gln Ala Phe Asn Gly Pro Phe Arg Tyr
                395                 400                 405

Gln Glu Asn Pro Arg Ala Ala Trp Leu Pro Ile Ala Asn Pro Ile
                410                 415                 420

Pro Asn Phe Gln Cys Gly Thr Leu Pro Glu Thr Gly Pro Asn Glu
                425                 430                 435

Asn Leu Thr Glu Arg Ser Leu Gln Asp Ala Gln Arg Leu Phe Leu
                440                 445                 450

Met Ser Glu Ala Val Gln Pro Val Thr Pro Glu Pro Cys Val Thr
                455                 460                 465

Gln Asp Ser Val Arg Phe Ser His Leu Val Val Asp Leu Val Gln
                470                 475                 480

Ala Lys Asp Thr Leu Tyr His Val Leu Tyr Ile Gly Thr Glu Ser
                485                 490                 495

Gly Thr Ile Leu Lys Ala Leu Ser Thr Ala Ser Arg Ser Leu His
                500                 505                 510

Gly Cys Tyr Leu Glu Glu Leu His Val Leu Pro Pro Gly Arg Arg
                515                 520                 525

Glu Pro Leu Arg Ser Leu Arg Ile Leu His Ser Ala Arg Ala Leu
                530                 535                 540

Phe Val Gly Leu Arg Asp Gly Val Leu Arg Val Pro Leu Glu Arg
                545                 550                 555

Cys Ala Ala Tyr Arg Ser Gln Gly Ala Cys Leu Gly Ala Arg Asp
                560                 565                 570

Pro Tyr Cys Gly Trp Asp Gly Lys Gln Gln Arg Cys Ser Thr Leu
```

-continued

```
                575                 580                 585

Glu Asp Ser Ser Asn Met Ser Leu Trp Thr Gln Asn Ile Thr Ala
                590                 595                 600

Cys Pro Val Arg Asn Val Thr Arg Asp Gly Gly Phe Gly Pro Trp
                605                 610                 615

Ser Pro Trp Gln Pro Cys Glu His Leu Asp Gly Asp Asn Ser Gly
                620                 625                 630

Ser Cys Leu Cys Arg Ala Arg Ser Cys Asp Ser Pro Arg Pro Arg
                635                 640                 645

Cys Gly Gly Leu Asp Cys Leu Gly Pro Ala Ile His Ile Ala Asn
                650                 655                 660

Cys Ser Arg Asn Gly Ala Trp Thr Pro Trp Ser Ser Trp Ala Leu
                665                 670                 675

Cys Ser Thr Ser Cys Gly Ile Gly Phe Gln Val Arg Gln Arg Ser
                680                 685                 690

Cys Ser Asn Pro Ala Pro Arg His Gly Gly Arg Ile Phe Val Gly
                695                 700                 705

Lys Ser Arg Glu Glu Arg Phe Cys Asn Glu Asn Thr Pro Cys Pro
                710                 715                 720

Val Pro Ile Phe Trp Ala Ser Trp Gly Ser Trp Ser Lys Cys Ser
                725                 730                 735

Ser Asn Cys Gly Gly Gly Met Gln Ser Arg Arg Arg Ala Cys Glu
                740                 745                 750

Asn Gly Asn Ser Cys Leu Gly Cys Gly Glu Phe Lys Thr Cys Asn
                755                 760                 765

Pro Glu Gly Cys Pro Glu Val Arg Arg Asn Thr Pro Trp Thr Pro
                770                 775                 780

Trp Leu Pro Val Asn Val Thr Gln Gly Gly Ala Arg Gln Glu Gln
                785                 790                 795

Arg Phe Arg Phe Thr Cys Arg Ala Pro Leu Ala Asp Pro His Gly
                800                 805                 810

Leu Gln Phe Gly Arg Arg Arg Thr Glu Thr Arg Thr Cys Pro Ala
                815                 820                 825

Asp Gly Ser Gly Ser Cys Asp Thr Asp Ala Leu Val Glu Val Leu
                830                 835                 840

Leu Arg Ser Gly Ser Thr Ser Pro His Thr Val Ser Gly Gly Trp
                845                 850                 855

Ala Ala Trp Gly Pro Trp Ser Ser Cys Ser Arg Asp Cys Glu Leu
                860                 865                 870

Gly Phe Arg Val Arg Lys Arg Thr Cys Thr Asn Pro Glu Pro Arg
                875                 880                 885

Asn Gly Gly Leu Pro Cys Val Gly Asp Ala Ala Glu Tyr Gln Asp
                890                 895                 900

Cys Asn Pro Gln Ala Cys Pro Val Arg Gly Ala Trp Ser Cys Trp
                905                 910                 915

Thr Ser Trp Ser Pro Cys Ser Ala Ser Cys Gly Gly Gly His Tyr
                920                 925                 930

Gln Arg Thr Arg Ser Cys Thr Ser Pro Ala Pro Ser Pro Gly Glu
                935                 940                 945

Asp Ile Cys Leu Gly Leu His Thr Glu Glu Ala Leu Cys Ala Thr
                950                 955                 960

Gln Ala Cys Pro Gly Trp Ser Pro Trp Ser Glu Trp Ser Lys Cys
                965                 970                 975
```

-continued

```
Thr Asp Asp Gly Ala Gln Ser Arg Ser Arg His Cys Glu Glu Leu
            980                 985                 990

Leu Pro Gly Ser Ser Ala Cys Ala Gly Asn Ser Ser Gln Ser Arg
            995                 1000                1005

Pro Cys Pro Tyr Ser Glu Ile Pro Val Ile Leu Pro Ala Ser Ser
            1010                1015                1020

Met Glu Glu Ala Thr Asp Cys Ala Gly Lys Arg Asn Arg Thr Tyr
            1025                1030                1035

Leu Met Leu Arg Ser Ser Gln Pro Ser Ser Thr Pro Leu Gln Ser
            1040                1045                1050

Leu Asp Ser Phe His Ile Leu Leu Gln Thr Ala Lys Leu Cys Trp
            1055                1060                1065

Gly Pro His Cys Phe Glu Met Gly Ser Ile Ser Ser Thr Trp Trp
            1070                1075                1080

Pro Arg Ala Ser Pro Ala Ser Trp Ala Leu Gly Ser
            1085                1090
```

<210> SEQ ID NO 97
<211> LENGTH: 3391
<212> TYPE: DNA
<213> ORGANISM: Homo Sapien

<400> SEQUENCE: 97

```
caagccctcc cagcatcccc tctcctgtgt tcctccccag ttctctactc        50

agagttgact gaccagagat ttatcagctt ggagggctgg aggtgtggat       100

ccatggggta gcctcaacgc atctgcccct ccaccccagc cagctcatgg       150

gccacgtggc ctggcccagc ctcagcaccc agggccagtg aacagagccc       200

tggctggagt ccaaacatgt ggggcctggt gaggctcctg ctggcctggc       250

tgggtggctg gggctgcatg gggcgtctgg cagccccagc ccgggcctgg       300

gcagggtccc gggaacaccc agggcctgct ctgctgcgga ctcgaaggag       350

ctgggtctgg aaccagttct ttgtcattga ggaatatgct ggtccagagc       400

ctgttctcat tggcaagctg cactcggatg ttgaccgggg agagggccgc       450

accaagtacc tgttgaccgg ggagggggca ggcaccgtat ttgtgattga       500

tgaggccaca ggcaatattc atgttaccaa gagccttgac cgggaggaaa       550

aggcgcaata tgtgctactg gcccaagccg tggaccgagc ctccaaccgg       600

cccctggagc cccccatcaga gttcatcatc aaagtgcaag acatcaacga      650

caatccaccc atttttcccc ttgggcccta ccatgccacc gtgcccgaga       700

tgtccaatgt cgggacatca gtgatccagg tgactgctca cgatgctgat       750

gaccccagct atgggaacag tgccaagctg gtgtacactg ttctggatgg       800

actgcctttc ttctctgtgg acccccagac tggagtggtg cgtacagcca       850

tccccaacat ggaccgggag acacaggagg agttcttggt ggtgatccag       900

gccaaggaca tgggcggcca catggggggg ctgtcaggca gcactacggt       950

gactgtcacg ctcagcgatg tcaacgacaa cccccccaag ttcccacaga      1000

gcctatacca gttctccgtg gtggagacag ctggacctgg cacactggtg      1050

ggccggctcc gggcccagga cccagacctg gggggacaacg ccctgatggc     1100

atacagcatc ctggatgggg aggggtctga ggccttcagc atcagcacag      1150
```

-continued

```
acttgcaggg tcgagacggg ctcctcactg tccgcaagcc cctagacttt      1200
gagagccagc gctcctactc cttccgtgtc gaggccacca acacgctcat      1250
tgacccagcc tatctgcggc gagggccctt caaggatgtg gcctctgtgc      1300
gtgtggcagt gcaagatgcc ccagagccac ctgccttcac ccaggctgcc      1350
taccacctga cagtgcctga gaacaaggcc ccggggaccc tggtaggcca      1400
gatctccgcg gctgacctgg actcccctgc cagcccaatc agatactcca      1450
tcctccccca ctcagatccg gagcgttgct tctctatcca gcccgaggaa      1500
ggcaccatcc atacagcagc acccctggat cgcgaggctc gcgcctggca      1550
caacctcact gtgctggcta cagagctcga cagttctgca caggcctcgc      1600
gcgtgcaagt ggccatccag accctggatg agaatgacaa tgctccccag      1650
ctggctgagc cctacgatac ttttgtgtgt gactctgcag ctcctggcca      1700
gctgattcag gtcatccggg ccctggacag agatgaagtt ggcaacagta      1750
gccatgtctc ctttcaaggt cctctgggcc ctgatgccaa ctttactgtc      1800
caggacaacc gagatggctc cgccagcctg ctgctgccct cccgccctgc      1850
tccaccccgc catgcccccct acttggttcc catagaactg tgggactggg      1900
ggcagccggc gctgagcagc actgccacag tgactgttag tgtgtgccgc      1950
tgccagcctg acggctctgt ggcatcctgc tggcctgagg ctcacctctc      2000
agctgctggg ctcagcaccg gcgccctgct tgccatcatc acctgtgtgg      2050
gtgccctgct tgccctggtg gtgctcttcg tggccctgcg gcggcagaag      2100
caagaagcac tgatggtact ggaggaggag gacgtccgag agaacatcat      2150
cacctacgac gacgagggcg gcggcgagga ggacaccgag gccttcgaca      2200
tcacggcctt gcagaacccg gacggggcgg cccccccggc gcccggccct      2250
cccgcgcgcc gagacgtgtt gccccgggcc cgggtgtcgc gccagcccag      2300
accccccggc cccgccgacg tggcgcagct cctggcgctg cggctccgcg      2350
aggcggacga ggaccccggc gtacccccgt acgactcggt gcaggtgtac      2400
ggctacgagg gccgcggctc ctcttgcggc tccctcagct ccctgggctc      2450
cggcagcgaa gccggcggcg cccccggccc cgcggagccg ctggacgact      2500
ggggtccgct cttccgcacc ctggccgagc tgtatggggc caaggagccc      2550
ccggcccccct gagcgcccgg gctggcccgg cccaccgcgg gggggggggca      2600
gcgggcacag gccctctgag tgagccccac ggggtccagg cgggcggcag      2650
cagcccaggg gccccaggcc tcctccctgt ccttgtgtcc ctccttgctt      2700
ccccggggca ccctcgctct cacctccctc ctcctgagtc ggtgtgtgtg      2750
tctctctcca ggaatctttg tctctatctg tgacacgctc ctctgtccgg      2800
gcctgggttt cctgccctgg ccctggccct gcgatctctc actgtgattc      2850
ctctccttcc tccgtggcgt tttgtctctg cagttctgaa gctcacacat      2900
agtctccctg cgtcttcctt gcccatacac atgctctgtg tctgtctcct      2950
gcccacatct cccttccttc tctctgggtc cctgtgactg gctttttgtt      3000
tttttctgtt gtccatccca aaatcaagag aaacttccag ccactgctgc      3050
ccaccctcct gcaggggatg ttgtgcccca gacctgcctg catggttcca      3100
tccattactc atggcctcag cctcatcctg gctccactgg cctccagctg      3150
```

```
agagagggaa ccagcctgcc tcccagggca agagctccag cctcccgtgt            3200

ggccgcctcc ctggagctct gcccagctgc cagcttcccc tgggcatccc            3250

agccctgggc attgtcttgt gtgcttcctg agggagtagg gaaaggaaag            3300

ggggaggcgg ctggggaagg ggaaagaggg aggaagggga ggggcctcca            3350

tctctaattt cataataaac aaacacttta ttttgtaaaa c                     3391


<210> SEQ ID NO 98
<211> LENGTH: 781
<212> TYPE: PRT
<213> ORGANISM: Homo Sapien

<400> SEQUENCE: 98

Met Trp Gly Leu Val Arg Leu Leu Leu Ala Trp Leu Gly Gly Trp
  1               5                  10                  15

Gly Cys Met Gly Arg Leu Ala Ala Pro Ala Arg Ala Trp Ala Gly
                 20                  25                  30

Ser Arg Glu His Pro Gly Pro Ala Leu Leu Arg Thr Arg Arg Ser
                 35                  40                  45

Trp Val Trp Asn Gln Phe Phe Val Ile Glu Glu Tyr Ala Gly Pro
                 50                  55                  60

Glu Pro Val Leu Ile Gly Lys Leu His Ser Asp Val Asp Arg Gly
                 65                  70                  75

Glu Gly Arg Thr Lys Tyr Leu Leu Thr Gly Glu Gly Ala Gly Thr
                 80                  85                  90

Val Phe Val Ile Asp Glu Ala Thr Gly Asn Ile His Val Thr Lys
                 95                 100                 105

Ser Leu Asp Arg Glu Glu Lys Ala Gln Tyr Val Leu Leu Ala Gln
                110                 115                 120

Ala Val Asp Arg Ala Ser Asn Arg Pro Leu Glu Pro Pro Ser Glu
                125                 130                 135

Phe Ile Ile Lys Val Gln Asp Ile Asn Asp Asn Pro Pro Ile Phe
                140                 145                 150

Pro Leu Gly Pro Tyr His Ala Thr Val Pro Glu Met Ser Asn Val
                155                 160                 165

Gly Thr Ser Val Ile Gln Val Thr Ala His Asp Ala Asp Asp Pro
                170                 175                 180

Ser Tyr Gly Asn Ser Ala Lys Leu Val Tyr Thr Val Leu Asp Gly
                185                 190                 195

Leu Pro Phe Phe Ser Val Asp Pro Gln Thr Gly Val Val Arg Thr
                200                 205                 210

Ala Ile Pro Asn Met Asp Arg Glu Thr Gln Glu Glu Phe Leu Val
                215                 220                 225

Val Ile Gln Ala Lys Asp Met Gly Gly His Met Gly Gly Leu Ser
                230                 235                 240

Gly Ser Thr Thr Val Thr Val Thr Leu Ser Asp Val Asn Asp Asn
                245                 250                 255

Pro Pro Lys Phe Pro Gln Ser Leu Tyr Gln Phe Ser Val Val Glu
                260                 265                 270

Thr Ala Gly Pro Gly Thr Leu Val Gly Arg Leu Arg Ala Gln Asp
                275                 280                 285

Pro Asp Leu Gly Asp Asn Ala Leu Met Ala Tyr Ser Ile Leu Asp
                290                 295                 300
```

-continued

Gly Glu Gly Ser Glu Ala Phe Ser Ile Ser Thr Asp Leu Gln Gly
305 310 315

Arg Asp Gly Leu Leu Thr Val Arg Lys Pro Leu Asp Phe Glu Ser
320 325 330

Gln Arg Ser Tyr Ser Phe Arg Val Glu Ala Thr Asn Thr Leu Ile
335 340 345

Asp Pro Ala Tyr Leu Arg Arg Gly Pro Phe Lys Asp Val Ala Ser
350 355 360

Val Arg Val Ala Val Gln Asp Ala Pro Glu Pro Pro Ala Phe Thr
365 370 375

Gln Ala Ala Tyr His Leu Thr Val Pro Glu Asn Lys Ala Pro Gly
380 385 390

Thr Leu Val Gly Gln Ile Ser Ala Ala Asp Leu Asp Ser Pro Ala
395 400 405

Ser Pro Ile Arg Tyr Ser Ile Leu Pro His Ser Asp Pro Glu Arg
410 415 420

Cys Phe Ser Ile Gln Pro Glu Glu Gly Thr Ile His Thr Ala Ala
425 430 435

Pro Leu Asp Arg Glu Ala Arg Ala Trp His Asn Leu Thr Val Leu
440 445 450

Ala Thr Glu Leu Asp Ser Ser Ala Gln Ala Ser Arg Val Gln Val
455 460 465

Ala Ile Gln Thr Leu Asp Glu Asn Asp Asn Ala Pro Gln Leu Ala
470 475 480

Glu Pro Tyr Asp Thr Phe Val Cys Asp Ser Ala Ala Pro Gly Gln
485 490 495

Leu Ile Gln Val Ile Arg Ala Leu Asp Arg Asp Glu Val Gly Asn
500 505 510

Ser Ser His Val Ser Phe Gln Gly Pro Leu Gly Pro Asp Ala Asn
515 520 525

Phe Thr Val Gln Asp Asn Arg Asp Gly Ser Ala Ser Leu Leu Leu
530 535 540

Pro Ser Arg Pro Ala Pro Pro Arg His Ala Pro Tyr Leu Val Pro
545 550 555

Ile Glu Leu Trp Asp Trp Gly Gln Pro Ala Leu Ser Ser Thr Ala
560 565 570

Thr Val Thr Val Ser Val Cys Arg Cys Gln Pro Asp Gly Ser Val
575 580 585

Ala Ser Cys Trp Pro Glu Ala His Leu Ser Ala Ala Gly Leu Ser
590 595 600

Thr Gly Ala Leu Leu Ala Ile Ile Thr Cys Val Gly Ala Leu Leu
605 610 615

Ala Leu Val Val Leu Phe Val Ala Leu Arg Arg Gln Lys Gln Glu
620 625 630

Ala Leu Met Val Leu Glu Glu Glu Asp Val Arg Glu Asn Ile Ile
635 640 645

Thr Tyr Asp Asp Glu Gly Gly Gly Glu Glu Asp Thr Glu Ala Phe
650 655 660

Asp Ile Thr Ala Leu Gln Asn Pro Asp Gly Ala Ala Pro Pro Ala
665 670 675

Pro Gly Pro Pro Ala Arg Arg Asp Val Leu Pro Arg Ala Arg Val
680 685 690

Ser Arg Gln Pro Arg Pro Pro Gly Pro Ala Asp Val Ala Gln Leu

-continued

```
                695                 700                 705

Leu Ala Leu Arg Leu Arg Glu Ala Asp Glu Asp Pro Gly Val Pro
                710                 715                 720

Pro Tyr Asp Ser Val Gln Val Tyr Gly Tyr Glu Gly Arg Gly Ser
                725                 730                 735

Ser Cys Gly Ser Leu Ser Ser Leu Gly Ser Gly Ser Glu Ala Gly
                740                 745                 750

Gly Ala Pro Gly Pro Ala Glu Pro Leu Asp Asp Trp Gly Pro Leu
                755                 760                 765

Phe Arg Thr Leu Ala Glu Leu Tyr Gly Ala Lys Glu Pro Pro Ala
                770                 775                 780

Pro
```

<210> SEQ ID NO 99
<211> LENGTH: 2855
<212> TYPE: DNA
<213> ORGANISM: Homo Sapien

<400> SEQUENCE: 99

```
gccaacactg gccaaacata tggggctgga atctcaacat cggtcactgg      50

gacctcaata tttggagccg gaaccccaca atttggaaca cagaccccaa     100

tatttggagc agaaccccaa gatttgacat ctaaaacctc aagcctggag     150

ctgaactctg aattctgggc ctgggacctt gaaatctggg actggatttc     200

cagtactgta ccctggaacc cactcttggg gacctgaacc ctgggattca     250

ggcctcaaat tccaagatct ggactgtggg attccaaggg gcctgaaccc     300

gagtttgggc ctgaagtcct tgctgcagac ctgagtgctt aaatctgggg     350

cttgagacct cccaatcttg actcagcacc ccaatatctg aatgcagaac     400

cccgggatcg gatctcagac tctaaacccc accgtttggc tgcttagcat     450

cccaagactg gacctgggag accctgaccc tgaacaaccc aaactggacc     500

cgtaaaactg gaccctagag gcccaatatt taggggtctg gaaccccgag     550

tattaaggtc tggagactcc gttgccacag atttgagccg agtcaggaca     600

cagtccctct acagaagcct tggggacagg aaaagcatga ccagatgctc     650

cctccagagc cctgacctct gactcccctg gagctaggac tctgctccct     700

ggggctgctt ctagctcagg acacccctgc ccgcgatggc catcctcccg     750

ttgctcctgt gcctgctgcc gctggcccct gcctcatccc caccccagtc     800

agccacaccc agcccatgtc cccgccgctg ccgctgccag acacagtcgc     850

tgcccctaag cgtgctgtgc ccaggggcag gcctcctgtt cgtgccaccc     900

tcgctggacc gccgggcagc cgagctgcgg ctggcagaca acttcatcgc     950

ctccgtgcgc cgccgcgacc tggccaacat gacaggcctg ctgcatctga    1000

gcctgtcgcg gaacaccatc cgccacgtgg ctgccggcgc cttcgccgac    1050

ctgcgggccc tgcgtgccct gcacctggat ggcaaccggc tgacctcact    1100

gggcgagggc cagctgcgcg gcctggtcaa cttgcgccac ctcatcctca    1150

gcaacaacca gctggcagcg ctggcggccg gcgccctgga tgattgtgcc    1200

gagacactgg aggacctcga cctctcctac aacaacctcg agcagctgcc    1250

ctgggaggcc ctgggccgcc tgggcaacgt caacacgttg ggcctcgacc    1300
```

-continued

```
acaacctgct ggcttctgtg cccggcgctt tttcccgcct gcacaagctg          1350

gcccggctgg acatgacctc caaccgcctg accacaatcc cacccgaccc          1400

actcttctcc cgcctgcccc tgctcgccag gccccggggc tcgcccgcct          1450

ctgccctggt gctggccttt ggcgggaacc ccctgcactg caactgcgag          1500

ctggtgtggc tgcgtcgcct ggcgcgggag gacgacctcg aggcctgcgc          1550

gtccccacct gctctgggcg gccgctactt ctgggcggtg ggcgaggagg          1600

agtttgtctg cgagccgccc gtggtgactc accgctcacc acctctggct          1650

gtgcccgcag gtcggccggc tgccctgcgc tgccgggcag tgggggaccc          1700

agagccccgt gtgcgttggg tgtcacccca gggccggctg ctaggcaact          1750

caagccgtgc ccgcgccttc cccaatggga cgctggagct gctggtcacc          1800

gagccgggtg atggtggcat cttcacctgc attgcggcca atgcagctgg          1850

cgaggccaca gctgctgtgg agctgactgt gggtccccca ccacctcctc          1900

agctagccaa cagcaccagc tgtgaccccc cgcgggacgg ggatcctgat          1950

gctctcaccc caccctccgc tgcctctgct tctgccaagg tggccgacac          2000

tgggcccccct accgaccgtg gcgtccaggt gactgagcac ggggccacag          2050

ctgctcttgt ccagtggccg gatcagcggc ctatcccggg catccgcatg          2100

taccagatcc agtacaacag ctcggctgat gacatcctcg tctacaggat          2150

gatcccggcg gagagccgct cgttcctgct gacggacctg gcgtcaggcc          2200

ggacctacga tctgtgcgtg ctcgccgtgt atgaggacag cgccacgggg          2250

ctcacggcca cgcggcctgt gggctgcgcc cgcttctcca ccgaacctgc          2300

gctgcggcca tgcggggcgc cgcacgctcc cttcctgggc ggcacgatga          2350

tcatcgcgct gggcggcgtc atcgtagcct cggtactggt cttcatcttc          2400

gtgctgctaa tgcgctacaa ggtgcacggc ggccagcccc ccggcaaggc          2450

caagattccc gcgcctgtta gcagcgtttg ctcccagacc aacggcgccc          2500

tgggccccac gcccacgccc gccccgcccg ccccggagcc cgcggcgctc          2550

agggcccaca ccgtggtcca gctggactgc gagccctggg ggcccggcca          2600

cgaacctgtg ggaccctagc caggcgcccc cccctctaag ggtcctctgg          2650

ccccacggac agcaggaccc ggacaccctg tgggacctgg cctcaaactc          2700

accaaatcgc tcatggtttt taaaactctg atggggaggg tgtcggggac          2750

accggggcaa aacaagaaag tcctattttt ccaaaaaaaa aaaaaaaaaa          2800

aaaaaaaaaa aaaaaaaaaa aaaaaaaaaa aaaaaaaaaa aaaaaaaaaa          2850

aaaaa                                                           2855
```

<210> SEQ ID NO 100
<211> LENGTH: 627
<212> TYPE: PRT
<213> ORGANISM: Homo Sapien

<400> SEQUENCE: 100

```
Met Ala Ile Leu Pro Leu Leu Leu Cys Leu Leu Pro Leu Ala Pro
  1               5                  10                  15

Ala Ser Ser Pro Pro Gln Ser Ala Thr Pro Ser Pro Cys Pro Arg
                 20                  25                  30

Arg Cys Arg Cys Gln Thr Gln Ser Leu Pro Leu Ser Val Leu Cys
```

-continued

```
                35                  40                  45

Pro Gly Ala Gly Leu Leu Phe Val Pro Pro Ser Leu Asp Arg Arg
                50                  55                  60

Ala Ala Glu Leu Arg Leu Ala Asp Asn Phe Ile Ala Ser Val Arg
                65                  70                  75

Arg Arg Asp Leu Ala Asn Met Thr Gly Leu Leu His Leu Ser Leu
                80                  85                  90

Ser Arg Asn Thr Ile Arg His Val Ala Ala Gly Ala Phe Ala Asp
                95                 100                 105

Leu Arg Ala Leu Arg Ala Leu His Leu Asp Gly Asn Arg Leu Thr
               110                 115                 120

Ser Leu Gly Glu Gly Gln Leu Arg Gly Leu Val Asn Leu Arg His
               125                 130                 135

Leu Ile Leu Ser Asn Asn Gln Leu Ala Ala Leu Ala Ala Gly Ala
               140                 145                 150

Leu Asp Asp Cys Ala Glu Thr Leu Glu Asp Leu Asp Leu Ser Tyr
               155                 160                 165

Asn Asn Leu Glu Gln Leu Pro Trp Glu Ala Leu Gly Arg Leu Gly
               170                 175                 180

Asn Val Asn Thr Leu Gly Leu Asp His Asn Leu Leu Ala Ser Val
               185                 190                 195

Pro Gly Ala Phe Ser Arg Leu His Lys Leu Ala Arg Leu Asp Met
               200                 205                 210

Thr Ser Asn Arg Leu Thr Thr Ile Pro Pro Asp Pro Leu Phe Ser
               215                 220                 225

Arg Leu Pro Leu Leu Ala Arg Pro Arg Gly Ser Pro Ala Ser Ala
               230                 235                 240

Leu Val Leu Ala Phe Gly Gly Asn Pro Leu His Cys Asn Cys Glu
               245                 250                 255

Leu Val Trp Leu Arg Arg Leu Ala Arg Glu Asp Asp Leu Glu Ala
               260                 265                 270

Cys Ala Ser Pro Pro Ala Leu Gly Gly Arg Tyr Phe Trp Ala Val
               275                 280                 285

Gly Glu Glu Glu Phe Val Cys Glu Pro Pro Val Val Thr His Arg
               290                 295                 300

Ser Pro Pro Leu Ala Val Pro Ala Gly Arg Pro Ala Ala Leu Arg
               305                 310                 315

Cys Arg Ala Val Gly Asp Pro Glu Pro Arg Val Arg Trp Val Ser
               320                 325                 330

Pro Gln Gly Arg Leu Leu Gly Asn Ser Ser Arg Ala Arg Ala Phe
               335                 340                 345

Pro Asn Gly Thr Leu Glu Leu Leu Val Thr Glu Pro Gly Asp Gly
               350                 355                 360

Gly Ile Phe Thr Cys Ile Ala Ala Asn Ala Ala Gly Glu Ala Thr
               365                 370                 375

Ala Ala Val Glu Leu Thr Val Gly Pro Pro Pro Pro Pro Gln Leu
               380                 385                 390

Ala Asn Ser Thr Ser Cys Asp Pro Pro Arg Asp Gly Asp Pro Asp
               395                 400                 405

Ala Leu Thr Pro Pro Ser Ala Ala Ser Ala Ser Ala Lys Val Ala
               410                 415                 420

Asp Thr Gly Pro Pro Thr Asp Arg Gly Val Gln Val Thr Glu His
               425                 430                 435
```

-continued

```
Gly Ala Thr Ala Ala Leu Val Gln Trp Pro Asp Gln Arg Pro Ile
                440                 445                 450

Pro Gly Ile Arg Met Tyr Gln Ile Gln Tyr Asn Ser Ser Ala Asp
                455                 460                 465

Asp Ile Leu Val Tyr Arg Met Ile Pro Ala Glu Ser Arg Ser Phe
                470                 475                 480

Leu Leu Thr Asp Leu Ala Ser Gly Arg Thr Tyr Asp Leu Cys Val
                485                 490                 495

Leu Ala Val Tyr Glu Asp Ser Ala Thr Gly Leu Thr Ala Thr Arg
                500                 505                 510

Pro Val Gly Cys Ala Arg Phe Ser Thr Glu Pro Ala Leu Arg Pro
                515                 520                 525

Cys Gly Ala Pro His Ala Pro Phe Leu Gly Gly Thr Met Ile Ile
                530                 535                 540

Ala Leu Gly Gly Val Ile Val Ala Ser Val Leu Val Phe Ile Phe
                545                 550                 555

Val Leu Leu Met Arg Tyr Lys Val His Gly Gly Gln Pro Pro Gly
                560                 565                 570

Lys Ala Lys Ile Pro Ala Pro Val Ser Ser Val Cys Ser Gln Thr
                575                 580                 585

Asn Gly Ala Leu Gly Pro Thr Pro Thr Pro Ala Pro Pro Ala Pro
                590                 595                 600

Glu Pro Ala Ala Leu Arg Ala His Thr Val Val Gln Leu Asp Cys
                605                 610                 615

Glu Pro Trp Gly Pro Gly His Glu Pro Val Gly Pro
                620                 625
```

<210> SEQ ID NO 101
<211> LENGTH: 1111
<212> TYPE: DNA
<213> ORGANISM: Homo Sapien

<400> SEQUENCE: 101

```
cgactccata accgtggcct tggccccagt cccccctgact tccggacttc        50

agaccagata ctgcccatat ccccttatga agtcttggcc aggcaacccc       100

tagggtgtac gttttctaaa gattaaagag gcggtgctaa gctgcagacg       150

gacttgcgac tcagccactg gtgtaagtca ggcgggaggt ggcgcccaat       200

aagctcaaga gaggaggcgg gttctggaaa aaggccaata gcctgtgaag       250

gcgagtctag cagcaaccaa tagctatgag cgagaggcgg gactctgagg       300

gaagtcaatc gctgccgcag gtaccgccaa tggcttttgg cgggggcgtt       350

ccccaaccct gccctctctc atgaccccgc tccgggatta tggccgggac       400

tgggctgctg gcgctgcgga cgctgccagg gcccagctgg gtgcgaggct       450

cgggcccttc cgtgctgagc cgcctgcagg acgcggccgt ggtgcggcct       500

ggcttcctga gcacggcaga ggaggagacg ctgagccgag aactggagcc       550

cgagctgcgc cgccgccgct acgaatacga tcactgggac gcggccatcc       600

acggcttccg agagacagag aagtcgcgct ggtcagaagc cagccgggcc       650

atcctgcagc gcgtgcaggc ggccgccttt ggccccggcc agaccctgct       700

ctcctccgtg cacgtgctgg acctggaagc ccgcggctac atcaagcccc       750

acgtggacag catcaagttc tgcggggcca ccatcgccgg cctgtctctc       800
```

ctgtctccca gcgttatgcg gctggtgcac acccaggagc cgggggagtg 850
gctggaactc ttgctggagc cgggctccct ctacatcctt aggggctcag 900
cccgttatga cttctcccat gagatccttc gggatgaaga gtccttcttt 950
ggggaacgcc ggattccccg gggccggcgc atctccgtga tctgccgctc 1000
cctccctgag ggcatggggc caggggagtc tggacagccg cccccagcct 1050
gctgaccccc agctttctac agacaccaga tttgtgaata aagttgggga 1100
atggacagcc t 1111

<210> SEQ ID NO 102
<211> LENGTH: 221
<212> TYPE: PRT
<213> ORGANISM: Homo Sapien

<400> SEQUENCE: 102

Met Ala Gly Thr Gly Leu Leu Ala Leu Arg Thr Leu Pro Gly Pro
1 5 10 15

Ser Trp Val Arg Gly Ser Gly Pro Ser Val Leu Ser Arg Leu Gln
20 25 30

Asp Ala Ala Val Val Arg Pro Gly Phe Leu Ser Thr Ala Glu Glu
35 40 45

Glu Thr Leu Ser Arg Glu Leu Glu Pro Glu Leu Arg Arg Arg Arg
50 55 60

Tyr Glu Tyr Asp His Trp Asp Ala Ala Ile His Gly Phe Arg Glu
65 70 75

Thr Glu Lys Ser Arg Trp Ser Glu Ala Ser Arg Ala Ile Leu Gln
80 85 90

Arg Val Gln Ala Ala Ala Phe Gly Pro Gly Gln Thr Leu Leu Ser
95 100 105

Ser Val His Val Leu Asp Leu Glu Ala Arg Gly Tyr Ile Lys Pro
110 115 120

His Val Asp Ser Ile Lys Phe Cys Gly Ala Thr Ile Ala Gly Leu
125 130 135

Ser Leu Leu Ser Pro Ser Val Met Arg Leu Val His Thr Gln Glu
140 145 150

Pro Gly Glu Trp Leu Glu Leu Leu Leu Glu Pro Gly Ser Leu Tyr
155 160 165

Ile Leu Arg Gly Ser Ala Arg Tyr Asp Phe Ser His Glu Ile Leu
170 175 180

Arg Asp Glu Glu Ser Phe Phe Gly Glu Arg Arg Ile Pro Arg Gly
185 190 195

Arg Arg Ile Ser Val Ile Cys Arg Ser Leu Pro Glu Gly Met Gly
200 205 210

Pro Gly Glu Ser Gly Gln Pro Pro Pro Ala Cys
215 220

<210> SEQ ID NO 103
<211> LENGTH: 3583
<212> TYPE: DNA
<213> ORGANISM: Homo Sapien

<400> SEQUENCE: 103
ctccccggcg ccgcaggcag cgtcctcctc cgaagcagct gcacctgcaa 50
ctgggcagcc tggaccctcg tgccctgttc ccgggacctc gcgcaggggg 100

-continued

```
cgccccggga cacccccctgc gggccgggtg gaggaggaag aggaggagga      150
ggaagaagac gtggacaagg acccccatcc tacccagaac acctgcctgc       200
gctgccgcca cttctcttta agggagagga aaagagagcc taggagaacc       250
atggggggct gcgaagtccg ggaatttctt ttgcaatttg gtttcttctt       300
gcctctgctg acagcgtggc caggcgactg cagtcacgtc tccaacaacc       350
aagttgtgtt gcttgataca acaactgtac tgggagagct aggatggaaa       400
acatatccat taaatgggtg ggatgccatc actgaaatgg atgaacataa       450
taggcccatt cacacatacc aggtatgtaa tgtaatggaa ccaaaccaaa       500
acaactggct tcgtacaaac tggatctccc gtgatgcagc tcagaaaatt       550
tatgtggaaa tgaaattcac actaagggat tgtaacagca tcccatgggt       600
cttggggact tgcaaagaaa catttaatct gttttatatg gaatcagatg       650
agtcccacgg aattaaattc aagccaaacc agtatacaaa gatcgacaca       700
attgctgctg atgagagttt tacccagatg gatttgggtg atcgcatcct       750
caaactcaac actgaaattc gtgaggtggg gcctatagaa aggaaaggat       800
tttatctggc ttttcaagac attggggcgt gcattgccct ggtttcagtc       850
cgtgttttct acaagaaatg ccccttcact gttcgtaact tggccatgtt       900
tcctgatacc attccaaggg ttgattcctc ctctttggtt gaagtacggg       950
gttcttgtgt gaagagtgct gaagagcgtg acactcctaa actgtattgt      1000
ggagctgatg gagattggct ggttcctctt ggaaggtgca tctgcagtac      1050
aggatatgaa gaaattgagg gttcttgcca tgcttgcaga ccaggattct      1100
ataaagcttt tgctgggaac acaaaatgtt ctaaatgtcc tccacacagt      1150
ttaacataca tggaagcaac ttctgtctgt cagtgtgaaa agggttattt      1200
ccgagctgaa aaagacccac cttctatggc atgtaccagg ccaccttcag      1250
ctcctaggaa tgtggttttt aacatcaatg aaacagccct tattttggaa      1300
tggagcccac caagtgacac aggagggaga aaagatctca catacagtgt      1350
aatctgtaag aaatgtggct tagacaccag ccagtgtgag gactgtggtg      1400
gaggactccg cttcatccca agacatacag gcctgatcaa caattccgtg      1450
atagtacttg actttgtgtc tcacgtgaat tacacctttg aaatagaagc      1500
aatgaatgga gtttctgagt tgagtttttc tcccaagcca ttcacagcta      1550
ttacagtgac cacggatcaa gatgcacctt ccctgatagg tgtggtaagg      1600
aaggactggg catcccaaaa tagcattgcc ctatcatggc aagcacctgc      1650
tttttccaat ggagccattc tggactacga gatcaagtac tatgagaaag      1700
aacatgagca gctgacctac tcttccacaa ggtccaaagc ccccagtgtc      1750
atcatcacag gtcttaagcc agccaccaaa tatgtatttc acatccgagt      1800
gagaactgcg acaggataca gtggctacag tcagaaattt gaatttgaaa      1850
caggagatga aacttctgac atggcagcag aacaaggaca gattctcgtg      1900
atagccaccg ccgctgttgg cggattcact ctcctcgtca tcctcacttt      1950
attcttcttg atcactggga gatgtcagtg gtacataaaa gccaagatga      2000
agtcagaaga gaagagaaga aaccacttac agaatgggca tttgcgcttc      2050
```

-continued

```
ccgggaatta aaacttacat tgatccagat acatatgaag acccatccct        2100

agcagtccat gaatttgcaa aggagattga tccctcaaga attcgtattg        2150

agagagtcat tggggcaggt gaatttggag aagtctgtag tgggcgtttg        2200

aagacaccag ggaaaagaga gatcccagtt gccattaaaa ctttgaaagg        2250

tggccacatg gatcggcaaa gaagagattt tctaagagaa gctagtatca        2300

tgggccagtt tgaccatcca aacatcattc gcctagaagg ggttgtcacc        2350

aaaagatcct tcccggccat tggggtggag gcgttttgcc ccagcttcct        2400

gagggcaggg tttttaaata gcatccaggc cccgcatcca gtgccagggg        2450

gaggatcttt gccccccagg attcctgctg gcagaccagt aatgattgtg        2500

gtggaatata tggagaatgg atccctagac tcctttttgc ggaagcatga        2550

tggccacttc acagtcatcc agttggtcgg aatgctccga ggcattgcat        2600

caggcatgaa gtatctttct gatatgggtt atgttcatcg agacctagcg        2650

gctcggaata tactggtcaa tagcaactta gtatgcaaag tttctgattt        2700

tggtctctcc agagtgctgg aagatgatcc agaagctgct tatacaacaa        2750

ctggtggaaa aatccccata aggtggacag ccccagaagc catcgcctac        2800

agaaaattct cctcagcaag cgatgcatgg agctatggca ttgtcatgtg        2850

ggaggtcatg tcctatggag agagacctta ttgggaaatg tctaaccaag        2900

atgtcattct gtccattgaa gaagggtaca gacttccagc tcccatgggc        2950

tgtccagcat ctctacacca gctgatgctc cactgctggc agaaggagag        3000

aaatcacaga ccaaaattta ctgacattgt cagcttcctt gacaaactga        3050

tccgaaatcc cagtgccctt cacaccctgg tggaggacat ccttgtaatg        3100

ccagagtccc ctggtgaagt tccggaatat cctttgtttg tcacagttgg        3150

tgactggcta gattctataa agatggggca atacaagaat aacttcgtgg        3200

cagcagggtt tacaacattt gacctgattt caagaatgag cattgatgac        3250

attagaagaa ttggagtcat acttattgga caccagagac gaatagtcag        3300

cagcatacag actttacgtt tacacatgat gcacatacag gagaagggat        3350

ttcatgtatg aaagtaccac aagcacctgt gttttgtgcc tcagcatttc        3400

taaaatgaac gatatcctct ctactactct ctcttctgat tctccaaaca        3450

tcacttcaca aactgcagtc ttctgttcag actataggca cacaccttat        3500

gtttatgctt ccaaccagga ttttaaaatc atgctacata aatccgttct        3550

gaataacctg caactaaaaa aaaaaaaaaa aaa                          3583
```

<210> SEQ ID NO 104
<211> LENGTH: 1036
<212> TYPE: PRT
<213> ORGANISM: Homo Sapien

<400> SEQUENCE: 104

```
Met Gly Gly Cys Glu Val Arg Glu Phe Leu Leu Gln Phe Gly Phe
  1               5                  10                  15

Phe Leu Pro Leu Leu Thr Ala Trp Pro Gly Asp Cys Ser His Val
                 20                  25                  30

Ser Asn Asn Gln Val Val Leu Leu Asp Thr Thr Thr Val Leu Gly
                 35                  40                  45
```

-continued

```
Glu Leu Gly Trp Lys Thr Tyr Pro Leu Asn Gly Trp Asp Ala Ile
                50                  55                  60

Thr Glu Met Asp Glu His Asn Arg Pro Ile His Thr Tyr Gln Val
                65                  70                  75

Cys Asn Val Met Glu Pro Asn Gln Asn Asn Trp Leu Arg Thr Asn
                80                  85                  90

Trp Ile Ser Arg Asp Ala Ala Gln Lys Ile Tyr Val Glu Met Lys
                95                  100                 105

Phe Thr Leu Arg Asp Cys Asn Ser Ile Pro Trp Val Leu Gly Thr
                110                 115                 120

Cys Lys Glu Thr Phe Asn Leu Phe Tyr Met Glu Ser Asp Glu Ser
                125                 130                 135

His Gly Ile Lys Phe Lys Pro Asn Gln Tyr Thr Lys Ile Asp Thr
                140                 145                 150

Ile Ala Ala Asp Glu Ser Phe Thr Gln Met Asp Leu Gly Asp Arg
                155                 160                 165

Ile Leu Lys Leu Asn Thr Glu Ile Arg Glu Val Gly Pro Ile Glu
                170                 175                 180

Arg Lys Gly Phe Tyr Leu Ala Phe Gln Asp Ile Gly Ala Cys Ile
                185                 190                 195

Ala Leu Val Ser Val Arg Val Phe Tyr Lys Lys Cys Pro Phe Thr
                200                 205                 210

Val Arg Asn Leu Ala Met Phe Pro Asp Thr Ile Pro Arg Val Asp
                215                 220                 225

Ser Ser Ser Leu Val Glu Val Arg Gly Ser Cys Val Lys Ser Ala
                230                 235                 240

Glu Glu Arg Asp Thr Pro Lys Leu Tyr Cys Gly Ala Asp Gly Asp
                245                 250                 255

Trp Leu Val Pro Leu Gly Arg Cys Ile Cys Ser Thr Gly Tyr Glu
                260                 265                 270

Glu Ile Glu Gly Ser Cys His Ala Cys Arg Pro Gly Phe Tyr Lys
                275                 280                 285

Ala Phe Ala Gly Asn Thr Lys Cys Ser Lys Cys Pro Pro His Ser
                290                 295                 300

Leu Thr Tyr Met Glu Ala Thr Ser Val Cys Gln Cys Glu Lys Gly
                305                 310                 315

Tyr Phe Arg Ala Glu Lys Asp Pro Pro Ser Met Ala Cys Thr Arg
                320                 325                 330

Pro Pro Ser Ala Pro Arg Asn Val Val Phe Asn Ile Asn Glu Thr
                335                 340                 345

Ala Leu Ile Leu Glu Trp Ser Pro Pro Ser Asp Thr Gly Gly Arg
                350                 355                 360

Lys Asp Leu Thr Tyr Ser Val Ile Cys Lys Lys Cys Gly Leu Asp
                365                 370                 375

Thr Ser Gln Cys Glu Asp Cys Gly Gly Gly Leu Arg Phe Ile Pro
                380                 385                 390

Arg His Thr Gly Leu Ile Asn Asn Ser Val Ile Val Leu Asp Phe
                395                 400                 405

Val Ser His Val Asn Tyr Thr Phe Glu Ile Glu Ala Met Asn Gly
                410                 415                 420

Val Ser Glu Leu Ser Phe Ser Pro Lys Pro Phe Thr Ala Ile Thr
                425                 430                 435

Val Thr Thr Asp Gln Asp Ala Pro Ser Leu Ile Gly Val Val Arg
```

-continued

```
                440                 445                 450

Lys Asp Trp Ala Ser Gln Asn Ser Ile Ala Leu Ser Trp Gln Ala
                455                 460                 465

Pro Ala Phe Ser Asn Gly Ala Ile Leu Asp Tyr Glu Ile Lys Tyr
                470                 475                 480

Tyr Glu Lys Glu His Glu Gln Leu Thr Tyr Ser Ser Thr Arg Ser
                485                 490                 495

Lys Ala Pro Ser Val Ile Ile Thr Gly Leu Lys Pro Ala Thr Lys
                500                 505                 510

Tyr Val Phe His Ile Arg Val Arg Thr Ala Thr Gly Tyr Ser Gly
                515                 520                 525

Tyr Ser Gln Lys Phe Glu Phe Glu Thr Gly Asp Glu Thr Ser Asp
                530                 535                 540

Met Ala Ala Glu Gln Gly Gln Ile Leu Val Ile Ala Thr Ala Ala
                545                 550                 555

Val Gly Gly Phe Thr Leu Leu Val Ile Leu Thr Leu Phe Phe Leu
                560                 565                 570

Ile Thr Gly Arg Cys Gln Trp Tyr Ile Lys Ala Lys Met Lys Ser
                575                 580                 585

Glu Glu Lys Arg Arg Asn His Leu Gln Asn Gly His Leu Arg Phe
                590                 595                 600

Pro Gly Ile Lys Thr Tyr Ile Asp Pro Asp Thr Tyr Glu Asp Pro
                605                 610                 615

Ser Leu Ala Val His Glu Phe Ala Lys Glu Ile Asp Pro Ser Arg
                620                 625                 630

Ile Arg Ile Glu Arg Val Ile Gly Ala Gly Glu Phe Gly Glu Val
                635                 640                 645

Cys Ser Gly Arg Leu Lys Thr Pro Gly Lys Arg Glu Ile Pro Val
                650                 655                 660

Ala Ile Lys Thr Leu Lys Gly Gly His Met Asp Arg Gln Arg Arg
                665                 670                 675

Asp Phe Leu Arg Glu Ala Ser Ile Met Gly Gln Phe Asp His Pro
                680                 685                 690

Asn Ile Ile Arg Leu Glu Gly Val Val Thr Lys Arg Ser Phe Pro
                695                 700                 705

Ala Ile Gly Val Glu Ala Phe Cys Pro Ser Phe Leu Arg Ala Gly
                710                 715                 720

Phe Leu Asn Ser Ile Gln Ala Pro His Pro Val Pro Gly Gly Gly
                725                 730                 735

Ser Leu Pro Pro Arg Ile Pro Ala Gly Arg Pro Val Met Ile Val
                740                 745                 750

Val Glu Tyr Met Glu Asn Gly Ser Leu Asp Ser Phe Leu Arg Lys
                755                 760                 765

His Asp Gly His Phe Thr Val Ile Gln Leu Val Gly Met Leu Arg
                770                 775                 780

Gly Ile Ala Ser Gly Met Lys Tyr Leu Ser Asp Met Gly Tyr Val
                785                 790                 795

His Arg Asp Leu Ala Ala Arg Asn Ile Leu Val Asn Ser Asn Leu
                800                 805                 810

Val Cys Lys Val Ser Asp Phe Gly Leu Ser Arg Val Leu Glu Asp
                815                 820                 825

Asp Pro Glu Ala Ala Tyr Thr Thr Thr Gly Gly Lys Ile Pro Ile
                830                 835                 840
```

-continued

```
Arg Trp Thr Ala Pro Glu Ala Ile Ala Tyr Arg Lys Phe Ser Ser
                845                 850                 855

Ala Ser Asp Ala Trp Ser Tyr Gly Ile Val Met Trp Glu Val Met
                860                 865                 870

Ser Tyr Gly Glu Arg Pro Tyr Trp Glu Met Ser Asn Gln Asp Val
                875                 880                 885

Ile Leu Ser Ile Glu Glu Gly Tyr Arg Leu Pro Ala Pro Met Gly
                890                 895                 900

Cys Pro Ala Ser Leu His Gln Leu Met Leu His Cys Trp Gln Lys
                905                 910                 915

Glu Arg Asn His Arg Pro Lys Phe Thr Asp Ile Val Ser Phe Leu
                920                 925                 930

Asp Lys Leu Ile Arg Asn Pro Ser Ala Leu His Thr Leu Val Glu
                935                 940                 945

Asp Ile Leu Val Met Pro Glu Ser Pro Gly Glu Val Pro Glu Tyr
                950                 955                 960

Pro Leu Phe Val Thr Val Gly Asp Trp Leu Asp Ser Ile Lys Met
                965                 970                 975

Gly Gln Tyr Lys Asn Asn Phe Val Ala Ala Gly Phe Thr Thr Phe
                980                 985                 990

Asp Leu Ile Ser Arg Met Ser Ile Asp Asp Ile Arg Arg Ile Gly
                995                 1000                1005

Val Ile Leu Ile Gly His Gln Arg Arg Ile Val Ser Ser Ile Gln
               1010                1015                1020

Thr Leu Arg Leu His Met Met His Ile Gln Glu Lys Gly Phe His
               1025                1030                1035

Val
```

<210> SEQ ID NO 105
<211> LENGTH: 2148
<212> TYPE: DNA
<213> ORGANISM: Homo Sapien

<400> SEQUENCE: 105

```
ggcggcgggc tgcgcggagc ggcgtcccct gcagccgcgg accgaggcag         50

cggcggcacc tgccggccga gcaatgccaa gtgagtacac ctatgtgaaa        100

ctgagaagtg attgctcgag gccttccctg caatggtaca cccgagctca        150

aagcaagatg agaaggccca gcttgttatt aaaagacatc ctcaaatgta        200

cattgcttgt gtttggagtg tggatccttt atatcctcaa gttaaattat        250

actactgaag aatgtgacat gaaaaaaatg cattatgtgg accctgacca        300

tgtaaagaga gctcagaaat atgctcagca agtcttgcag aaggaatgtc        350

gtcccaagtt tgccaagaca tcaatggcgc tgttatttga gcacaggtat        400

agcgtggact tactcccttt tgtgcagaag gcccccaaag acagtgaagc        450

tgagtccaag tacgatcctc cttttgggtt ccggaagttc tccagtaaag        500

tccagaccct cttggaactc ttgccagagc acgacctccc tgaacacttg        550

aaagccaaga cctgtcggcg ctgtgtggtt attggaagcg gaggaatact        600

gcacggatta gaactgggcc acaccctgaa ccagttcgat gttgtgataa        650

ggttaaacag tgcaccagtt gagggatatt cagaacatgt tggaaataaa        700

actactataa ggatgactta tccagagggc gcaccactgt ctgaccttga        750
```

-continued

```
atattattcc aatgacttat ttgttgctgt tttatttaag agtgttgatt          800

tcaactggct tcaagcaatg gtaaaaaagg aaaccctgcc attctgggta          850

cgactcttct tttggaagca ggtggcagaa aaaatcccac tgcagccaaa          900

acatttcagg attttgaatc cagttatcat caaagagact gcctttgaca          950

tccttcagta ctcagagcct cagtcaaggt tctggggccg agataagaac         1000

gtccccacaa tcggtgtcat tgccgttgtc ttagccacac atctgtgcga         1050

tgaagtcagt ttggcgggtt ttggatatga cctcaatcaa cccagaacac         1100

ctttgcacta cttcgacagt caatgcatgg ctgctatgaa ctttcagacc         1150

atgcataatg tgacaacgga aaccaagttc ctcttaaagc tggtcaaaga         1200

gggagtggtg aaagatctca gtggaggcat tgatcgtgaa ttttgaacac         1250

agaaaacctc agttgaaaat gcaactctaa ctctgagagc tgtttttgac         1300

agccttcttg atgtatttct ccatcctgca gatactttga agtgcagctc         1350

atgtttttaa cttttaattt aaaaacacaa aaaaaatttt agctcttccc         1400

actttttttt tcctatttat ttgaggtcag tgtttgtttt tgcacaccat         1450

tttgtaaatg aaacttaaga attgaattgg aaagacttct caaagagaat         1500

tgtatgtaac gatgttgtat tgatttttaa gaaagtaatt taatttgtaa         1550

aacttctgct cgtttacact gcacattgaa tacaggtaac taattggaag         1600

gagaggggag gtcactcttt tgatggtggc cctgaacctc attctggttc         1650

cctgctgcgc tgcttggtgt gacccacgga ggatccactc ccaggatgac         1700

gtgctccgta gctctgctgc tgatactggg tctgcgatgc agcggcgtga         1750

ggcctgggct ggttggagaa ggtcacaacc cttctctgtt ggtctgcctt         1800

ctgctgaaag actcgagaac caaccaggga agctgtcctg gaggtccctg         1850

gtcggagagg gacatagaat ctgtgacctc tgacaactgt gaagccaccc         1900

tgggctacag aaaccacagt cttcccagca attattacaa ttcttgaatt         1950

ccttggggat tttttactgc cctttcaaag cacttaagtg ttagatctaa         2000

cgtgttccag tgtctgtctg aggtgactta aaaaatcaga acaaaacttc         2050

tattatccag agtcatggga gagtacaccc tttccaggaa taatgttttg         2100

ggaaacactg aaatgaaatc ttcccagtat tataaattgt gtatttaa           2148
```

<210> SEQ ID NO 106
<211> LENGTH: 362
<212> TYPE: PRT
<213> ORGANISM: Homo Sapien

<400> SEQUENCE: 106

```
Met Arg Arg Pro Ser Leu Leu Leu Lys Asp Ile Leu Lys Cys Thr
  1               5                  10                  15

Leu Leu Val Phe Gly Val Trp Ile Leu Tyr Ile Leu Lys Leu Asn
                 20                  25                  30

Tyr Thr Thr Glu Glu Cys Asp Met Lys Lys Met His Tyr Val Asp
                 35                  40                  45

Pro Asp His Val Lys Arg Ala Gln Lys Tyr Ala Gln Gln Val Leu
                 50                  55                  60

Gln Lys Glu Cys Arg Pro Lys Phe Ala Lys Thr Ser Met Ala Leu
                 65                  70                  75
```

-continued

Leu Phe Glu His Arg Tyr Ser Val Asp Leu Leu Pro Phe Val Gln
80 85 90

Lys Ala Pro Lys Asp Ser Glu Ala Glu Ser Lys Tyr Asp Pro Pro
95 100 105

Phe Gly Phe Arg Lys Phe Ser Ser Lys Val Gln Thr Leu Leu Glu
110 115 120

Leu Leu Pro Glu His Asp Leu Pro Glu His Leu Lys Ala Lys Thr
125 130 135

Cys Arg Arg Cys Val Val Ile Gly Ser Gly Gly Ile Leu His Gly
140 145 150

Leu Glu Leu Gly His Thr Leu Asn Gln Phe Asp Val Val Ile Arg
155 160 165

Leu Asn Ser Ala Pro Val Glu Gly Tyr Ser Glu His Val Gly Asn
170 175 180

Lys Thr Thr Ile Arg Met Thr Tyr Pro Glu Gly Ala Pro Leu Ser
185 190 195

Asp Leu Glu Tyr Tyr Ser Asn Asp Leu Phe Val Ala Val Leu Phe
200 205 210

Lys Ser Val Asp Phe Asn Trp Leu Gln Ala Met Val Lys Lys Glu
215 220 225

Thr Leu Pro Phe Trp Val Arg Leu Phe Phe Trp Lys Gln Val Ala
230 235 240

Glu Lys Ile Pro Leu Gln Pro Lys His Phe Arg Ile Leu Asn Pro
245 250 255

Val Ile Ile Lys Glu Thr Ala Phe Asp Ile Leu Gln Tyr Ser Glu
260 265 270

Pro Gln Ser Arg Phe Trp Gly Arg Asp Lys Asn Val Pro Thr Ile
275 280 285

Gly Val Ile Ala Val Val Leu Ala Thr His Leu Cys Asp Glu Val
290 295 300

Ser Leu Ala Gly Phe Gly Tyr Asp Leu Asn Gln Pro Arg Thr Pro
305 310 315

Leu His Tyr Phe Asp Ser Gln Cys Met Ala Ala Met Asn Phe Gln
320 325 330

Thr Met His Asn Val Thr Thr Glu Thr Lys Phe Leu Leu Lys Leu
335 340 345

Val Lys Glu Gly Val Val Lys Asp Leu Ser Gly Gly Ile Asp Arg
350 355 360

Glu Phe

<210> SEQ ID NO 107
<211> LENGTH: 1399
<212> TYPE: DNA
<213> ORGANISM: Homo Sapien

<400> SEQUENCE: 107
tgacgcgggg cgccagctgc caacttcgcg cgcggagctc cccggcggtg 50
cagtcccgtc ccggcggcgc gggcggcatg aagactagcc gccgcggccg 100
agcgctcctg gccgtggccc tgaacctgct ggcgctgctg ttcgccacca 150
ccgctttcct caccacgcac tggtgccagg gcacgcagcg ggtccccaag 200
ccgggctgcg gccagggcgg gcgcgccaac tgccccaact cgggcgccaa 250
cgccacggcc aacggcaccg ccgccccgc cgccgccgcc gccgccgcca 300

-continued

```
ccgcctcggg gaacggcccc cctggcggcg cgctctacag ctgggagacc          350

ggcgacgacc gcttcctctt caggaatttc cacaccggca tctggtactc          400

gtgcgaggag gagctcagcg ggcttggtga aaaatgtcgc agcttcattg          450

acctggcccc ggcgtcggag aaaggcctcc tgggaatggt cgcccacatg          500

atgtacacgc aggtgttcca ggtcaccgtg agcctcggtc ctgaggactg          550

gagaccccat tcctgggact acgggtggtc cttctgcctg gcgtggggct          600

cctttacctg ctgcatggca gcctctgtca ccacgctcaa ctcctacacc          650

aagacggtca ttgagttccg gcacaagcgc aaggtctttg agcagggcta          700

ccgggaagag ccgaccttca tagaccctga ggccatcaag tacttccggg          750

agaggatgga gaagagggac gggagcgagg aggactttca cttagactgc          800

cgccacgaga gataccctgc ccgacaccag ccacacatgg cggattcctg          850

gccccggagc tccgcacagg aagcaccaga gctgaaccga cagtgctggg          900

tcttggggca ctgggtgtga ccaagacctc aacctggccc gcggacctca          950

ggccatcgct ggcaccagcc cctgctgcaa gaccaccaga gtggtgcccc         1000

cagaaccctg gcctgtgtgc cgtgaactca gtcagcctgc gtgggagatg         1050

ccaggcctgt cctgcccatc gctgcctggg tcccatggcc ttggaaatgg         1100

ggccagggca ggcccaaggg aatgcacagg gctgcacaga gtgactttgg         1150

gacagcagcc ccggactctt gccatcatca catgagccct gctgggcaca         1200

gctgcgatgc caggagacac atggccactg gccactgaat ggctggcacc         1250

cacaagccag tcaggtgccc agaggggcag agccctttgg ggggcagaga         1300

gtggcttcct gaaggagggg gcagtggcgc aggcactgca ggggtgtcac         1350

acagcaggca cacagcaggg gctcaataaa tgcttgttga acttgtttt          1399
```

<210> SEQ ID NO 108
<211> LENGTH: 280
<212> TYPE: PRT
<213> ORGANISM: Homo Sapien

<400> SEQUENCE: 108

```
Met Lys Thr Ser Arg Arg Gly Arg Ala Leu Leu Ala Val Ala Leu
  1               5                  10                  15

Asn Leu Leu Ala Leu Leu Phe Ala Thr Thr Ala Phe Leu Thr Thr
                 20                  25                  30

His Trp Cys Gln Gly Thr Gln Arg Val Pro Lys Pro Gly Cys Gly
                 35                  40                  45

Gln Gly Gly Arg Ala Asn Cys Pro Asn Ser Gly Ala Asn Ala Thr
                 50                  55                  60

Ala Asn Gly Thr Ala Ala Pro Ala Ala Ala Ala Ala Ala Ala Thr
                 65                  70                  75

Ala Ser Gly Asn Gly Pro Pro Gly Gly Ala Leu Tyr Ser Trp Glu
                 80                  85                  90

Thr Gly Asp Asp Arg Phe Leu Phe Arg Asn Phe His Thr Gly Ile
                 95                 100                 105

Trp Tyr Ser Cys Glu Glu Glu Leu Ser Gly Leu Gly Glu Lys Cys
                110                 115                 120

Arg Ser Phe Ile Asp Leu Ala Pro Ala Ser Glu Lys Gly Leu Leu
                125                 130                 135
```

-continued

```
Gly Met Val Ala His Met Met Tyr Thr Gln Val Phe Gln Val Thr
                140                 145                 150

Val Ser Leu Gly Pro Glu Asp Trp Arg Pro His Ser Trp Asp Tyr
                155                 160                 165

Gly Trp Ser Phe Cys Leu Ala Trp Gly Ser Phe Thr Cys Cys Met
                170                 175                 180

Ala Ala Ser Val Thr Thr Leu Asn Ser Tyr Thr Lys Thr Val Ile
                185                 190                 195

Glu Phe Arg His Lys Arg Lys Val Phe Glu Gln Gly Tyr Arg Glu
                200                 205                 210

Glu Pro Thr Phe Ile Asp Pro Glu Ala Ile Lys Tyr Phe Arg Glu
                215                 220                 225

Arg Met Glu Lys Arg Asp Gly Ser Glu Glu Asp Phe His Leu Asp
                230                 235                 240

Cys Arg His Glu Arg Tyr Pro Ala Arg His Gln Pro His Met Ala
                245                 250                 255

Asp Ser Trp Pro Arg Ser Ser Ala Gln Glu Ala Pro Glu Leu Asn
                260                 265                 270

Arg Gln Cys Trp Val Leu Gly His Trp Val
                275                 280
```

<210> SEQ ID NO 109
<211> LENGTH: 2964
<212> TYPE: DNA
<213> ORGANISM: Homo Sapien

<400> SEQUENCE: 109

```
gattaccaag caagaacagc taaaatgaaa gccatcattc atcttactct          50

tcttgctctc ctttctgtaa acacagccac caaccaaggc aactcagctg         100

atgctgtaac aaccacagaa actgcgacta gtggtcctac agtagctgca         150

gctgatacca ctgaaactaa tttccctgaa actgctagca ccacagcaaa         200

tacaccttct ttcccaacag ctacttcacc tgctcccccc ataattagta         250

cacatagttc ctccacaatt cctacacctg ctcccccat aattagtaca          300

catagttcct ccacaattcc tatacctact gctgcagaca gtgagtcaac         350

cacaaatgta aattcattag ctacctctga cataatcacc gcttcatctc         400

caaatgatgg attaatcaca atggttcctt ctgaaacaca aagtaacaat         450

gaaatgtccc ccaccacaga agacaatcaa tcatcagggc ctcccactgg         500

caccgcttta ttggagacca gcaccctaaa cagcacaggt cccagcaatc         550

cttgccaaga tgatccctgt gcagataatt cgttatgtgt taagctgcat         600

aatacaagtt tttgcctgtg tttagaaggg tattactaca actcttctac         650

atgtaagaaa ggaaaggtat tccctgggaa gatttcagtg acagtatcag         700

aaacatttga cccagaagag aaacattcca tggcctatca agacttgcat         750

agtgaaatta ctagcttgtt taaagatgta tttggcacat ctgtttatgg         800

acagactgta attcttactg taagcacatc tctgtcacca agatctgaaa         850

tgcgtgctga tgacaagttt gttaatgtaa caatagtaac aattttggca         900

gaaaccacaa gtgacaatga gaagactgtg actgagaaaa ttaataaagc         950

aattagaagt agctcaagca actttctaaa ctatgatttg acccttcggt        1000
```

-continued

```
gtgattatta tggctgtaac cagactgcgg atgactgcct caatggttta      1050
gcatgcgatt gcaaatctga cctgcaaagg cctaacccac agagcccttt      1100
ctgcgttgct tccagtctca agtgtcctga tgcctgcaac gcacagcaca      1150
agcaatgctt aataaagaag agtggtgggg cccctgagtg tgcgtgcgtg      1200
cccggctacc aggaagatgc taatgggaac tgccaaaagt gtgcatttgg      1250
ctacagtgga ctcgactgta aggacaaatt tcagctgatc ctcactattg      1300
tgggcaccat cgctggcatt gtcattctca gcatgataat tgcattgatt      1350
gtcacagcaa gatcaaataa caaaacgaag catattgaag aagagaactt      1400
gattgacgaa gactttcaaa atctaaaact gcggtcgaca ggcttcacca      1450
atcttggagc agaagggagc gtctttccta aggtcaggat aacggcctcc      1500
agagacagcc agatgcaaaa tccctattca agccacagca gcatgccccg      1550
ccctgactat tagaatcata agaatgtgga acccgccatg gcccccaacc      1600
aatgtacaag ctattattta gagtgtttag aaagactgat ggagaagtga      1650
gcaccagtaa agatctggcc tccgggggttt ttcttccatc tgacatctgc     1700
cagcctctct gaatggaagt tgtgaatgtt tgcaacgaat ccagctcact      1750
tgctaaataa gaatctatga cattaaatgt agtagatgct attagcgctt      1800
gtcagagagg tggttttctt caatcagtac aaagtactga gacaatggtt      1850
agggttgttt tcttaattct tttcctggta gggcaacaag aaccatttcc      1900
aatctagagg aaagctcccc agcattgctt gctcctgggc aaacattgct      1950
cttgagttaa gtgacctaat tcccctggga gacatacgca tcaactgtgg      2000
aggtccgagg ggatgagaag ggatacccac catctttcaa gggtcacaag      2050
ctcactctct gacaagtcag aatagggaca ctgcttctat ccctccaatg      2100
gagagattct ggcaaccttt gaacagccca gagcttgcaa cctagcctca      2150
cccaagaaga ctggaaagag acatatctct cagctttttc aggaggcgtg      2200
cctgggaatc caggaacttt ttgatgctaa ttagaaggcc tggactaaaa      2250
atgtccacta tggggtgcac tctacagttt ttgaaatgct aggaggcaga      2300
aggggcagag agtaaaaaac atgacctggt agaaggaaga gaggcaaagg      2350
aaactgggtg gggaggatca attagagagg aggcacctgg gatccacctt      2400
cttccttagg tcccctcctc catcagcaaa ggagcacttc tctaatcatg      2450
ccctcccgaa gactggctgg gagaaggttt aaaaacaaaa aatccaggag      2500
taagagcctt aggtcagttt gaaattggag acaaactgtc tggcaaaggg      2550
tgcgagaggg agcttgtgct caggagtcca gccgcccagc ctcggggtgt      2600
aggtttctga ggtgtgccat tggggcctca gccttctctg gtgacagagg      2650
ctcagctgtg gccaccaaca cacaaccaca cacacacaac cacacacaca      2700
aatgggggca accacatcca gtacaagctt ttacaaatgt tattagtgtc      2750
ctttttttatt tctaatgcct tgtcctctta aaagttattt tatttgttat     2800
tattatttgt tcttgactgt taattgtgaa tggtaatgca ataaagtgcc      2850
tttgttagat ggtgaaaaaa aaaaaaaaaa aaaaaaaaaa aaaaaaaaaa      2900
aaaaaaaaaa aaaaaaaaaa aaaaaaaaaa aaaaaaaaaa aaaaaaaaaa      2950
aaaaaaaaaa aaaa                                             2964
```

<210> SEQ ID NO 110
<211> LENGTH: 512
<212> TYPE: PRT
<213> ORGANISM: Homo Sapien

<400> SEQUENCE: 110

```
Met Lys Ala Ile Ile His Leu Thr Leu Leu Ala Leu Leu Ser Val
  1               5                  10                  15

Asn Thr Ala Thr Asn Gln Gly Asn Ser Ala Asp Ala Val Thr Thr
                 20                  25                  30

Thr Glu Thr Ala Thr Ser Gly Pro Thr Val Ala Ala Ala Asp Thr
                 35                  40                  45

Thr Glu Thr Asn Phe Pro Glu Thr Ala Ser Thr Thr Ala Asn Thr
                 50                  55                  60

Pro Ser Phe Pro Thr Ala Thr Ser Pro Ala Pro Pro Ile Ile Ser
                 65                  70                  75

Thr His Ser Ser Ser Thr Ile Pro Thr Pro Ala Pro Pro Ile Ile
                 80                  85                  90

Ser Thr His Ser Ser Ser Thr Ile Pro Ile Pro Thr Ala Ala Asp
                 95                 100                 105

Ser Glu Ser Thr Thr Asn Val Asn Ser Leu Ala Thr Ser Asp Ile
                110                 115                 120

Ile Thr Ala Ser Ser Pro Asn Asp Gly Leu Ile Thr Met Val Pro
                125                 130                 135

Ser Glu Thr Gln Ser Asn Asn Glu Met Ser Pro Thr Thr Glu Asp
                140                 145                 150

Asn Gln Ser Ser Gly Pro Pro Thr Gly Thr Ala Leu Leu Glu Thr
                155                 160                 165

Ser Thr Leu Asn Ser Thr Gly Pro Ser Asn Pro Cys Gln Asp Asp
                170                 175                 180

Pro Cys Ala Asp Asn Ser Leu Cys Val Lys Leu His Asn Thr Ser
                185                 190                 195

Phe Cys Leu Cys Leu Glu Gly Tyr Tyr Tyr Asn Ser Ser Thr Cys
                200                 205                 210

Lys Lys Gly Lys Val Phe Pro Gly Lys Ile Ser Val Thr Val Ser
                215                 220                 225

Glu Thr Phe Asp Pro Glu Glu Lys His Ser Met Ala Tyr Gln Asp
                230                 235                 240

Leu His Ser Glu Ile Thr Ser Leu Phe Lys Asp Val Phe Gly Thr
                245                 250                 255

Ser Val Tyr Gly Gln Thr Val Ile Leu Thr Val Ser Thr Ser Leu
                260                 265                 270

Ser Pro Arg Ser Glu Met Arg Ala Asp Asp Lys Phe Val Asn Val
                275                 280                 285

Thr Ile Val Thr Ile Leu Ala Glu Thr Thr Ser Asp Asn Glu Lys
                290                 295                 300

Thr Val Thr Glu Lys Ile Asn Lys Ala Ile Arg Ser Ser Ser Ser
                305                 310                 315

Asn Phe Leu Asn Tyr Asp Leu Thr Leu Arg Cys Asp Tyr Tyr Gly
                320                 325                 330

Cys Asn Gln Thr Ala Asp Asp Cys Leu Asn Gly Leu Ala Cys Asp
                335                 340                 345

Cys Lys Ser Asp Leu Gln Arg Pro Asn Pro Gln Ser Pro Phe Cys
```

-continued

```
                350                 355                 360

Val Ala Ser Ser Leu Lys Cys Pro Asp Ala Cys Asn Ala Gln His
                365                 370                 375

Lys Gln Cys Leu Ile Lys Lys Ser Gly Gly Ala Pro Glu Cys Ala
                380                 385                 390

Cys Val Pro Gly Tyr Gln Glu Asp Ala Asn Gly Asn Cys Gln Lys
                395                 400                 405

Cys Ala Phe Gly Tyr Ser Gly Leu Asp Cys Lys Asp Lys Phe Gln
                410                 415                 420

Leu Ile Leu Thr Ile Val Gly Thr Ile Ala Gly Ile Val Ile Leu
                425                 430                 435

Ser Met Ile Ile Ala Leu Ile Val Thr Ala Arg Ser Asn Asn Lys
                440                 445                 450

Thr Lys His Ile Glu Glu Glu Asn Leu Ile Asp Glu Asp Phe Gln
                455                 460                 465

Asn Leu Lys Leu Arg Ser Thr Gly Phe Thr Asn Leu Gly Ala Glu
                470                 475                 480

Gly Ser Val Phe Pro Lys Val Arg Ile Thr Ala Ser Arg Asp Ser
                485                 490                 495

Gln Met Gln Asn Pro Tyr Ser Ser His Ser Ser Met Pro Arg Pro
                500                 505                 510

Asp Tyr


<210> SEQ ID NO 111
<211> LENGTH: 943
<212> TYPE: DNA
<213> ORGANISM: Homo Sapien

<400> SEQUENCE: 111

ctgggacttg gctttctccg gataagcggc ggcaccggcg tcagcgatga        50

ccgtgcagag actcgtggcc gcggccgtgc tggtggccct ggtctcactc       100

atcctcaaca acgtggcggc cttcacctcc aactgggtgt gccagacgct       150

ggaggatggg cgcaggcgca gcgtggggct gtggaggtcc tgctggctgg       200

tggacaggac ccggggaggg ccgagccctg ggccagagc cggccaggtg        250

gacgcacatg actgtgaggc gctgggctgg ggctccgagg cagccggctt       300

ccaggagtcc cgaggcaccg tcaaactgca gttcgacatg atgcgcgcct       350

gcaacctggt ggccacggcc gcgctcaccg caggccagct caccttcctc       400

ctggggctgg tgggcctgcc cctgctgtca cccgacgccc cgtgctggga       450

ggaggccatg gccgctgcat tccaactggc gagttttgtc ctggtcatcg       500

ggctcgtgac tttctacaga attggcccat acaccaacct gtcctggtcc       550

tgctacctga acattggcgc ctgccttctg gccacgctgg cggcagccat       600

gctcatctgg aacattctcc acaagaggga ggactgcatg gcccccggg        650

tgattgtcat cagccgctcc ctgacagcgc gctttcgccg tgggctggac       700

aatgactacg tggagtcacc atgctgagtc gcccttctca gcgctccatc       750

aacgcacacc tgctatcgtg gaacagccta gaaaccaagg gactccacca       800

ccaagtcact tcccctgctc gtgcagaggc acgggatgag tctgggtgac       850

ctctgcgcca tgcgtgcgag acacgtgtgc gtttactgtt atgtcggtca       900

tatgtctgta cgtgtcgtgg gccaacctcg ttctgcctcc agc              943
```

<210> SEQ ID NO 112
<211> LENGTH: 226
<212> TYPE: PRT
<213> ORGANISM: Homo Sapien

<400> SEQUENCE: 112

Met Thr Val Gln Arg Leu Val Ala Ala Ala Val Leu Val Ala Leu
1 5 10 15

Val Ser Leu Ile Leu Asn Asn Val Ala Ala Phe Thr Ser Asn Trp
20 25 30

Val Cys Gln Thr Leu Glu Asp Gly Arg Arg Arg Ser Val Gly Leu
35 40 45

Trp Arg Ser Cys Trp Leu Val Asp Arg Thr Arg Gly Gly Pro Ser
50 55 60

Pro Gly Ala Arg Ala Gly Gln Val Asp Ala His Asp Cys Glu Ala
65 70 75

Leu Gly Trp Gly Ser Glu Ala Ala Gly Phe Gln Glu Ser Arg Gly
80 85 90

Thr Val Lys Leu Gln Phe Asp Met Met Arg Ala Cys Asn Leu Val
95 100 105

Ala Thr Ala Ala Leu Thr Ala Gly Gln Leu Thr Phe Leu Leu Gly
110 115 120

Leu Val Gly Leu Pro Leu Leu Ser Pro Asp Ala Pro Cys Trp Glu
125 130 135

Glu Ala Met Ala Ala Ala Phe Gln Leu Ala Ser Phe Val Leu Val
140 145 150

Ile Gly Leu Val Thr Phe Tyr Arg Ile Gly Pro Tyr Thr Asn Leu
155 160 165

Ser Trp Ser Cys Tyr Leu Asn Ile Gly Ala Cys Leu Leu Ala Thr
170 175 180

Leu Ala Ala Ala Met Leu Ile Trp Asn Ile Leu His Lys Arg Glu
185 190 195

Asp Cys Met Ala Pro Arg Val Ile Val Ile Ser Arg Ser Leu Thr
200 205 210

Ala Arg Phe Arg Arg Gly Leu Asp Asn Asp Tyr Val Glu Ser Pro
215 220 225

Cys

<210> SEQ ID NO 113
<211> LENGTH: 1389
<212> TYPE: DNA
<213> ORGANISM: Homo Sapien

<400> SEQUENCE: 113
gactttacca ctactcgcta tagagccctg gtcaagttct ctccacctct 50
ctatctatgt ctcagtttct tcatctgtaa catcaaatga ataataatac 100
caatctccta gacttcataa gaggattaac aaagacaaaa tatgggaaaa 150
acataacatg gcgtcccata attattagat cttattattg acactaaaat 200
ggcattaaaa ttaccaaaag gaagacagca tctgtttcct ctttggtcct 250
gagctggtta aaaggaacac tggttgcctg aacagtcaca cttgcaacca 300
tgatgcctaa acattgcttt ctaggcttcc tcatcagttt cttccttact 350
ggtgtagcag gaactcagtc aacgcatgag tctctgaagc ctcagagggt 400

-continued

```
acaatttcag tcccgaaatt ttcacaacat tttgcaatgg cagcctggga           450

gggcacttac tggcaacagc agtgtctatt ttgtgcagta caaaatatat           500

ggacagagac aatggaaaaa taaagaagac tgttggggta ctcaagaact           550

ctcttgtgac cttaccagtg aaacctcaga catacaggaa ccttattacg           600

ggagggtgag ggcggcctcg gctgggagct actcagaatg gagcatgacg           650

ccgcggttca ctccctggtg ggaaacaaaa atagatcctc cagtcatgaa           700

tataacccaa gtcaatggct ctttgttggt aattctccat gctccaaatt           750

taccatatag ataccaaaag gaaaaaaatg tatctataga agattactat           800

gaactactat accgagtttt tataattaac aattcactag aaaaggagca           850

aaaggtttat gaaggggctc acagagcggt tgaaattgaa gctctaacac           900

cacactccag ctactgtgta gtggctgaaa tatatcagcc catgttagac           950

agaagaagtc agagaagtga agagagatgt gtggaaattc catgacttgt          1000

ggaatttggc attcagcaat gtggaaattc taaagctccc tgagaacagg          1050

atgactcgtg tttgaaggat cttatttaaa attgtttttg tattttctta          1100

aagcaatatt cactgttaca ccttggggac ttctttgttt acccattctt          1150

ttatccttta tatttcattt gtaaactata tttgaacgac attccccccg          1200

aaaaattgaa atgtaaagat gaggcagaga ataaagtgtt ctatgaaatt          1250

cagaacttta tttctgaatg taacatccct aataacaacc ttcattcttc          1300

taatacagca aaataaaaat ttaacaacca aggaatagta tttaagaaaa          1350

tgttgaaata attttttaa aatagcatta cagactgag                      1389
```

<210> SEQ ID NO 114
<211> LENGTH: 231
<212> TYPE: PRT
<213> ORGANISM: Homo Sapien

<400> SEQUENCE: 114

```
Met Met Pro Lys His Cys Phe Leu Gly Phe Leu Ile Ser Phe Phe
  1               5                  10                  15

Leu Thr Gly Val Ala Gly Thr Gln Ser Thr His Glu Ser Leu Lys
                 20                  25                  30

Pro Gln Arg Val Gln Phe Gln Ser Arg Asn Phe His Asn Ile Leu
                 35                  40                  45

Gln Trp Gln Pro Gly Arg Ala Leu Thr Gly Asn Ser Ser Val Tyr
                 50                  55                  60

Phe Val Gln Tyr Lys Ile Tyr Gly Gln Arg Gln Trp Lys Asn Lys
                 65                  70                  75

Glu Asp Cys Trp Gly Thr Gln Glu Leu Ser Cys Asp Leu Thr Ser
                 80                  85                  90

Glu Thr Ser Asp Ile Gln Glu Pro Tyr Tyr Gly Arg Val Arg Ala
                 95                 100                 105

Ala Ser Ala Gly Ser Tyr Ser Glu Trp Ser Met Thr Pro Arg Phe
                110                 115                 120

Thr Pro Trp Trp Glu Thr Lys Ile Asp Pro Pro Val Met Asn Ile
                125                 130                 135

Thr Gln Val Asn Gly Ser Leu Leu Val Ile Leu His Ala Pro Asn
                140                 145                 150
```

-continued

```
Leu Pro Tyr Arg Tyr Gln Lys Glu Lys Asn Val Ser Ile Glu Asp
                155                 160                 165

Tyr Tyr Glu Leu Leu Tyr Arg Val Phe Ile Ile Asn Asn Ser Leu
                170                 175                 180

Glu Lys Glu Gln Lys Val Tyr Glu Gly Ala His Arg Ala Val Glu
                185                 190                 195

Ile Glu Ala Leu Thr Pro His Ser Ser Tyr Cys Val Val Ala Glu
                200                 205                 210

Ile Tyr Gln Pro Met Leu Asp Arg Arg Ser Gln Arg Ser Glu Glu
                215                 220                 225

Arg Cys Val Glu Ile Pro
                230


<210> SEQ ID NO 115
<211> LENGTH: 43
<212> TYPE: DNA
<213> ORGANISM: Artificial Sequence
<220> FEATURE:
<223> OTHER INFORMATION: Synthetic Oligonucleotide Probe

<400> SEQUENCE: 115

tgtaaaacga cggccagtta aatagacctg caattattaa tct                       43


<210> SEQ ID NO 116
<211> LENGTH: 41
<212> TYPE: DNA
<213> ORGANISM: Artificial Sequence
<220> FEATURE:
<223> OTHER INFORMATION: Synthetic Oligonucleotide Probe

<400> SEQUENCE: 116

caggaaacag ctatgaccac ctgcacacct gcaaatccat t                         41
```